US008962263B2

(12) United States Patent
Perez et al.

(10) Patent No.: US 8,962,263 B2
(45) Date of Patent: *Feb. 24, 2015

(54) METHODS AND COMPOSITIONS FOR DETECTING THE ACTIVATION STATE OF MULTIPLE PROTEINS IN SINGLE CELLS

(75) Inventors: Omar D. Perez, Stanford, CA (US); Garry P. Nolan, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/094,735

(22) Filed: Apr. 26, 2011

(65) Prior Publication Data

US 2012/0309026 A1 Dec. 6, 2012

Related U.S. Application Data

(60) Division of application No. 12/372,670, filed on Feb. 17, 2009, now Pat. No. 8,148,094, which is a continuation of application No. 10/193,462, filed on Jul. 10, 2002, now Pat. No. 7,563,584.

(60) Provisional application No. 60/304,434, filed on Jul. 10, 2001, provisional application No. 60/310,141, filed on Aug. 2, 2001.

(51) Int. Cl.
*G01N 33/574* (2006.01)
*G01N 33/557* (2006.01)
(Continued)

(52) U.S. Cl.
CPC ............ *G01N 33/5302* (2013.01); *C12Q 1/485* (2013.01); *G01N 33/5008* (2013.01);
(Continued)

(58) Field of Classification Search
USPC .......... 435/1, 4, 6, 7.1, 7.21, 7.23, 7.24, 7.92, 435/8, 18, 23, 40.5, 375, 973, 1.1; 436/503, 436/519, 538, 546, 10, 17, 37, 56, 63, 64, 436/172, 174; 422/82.05
See application file for complete search history.

(56) References Cited

U.S. PATENT DOCUMENTS

| 4,469,863 A | 9/1984 | Ts'o et al. |
| 4,568,649 A | 2/1986 | Bertoglio-Matte et al. |

(Continued)

FOREIGN PATENT DOCUMENTS

| WO | 99/44067 | 9/1999 |
| WO | 99/54494 | 10/1999 |

(Continued)

OTHER PUBLICATIONS

Cell-cycle-dependent activation of mitogen-mitogen activated protein kinase kinase (MEK-1/2) in myeloid leukemia cell lines and induction of growth inhibition and apoptosis by inhibitors of RAS signaling. Blood 97 (6): 1823-1834 (Mar. 15, 2001).*

(Continued)

*Primary Examiner* — Gail R Gabel
(74) *Attorney, Agent, or Firm* — Bozicevic, Field & Francis LLP; Bret E. Field

(57) ABSTRACT

The invention provides methods and compositions for simultaneously detecting the activation state of a plurality of proteins in single cells using flow cytometry. The invention further provides methods and compositions of screening for bioactive agents capable of coordinately modulating the activity of a plurality of proteins in single cells. The methods and compositions can be used to determine the protein activation profile of a cell for predicting or diagnosing a disease state, and for monitoring treatment of a disease state.

15 Claims, 101 Drawing Sheets

(51) Int. Cl.
  *G01N 33/53* (2006.01)
  *C12Q 1/48* (2006.01)
  *G01N 33/50* (2006.01)
  *G01N 33/543* (2006.01)
  *G01N 33/573* (2006.01)
  *G01N 33/58* (2006.01)

(52) U.S. Cl.
  CPC ........ *G01N33/5041* (2013.01); *G01N 33/5091* (2013.01); *G01N 33/5094* (2013.01); *G01N 33/54313* (2013.01); *G01N 33/573* (2013.01); *G01N 33/582* (2013.01); *G01N 2333/91205* (2013.01); *G01N 2333/96466* (2013.01); *Y10S 435/973* (2013.01)
  USPC ........... 435/7.23; 435/1.1; 435/7.1; 435/7.21; 435/7.24; 435/23; 435/40.5; 435/375; 435/973; 436/517; 436/519; 436/546; 436/10; 436/63; 436/64; 436/172; 436/174; 422/82.05

(56) References Cited

U.S. PATENT DOCUMENTS

| | | | |
|---|---|---|---|
| 4,979,824 A | 12/1990 | Mathies et al. | |
| 5,034,506 A | 7/1991 | Summerton et al. | |
| 5,137,809 A | 8/1992 | Loken et al. | |
| 5,216,414 A | 6/1993 | Fukutani et al. | |
| 5,234,816 A | 8/1993 | Terstappen | |
| 5,235,033 A | 8/1993 | Summerton et al. | |
| 5,386,023 A | 1/1995 | Sanghvi et al. | |
| 5,599,681 A | 2/1997 | Epstein et al. | |
| 5,602,240 A | 2/1997 | De Mesmaeker et al. | |
| 5,637,684 A | 6/1997 | Cook et al. | |
| 5,644,048 A | 7/1997 | Yau | |
| 5,919,646 A | 7/1999 | Okun et al. | |
| 5,968,738 A | 10/1999 | Anderson et al. | |
| 5,998,212 A | 12/1999 | Corio et al. | |
| 6,280,967 B1 | 8/2001 | Ransom et al. | |
| 6,379,917 B1 | 4/2002 | Okun et al. | |
| 6,495,333 B1 | 12/2002 | Willmann et al. | |
| 6,558,916 B2 | 5/2003 | Veerapandian et al. | |
| 6,592,822 B1 | 7/2003 | Chandler | |
| 6,673,554 B1 | 1/2004 | Kauvar | |
| 6,733,743 B2 | 5/2004 | Jordan | |
| 6,806,056 B2 | 10/2004 | Glickman et al. | |
| 6,821,740 B2 | 11/2004 | Darzynkiewicz et al. | |
| 6,872,574 B2 | 3/2005 | Cravatt et al. | |
| 6,906,320 B2 | 6/2005 | Sachs et al. | |
| 6,958,221 B2 | 10/2005 | Veerapandian et al. | |
| 6,972,198 B2 * | 12/2005 | Craig et al. .................. | 436/164 |
| 7,001,725 B2 | 2/2006 | Singh et al. | |
| 7,018,850 B2 | 3/2006 | Raymond et al. | |
| 7,070,943 B2 * | 7/2006 | Darzynkiewicz et al. ..... | 435/7.2 |
| 7,102,005 B2 | 9/2006 | Agnew et al. | |
| 7,183,385 B2 | 2/2007 | Comb et al. | |
| 7,236,888 B2 | 6/2007 | Allbritton et al. | |
| 7,300,753 B2 | 11/2007 | Rush et al. | |
| 7,316,897 B2 | 1/2008 | Bisconte de Saint Julien et al. | |
| 7,326,577 B2 | 2/2008 | Shults et al. | |
| 7,329,502 B2 | 2/2008 | Staudt et al. | |
| 7,351,546 B2 | 4/2008 | Willmann et al. | |
| 7,392,199 B2 | 6/2008 | Karlov et al. | |
| 7,393,656 B2 | 7/2008 | Perez et al. | |
| 7,419,777 B2 | 9/2008 | Bacus | |
| 7,563,584 B2 | 7/2009 | Perez et al. | |
| 7,695,924 B2 | 4/2010 | Perez et al. | |
| 7,803,523 B2 | 9/2010 | Chow et al. | |
| 7,894,992 B2 | 2/2011 | Shaughnessy et al. | |
| 7,939,278 B2 | 5/2011 | Perez et al. | |
| 7,939,331 B2 | 5/2011 | Leite et al. | |
| 8,187,885 B2 | 5/2012 | Purvis, Jr. | |
| 8,206,939 B2 | 6/2012 | Perez et al. | |
| 8,214,157 B2 | 7/2012 | Moser et al. | |
| 8,227,202 B2 | 7/2012 | Fantl et al. | |
| 8,242,248 B2 | 8/2012 | Soper et al. | |
| 8,309,315 B2 | 11/2012 | Cao et al. | |
| 8,333,970 B2 | 12/2012 | Aukerman et al. | |
| 8,394,599 B2 | 3/2013 | Perez et al. | |
| 2002/0028450 A1 | 3/2002 | Greene et al. | |
| 2002/0127604 A1 | 9/2002 | Albritton et al. | |
| 2002/0197658 A1 | 12/2002 | Delaney et al. | |
| 2003/0148321 A1 | 8/2003 | Pecker et al. | |
| 2003/0190688 A1 | 10/2003 | Crosby et al. | |
| 2003/0190689 A1 | 10/2003 | Crosby et al. | |
| 2003/0219827 A1 | 11/2003 | Comb et al. | |
| 2004/0063088 A1 | 4/2004 | Berg et al. | |
| 2004/0072184 A1 | 4/2004 | Yoganathan et al. | |
| 2004/0126784 A1 | 7/2004 | Hitoshi et al. | |
| 2004/0137539 A1 | 7/2004 | Bradford | |
| 2004/0170995 A1 | 9/2004 | Lograsso et al. | |
| 2004/0180380 A1 | 9/2004 | Lee et al. | |
| 2004/0219592 A1 | 11/2004 | Berg et al. | |
| 2004/0224371 A1 | 11/2004 | DeMatos et al. | |
| 2004/0229284 A1 | 11/2004 | Luciw et al. | |
| 2004/0241636 A1 | 12/2004 | Michnick et al. | |
| 2004/0248151 A1 | 12/2004 | Bacus et al. | |
| 2005/0009112 A1 | 1/2005 | Edgar et al. | |
| 2005/0042694 A1 | 2/2005 | Darzynkiewicz et al. | |
| 2005/0074834 A1 | 4/2005 | Chaplen et al. | |
| 2005/0084924 A1 | 4/2005 | Shults et al. | |
| 2005/0131006 A1 | 6/2005 | Mukherjee et al. | |
| 2005/0216961 A1 | 9/2005 | Delaney | |
| 2005/0250127 A1 | 11/2005 | Fisher et al. | |
| 2005/0281743 A1 | 12/2005 | Delaney | |
| 2006/0029944 A1 | 2/2006 | Huang et al. | |
| 2006/0035211 A1 | 2/2006 | Levinson et al. | |
| 2006/0040338 A1 | 2/2006 | Westwick et al. | |
| 2006/0046249 A1 | 3/2006 | Huang et al. | |
| 2006/0073474 A1 | 4/2006 | Perez et al. | |
| 2006/0216760 A1 | 9/2006 | Dieterich et al. | |
| 2007/0009923 A1 | 1/2007 | Nolan et al. | |
| 2007/0105165 A1 | 5/2007 | Goolsby et al. | |
| 2007/0196869 A1 | 8/2007 | Perez et al. | |
| 2008/0254489 A1 | 10/2008 | Perez et al. | |
| 2009/0068681 A1 | 3/2009 | Perez et al. | |
| 2009/0081699 A1 | 3/2009 | Perez et al. | |
| 2009/0098594 A1 | 4/2009 | Fantl et al. | |
| 2009/0148462 A1 | 6/2009 | Chevrier et al. | |
| 2009/0269773 A1 | 10/2009 | Fantl et al. | |
| 2009/0269800 A1 | 10/2009 | Covey et al. | |
| 2009/0291458 A1 | 11/2009 | Cohen et al. | |
| 2010/0006787 A1 | 1/2010 | Nakata et al. | |
| 2010/0009364 A1 | 1/2010 | Fantl et al. | |
| 2010/0014741 A1 | 1/2010 | Banville et al. | |
| 2010/0030719 A1 | 2/2010 | Covey et al. | |
| 2010/0042351 A1 | 2/2010 | Covey et al. | |
| 2010/0086951 A1 | 4/2010 | Hedley et al. | |
| 2010/0099109 A1 | 4/2010 | Fantl et al. | |
| 2010/0105074 A1 | 4/2010 | Covey et al. | |
| 2010/0151472 A1 | 6/2010 | Nolan et al. | |
| 2010/0184092 A1 | 7/2010 | Perez et al. | |
| 2010/0204973 A1 | 8/2010 | Parkinson et al. | |
| 2010/0209929 A1 | 8/2010 | Fantl et al. | |
| 2010/0215644 A1 | 8/2010 | Fantl et al. | |
| 2010/0233733 A1 | 9/2010 | Fantl | |
| 2010/0285594 A1 | 11/2010 | Purvis, Jr. | |
| 2010/0297676 A1 | 11/2010 | Fantl et al. | |
| 2011/0020839 A1 | 1/2011 | Perez et al. | |
| 2011/0059861 A1 | 3/2011 | Nolan et al. | |
| 2011/0104717 A1 | 5/2011 | Fantl et al. | |
| 2011/0201018 A1 | 8/2011 | Perez et al. | |
| 2011/0201019 A1 | 8/2011 | Perez et al. | |
| 2011/0207145 A1 | 8/2011 | Perez et al. | |
| 2011/0207146 A1 | 8/2011 | Perez et al. | |
| 2011/0207149 A1 | 8/2011 | Perez et al. | |
| 2011/0250614 A1 | 10/2011 | Perez et al. | |
| 2011/0262468 A1 | 10/2011 | Fantl et al. | |
| 2011/0269154 A1 | 11/2011 | Fantl et al. | |
| 2011/0269634 A1 | 11/2011 | Perez et al. | |
| 2012/0070849 A1 | 3/2012 | Perez et al. | |

(56) References Cited

U.S. PATENT DOCUMENTS

| | | | |
|---|---|---|---|
| 2012/0157340 A1 | 6/2012 | Cesano et al. | |
| 2012/0309026 A1* | 12/2012 | Perez et al. | 435/7.21 |
| 2013/0071860 A1 | 3/2013 | Hale et al. | |

FOREIGN PATENT DOCUMENTS

| | | |
|---|---|---|
| WO | 2007/056192 | 5/2007 |
| WO | 2009/025847 | 2/2009 |
| WO | 2010/006291 | 1/2010 |
| WO | 2010/028277 | 3/2010 |
| WO | 2010/045651 | 4/2010 |
| WO | 2010/135608 | 11/2010 |

OTHER PUBLICATIONS

Wang; et al. "Regulation of Rb and E2F by signal transduction cascades: divergent effects of JNK1 and p38 kinases", The EMBO Journal (Mar. 1999), 18(6):1559-1570.

U.S. Appl. No. 13/094,737, filed Apr. 26, 2011, Perez et al.

U.S. Appl. No. 13/098,902, filed May 2, 2011, Perez et al.

Aziz, et al. Modulation of endothelial cell expression of ICAM-1, E-selectin, and VCAM-1 by beta-estradiol, progesterone, and dexamethasone. Cell Immunol. Jan. 10, 1996;167(1):79-85.

Fiering, S. N. et al. "Improved FAGS-gal:flow cytometric analysis and sorting of viable eukaryotic cells expressing reporter gene constructs." Cytometry, 12:291-301. (1991).

Fine, J. S., and Kruisbeek, A. M. (1991). "The role of LFA-1IICAM-1 interactions during murine T lymphocyte development." J Immunol 147. 2852-2859.

Geiger, C., et al. (2000). "Cytohesin-1 regulates beta-2 integrin-mediated adhesion through both ARF-GEF function and interaction with LFA-1." Embo J 19, 2525-2536.

Griffioen, A. W., et al. (1996). "Endothelial intercellular adhesion molecule-1 expression is suppressed in human malignancies: the role of angiogenic factors." Cancer Res 56,111 1-1 7.

Griffioen, A. W., et al. (1996). "Tumor angiogenesis is accompanied by a decreased inflammatory response of tumor-associated endothelium." Blood 88,667-73.

Haswell, L. E., et al., "Analysis of the oligomeric requirement for signaling by CD40 using soluble multimeric forms of its ligands, CD154", Eur. J. Immunol., 2001, 31(10):3094-3100.

Helander, T. S., et al. (1996). :ICAM-2 redistributed by ezrin as a target for killer cells. Nature 382, 265-8.

Hogg, N., et al. (1999). "A novel leukocyte adhesion deficiency caused by expressed but nonfunctional beta2 integrins Mac-1 and LFA-1." J Clin Invest 103, 97-106.

Igietseme, J. U., eta. (1999). "The intercellular adhesion molecule type-I is required for rapid activation of T helper type 1 lymphocytes that control early acute phase of genital chlamydia1 infection in mice." Immunology 98, 510-8.

Iyer, S. B., et al. (1998). "Quantitation of CD38 expression using QuantiBRITETM beads." Cytometry 33, 206-12.

Jiang, K., et al. (2000). "Pivotal role of phosphoinositide-3 kinase in regulation of cytotoxicity in natural killer cells." Nat Immunol 1, 419-425.

Johnson, V. L., et al. (2000). "Effector caspases are dispensable for the early nuclear morphological changes during chemical-induced apoptosis." J Cell Sci 11 3, 2941-53.

Kennedy, S. G., et al. (1999). "AktlProtein kinase B inhibits cell death by preventing the release of cytochrome c from mitochondria." Mol Cell Biol 19, 5800-10.

Kliche, S., et al. (2001). "Signaling by human herpesvirus 8 kaposin A through direct membrane recruitment of cytohesin-1." Mol Cell 7, 833-843.

Kulik, G. et al. (1997). "Antiapoptotic signalling by the insulin-like growth factor I receptor, phosphatidylinositol 3-kinase, and Akt." Mol Cell Biol 17,1595-606.

Lecoeur, H., et al. (2001). "A novel flow cytometric assay for quantitation and multiparametric characterization of cell-mediated cytotoxicity." J Immunol Methods 253, 177-1 87.

Lenkei, R., et al. (1998). "Performance of calibration standards for antigen quantitation with flow cytometry." Cytometry 33,188-96.

Lub, M., et al. (1997). "Dual role of the actin cytoskeleton in regulating cell adhesion mediated by the integrin lymohocvte function-associated molecule-I ." Mol Biol Cell 8, 341-351.

Matsumoto, G., et al. (2000). "Adhesion mediated by LFA-1 is required for efficient IL-12-induced NK and NKT cell cytotoxicity." Eur J Immunol 30, 3723-3731.

McDowall, A., et al. (1998). "The I domain of integrin leukocyte function-associated antigen-1 is involved in a conformational change leading to high affinity binding to ligand intercellular adhesion molecule 1 (ICAM-1)." J Biol Chem 273,27396-27403.

Miller, J., et al. (1995). "Intercellular adhesion molecule-1 dimerization and its consequences for adhesion mediated by lymphocyte function associated-1 ." J Exp Med 182, 1231-41.

Morgan, M. M., et al. (2001). "Superantigen-induced T cell:B cell conjugation is mediated by LFA-1 and requires sinnalinn through Lck, but not ZAP-70." J Immunol 167, 5708-5718.

Moser, C. et al. (2002). "Improved outcome of chronic *Pseudomonas aeruginosa* lung infection is associated with induction of a Thl-dominated cytokine response." Clin Exp Immunol 127, 206-213.

Mukai, S., et al. (1999). "Critical role of CDI a (LFA-1) in therapeutic efficacy of systemically transferred antitumor effector T cells." Cell Immunol 192, 122-1 32.

Neeson, P. J., et al. (2000). "Characterization of activated lymphocyte-tumor cell adhesion." J Leukoc Biol 67, 847-855.

Nielsen, S. D., et al. "Expression of the activation antigen CD69 predicts functionality of in vitro expanded peripheral blood mononuclear cells (PBMC) from healthy donors and HIV-infected patients." Clin Exp Immunol 114, 66-72. (1 998).

Nishimura, T., et al. (1999). "Distinct role of antigen-specific T helper type 1 (Thl) and Th2 cells in tumor eradication in vivo." J Exp Med 190, 61 7-627.

Nolan, G. P., et al. "Fluorescence activated cell analysis and sorting of viable mammalian cells based on beta-D-galactosidase activitvafter transduction of *Escherichia coli* lacZ." Proc Natl Acad Sci U S A 85, 2603-7. (1988).

Olsen, M. J. et al. "Function-based isolation of novel enzymes from a large library." Nat Biotechnol 18,1071-4; (2000).

Onishi, M., et al. (1996). "Applications of retrovirus-mediated expression cloning." Exp Hematol 24,324-9.

Perez, 0. D., and Nolan, G. P. (2002). "Simultaneous measurement of multiple active kinase states using polychromatic flow cytometry." Nat Biotechnol 20, 155-1 62.

Perez, 0. D., eta;. (2002). "Activation of the PKBIAKT Pathway by ICAM-2." Immunity 26, 51-65.

Peterson, E. J., et al. (2001). "Coupling of the TCR to integrin activation by Slap-130IFyb." Science 293, 2263-2265.

Benekli, et al. Signal transducer and activator of transcription proteins in leukemias. Blood. Apr. 15, 2003;101(8):2940-54.

Khalidi, et al. The immunophenotype of adult acute myeloid leukemia: high frequency of lymphoid antigen expression and comparison of immunophenotype, French-American-British classification, and karyotypic abnormalities. Am J Clin Pathol. Feb. 1998;109(2):211-20.

Irish, et al. Single cell profiling of potentiated phospho-protein networks in cancer cells. Cell. Jul. 23, 2004;118(2):217-28.

Soiling, et al. Free light chains of immunoglobulins in serum from patients with leukaemias and multiple myeloma. Scand J Haematol. Apr. 1982;28(4):309-18.

Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

Kindler, et al., "Identification of a novel activating mutation (Y842C) within the activation loop of FLT3 in a patient with AML", Blood (2003), 102(11):239B-240B and 45th Annual Meeting of the American Society of Hematology San Diego, CA, USA. Dec. 6-9, 2003. Abstract 4681.

(56) References Cited

OTHER PUBLICATIONS

Radoja, S., et al. (2001). "CD8+ tumor-infiltrating T cells are deficient in perforin-mediated cytolytic activity due to defective microtubule-organizing center mobilization and lytic granule exocytosis." J Immunol 167, 5042-5051.

Risso, A. et al. "CD69 in resting and activated T lymphocytes. Its association with a GTP binding protein and biochemical requirements for its expression." J Immunol 146, 41 05-14. (1991).

Salomon, B., and Bluestone, J. A. (1998). "LFA-1 interaction with ICAM-1 and ICAM-2 regulates Th2 cytokine production." J Immunol 161, 5138-5142.

Scharffetter-Kochanek, K., et al. (1998). "Spontaneous skin ulceration and defective T cell function in CD18 null mice." J Exp Med 188, 119-131.

Shibuya, K., et al. (1999). "Physical and functional association of LFA-1 with DNAM-1 adhesion molecule." Immunity 11, 615-623.

Shier, P., et al. (1999). "Defective CD8+ T cell activation and cytolytic function in the absence of LFA-1 cannot be restored by increased TCR signaling." J Immunol 163,4826-4832.

Soede, R. D., et al. (1999). "LFA-1 to LFA-1 signals involve zeta-associated protein-70 (ZAP-70) tyrosine kinase: relevance for invasion and migration of a T cell hybridoma." J Immunol 163,4253-4261.

Somersalo, K., et al. (1995). "Activation of natural killer cell migration by leukocyte integrin-binding peptide from intracellular adhesion molecule-2 (ICAM-2)." J Biol Chem 270, 8629-8636.

Song, X., et al. "Flow cytometry-based biosensor for detection of multivalent proteins." Anal Biochem 284, 35-41. (2000).

Staquet, M. J., et al. (1995). "Expression of ICAM-3 on human epidermal dendritic cells." Immunobiology 192, 249-61.

Starling, G. C., et al. (1995). "Intercellular adhesion molecule-3 is the predominant co-stimulatory ligand for leukocyte function antigen-I on human blood dendritic cells." Eur J Immunol25, 2528-2532.

Sugai, T., et al. (2000). "Allelic losses of 17p, 5q, and 18q loci in diploid and aneuploid populations of multiploid colorectal carcinomas." Hum Pathol 31, 925-30.

Tanaka Y, et al. "Intercellular adhesion molecule 1 underlies the functional heterogeneity of synovial cells in patients with rheumatoid arthritis: involvement of cell cycle machinery." Arthritis Rheum. Nov. 2000;43(11):2513-22.

Taylor, R.P., et al., "Complement-Opsonized IgG Antibody/dsDNA Immune Complexes Bind to CR1 Clusters on Isolated Human Erythrocytes", Clinical Immunology and Immunopathology, 1991, 61 :143-160.

Weber, K. S., et al. (2001). "Cytohesin-I is a dynamic regulator of distinct LFA-1 functions in leukocyte arrest and transmigration triggered by chemokines." Curr Biol 11, 1969-1 974.

Yu, T. K., et al. (2000). "11-2 activation of NK cells: involvement of MKKIIZERK but not p38 kinase pathway." J Immunol 164, 6244-6251.

Krutzik et al. "Analysis of Protein Phosphorylation and Cellular Signaling Events by Flow Cytometry: Techniques and Clinical Applications," Clinical Immunology (2004) 110:206-221.

Pettersen et al. "CD47 Signals T Cell Death," The American Association of Immunologists (1999)—162:7031-7040.

Perez, Omar; et al., "Methods for the simultaneous determination of the activation state of multiple proteins", U.S. Appl. No. 60/304,434, filed Jul. 10, 2001.

Nolan, Garry; et al., "Methods for determining kinase activity", U.S. Appl. No. 60/310,141, filed Aug. 2, 2001.

Perez OD, Mitchell D, Jager GC, Nolan GP. LFA-1 signaling through p44/42 is coupled to perforin degranulation in CD56+CD8+ natural killer cells. Blood. Aug. 15, 2004;104(4):1083-93.

Perez OD, Krutzik PO, Nolan GP. Flow cytometric analysis of kinase signaling cascades. Methods in Molecular Biology. 2004;263:67-94.

Perez OD, Mitchell D, Jager GC, South S, Murriel C, McBride J, Herzenberg LA, Kinoshita S, Nolan GP. Leukocyte functional antigen 1 lowers T cell activation thresholds and signaling through cytohesin-1 and Jun-activating binding protein 1. Nature Immunology. Nov. 2003;4(11):1083-92.

Krutzik PO, Nolan GP. Intracellular phospho-protein staining techniques for flow cytometry: monitoring single cell signaling events. Cytometry (A). Oct. 2003;55(2):61-70.

Belloc; et al., "Flow Cytometry Detection of Caspase 3 Activation in Preapoptotic Leukemic Cells", Cytometry (2000), 40:151-160.

Demirovic, PIP3 and PIP2: Complex Roles at the Cell Surface, Cell (2000), 100:603-606.

De Rosa, Stephen C.; et al., "11-color, 13-parameter flow cytometry: Identification of human naive T cells by phenotype, function, and T-cell receptor diversity", Nature Medicine, Feb. 2001, 7(2): 245-8.

Koester; et al., Intracellular Markers, Journal of Immunological Methods, 2000, 243:99-106.

Krutzik, Peter O.; et al, "Intracellular phospho-protein staining techniques for flow cytometry: monitoring single cell signaling events", Cytometry (A), Oct. 2003, 55(2):61-70.

Morgan, Michael A.; et al., "Cell-cycle-dependent activation of mitogen-activated protein kinase kinase (MEK-1/2) in myeloid leukemia cell lines and induction of growth inhibition and apoptosis by inhibitors of RAS signaling", Neoplasia, Blood, Mar. 15, 2001, vol. 97, No. 6, pp. 1823-1834, The American Society of Hematology.

Perez, Omar D.; et al, "Leukocyte functional antigen 1 lowers T cell activation thresholds and signaling through cytohesin-1 and Jun-activating binding protein 1", Nature Immunology, Nov. 2003, 4(11):1083-92.

Perez, Omar D.; et al., "LFA-1 signaling through p44/42 is coupled to perforin degranulation in CD56+CD8+ natural killer cells", Blood, Aug. 15, 2004, 104(4):1083-93.

Perez, Omar D.; et al, "Flow cytometric analysis of kinase signaling cascades", Methods in Molecular Biology, 2004, 263:67-94.

Allende, L. M., et al., (2000). "A novel CD18 genomic deletion in a patient with severe leucocyte adhesion deficiency: a possible CD21lymphocyte function-associated antigen-1 functional association in humans." Immunology 991440-50.

Anderson, M. T. et al. "Simultaneous fluorescence-activated cell sorter analysis of two distinct transcriptional elements within a single cell using engineered green fluorescent proteins." Proc Natl Acad Sci U S A 93, 8508-11 (1996).

Bleijs, D. A., et al. (2001). "A single amino acid in the cytoplasmic domain of the beta 2 integrin lymphocyte function-associated antigen-1 regulates avidity-dependent inside-out signaling." J Biol Chem 276, 10338-1 0346.

Cairo, C.W., et al., "Control of Multivalent Interactions by Binding Epitope Density", J. Am. Chem. Soc., 2002, 124(8):1615-1619.

Cochran, J. R., et al., "Receptor clustering and transmembrane signaling in T cells", TRENDS in Biochemical Sciences, May 2001, 26(5):304-310.

Colucci, F., et al. (1999). "Redundant role of the Syk protein tyrosine kinase in mouse NK cell differentiation." J Immunol 163. 1769-17 74.

Damle, N. K., et al. (1992~)".D ifferential regulatory effects of intercellular adhesion molecule-1 on costimulation by the CD28 counter-receptor 87." J Immunol 149, 2541-2548.

Dantuma, N. P., et al. "Short-lived green fluorescent proteins for quantifying ubiquitin/proteasome-dependent proteolysis in living cells." Nat Biotechnol 18, 538-43. (2000).

Davis, K. A., et al. (1998). "Determination of CD4 antigen density on cells: role of antibody valency, avidity, clones, and conjugation." Cytometry 33,197-205.

De Fougerolles, A. R., et al. (1995). "Heterogenous glycosylation of ICAM-3 and lack of interaction with Mac-1 and p150,95." Eur J Immunol 25,1008-12.

De Fougerolles, et al. (1991). "Characterization of ICAM-2 and evidence for a third counter-receptor for LFA-1." Exp Med 174. 253-67.

De Rosa, S. C., et al. "1 1-color, 13-parameter flow cytometry: Identification of human naive T cells by phenotype, function, and T-cell receptor diversitv." Nat Med 7. 245-248. (2001 ).

Deeths, M. J., and Mescher, M. F. (1 999). "ICAM-1 and 87-1 provide similar but distinct costimulation for CD8+ T cells, while CD4+ T cells are poorlv costimulated by ICAM-1." Eur J Immunol 29, 45-53.

Devine, L., et al. "Role of LFA-1, ICAM-1, VLA4 and VCAM-1 in lymphocyte migration across retinal pigment epithelial monolayers in vitro." Immunology 88, 456-62, 1998.

(56) References Cited

OTHER PUBLICATIONS

Diacovo, T. G., et al. (1994). "A functional integrin ligand on the surface of platelets: intercellular adhesion molecule-2." J Clin Invest 94,1243-51.
Dikic, I., et al. (1996). "A role for Pyk2 and Src in linking G-protein-coupled receptors with MAP kinase activation." Nature 383, 547-50.
Donskov, F., et al. (1996). "Expression and function of LFA-1 on A-NK and T-LAK cells: role in tumor target killing and migration into tumor tissue." Nat Immun 15, 134-146.
U.S. Appl. No. 13/453,636, filed Apr. 23, 2012, Purvis Jr.
U.S. Appl. No. 13/464,254, filed May 4, 2012, Moser et al.
U.S. Appl. No. 13/473,829, filed May 17, 2012, Fantl et al.
U.S. Appl. No. 13/493,857, filed Jun. 11, 2012, Fantl et al.
U.S. Appl. No. 13/544,053, filed Jul. 9, 2012, Soper et al.
Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.
Kumar, et al. 2-methoxyestradiol blocks cell-cycle progression at G(2)/M phase and inhibits growth of human prostate cancer cells. Mol Carcinog. Jul. 2001;31(3):111-24.
Mack, et al. Detection of caspase-activation in intact lymphoid cells using standard caspase substrates and inhibitors. J Immunol Methods. Jul. 31, 2000;241(1-2):19-31.
Apperley; et al. "Bone marrow transplantation for chronic myeloid leukaemia in first chronic phase: importance of a graft-versus-leukaemia effect", British Journal of Haematology (Jun. 1988), 69(2):239-245.
Bagrintseva; et al., "FLT3-ITD-TKD dual mutants associated with AML confer resistance to FLT3 PTK inhibitors and cytotoxic agents by overexpression of Bcl-x(L)", Blood (May 2005), 105(9):3679-3685.
Bartram; et al., "Translocation of c-abl oncogene correlates with the presence of a Philadelphia chromosome in chronic myelocytic leukaemia", Nature (Nov. 1983), 306(5940):277-280.
Benati; et al., "SRC family kinases as potential therapeutic targets for malignancies and immunological disorders", Curr Med Chem (2008), 15(12): 1154-1165.
Bene; et al., "Detection of receptor clustering by flow cytometric fluorescence anisotropy measurements", Cytometry (Aug. 2000), 40(4):292-306.
Birkenkamp; et al., "Regulation of constitutive STAT5 phosphorylation in acute myeloid leukemia blasts", Leukemia (Dec. 2001), 15(12):1923-1931.
Caligaris-Cappio; et al., "Infrequent normal B lymphocytes express features of B-chronic lymphocytic leukemia", J Exp Med (Feb. 1982), 155(2):623-628.
Calò; et al., "STAT proteins: from normal control of cellular events to tumorigenesis", J Cell Physiol (Nov. 2003), 197 (2):157-168.
Cantley; et al., "Oncogenes and signal transduction", Cell (Jan. 1991), 64(2):281-302.
Castillo; et al., "Proliferative response of mantle cell lymphoma cells stimulated by CD40 ligation and IL-4", Leukemia (Feb. 2000), 14(2):292-298.
Chow; et al., "Constitutive phosphorylation of the S6 ribosomal protein via mTOR and ERK signaling in the peripheral blasts of acute leukemia patients", Experimental hematology (2006), 34(9):1182-1190.
Chung; et al., "The biology of Abl during hemopoietic stem cell differentiation and development", Oncogene (Apr. 1995), 10(7):1261-1268.
Clark; et al., "Regulation of human B-cell activation and adhesion", Annu Rev Immunol (1991), 9:97-127.
Countouriotis; et al., "Cell surface antigen and molecular targeting in the treatment of hematologic malignancies", Stem Cells (2002), 20(3):215-229.
Crans-Vargas; et al., "CREB as a prognostic marker in acute leukemia", Blood (Nov. 2001); 98(11 part 1):316a, abstract only.
Cuenda; et al., "p38 MAP-kinases pathway regulation, function and role in human diseases", Biochimica et Biophysica Acta. (Aug. 2007), 1773(8):1358-1375.
Czech; et al., "PIP2 and PIP3: complex roles at the cell surface", Cell (Mar. 2000), 100(6):603-606.
Di Bacco; et al., "Molecular abnormalities in chronic myeloid leukemia: deregulation of cell growth and apoptosis", Oncologist (2000), 5(5):405-415.
Erlanson and Landberg, "Flow cytometric quantification of cyclin E in human cell lines and hematopoietic malignancies", Cytometry (Jul. 1998), 32(3):214-222.
Friedman; et al., "Bayesian network classifiers", Machine Learning (1997), 29:131-163.
Friedman; et al., "Inferring cellular networks using probabilistic graphical models", Science (Feb. 2004), 303(5659):799-805.
Friedman; et al., "Using Bayesian networks to analyze expression data", Journal of Computer Biology (2000), 7(3-4):601-620.
Garrido; et al., "Three-color versus four-color multiparameter cell cycle analyses of primary acute myeloid leukemia samples", Cytometry (Apr. 2000), 42(2):83-94.
Hartemink; et al., "Using graphical models and genomic expression data to statistically validate models of genetic regulatory networks", Pacific Symposium on Biocomputing (2001), 422-433.
Hunter; et al., "Cooperation between oncogenes", Cell (Jan. 1991), 64(2):249-270.
Irish; et al., "Mapping normal and cancer cell signalling networks: towards single-cell proteomics", Nat Rev Cancer (Feb. 2006), 6(2):146-155.
Kishimoto; et al., "Signal transduction through homo- or heterodimers of gpl30", Stem Cells. 1994;12(Suppl):37-44; abstract only.
Kornblau; et al., "Dynamic single-cell network profiles in acute myelogenous leukemia are associated with patient response to standard induction therapy", Clin Cancer Res (Jul. 2010), 16(14):3721-3733.
Krutzik; et al., "High-content single-cell drug screening with phosphospecific flow cytometry", Natural Chemical Biology (Feb. 2008). 4(2):132-142.
Liu; et al., "Overexpression of cyclin D1 in accelerated-phase chronic myeloid leukemia", Leuk Lymphoma (Dec. 2004), 45(12):2419-2425.
Ingley; et al., "Src family kinases: regulation of their activities, levels and identification of new pathways", Biochim Biophys Acta. (Jan. 2008), 1784(1):56-65.
Marvin; et al., "Normal bone marrow signal transduction profiles: a requisite for enhanced detection of signaling dysregulations in AML", Blood (Jan. 2011), doi:10.1182/blood-2010-10-316026.
Mørkve; et al., "Quantitation of biological tumor markers (p53, c-myc, Ki-67 and DNA ploidy) by multiparameter flow cytometry in non-small-cell lung cancer", Int J Cancer (Dec. 1992), 52(6):851-855.
Neben; et al., "Gene expression patterns in acute myeloid leukemia correlate with centrosome aberrations and numerical chromosome changes", Oncogene (Mar. 2004), 23(13):2379-2384.
Neote; et al., "Molecular cloning, functional expression, and signaling characteristics of a C—C chemokine receptor", Cell. (Feb. 1993), 12;72(2):415-425.
Norris; et al., "Multivariate analysis and reverse engineering of signal transduction pathways", Master thesis: The University of British Columbia (Apr. 2002), pp. 152.
Nurse; et al., "Universal control mechanism regulating onset of M-phase", Nature (Apr. 1990), 344(6266):503-508.
Pallis; et al., "Flow cytometric measurement of phosphorylated STAT5 in AML: lack of specific association with FLT3 internal tandem duplications", Leuk Res (Sep. 2003), 27(9):803-805.
Pascual; et al., "Analysis of somatic mutation in five B cell subsets of human tonsil", J Exp Med (Jul. 1994), 180(1):329-339.
Pe'Er; et al., "Inferring subnetworks from perturbed expression profiles", Bioinformatics (2001), 17(Suppl 1):S215-224.
Rezaei; et al., "Leukemia markers expression of peripheral blood vs bone marrow blasts using flow cytometry", Med Sci Monit (Aug. 2003), 9(8):CR359-362.

(56) References Cited

OTHER PUBLICATIONS

Rosen; et al., "Functional characterization of FLT3 receptor signaling deregulation in acute myeloid leukemia by single cell network profiling (SCNP)", PLoS One (Oct. 2010), 5(10):e13543.

Sachs; et al., "Analysis of signaling pathways in human T-cells using bayesian network modeling of single cell data", Proceedings of the 2004 IEEE computational systems bioinformatics conferences (2004), pp. 644, abstract only.

Sachs; et al., "Bayesian network approach to cell signaling pathway modeling", Science's STKE (Sep. 2002), 2002(148):pe38.

Sachs; et al., "Causal protein-signaling networks derived from multiparameter single-cell data", Science (Apr. 2005), 308(5721):523-529.

Schlessinger; et al., "Growth factor signaling by receptor tyrosine kinases", Neuron (Sep. 1992), 9(3):383-391.

Schulz; et al., "Single-cell phospho-protein analysis by flow cytometry", Curr Protoc Immunol (2007), Chapter 8:Unit 8.17.

Shankar; et al., "CREB is amplified in AML blasts and is associated with an increased risk of relapse and decreased event-free survival", Blood (2004), 104(11 part 1):166A, abstract only.

Shankar; et al., "Role of cyclic AMP response element binding protein in human leukemias", Cancer (Nov. 2005), 104(9):1819-1824.

Shankar; et al., "The role of CREB as a proto-oncogene in hematopoiesis and in acute myeloid leukemia", Cancer Cell (Apr. 2005), 7(4):351-362.

Fang; et al., "CGP57148B (STI-571) induces differentiation and apoptosis and sensitizes Bcr-Abl-positive human leukemia cells to apoptosis due to antileukemic drugs", Blood (Sep. 2000), 96(6):2246-53.

Hagiwara; et al. "Tyrosine Phosphorylation of Proteins in Primary Human Myeloid Leukemic Cells Stimulated by Macrophage Colony-Stimulating Factor: Analysis by Disease Type and Comparison With Normal Human Hematopoietic Cells", Int J Hematol (Jan. 2007), 73(1)100-107.

Xu; et al. "Tandem duplication of the FLT3 gene is found in acute lymphoblastic leukaemia as well as acute myeloid leukaemia but not in myelodysplastic syndrome or juvenile chronic myelogenous leukaemia in children", Br J Haematol (Apr. 1999), 105(1):155-162 (abstract only).

Shankaran; et al., "IFNgamma and lymphocytes prevent primary tumour development and shape tumour immunogenicity", Nature (Apr. 2001), 410(6832):1107-1111.

Spiekermann; et al., "Overexpression and constitutive activation of FLT3 induces STAT5 activation in primary acute myeloid leukemia blast cells", Clin Cancer Res (Jun. 2003), 9(6):2140-2150.

Szegedi; et al., "A new method to localize acid phosphatase using the confocal laser-scanning microscope", Pathol Oncol Res (1998), 4(3):217-223.

Tanner; et al., "Multiplex bio-assay with inductively coupled plasma mass spectrometry: Towards a massively multivariate single-cell technology", Spectrochimia Acta Part B. (2007), 62(3):188-95.

Tefferi; et al., "JAK and MPL mutations in myeloid malignancies. Leuk Lymphoma", (Mar. 2008), 49(3):388-397.

Trinchieri; et al., "Biology of natural killer cells", Adv Immunol (1989), 47:187-376.

Tse; et al., "Intracellular antibody capture technology: application to selection of intracellular antibodies recognising the BCR-ABL oncogenic protein", J Mol Biol. (Mar. 2002), 15;317(1):85-94.

Woolf; et al., "Bayesian analysis of signaling networks governing embryonic stem cell fate decisions", Bioinformatics (Mar. 2005), 21(6):741-753.

Zheng; et al., "Regulation of STAT3 and STAT5 in the differentiation of FLT3/ITD expressing 32Dcl3 cells induced by G-CSFS and CEP-701", Blood 44th Annual Meeting of the American Society of Hematology (Dec. 2002), 100(110): Abstract 2935.

Zupo; et al., "CD38 expression distinguishes two groups of B-cell chronic lymphocytic leukemias with different responses to anti-IgM antibodies and propensity to apoptosis", Blood (Aug. 1996), 88(4):1365-1374.

Lunghi; et al. "Downmodulation of ERK activity inhibits the proliferation and induces the apoptosis of primary acute myelogenous leukemia blasts", Leukemia (Sep. 2003), 17(9):1783-1793.

* cited by examiner

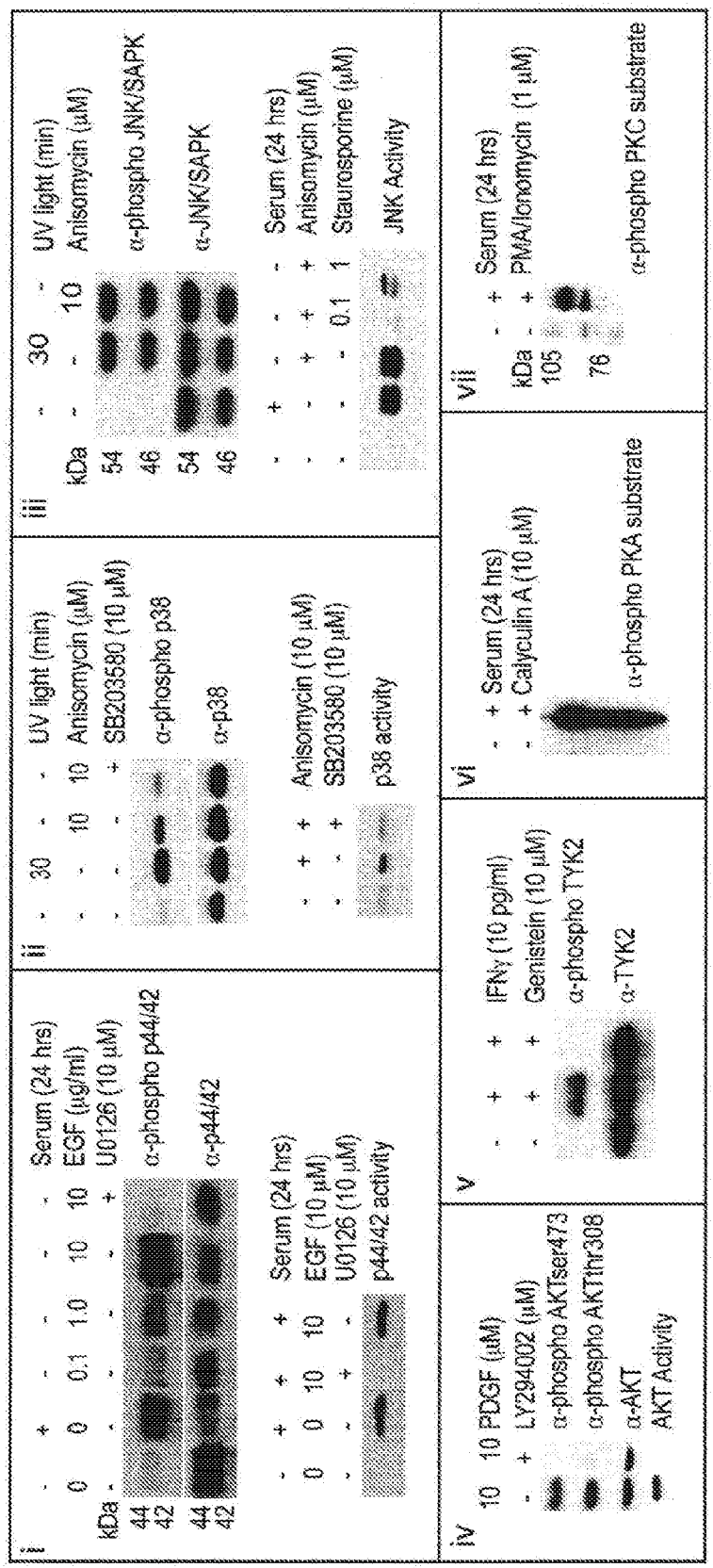
FIG._1A

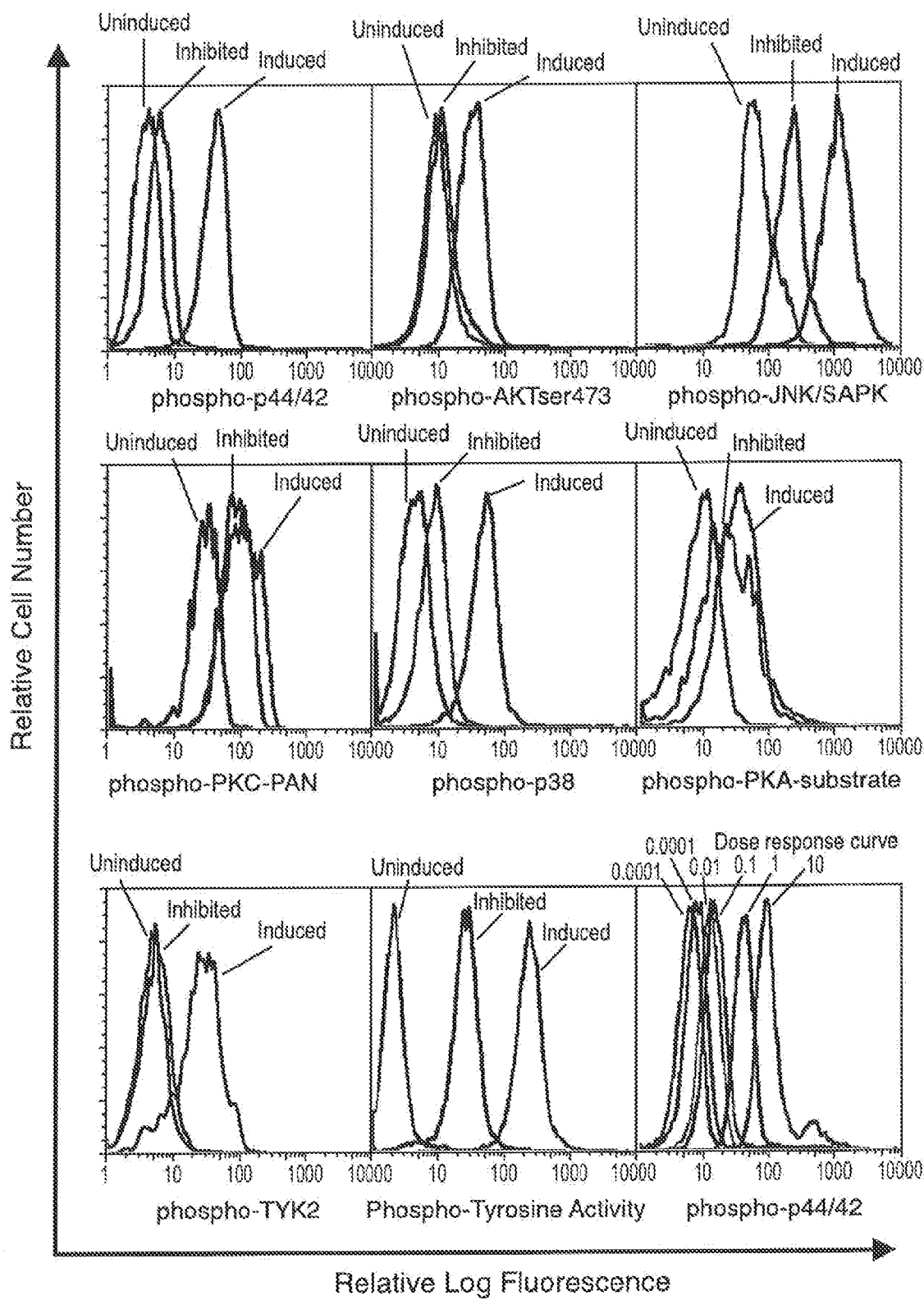
FIG._1B

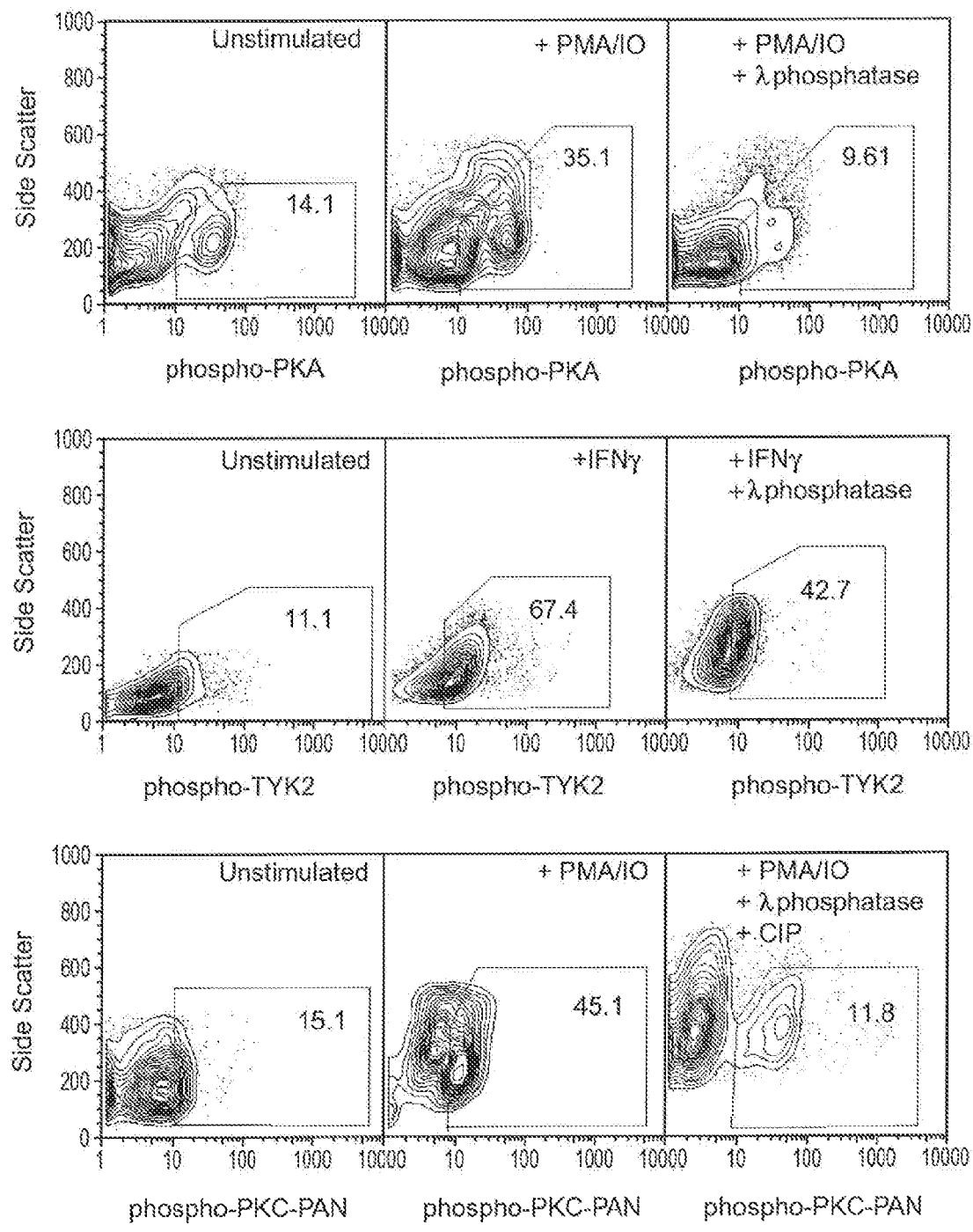
FIG._1C

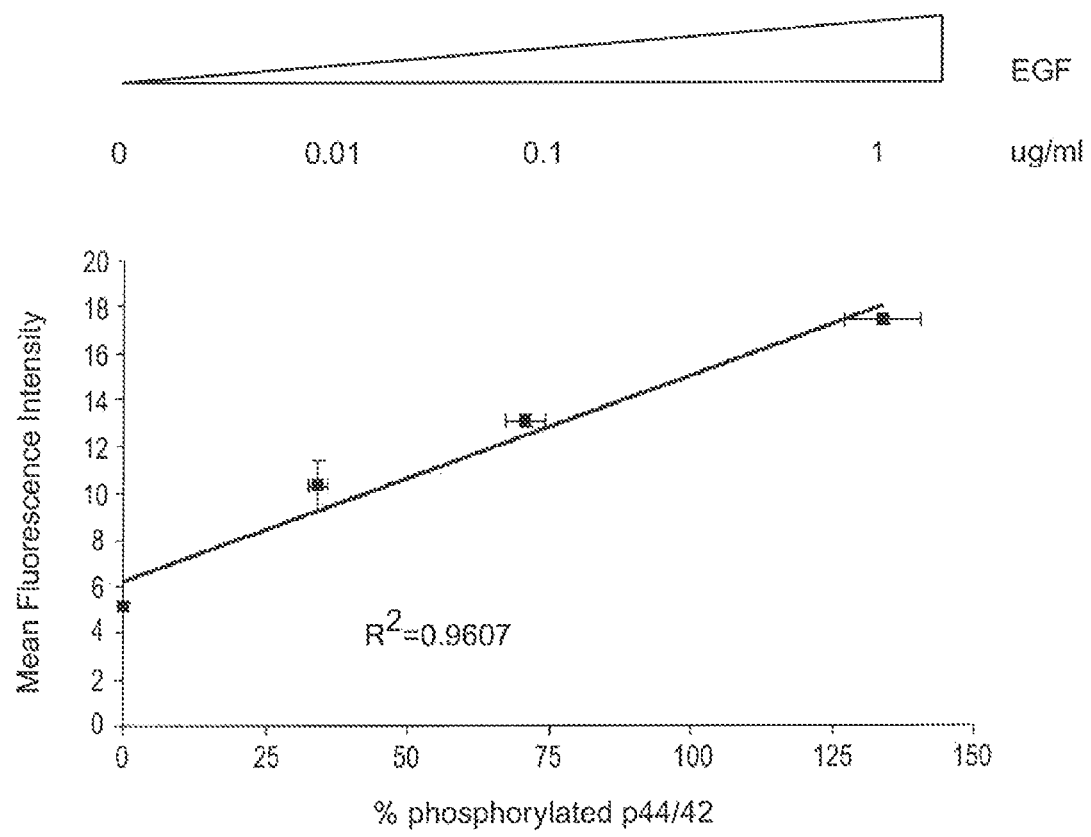
FIG._1D

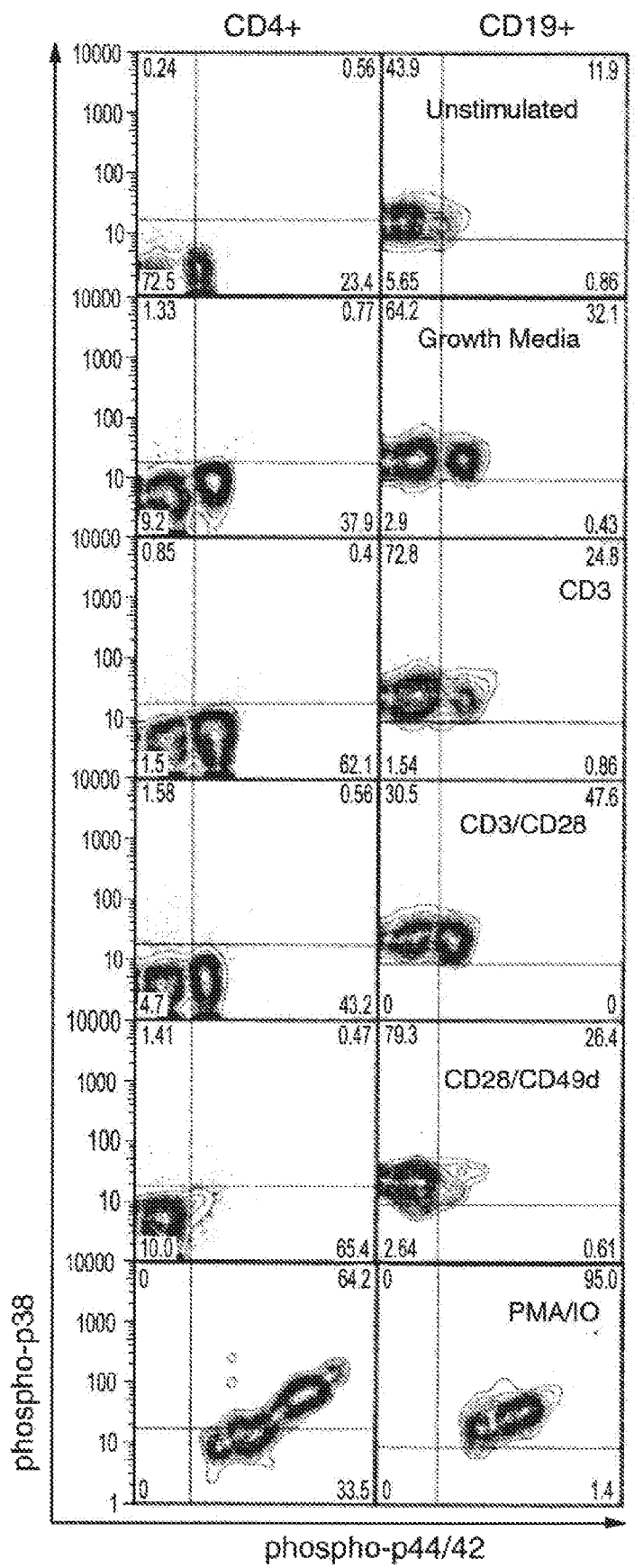
FIG._2A

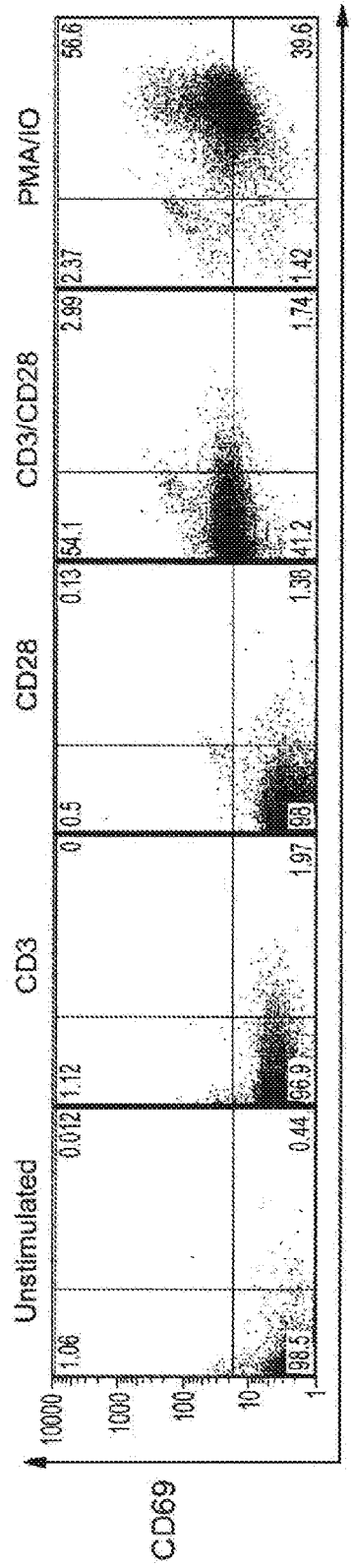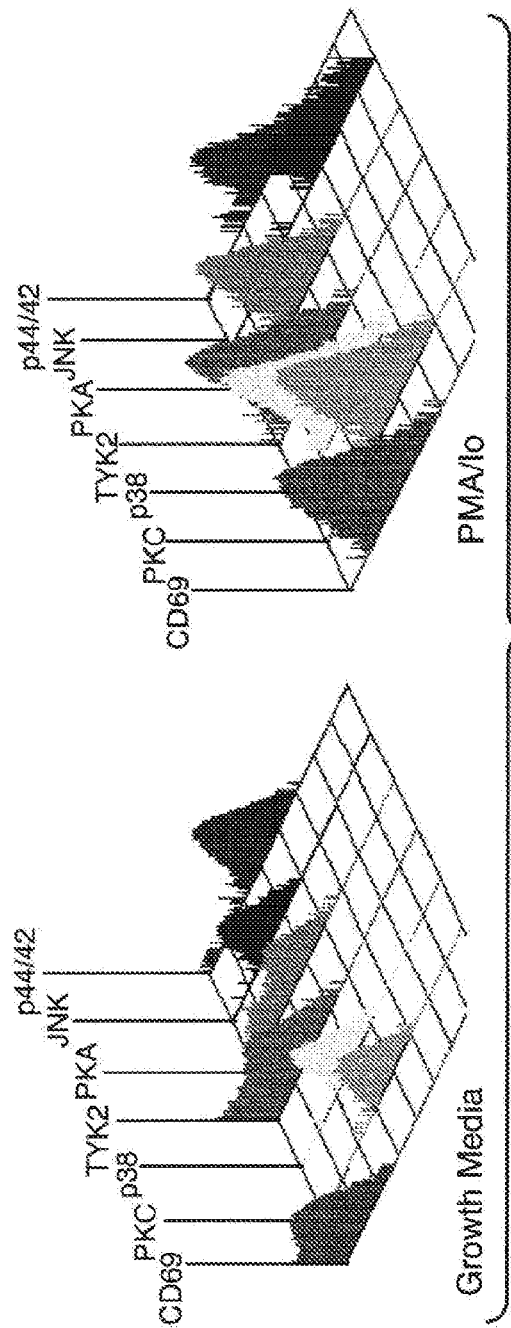

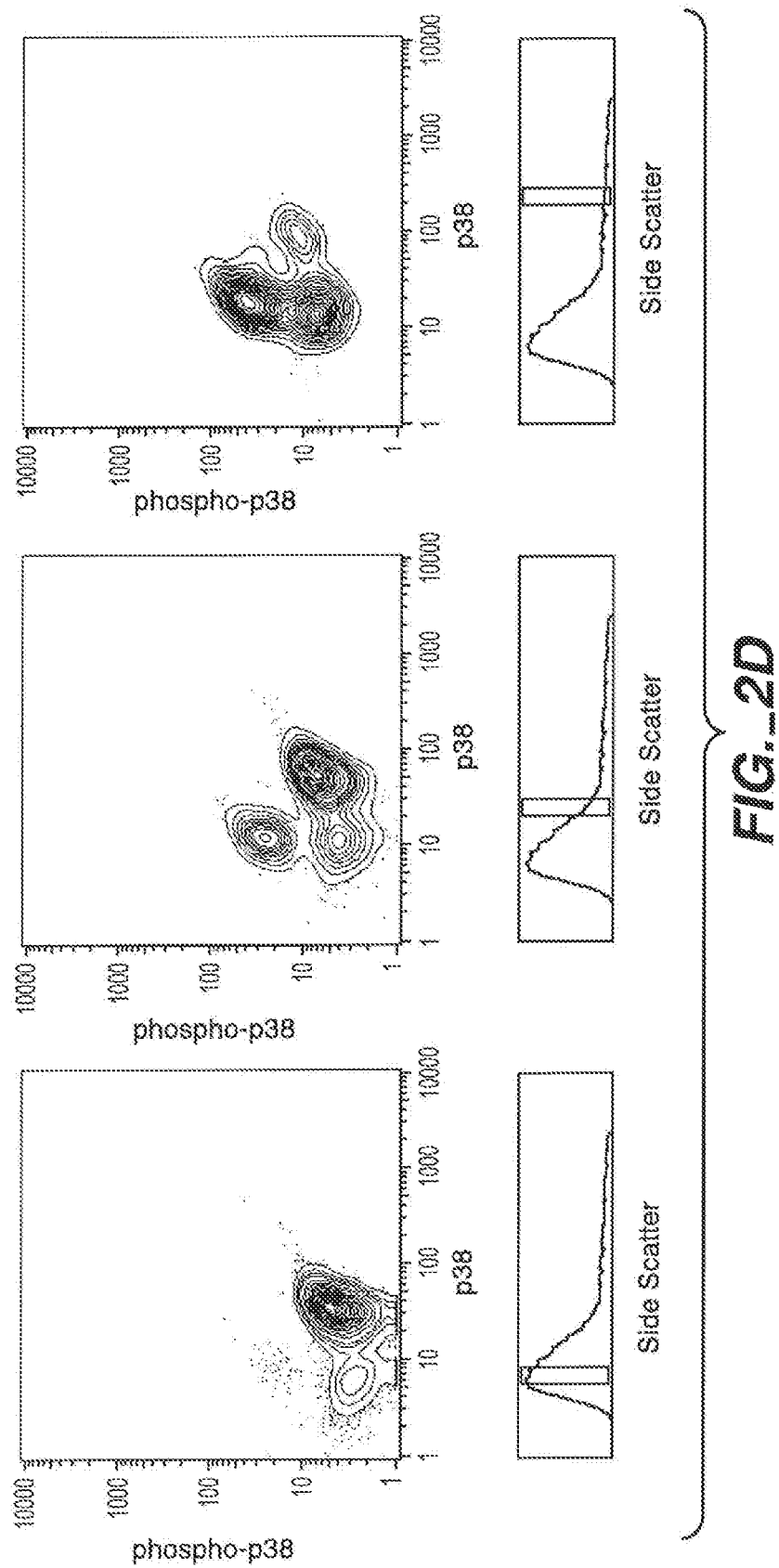

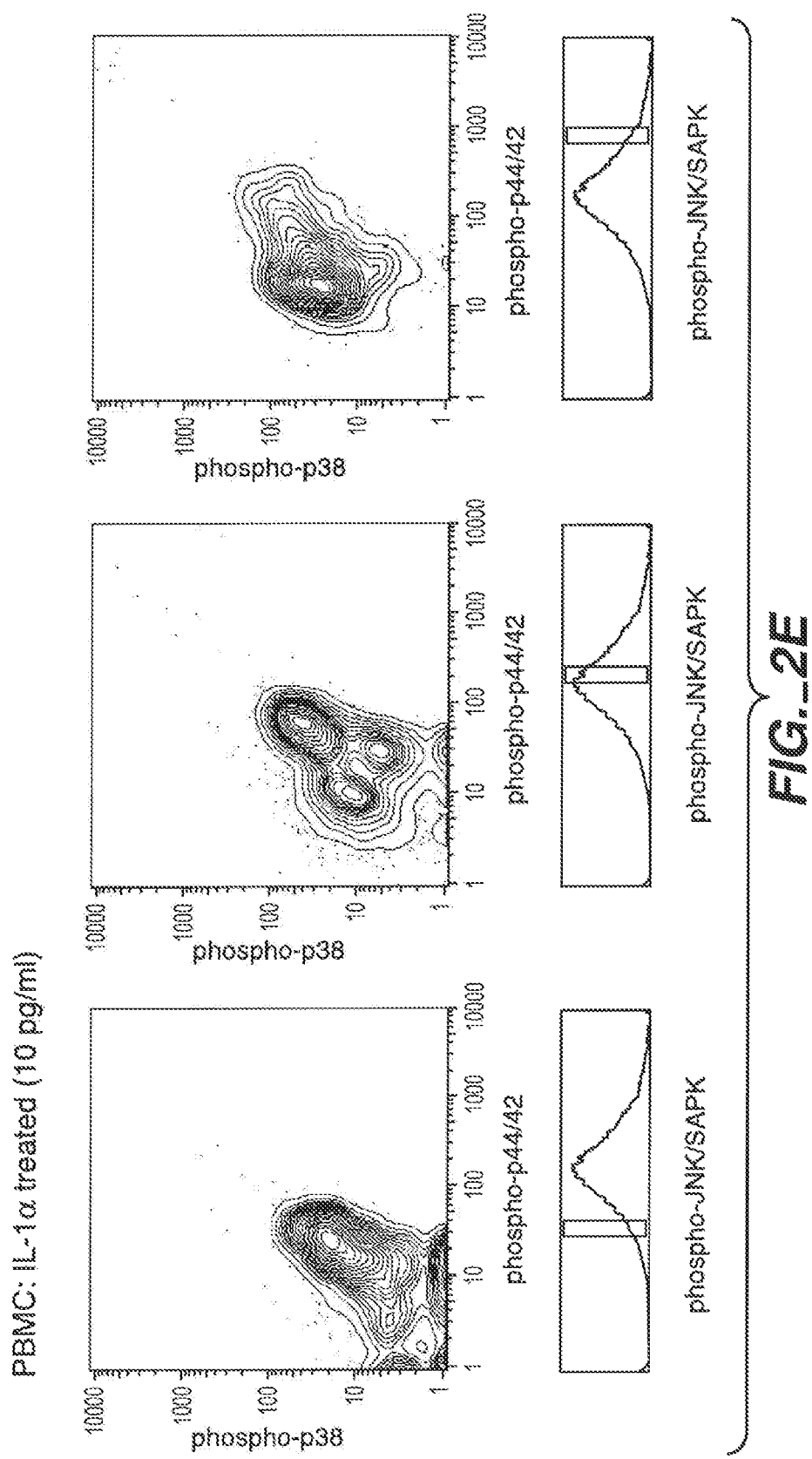
FIG._2E

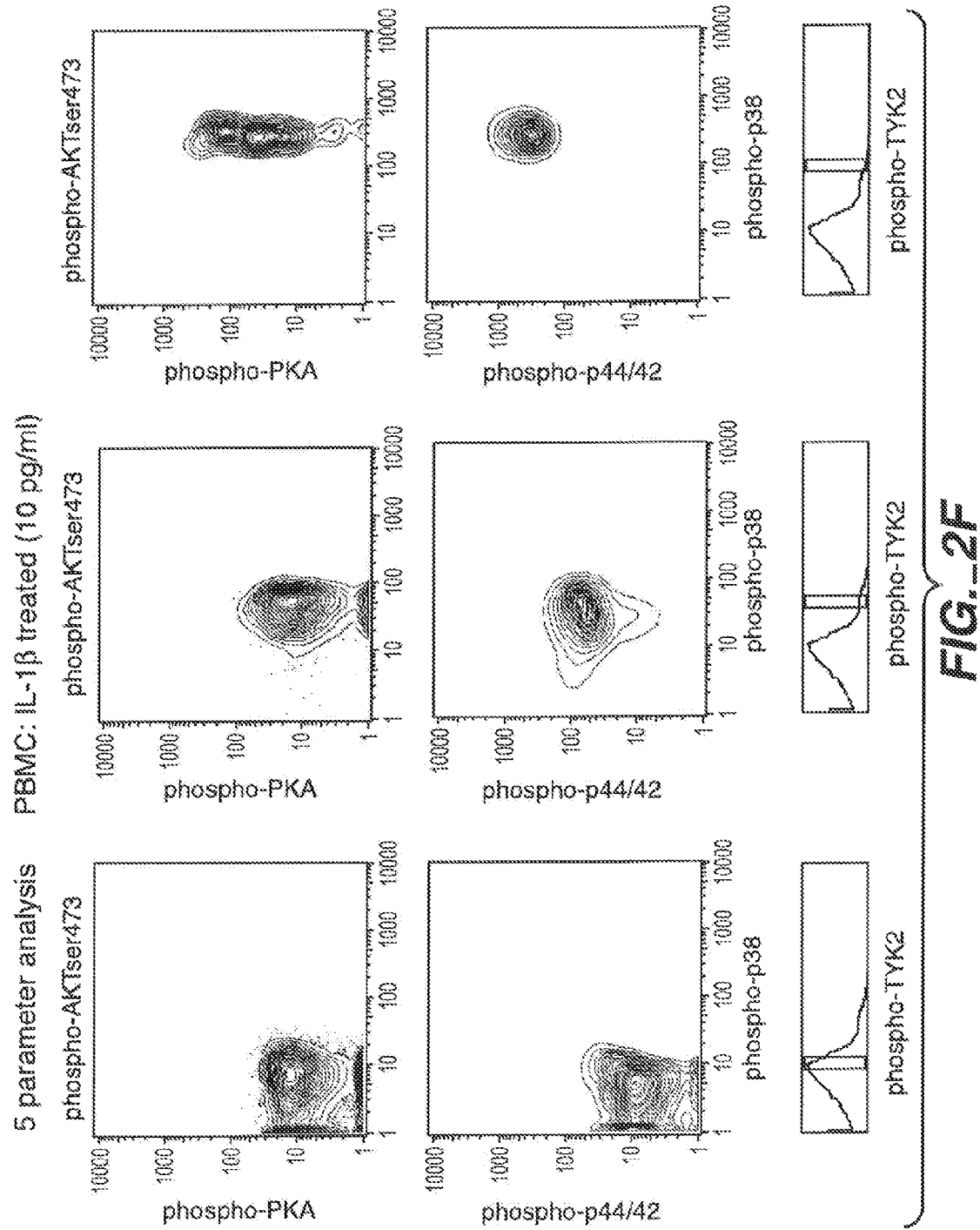
FIG._2F

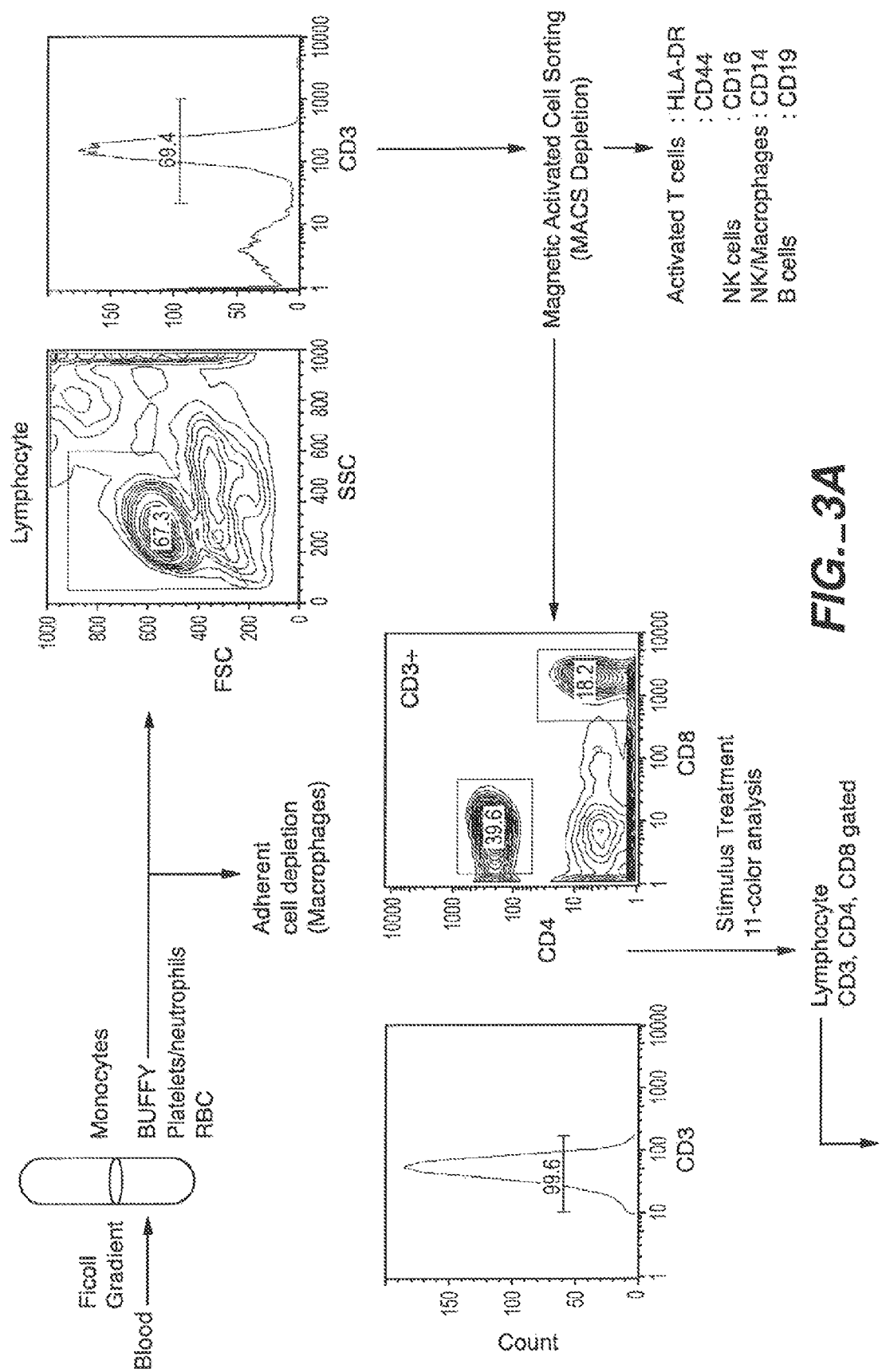
FIG._3A

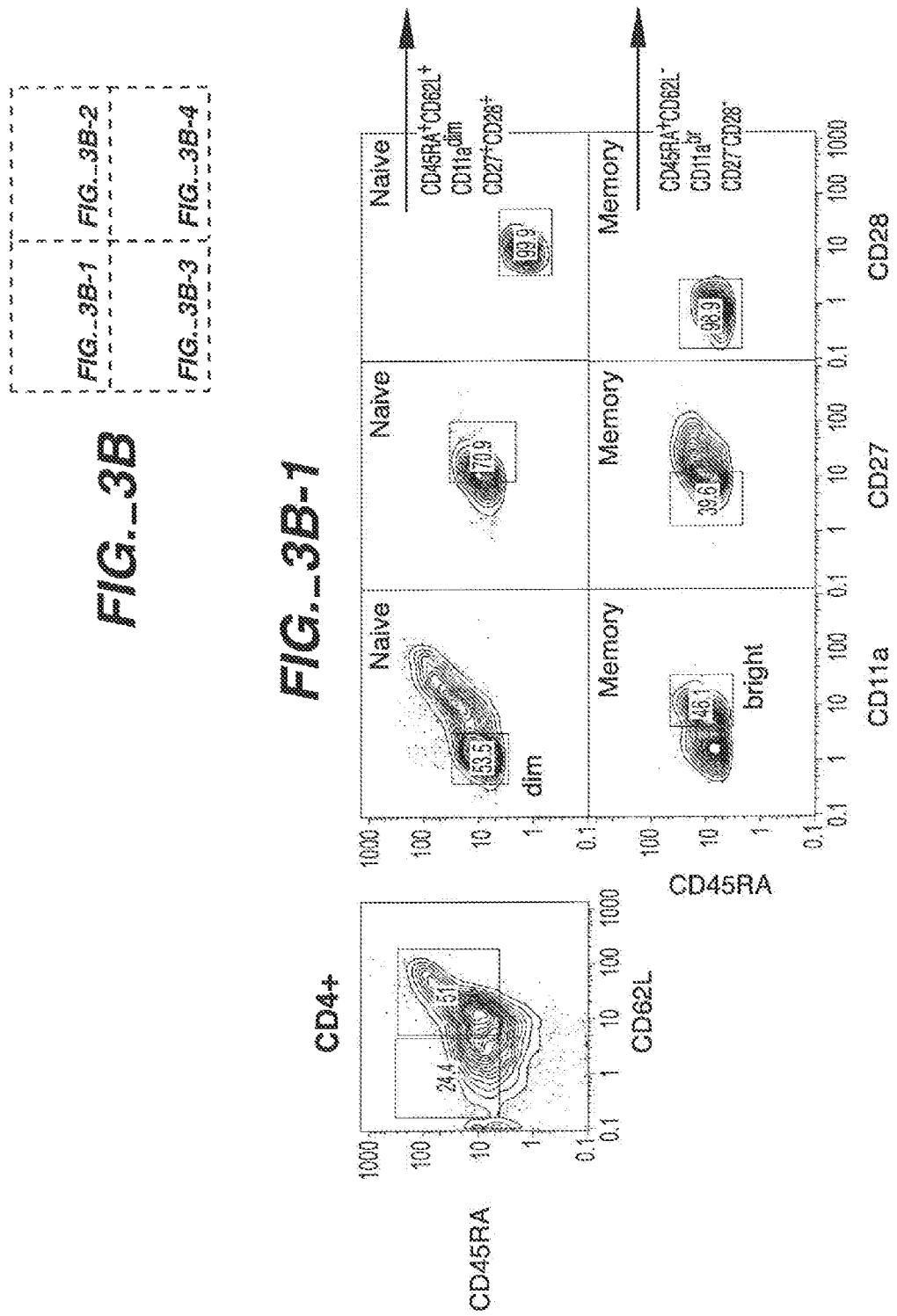

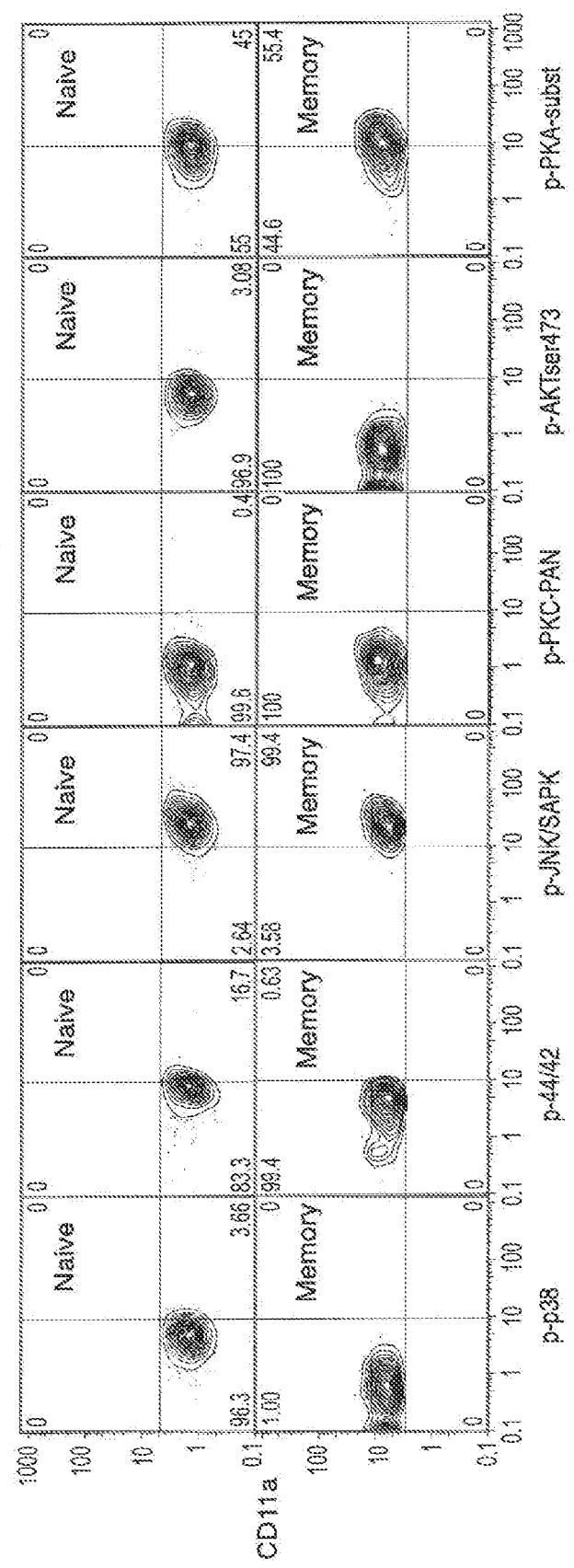
FIG._3B-2

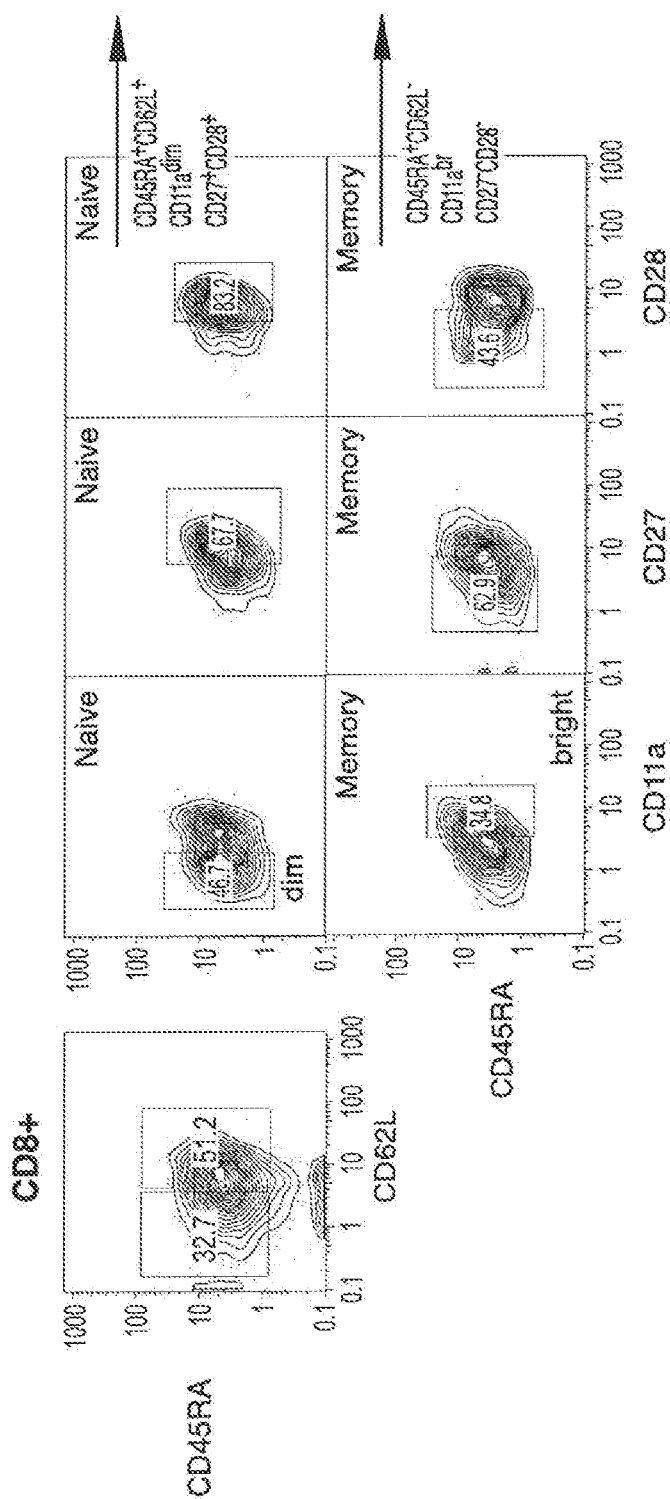
FIG._3B-3

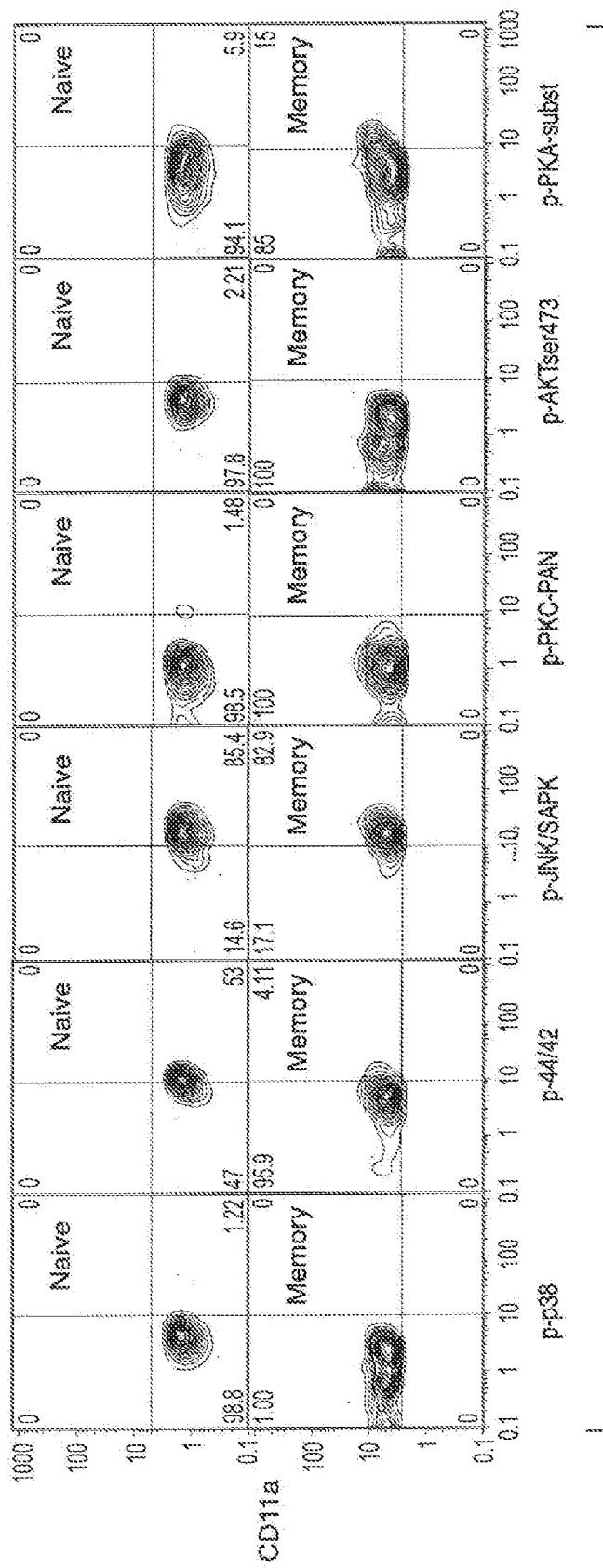
FIG._3B-4

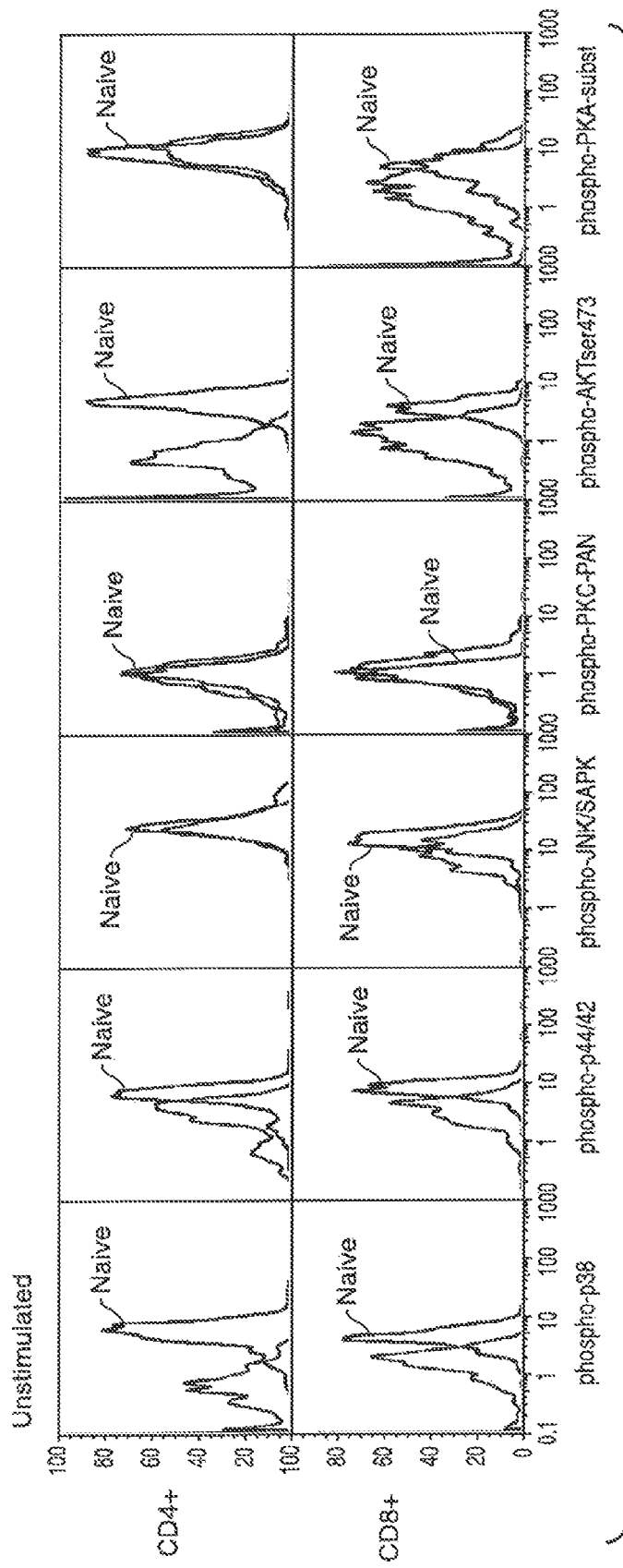
FIG._4A

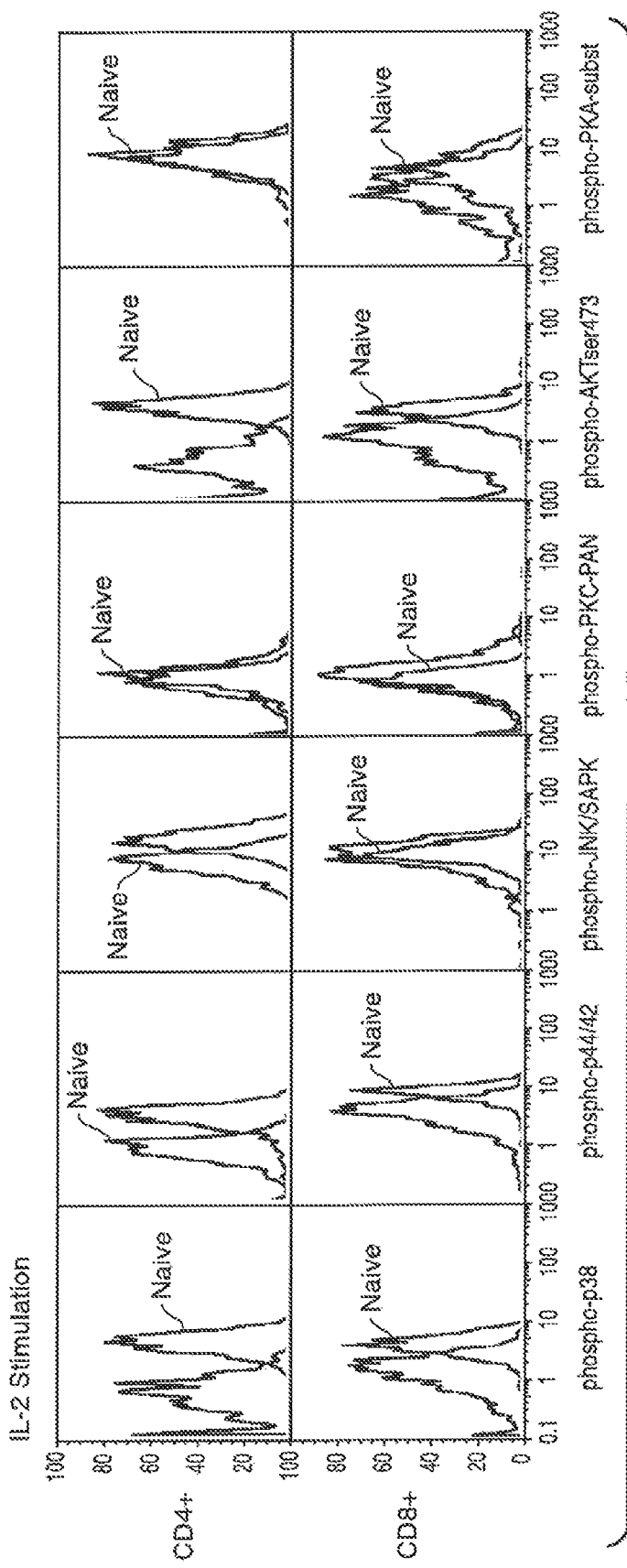
FIG._4D

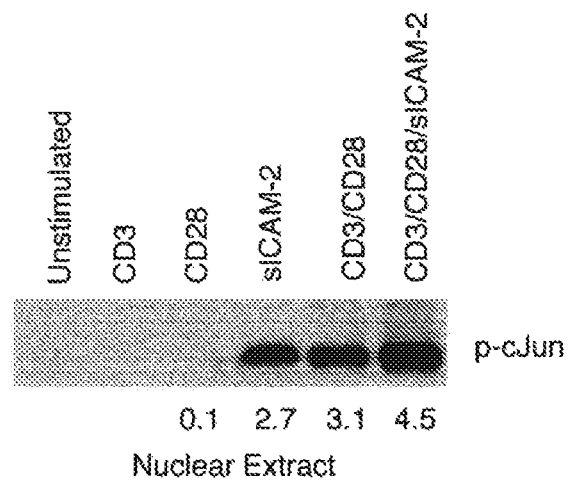
FIG._6A
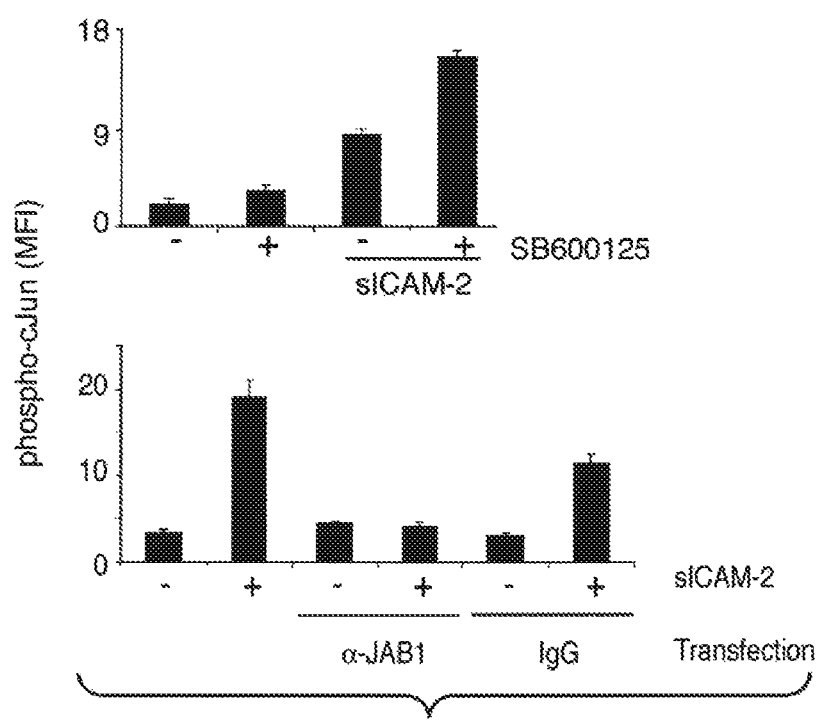
FIG._6B

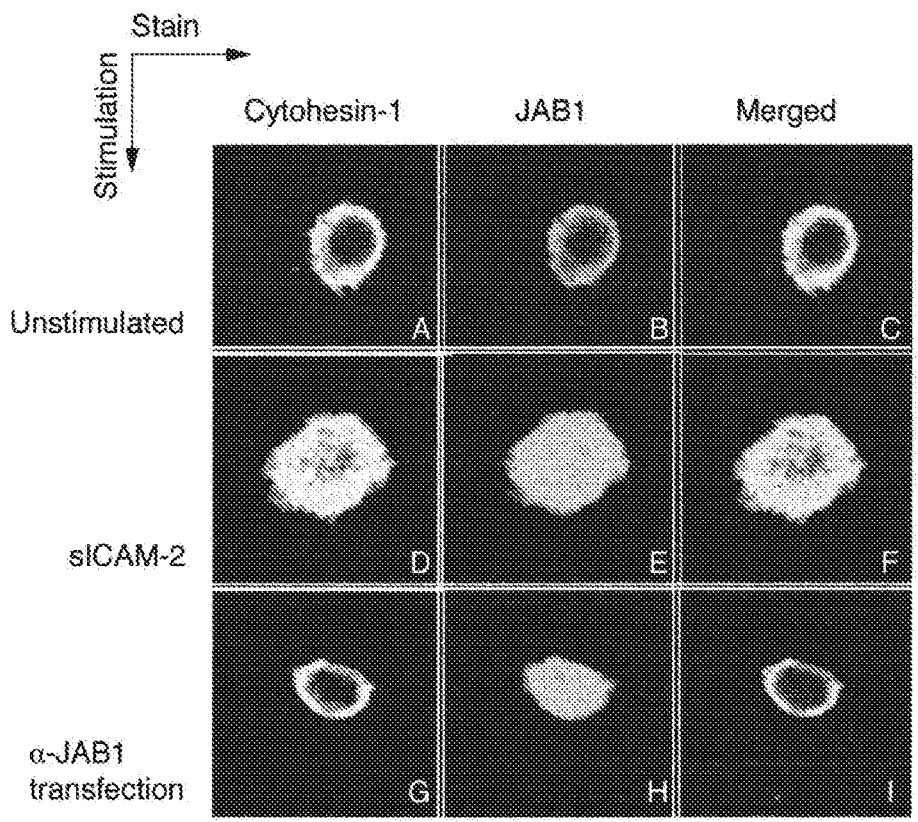
*FIG._6C*
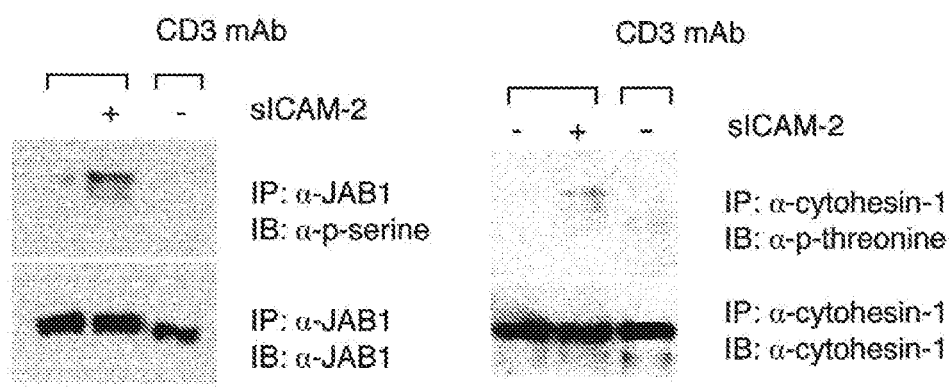
*FIG._6D*

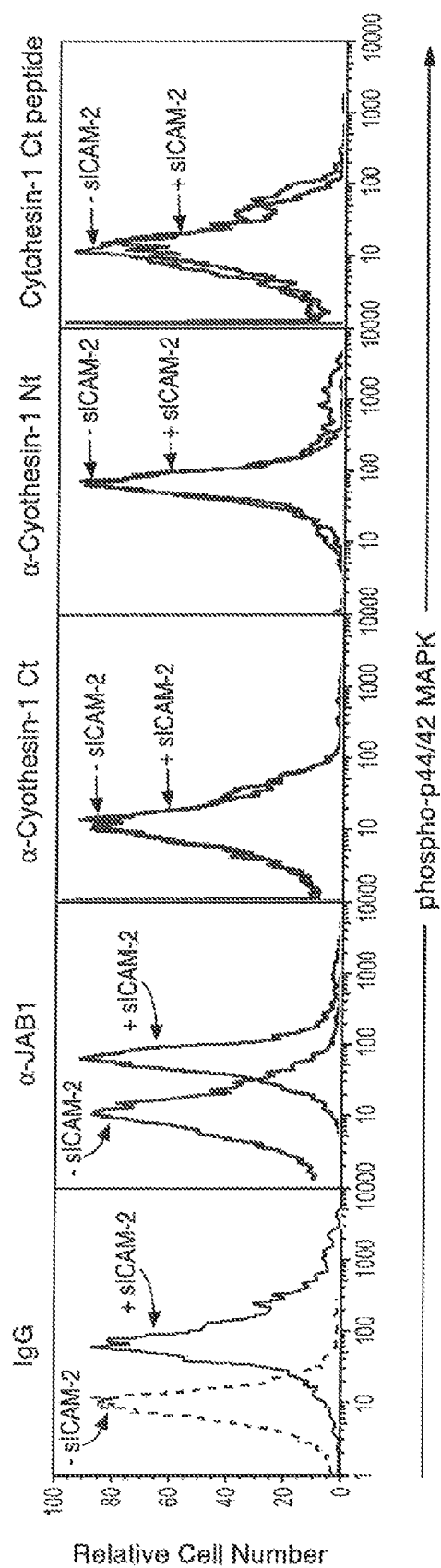
FIG._6E

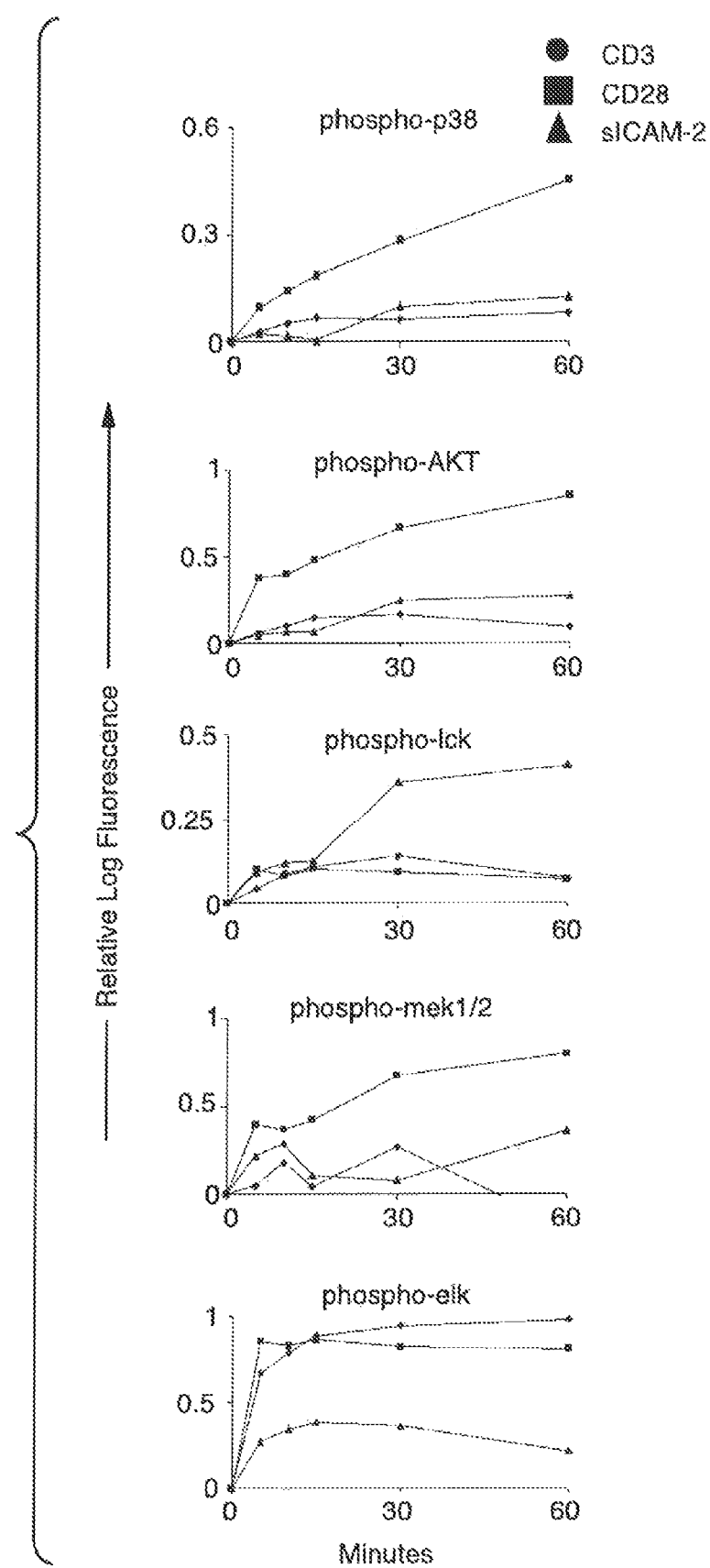
FIG._6F

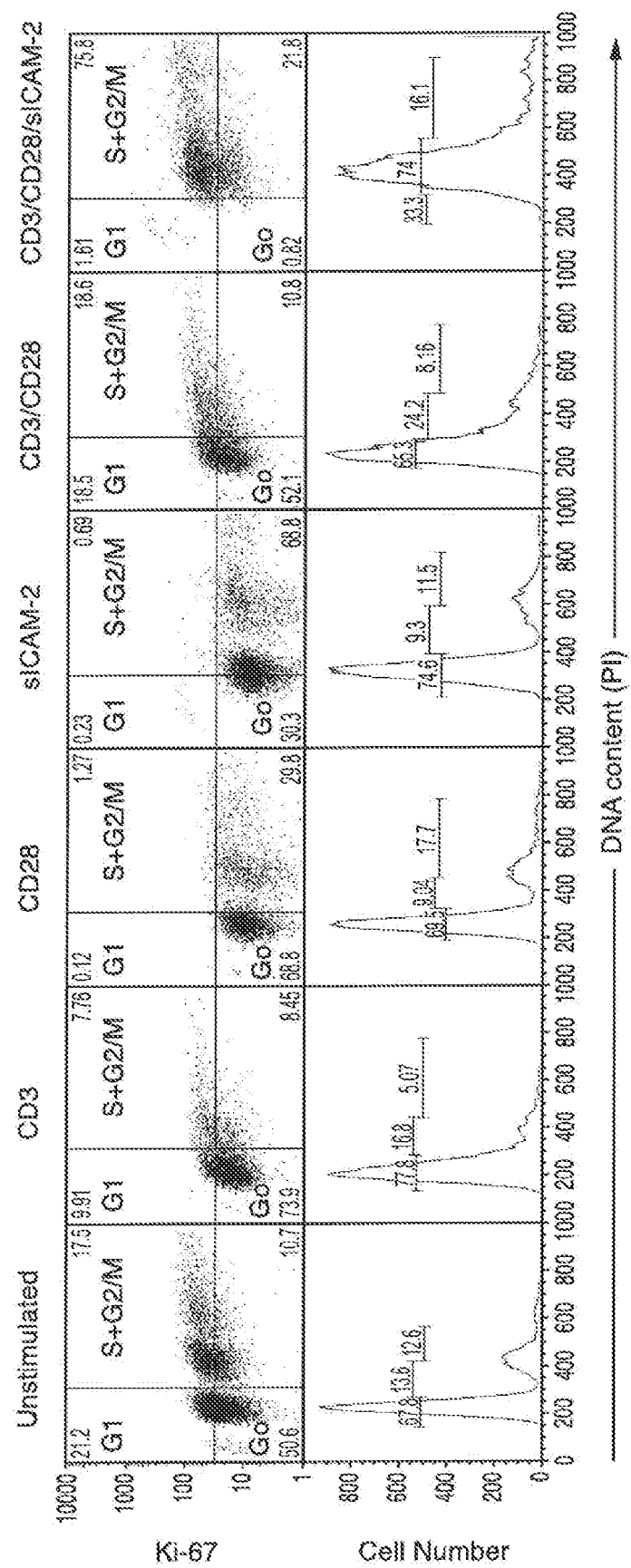
FIG._7B

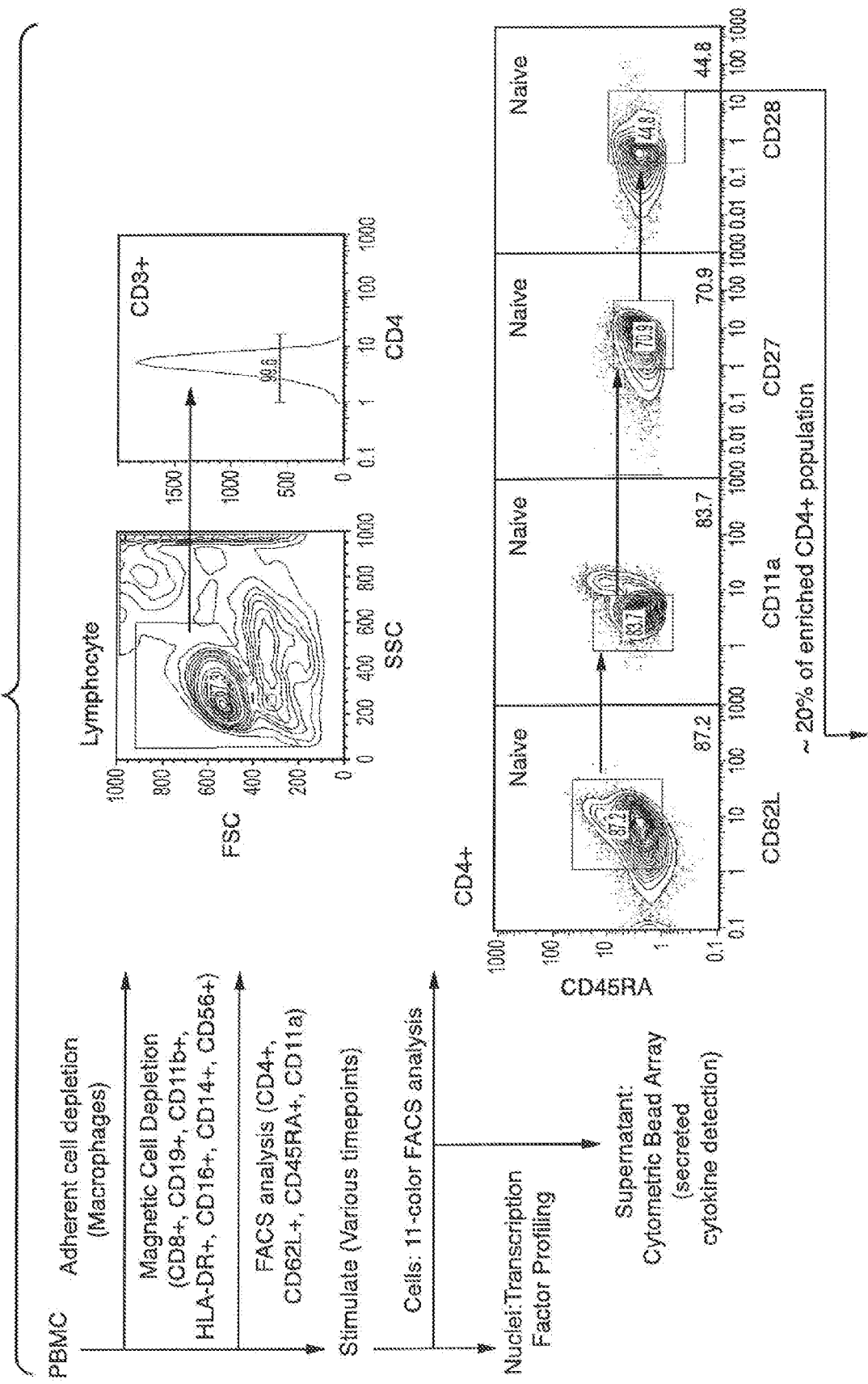
FIG._8A-1

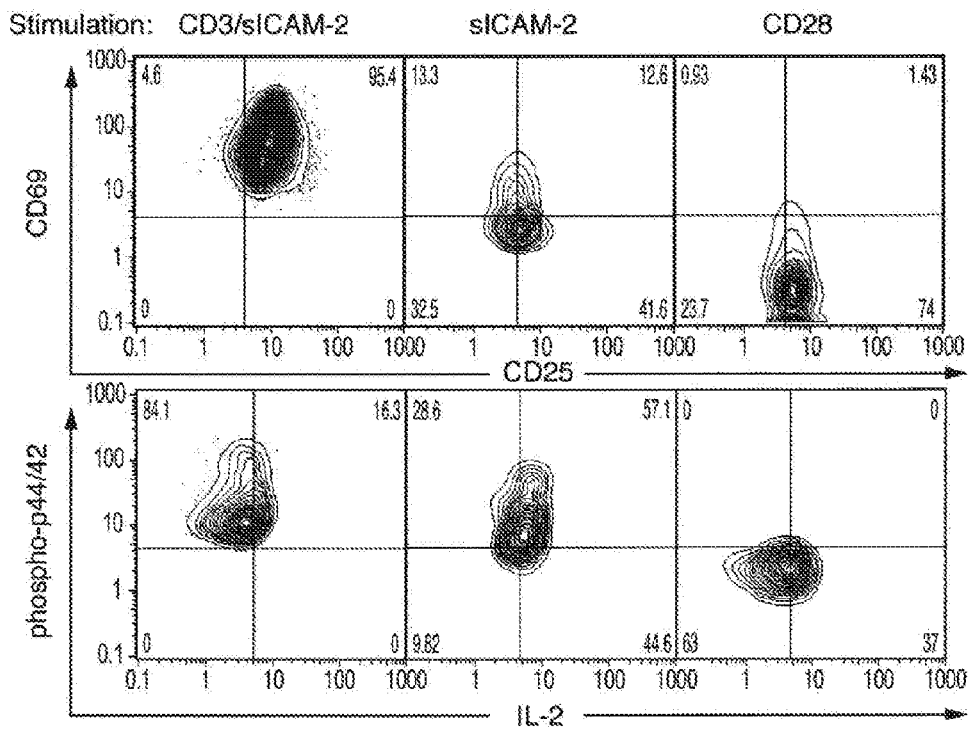
FIG._8B
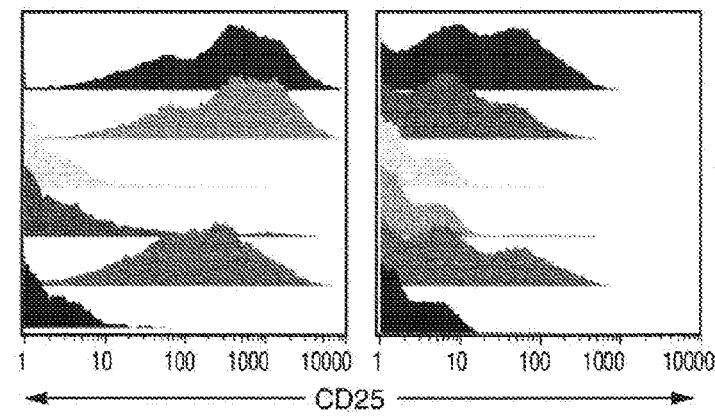
FIG._8C

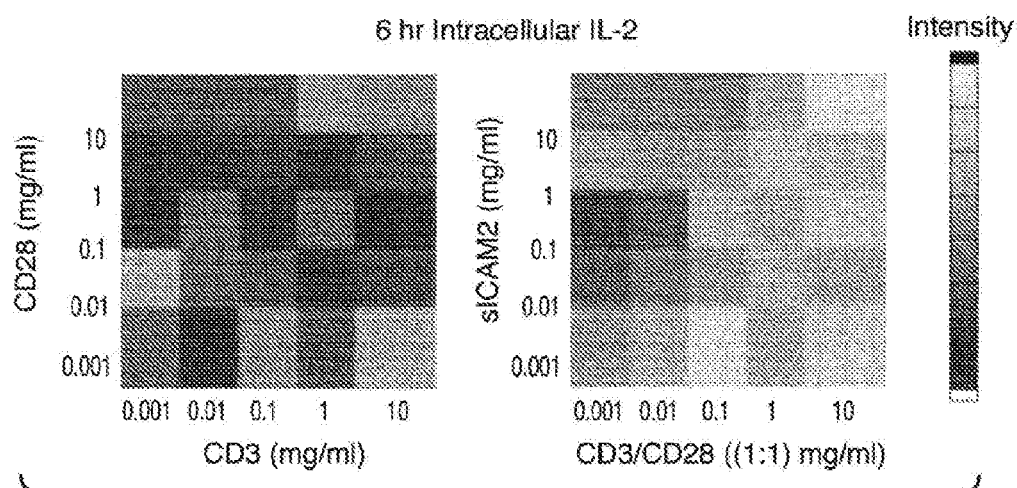
FIG._9A
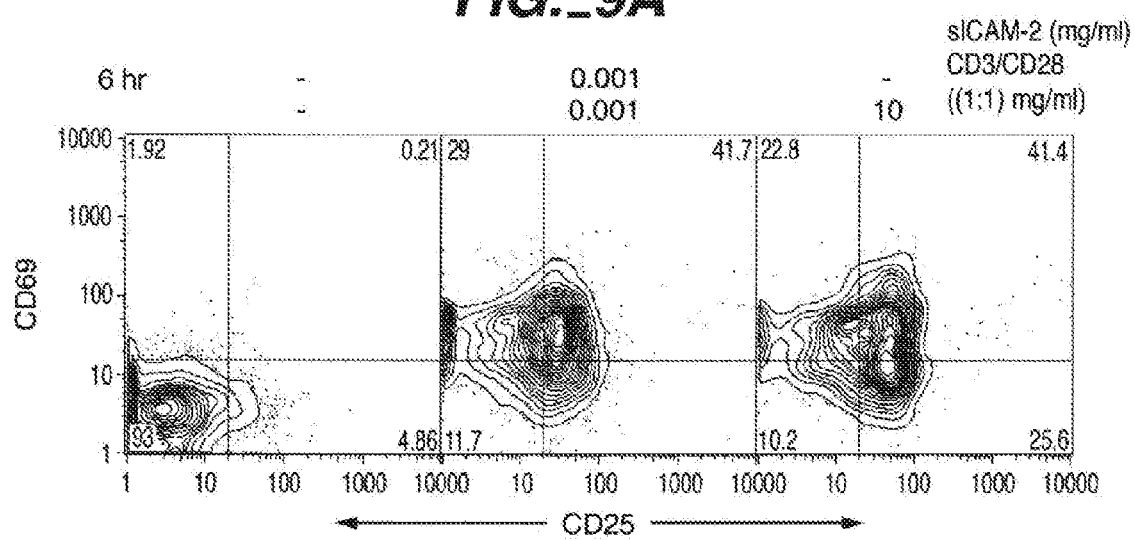
FIG._9B
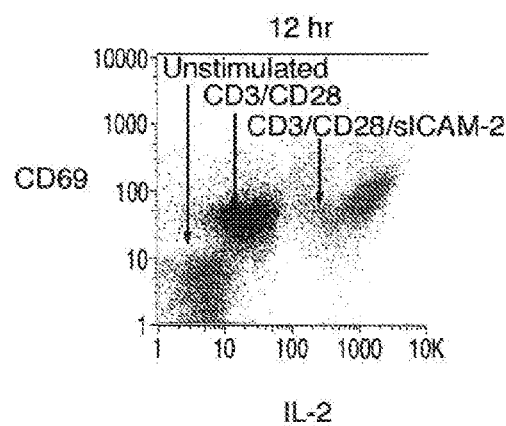
FIG._9C

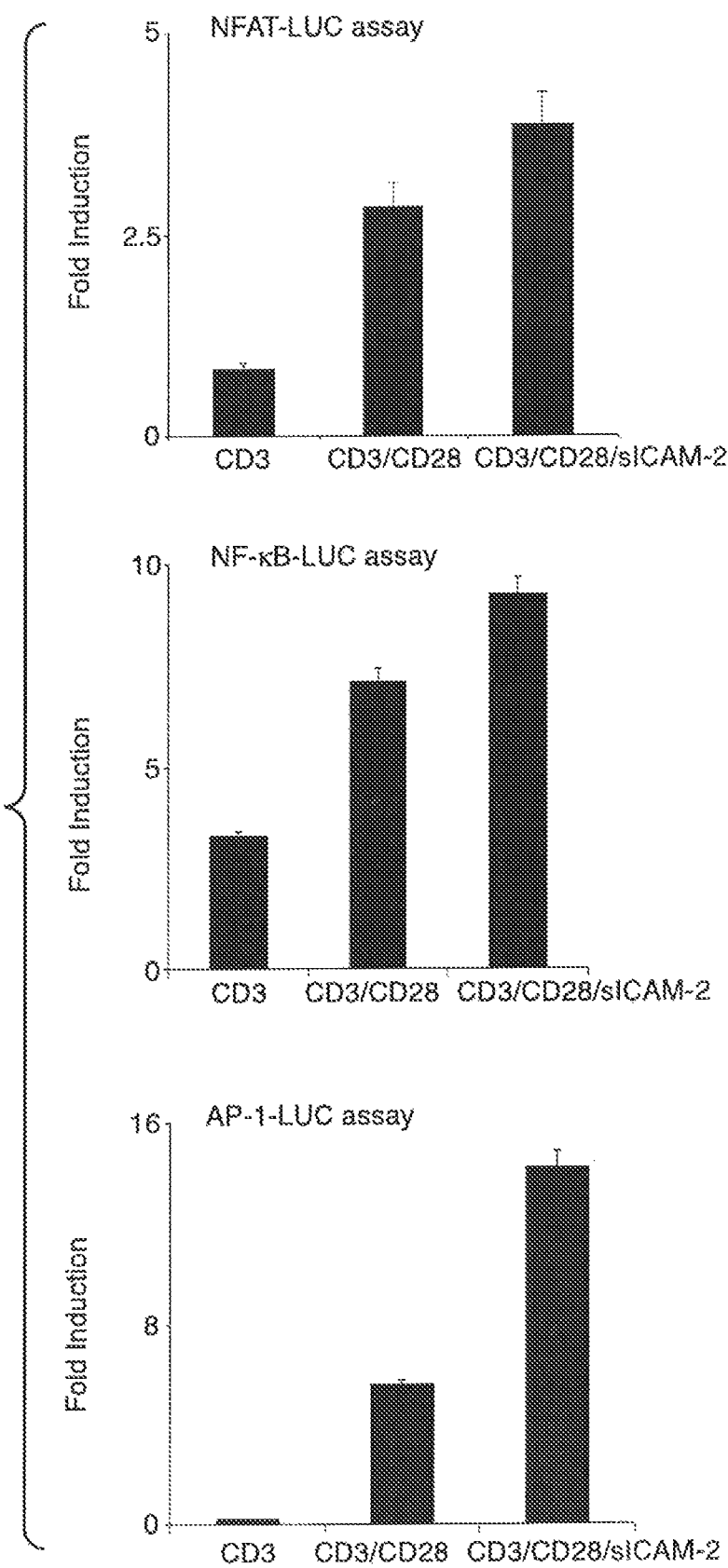
FIG._10A

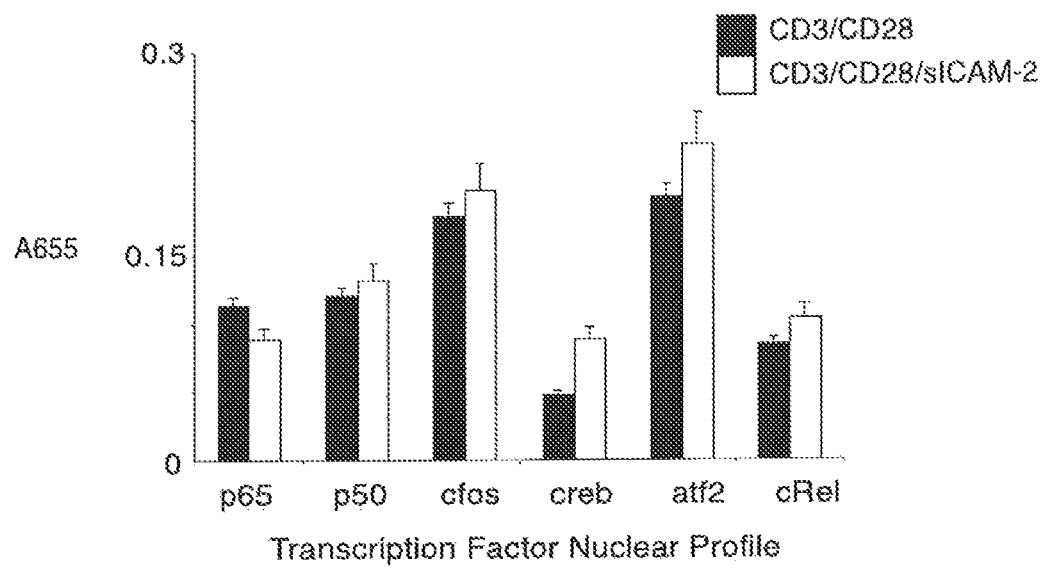
FIG._10B
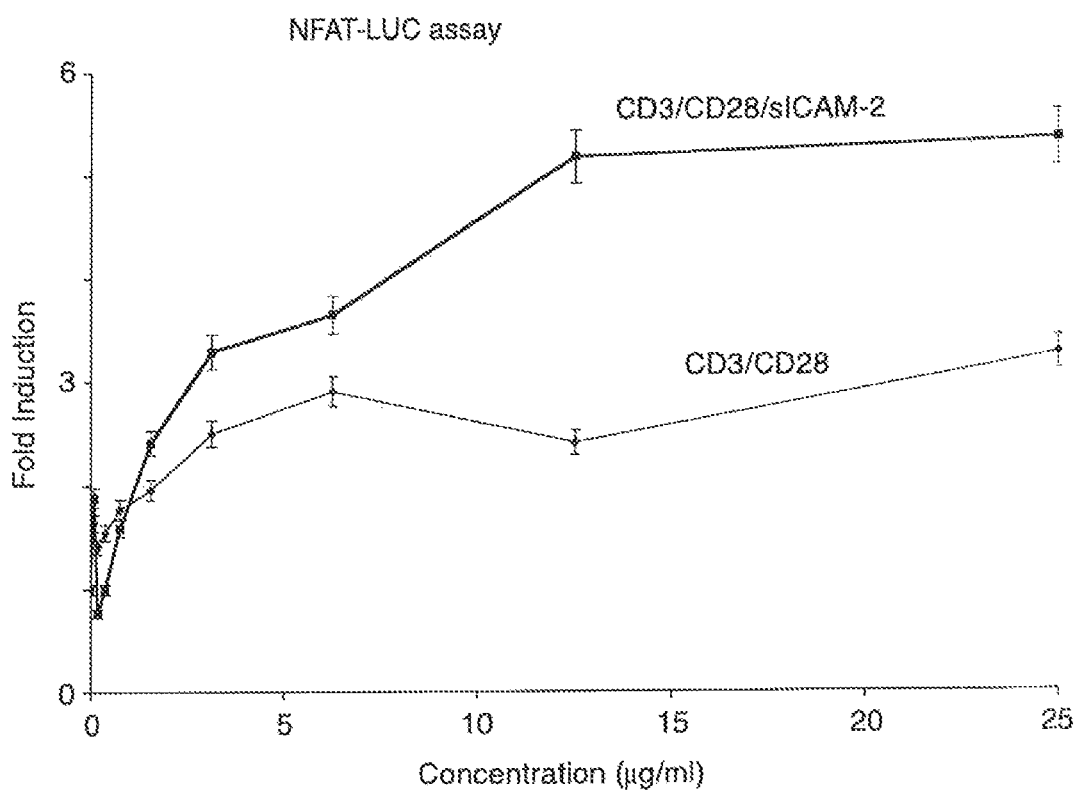
FIG._10C

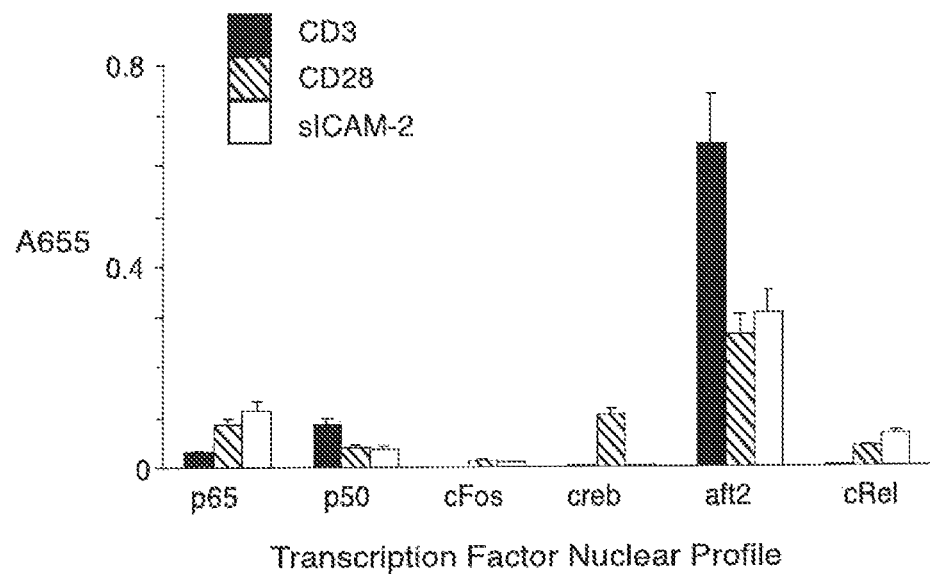
FIG._10D
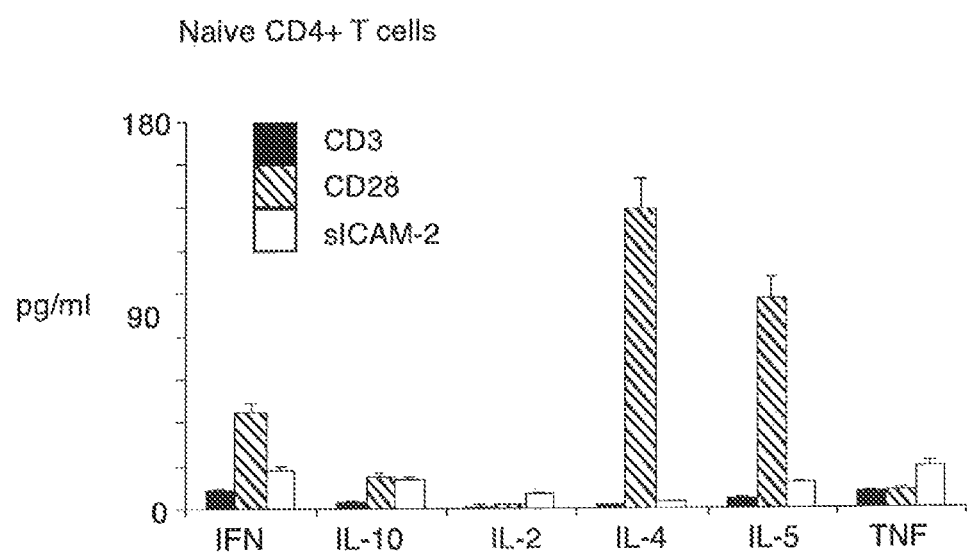
FIG._10E

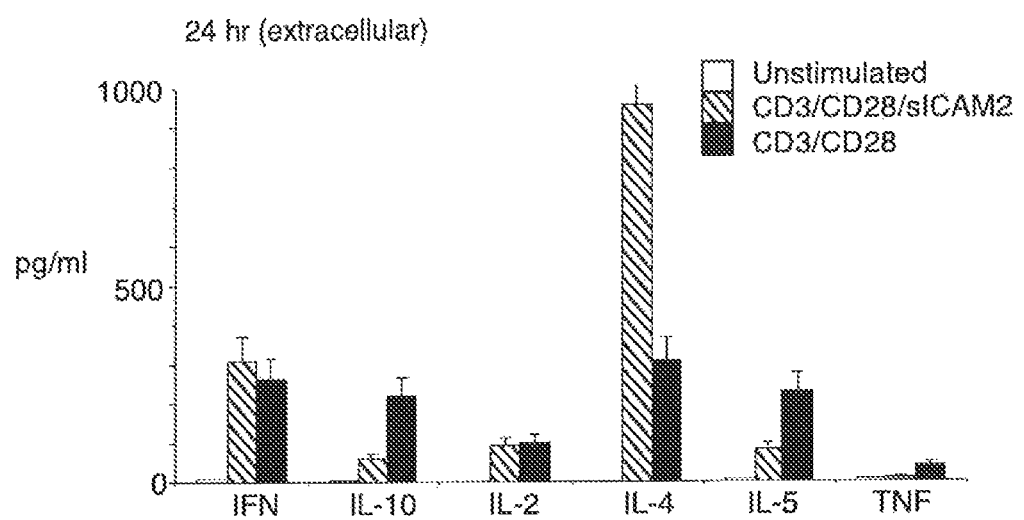
FIG._12

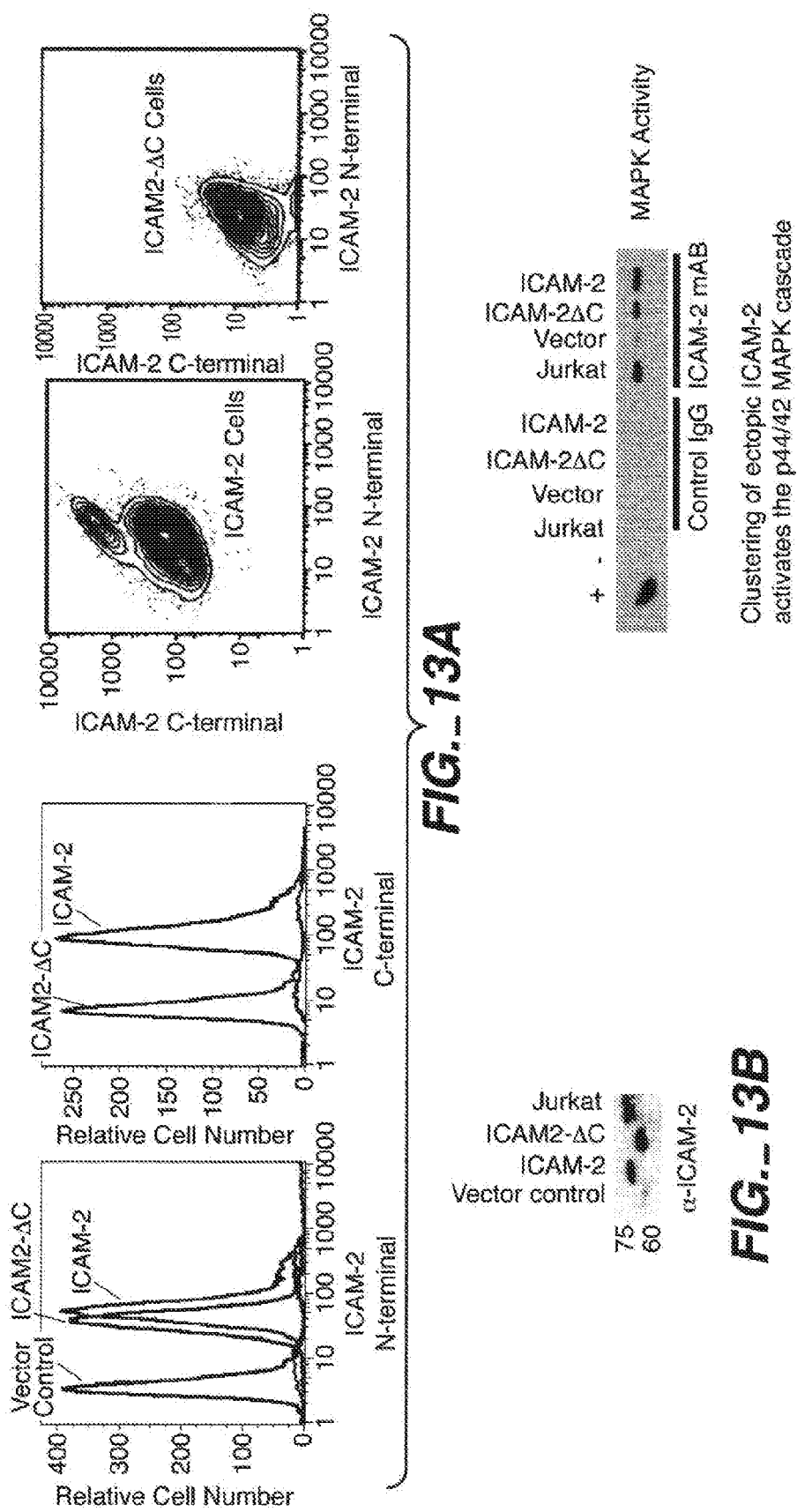

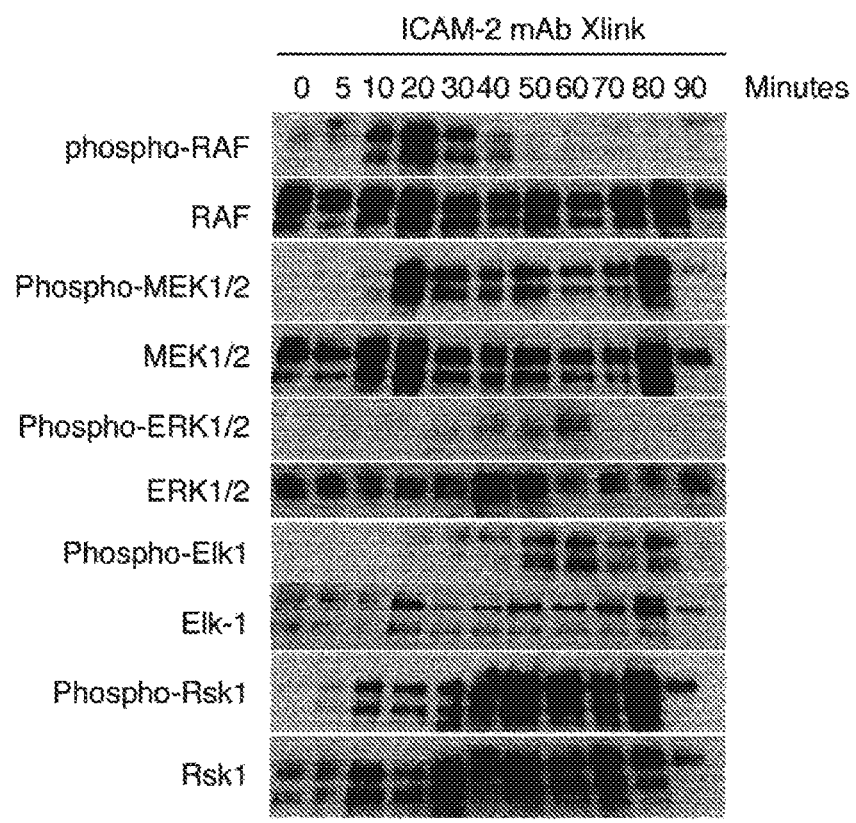
FIG._13C

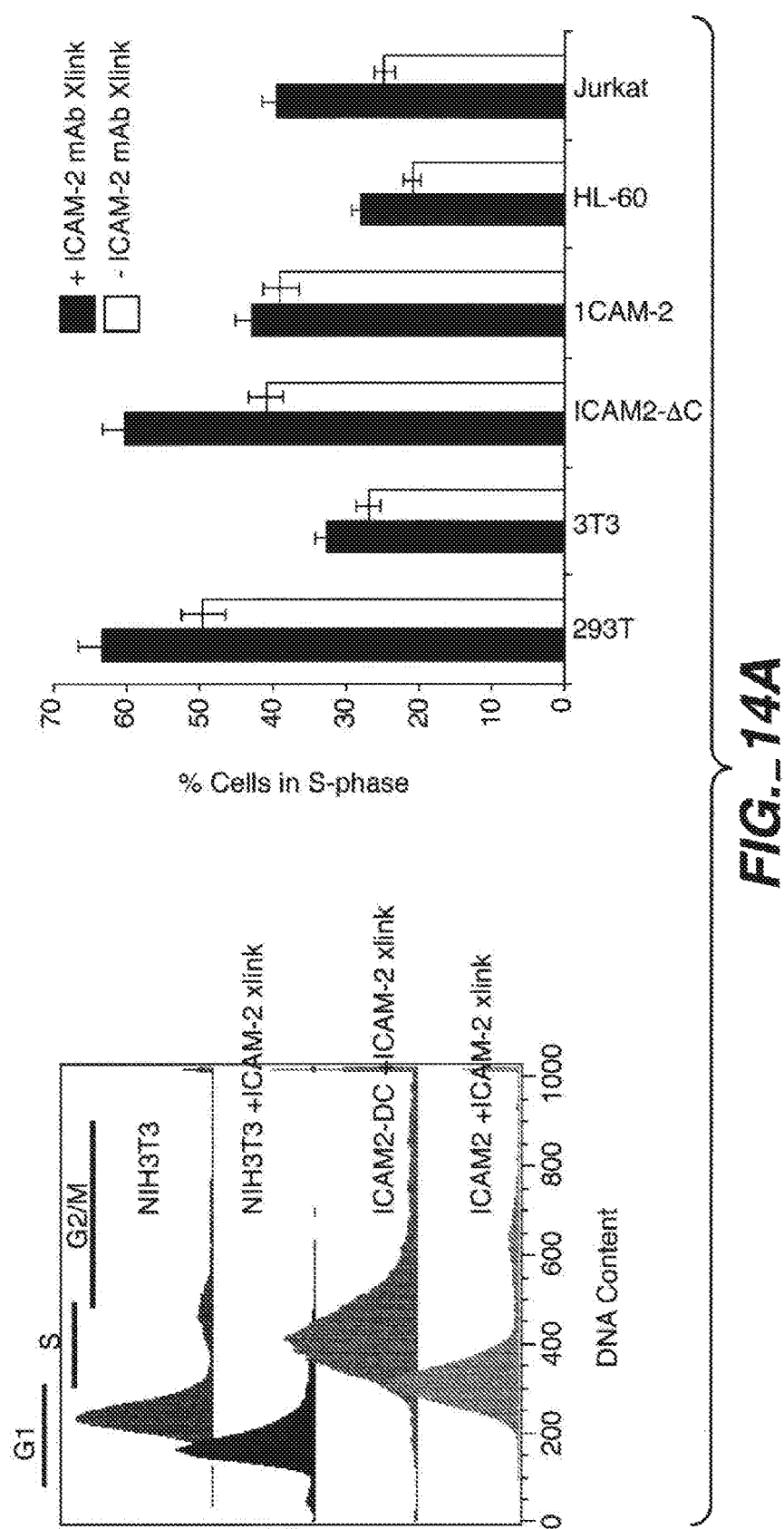
FIG._14A

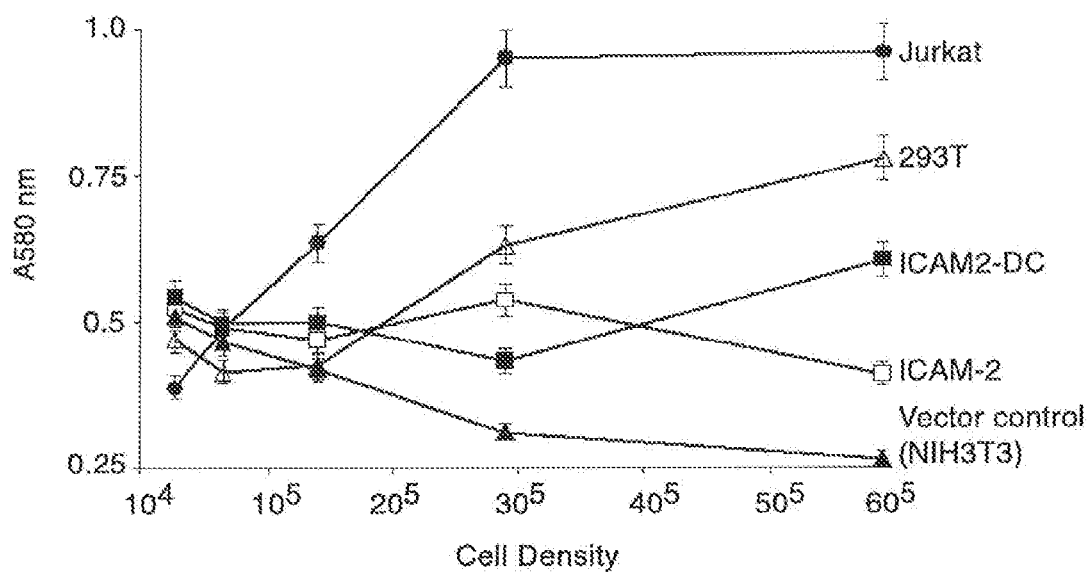
FIG._14B
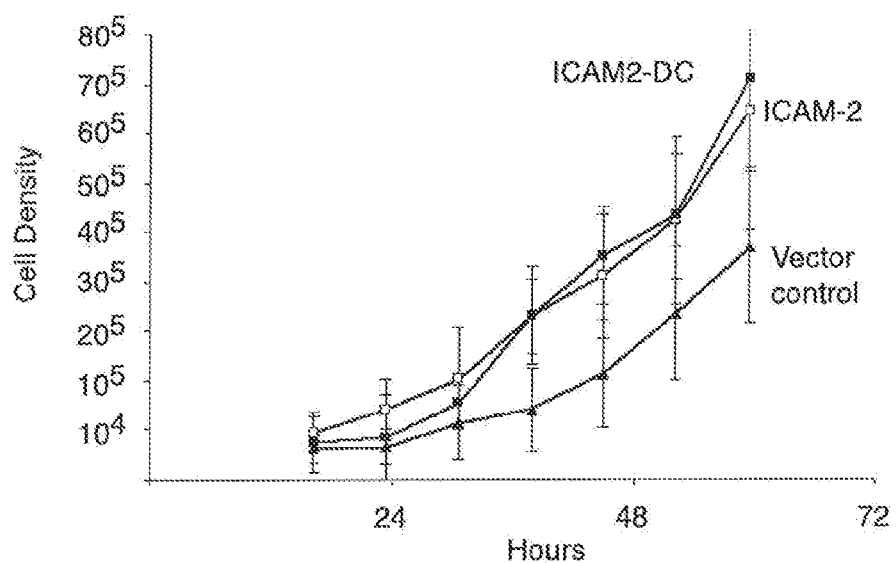
FIG._14C

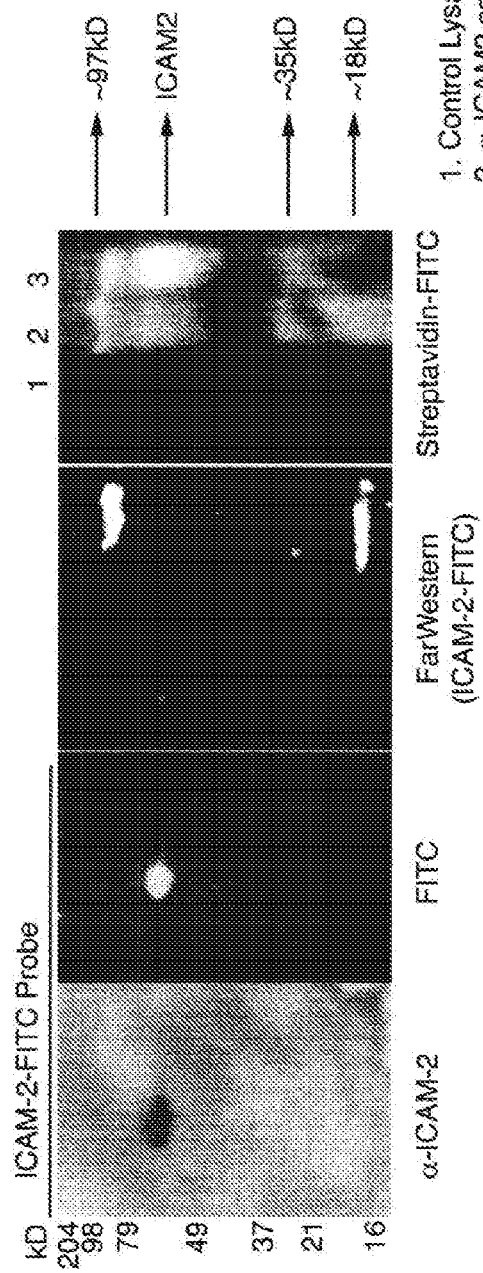
FIG._15A
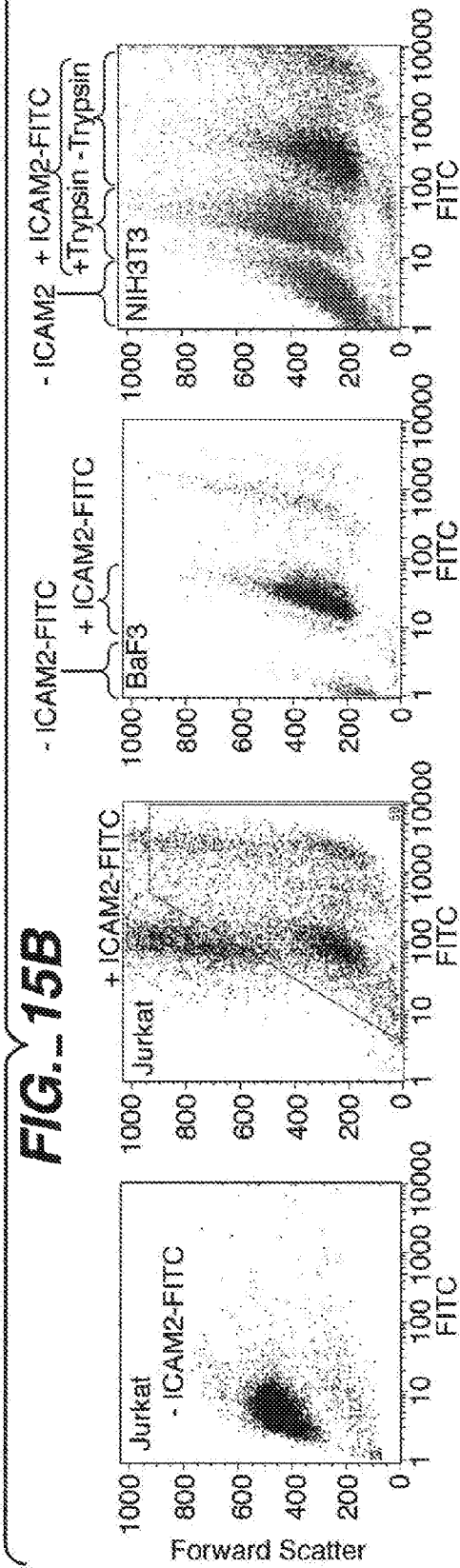
FIG._15B

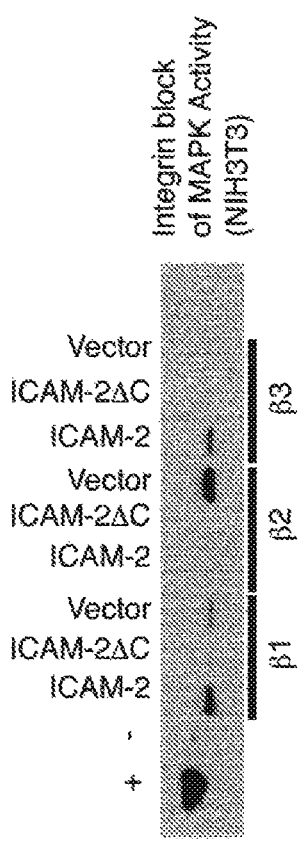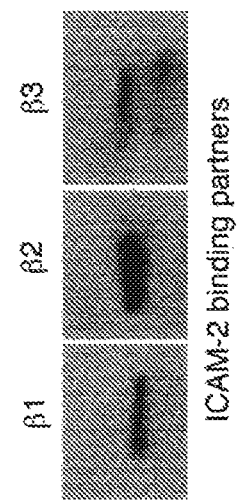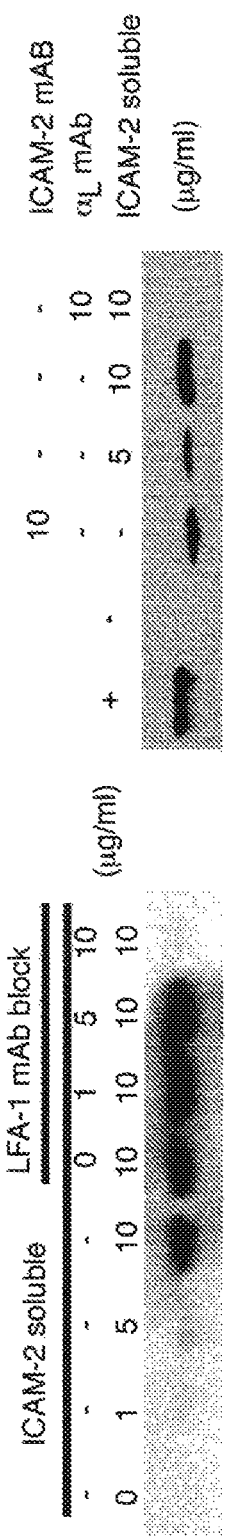
FIG. 15C
FIG. 15D
FIG. 15F

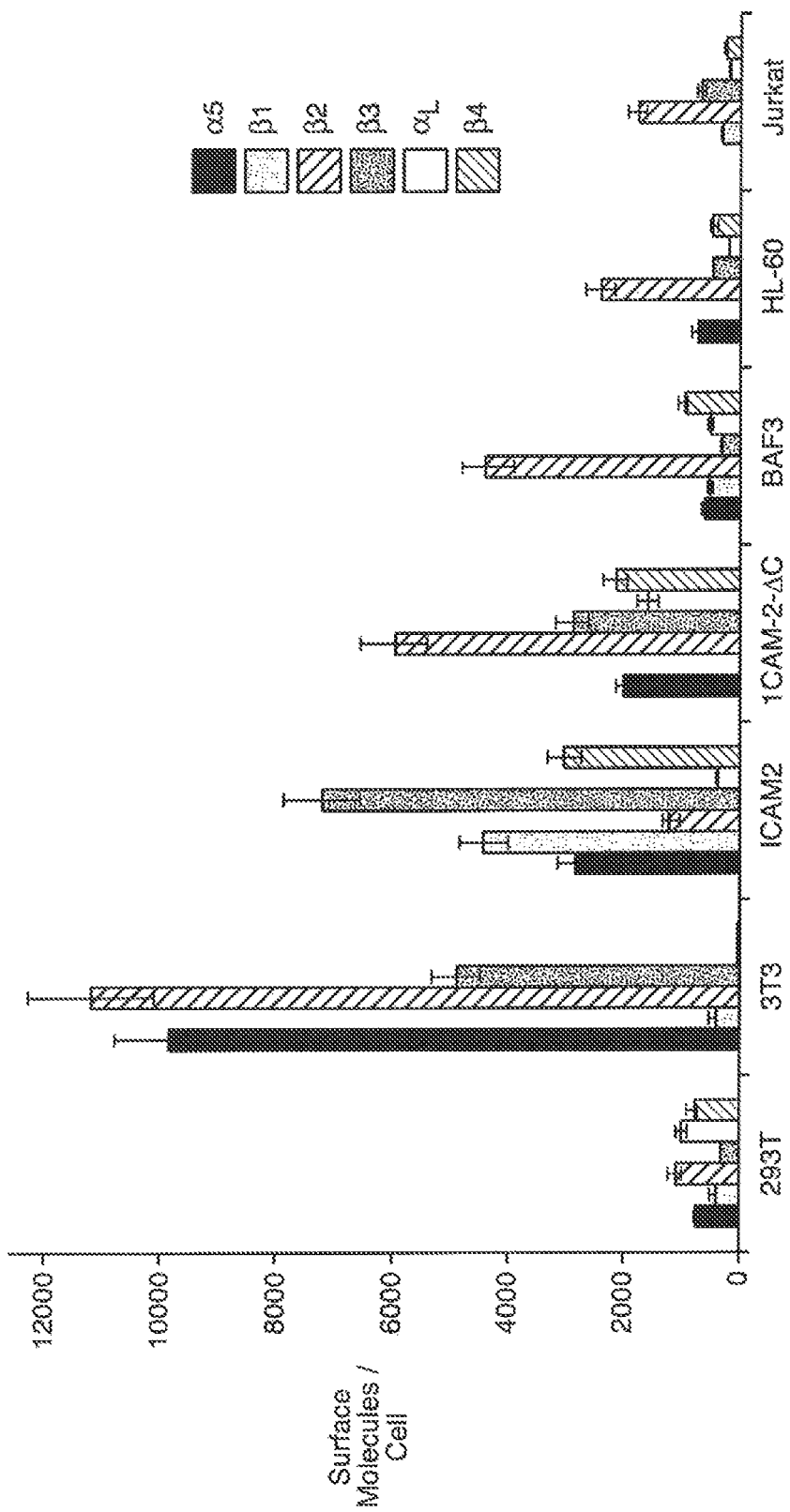

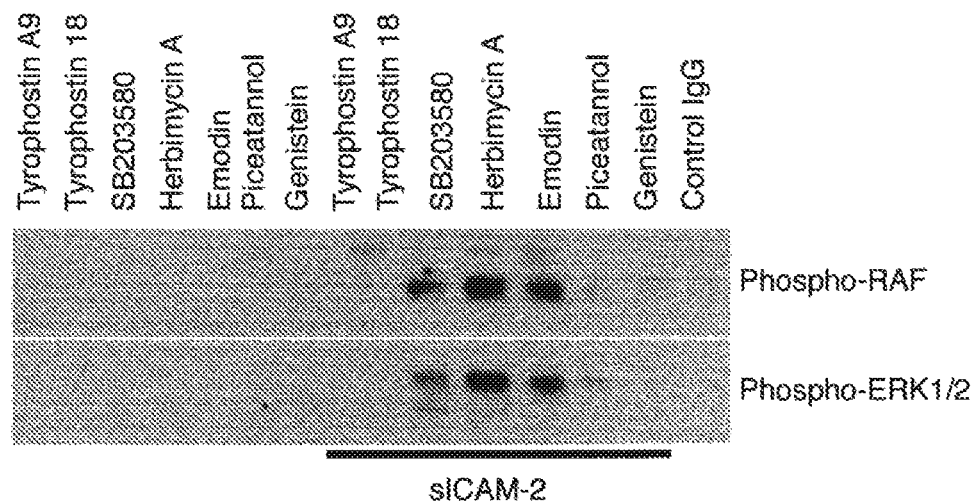
*FIG._16A*
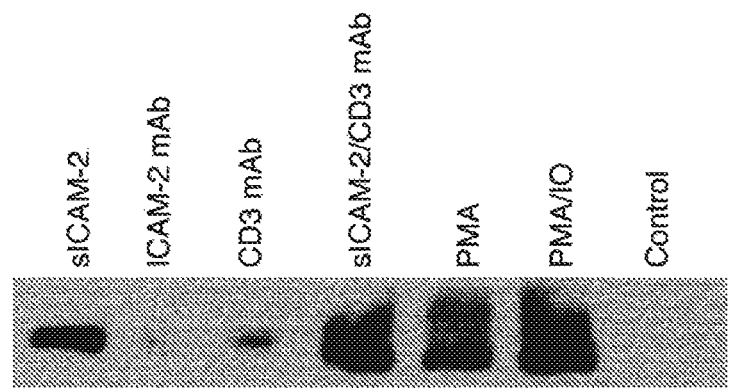
IP: Anti-phosphotyrosine
Blot: PYK2
*FIG._16C*

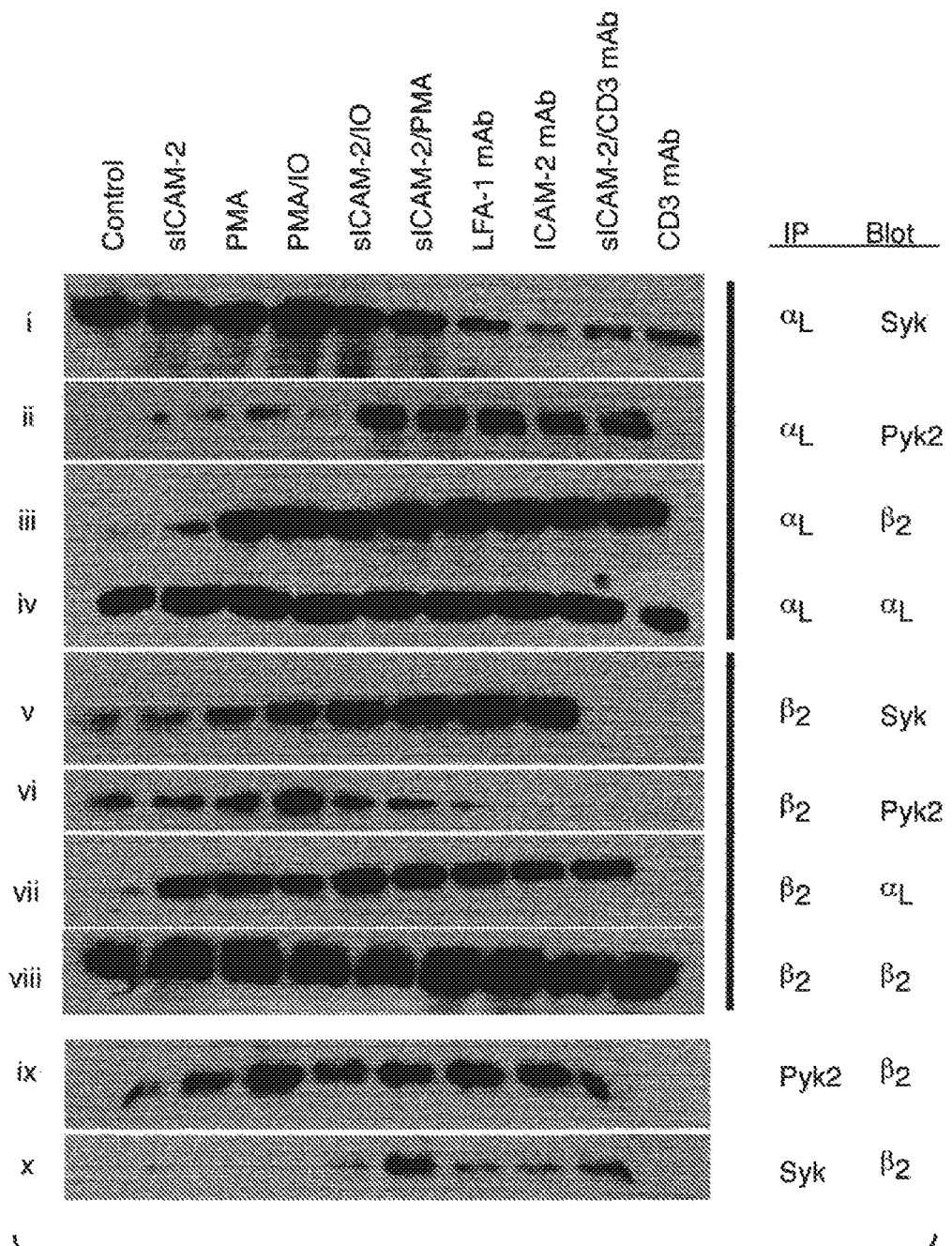
FIG._16B

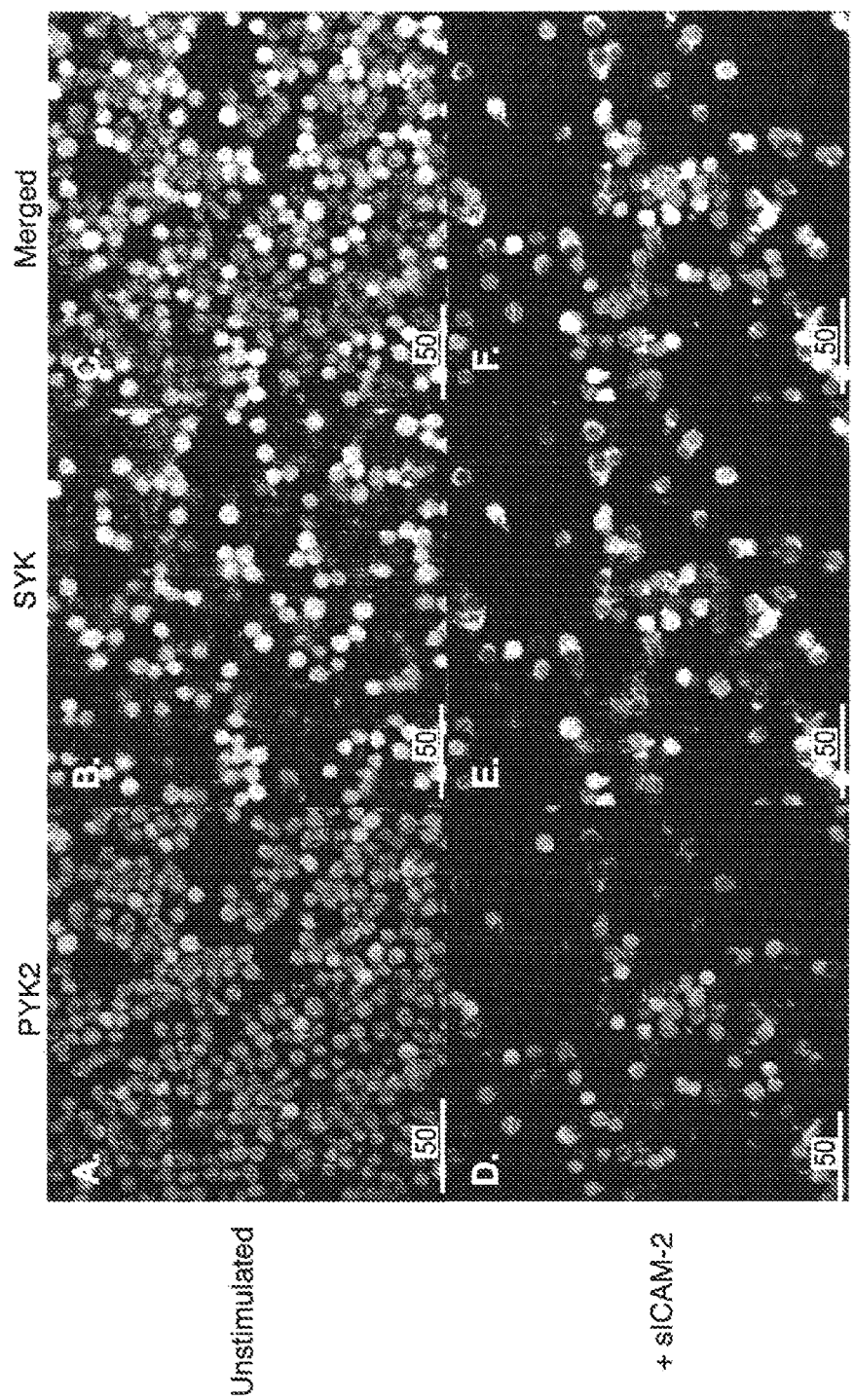
FIG._17A

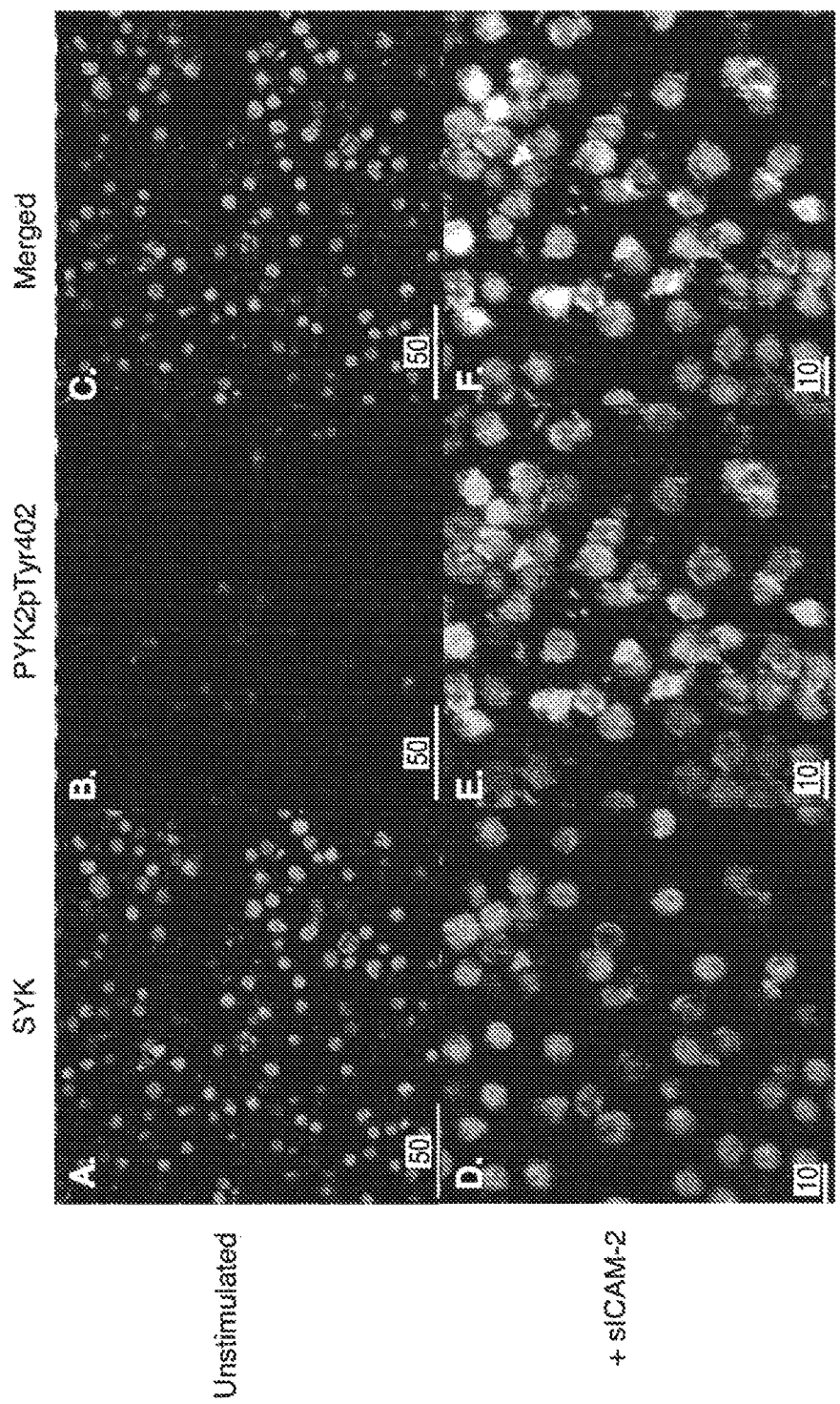
FIG._17B

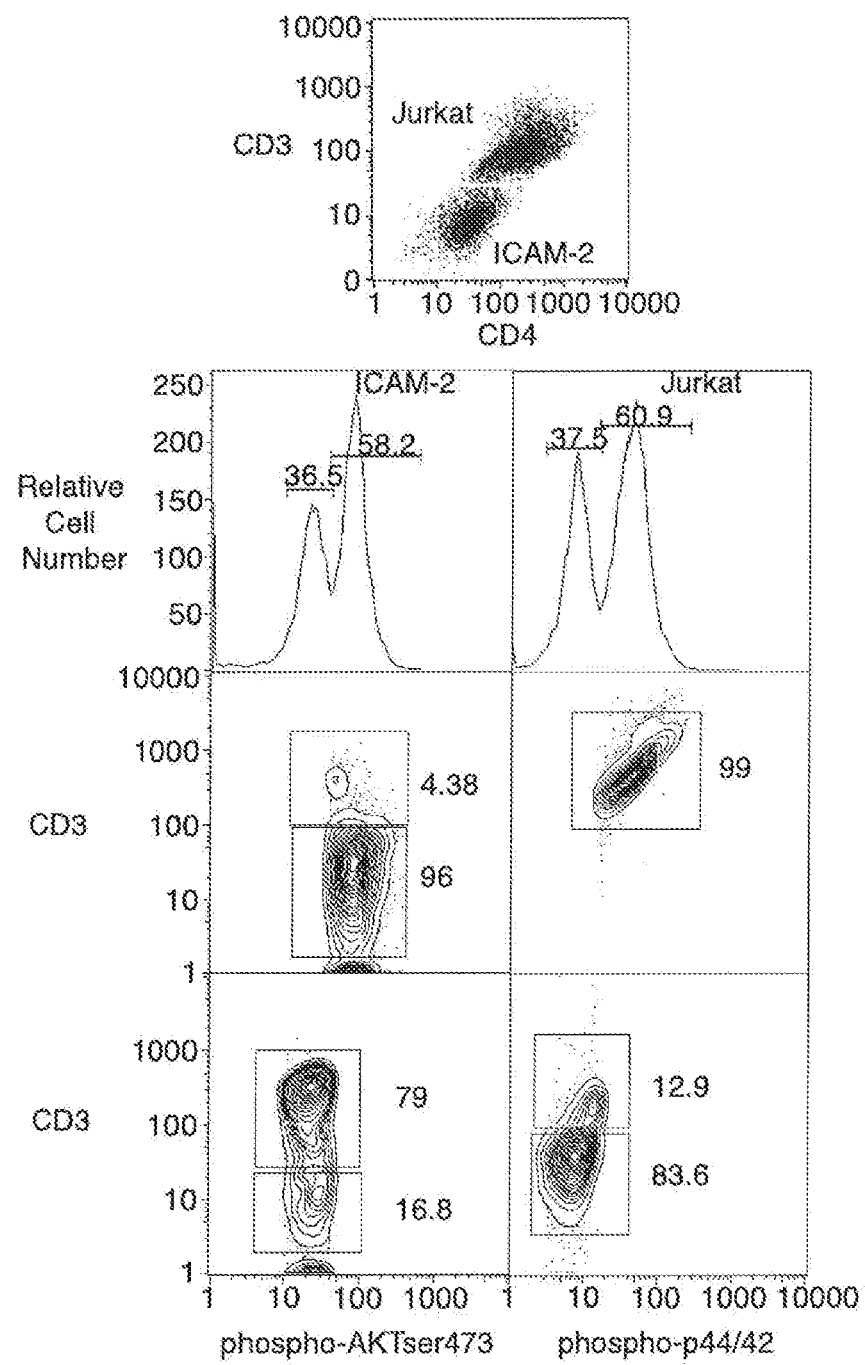
FIG._18A

1. Infect 3T3 cells
   with cDNA library
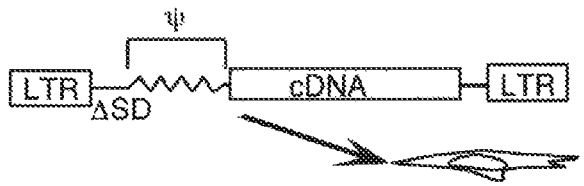
2. Treat with staurosporine for
   24 hours. Grow out survivors
   for one week. Repeat x 3.
3. Infect surviving cells with MMLV
   to rescue proviruses as infectious particles
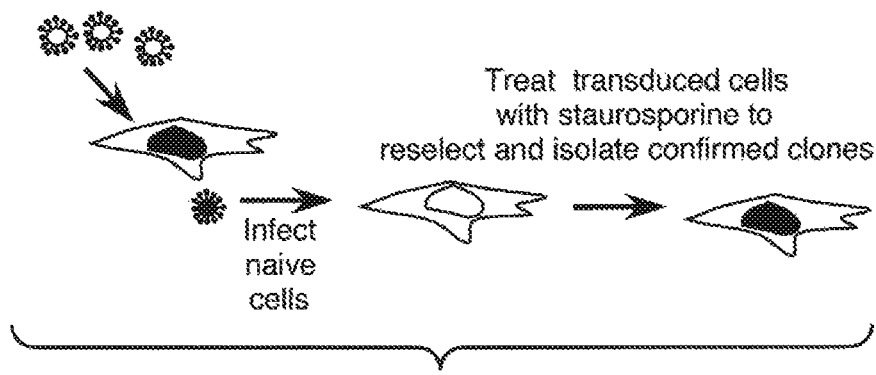
*FIG._19A*
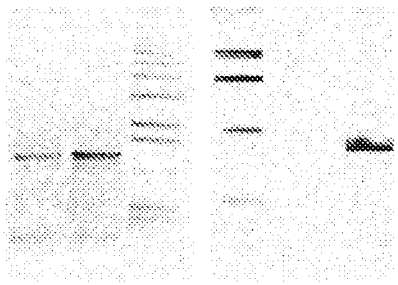
*FIG._19B*
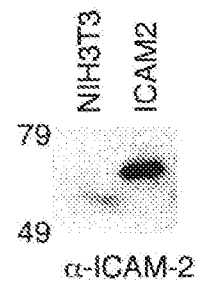
*FIG._19C*

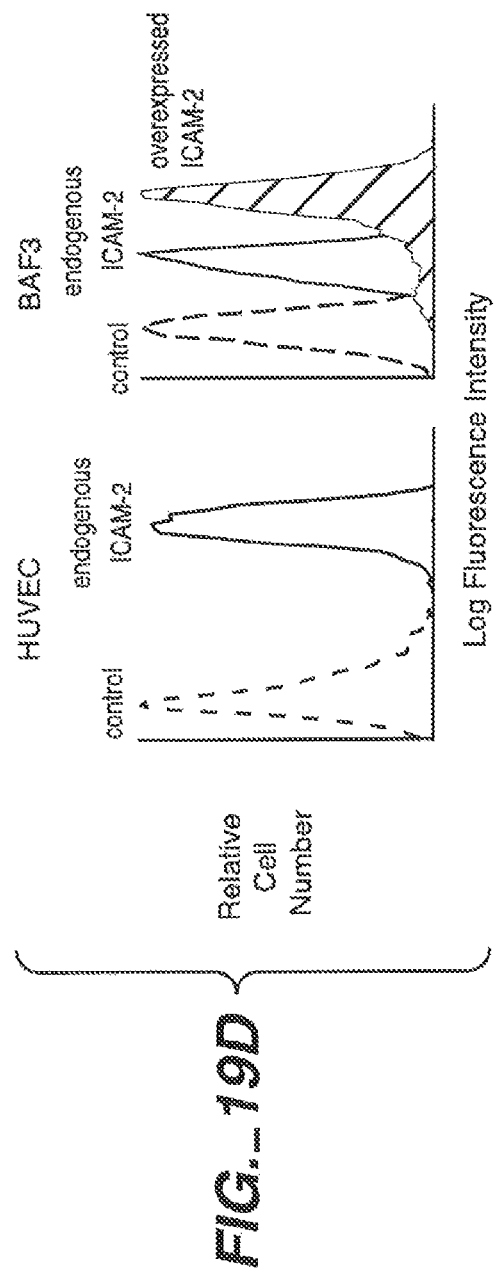
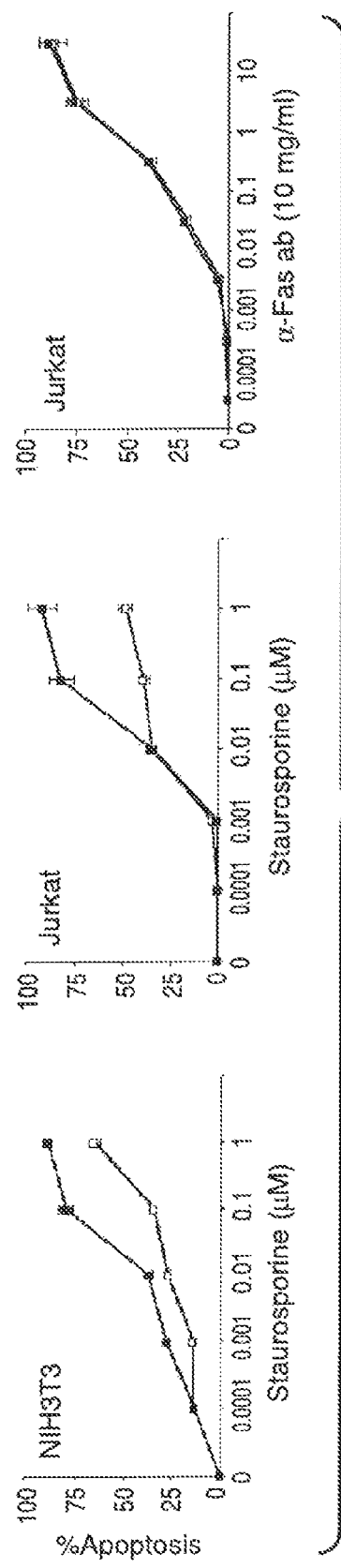
FIG._19D
FIG._19E

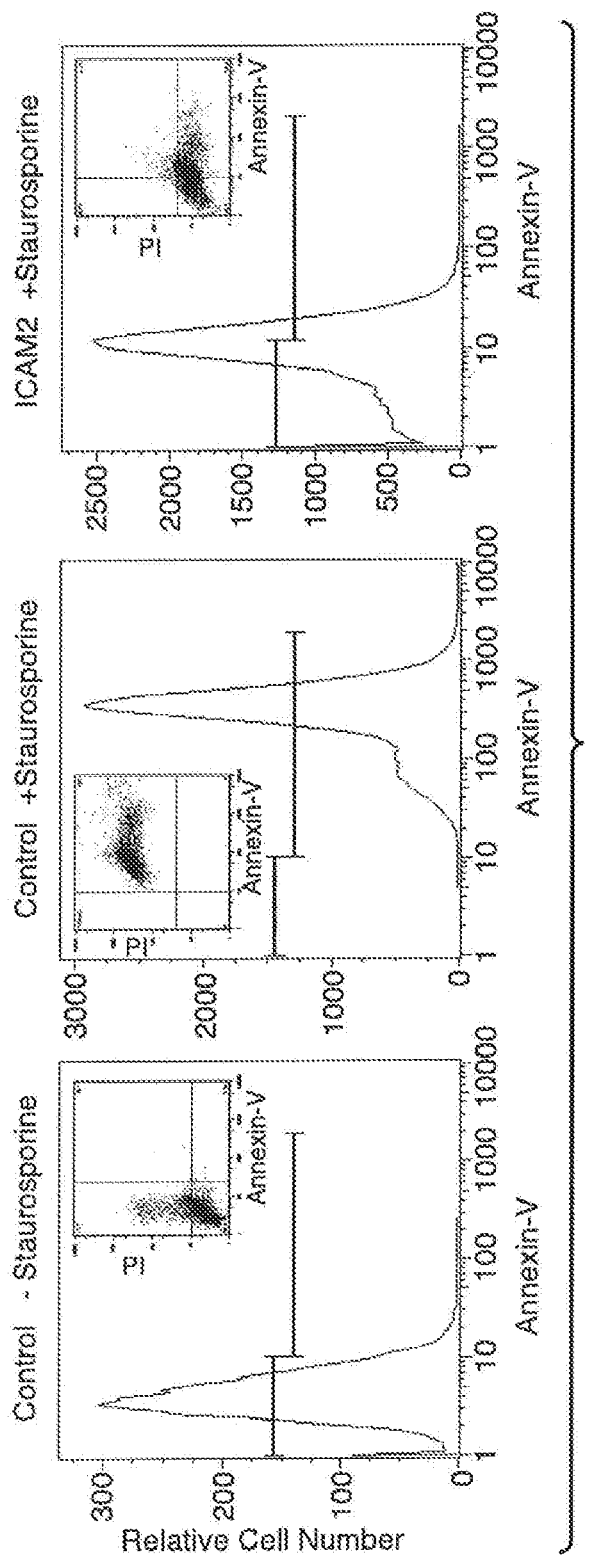
FIG._20A

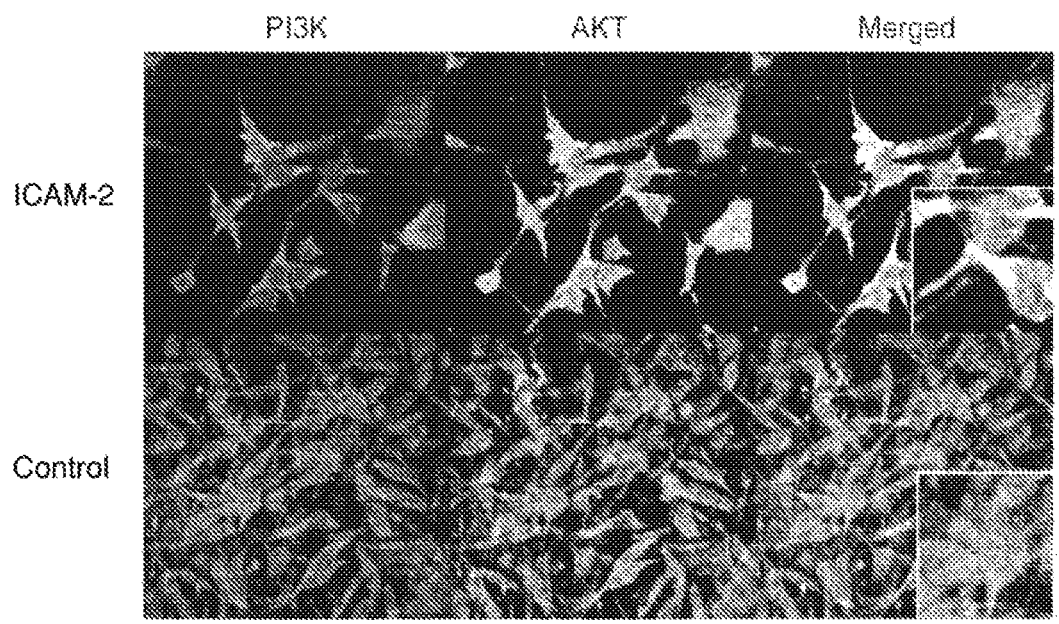
FIG._21B
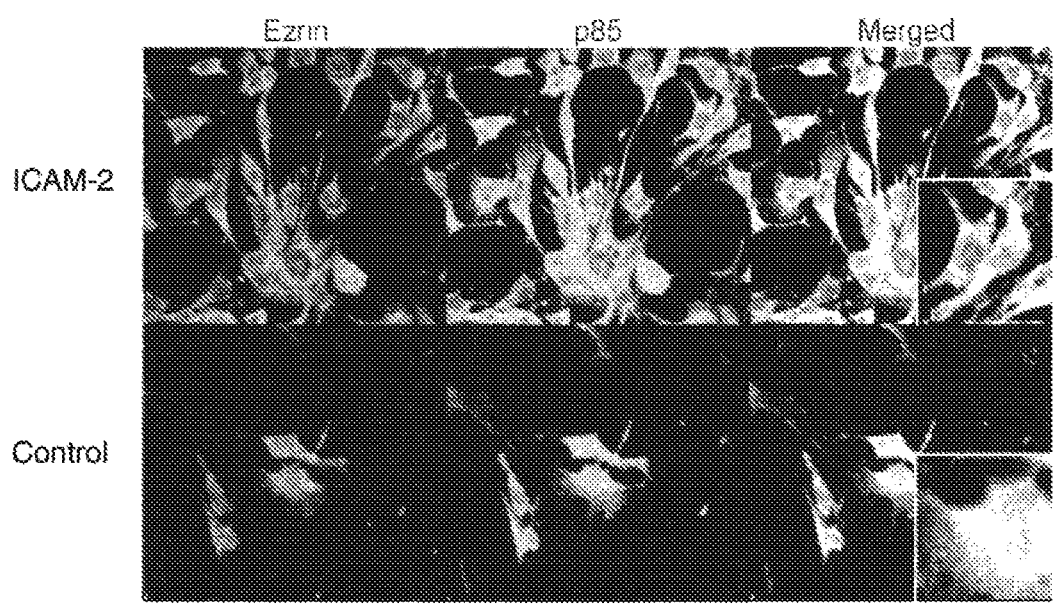
FIG._21C

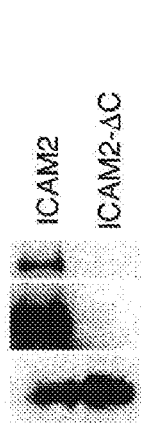
*FIG._22A*
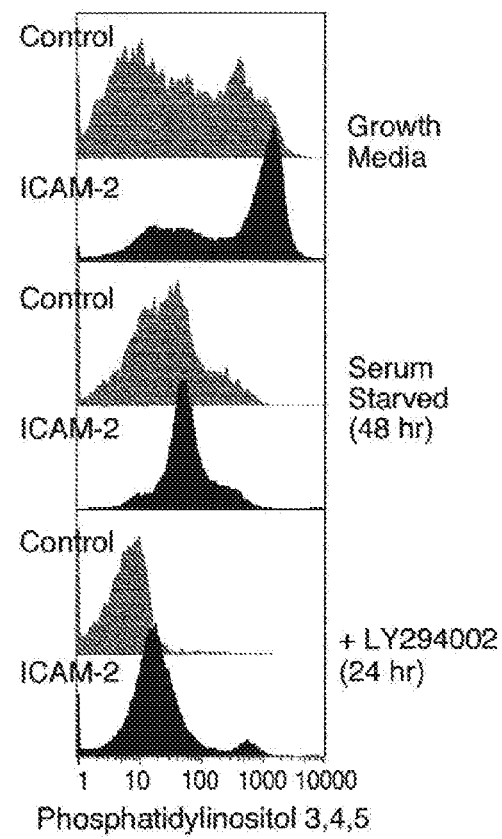
*FIG._22B*
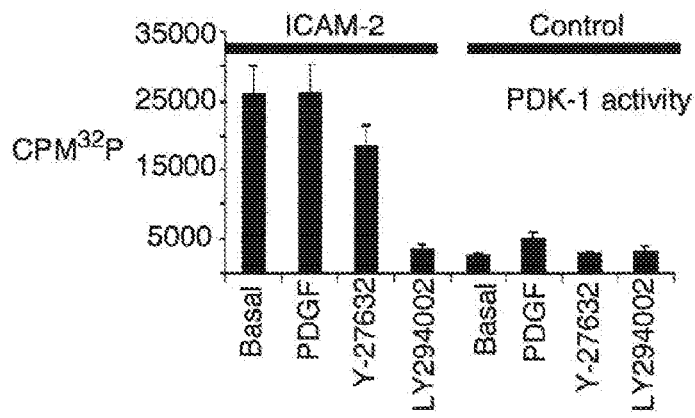
*FIG._22C*
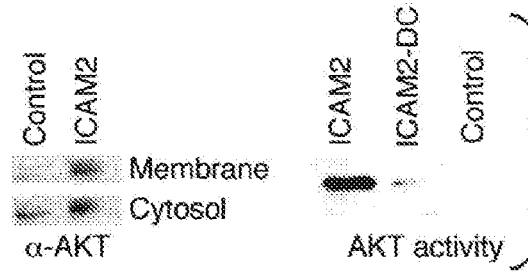
*FIG._22D*

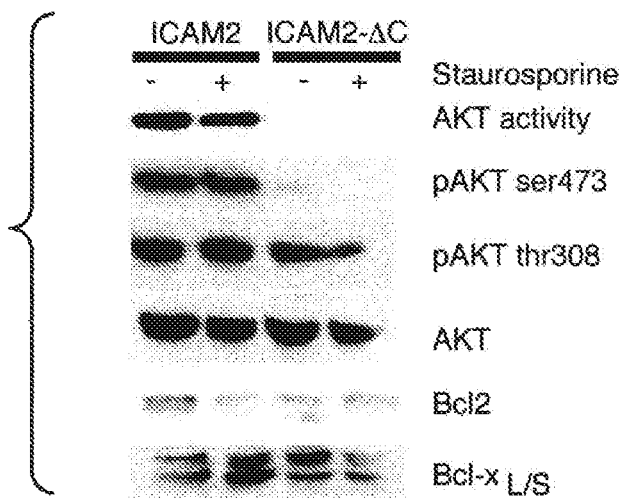
FIG._22E
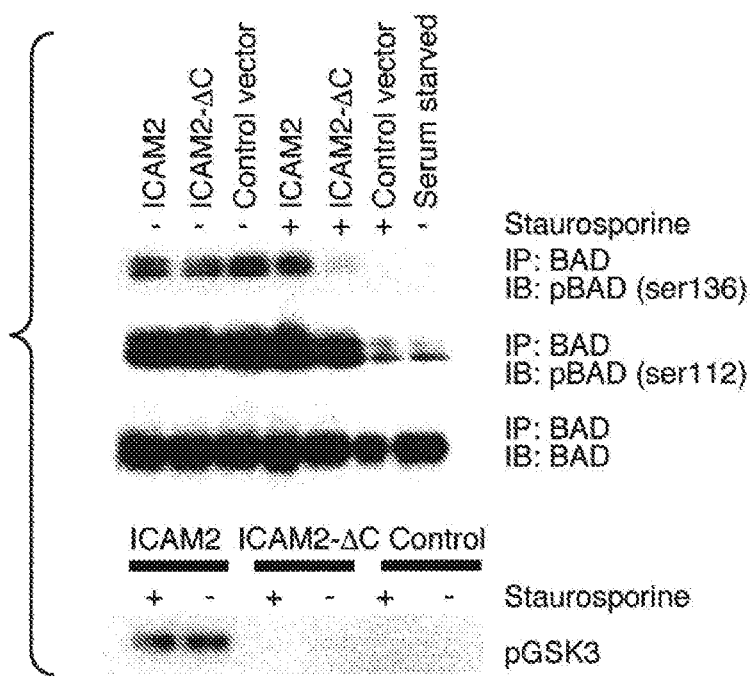
FIG._22F

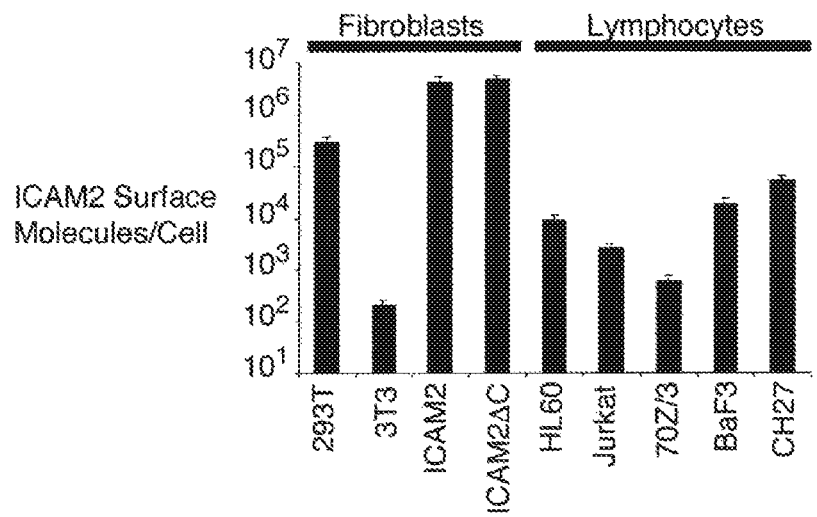
FIG._23A
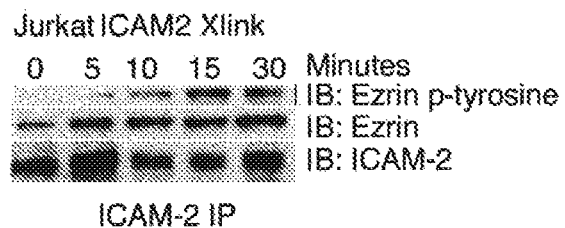
FIG._23B
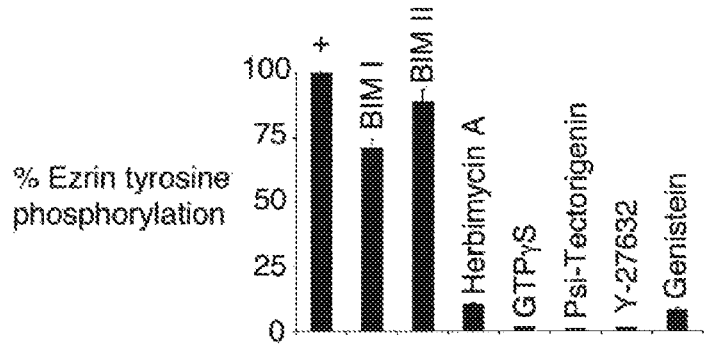
FIG._23C

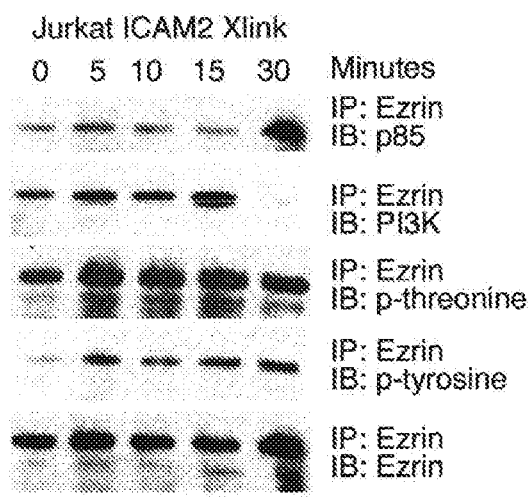
FIG._23D
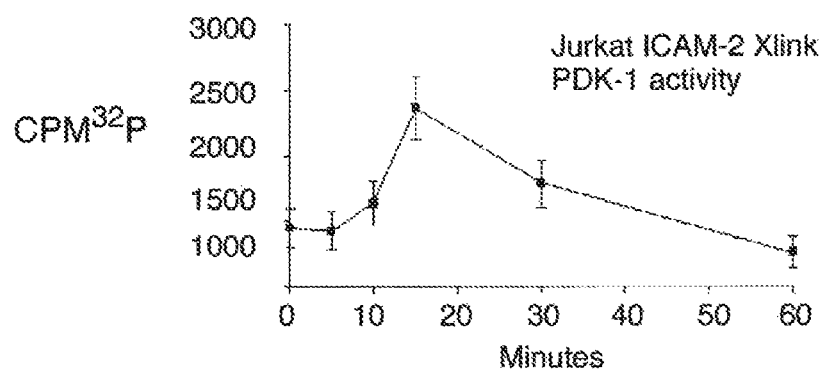
FIG._23E
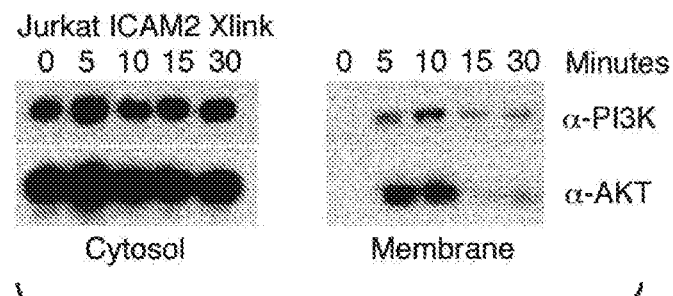
FIG._23F

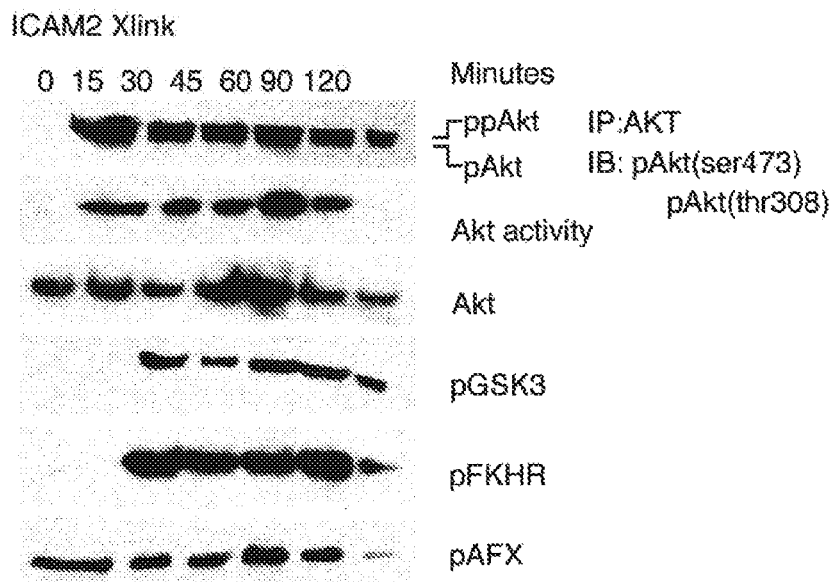
FIG._24A
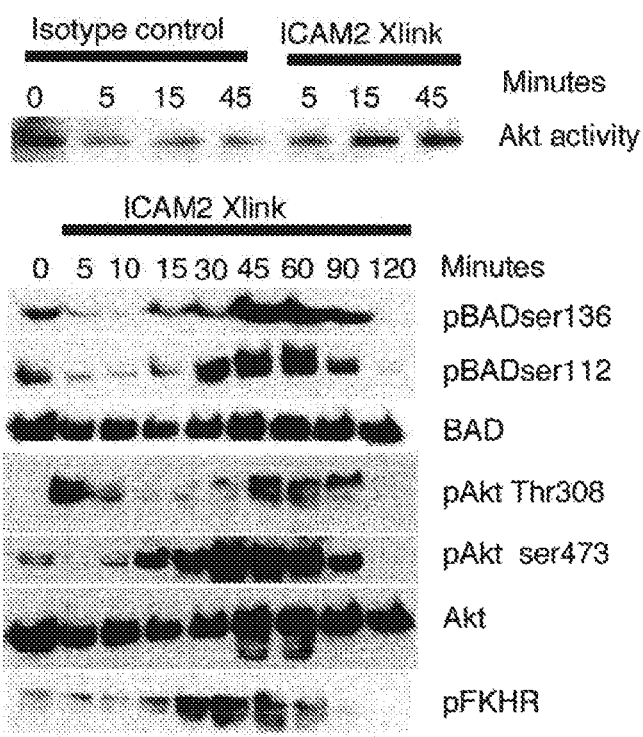
FIG._24B

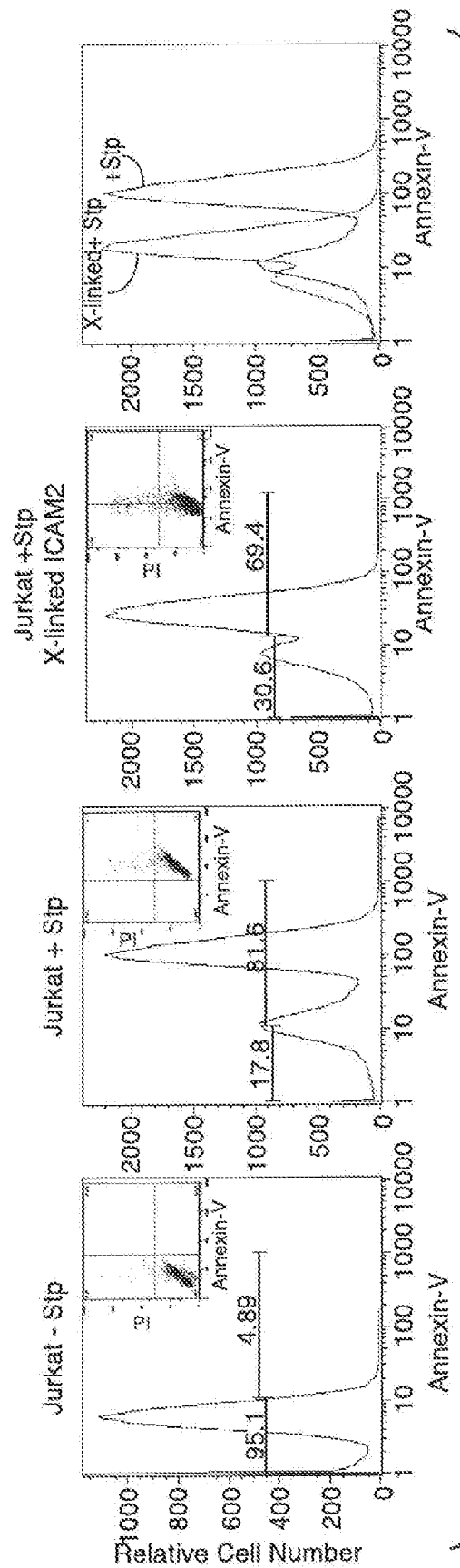
FIG._24C

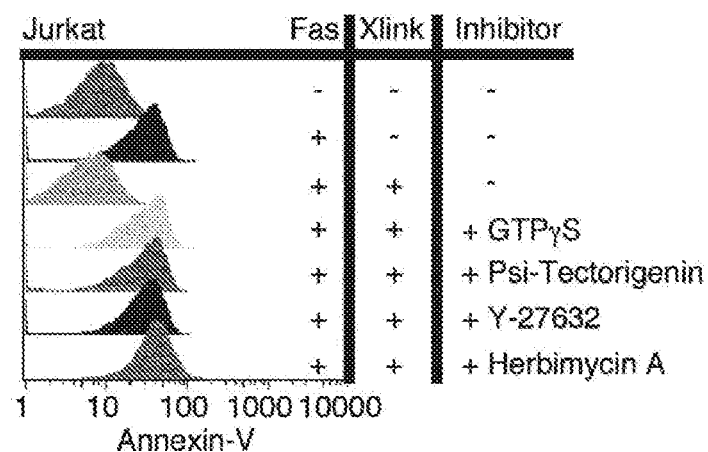
FIG._24D
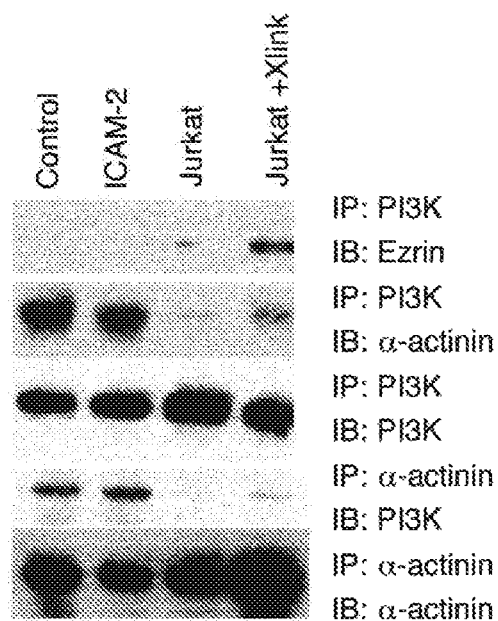
FIG._24E

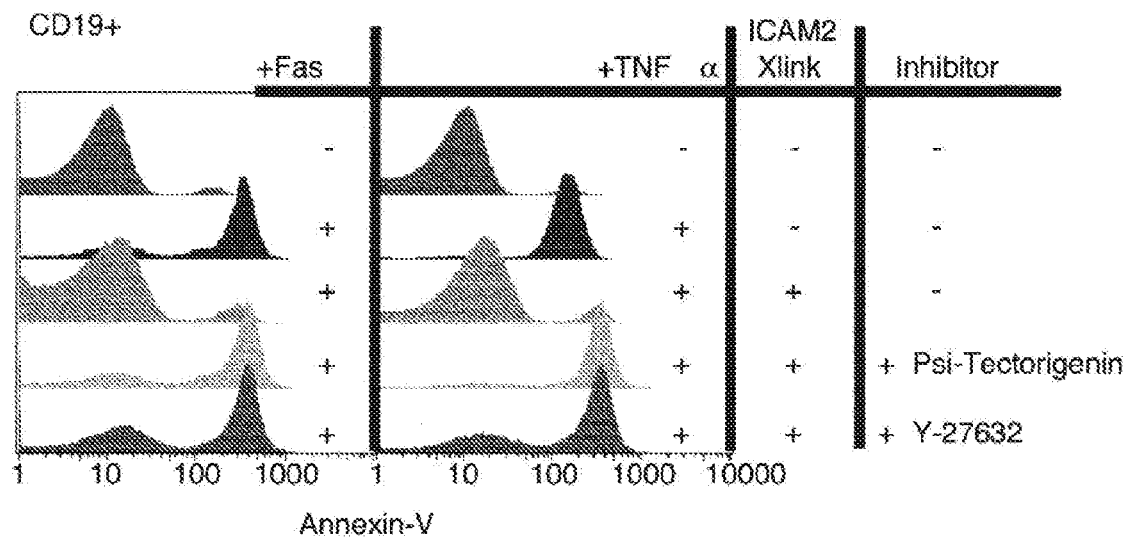
FIG._25D
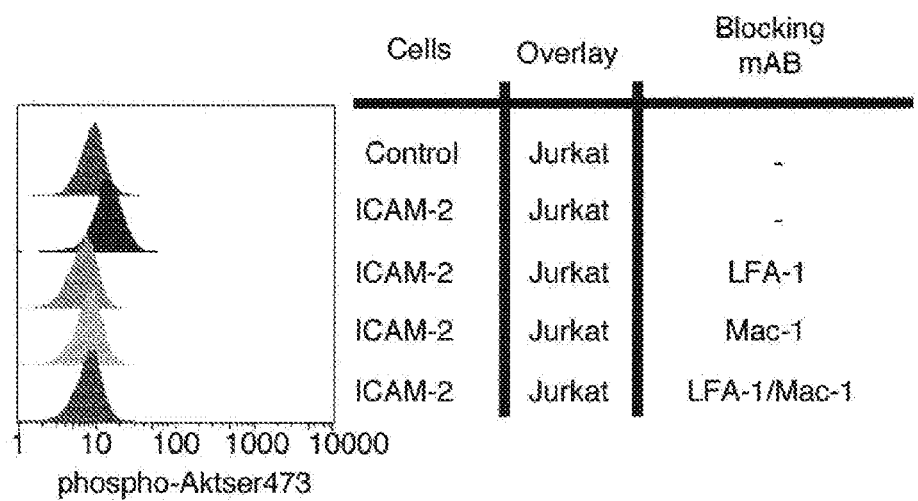
FIG._25E

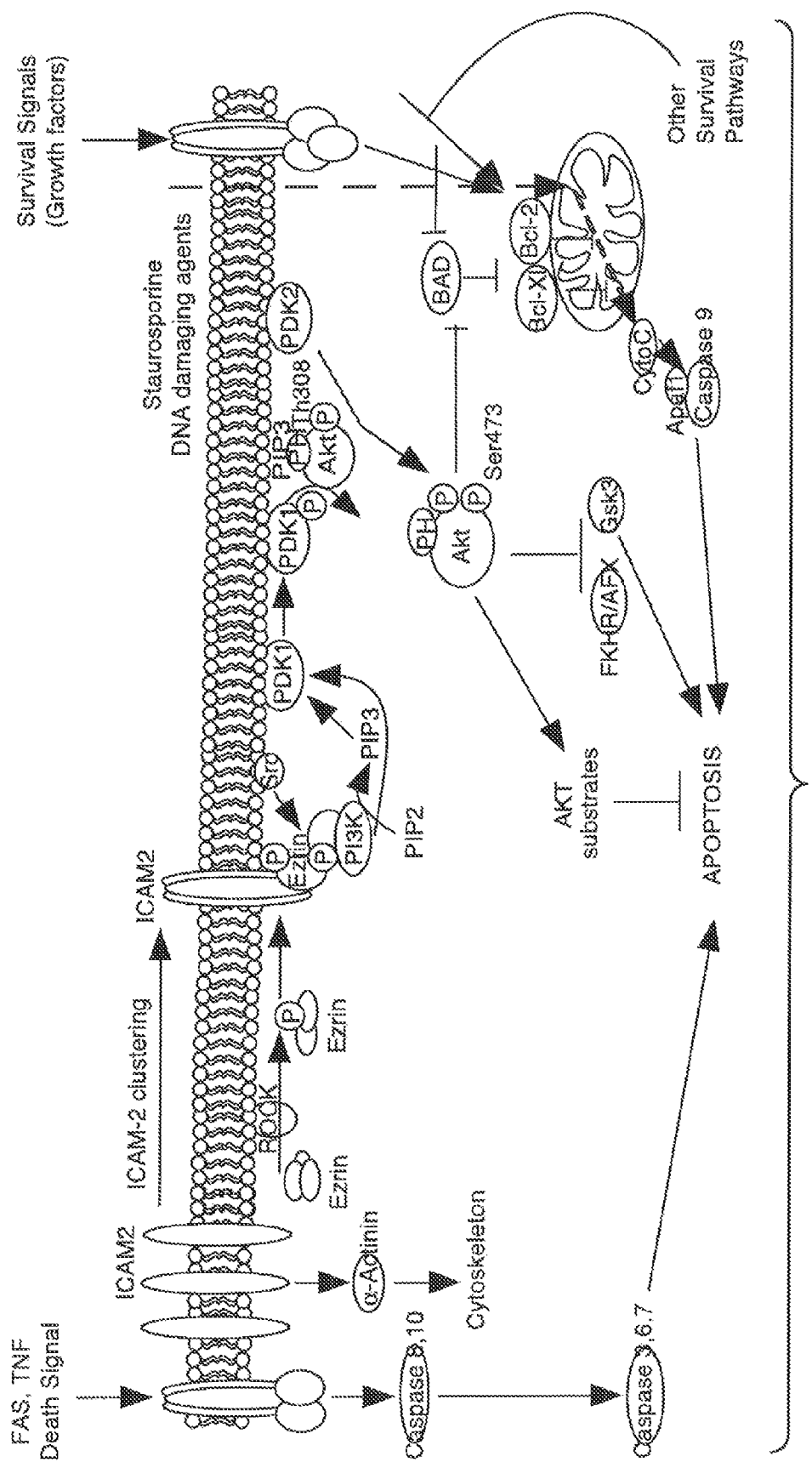
FIG._25F

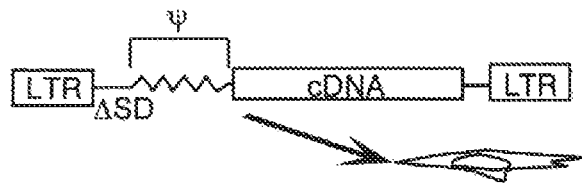
1. Infect 3T3 cells with cDNA library
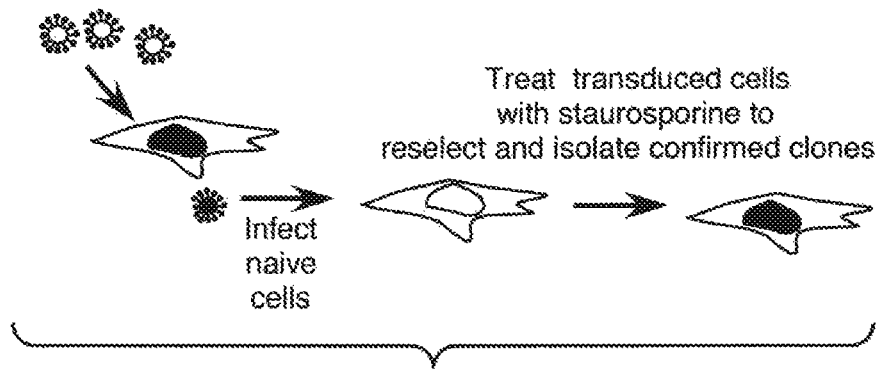
2. Treat with staurosporine for 24 hours. Grow out survivors for one week. Repeat × 3.
3. Infect surviving cells with MMLV to rescue proviruses as infectious particles.
*FIG._26A*
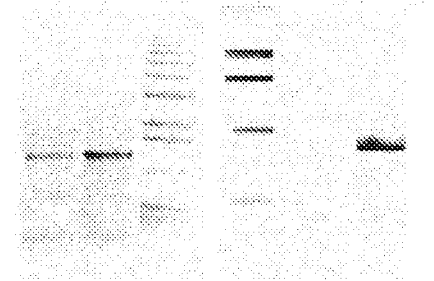
*FIG._26B*

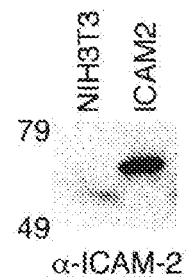
FIG._27A
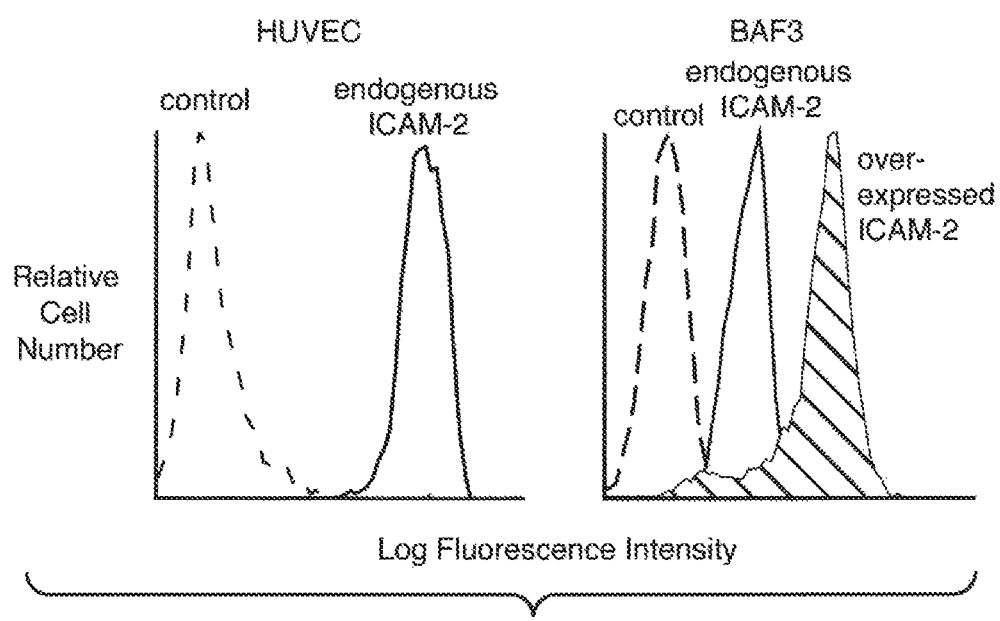
FIG._27B

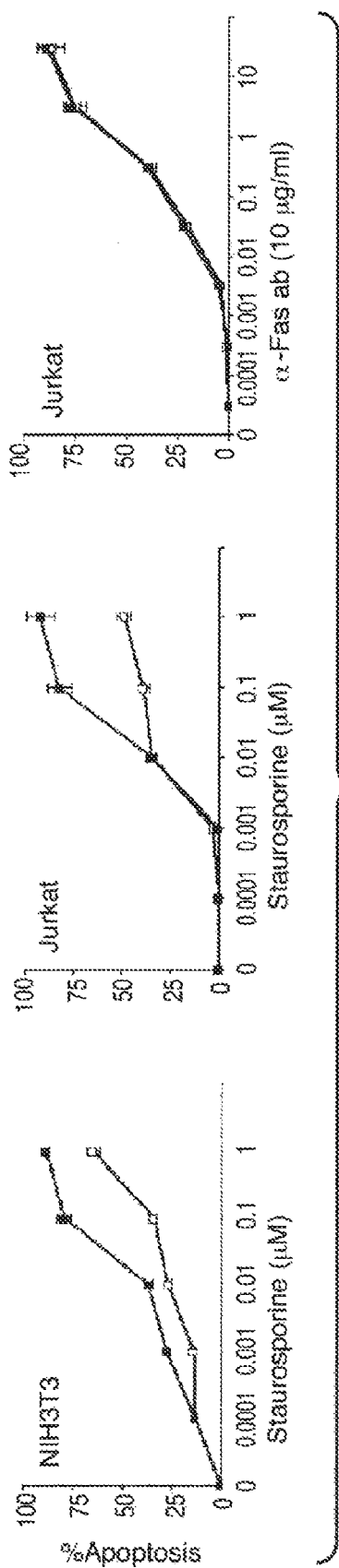
FIG.—27C
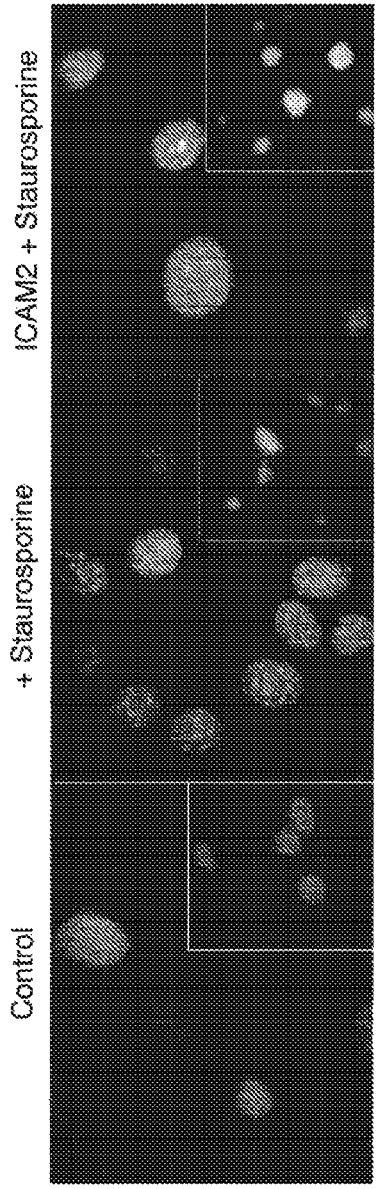
FIG.—27D

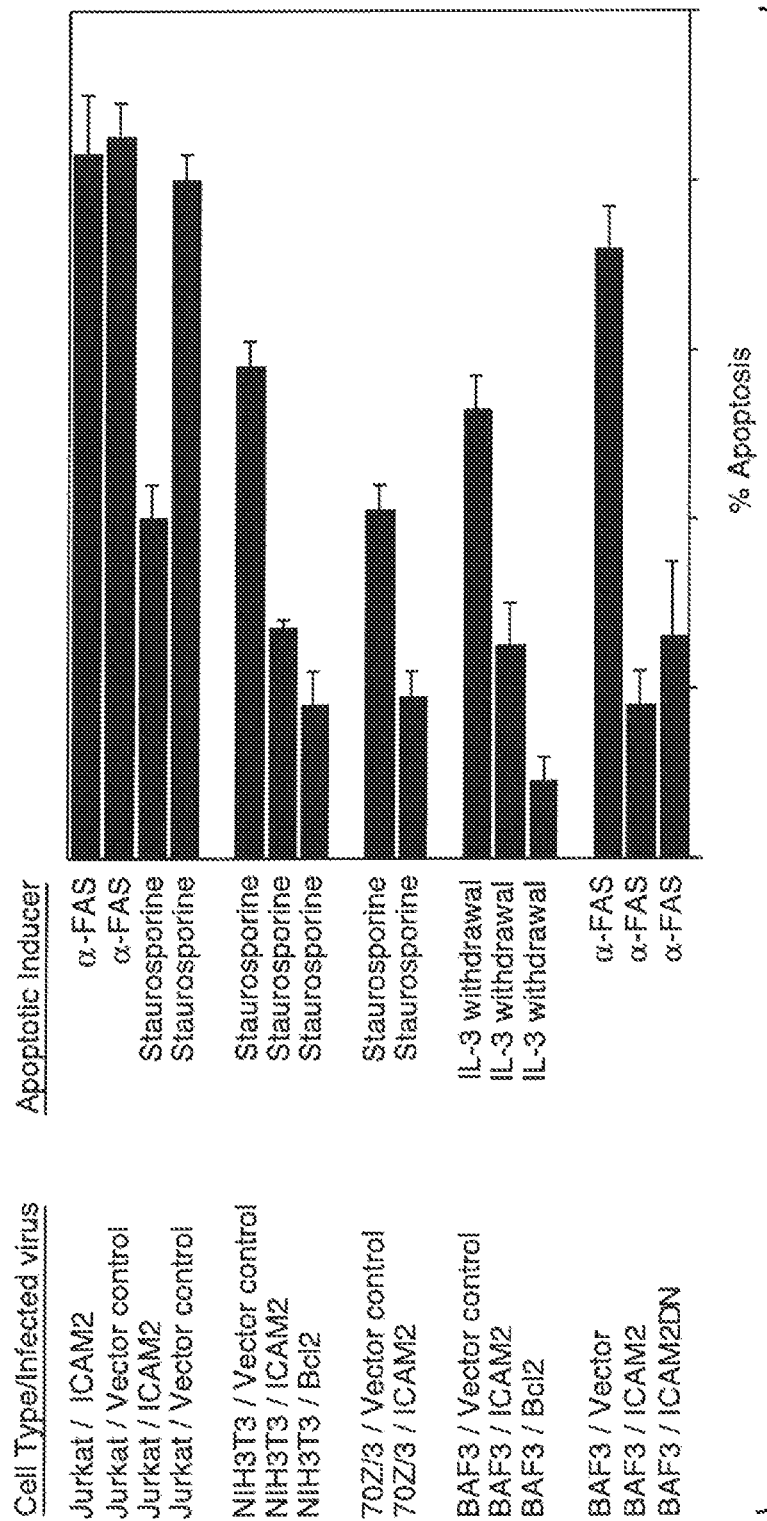

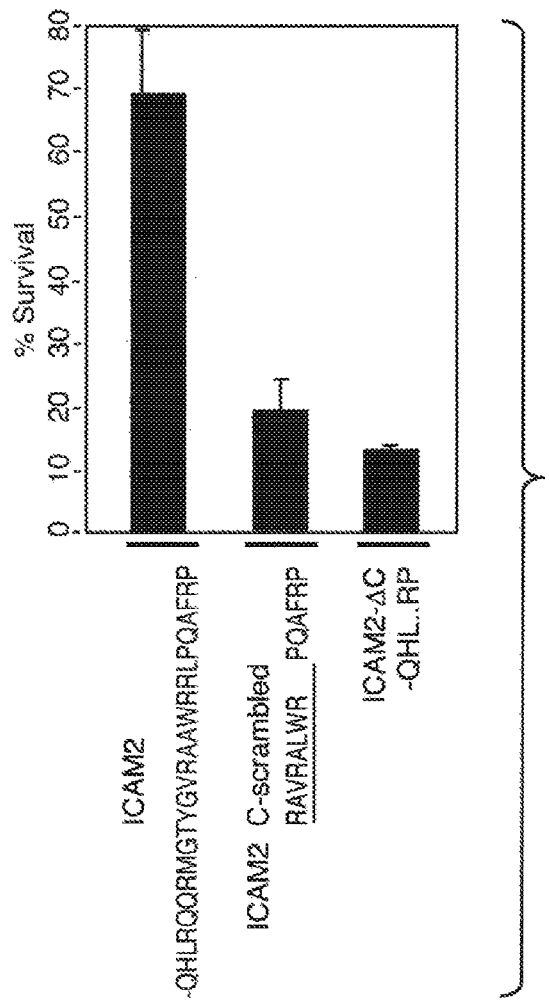
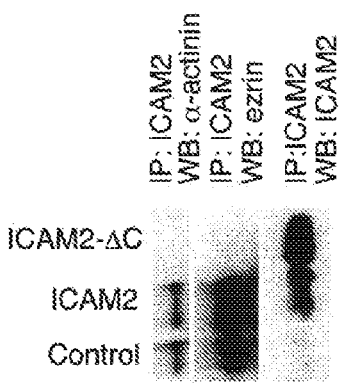
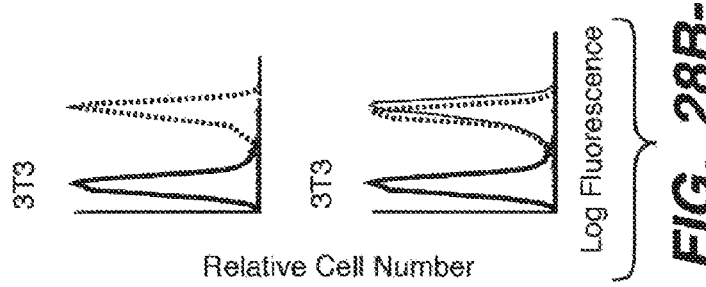
FIG. _28B-2
FIG. _28C
FIG. _28B-1

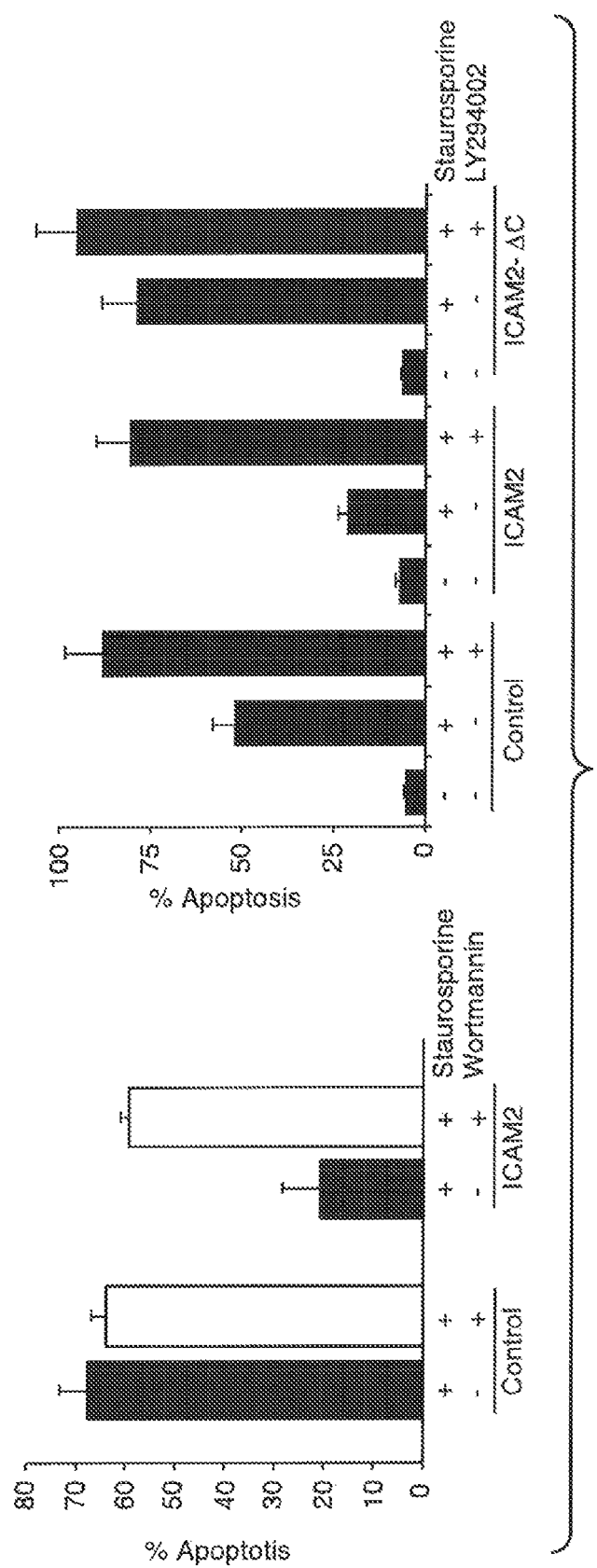
FIG._29A

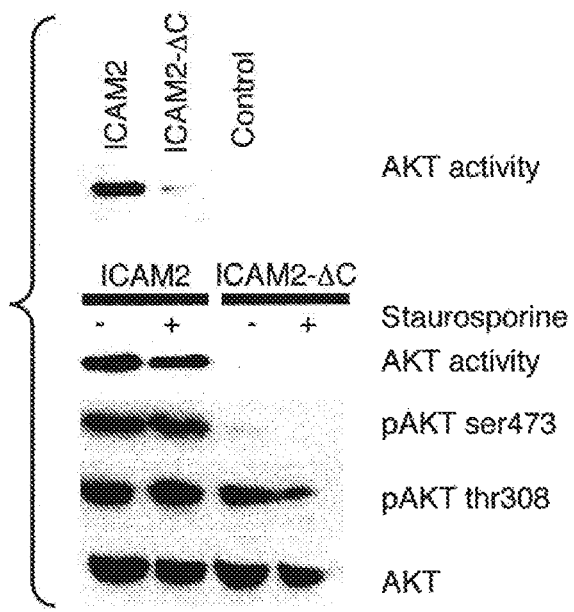
*FIG._30A*
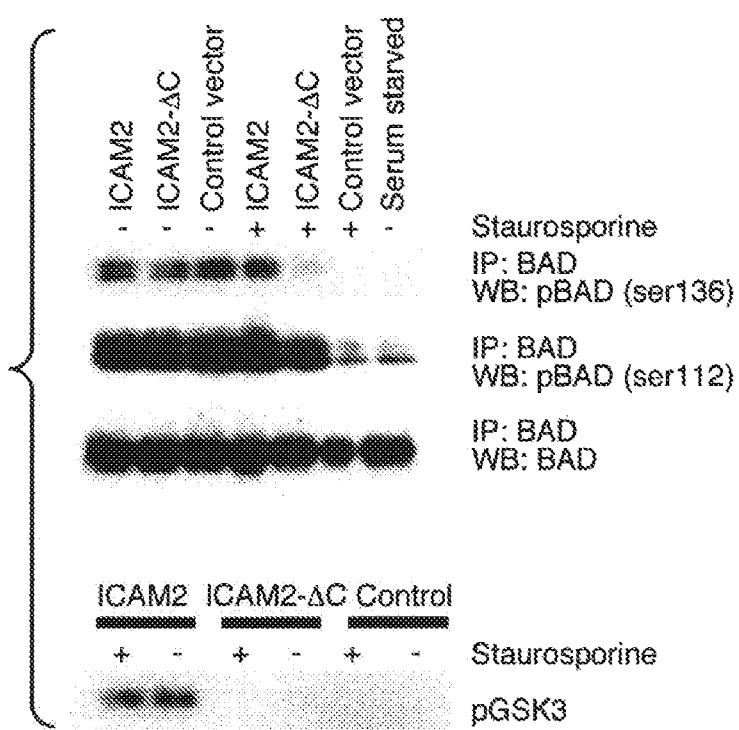
*FIG._30B*

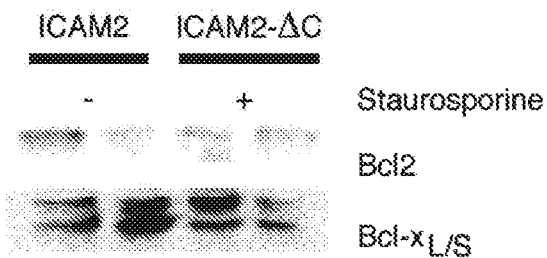
FIG._30C
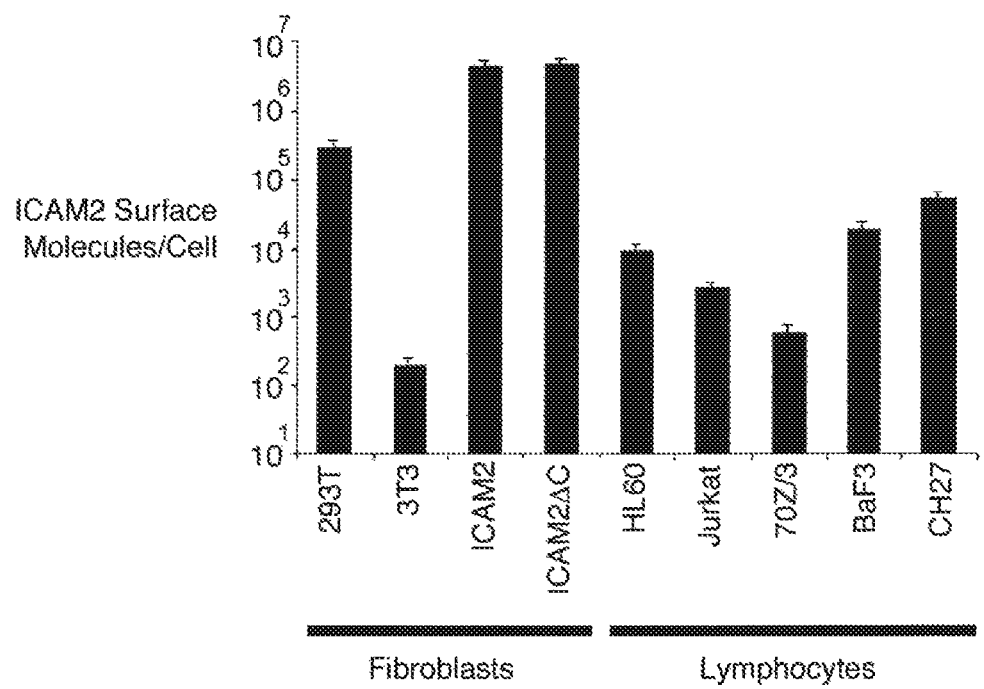
FIG._30D

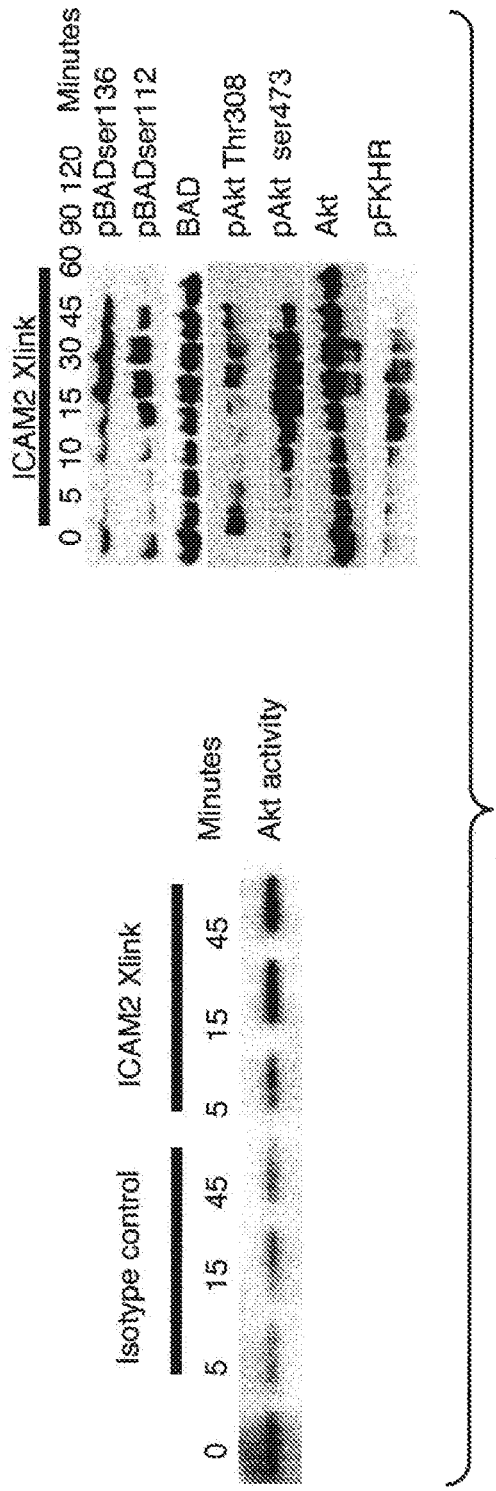
FIG._31A

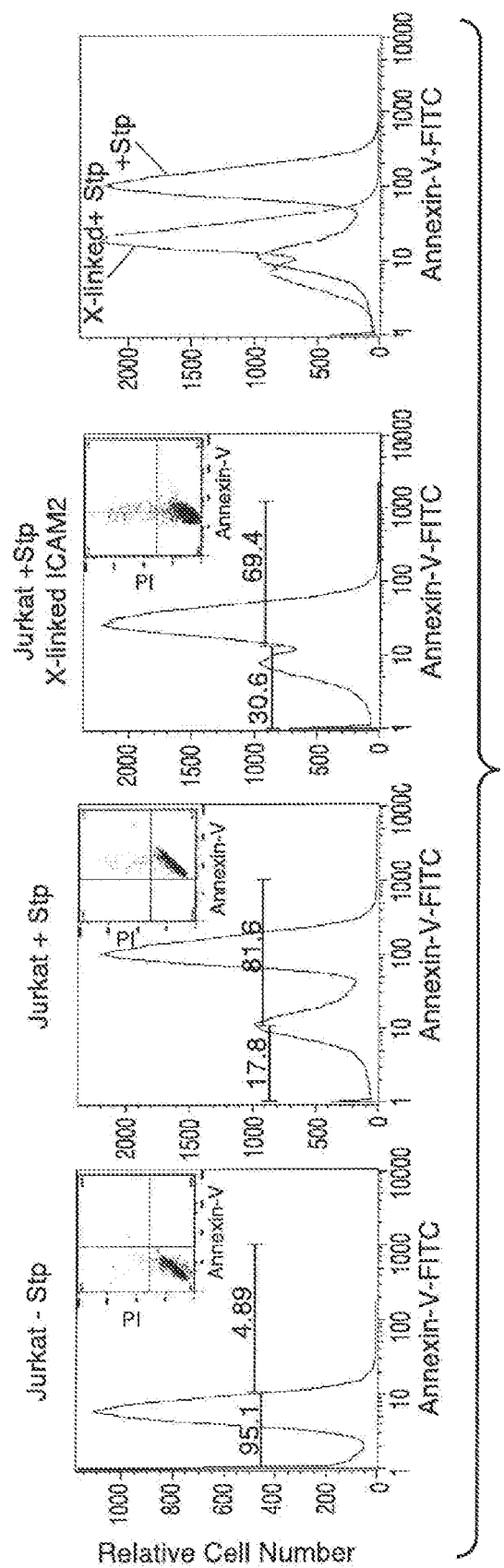
FIG._31B

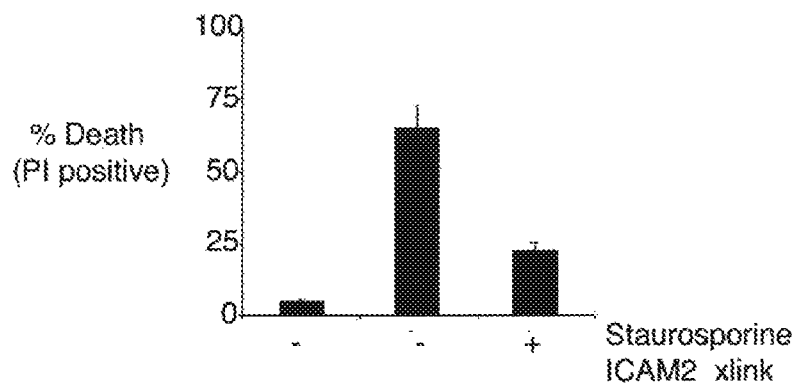
FIG._31C
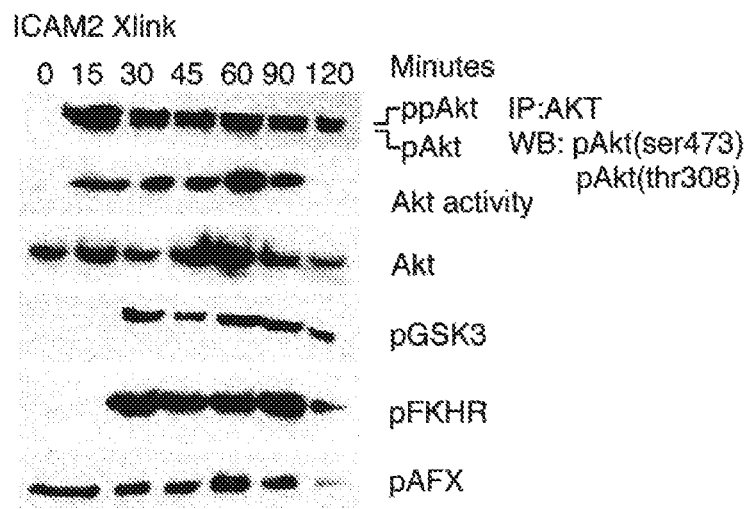
FIG._31D

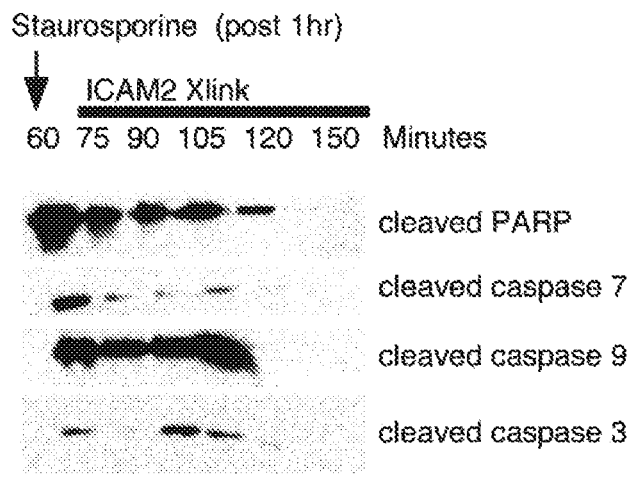
FIG._31E
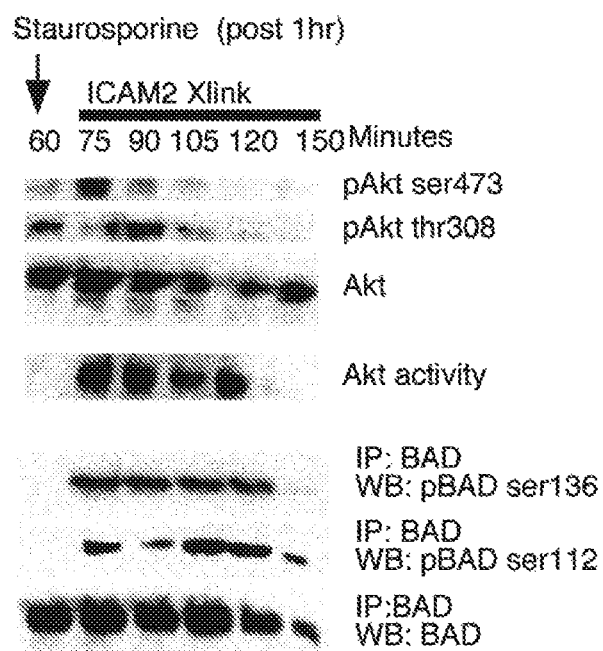
FIG._31F

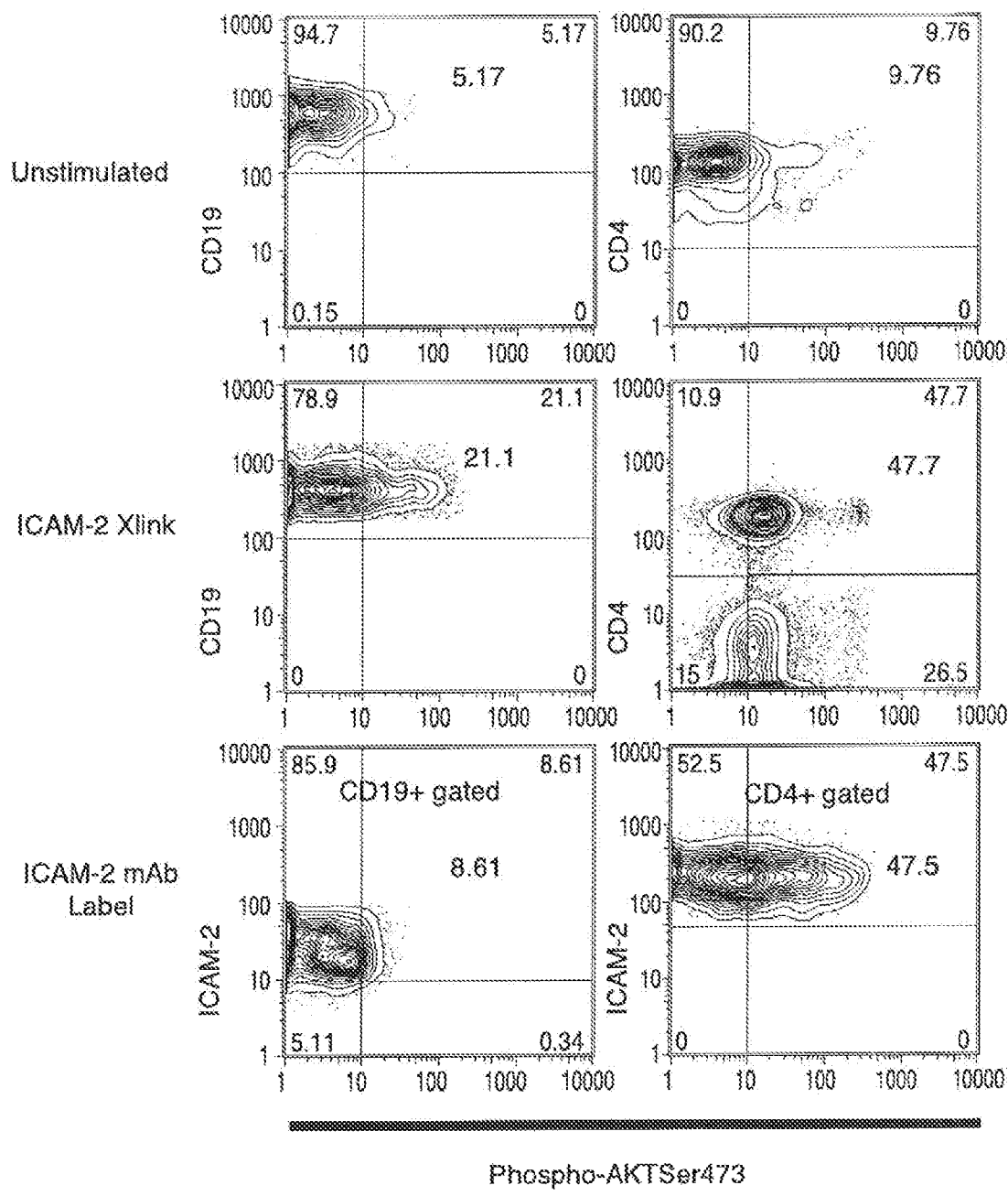
FIG._32A

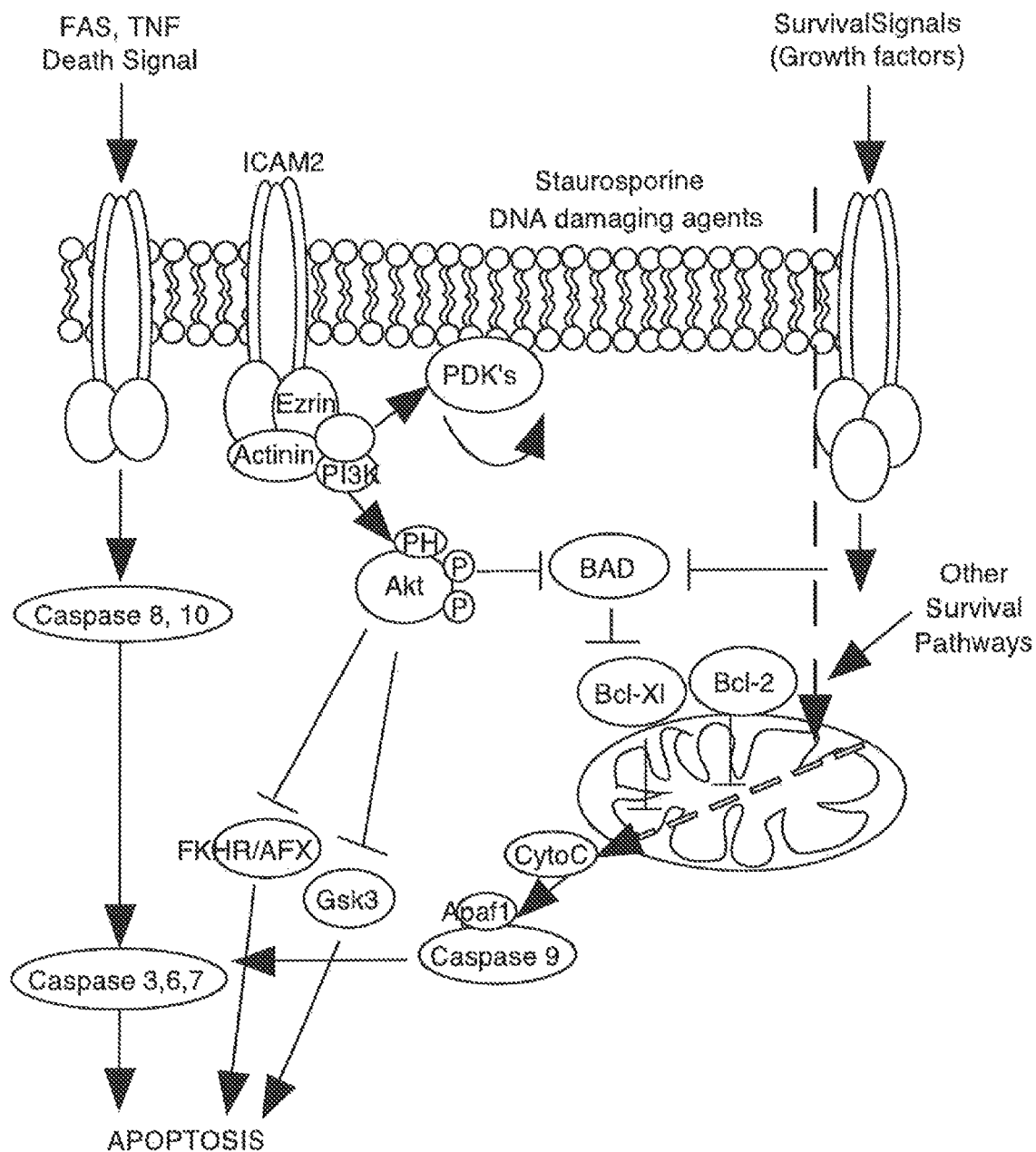
FIG._32C

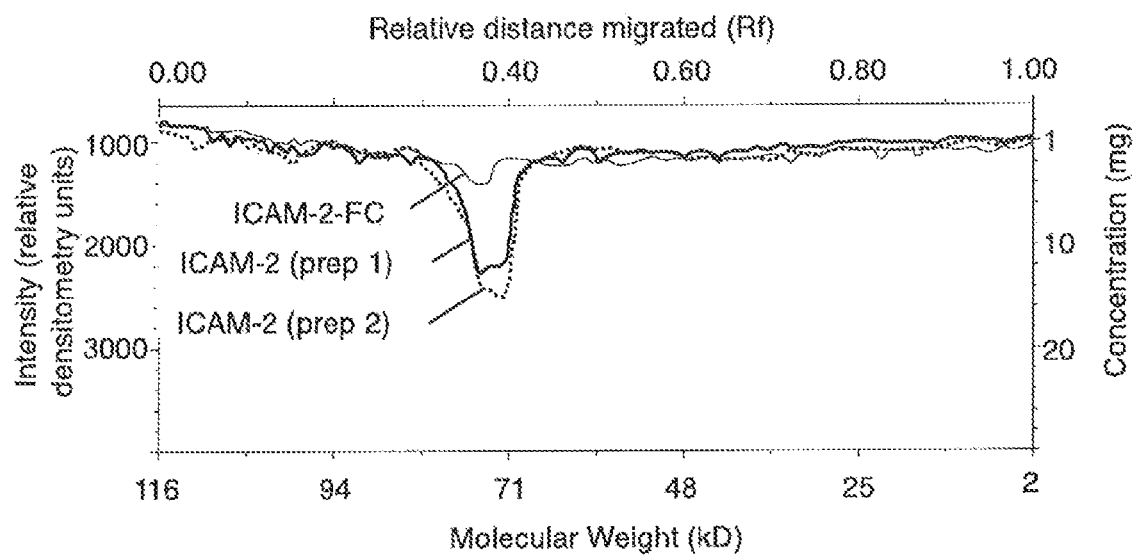
FIG._33A
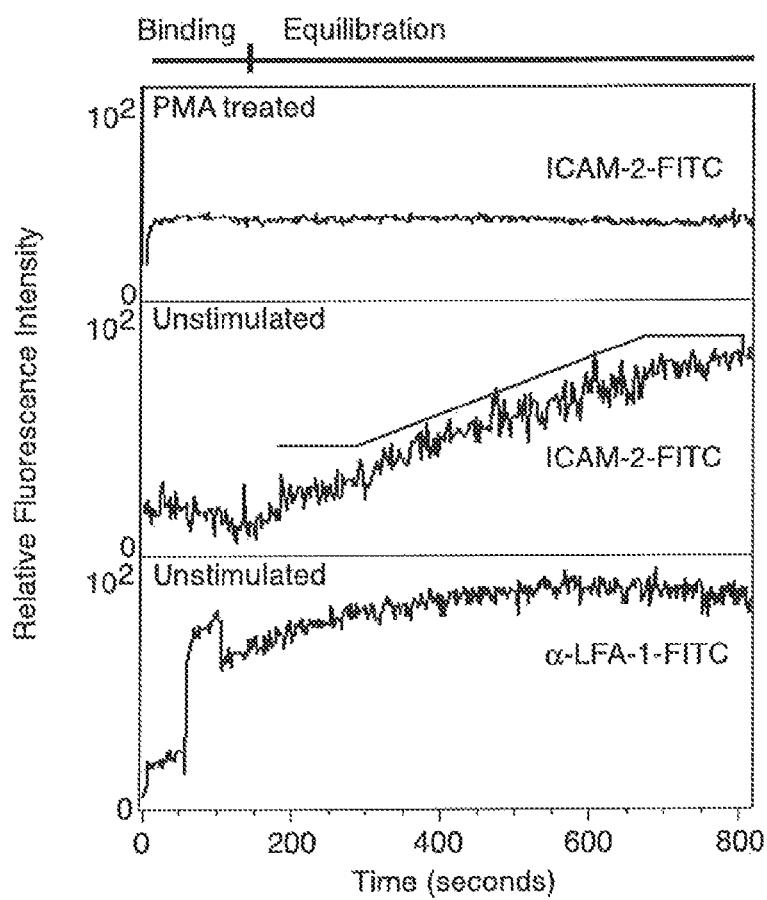
FIG._33B

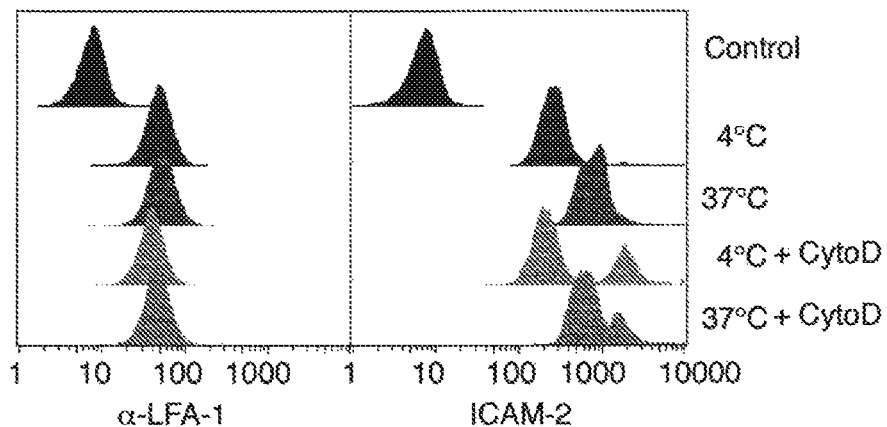
FIG._33C
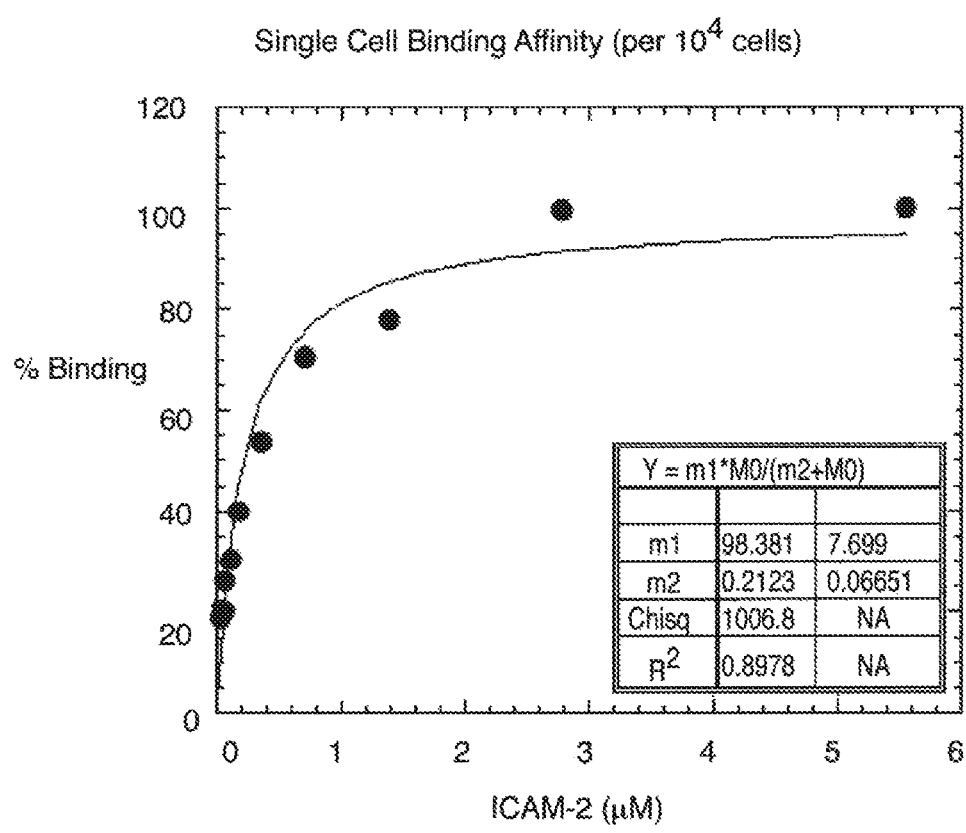
FIG._33D

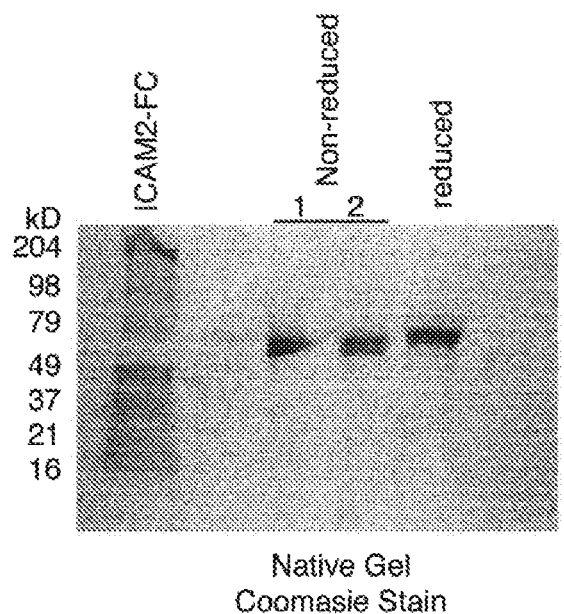
FIG. _33E
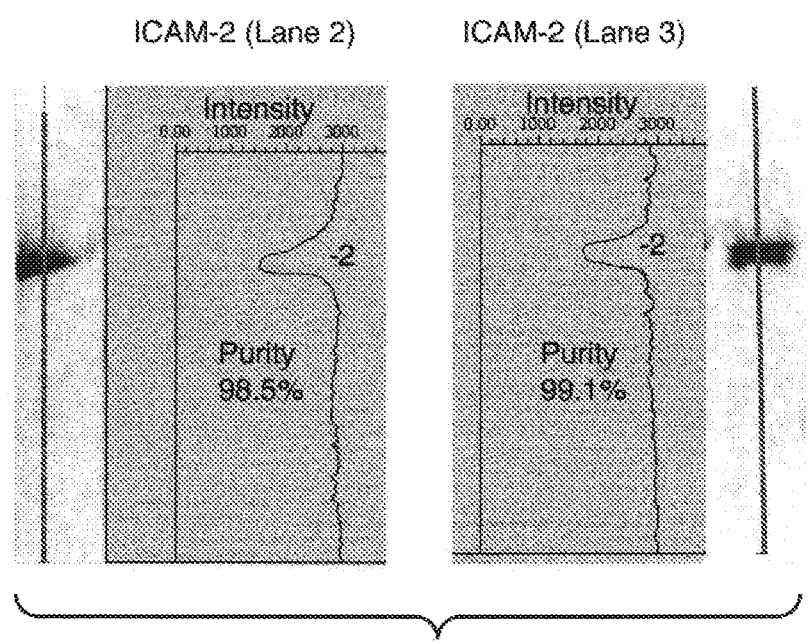
FIG. _33F

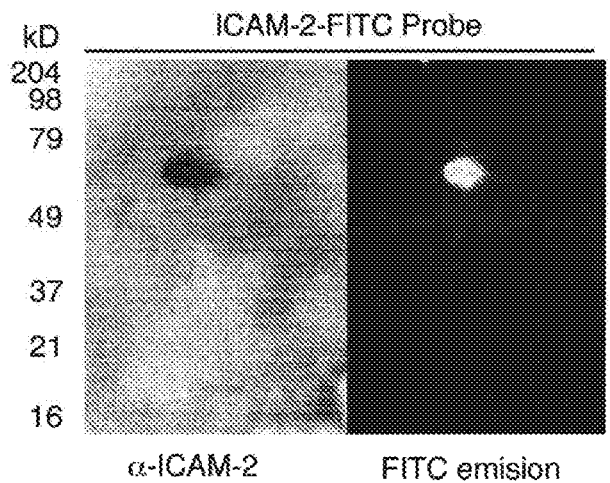
FIG._33G
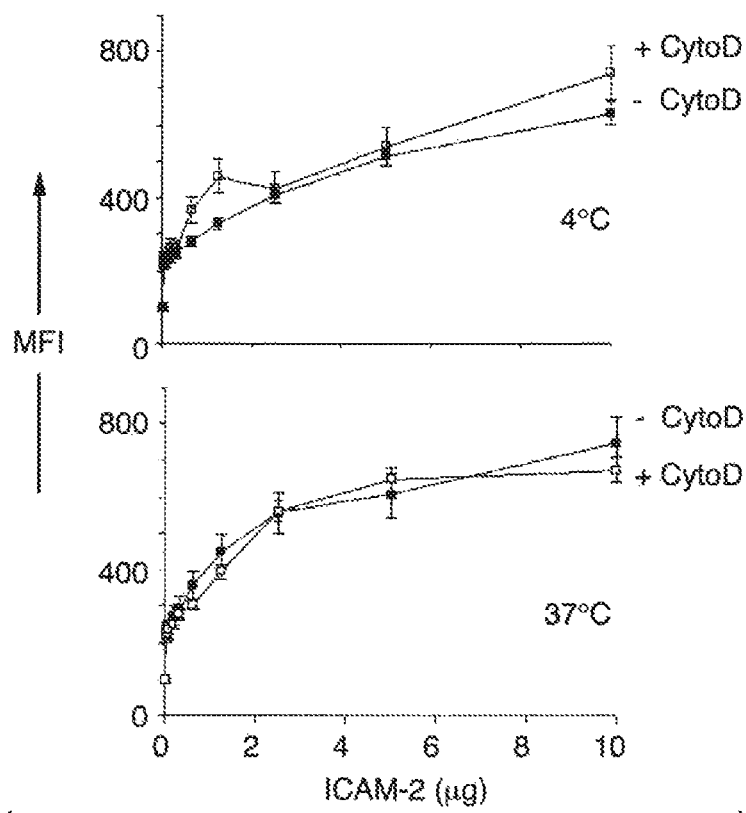
FIG._33H

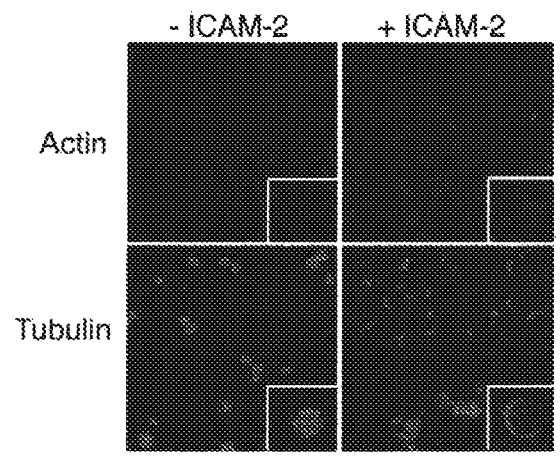
FIG._34A
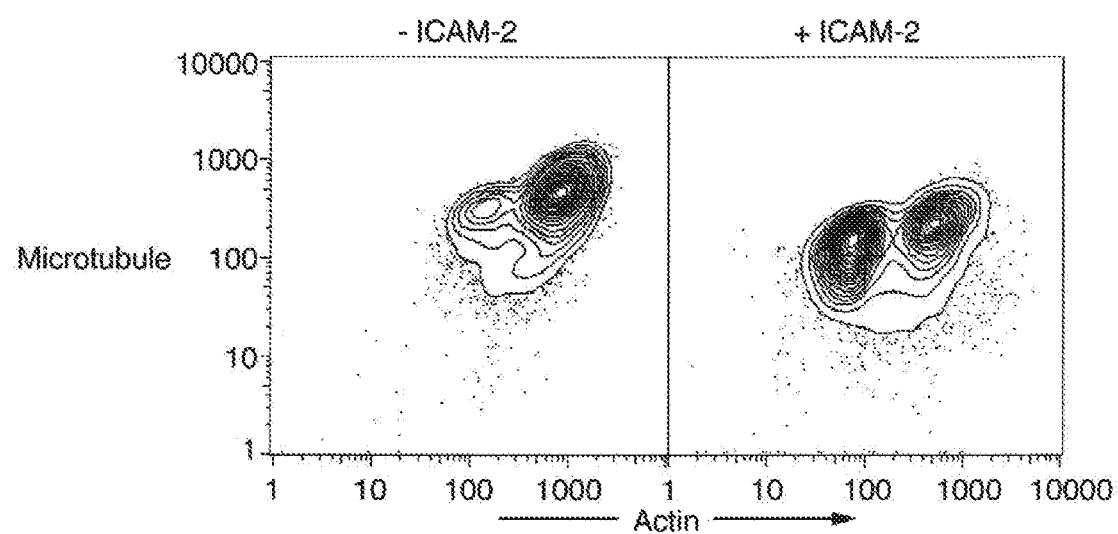
FIG._34B

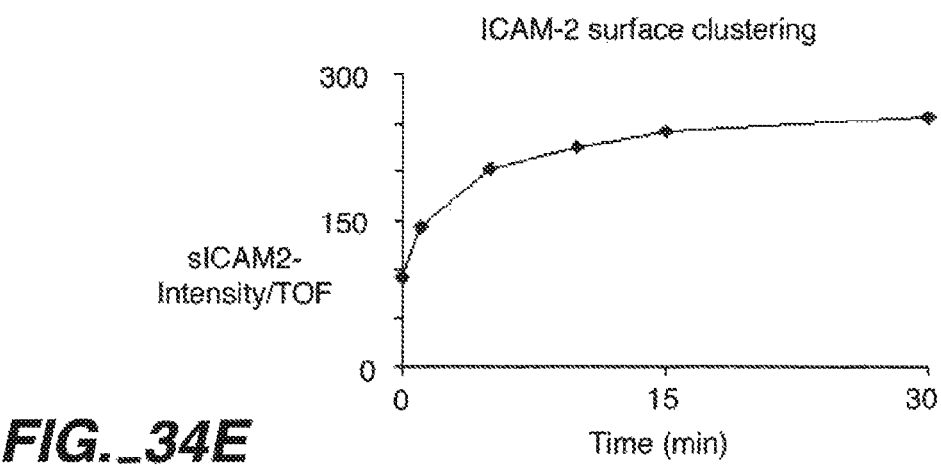
FIG._34E
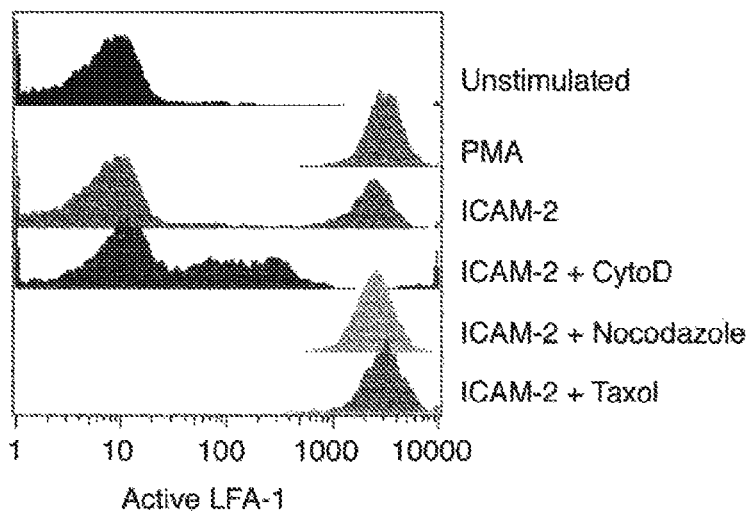
FIG._34F
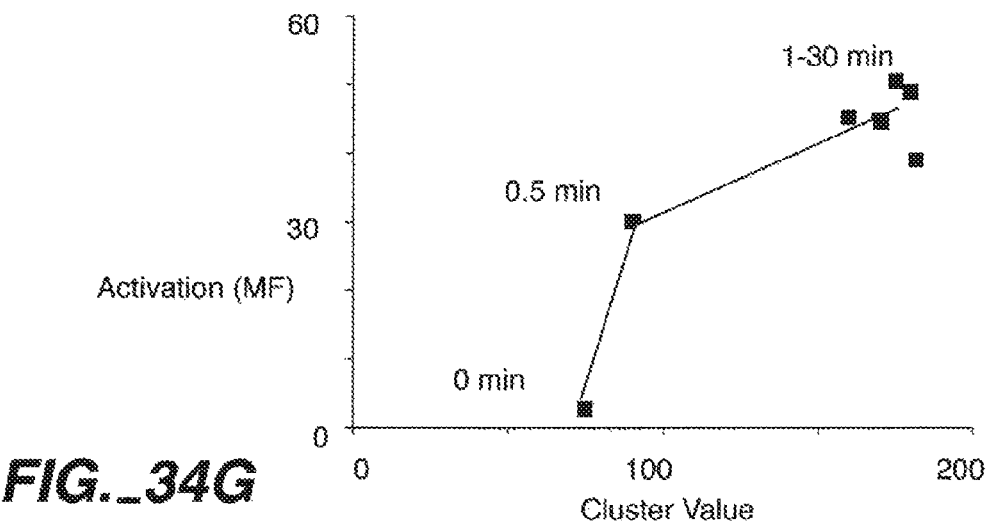
FIG._34G

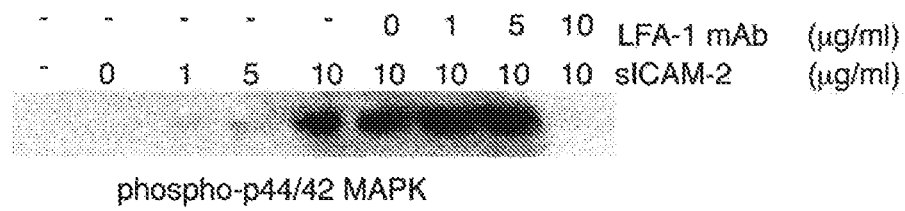
*FIG._34H*
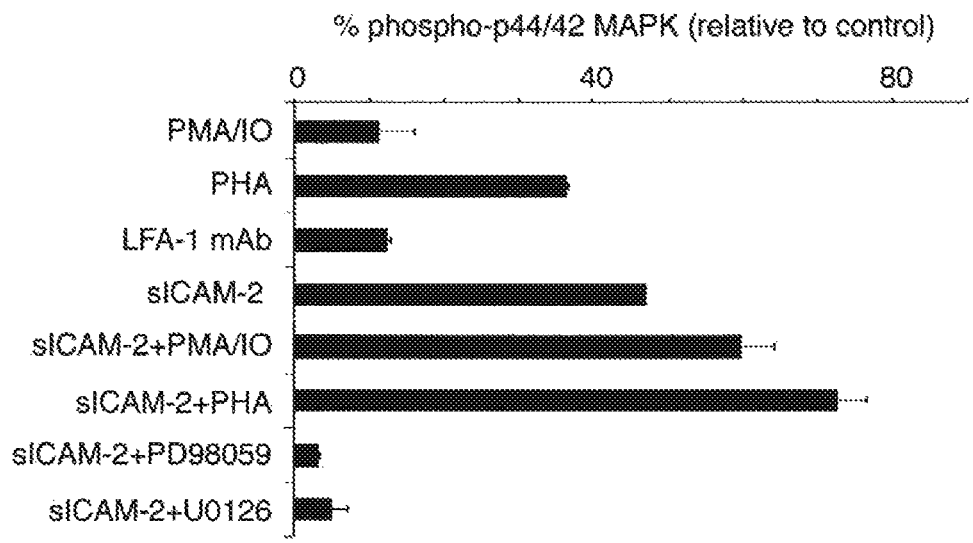
*FIG._34I*

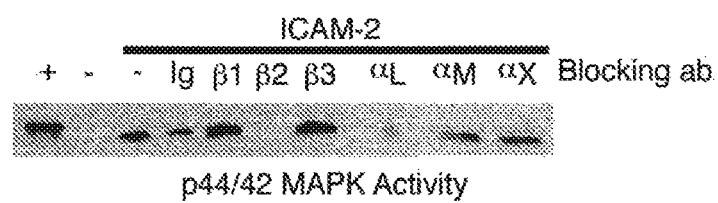
FIG._35C
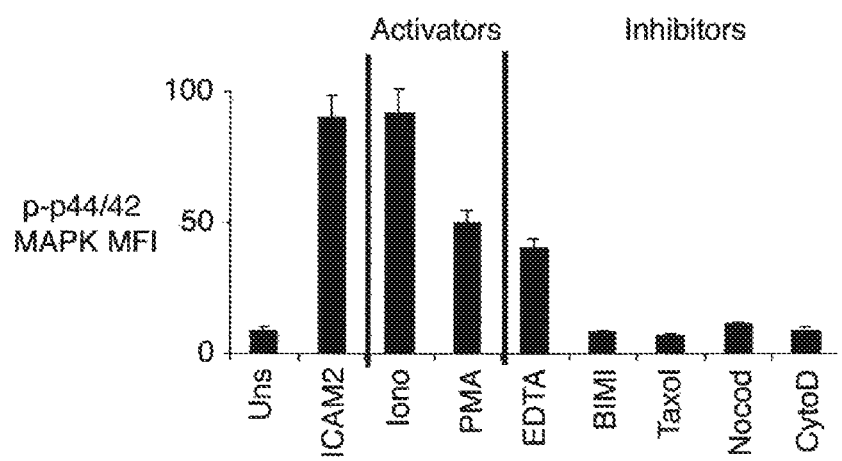
FIG._35D

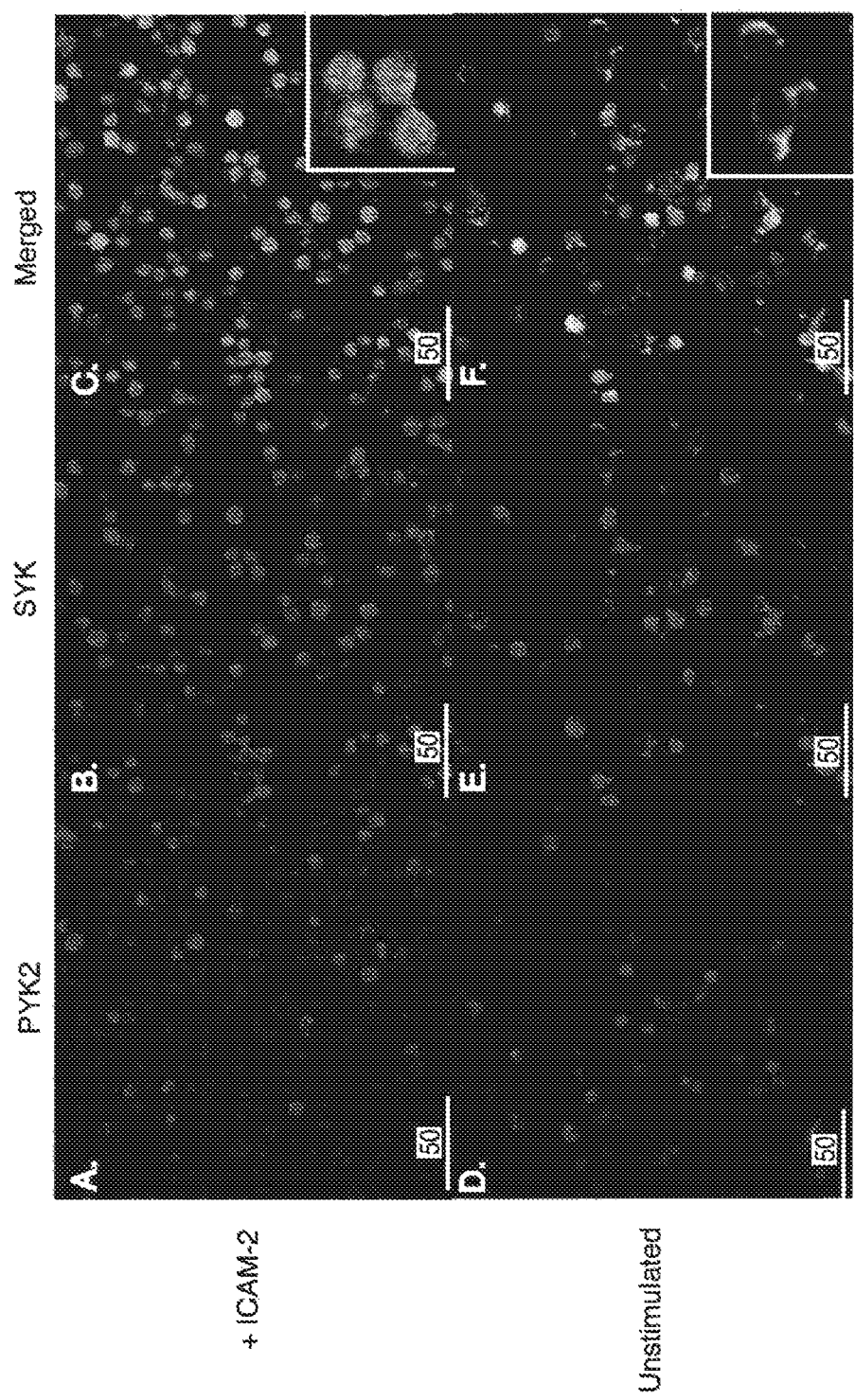
FIG._35E

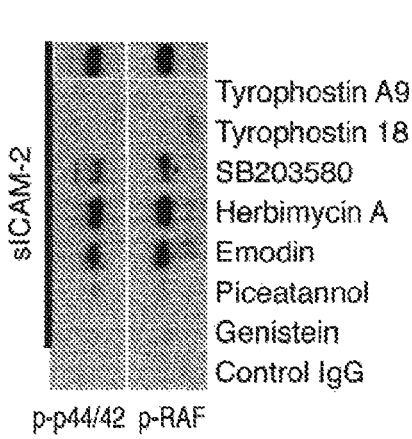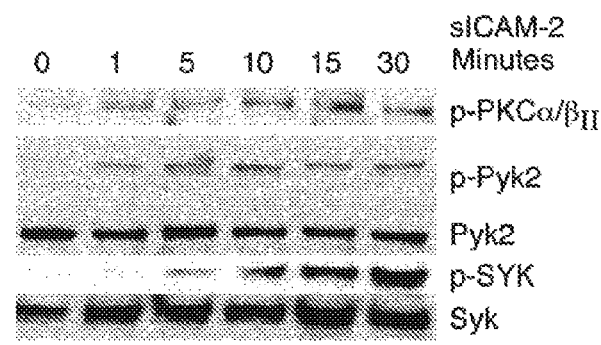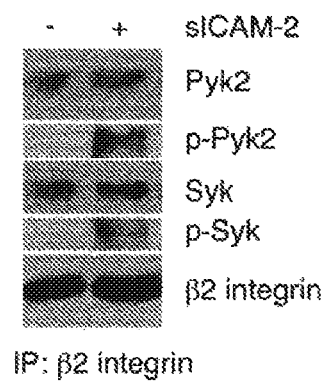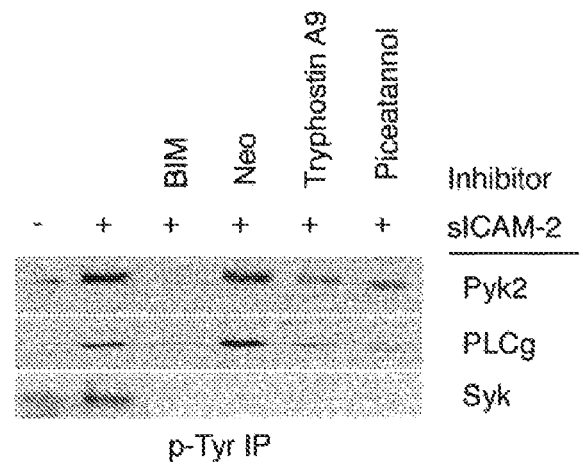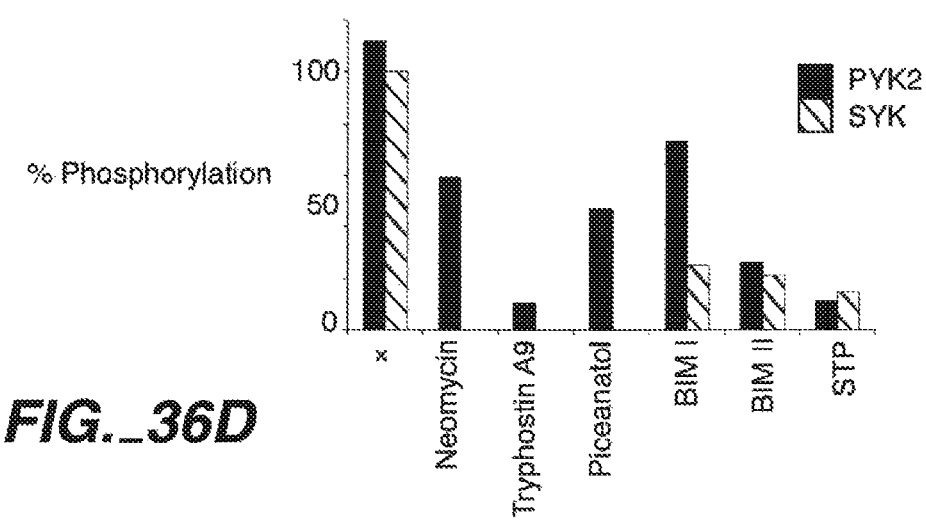
FIG._36A
FIG._36B
FIG._36C
FIG._36D
FIG._36E

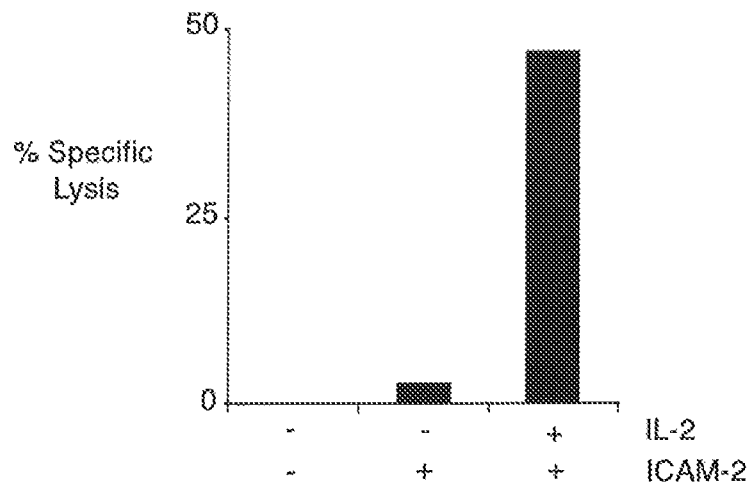
FIG._37A
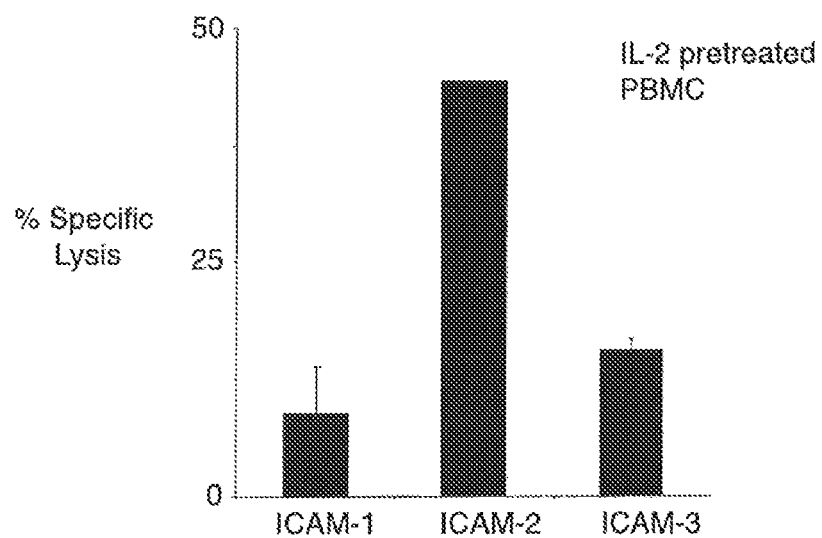
FIG._37B

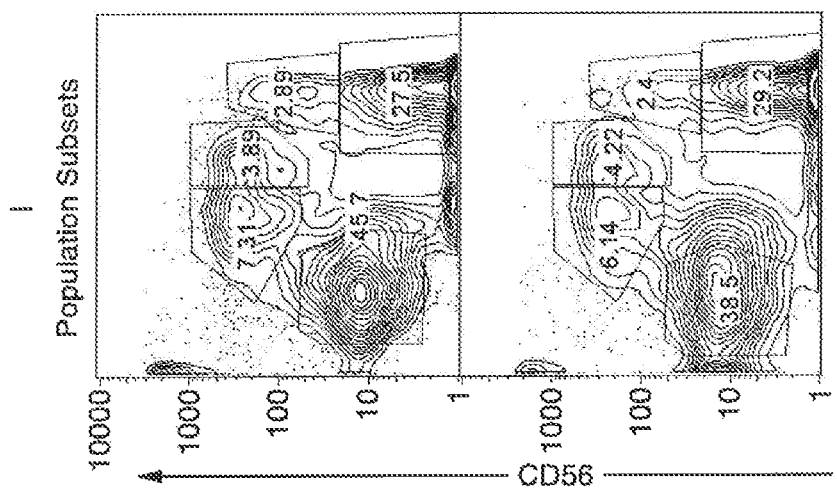
FIG._38A-1

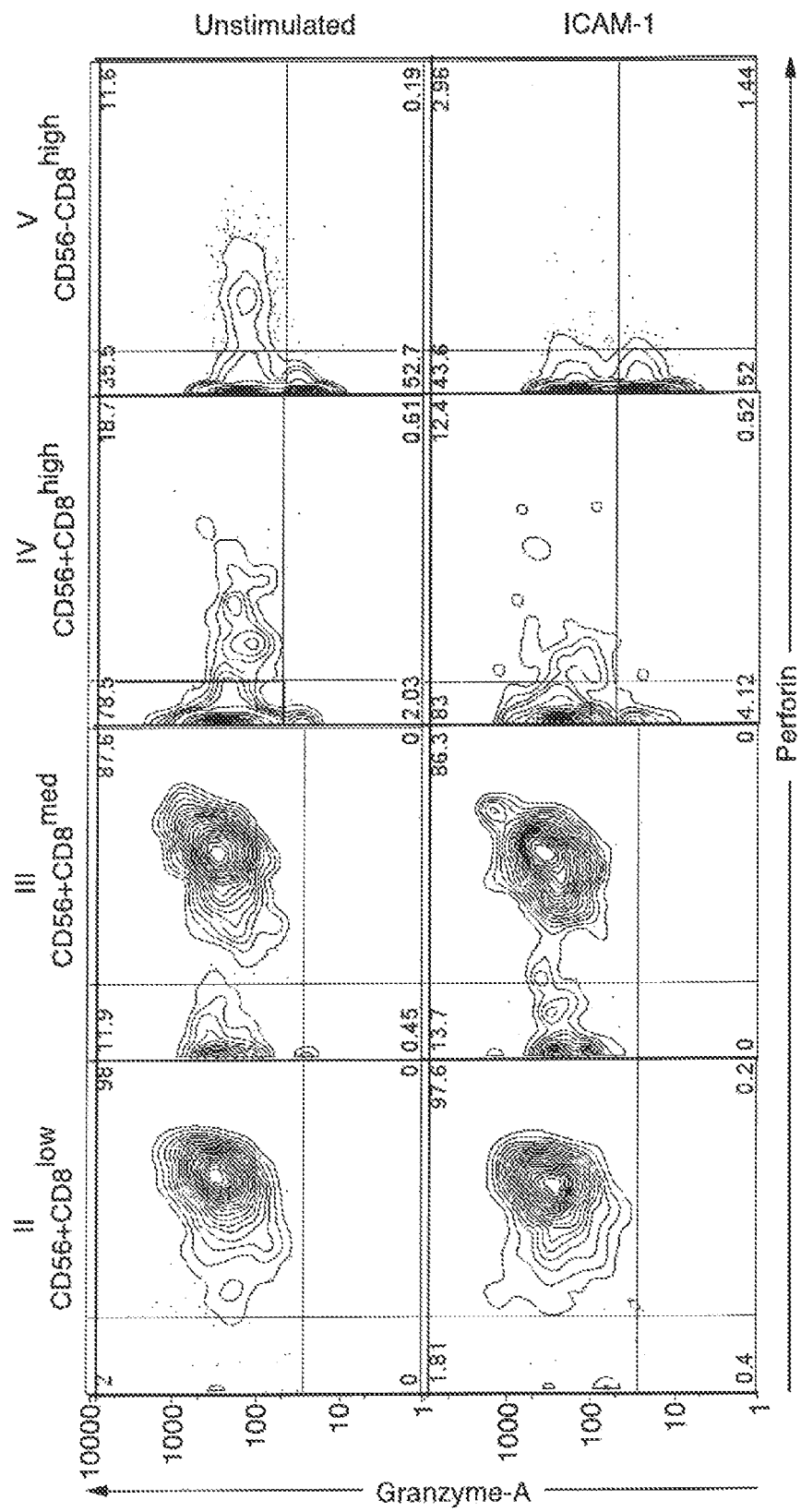
FIG._38-A2

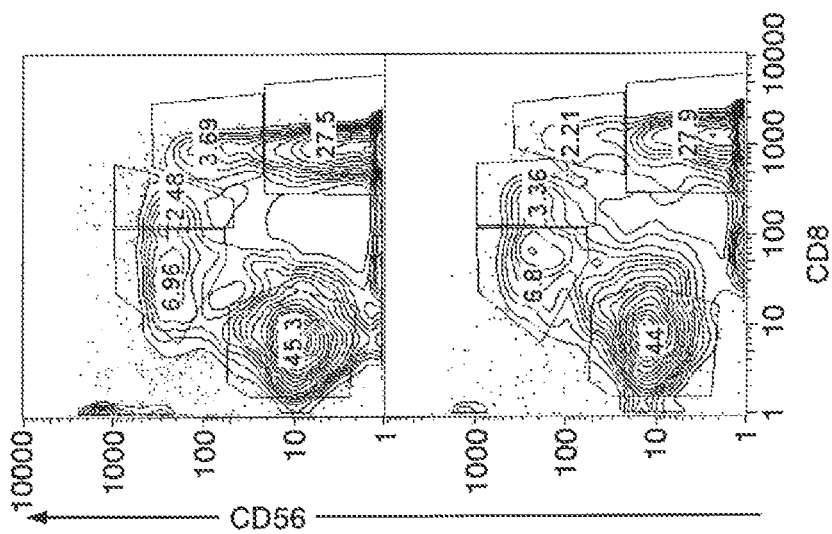
FIG._38A-3

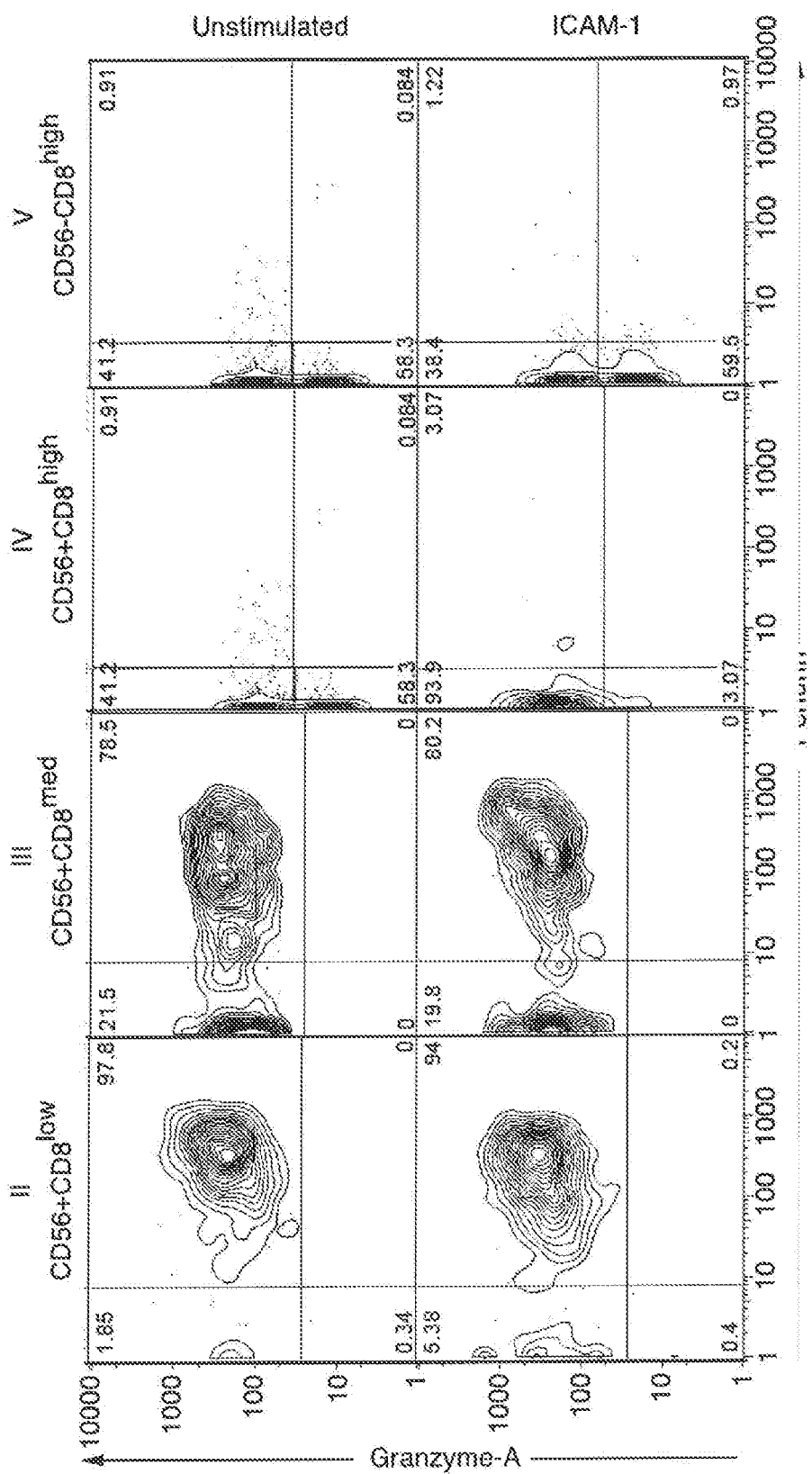
FIG._38-A4

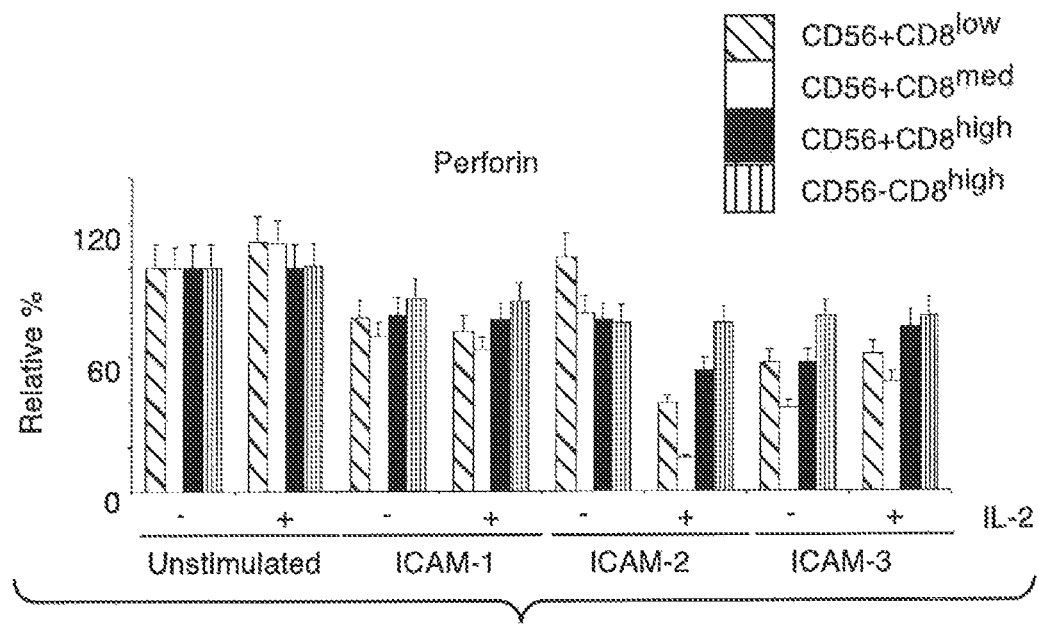
FIG._38B
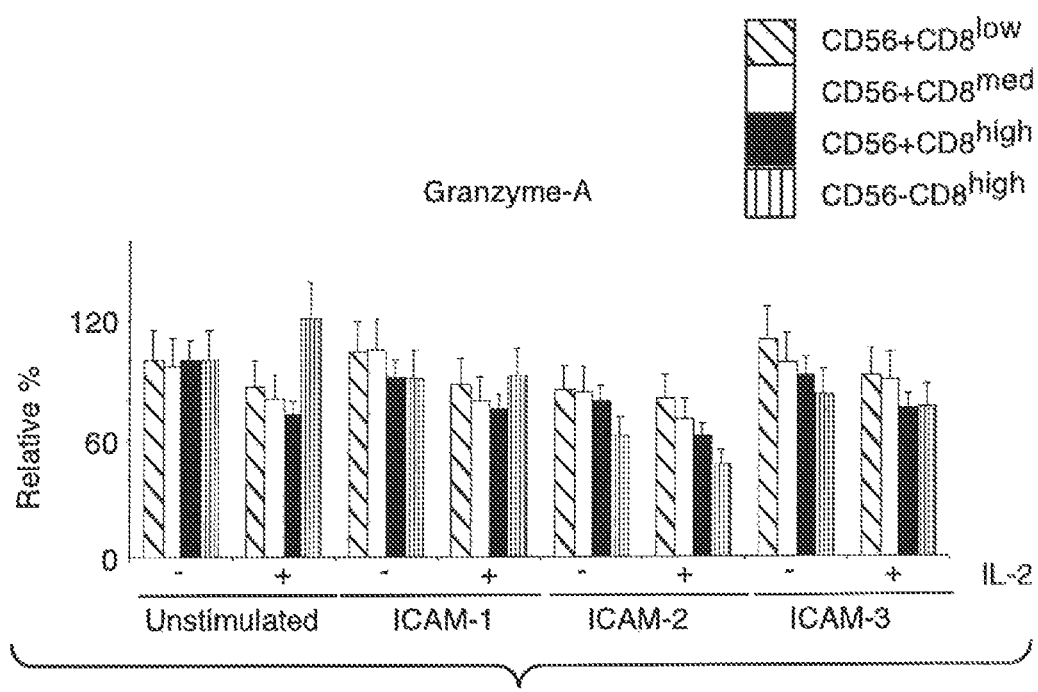
FIG._38C

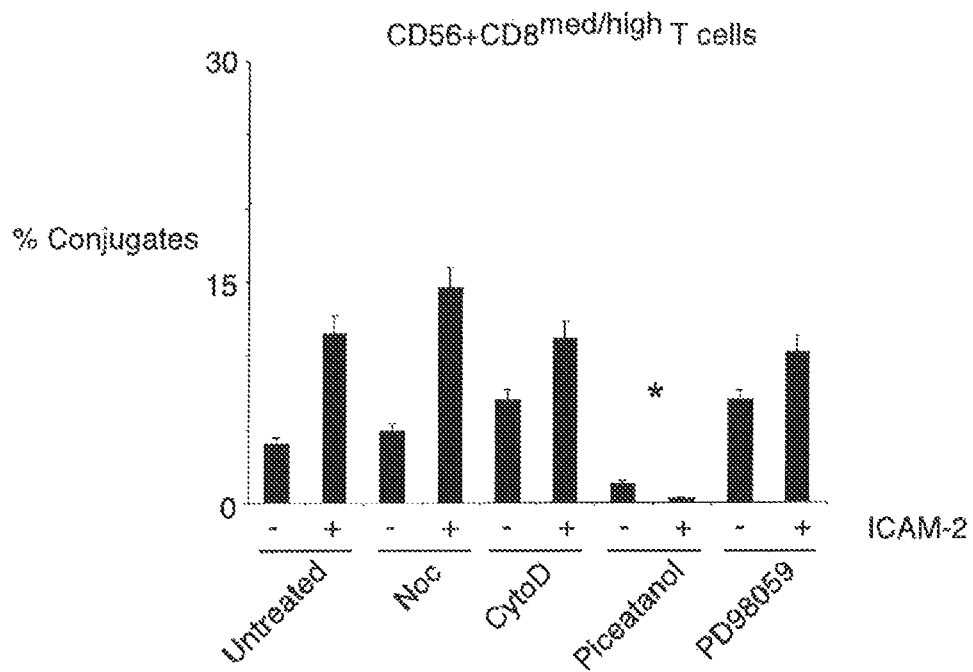
FIG._39A
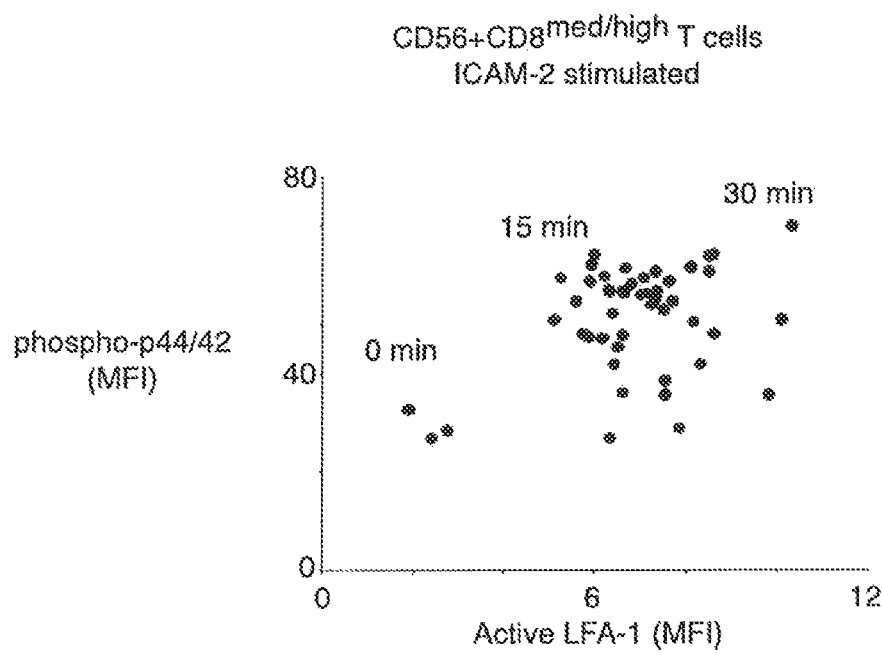
FIG._39B

METHODS AND COMPOSITIONS FOR DETECTING THE ACTIVATION STATE OF MULTIPLE PROTEINS IN SINGLE CELLS

This application is a divisional of U.S. application Ser. No. 12/372,670, filed Feb. 17, 2009, now U.S. Pat. No. 8,148,094, which is a continuation of U.S. application Ser. No. 10/193,462, filed Jul. 10, 2002, now U.S. Pat. No. 7,563,584, which claims the benefit of United States provisional applications Ser. No. 60/304,434, filed Jul. 10, 2001, and Ser. No. 60/310,141, filed Aug. 2, 2001, all of which are hereby incorporated by reference.

The invention was made with United States Government support under Grant Numbers AI039646, AR044565, AI035304, AR062227, and AI41520, awarded by the National Institutes of Health. The United States Government has certain rights in the invention.

FIELD OF THE INVENTION

The invention relates generally to the field of protein detection using flow cytometry. More specifically, the invention relates to simultaneously detecting the activation states of multiple proteins in single cells using flow cytometry and, more particularly, using polychromatic flow cytometry.

BACKGROUND OF THE INVENTION

Proteins are the major components of cells. The spatiotemporal expression pattern and the subcellular localization of proteins determines the shape, structure, and function of cells. Proteins are assembled from 20, different amino acids, each with a distinct side chain and chemical property. This provides for enormous variety in the chemical properties of proteins and the activities they exhibit.

In addition, many proteins are dynamically regulated such that their activity is altered in response to certain intrinsic or extrinsic cues. One form of regulation involves covalent modification of the regulated protein. An example of such a covalent modification is the substitution of a phosphate group for a hydroxyl group in the side chain of an amino acid (phosphorylation). Such modification is often associated with an alteration in the activity of a protein. Protein kinases can recognize specific protein substrates and catalyze the phosphorylation of serine, threonine, or tyrosine residues on their protein substrates. Such substrate proteins capable of being phosphorylated are referred to as phosphoproteins. Once phosphorylated, a substrate protein may have its phosphorylated residue converted back to a hydroxylated one by the action of a protein phosphatase which specifically recognizes the substrate protein. Protein phosphatases catalyze the replacement of phosphate groups by hydroxyl groups on serine, threonine, or tyrosine residues. Through the action of kinases and phosphatases a protein may be reversibly phosphorylated on a multiplicity of residues and its activity may be regulated thereby.

Many kinases and phosphatases are known and play important roles in signal transduction. Many kinases and phosphatases are phosphoproteins, the kinase and phosphatase activities of which are regulated by phosphorylation. The phosphorylation of kinases and phosphatases is often regulated by other or same type kinases and phosphatases. In this way, the regulators of signal transduction are themselves regulated as part of a signaling cascade.

Many intracellular kinases and phosphatases transduce signals in response to extracellular signals that stimulate receptors at the cell surface. As a result, extracellular signals induce changes in the phosphorylation and activation states of many proteins in receptive cells. For example, many mitogens induce JNK and MAPK signaling activity which causes cell to proliferate. As another example, neurotrophic factors have been shown to induce AKT signaling activity which supports neuronal survival. In addition, many diseases, such as cancer, are associated with an alteration in the activation state of many signaling proteins. In many instances, the signaling activity observed in cancer cells is reminiscent of growth factor stimulated signaling activity in non-cancer cells.

Some lipids of the cell membrane are also substrates for kinases. For example, phosphatidylinositol 3-kinase (PI3K) specifically recognizes phosphatidylinositol 4,5-diphosphate (PIP2) and catalyzes its phosphorylation at the 3' position of the inositol moiety. PIP2, is generated by the activity of another kinase, phosphatidylinositol 4-kinase which catalyzes phosphorylation of phosphatidylinositol at the 4' and 5' positions of the inositol moiety. PI3K regulates a variety of cellular functions and is activated by growth factors such as nerve growth factor (NGF), platelet derived growth factor (PDGF), insulin receptor substrate 1, (IRS-1) and CD28. Many of the proteins that activate PI3K also activate GTPases, predominantly the ras family, which in turn activate PI3K by binding to its p110, subunit. The direct pathway from tyrosine phosphorylated receptors to PI3K and activation of PI3K by GTPase proteins function synergistically. PI3K is a heterodimeric enzyme composed of a catalytic subunit (p110) and a regulatory subunit. Several genes encoding regulatory subunits of PI3K have been identified, including p85α and p85β. In addition, a number of splice variants of p85α are known (including p55α and p50α).

It is understood that kinase signaling cascades play an important role in nearly every critical decision process in cells (for review see Hunter, Cell 100:113-127, 2000). Determining the role of specific signal transduction pathways in a given system has been aided by the advent of pharmacological inhibitors for specific kinases. However, monitoring activities for such kinases, for example, protein kinase B/AKT, cJun-N-terminal kinase (JNK), p38, mitogen activated protein kinase (p38), p44/42, ERK1/2, (ERK), PKA, PKC or TYK2, or others, is usually dependent upon in vitro kinase assays or more recently by immunoblotting to determine the phosphorylation state of these proteins using phospho-specific antibodies. To date it has not been possible to correlate rare subpopulations of cells with the activation state of kinases in important signaling pathways.

Another form of protein regulation involves proteolytic cleavage of a peptide bond. While random or misdirected proteolytic cleavage may be detrimental to the activity of a protein, many proteins are activated by the action of proteases that recognize and cleave specific peptide bonds. Many proteins derive from precursor proteins, or pro-proteins, which give rise to a mature isoform of the protein following proteolytic cleavage of specific peptide bonds. Many growth factors are synthesized and processed in this manner, with a mature isoform of the protein typically possessing a biological activity not exhibited by the precursor form. Many enzymes are also synthesized and processed in this manner, with a mature isoform of the protein typically being enzymatically active, and the precursor form of the protein being enzymatically inactive. This type of regulation is apparently not reversible. Thus, to inhibit the activity of a proteolytically activated protein, mechanisms other than de-cleavage must be used. It is the case that many proteolytically activated proteins are relatively short lived proteins.

Among the enzymes that are proteolytically activated are the caspases. The caspases are an important class of proteases that mediate programmed cell death (referred to in the art as "apoptosis"). Caspases are constitutively present in most cells, residing in the cytosol as a single chain proenzyme. These are activated to fully functional proteases by a first proteolytic cleavage to divide the chain into large and small caspase subunits and a second cleavage to remove the N-terminal domain. The subunits assemble into a tetramer with two active sites (Green, Cell 94:695-698, 1998).

Antibodies are particularly useful for the study of proteins. Antibodies are a large family of glycoproteins that specifically bind antigens, and do so with a high affinity. Antibodies comprise a constant domain and a variable domain. The variable domain of an antibody binds to antigen. Polyclonal antibodies comprise a multiplicity of variable region types. Monoclonal antibodies comprise a single type of variable region, and are thus more likely to specifically bind to fewer proteins. Monoclonal and polyclonal antibodies are routinely generated by means known in the art, and have been raised against many known proteins for use in both research and therapy. Antibodies may be used to determine the presence of antigens or proteins to which they specifically bind. Well known immunochemical methods that employ this approach include Western blotting, immunoprecipitation, and enzyme linked immunoassay (ELISA).

In particular, antibodies may be used to determine the presence of a specific isoform of a protein, especially, when the isoform possesses an antigen not present in other isoforms of the protein, or when the isoform lacks an antigen not present in other isoforms of the protein. Thus, the isoform can be antigenically distinct from other isoforms of the same protein. The antigenically distinct isoform may uniquely possess or lack a covalently attached moiety, or may be in a conformation distinct from other isoforms and thereby present the same amino acid sequence in an antigenically distinguishable way.

For example, the determination of PI3K activity has typically involved immunoprecipitation of PI3K and an in vitro enzymatic assay using phospholipids and labeled ATP. Recently, antibodies that specifically bind to phosphatidylinositol 4,5-diphosphate and phosphatidylinositol 3,4,5-triphosphate have been developed (Molecular Probes, A-21327, anti-phosphatidylinositol 4,5-diphosphate, mouse IgM monoclonal 2C11; A-21328, anti-phosphatidylinositol 3,4,5-triphosphate, mouse IgM monoclonal RC6F8). These antibodies serve as useful tools for the detection of PI3K substrate (PIP2) and product (PIP3), and can be used to determine the activity of PI3K.

Biochemical investigations of protein expression and function have traditionally focused on one or a few proteins at a time. This has largely been due to limitations imposed by the available investigative techniques. It is well understood that a cell's normal and abnormal physiology is the product of a large number of proteins participating in a large number of molecular interactions. For the purposes of designing treatments and cures, an understanding of the mechanisms underlying disease is desired. Such an understanding requires consideration of multiple proteins and their molecular interactions over time. In this regard, one important experimental hurdle is how to analyze large numbers of proteins in a single experiment, for example to determine a protein expression profile and, more specifically, active protein profiling for a single protein sample, or even for a single cell.

In addition to qualitative measurements of protein expression in cells, quantitative measures of protein expression are desirable. It is well known that many proteins can function differently at different expression levels, and such differences in protein function can lead to differences in cell physiology.

It is highly desirable to determine expression levels of particular isoforms of proteins in a sample, given that different isoforms of a protein can have different activities. For example, proteins involved in signal transduction can often exist in two or more forms, and it is usually a particular form of the signaling protein that transmits a signal that mediates the effects of a signaling pathway. Conversion from one form to another is often used to turn a signal on or off through a change in protein activity.

In addition, in order to study protein expression and function, it is often necessary to immobilize proteins on a solid support. In Western blot analysis, proteins of interest are first separated by electrophoresis and then transferred and immobilized onto a nitrocellulose or a polyvinylidene difluoride (PVDF) membrane. In the phage display screening of a protein expression library, several hundred thousand proteins expressed by phages are immobilized on membranes. In both Western blotting and phage display screening, proteins are immobilized non-covalently. The protein of interest is then selected by its unique property, i.e., interaction with an antibody. In some other applications such as immunoprecipitation and affinity purification, agents (e.g., antibodies, ligands) are covalently conjugated onto solid supports (e.g., agarose beads) through their primary amines, sulfhydryls or other reactive groups. In general, proteins retain their abilities of interacting with other proteins or ligands after immobilization. However, even with the immobilization of a multiplicity of proteins from a sample, the problems of simultaneous detection of protein expression, protein form, and protein level for a multiplicity of proteins remains.

Thus, an object of the present invention is to overcome the problems described above. Accordingly, the present invention provides an approach for the simultaneous determination of the activation states of a plurality of proteins in single cells. This approach permits the rapid detection of heterogeneity in a complex cell population based on protein activation states, and the identification of cellular subsets that exhibit correlated changes in protein activation within the cell population. Moreover, this approach allows the correlation of cellular activities or properties, such as surface molecule expression or cell granularity, with protein activation at the single cell level.

SUMMARY OF THE INVENTION

In accordance with the above objects, the present invention provides methods and compositions for simultaneously detecting the activation state of a plurality of activatable proteins in single cells using flow cytometry. The invention further provides methods and compositions of screening for bioactive agents capable of coordinately modulating the activity or activation state of a plurality of activatable proteins in single cells. The methods and compositions can be used to determine the protein activation profile of a cell for predicting or diagnosing a disease state, and for monitoring treatment of a disease state. Further, the methods and compositions of the present invention can be used optionally to sequentially detect the activation state of a plurality of activatable proteins in single cells. In addition, the methods and compositions of the present invention can be used optionally detect the activation state of a single protein or modulate the activity or activation state of a single protein.

The invention provides populations of cells, single cells, cell lysates, proteins, and samples comprising populations of cells, single cells, cell lysates, proteins useful in the methods of the present invention. In particular, the invention provides activatable proteins and activation state-specific antibodies that bind to a specific isoform of an activatable protein. In one aspect, the activation state-specific antibodies are conjugated to a label, preferably a fluorescent label, and more preferably a FRET label.

In one aspect, the invention provides methods of detecting the activation state of at least a first and a second activatable protein in single cells, the method comprising the steps of: a) providing a population of cells comprising the first and the second activatable proteins; b) contacting the population of cells with a plurality of activation state-specific antibodies, wherein the plurality of activation state-specific antibodies comprise: i) at least one first activation state-specific antibody that is capable of binding to a corresponding isoform of the first activatable protein in the population of cells; and ii) at least one second activation state-specific antibody that is capable of binding to a corresponding isoform of the second activatable protein in the population of cells; and c) using flow cytometry to detect the binding of the first and second activation state-specific antibodies in single cells of the population of cells, wherein the binding of the first activation state-specific antibody is indicative of a specific activation state of the first activatable protein, and the binding of the second activation state-specific antibody is indicative of a specific activation state of the second activatable protein.

In a further aspect, the first activatable protein is a kinase. Also in a further aspect, the first activatable protein is a caspase.

In a further aspect, the first activatable protein is a first kinase and the second activatable protein is a second kinase. Also in a further aspect, the isoform of the first kinase is a first phosphorylated kinase, and the isoform of the second kinase is a second phosphorylated kinase. In another aspect, the first activation site-specific antibody binds to the first phosphorylated kinase, and the second activation site-specific antibody binds the second phorphorylated kinase.

In a further aspect, the first activatable protein is a first caspase and the second activatable protein is a second caspase. Also in a further aspect, the isoform of the first caspase is a cleaved product of a first pro-caspase, and the isoform of the second caspase is a cleaved product of a second pro-caspase. In another aspect, the plurality of activation site-specific antibodies comprise a first activation site-specific antibody that binds to the isoform of the first caspase, and a second activation site-specific antibody that binds to the isoform of the second caspase.

In another aspect, the invention provides methods of detecting the activation state of at least a first activatable protein in single cells, the method comprising the steps of: a) providing a population of cells comprising at least the first activatable protein; b) contacting the population of cells with a plurality of substrates; wherein the plurality of substrates comprise at least a first substrate that is capable of being modified by a corresponding isoform of the first activatable protein in the population of cells; and c) using flow cytometry to detect the modification of the first substrate in single cells of the population of cells, wherein the modification is indicative of a specific activation state of the first activatable protein.

In a further aspect, the population of cells further comprises a second activatable protein; the plurality of substrates further comprise a second substrate that is capable of being modified by a corresponding isoform of the second activatable protein in the population of cells; and step c) further comprises using the flow cytometry to detect the modification of the second substrate in single cells of the population of cells, wherein the modification of the second substrate is indicative of a specific activation state of the second activatable protein.

In another aspect, the invention provides methods of detecting a protein activation state profile of single cells based on the activation state of at least a first activatable protein in the cells, the method comprising the steps of: a) providing a population of cells comprising at least the first activatable protein; b) contacting the population of cells with a plurality of substrates; wherein the plurality of substrates comprise at least a first substrate that is capable of being modified by a corresponding isoform of the first activatable protein in the population of cells; c) contacting the population of cells with a plurality of activation state-specific antibodies, wherein the activation state-specific antibodies comprise at least one first activation state-specific antibody that is capable of binding to a corresponding isoform of the first activatable protein in the population of cells; and d) using flow cytometry to simultaneously detect: i) the binding of the first activation state-specific antibody in single cells of the population of cells, wherein the binding of the first activation state-specific antibody is indicative of a specific activation, state of the first activatable protein; and ii) the modification of the first substrate the single cells, wherein the modification is indicative of the specific activation state of the first activatable protein.

In a further aspect, the population of cells further comprises a second activatable protein; the plurality of substrates further comprises a second substrate that is capable of being modified by a corresponding isoform of the second activatable protein in the population of cells; and step d) further comprises using the flow cytometry to detect the modification of the second substrate in the single cells, wherein the modification is indicative of a specific activation state of the second activatable protein.

In a further aspect, the plurality of activation state-specific antibodies further comprises a second activation state-specific antibody that is capable of binding to a corresponding isoform of the second activatable protein in the population of cells, and step c) further comprises using the flow cytometry to detect the binding of the second activation state-specific antibody the single cells of the population of cells, wherein the binding of the second activation state-specific antibody is indicative of the specific activation state of the second activatable protein.

In another aspect, the invention provides methods of screening for a bioactive agent capable of modulating the activity of at least a first activatable protein in cells, the method comprising: a) providing a population of cells, each of the cells comprising at least the a first activable protein, a second activatable protein, and a third activatable protein, wherein the first activable protein can activate the second activatable protein thereby forming a specific isoform of the second activable protein (isoform-2), and wherein the second activable protein can activate the third activatable protein thereby forming a specific isoform of the third activatable protein (isoform-3); b) contacting the cells with a second activation state-specific antibody, a third activation state-specific antibody, and a candidate bioactive agent, wherein the second activation state-specific antibody is capable of binding to the isoform-2, and wherein the third activation state-specific antibody is capable of binding to the isoform-3; c) using fluorescent activated cell sorting (FACS) to sort single cells of the population of cells based on the presence of the isoform-2, and the isoform-3; and d) determining the ratio of the isoform-2, to the isoform-3, in the single cells in the presence and absence of the candidate bioactive agent, wherein a difference in the ratio of the isoform-2, to the isoform-3, in the presence and absence of the candidate bioactive agent is indicative of the ability of the candidate bioactive agent to modify the activity of the first activable protein.

In a further aspect, the first activatable protein is activated by an activating agent.

In a further aspect, the first activatable protein is a caspase. In another aspect, the first activatable protein is a kinase; in an additional aspect, the kinase is PI3K; and in a further aspect the PI3K is activated by a growth factor or by activation of a cell surface receptor.

In a further aspect, the kinase is PI3K; the second activatable protein is PIP2; the third activatable protein is PIP3; the isoform-2, is PIP 4,5, bisphosphate; and the isoform-3, is PIP 3,4,5.

In a further aspect, the first activatable protein is ICAM-2; the activity is apoptosis; the second activatable lipid is PIP2; the third activatable protein is PIP3; the isoform-2, is PIP 4,5 bisphosphate; and the isoform-3, is PIP 3,4,5. In a further aspect step a) further comprises clustering the ICAM-2, ICAM-3, or ICAM-1.

In a further aspect, the plurality of activation state-specific antibodies comprise at least one antibody selected from a group of antibodies consisting of: anti-AKT-phospho-Ser473, anti-AKT phospho-Thr308, anti-p44/42, MAPK phospho-Thr202/Tyr204, anti-TYK2, phospho-Tyr1054/1055, anti-p38, MAPK phospho-Thr180/Tyr182, anti-JNK/SAPK phospho-Thr183/Tyr185, anti-phospho-tyrosine, anti-phospho-threonine, anti-PIP2, and anti-PIP3.

In a further aspect, of the step a) further comprises contacting the population of cells with an agent that induces the activation of at least the first activatable protein.

In a further aspect, step a) further comprises contacting the population of cells with an agent that induces the activation of at least one of the first and the second activatable proteins.

The method according to any of claims 15-22, wherein step a) further comprises contacting the population of cells with an agent that induces the activation of at least one of the first, the second, and the third activatable proteins.

In a further aspect, the methods further comprises sorting the single cells based on the activation state of the first activatable protein, and the activation state of the second activatable protein.

In a further aspect, the first activation state-specific antibody comprises a first label, wherein the second activation state-specific antibody comprises a second fluorescent label and, wherein the sorting is by fluorescent activated cell sorting (FACS).

In a further aspect, the first activation state-specific antibody comprises a first FRET label; the second activation state-specific antibody comprises a second FRET label and the sorting is by fluorescent activated cell sorting (FACS).

In a further aspect, the first activation state-specific antibody comprises a FRET label; the second activation state-specific antibody comprises a label; and the sorting is by fluorescent activated cell sorting (FACS).

In a further aspect, step a) further comprises fixing the cells.

In a further aspect, the cells are mammalian cells.

BRIEF DESCRIPTION OF THE DRAWINGS

FIG. 1 depicts the results of experiments demonstrating that phospho-specific antibodies correlate with kinase activity. A) Phospho specific antibodies for i) p44/42, ii) p38, iii) JNK/SAPK, iv) AKTser473/AKTthr308, v) TYK2, vi) PKA-substrate, and vii) PKC-PAN substrate were tested for phospho-specificity by specific kinase inducing and inhibitory conditions. The inducing conditions for kinase are shown as well as specific inhibitor(s) of the pathway. The ability of the kinase to have activity upon a known substrate is shown beneath each phospho-western set. Non-phospho specific antibodies for AKT, p38, SAPK/JNK, p44/42, MAPK, and TYK2, reflect total kinase present. Kinase activity was determined under conditions found to elicit phosphorylation of respective kinase and correlated with the phosphorylated state of the kinase as detected by phospho-specific antibodies. Given the nature of the phospho-PKA substrate and phospho-PKC-PAN substrate antibodies, direct kinase activities could not be measured. Conditions used determined a general activation of PKC and PKA, since both antibodies recognize multiple PKC and PKA target proteins in the phosphorylated form of their respective kinase substrate recognition motif. Immunoblots/kinase assays for AKT, p44/42, p38, and JNK kinases were performed in NIH3T3, and data for TYK2, PKC, and PKA were performed in Jurkat cells (see Material and Methods for elaboration on treatment conditions).

Figure 4B:
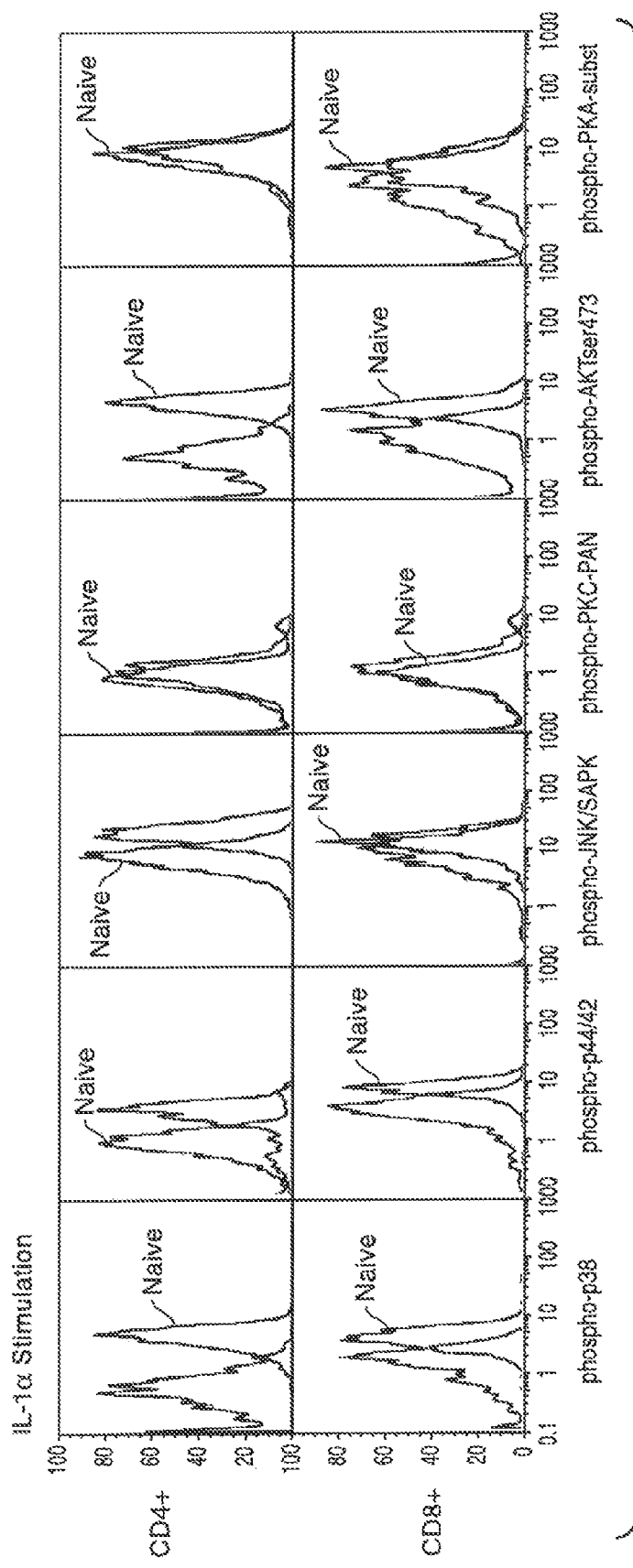

B) Jurkat cells were treated with a kinase inducing agent (induced), or kinase inhibitor (inhibited) before induction conditions as diagrammed in Table 2. Cells were prepared for intracellular FACS staining and analyzed for kinase activities noted in the figures by log fluorescence of phospho-specific antibody-fluorophore conjugate. Plot overlays illustrate shifts respective of either increased or decreased kinase activity. The bottom right panel represents a dose response curve of EGF treatment as measured by phospho-ERK activity (0.001, 0.01, 0.1, 1.0, 10 µg/ml). The inhibitors and activators used were the following: p44/42, (ERK1/2), was activated with epidermal growth factor (EGF) and inhibited with MEK1/2, inhibitor U0126[21-23]*; AKT activation was achieved by addition of growth media and platelet derived growth factor and inhibited by incubation with PI3K kinase inhibitor LY294002[20]*; JNK was activated by anisomycin[29]* and inhibited by staurosporine; p38, MAPK was activated by anisomycin[29]* and inhibited with compound SB203580[24,29]*; PKA was activated by phorbal 12, myristalated 13-acetate (PMA) and phospho detection was made possible by incubation with protein phosphatase inhibitor calyculin A[25]*; PKC was activated by ionomycin (10) and inhibited using bisindolymaleimide II[26,27]*; TYK2 activity was induced by interferon γ (IFNγ) and inhibited using the general tyrosine kinase inhibitor genistein[26,3]*. *See the corresponding reference number and cite in Example 1, under "References."

C) TYK2, PKA and PKC substrate probes are phospho specific. Treatment of stimulated samples (stated above) with lambda phosphatase prior to intracellular staining decreased detection by phospho-TYK2, and phospho-PKA substrate probes. Treatment of cells with calf intestinal phosphatase in addition to lambda phosphatase was required for decreased detection of phosphorylated PKC substrates.

D) Phosphorylation of p44/42, correlates with mean fluorescent intensity as measured by flow cytometry. Semiquantitative analysis of p44/42, phosphorylation as measured by both phospho specific detection and mean fluorescence intensity (MFI) by phospho-p44/42, kinase probe. Jurkat cells were subjected to a dose response curve of EGF at the indicated concentrations for 30, minutes, and assessed for p44/42, phosphorylation by both immunoblotting with phospho-specific antibodies and flow cytometry with developed p44/42, kinase probe. Y error bars are standard deviation for MFI values. X error bars are standard deviation for percent phosphorylated relative to unstimulated control. Values displayed are representative of 3 independent experiments. Error bars not visible are concealed by data point.

FIG. 2 depicts the results of experiments demonstrating that multi-dimensional analysis provides insights into signaling networks as induced by differing stimuli.

A) Differential kinase activity within CD4+, and CD19+, lymphocyte subsets. PBMC were treated with the indicated stimulus for 1, hour and prepared for intracellular kinase phosphorylation status determination by flow cytometry. Both hyper and hypo responses can be observed with respect to p44/42, activity in CD4+, upon different stimuli.

B) T cell activation measured by CD69, presents differential p44/42, kinase activity to CD3/CD28 and PMA/ionomycin stimulation. The stimulation conditions are shown in the Figure.

C) Multiple kinase activities measured in artificial T cell stimulation. Jurkat cells in growth media and PMA/ionomycin (IO) treated were prepared for intracellular kinase phosphorylation status determination by flow cytometry. CD69, expression serves to indicate T cell activation. X-axis corresponds to log fluorescence values, Y-axis corresponds relative cell number.

D) Phosphorylation of p38, as a function of cell granularity. Simultaneous measurement of phosphorylated and non-phosphorylated p38, exemplifies a shift from non-phosphorylated to phosphorylated p38, as cell granularity increases (indicated by the open bar in the side scatter parameter).

E) 3-parameter analysis of p44/42, and p38, kinase activity as a function of JNK activity illustrate potential mapping of signaling crosstalk. PBMC were treated with IL-1α. JNK, p44/42, and p38 activity was simultaneously measured by flow cytometry. Open bar in phospho-JNK/SAPK plot indicates intensity of JNK activation.

F) 5-parameter analysis of AKT, p38, PKA, and p44/42, activity as a function of TYK2, activity in IL-1β treated PBMC. At initiation of TYK2, activity, all 4, kinase activities are not detectable. Synchronous activation of p38, p44/42, and AKT activity is observed at a greater level of TYK2 activity. PKA activity is observed at a greater level of p38, and p44/42, activity.

FIG. 3 shows a flow diagram of resting T cell isolation, preparation, and analysis by polychromatic flow cytometry (11-color, 13, parameter).

A) Isolation of lymphocytes was achieved by a Ficoll-plaque gradient and depleted for adherent cells. Flow cytometry plots illustrate typical lymphocyte gate and presence of CD3- populations. Magnetically activated cell sorting eliminated activated T cells, NK cells, remaining macrophages, and B cells, enriching for resting T cells. The enriched population was assessed prior to stimulation to ensure presence of CD4+and CD8+cells. Stimulation to IL-1α, IL-1β, or IL-2, was performed and cells were prepared for flow cytometry using stains depicted in Table 1. Occasionally, downregulation of some surface markers was observed to certain stimuli and is presented by receptor downregulation of key molecules, namely CD3, CD4, CD8, (apparent when comparing flow cytometry plots of these markers prior to stimulus treatment). B) An example of memory and naive gating by 5, differentiation markers is depicted for both CD4+(3B-1, 3B-2) and CD8+(3B-3, 3B-4) T cells. Appropriate placement of CD45RA gate was done according to De Rosa et al and was carried out separately for CD4+and CD8+populations. After identification of naive and memory cells by multiple-gating according to differentiation markers, intracellular kinase activity was determined. Kinase profiles are plotted against CD11a markers, although they are gated for all naive and memory markers. Assessment of multiple kinase activities was made possible by combining two 11-color experiments.

Figure 4C:
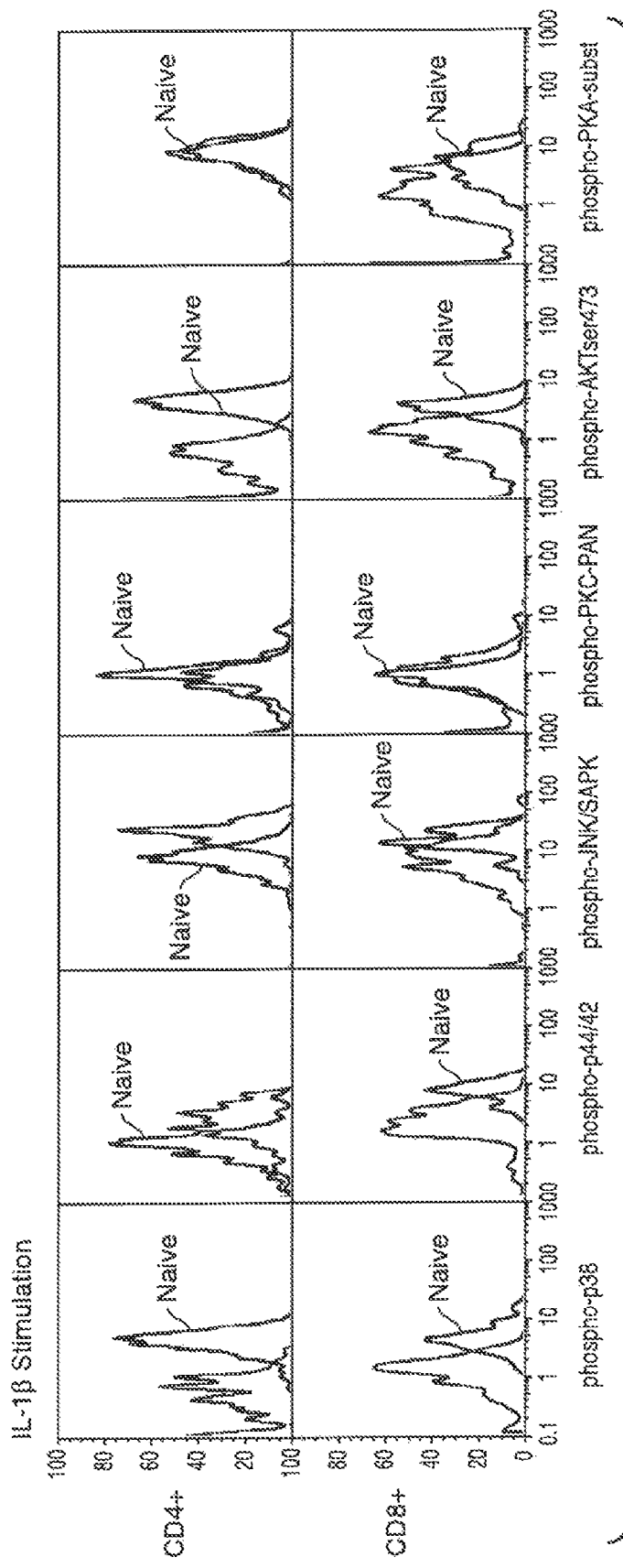

FIG. 4 depicts the results of experiments demonstrating that signaling profiles are readily discernible in particular lymphocyte subsets using polychromatic flow cytometry.

Naive and memory T cell kinase profiles are overlayed for direct comparison: A) Unstimulated; B) IL-1α, stimulated; C) IL-1β stimulated; and D) IL-2, stimulated. Mechanisms involving threshold dependent kinase activation can be observed when kinase phosphorylation approaches but does not exceed Log 10 fluorescence intensity (value defined from inhibitor/inducer experiments FIG. 2) in CD8+naive cells. Hyporesponses can be seen for IL-1αCD4+naive cells.

Figure 5:
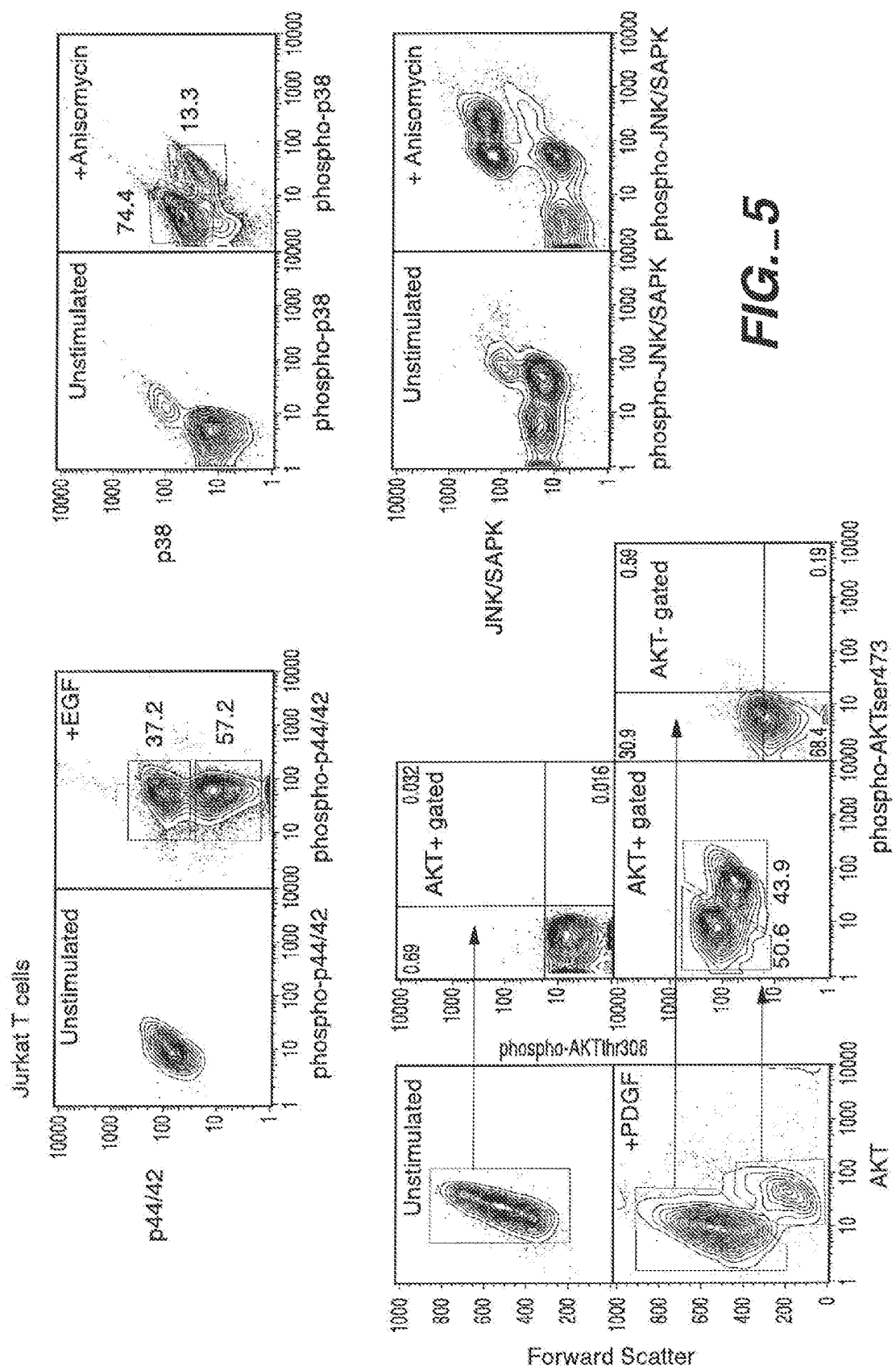

FIG. 5 depicts the results of experiments monitoring intensities of both active and non-active kinases by flow cytometry Phospho and non-phospho-specific probes for p44/42, p38, AKT, TYK2, and JNK detect respective kinase in its native state. Jurkat cells were treated to the following: AKT activity stimulated with PDGF, MAPK activity stimulated with EGF, p38, and JNK activity stimulated with anisomycin—for 10, minutes to induce initial activation of respective kinase with inducers as per the concentrations stated in Table 2. Phospho-p44/42, phospho-p38, phospho-AKTser473, and phosphoAKTthr308, and phospho-JNK/SAPK detected distinct populations upon a given stimulus in respect to their non-phospho specific counterparts. AKT positive cells were gated and plotted against AKTser473—and AKTthr308, phosphorylation plot as denoted in panel. Unstimulated cells for all non-phospho specific kinases are appropriately displayed for comparison.

FIG. 6 depicts the results of experiments demonstrating that LFA-1, stimulus induces JAB1, and Cytohesin-1, release and phosphorylation in human naïve CD4+, T cells. A) Phospho-cJun immunoblot of nuclear extracts from cells stimulated with CD3, CD28, and sICAM-2, (5, μg/ml, 30 min). B) Single cell analysis of phospho-cJun(S63) in α-JAB1, IgG transfected and untransfected cells. The median fluorescence intensity is plotted±SD. C) Confocal of JAB1, and cytohesin-1, in unstimulated (panel A-C), LFA-1, stimulated (sICAM-2 5, μg/ml) (panel D-F), and α-JAB1 transfected cells (G-I). Panels G-I were not stained with α-JAB1, antibody. D) Immunoprecipitates of JAB1, and Cytohesin-1, from unstimulated, sICAM-2, and CD3, (5, μg/ml, 30, min) stimulated cells were immunostained for phospho-serine and phospho-threonine and subsequently stripped and stained for α-JAB1, and α-cytohesin-1, respectively. E) Flow cytometric detection of phospho-p44/42(T202/Y204) in IgG, a-JAB1, α-cytohesin-1, N-terminal, α-cytohesin-1, C-terminal, and C-terminal cytohesin-1, peptide transfected cells stimulated with sICAM-2, (5, μg/ml, 30, min).

F) depicts the results of experiments demonstrating: A) Kinetic analyses of CD3, CD28, and LFA-1, stimulus of phospho-p38(T180/Y182), phospho-AKT(S473), phospho-Lck(S158), phospho-mek1/2(S217/221), phospho-elk(S38) by flow cytometry. We observed phospho-AKT, phospho-p38, and phospho-mek1/2, to be induced by CD28, stimulation to a greater extent than CD3, or LFA-1, stimulus. These reports are consistent with recent findings suggesting the activation of these pathways by CD28, stimulation (Kane et al., 2001; Li et al., 2001). We noted that phospho-lck was induced over time in the LFA-1, stimulus differentially with respect to CD3 and CD28, stimulation. Phosphorylation of elk-1, was imparted by CD3, and CD28, stimulation, and to a lesser degree by LFA-1, stimulus.

FIG. 7 depicts the results of experiments demonstratin CD3/CD28/LFA-1, signaling in human naïve T cells by phospho-protein antibody array. A) Differential phospho-protein profile of CD3/CD28/LFA-1, vs. C3/CD28, stimulated naïve CD4+, T cells. Ratios of the fluorescent phospho-protein array were calculated from the following equation where MFI equals mean fluorescent intensity: Log, (see Materials and Methods). Fold-phosphorylation is depicted by the fluorescence intensity scale where green corresponds to high and red corresponds to low. B) Cell cycle analysis of CD4+, T cells stimulated with CD3, CD28, and sICAM-2. Cells in G0, G1, S+G2/M phases of the cell cycle were determined using double staining for expression of Ki-67 and DNA content. Low Ki-67− signals were considered cells in G0, Ki-67+, signals with 2n DNA were considered cells in G1, and Ki-67+, signals with 2n DNA were considered to be in S or G2/M.

Figure 8A:
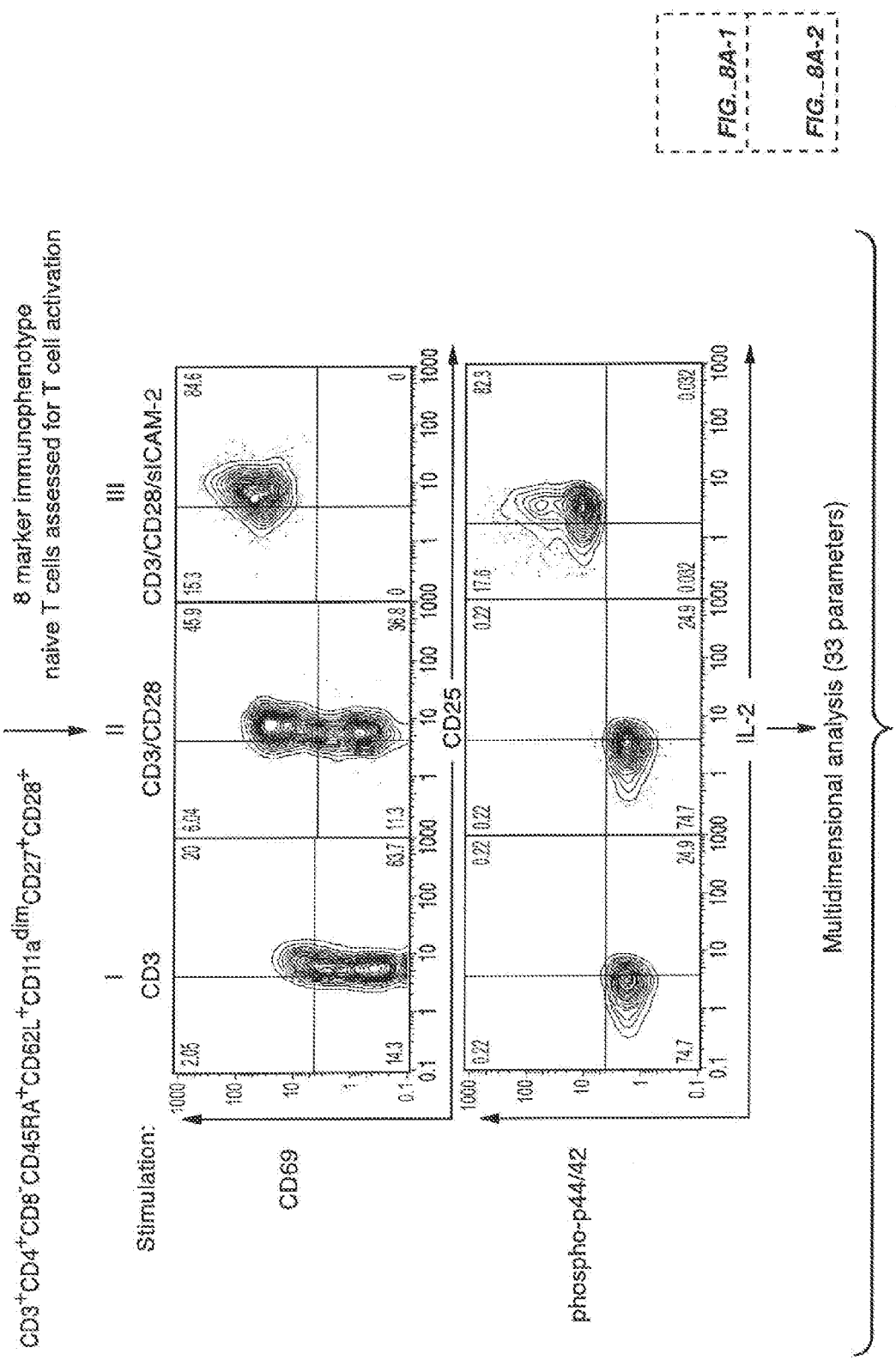

FIG. 8 A-1 )shows a flow diagram depicting multidimensional analysis of naive CD4+T cells. A-2) Magnetic cell sorting, 13-parameter flow cytometry, transcription factor profiling, and cytokine bead arrays were multiplexed to determine stimulations effect on immunophenotyped naive human CD4+T cells (CD3$^+$, CD4$^+$, CD8$^-$CD45RA$^+$, CD62L$^+$, CD11a$^{dim}$CD27$^+$, CD28$^+$, ). Intracellular levels of cytokines and phospho-proteins were correlated with surface phenotypes/activation markers as indicated in figure. B) demonstrates that the cells are naive gated CD4+T cells (as indicated by 5, differentiation markers) for individual stimulations of sICAM-2, and CD28, as well as the CD31/sCAM-2 combination. C) CD25, expression post 24, and 48, hr stimulus (as indicated, 10, μg/ml).

FIG. 9 depicts the results of experiments demonstratin T cell activation as monitored by intracellular IL-2, and surface CD25, and CD69, markers. A) Intracellular detection of IL-2, of titration of CD3/CD28, vs. LFA-1, stimulus or CD3, vs. CD28, stimulus for 6, hours. Median Fluorescent intensity is plotted as a visual array. B) Bivariate analysis of CD69, and CD25 expression in unstimulated, CD3/CD28/LFA-1, (0.001, μg/ml, 1:1:1) stimulated, and CD3/CD28, (10 μg/ml) stimulated CD4, T cells. C) Bivariate plot of CD69, expression and intracellular detection of IL-2, post 12, hour stimulation of unstimulated, CD3/CD28, and CD3/CD28/LFA-1, stimulation.

FIG. 10 depicts the results of experiments demonstrating the profiling of transcription factor nuclear localization and activity. A) Reporter gene assays of NFAT-luciferase, NF-κB-luciferase, and AP-1-luciferase transfected Jurkat cells. CD3, CD3/CD28, and CD3/CD28/LFA-1, stimulus was performed (6, hr, 10, μg/ml) and fold luciferase activity is plotted. B) Nuclear profile of transcription factors (as indicated in figure) to CD3, CD28, and LFA-1, stimulus (10, μg/ml, 12, hr). Nuclear extracts (5, μg/ml) were hybridized to transcription factor specific consensus sequence DNA coated plates, and detected by ELISA. Values were normalized to negative control and displayed as absorbance units of 655, nm. Nuclear profile of CD3/CD28, and CD3/CD28/sICAM-2 stimulated cells (as described above). C) NFAT-luciferase reporter activity on CD3/CD28, and CD3/CD28/LFA-1, titrations (as indicated) as described above. D-E) depict the results of experiments demonstrating the transcription factor profiling and cytometric bead array of CD3, CD28, and LFA-1, stimulation. A) Nuclear extracts of stimulated cells were prepared and hybridized to 96, well plates coated with consensus sequences to p65, p50, cFos, creb, atf2, and cRel. Bound protein was detected using standard ELISA techniques. CD3, stimulation presented low levels of the NF-κB subunits p65, and p50, and no detectable levels of cFos, cRel, CREB, effects of which were similar to LFA-1, stimulation. However, CD3, stimulation alone presented higher levels of aft2, than CD28, and LFA-1, stimulus. CD28, stimulation alone presented low levels of the NF-κB p65, and p50, subunits, with elevated levels of CREB. LFA-1, stimulation presented slightly higher levels of NF-κB p65, subunit and cRel. B) Cytometric bead array (CBA) for secreted IFNγ, IL-10, IL-2, IL-4, IL-5, IL-2, and TNFα to CD3/CD28, and CD3/CD28/LFA-1, stimulus (10 μg/ml, 16, hr). Values were computed to standard curve using recombinant cytokines and were simultaneously measured from the supernatant of treated cells. Measurement of cytokine secretion after CD3, and LFA-1, stimulus alone did not report significant cytokine secretion CD28 stimulation gave elevated levels of IL-4, and IL-5, with low levels of IFNγ.

Figure 11:
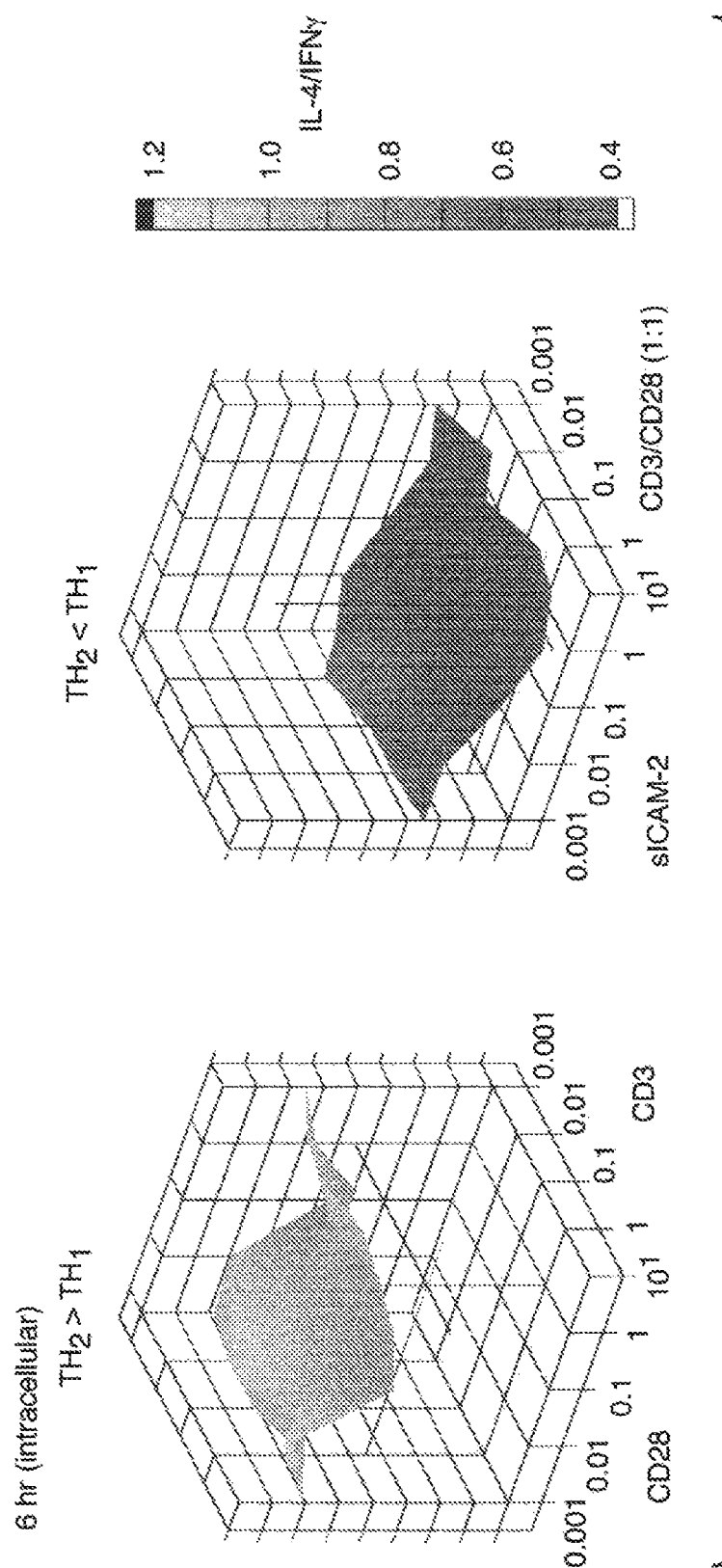

FIG. 11 depicts the results of experiments demonstrating the intracellular production of IL-4 and IFNγ in human naïve CD4, T cells. Intracellular levels of IFNγ and IL-4, post 6, hr stimulus of titrations of CD3, vs. CD28, and CD3/CD28, vs. LFA-1, stimulus. Median fluorescence values were normalized to unstimulated cells, and log ratios of IL-4/IFNγ were computed and plotted as intensity contour plots. Intensity levels are depicted in range indicator (right).

FIG. 12 depicts the results of experiments demonstrating cytometric bead arrays and Cytometric bead array (CBA) for secreted IFNγ, IL-10, IL-2, IL-4, IL-5, IL-5, and TNFα to CD3/CD28, and CD3/CD28/LFA-1, stimulus (10, μg/ml, 16, hr). Values were computed to a standard curve using recombinant cytokines and were simultaneously measured from the supernatant of treated cells using CBA arrays from PharMingen.

FIG. 13 depicts the results of experiments demonstrating clustering of ectopic ICAM-2, in NIH3T3, activated the p44/42, MAPK cascade. A) ICAM-2, and ICAM2-AC retroviral expression vectors target to the cell surface. Plasma membrane targeting of ICAM-2, and ICAM2-AC transduced NIH3T3, was verified by flow cytometry using specific anti-human antibodies to respective termini. B) Western-blot verified ICAM-2, and ICAM2-AC expression to compare with endogenous ICAM-2, from Jurkat cells. C) p44/42, MAPK cascade is initiated upon surface ICAM-2, clustering. Serum starved ICAM-2, cells were ICAM-2, crosslinked (10, μg/ml) for the indicated time by an anti-human ICAM-2, monoclonal antibody. Cell lysates were harvested and subjected to standard electrophoretic and immunoblotting protocols. Phospho specific antibodies for RAF, MEK, p44/42, MAPK (ERK1/2), Elk-1, and Rsk1, were used to detect phosphorylated proteins. Blots were then stripped and reprobed using a normalizing antibody (non-phospho specific antibody) to the each respective kinase. D) ICAM-2, clustering induces p44/42, MAPK activity as determine by p44/42, MAPK kinase activity assay. Serum starved cells were crosslinked for ICAM-2, (10, μg/ml) for 30, minutes and assessed for p44/42, MAPK activity. Positive and negative denoted lanes indicate internal MAPK kinases controls and a control IgG served as a negative control for induction condition.

FIG. 14 depicts the results of experiments demonstrating that p44/42, MAPK activity mediates enhanced growth kinetics. A) Cell cycle re-entry in initiated upon ICAM-2, clustering. Cells were serum starved for 72, hours to synchronize cells in the absence of chemical agents and subsequently ICAM-2, crosslinked (10, μg/ml, 18, hrrs) and subjected to cell cycle analysis by flow cytometry. Errors bars denote standard deviation of triplicate experiments. Gating for specific cell cycle stages is presented (left). B) Contact inhibition induced cell cycle arrest as measured by the MTT cell viability assay. Indicated cell types were seeded in a 96, well plate at increasing cell density as indicated and cellular respiration was measured by incubating the cells with the MTT reagent. Detection of product was done by reading absorbance at 580, nm 4, hrs post an initial 2-hour settling period. Error bars denote standard deviation of triplicate experiments. C)

Growth kinetics monitored by cell density over time. Indicated cell types were seeded at $10^4$, cells and cell density was monitored by standard clonogenic assay over the indicated time period. Error bars denote standard deviation of triplicate experiments.

FIG. 15 depicts the results of experiments demonstrating that ICAM-2, binds surface β1, β2, and β3, integrins. A) Affinity chromatography detects several ICAM-2, interacting surface proteins. An ICAM-2FITC probe was generated by immuno-depletion of ICAM-2, from transduced NIH3T3, chemically conjugated to FITC (1st and 2nd panels), and tested by anti-ICAM-2, immunoblot and fluorescent labeling. A farwestern approach utilizing ICAM-2-FITC as a labeled probe detects a 96, and 16, kdA interacting protein bands in ICAM-2, lysates (3rd panel). Surface proteins of ICAM-2, and vector control cells were biotinylated and subjected to affinity chromatography dual column system utilizing a constructed ICAM-2, coupled solid support and a streptavidin-agarose support. Several protein bands were identified that are both ICAM-2, interacting and surface expressed (biotinylation detected by streptavidinFITC) ($4^{th}$, panel). B) ICAM-2, soluble protein binds to the surface of cells. The ICAM-2-FITC probe was used to label NIH3T3, Jurkat, and BaF3, cells and was detected by flow cytometry. Prior treatment of cells with trypsin attenuated the ICAM-2-FITC binding (right panel). C) ICAM-2, interacts with β1, β2, and β3, integrins. Final elusions from the ICAM-2, solid support and subsequent streptavidin-agarose column passage were immunoblotted for β-integrins using monoclonal antibodies. Detection of β1, β2, and β3 refined and verified the mass spectrometry reading of the MALDLMS analysis. D) ICAM-2 interaction with β2, integrin induces p44/42, MAPK kinase activity. Beta-1, β2, and β3, integrin were blocked with monoclonal antibodies in serum starved cells prior to ICAM-2, crosslinking in ICAM-2, ICAM2-AC, and vector control cells. E) Integrin profile assessment by quantitative flow cytometry. Alpha-5, αL, β1, β2, β3, β4, monoclonal antibodies were conjugated to phycoerythrin (PE) and quantitated using QuantiBRiTE PE beads by flow cytometry (see materials and methods for elaboration). Linear regression analysis of fluorescent signal as a function of a standard antigen concentration curve allows quanititation of the number of surface molecules per cell. Error bars denote standard deviation of triplicate experiments. F) Soluble ICAM-2, induced p44/42 MAPK phosphorylation and activity is blocked by antibodies to αL integrin. ICAM-2, soluble protein was incubated for 30, minutes in serum starved Jurkat cells at the indicated concentrations in the presence or absence of monoclonal antibody pre-treatment to αL (similar to mAb blocking experiments). Immunoblot for phospho-p44/42, MAPK (left) and p44/42, MAPK activity assay (right).

FIGS. 16A to 16C depict the results of experiments demonstrating that ICAM-2/LFA-1, interaction is transmitted to Raf by PYK2, and SYK. Inhibitor screens using various pharmacological inhibitors to Src related kineses identify PYK2, and SYK to be necessary in relaying the ICAM-2, induced signal to Raf and p44/42, MAPK kinase. Serum starved cells were treated with 10, μM of indicated compound 30, minutes prior to being ICAM-2, crosslinked for 30, minutes (10, μg/ml) and assessed for phosphorylated Raf and p44/42, MAPK using phospho specific antibodies in standard immunoblot procedures. Control IgG dissolved in 0.1% DMSO served as negative control. Blots are representative of triplicate experiments. B) SYK and PYK interaction with LFA-1, subunits is intensified upon ICAM-2, interaction. Co-immunoprecipitation experiments were performed immunoprecipitating αL and β2, integrin and immunoblotting for the presence of SYK and PYK as a function of a stimulus for 30, minutes as indicated (antibodies used at 10, μg/ml, compounds used at 1, μM and control 19, served as negative control). Reciprocal co-immunoprecipitations confirm PYK and SYK associations with β2, integrin (bottom panel). C) PYK2, is phosphorylated in the presence of ICAM-2, or additional stimuli as determined by an anti-phosphotyrosine immunoprecipitation and subsequent immunoblot for PYK2.

FIG. 17 depicts result from experiments demonstrating that confocal microscopy reveals cellular the redistribution of PYK2, and SYK to the surface membrane in Jurkat cells after ICAM-2 interaction with LFA-1, and subsequent phosphorylation of PYK2. Jurkat cells were treated with soluble ICAM-2, protein (10, μg/ml) or bovine serum albumin (Unstimulated, 10, μg/ml) for 10 minutes and prepared for confocal microscopy (see material and methods). A) Cells were stained for PYK2, SYK2, and B) phosphorylated PYK2, at tyrosine 402, (denoted as PYK2 pTyr402). In FIGS. 17A and B, panels A-C represent unstimulated cells and panels D-F represent ICAM-2, treated cells. Arrows serve to highlight marked differences in cellular distribution of PYK2, and SYK. Scale bar is denoted in lower left corner of panels (in micrometers). Panels D-F are at a higher magnification to see distribution differences clearly.

Figure 18B:
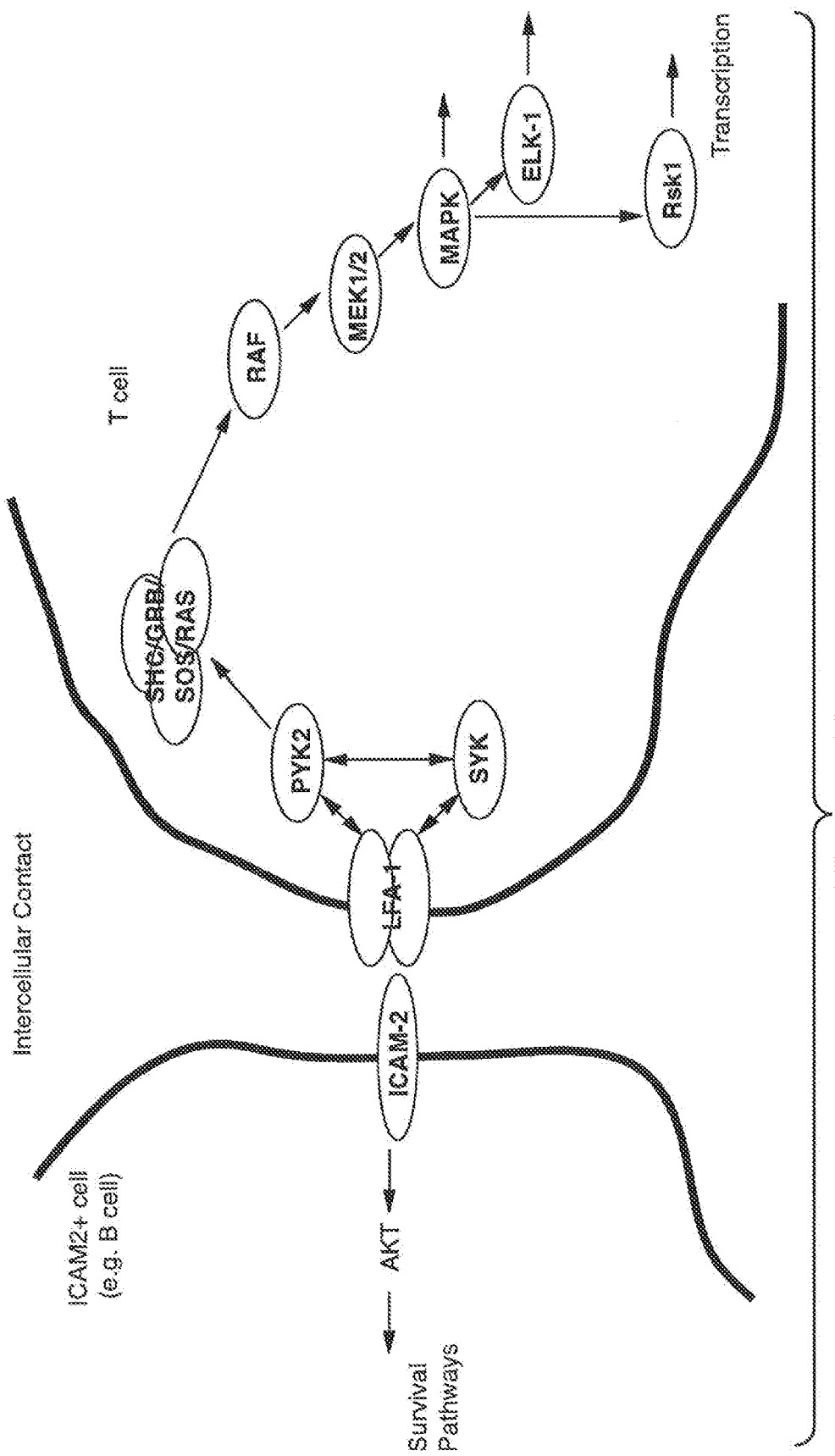

FIG. 18 depicts result from experiments demonstrating that cell-to-cell contact initiates p44/42 MAPK activity in LFA-1, expressing and AKT activity in ICAM-2, expressing cells as determined by flow cytometry based kineses assays. A) Jurkat cells and retrovirally transduced ICAM-2, cells were mixed for 30, minutes and subjected for flow cytometry by surface staining for CD3, and CD4 surface markers, and stained intracellularly for phospho-p44/42, MAPK and phospho-AKT using fluorescently conjugated phospho-specific monoclonal antibodies (see materials and methods for elaboration). Gating on high and low phosphorylated AKT and p44/42, MAPK populations, as determined for fluorescence log intensity, were analyzed according to the CD3, and CD4, surface markers. Plots depict CD3, vs. phospho-AKTser473, or phospho-p44/42, but are similar for CD4. B) Model of signaling pathways initiated upon intercellular ICAM-2/LFA-1, interaction. LFA-1, upon engagement of ICAM-2, activates the RAF/MEK/MAPK cascade, mediated through PYK2, and SYK. ICAM-2, expressing cells activate the AKT survival pathway as ICAM-2, is clustered on the cell surface.

FIG. 19 depicts the results of experiments demonstrating that a retroviral library screen for anti-apoptotic molecules to staurosporine induced apoptosis identifies ICAM-2. A) cDNA library screening scheme. $10^7$, NIH3T3, cells were infected with a Jurkat T cell retroviral cDNA library and treated with staurosporine (1, μM) for 24, hours to induce apoptosis (Stolzenberg et al., 2000). Surviving clones were grown out for one week and subjected to a repeat selection three times. To determine which viral integrants encoded an antiapoptotic function, a phenotypic transfer assay was performed. An aliquot of the surviving cell population was infected with native Moloney murine leukemia virus (MMLV). This rescued the replication-defective viral vector proviruses, generating infectious particles. NIH3T3, cells were infected with the rescued viral vectors and treated with staurosporine to confirm the anti-apoptotic phenotype. B) Complexity of populations surviving staurosporine induced apoptotic screen. RT-PCR was performed to assess the complexity of the surviving populations. Surviving population (1°) exhibited several discrete bands and the post-transfer population(2°) exhibited a single band. M-molecular weight marker. A negative control vector (LacZ), initially spiked into the library at 10% was undetectable, while an independent infection of a Bcl-2-expressing vector was readily detected. C) Retroviral vector encoding ICAM-2, western blot analysis in infected NIH3T3. D) Retroviral vector encoding ICAM-2 ectopically expresses surface ICAM-2. Right Panel: BaF3, pro-B-cells infected with a retroviral vector construct encoding ICAM-2, or vector control and assayed for either endogenous and expressed ICAM-2, surface expression levels by flow cytometry. Left Panel: HUVEC cells stained for endogenous ICAM-2, expression by flow cytometry. E) Dose response curves of ICAM-2 transduced NIH3T3, and Jurkat T-cells to treatment of staurosporine or anti-Fas antibody for 24 hours. Open squares: ICAM-2, expressing cells. Closed squares: control cells expressing vector alone. The proportion of apoptotic cells in each culture without staurosporine or anti-Fas mAb was less then 3%. The percentage of apoptotic cells is expressed as the mean (bar)±SD of triplicate cultures.

FIG. 20 depicts the results of experiments demonstrating that the overexpression of ICAM-2 results in a broadly acting anti-apoptotic phenotype. A) Effect of ICAM-2, on staurosporine induced apoptosis was assessed by annexin-V binding assay. ICAM-2, expressing NIH3T3, and vector control NIH3T3, were subjected to an annexin-V binding assay in the presence or absence of staurosporine (1, µM, 24, hrs). DMSO vehicle served as the negative control. The proportion of apoptotic cells in each culture without staurosporine was 5%+/−1.2. B) Effects of ICAM-2 overexpression in Jurkat, NIH3T3, 70Z/3, and BaF3, cells in the context of different apoptotic inducers. Infected cells were treated with either staurosporine (1µl, M), anti-Fas antibody (5 µg/ml), or deprived of IL-3, for 24, hours as indicated and evaluated for apoptosis as described (Jacobson and Raff, 1995). Cells were infected with retroviral constructs encoding ICAM-2, ICAM2-AN, vector control, or Bcl-2, and subjected to apoptose as indicated (24, hrs, 70Z/3, cells: 0.2, µM STP, 4, hrs). The percentage of apoptotic cells is expressed as the mean (bar)+/−SD of triplicate cultures. C) The α-actinin binding site is required for survival. ICAM-2, wild-type sequence (red line); ICAM2ΔC, cytoplasmic domain deletion (solid, thin line); ICAM-2 C-scrambled, full length with scrambled [a]α-actinin binding site (hatched line) were FACS sorted by an anti-ICAM-2-FITC monoclonal antibody (IC2/2), and incubated with etoposide (100 µM, 24, hrs). Viable cells were scored after a 24, hr recovery period following etoposide treatment. The percentage of surviving cells is expressed as the mean (bar)+/−SD of triplicate cultures.

Figure 21A:
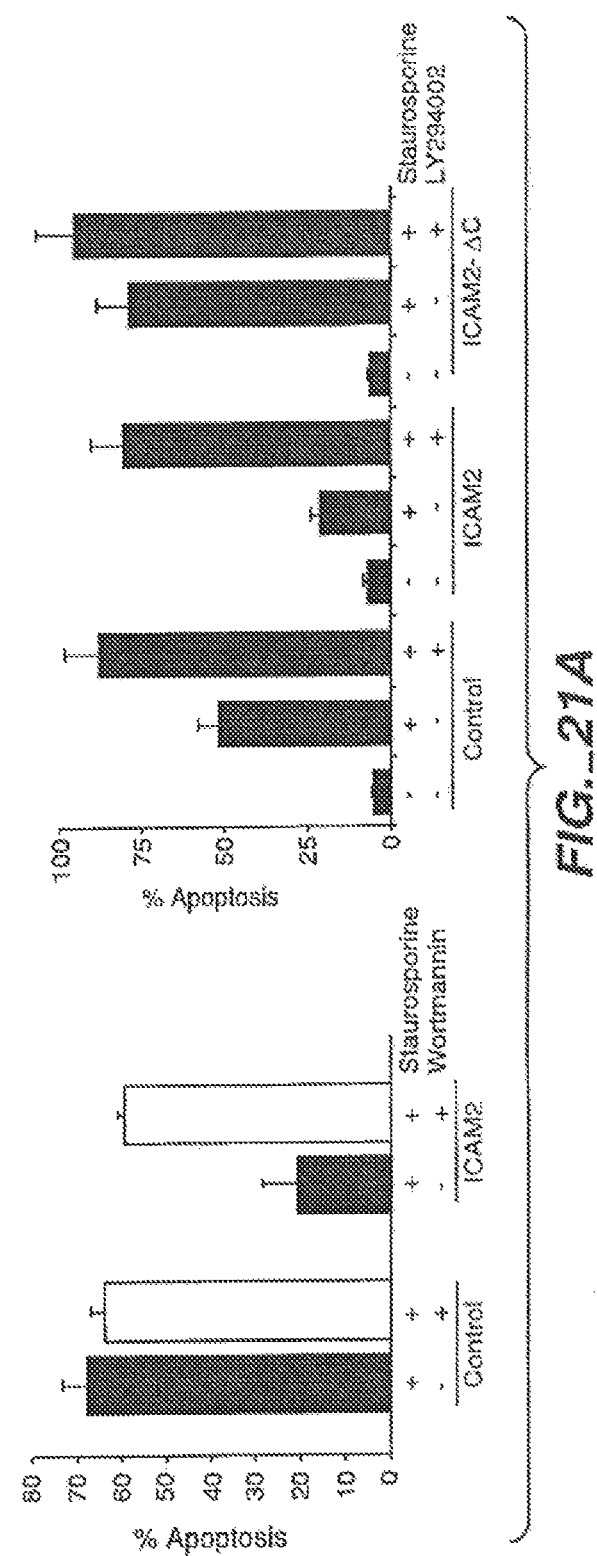

FIG. 21 depicts the results of experiments demonstrating that PI3-kinase is necessary for ICAM-2's anti-apoptotic effect. A) Pharmacological inhibitors of PI3K abrogate ICAM-2's anti-apoptotic. ICAM-2, or vector transduced BaF3, cells were treated with staurosporine (1, µM) with (unfilled) or without (filled) the addition of 100, nM wortmannin for 24, hours (left bar graph). Apoptosis was determined by nuclear staining and fluorescence microscopy (left bar graph) and by annexin-V binding assay (right bar graph). The proportion of apoptotic cells in each culture without staurosporine was 8%+/−2. The percentage of apoptotic cells is expressed as the mean (bar)+SD of triplicate cultures. ICAM-2, 1CAM2-AC, or vector transduced NIH3T3, were treated with staurosporine (1µl, M) in the presence or absence of 10, µM LY294002, for 24, hours (right bar graph). DMSO vehicle served as negative control. The percentage of apoptotic cells is expressed as the mean (bar)+/−SD of triplicate cultures. B) Confocal images of PI3K and AKT localization in ICAM-2, (top) or vector control cells (bottom). C) Confocal images of ezrin and the p85, subunit of PI3K (green) localization in ICAM-2, (top) or vector control cells (bottom).

FIG. 22 depicts the results of experiments demonstrating that ICAM-2, signal results in phosphatidylinositol 3,4,5, triphosphate production, PDK-1, and AKT activation, and subsequent phosphorylation of AKT downstream effectors. A) ICAM-2, interacts with α-actinin and ezrin. ICAM-2, ICAM2-ΔC or control cells were immunoprecipiated for ICAM-2, and immunoblotted for either a-actinin or ezrin. Control lysates were not subjected to immunoprecipitation and reflect positive controls for detected interacting protein. B) ICAM-2, cells exhibit high levels of phosphatidylinositol 3,4,5, triphosphate. ICAM-2, and control cells were serum starved (48, hrs), treated with LY294002, (10, µM, 24, hrs), or cultured in growth media, and prepared for intracellular detection of phosphatidyinositol 3,4,5, triphosphate detection by flow cytometry. C) PDK-1, I kinase levels are elevated in ICAM-2, cells and are partially inhibited by Y-27632. PDK-1 kinase was immunoprecipitated from cells incubated with the indicated compounds (10, µM, 1, hr) and subjected to an immuno-kinase reaction with inactive SGK enzyme and peptide substrate. Phosphotransfer of ATP to peptide substrate was detected by scintillation counting and presented as counts per minute CPM. D) Immunoblot for AKT in membrane/cytosol fractions of ICAM-2, and controls cells and AKT kinase activity. E) AKT kinase level and dual phosphorylation at serine 473 and threonine 308, are sustained in ICAM-2, cells in the presence of staurosporine. F) The AKT kinase substrates BAD and GSK3, remain phosphorylated in ICAM-2-expressing cells following staurosporine treatment. Extracts from ICAM-2, ICAM-2ΔC and control vector cells treated with DMSO-vehicle (−) or 1, µM staurosporine (+) were assayed for BAD and GSK3, phosphorylation by immunoblotting as indicated.

FIG. 23 depicts the results of experiments demonstrating that ligation of endogenous ICAM-2 induces tyrosine phosphorylation of ezrin and recruits PI3K to the membrane, resulting in PDK-1 and AKT kinase activation. A) Expression levels of ICAM-2, vary across cell lines of different origins. Quantitative flow cytometry analysis was performed to assess the number of ICAM-2 surface molecules across transformed and untransformed fibroblasts, lymphocytes of T-cell and different B-cell differentiation states and myeloid lineages (see Material and Methods for elaboration). The number of surface molecules/cell is expressed as the mean (bar)+/−SD of triplicate experiments. B) Crosslinking of endogenous ICAM-2, induces ezrin tyrosine phosphorylation and enhanced ICAM-2, interaction. Jurkat cells were crosslinked for ICAM-2 using monoclonal antibody for the indicated times and subjected to immunoprecipitation/immunoblotting as indicated. C) Inhibition of ezrin phosphotyrosine by chemical inhibitors of src and Rho-dependent kinases. D) Ezrin phosphorylation and enhanced interaction with the p85, subunit of PI3K as a function of ICAM-2. Determined as described above. E) PDK-1, activity as a function of ICAM-2, ligation, as described above). F) PI3K and AKT localize to the membrane as a function of ICAM-2, ligation. Membrane/cytosolic fractionation was performed on ICAM-2, ligated Jurkat cells as a function of time and subjected to immunoblotting for PI3K and AKT.

FIG. 24 depicts the results of experiments demonstrating that ligation of endogenous ICAM-2 induced AKT activation in lymphoid cells conferring cell survival. A) ICAM-2, crosslinking induced AKT activity in Jurkat T cells and subsequent phosphorylation of GSK3, FKHR, and AFX as a function of time. Serum starved Jurkat T cells were incubated with either isotype control or anti-human ICAM-2, (10, µg/ml) for the indicated times. AKT kinase activity was determined as described. Immunoblot analysis verified AKT dual phosphorylation, FKHR and GSK3 phosphorylation, and BAD phosphorylation as a function of ICAM-2, crosslinking. B) ICAM-2 crosslinking induces AKT activity in BaF3, pre-B cells. C) ICAM-2, clustering on Jurkat T cells treated with staurosporine (1, μm for 6, hours) shows a decrease in apoptosis as measured by flow cytometry annexin-V binding assay. ICAM-2, was crosslinked on 106, Jurkat T cells using an ICAM-2, mAb (10, μg/ml) 30, minutes prior to treatment with staurosporine (+) or DMSO vehicle (−). Apoptosis was determined by flow cytometry using annexin-V binding assay. D) ICAM-2, survival signal is abrogated in the presence of GTPγS, Psi-tectorigenin, Y-27632, and herbimycin A. Jurkat cells were incubated with indicated inhibitor (10, μM, 1, hour) prior to being crosslinked for ICAM-2, (10, μg/ml, one hour) and treated with anti-Fas (50, ng/ml, 8, hours). Cells were assessed for apoptosis by annexin-V binding assay. E) ICAM-2, crosslinking induces ezrin association with PI3K. ICAM-2, vector control, Jurkat and Jurkat cells crosslinked for ICAM-2, (10, μg/ml, 15 minutes) were subjected to immunoprecipitation and subsequent immunoblotting as indicated.

FIG. 25 depicts the results of experiments demonstrating that ligation of ICAM-2, induces AKT activity and protects primary B cells from apoptosis. A) Human peripheral blood monocytes were crosslinked for ICAM-2, (10, μg/ml 45, minutes) prior to being subjected to apoptosis by treatment with TNFα 200, ng/ml plus 1, μg/ml cycloheximide) and anti-Fas antibody (10, ng/ml CH11) for 12 hours. Multi-parameter FACS analysis illustrates ICAM-2, induced AKT activity in CD4+, and CD19+, populations protects from apoptosis. (1×10⁶, events collected to enumerate a minimum of 80,000, CD19+, cells). B) PBMC were crosslinked for ICAM-1, -2, -3, CD43, or CD44, (10, μg/ml 45 minutes) and subjected to phosphatidylinositoi detection of phosphatidylinositol 3,4,5 triphosphate, phosphatidylinositol 4,5, bisphosphate, or phospho-AKTser473, detection by flow cytometry. Cell subsets are gated and displayed as indicated. C) PBMC were crosslinked for ICAM-1, -2, -3, CD43, or CD44, (10, μg/ml 45, minutes) prior to being induced to apoptose as described above. Apoptosis was measured by annexin-V binding detected by flow cytometry, and gated for CD19+, cells. D) PBMC was crosslinked for ICAM-2, prior to being induced to apoptose as described above in the presence or absence of inhibitory compounds Psi-tectorigenin and Y-27632, (10, μM, 30, minutes). Apoptosis was measured by annexin-V binding assay. E) LFA-1, overlay assay. LFA-1+, Jurkat cells were overlayed on either vector control or ICAM-2, expressing cells after being treated with LY294002, (2, μM, one hour). Some Jurkat samples were treated with monoclonal antibodies to LFA-1, or Mac-1, (5, μg/ml, 30, minutes) prior to being overlayed on ICAM-2, or vector control. Cells were mixed for 30, minutes at 37° C., and then subjected for flow cytometry. Jurkat cells were gated and removed from displayed analysis of phospho-AktSer473, ICAM-2, cells F) Model for ICAM-2, mediated cell survival signal. ICAM-2, oligomerization recruits and phosphorylates ezrin through a Src/Rho dependent mechanism. This results in recruitment of PI3K to the membrane through ezrin's interaction with the p85, regulatory subunit of PI3K. Membrane translocation of PI3K generates phosphatidylinositol 3,4,5, triphosphates that activate PDK-1, and recruit AKT to the plasma membrane by binding to its PH domain. Translocation of cytosolic AKT to the membrane allows PDK1/2, to phosphorylate AKT at ser473, and thr308, activating AKT. AKT subsequently phosphorylates downstream effectors GSK3, BAD, FKHR (and potentially others depending on the cell type). Phosphorylation of these effectors can block apoptosis alone or synergistically to generate a survival signal.

FIG. 26 depicts the results of experiments demonstrating the retroviral library screen for anti-apoptotic molecules to staurosporine induced apoptosis. A) cDNA library screening scheme. 10⁷, NIH3T3, cells were infected with a Jurkat T cell retroviral cDNA library and treated with staurosporine (1, μM) for 24, hours to induce apoptosis (Stolzenberg et al., 2000). Surviving clones were grown out for one week and subjected to a repeat selection three times. To determine which viral integrants encoded an anti-apoptotic function, a phenotypic transfer assay was performed. An aliquot of the surviving cell population was infected with native Moloney murine leukemia virus (MMLV). This rescued the replication-defective viral vector proviruses, generating infectious particles. NIH3T3, cells were infected with the rescued viral vectors and treated with staurosporine to confirm the anti-apoptotic phenotype. B) Complexity of populations surviving staurosporine induced apoptotic screen. RT-PCR was performed to assess the complexity of the surviving populations. Surviving population (1°) exhibited several discrete bands and the post-transfer population (2°) exhibited a single band. M-molecular weight marker. A negative control vector (LacZ, initially spiked into the library at 10% was undetectable, while an independent infection of a BcL2-expressing vector was readily detected.

FIG. 27 depicts the results of experiments demonstrating that overexpression of ICAM-2 inhibits staurosporine induced apoptosis. A) Retroviral vector encoding ICAM-2, western blot analysis in infected NIH3T3. B) Retroviral vector encoding ICAM-2, ectopically expresses surface ICAM-2. Right Panel: BaF3, pro-B-cells infected with a retroviral vector construct encoding ICAM-2, or vector control and assayed for either endogenous and expressed ICAM-2, surface expression levels by flow cytometry. Left Panel: HUVEC cells stained for endogenous ICAM-2 expression by flow cytometry. C) Dose response curves of ICAM-2, transduced NIH3T3, and Jurkat T-cells to treatment of staurosporine or anti-Fas antibody for 24, hours. Open squares: ICAM-2, expressing cells. Closed squares: control cells expressing vector alone. The proportion of apoptotic cells in each culture without staurosporine or anti-Fas mAb was less then 3%. The percentage of apoptotic cells is expressed as the mean (bar) ±SD of triplicate cultures. D) Pyknotic nuclei of negative control NIH3T3, vector control (−STP), positive control NIH3T3, vector control (+STP), and ICAM-2, expressing NIH3T3, Nuclei were stained with Hoescht (5, μg/ml) and acridine orange (25, μM) and ethidium bromide (25, μM). Inserts indicate degree of cell death or cell viability. E) Effect of ICAM-2, on staurosporine induced apoptosis was assessed by annexin-V binding assay ICAM-2, expressing NIH3T3, and vector control NIH3T3, were subjected to an annexn-V binding assay in the presence or absence of staurosporine (1, μM, 24, hr). DMSO vehicle served as the negative control. The proportion of apoptotic cells in each culture without staurosporine was 5%±1.2.

FIG. 28 depicts the results of experiments demonstrating that ICAM-2, mediates an anti-apoptotic effect. A) Effects of ICAM-2, overexpression in Jurkat, NIH3T3, 70Z/3, and BaF3 cells in the context of different apoptotic inducers. Infected cells were treated with either staurosporine (1, μM), anti-Fas antibody (5, μg/ml), or deprived of IL-3, for 24, hours as indicated and evaluated for apoptosis as described (Jacobson and Raff, 1995). Jurkat T cells were infected with retroviral constructs encoding ICAM-2, or vector control. Mouse pre-B 70Z/3, cells were infected with a retroviral vector construct encoding ICAM-2, or vector control and treated with staurosporine (0.2, μM) for 4, hours and evaluated for apoptosis. IL-3-dependent BaF3, cells were infected with retroviral vector constructs encoding ICAM-2, ICAM2-ΔN, or Bcl2. To induce apoptosis, cells were maintained in IL-3-deficient medium for 24, hours. BaF3-cells expressing retroviral vector encoded ICAM-2, or an in-frame deletion of the extracellular domain were treated with anti-mouse Fas for 24, hours and evaluated for cell death. The percentage of apoptotic cells is expressed as the mean (bar)±SD of triplicate cultures. B) The α-actinin binding site is required for survival. NIH3T3, cells were transduced with ICAM-2, encoding retroviral constructs: ICAM-2, wild-type sequence (hatched line); ICAM-2ΔC, cytoplasmic domain deletion (solid, thin line); ICAM-2, C-scrambled, full length with scrambled α-actinin binding site (hatched line). Transduced cells were labeled with a fluorescently conjugated anti-ICAM-2, monoclonal antibody that recognized only the native protein (IC2/2). Cells were then purified by FACS (MoFlo, Cytomation, Ft. Collins, Colo.). Sorted cells were cultured and then cells were challenged with 100 μM etoposide for 24, hours. The surviving cells were allowed to recover for 24, hours following removal of the drug and the number of viable cells was scored. The percentage of surviving cells is expressed as the mean (bar) ±SD of triplicate cultures. C) α-actinin and ezrin both co-immunoprecipitate with ICAM-2, and interact with the C-terminus of ICAM-2. ICAM-2, was immunoprecipitated from ICAM-2, ICAM2-ΔC, and vector control transduced NIH3T3. Immunoprecipitates were resolved by SDS-PAGE and subjected to immoblotting for α-actinin, ezrin, and ICAM-2

Figure 29B:
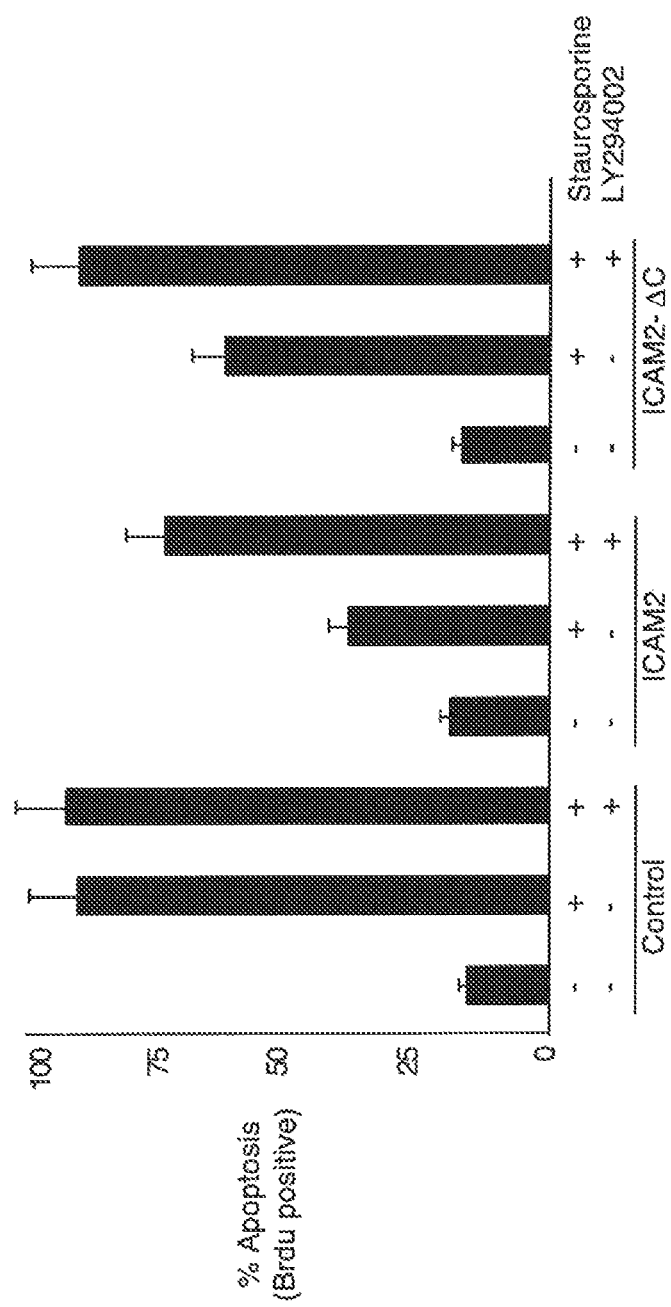

FIG. 29 depicts the results of experiments demonstrating that pharmacological inhibitors of PI3K abrogate ICAM-2's anti-apoptotic effect. A) The anti-apoptotic effect of ICAM-2, is both wortmannin and LY294002, sensitive. ICAM-2, or vector transduced BaF3, cells were treated with staurosporine (1, μM) with (unfilled) or without (filled) the addition of 100, nM wortmannin for 24 hours. Apoptosis was determined by nuclear staining and fluorescence microscopy (left bar graph) and by annexin-V binding assay (right bar graph). The proportion of apoptotic cells in each culture without staurosporine was 8%±2. The percentage of apoptotic cells is expressed as the mean (bar)±SD of triplicate cultures. ICAM-2, ICAM2-ΔC, or vector transduced NIH3T3, were treated with staurosporine (1, μM) in the presence or absence of 10, μM LY294002, for 24, hours. DMSO vehicle served as negative control. The percentage of apoptotic cells is expressed as the mean (bar)±SD of triplicate cultures. B) ICAM-2, expressing NIH3T3, cells are sensitive to apoptosis in the presence of PI3K inhibitor LY294002. BrdU TUNEL assay was performed in staurosporine (1, μM) or LY294002, (10, μM) treated ICAM-2, ICAM2-ΔC, and control vector transduced NIH3T3, cells. The percentage of apoptotic cells is expressed as the mean (bar)±SD of triplicate cultures.

FIG. 30 depicts the results of experiments demonstrating that ICAM-2, induces AKT kinase activity and phosphorylation of BAD and GSK. A) AKT kinase levels and dual phosphorylation at serine 473, and threonine 308, are elevated in ICAM-2, expressing cells and sustained in the presence of staurosporine. AKT kinase was immunoprecipitated from ICAM-2, ICAM-2ΔC and control vector (pBMN-Z-IN-GFP) expressing NIH3T3, fibroblasts in the presence or absence of staurosporine (with 1, μM staurosporine (+) or DMSO-vehicle (−) and incubated with a GSK protein substrate. Phosphorylated GSK was identified by anti-phospho-GSK specific immunoblotting. B) The AKT kinase substrates BAD, FKHR, and GSK3, remain phosphorylated in ICAM-2-expressing cells following staurosporine treatment Extracts from ICAM-2, ICAM-2ΔC and control vector expressing NIH3T3, fibroblasts treated with DMSO-vehicle (−) or 1, μM staurosporine (+) were assayed for BAD and GSK3, phosphorylation and by immunoprecipitating BAD or GSK3, and immunoblotting with phospho-BAD, or phospho-GSK3, specific antibodies. C) ICAM-2's anti-apoptotic effect is independent of Bcl-2, or Bcl-$X_{L/S}$, as determined by immunoblotting. ICAM-2, or ICAM2-ΔC transduced NIH3T3, were treated with DMSO vehicle (−) or 1, μM staurosporine (+) for 24, hours and assayed for Bcl2, and Bcl-$X_{L/S}$, expression by immunoblotting. D) Expression levels of ICAM-2, vary across cell lines of different origins. Quantitative flow cytometry analysis was performed to assess the number of ICAM-2, surface molecules across transformed and untransformed fibroblasts, lymphocytes of T-cell and different B-cell differentiation states, and myeloid lineages. Geometric mean fluorescence values were calibrated to standard curve derived from geometric mean fluorescence values of beads labeled with known amounts of phycoeyrthrin molecules (see experimental procedures for elaboration). The number of surface molecules/cell is expressed as the mean (bar)±SD of triplicate experiments.

FIG. 31 depicts the results of experiments demonstrating that cross-linking of endogenous ICAM-2, induces AKT activation in BaF3, B-cells and protects Jurkat T cells from apoptosis. A) Cross-linking ICAM-2, with monoclonal anti-ICAM2, antibody induced AKT activity. Serum starved BaF3, preB cells were incubated with either normal rat IgG2, (isotype control) or anti-mouse ICAM-2, at 10, μg/ml for the indicated times. AKT kinase activity was determined as described. immunoblot analysis was performed to verify AKT dual phosphorylation, FKHR phosphorylation, and BAD phosphorylation as a function of ICAM-2, crosslinking. Isotype control did not induce AKT phosphorylation or phosphorylation of FKHR or BAD (data not shown). B) ICAM-2, clustering on Jurkat T cells treated with staurosporine (1, μm for 6, hours) shows a decrease in apoptosis as measured by flow cytometry annexin-V binding assay. ICAM-2, was crosslinked on $10^6$, Jurkat T-cells using a monoclonal anti-ICAM-2, antibody (10, μg/ml) 30, minutes prior to treatment with staurosporine (+) or DMSO vehicle (−). Apoptosis was determined by flow cytometry using annexin-V binding assay. (100,000, events collected). C) ICAM-2, crosslinking on Jurkat T cells decreases percentage of death in staurosporine treatment. The percentage of dead cells is expressed as the mean (bar)±SD of triplicate experiments. D) ICAM-2, cross-linking induces AKT activity in Jurkat T cells and subsequent phosphorylation of GSK3, FKHR, AFX as a function of time. E) ICAM-2, crosslinking can overcome staurosporine induce apoptosis. $10^6$, Jurkat T-cells were treated with staurosporine (1, μM) for one hour as indicated by (+) to induce apoptosis. After one hour of staurosporine induced apoptosis, ICAM-2, was crosslinked using a monoclonal anti-ICAM2, antibody (10, μg/ml) for the indicated times. Attenuation of cleaved caspases was not observed in isotype control (10, μg/ml) (data not shown). F) ICAM-2, cross-linking induces AKT activity, subsequent phosphorylation of BAD, and is sufficient to override apoptotic induction by staurosporine. Jurkat cells were treated as mentioned above. AKT activity was determined by AKT kinase assay and detection of dually phosphorylation AKT by immunoblotting with phospho-specific antibodies against ser473, and thr308. BAD phosphorylation was detected by immunoprecipitation for BAD, followed by immunoblotting with phospho-specific antibodies ser112, and ser136. Isotype control (10, μg/ml) did not generate AKT activation (data not shown).

FIG. 32 depicts the results of experiments demonstrating that resistance to TNFα and Fas induced apoptosis in primary human CD4+, and CD19+, cells is mediated by active AKT following ICAM-2, crosslinking. A) Human periperal blood monocytes were assayed for AKT activity following ICAM-2, clustering using monoclonal antibodies (middle panel) or antiIICAM-2, labeled antibodies (bottom panel) and subsequently gated for CD4, or CD19, markers (50,000, events collected). B) Human peripheral blood monocytes were crosslinked for ICAM-2, (10, µg/ml 45 minutes) prior to being subjected to apoptosis by treatment with TNFα 200, ng/ml plus 1, µg/ml cycloheximide) and anti-Fas antibody (10, ng/ml CH11) for 12, hours. Multi-parameter FACS analysis illustrates ICAM-2, induced AKT activity in CD4+, and CD19+, populations protects from apoptosis. ($1\times10^6$, events collected to enumerate a minimum of 80,000, CD19+, cells). C) Model for ICAM-2, mediated anti-apoptotic signaling. ICAM-2, binds intracellular linker proteins α-actinin and ezrin, which recruit PI3K to the plasma membrane. PI3K generates inositol phosphates that recruit AKT to the plasma membrane by binding to its PH domain. Translocation of cytosolic AKT to the membrane allows PDK1/2, to phosphorylate AKT at ser473, and thr308, activating AKT. AKT subsequently phosphorylates downstream effectors GSK3, BAD, FKHR (and potentially others depending on the cell type). Phosphorylation of these effectors can block apoptosis alone or synergistically to generate a survival signal.

FIG. 33 depicts results demonstrating that soluble ICAM-2, binding induces LFA-1, clustering and cytoskeletal polarization. A) Purified human ICAM-2, from retrovirally transduced NIH3T3, (see materials and methods) was tested for purity, size, and aggregate formation by native gel electrophoresis and gel filtration. Analysis of purified ICAM-2, from two different preps and ICAM2-FC from NSO cells. Molecular weight was calculated using relative distance migration from a molecular weight standard. Concentration was determined using serial dilutions of BSA as a standard. Molecular weight and concentration are displayed in the figure. B) ICAM-2, ligand binding to cell surface as a function of time. $5\times10^6$, unstimulated and PMA stimulated (1, µg/ml, 30, min) Jurkat T cells were incubated with ICAM-2-FITC or LFA-1-FITC antibody (1, µg/ml) and subjected to time dependent flow cytometry. Mean fluorescence intensity was plotted per time of a gated homogenous cell population. Flow rate was maintained at 200-300, cells/second, with fluorescence intensity values acquired at 10, millisecond intervals for 1200, seconds. C) Flow cytometric analysis of ICAM-2-FITC and a-LFA-1-FITC surface binding on cytochalisin D treated (10, µM, 30, min) Jurkat cells at 37° C. and 4° C. D) Curve fit analysis of ICAM-2-FITC binding per $10^4$, cells. Jurkat cells were incubated with ICAM-2-FITC at 37° C. for 30, min at indicated concentrations in 50, µL volume. Cells were washed 1×, and analyzed for mean fluorescent intensity (MFI) of $10^4$, cells. Percent ICAM-2-FITC bound was calculated from the following equation: $100\times[(MFI_{[x]}-MFI_{unstained})/(MFI_{[saturated]}-MFI_{unstained})]$ where [x]=ICAM-2-FITC concentration and [saturated]=concentration that saturated binding. Values were fit to the equation Y=m1*M0/(m2+M0) (see materials and methods).

E-H) depicts soluble ICAM-2, and ICAM-2-FITC generation. E) Native gel electrophoresis of purified ICAM-2. Gel was coomasie stained and purified ICAM-2 did not display aggregates (after gel filtration, we found that the added glycerol in the purification step eliminated higher molecular weight species formation). F) a Purity analysis of ICAM-2 by native PAGE. Quantity was determined from densitometry measurements of entire lane. Percent purity was determined from calculating density of band relative to total density of the lane. ICAM-2, from prep one (left) and from prep 2 (right). Purity was greater than 98%. G) ICAM-2, was conjugated to FITC and purified conjugate (by spin chromatography) was immunoblotted with anti-ICAM-2, antibody (left panel) and subsequently verified for fluorescent conjugation in gel (right panel). H) Treatment of cells with cytochalisin D at low concentrations at 4° C led to enhanced ICAM-2, binding in a subset of cells and saturated at 37° C. Titration of ICAM-2-FITC surface binding at 37° C and 4° C in cytochalisin D treated (10, mM, 30, min) and untreated Jurkat cells by flow cytometry. Median Fluorescence Intensity (MFI) is plotted as a function of ICAM-2-FITC concentration.

FIG. 34 depicts the results of experiments demonstrating the simultaneous detection of ICAM-2, induced LFA-1, clustering, activation, and actin/microtubule reorganization. A) Confocal microscopy of actin and microtubule architecture upon ICAM-2, stimulus (10, µg/ml, 30, min) in Jurkat cells. Actin was stained by phalloidin-alexa633, and tubulin by taxol-alexa546. Inserts display enlarged cell image of representative treatment B) Flow cytometric staining for actin and microtubules as described above. C) Left: Fluorescence topography analysis of ICAM-2-FITC (1 µg/ml, time as indicated) surface distribution. Intensity color gradient depicts high and low fluorescent intensity values. Right: Confocal microscopy of ICAM-2-FITC surface binding (10 µg/ml, 30, min) and anti-β2-alexa568, (clone CTB104). D) Staining for ICAM-2-FITC surface binding (fluorescence intensity) and surface distribution (fluorescence pulse) in cytochalisin D treated Jurkat cells at 37° C. and 4° C. by flow cytometry. E) Values for ICAM-2-FITC fluorescence intensity per time-of-flight per cell as described in text. F) Flow cytometric staining for LFA-1 activation by mAb24-alexa633. Stimuli as indicated (10, µM, 30, min), PMA (1, µg/ml) prior to ICAM-2, stimulation (10, µg/ml, 30, min). Staining was performed at 37° C. G) Mean fluorescence intensity (MFI) values of mAb24-633, and ICAM-2, cluster values, computed as described above, as a function of time.

H-I) depict ICAM-2, induced p44/42, MAPK phosphorylation, and inhibition by LFA-1, mAb and comparison with other stimuli. H) Phospho-p44/42, MAPK immunoblot of total lysates from Jurkat cells stimulated with ICAM-2, (concentrations indicated in figure, 30, min) and subsequently blocked with increasing concentrations of LFA-1, mAb. I) Comparison of phospho-p44/2, MAPK induction to stimuli using FACS based detection of phospho-p44/42, MAPK. Stimuli were either 1 mg/ml (PHA, PMA, ionomycin), 10, mg/ml (LFA-1, mAb and ICAM-2), or 10, mM for PD98059, and U0126. Chemical inhibition was done 30, min prior to stimulation. Data is presented as percent phospho-p44/24, MAPK positive cells relative to unstimulated cells. Note the difference between LFA-1, mAb crosslinking and ICAM-2, stimulation.

FIG. 35 depicts the results of experiments demonstrating ICAM-2, induced p44/42, MAPK activation via LFA-1, interaction. A) Mean fluorescent intensity values (MFI) of ICAM-2-FITC (adhesion) and mAb24-Alexa633, (LFA-1, activation) in treated Jurkat cells (as above). Control unstimulated and/or compound pretreated values were subtracted. B) Top panel: Intracellular phospho-p44/42, MAPK detection as a function of ICAM-2, dose in Jurkat cells by flow cytometry (see Material and Methods). Mean fluorescent intensity values (MFI) were plotted±standard deviation (SD). Bottom panel: ICAM-2, treated Jurkat cells were stained for intracellular phospho-p44/42, MAPK as described above. mAbs to β2, and $α_L$, integrins (10, µg/ml, 10, minutes) were titrated prior to ICAM-2, treatment as indicated and plotted for MFI±SD. C) ICAM-2, induced p44/42, MAPK activity is blocked by β2, and $α_L$, integrin antibodies as determined by a p44/42 MAPK kinase assay. Conditions for induction and inhibition are as described above. Recombinant active p44/ 42, MAPK served as an internal positive control (denoted by "+"). D) Inhibition and activation profile for intracellular phospho-p44/42, by flow cytometry in the presences of chemical agents (10, μM), EDTA (1, mM), or PMA, ionomycin and ICAM-2, stimulus (as indicated above). MFI values±SD are plotted.

E) depicts that sICAM-2, induces Pyk2, and Syk membrane localization. Confocal Microscopy of Jurkat cells treated with ICAM-2, protein (10, mg/ml) or bovine serum albumin (Unstimulated, 10 mg/ml) for 10, minutes and prepared for confocal microscopy (see material and methods). Cells were stained for Pyk2, and Syk. Panels A-C represents unstimulated cells and panels D-F represent ICAM-2, treated cells. Scale bar is denoted in lower left corner of panels (in micrometers).

FIG. 36 depicts the results of experiments demonstrating ICAM-2, induced phosphorylation of Pyk2, and Syk, and β2, integrin association. A) Phospho-raf and phospho-p44/42, immunoblot inhibition profile by tyrosine kinase inhibitors. $1×10^6$, cells were treated with indicated compound (10, μM, 30, min) and then stimulated with ICAM-2, (10, μg/ml, 30, min). Cell lysates were immunoblotted for phospho-raf and phospho-p44/42. Compound alone did not induce detectable phosphorylation. B) Pyk2, and Syk are phosphorylated and co-immunoprecipitate with β2, integrin upon ICAM-2, stimulus. Phospho-specificity was determined by phospho-PykpY402, and phospho-syk (Tyr525/526) antibodies. C) Kinetic analyses of the phosphorylation state of PKCα/β, Pyk2, and Syk as a function of ICAM-2, stimulus per time. Cells were treated and processed as above. Phospho-specific $PKCα/β_{II}$, (Thr638) and the following antibodies were used; Pyk2, and Syk were first immunoprecipitated, probed with anti-phosphotyrosine antibody (PY20), stripped and subsequently probed with indicated non-phospho specific antibody. Immunoblots are representative of triplicate experiments.

E) depicts that LFA-1, induced phosphorylation of Pyk2, and Syk is dependent on PKC. We screened for the inhibition of sICAM-2, induced Pyk2, and Syk phosphorylation by chemical inhibitors to tyrosine kinases using a phospho-tyrosine based ELISA. Pyk2, phosphorylation was abrogated in the presence of PKC inhibitors bisindolymaleimide II (BIM II) and staurosporine (STP), in addition to tyrphostin A9, a specific Pyk2, inhibitor. a Pyk2, phosphorylation was also affected by inhibitors of phospholipase Cg (neomycin), inhibitors of Syk (piceatannol), and PKC inhibitor BIM I. Syk phosphorylation was completely abolished by inhibition of Pyk2, PLCg1, and strongly affected by PKC inhibitors. Thus, both Pyk2, and Syk phosphorylations were dependent on PKC activity, while Syk phosphorylation was additionally dependent on PLCg1, and Pyk2, activity. It was not possible to assess specific PKC isozymes by this method.

A chemical genetic approach was undertaken to determine the hierarchy of PKC, Pyk2, PLCg1, and Syk activities in response to sICAM-2, stimulus by verifying phosphorylation status of each kinase in the presence of respective chemical inhibitors. Inhibition of PKC with BIM II abrogated phosphorylation of Pyk2, PLCg1, and Syk. Inhibition of PLCg1, by neomycin abrogated phosphorylation of Syk, with no inhibition observed for Pyk2. Inhibition of Syk by piceatannol did not block phosphorylation of Pyk2, or PLCg1. These observations suggest that PKC activation is upstream of PYK2, PLCg, and SYK activities, and also that SYK activity is consequential to PYK2 and PLCg1, activity. Thus, the upstream signaling events from LFA-1, to Raf-1, appear to involve PKC/Pyk2/PLCg1/Syk. However, we acknowledge that phospho-protein immunoprecipitation techniques do not exclude the possibility of these molecules existing in complexes. We are currently pursuing these complexes in a separate study.

FIG. 37 depicts the results of experiments demonstrating that ICAM-2, induces cytotoxic lymphocyte activity in IL-2, activated human PBMC. A) PBMC were either treated with ICAM-2, (10 μg/ml) in the presence of IL-2, for 12, hr and then incubated with CFSE labeled target HL60, cells at a 50:1, E:T ratio for 4, hrs. Remaining HL60, cells were quantified by flow cytometry. B) PBMC were treated with IL-2, (100, U/ml, 12, hrs) and treated with ICAM-1,-2, or 3, FC proteins (10, μg/ml) and used in a cytotoxicity assay as described above. Results are representative of 4, independent experiments.

FIG. 38 depicts the results of experiments demonstrating ICAM-2, exhibits differences to ICAM-1 and ICAM-3, in mediating perforin and granzyme release from $CD56^+$, $CD8^+$, cytotoxic lymphocytes subsets. IL-2, activated PBMC (shown in A-1 and A-3) were mock-treated (IgG) (A-2), ICAM-1, (A2), ICAM-2, (A4), or ICAM-3, (A4) treated (10, μg/ml of FC fusion protein) for 12 hrs prior to incubation with target HL60, cells at a 50:1, E:T ratio for 4, hrs. Cells were then prepared for flow cytometry with CD8-CY5PE, CD56-PE surface stains, and perforin-CY5, and granzyme-A-FITC intracellular stains. Cells were gated for $CD56^{+CD8^{low}}$, $CD56^{+CD8^{med}}$, $CD56^+$, $CD8^{high}$, $CD56^-$, $CD8^-$, , $CD56^{--}$ $CD8^{high}$, populations as shown in A-1 and A-3 and population frequencies within appropriate gate. A-2 and A-4 are subset gated populations displayed for perforin and granzyme-A log fluorescent intensities. Results are representative of 3 independent experiments and were similar at 25:1 and 12.5:1 E:T ratios (data not shown). Manual calibration was performed. B) CD56CD8, population subsets were gated (as indicated) and displayed for intracellular perforin for ICAM-1, -2, -3, stimulated cells. Perforin percentage was calculated from the following equation where MFI equals mean fluorescent intensity: $100×[(MFI_{experimental}−MFI_{isotype\ mAb})/(MFI_{control}−MFI_{isotype\ mAb})]$ Unstimulated cells were used as control. C) Intracellular granzyme-A values were calculated and displayed as described above.

FIG. 39 depicts the results of experiments demonstrating that ICAM-2, induced LFA-1, mediated p44/42, MAPK correlates with LFA-1, activation in human $CD56^+$, $CD8^+$, cells. A) Conjugate formation of CFSE labeled HL60, cells and $CD56^+$, $CD8^+$, cells. Conjugate flow cytometric based assay was performed on PBMC treated with indicated chemicals (10, μM, 30, min) prior to treatment with ICAM-2, (10, μg/ml, 30, min). CFSE labeled HL60, cells were incubated at 25:1, E:T ratio for 5, min, and fixed with 1% paraformaldehyde. Cells were then immunolabeled with CD8 and CD56, antibodies, gated for $CD8^+$, $CD56^+$, cell populations and percent HL60, fluorescence was made relative to total HL60, cells. B) IL-2, activated PBMC were either treated with ICAM-2, (10 μg/ml, 30, min) or mock-treated (IgG) and stained for active-LFA-1, (mAb24-Alexa633), phospho-p44/42-Ax488, CD8-CY5PE, and CD56-PE. $CD56^+$, $CD8^+$, cell populations are gated and displayed for active LFA-1, vs. phospho-p44/42. The mean fluorescent intensities (MFI) of mAb24-Ax633 and phospho-44/42-Ax488, were computed and displayed over time as described above.

DETAILED DESCRIPTION OF THE INVENTION

Intracelluar assays of signaling systems have been limited by an inability to correlate functional subsets of cells in complex populations based on the activity of signaling agents, for example, the activity of kinases. Such correlations are important for distinguishing changes in signaling status that arise in rare cell subsets during signaling or in disease manifestations. The present invention solves these problems by providing methods and compositions for simultaneously detecting the activation state of a plurality of activatable proteins in single cells using flow cytometry. The invention further provides methods and compositions of screening for bioactive agents capable of coordinately modulating the activity or activation state of a plurality of activatable proteins in single cells. The methods and compositions can be used to determine the protein activation profile of a cell for predicting or diagnosing a disease state, and for monitoring treatment of a disease state. Further, the methods and compositions of the present invention can be used optionally to sequentially detect the activation state of a plurality of activatable proteins in single cells. In addition, the methods and compositions of the present invention can be used optionally to detect the activation state of a single protein or modulate the activity or activation state of a single protein in single cells.

The methods and compositions of the present invention may be used to detect any particular protein isoform in a sample that is antigenically detectable and antigenically distinguishable from other isoforms of the protein which are present in the sample. For example, as demonstrated (see, e.g., the Examples) and described herein, the activation state-specific antibodies of the present invention can be used in the present methods to identify distinct signaling cascades of a subset or subpopulation of complex cell populations; and the ordering of protein activation (e.g., kinase activation) in potential signaling hierarchies. Further, in the methods of the present invention, the use of flow cytometry, particularly polychromatic flow cytometry, permits the multi-dimensional analysis and functional assessment of the signaling pathway in single cells.

As used herein, the term "activation state-specific antibody" or "activation state antibody" or grammatical equivalents thereof, refer to an antibody that specifically binds to a corresponding and specific antigen. Preferably, the corresponding and specific antigen is a specific isoform of an activable protein. Also preferably, the binding of the activation state-specific antibody is indicative of a specific activation state of a specific activatable protein. Thus, in preferred embodiments, the binding of an activation state-specific antibody to a corresponding isoform of an activatable protein is indicative of the identity of the activatable protein and of the activation state of the activatable protein.

In a preferred embodiment, the activation state-specific antibody is a peptide comprising a recognition structure that binds to a target structure on an activatable protein. A variety of recognition structures are well known in the art and can be made using methods known in the art, including by phage display libraries (see e.g., Gururaja et al. Chem. Biol. (2000) 7:515-27; Houimel et al., Eur. J. Immunol. (2001) 31:3535-45; Cochran et al. J. Am. Chem. Soc. (2001) 123:625-32; Houimel et al. Int. J. Cancer (2001) 92:748-55, each incorporated herein by reference). In a preferred embodiment, the activation state-specific antibody comprises the following recognition structure: SKVILFE (SEQ ID NO: 01)—random peptide loop—SKVILFE (SEQ ID NO: 01). Antibodies having such recognition structures can bind with high affinity to specific target structures. Further, fluorophores can be attached to such antibodies for use in the methods of the present invention.

A variety of recognitions structures are known in the art (e.g., Cochran et al., J. Am. Chem. Soc. (2001) 123:625-32; Boer et al., Blood (2002) 100:467-73, each expressly incorporated herein by reference)) and can be produced using methods known in the art (see e.g., Boer et al., Blood (2002) 100:467-73; Gualillo et al., Mol. Cell. Endocrinol. (2002) 190:83-9, each expressly incorporated herein by reference)), including for example combi chem methods for producing recognition structures such as polymers with affinity for a target structure on an activable protein (see e.g., Barn et al., J. Comb. Chem. (2001) 3:534-41; Ju et al., Biotechnol. (1999) 64:232-9, each expressly incorporated herein by reference). In another preferred embodiment, the activation state-specific antibody is a protein that only binds to an isoform of a specific activatable protein that is phosphorylated and does not bind to the isoform of this activatable protein when it is not phosphorylated or nonphosphorylated. In another preferred embodiment the activation state-specific antibody is a protein that only binds to an isoform of an activatable protein that is intracellular and not extracellular, or vice versa.

In a preferred embodiment, the recognition structure is an anti-laminin single-chain antibody fragment (scFv) (see e.g., Sanz et al., Gene Therapy (2002) 9:1049-53; Tse et al., J. Mol. Biol. (2002) 317:85-94, each expressly incorporated herein by reference).

As used herein, the terms "polypeptide" and "protein" may be used interchangeably and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

As used herein, an "activatable protein" or "substrate" or "substrate protein" or "protein substrate" grammatical equivalents thereof, refers to a protein that has at least one isoform (and in some cases two or more isoforms) that corresponds to a specific form of the protein having a particular biological, biochemical, or physical property, e.g., an enzymatic activity, a modification (e.g., post-translational modification), or a conformation. The activable protein can be activated or nonactivated with respect to a particular biological activity, modification, or conformation. Specifically, the "activated" or "active" form of the activatable protein has the particular biological activity, modification, or conformation, whereas the "non-activated" or "non-active" form of the activatable protein does not have (or has a lesser or diminished level of) the particular biological activity, modification, or conformation, respectively. In some embodiments, there may be more than one isoform associated with activity or activation state; for example, there may be an isoform associated with an "open" conformation available for substrate binding, a second "transition state" isoform, and an isoform devoid of activity (e.g., where the activity is inhibited). Examples of activatable proteins include, but are not limited to, phosphoproteins and phospho-lipids. Further examples of activatable proteins include, but are not limited to, kinases, phosphatases, PIP2, PIP3, and proteases such as cysteine and serine proteases, including, but not limited to caspases, cathepsins and a variety of well known serine proteases.

In a preferred embodiment, the biological, biochemical, or physical property (e.g. enzymatic activity, modification, or conformation) of the activatable protein is inducible or "activatable" by an activating agent or by cell signaling events. Examples of activating agents include, but are not limited to, kinases, phosphatases, proteases (e.g., caspases), and hormones. Examples of cell signaling events include, but are not limited to, receptor clustering or binding of a cognate molecule or ligand.

As used herein, an "isoform" or grammatical equivalents thereof, refers to a form of an activatable protein having a specific, and preferably detectable, biological activity, modification, or conformation. The isoform can be an activated (or active) form, or non-activated (or not active) form of an activatable protein. As mentioned, in preferred embodiments, the binding of an activation state-specific antibody to a corresponding isoform of an activable protein is indicative of the identity of the activatable protein and of the activation state of the activatable protein. In a preferred embodiment, the invention provides methods for determining a protein isoform profile which comprise determining the presence of an isoform of an activatable protein that is activated (or activated isoform).

In a preferred embodiment, the activated isoform or activated state of an activable protein is a form of the activable protein having a particular or specific biological, biochemical, or physical property that is not possessed by at least one other isoform of activatable protein. Examples of such properties include, but are not limited to, enzymatic activity (e.g., kinase activity and protease activity), and protein binding activity. Thus, such particular or specific properties or activities are associated with an activated isoform of an activatable protein. Such properties or activities are sometimes referred to herein as activation state activities.

An example of activation state activity is kinase activity for an activated protein kinase. As used herein, a protein kinase may refer to a protein that when activated is capable of catalyzing the phosphorylation of amino acids, or derivatives thereof, which possess an hydroxyl group. Preferred kinases are those which are capable of catalyzing the phosphorylation of serine, threonine, and tyrosine residues. Kinase activity may be determined by supplying a substrate for phosphorylation by kinase, a source of phosphate usable by kinase, and determining the phosphorylation of substrate in the presence of kinase.

Another example of activation state activity is protease activity for an activated protease. As used herein, a protease may refer to a protein that when activated is capable of hydrolyzing a peptide bond within a polypeptide comprising an amino acid sequence. Preferred proteases are the family of cysteine proteases known as caspases. Caspase activity may be determined by providing a substrate of a caspase and determining the cleavage of substrate in the presence of caspase. Other cysteine proteases having activations states that may be monitored using the methods of the invention include, but are not limited to, *cathespins*. Similarly, an additional class of proteases that may be monitored using the methods of the invention include serine proteases, of which a wide variety of suitable classes are known.

The antigenicity of an activated isoform of an activatable protein is distinguishable from the antigenicity of non-activated isoform of an activable protein or from the antigenicity of an isoform of a different activation state. In a preferred embodiment, an activated isoform of a protein possesses an epitope that is absent in a non-activated isoform of a protein, or vice versa. In another preferred embodiment, this difference is due to covalent addition of moieties to a protein, such as phosphate moieties, or due to a structural change in a protein, as through protein cleavage, or due to an otherwise induced conformational change in a protein which causes the protein to present the same sequence in an antigenically distinguishable way. In another preferred embodiment, such a conformational change causes an activated isoform of a protein to present at least one epitope that is not present in a non-activated isoform, or to not present at least one epitope that is presented by a non-activated isoform of the protein. In some embodiments, the epitopes for the distinguishing antibodies are centered around the active site of the enzyme, although as is known in the art, conformational changes in one area of a protein may cause alterations in different areas of the protein as well.

Among proteins that are capable of existing in a non-activated isoform and an activated isoform, which isoforms are antigenically distinguishable, are kinases. Kinases are enzymes that catalyze protein phosphorylation on serine, threonine, or tyrosine residues. The majority of kinases are phosphoproteins that are reversibly phosphorylated as a form of activity regulation. In the phosphorylated form (phosphorylated isoform), protein kinases are typically enzymatically active kinases. In the un-phosphorylated form, protein kinases are typically enzymatically inactive.

Many antibodies, many of which are commercially available (for example, see Cell Signaling Technology, www(dot)cellsiganal(dot)com, the contents which are incorporated herein by reference). have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein kinases and are sometimes referred to herein as kinase activation state antibodies or grammatical equivalents thereof. Particularly preferred antibodies for use in the present invention include: phospho-AKT Ser473, monoclonal anti-4E2, phospho-p44/42, MAP kinase (Thr202/Tyr204) monoclonal antibody, phospho-TYK2, (Tyr1054/1055) antibody, phospho-p38, MAP kinase (Thr180/Tyr182) monoclonal antibody 28B10, phospho-PKC-PAN substrate antibody, phospho-PKA-substrate, phospho-SAPK/JNK (Thr183/Tyr185) G9, monoclonal antibody, phospho-tyrosine monoclonal antibody (P-tyr-100), p44/42, MAPK, p38, MAPK, JNK/SAPK, and phospho-AKT-Thr308.

The present invention provides methods for the determination of a kinase activation state profile for a sample which comprise simultaneously determining the presence of activated isoforms of a multiplicity of kinases using a multiplicity of antibodies that specifically bind to active, phosphorylated isoforms of the multiplicity of kinases.

Another example of proteins that are capable of existing in a non-activated isoform and an activated isoform, which isoforms are antigenically distinguishable, are caspases. Caspases are proteases that catalyze the hydrolysis of peptide bonds within proteins. Caspases are synthesized as pro-caspases which are proteolytically inactive precursors of caspases. A pro-caspase is specifically cleaved by protease to yield an active caspase. As is known in the art, this is known to be true for a variety of other proteases, including both cysteine and serine proteases such as cathepsins, tissue plasminogen activators, etc., that are known to exist as pro-proteases, as is well known in the art.

The present invention provides methods for the determination of a caspase activation state profile for a sample which comprise simultaneously determining the presence of activated isoforms of a multiplicity of caspases using a multiplicity of antibodies that specifically bind to a multiplicity of caspases but not to the correlating pro-caspases from which they may be derived. For example, antibodies which specifically bind to caspases but do not specifically bind to pro-caspases from which caspases are derived are useful in the methods of the invention. Many such antibodies are commercially available (for example, see Cell Signaling Technology, www(dot)cellsignal(dot)com, the contents of which are incorporated herein by reference).

Additional means for determining kinase activation are provided by the present invention. Substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

In a preferred embodiment, the present invention provides methods for determining a kinase activation state profile for a sample, comprising providing a population of cells comprising a plurality of activatable proteins and contacting the cells with at least one non-phosphorylated protein kinase substrate under conditions which provide for phosphorylation of the substrate by activated kinase if present, and determining the presence of phosphorylated protein kinase substrate using a phospho-substrate antibody that binds specifically to the phosphorylated substrate. In a preferred embodiment, the present invention provides methods for determining a kinase activation state profile for a sample which comprises the use of a multiplicity of protein kinase substrates, a multiplicity of phospho-substrate antibodies, and a multiplicity of activation state antibodies to simultaneously determine the activation state of a multiplicity of kinases.

In another embodiment, the present invention provides methods for determining the activation state of one or more protein kinases and one or more caspases in a sample by combining the methods described for determining the activation state profile of each provided herein. Preferably, the sample comprises a population of cells, a cell, cell lysate, or proteins.

Similarly, the invention provides methods utilizing any and all other combinations of kinases and proteases (e.g., kinases and caspases, kinases and cathepsins, kinases and serine proteases, caspases and cathepsins, etc.).

In a further embodiment, a protein activation state profile is determined using a multiplicity of activation state antibodies that are immobilized. Antibodies may be non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included.

The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the antibody on the surface, etc. Following binding of the antibody, excess unbound material is removed by washing. The sample receiving areas may then be blocked through incubation with bovine serum albumin (BSA), casein or other innocuous protein or other moiety.

In a preferred embodiment, an epitope-recognizing fragment of an activation state antibody rather than the whole antibody is used. In another preferred embodiment, the epitope-recognizing fragment is immobilized. In another preferred embodiment, the antibody light chain which recognizes an epitope is used. A recombinant nucleic acid encoding a light chain gene product which recognizes an epitope may be used to produce such an antibody fragment by recombinant means well known in the art.

A chip analogous to a DNA chip can be used in the methods of the present invention. Arrayers and methods for spotting nucleic acid to a chip in a prefigured array are known. In addition, protein chips and methods for synthesis are known. These methods and materials may be adapted for the purpose of affixing activation state antibodies to a chip in a prefigured array.

In a preferred embodiment, such a chip comprises a multiplicity of kinase activation state antibodies, and is used to determine a kinase activation state profile for a sample. In a preferred embodiment, such a sample is a cell extract. In such a method, detection of activated kinase is by "sandwich assay" as known in the art. Briefly, a sample, preferably a cell extract, is passed over a the chip under conditions which allow the multiplicity of immobilized kinase activation state antibodies to simultaneously bind to a multiplicity of activated kinases if present in the sample. The immobilized antibody-kinase complex is optionally washed and contacted with a second plurality of antibodies comprising non-activation state antibodies that are capable of specifically binding to activated kinases while the kinases are specifically bound to kinase activation state specific antibodies. Such non-activation state specific antibodies specifically bind to activated kinases via an epitope that is not recognized by the kinase activation state specific antibody. Binding of the non-activation state specific antibodies to the activation state antibody-activated kinase complex is determined and reveals the presence of activated kinase in sample. As will be appreciated, the determination of binding of second antibody in the sandwich assay can be accomplished in many different ways. Preferably, the multiplicity of non-activation state specific antibodies are uniquely labeled to facilitate detection.

In an alternative embodiment, a chip comprises a multiplicity of non-activation state specific antibodies. Such a chip is contacted with sample, preferably cell extract, and a second multiplicity of antibodies comprising kinase activation state specific antibodies is used in the sandwich assay to simultaneously determine the presence of a multiplicity of activated kinases in sample. Preferably, the multiplicity of activation state specific antibodies are uniquely labeled to facilitate detection.

In a preferred embodiment, one or more components of the methods of the present invention comprise a tag. By "tag" is meant an attached molecule or molecules useful for the identification or isolation of the attached molecule(s), which are preferably substrate molecules. For example, a tag can be an attachment tag or a label tag. Components having a tag are referred to as "tag-X", wherein X is the component. Preferably, the tag is covalently bound to the attached component. When more than one component of a combination has a tag, the tags will be numbered for identification, for example, "tag1-antibody", "tag1-protein", and "tag1-substrate". Components may comprise more than one tag, in which case each tag will be numbered, for example "tag 1,2-antibody", "tag1, 2-protein", and "tag1,2-substrate". Preferred tags include, but are not limited to, a label, a partner of a binding pair, and a surface substrate binding molecule (or attachment tag). As will be evident to the skilled artisan, many molecules may find use as more than one type of tag, depending upon how the tag is used.

By "label" is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. Preferred labels include, but are not limited to, fluorescent labels, label enzymes and radioisotopes.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705, and Oregon green. Suitable optical dyes are described in the 1996, Molecular Probes Handbook by Richard P. Haugland, hereby expressly incorporated by reference. Suitable fluorescent labels also include, but are not limited to, green fluorescent protein (GFP; Chalfie, et al., *Science* 263 (5148):802-805, (Feb. 11, 1994); and EGFP; Clontech-Genbank Accession Number U55762), blue fluorescent protein (BFP; 1. Quantum Biotechnologies, Inc. 1801, de Maisonneuve Blvd. West, 8th Floor, Montreal (Quebec) Canada H3H 1J9; 2. Stauber, R. H. Biotechniques 24(3):462-471, (1998); 3. Heim, R. and Tsien, R. Y. Curr. Biol. 6:178-182, (1996)), enhanced yellow fluorescent protein (EYFP; 1. Clontech Laboratories, Inc., 1020, East Meadow Circle, Palo Alto, Calif. 94303), luciferase (Ichiki, et al., *J. Immunol.* 150(12): 5408-5417, (1993)), β-galactosidase (Nolan, et al., *Proc Natl Acad Sci USA* 85(8):2603-2607, (April 1988)) and *Renilla*, WO 92/15673; WO 95/07463; WO 98/14605; WO 98/26277; WO 99/49019; U.S. Pat. No. 5,292,658; U.S. Pat. No. 5,418, 155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925, 558). All of the above-cited references are expressly incorporated herein by reference.

Particularly preferred labels for use in the present invention include: ALEXA FLUOR® dyes (sulfonated amino-coumarin or rhodamine) (ALEXA FLUOR® 350, ALEXA FLUOR® 430, ALEXA FLUOR® 488, ALEXA FLUOR® 546, ALEXA FLUOR® 568, ALEXA FLUOR® 594, ALEXA FLUOR® 633, ALEXA FLUOR® 660, ALEXA FLUOR® 680), CASCADE BLUE® (pyrenyloxytrisulfonic acid), CASCADE YELLOW™ and R-phycoerythrin (PE) (Molecular Probes) (Eugene, Oreg.), FITC, Rhodamine, and TEXAS RED® (tetramethylrhodamines with extra iulolidine rinds) (Pierce, Rockford, Ill.), Cy5, Cy5.5, Cy7, (Amersham Life Science, Pittsburgh, Pa.). Tandem conjugate protocols for Cy5PE, Cy5.5PE, Cy7PE, Cy5.5APC, Cy7APC can be found at www(dot)drmr(dot)com/abcon. Quantitation of fluorescent probe conjugation may be assessed to determine degree of labeling and protocols including dye spectral properties can be found at www(dot)metazoa(dot)com/UPL3419.

In another preferred embodiment, the fluorescent label is a GFP and, more preferably, a *renilla, ptilosarcus*, or *aequorea*, species of GFP.

In preferred embodiments, multiple fluorescent labels are employed in the methods and compositions of the present invention. In a preferred embodiment, at least two fluorescent labels are used which are members of a fluorescence resonance energy transfer (FRET) pair.

FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Förster radius ($R_0$), which is typically 10-100, Å. Changes in the fluorescence emission spectrum comprising FRET pairs can be detected, indicating changes in the number of that are in close proximity (i.e., within 100, Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescien, IAEDANS/fluorescein, fluorescein/tetramethylrhodamine, fluorescen/LC Red 640,fluorescein/Cy 5, fluorescein/Cy 5.5 and fluorescein/LC Red 705.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, TAMRA, DABCYL, QSY™ 7, and QSY™ 33, (QSY™ are fluorescein derivatives). Useful fluorescent donor/quencher pairs include, but are not limited to EDANS/DABCYL, TEXAS RED® /DABCYL, BODIPY/DABCYL, Lucifer yellow/DABCYL, coumarin/DABCYL and fluorescein/ QSY™ 7, dye.

The skilled artisan will appreciate that FRET and fluorescence quenching allow for monitoring of binding of labeled molecules over time, providing continuous information regarding the time course of binding reactions.

By "label enzyme" is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., *Previews* 247:6-9, (1998), Young, *J. Virol. Methods* 24:227-236, (1989), which are each hereby incorporated by reference in their entirety.

By "radioisotope" is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

As mentioned, labels may be indirectly detected, that is, the tag is a partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avid (or biotin/streptavidin) and calmodulin binding protein (CBP)/calmodulin. Other suitable binding pairs include polypeptides such as the FLAG-peptide [Hopp et al., *BioTechnoloqy*, 6:1204-1210, (1988)]; the KT3, epitope peptide [Martin et al., *Science*, 255:192-194, (1992)]; tubulin epitope peptide [Skinner of al., *J. Biol. Chem.*, 266: 15163-15166, (1991)]; and the T7, gene 10, protein peptide tag [Lutz-Freyermuth et al., *Proc. Natl. Acad. Sci. USA*, 87:6393-6397, (1990)] and the antibodies each thereto. As will be appreciated by those in the art, binding pair partners may be used in applications other than for labeling, as is described herein.

As will be appreciated by those in the art, a partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5, substrate [Field et al., *Mol. Cell. Biol.*, 8:2159-2165, (1988)]; the c-myc tag and the 8F9, 3C7, 6E10, G4, B7, and 9E10, antibody substrates thereto [Evan et al., *Molecular and Cellular Biology*, 5:3610-3616, (1985)]; and the Herpes Simplex virus glycoprotein D (gD) tag and its antibody substrate [Paborsky et al., *Protein Engineering*, 3(6):547-553, (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin. Production of antibody-embedded substrates is well known; see Slinkin et al., *Bioconj. Chem.* 2:342-348, (1991); Torchilin et al., supra; Trubetskoy et al. *Bioconj. Chem.* 3:323-327, (1992); King et al., *Cancer Res.* 54:6176-6185, (1994); and Wilbur et al., *Bioconjugate Chem.* 5:220-235 (1994) (all of which are hereby expressly incorporated by reference), and attachment of or production of proteins with antigens is described above. Calmodulin-embedded substrates are commercially available, and production of proteins with CBP is described in Simcox et al., Strategies 8:40-43, (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of tag-labeled proteins is well known in the art and kits for such production are commercially available (for example, from Kodak and Sigma). Examples of tag labeled proteins include, but are not limited to, a Flag-polypeptide and His-polypeptide. Methods for the production and use of tag-labeled proteins are found, for example, in Winston et al., *Genes and Devel.* 13:270-283, (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., *Molec. Cell* 3:535-541, (1999), which is hereby incorporated by reference in its entirety.

Production of proteins having tags by recombinant means is well known, and kits for producing such proteins are commercially available. For example, such a kit and its use is described in the QIAexpress Handbook from Qiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment. The covalent attachment of the tag may be either direct or via a linker. In one embodiment, the linker is a relatively short coupling moiety, that is used to attach the molecules. A coupling moiety may be synthesized directly onto a component of the invention and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. In a preferred embodiment, the tag is attached to the amino or carboxl terminus of the polypeptide. As will be appreciated by those in the art, the above description of the covalent attachment of a label applies to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a protein, amino modified or hydrazine modified tags will be used for coupling via carbodiimide chemistry, for example using 1-ethyl-3-(3-dimethylaminopropyl)-carbodiimide (EDAC) as is known in the art (see Set 9, and Set 11, of the Molecular Probes Catalog, supra; see also the Pierce 1994, Catalog and Handbook, pages T-155, to T-200, both of which are hereby incorporated by reference). In one embodiment, the carbodiimide is first attached to the tag, such as is commercially available for many of the tags described herein.

Antibody conjugation may be preformed using standard procedures( http(colon)//drmr(dot)com(dot)abcon) or by using protein-protein/protein-dye crosslinking kits from Molecular Probes (Eugene, Oregon).

Using the example of two activation state specific antibodies, by "uniquely labeled" is meant that a first activation state antibody recognizing a first activated kinase comprises a first label, and second activation state antibody recognizing a second activated kinase comprises a second label, wherein the first and second label are detectable and distinguishable, making the first antibody and the second antibody uniquely labeled.

Non-activation state antibodies may also be used in the present invention. In a preferred embodiment, non-activation state antibodies bind to epitopes in both activated and non-activated forms of a protein. Such antibodies may be used to determine the amount of non-activated plus activated protein in a sample. In another preferred embodiment, non-activation state antibodies bind to epitopes present in non-activated forms of a protein but absent in activated forms of a protein. Such antibodies may be used to determine the amount of non-activated protein in a sample. Both types of non-activation state antibodies may be used to determine if a change in the amount of activation state protein, for example from samples before and after treatment with a candidate bioactive agent as described herein, coincide with changes in the amount of non-activation state protein. For example, such antibodies can be used to determine whether an increase in activated protein is due to activation of non-activation state protein, or due to increased expression of protein, or both.

In another preferred embodiment, antibodies are immobilized using beads analogous to those known and used for standardization in flow cytometry. Attachment of a multiplicity of activation state specific antibodies to beads may be done by methods known in the art and/or described herein. Such conjugated beads may be contacted with sample, preferably cell extract, under conditions which allow for a multiplicity of activated kinases, if present, to bind to the multiplicity of immobilized antibodies. A second multiplicity of antibodies comprising non-activation state antibodies which are uniquely labeled may be added to the immobilized activation state specific antibody-activated kinase complex and the beads may be sorted by FACS on the basis of the presence of each label, wherein the presence of label indicates binding of corresponding second antibody and the presence of corresponding activated kinase.

In a preferred embodiment, the present invention provides methods for determining a protein activation state profile for a single cell. The methods comprise sorting cells by FACS on the basis of the activation state of at least two proteins. Activation state-specific antibodies are used to sort cells on the basis of protein activation state.

When using fluorescent labeled components in the methods and compositions of the present invention, it will recognized that different types of fluorescent monitoring systems, e.g., FACS systems, can be used to practice the invention. Preferably, FACS systems are used or systems dedicated to high throughput screening, e.g 96, well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In a preferred embodiment, flow cytometry is used to detect fluorescence. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference).

In a preferred embodiment, FRET is used as a way of monitoring the activation state of proteins inside a cell. The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker can increase the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The ratio-metric fluorescent reporter system described herein has significant advantages over existing reporters for protein integration analysis, as it allows sensitive detection and isolation of both expressing and non-expressing single living cells. In a preferred embodiment, the assay system uses a non-toxic, non-polar fluorescent substrate which is easily loaded and then trapped intracellularly. Modification of the fluorescent substrate by a cognate protein yields a fluorescent emission shift as substrate is converted to product. Because the reporter readout is ratiometric it is unique among reporter protein assays in that it controls for variables such as the amount of substrate loaded into individual cells. The stable, easily detected, intracellular readout eliminates the need for establishing clonal cell lines prior to expression analysis. This system and other analogous flow sorting systems can be used to isolate cells having a particular protein activation profile from pools of millions of viable cells.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety FACS systems are known in the art and can be used in the methods of the invention (see e.g., WO99/54494, filed Apr. 16, 1999; U.S.A.N. 20010006787, filed Jul. 5, 2001, each expressly incorporated herein by reference).

In a preferred embodiment, a FACS cell sorter (e.g. a FACSVantage™ Cell Sorter, Becton Dickinson Immunocytometry Systems, San Jose, Calif.) is used to sort and collect cells based on their protein activation profile (positive cells). The cells are first contacted with fluorescent-labeled activation state-specific antibodies directed against specific isoforms of specific activatable proteins. In one embodiment, the amount of bound antibody on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell sorting procedures are described in detail, for example, in the FACSVantage™ Training Manual, with particular reference to sections 3-11, to 3-28, and 10-1, to 10-17.

In another embodiment, positive cells can be sorted using magnetic separation of cells based on the presence of an isoform of an activatable protein. In such separation techniques, cells to be positively selected are first contacted with specific binding agent (e.g., an antibody or reagent that binds an isoform of an activatable protein). The cells are then contacted with retrievable particles (e.g., magnetically responsive particles) which are coupled with a reagent that binds the specific binding agent (that has bound to the positive cells). The cell-binding agent-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual.

In a preferred embodiment, methods for the determination of a kinase activation state profile for a single cell are provided. The methods comprise providing a population of cells and sorting the population of cells by FACS. Preferably, cells are separated on the basis of the activation state of at least two kinases. In a preferred embodiment, a multiplicity of kinase activation state antibodies (sometimes referred to herein as kinase activation state specific antibodies) are used to simultaneously determine the activation state of a multiplicity of kinases. Particularly preferred is the use of at least two, preferably more than two, preferably all of the following kinase activation state antibodies: anti-AKT-phospho-Ser473, anti-AKT phospho-Thr308, anti-p44/42, MAPK phospho-Thr202/Tyr204, anti-TYK2, phospho-Tyr1054/1055, anti-p38, MAPK phospho-Thr180/Tyr182, anti-JNK/SAPK phospho-Thr183/Tyr185, anti-phospho-tyrosine, anti-phospho-threonine.

In addition to the direct detection of phosphorylated kinases in single cells, the methods provide for the detection of activated kinases in single cells using specific substrates for kinases and phospho-substrate antibodies as described herein. In a preferred embodiment, cells are contacted with at least two such substrates, contacted with phospho-substrate antibodies, and then sorted on the basis of kinase activation using a FACS machine. Particularly preferred are phospho-substrate antibodies that specifically bind to PKC substrate PAN phospho-substrate (which is a substrate for α, βI, βII, and δ isoforms of PKC only when phosphorylated at a carboxy terminal residue homologous to Ser660, of PKCβII), and phospho-substrate antibodies that specifically bind to PKA phospho-substrate (consensus phosphorylation site of PKA phosphorylation of threonine with arginine at −3, position).

In another preferred embodiment, a combination of kinase activation state antibodies that specifically bind to phosphorylated kinases, specific substrates for kinases, and phospho-substrate antibodies are used to determine a kinase activation state profile for a single cell. The methods comprise sorting cells on the basis of the activation state of at least two kinases using a FACS machine. Activation of at least two kinases is determined using at least one kinase activation state antibody and at least one specific substrate for a kinase and at least one phospho-substrate antibody for the measurement of the at least one phosphorylated substrate. Preferably, a kinase activation state antibody is selected from the group consisting of anti-AKT-phospho-Ser473, anti-AKT phospho-Thr308, anti-p44/42, MAPK phospho-Thr202/Tyr204, anti-TYK2, phospho-Tyr1054/1055, anti-p38, MAPK phospho-Thr180/Tyr182, anti-JNK/SAPK phospho-Thr183/Tyr185, anti-phospho-tyrosine, anti-phospho-threonine. Preferably, a phospho-substrate antibody is selected from an antibody that specifically binds to PKC substrate PAN phospho-substrate (which is a substrate for α, βI, βII, and δ isoforms of PKC only when phosphorylated at a carboxy terminal residue homologous to Ser660, of PKCβII), and an antibody that specifically binds to PKA phospho-substrate (consensus phosphorylation site of PKA phosphorylation of threonine with arginine at −3, position).

In a preferred embodiment, cell sorting by FACS on the basis of the activation state of at least two proteins, preferably kinases and/or caspases, is combined with a determination of other FACS readable outputs, such as the presence of surface markers, granularity and cell size to provide a correlation between the activation state of a multiplicity of proteins and other cell qualities measurable by FACS for single cells.

As will be appreciated, the present invention also provides for the ordering of protein activation events in signal transduction. Particularly, the present invention allows the artisan to construct a kinase activation heirarchy based on the correlation of levels of activation of a multiplicity of kinases within single cells.

The present invention may also be used to determine the presence of cellular subsets, based on correlated protein activation, preferably kinase activation, within complex cellular mixtures such as peripheral blood mononuclear cells. These subsets may represent different differentiation or activation states or different cell lineages or sublineages.

It will also be recognized that a homogeneous cell population is desirable for studying signal transduction in order that variances in signaling between cells not qualitatively and quantitatively mask signal transduction events. The ultimate homogeneous system is the single cell. The present invention provides methods for the analysis of signal transduction in single cells, where the activated state of the signal transducing proteins involved is antigenically distinguishable from a non-activated state.

As will be appreciated, these methods provide for the identification of distinct signaling cascades for both artificial and stimulatory conditions in complex cell populations, such a peripheral blood mononuclear cells, or naive and memory lymphocytes.

The methods provided herein may also involve the use of specific inhibitors of particular kinases. The methods provided herein may also involve the use of specific inhibitors of caspases. The methods provided herein may also involve the use of other pharmacological inhibitors of signaling pathways. These inhibitors may be used as controls to ensure that antibodies specifically bind to activated isoforms of proteins. For example, an inhibitor of a kinase known to phosphorylate and activate a second kinase may be used to inhibit phosphorylation of the second kinase and examine whether an antibody specifically recognizes a phosphorylated isoform of the second kinase. Alternatively, the inhibitors may be used to further probe signaling pathways and correlations in protein activity, particularly in single cells.

In a preferred embodiment, methods for the determination of a caspase activation state profile for a single cell are provided. The methods comprise providing a population of cells and sorting the population of cells by FACS. Preferably, cells are separated on the basis of the activation state of at least one caspase. In a preferred embodiment, caspase cleavage product antibodies as described herein are used to determine the activation state of at least one caspase.

In a preferred embodiment, a method for screening for a bioactive agent capable of modulating kinase activity is provided which comprises contacting a cell with a candidate bioactive agent and determining kinase activation in said cell by cell sorting said cell by FACS.

In a preferred embodiment, the method comprises contacting a plurality of cells with a plurality of candidate bioactive agents and sorting the cells by FACS on the basis of the activation of at least one kinase.

In a preferred embodiment, a method for screening for a bioactive agent capable of modulating caspase activity is provided which comprises contacting a cell with a candidate bioactive agent and determining caspase activation in said cell by cell sorting said cell by FACS.

In a preferred embodiment, the method comprises contacting a plurality of cells with a plurality of candidate bioactive agents and sorting the cells by FACS on the basis of the activation of at least one caspase.

By "candidate bioactive agent", "candidate agent", "candidate modulator", "candidate modulating agent", or "exogeneous compound" or grammatical equivalents herein is meant any molecule, e.g., protein, small organic molecule, carbohydrates (including polysaccharides), polynucleotide, lipids, etc. Generally a plurality of assay mixtures can be run in parallel with different agent concentrations to obtain a differential response to the various concentrations. Typically, one of these concentrations can serve as a negative control, i.e., at zero concentration or below the level of detection. In addition, positive controls can be used.

Candidate agents encompass numerous chemical classes. In a preferred embodiment, the candidate agents are small molecules. In another preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate agents are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate agent prior to the assay. Using the methods of the present invention, any candidate agents can be screened for the ability to modulate (e.g., increase or decease) the activity of an activatable protein. In addition, as is known in the art, coding tags using split synthesis reactions may be used to essentially identify the chemical moieties tested.

Alternatively, a preferred embodiment utilizes libraries of natural compounds, as candidate agents, in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate agents include proteins, nucleic acids, and chemical moieties.

In a preferred embodiment, the candidate agents are proteins, as defined above. In a preferred embodiment, the candidate agents are naturally occurring proteins or fragments of naturally occurring proteins. Thus, for example, cellular extracts containing proteins, or random or directed digests of proteinaceous cellular extracts, may be tested, as is more fully described below. In this way libraries of prokaryotic and eukaryotic proteins may be made for screening against any number of candidate agents. Particularly preferred in this embodiment are libraries of bacterial, fungal, viral, and mammalian proteins, with the latter being preferred, and human proteins being especially preferred.

In a preferred embodiment, the candidate agents are peptides of from about 2, to about 50, amino acids, with from about 5, to about 30, amino acids being preferred, and from about 8, to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular activatable protein. Accordingly, an interaction library must be large enough so that at least one of its members will have a structure that interacts with an activatable protein or other specific components of the signal transduction pathway involving the activable protein. Although it is difficult to gauge the required absolute size of an interaction library, nature provides a hint with the immune response: a diversity of $10^7$-$10^6$, different antibodies provides at least one combination with sufficient affinity to interact with most potential antigens faced by an organism. Published in vitro selection techniques have also shown that a library size of $10^7$, to $10^8$, is sufficient to find structures with affinity for a target. A library of all combinations of a peptide 7, to 20, amino acids in length, such as generally proposed herein, has the potential to code for $20^7$ ($10^9$) to $20^{20}$. Thus, with libraries of $10^7$, to $10^8$, different molecules the present methods allow a "working" subset of a theoretically complete interaction library for 7, amino acids, and a subset of shapes for the $20^{20}$, library. Thus, in a preferred embodiment, at least $10^6$, preferably at least $10^7$, more preferably at least $10^8$, and most preferably at least $10^9$, different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3, domains, serines, threonines, tyrosines or histidines for phosphorylation sites, etc., or to purines, etc.

In a preferred embodiment, the bias is towards peptides or nucleic acids that interact with known classes of molecules. For example, when the candidate agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus*, oocytes following stimulation. And, short SH-3, target peptides have been used as psuedosubstrates for specific binding to SH-3, proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well.

Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2, domains, SH-3, domains, Pleckstrin, death domains, protease cleavage/recognition sites, enzyme inhibitors, enzyme substrates, and Traf.

In a preferred embodiment, the candidate modulating agent is a polypeptide. In another preferred embodiment, the polypeptide is a cyclic peptide having at least 4, to 20, amino acids. Also in another preferred embodiment, the polypeptide is a catalytically inactive polypeptide. Examples of catalytically inactive polypeptides include, but are not limited to, catalytically inactive activable proteins and, more specifically a catalytically inactive kinases (e.g., PI3K) or caspases. In a further aspect, the candidate modulating agent is peptide fragment of an activatable protein, wherein the peptide fragment comprises an amino acid sequence that is a subsequence of the full-length amino acid sequence of the activable protein.

In a preferred embodiment, the candidate agents are nucleic acids. With reference to candidate agents, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925, (1993) and references therein; Letsinger, J. Org. Chem. 35:3800, (1970); Sprinzl et al., Eur. J. Biochem. 81:579, (1977); Letsinger et al., Nucl. Acids Res. 14:3487, (1986); Sawai et al, Chem. Lett. 805, (1984), Letsinger et al., J. Am. Chem. Soc. 110: 4470, (1988); and Pauwels et al., Chemica Scripta 26:141 91986)), phosphorothioate (Mag et al., Nucleic Acids Res. 19:1437, (1991); and U.S. Pat. No. 5,644,048), phosphorodithioate (Briu et al., J. Am. Chem. Soc. 111:2321, (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895, (1992);

Meier et al., Chem. Int. Ed. Engl. 31:1008, (1992); Nielsen, Nature, 365:566, (1993); Carlsson et al., Nature 380:207, (1996), all of which are incorporated by reference). Other analog nucleic acids include those with positive backbones (Denpcy et al., Proc. Natl. Acad. Sci. USA 92:6097, (1995); non-ionic backbones (U.S. Pat. Nos. 5,386,023, 5,637,684, 5,602,240, 5,216,141, and 4,469,863; Kiedrowshi et al., Angew. Chem. Intl. Ed. English 30:423, (1991); Letsinger et al., J. Am. Chem. Soc. 110:4470, (1988); Letsinger et al., Nucleoside & Nucleotide 13:1597, (1994); Chapters 2, and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395, (1994); Jeffs et al., J. Biomolecular NMR 34:17, (1994); Tetrahedron Lett. 37:743, (1996)) and non-ribose backbones, including those described in U.S. Pat. Nos. 5,235,033, and 5,034,506, and Chapters 6, and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid candidate agent may be naturally occurring nucleic acids, random nucleic acids, or "biased" random nucleic acids. For example, digests of prokaryotic or eukaryotic genomes may be used as is outlined above for proteins. Where the ultimate expression product is a nucleic acid, at least 10, preferably at least 12, more preferably at least 15, most preferably at least 21, nucleotide positions need to be randomized, with more preferable if the randomization is less than perfect. Similarly, at least 5, preferably at least 6, more preferably at least 7, amino acid positions need to be randomized; again, more are preferable if the randomization is less than perfect.

In a preferred embodiment, the candidate modulating agent is a mutant cDNA encoding a catalytically inactive polypeptide. Examples of such catalytically inactive polypeptides include, but are not limited to, catalytically inactive activatable proteins and, more specifically, catalytically inactive kinases (e.g., PI3K) or caspases.

In a preferred embodiment, the candidate modulating agent is an RNA, for example an antisense RNA or siRNA (small inhibitory RNA). In another preferred embodiment, the siRNA cleaves RNA encoding an activatable protein. The siRNAs can be prepared using the methods described herein and known in the art.

In a preferred embodiment, the candidate agents are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate agent at a time, e.g., by combining the candidate agents in the methods of the present invention. Thus, the library of candidate agents used may include only one type of agent (i.e. peptides), or multiple types (peptides and organic agents).

By "combining" is meant the combining of the various components in a reaction mixture in vitro or in a cell in vivo under conditions which promote an activity that is detectable using known methods or using the methods of the present invention (e.g., the binding of an antibody to a corresponding antigen or isoform of an activatable protein, or activation state of an activatable protein).

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

In a preferred embodiment, the reaction mixture or cells are contained in a well of a 96, well plate or other commercially available multiwell plate. In an alternate preferred embodiment, the reaction mixture or cells are in a FACS machine. Other multiwell plates useful in the present invention include, but are not limited to 384, well plates and 1536, well plates. Still other vessels for containing the reaction mixture or cells and useful in the present invention will be apparent to the skilled artisan.

The addition of the components of the assay for detecting the activation state or activity of an activatable protein, or modulation of such activation state or activity, may be sequential or in a predetermined order or grouping under conditions appropriate for the activity that is assayed for. Such conditions are described here and known in the art. Moreover, further guidance is provided below (see, e.g., in the Examples).

In a preferred embodiment, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96, well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of heat exchangers such as controlled blocks or platforms to provide accurate temperature control of incubating samples from 0° to 100° C.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluoroescence resonance energy transfer (FRET), luminescence, quenching, two-photon excitation, and intensity redistribution; CCD cameras to capture and transform data and images into quantifiable formats; and a computer workstation.

In a preferred embodiment, the detecting is by FACS. In another aspect, the detecting is by high pressure liquid chromatography (HPLC), for example, reverse phase HPLC, and in a further aspect, the detecting is by mass spectromety.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Functional Signaling Analysis in Single Cells: Simultaneous Measurement of Multiple Kinase Activities Using Polychromatic Flow Cytometry Intracellular assays of signaling systems has been limited by an inability to correlate functional subsets of cells in complex populations based on kinase activity. Such correlations could be important to distinguish changes in signaling status that arise in rare cell subsets during signaling or in disease manifestation. In this Example, using the methods and compositions of the present invention, the present inventors (also referred to herein as "we") demonstrate the ability to simultaneously detect the kinase activities of members of the mitogen activated protein kineses family (p38, MAPK, p44l42, MAPK, JNK/SAPK), members of cell survival pathways (PKA, AKT/PKB), and members of T-cell activation pathways (TYK2, PKC) in subpopulations of complex cell populations by multi-parameter flow cytometric analysis. Further, in this Example the present inventors demonstrate the utility of these probes in identifying distinct signaling cascades for: 1) both artificial and physiological stimulatory conditions of peripheral blood mononuclear cells (PBMC); 2) cytokine stimulation in human memory and naive lymphocyte subsets as identified by 5, differentiation markers; and 3) ordering of kinase activation in potential signaling hierarchies. Polychromatic flow cytometric kinase activity measurements (PFC-KA) demonstrate that multi-dimensional analysis of signaling pathway interplay can provide functional signaling pathway assessment on a single cell level.

Introduction

The study of multiple activated signaling pathways in complex populations of cells, such as peripheral blood, at the single cell level has not been previously possible. Multiparameter flow cytometric analysis allows for small subpopulations—representing different cellular subsets, differentiation or activation states—to be discerned using cell surface markers Downstream activation of signaling pathways can be read out by reporter systems that include intracellular detection of enzyme activity for β-galactoside[1,2], and β-glucuronidase[3], to study transcription from defined promoter(s) and green fluorescent proteins (GFP). Interactions between proteins can be determined by both Fluorescence Resonance Energy Transfer and Bioluminescence Resonance Energy Transfer[4,5,6,7]. In either of these latter cases, the activation of the signaling system is determined through overexpression of reporter proteins-as such the endogenous kinase activation states are not accessible.

It is understood that kinase signaling cascades play an important role in nearly every critical decision process in cells[8]. Determining the role of specific signal transduction pathways in a given system has been aided by the advent of pharmacological inhibitors for specific kinases. However, monitoring activities for such kinases as Protein Kinase B/AKT, c-Jun-N-terminal Kinase (JNK), p38, mitogen activated protein kinase (p38), p44l42, ERK1/2, (ERK) activity, PKA activity, PKC activity, or TYK2, activity is usually dependent upon in vitro kinase assays or, more recently, by immunoblotting to determine their phosphorylation state using phospho-specific antibodies. To date it has not been possible to correlate rare subpopulations with the activation state of kinases in important signaling paths. With the recent advent of 11-color flow cytometry[9] we sought to dissect biologically relevant subsets of cells based on defined kinase activation states.

Phospho-specific monoclonal, phospho-substrate specific polyclonal, and cognate (nonphospho-specific) kinase antibodies were conjugated to fluorophores (see Table 1, herein; and Table 1, legends below) as probes for specific kinase activities. Each antibody was tested for phospho-specificity prior to conjugation by treating cells with appropriate kinase inducing agents or specific kinase inhibitors (see Table 2, herein; and Table 2, legends below) and subjected to traditional western blot analysis and kinase activity assays (FIG. 1A). Antibodies exhibiting specificity for the phosphorylated state of the kinase were: AKT phospho-Ser473, AKT phospho-Thr308, p44/42, MAPK phosphoThr202, Tyr204, TYK2, phospho-Tyr1054/1055, p38 MAPK phosho-Thr1B0, Tyr182, PKC-PAN phospho-substrate (detects PKCα, βI, β11, and δ isoforms only when phosphorylated at a carboxy terminal residue homologous to ser660, of PKCβ 11), PKA phospho-substrate (consensus phosphorylation site of PKA phosphorylation of threonine with arginine at −3, position), JNK/SAPK phospho-Thr183/Tyr185, phosphotyrosine (p-tyr-100) and phoso-threonine. All kinase activation states were verified using specific inhibitors for the upstream kinase known to phosphorylate the cognate kinase (FIG. 1A). The inhibitors applied are listed in Table 2.

FACS based detection of kinase activity, after 24-hour serum-starvation, was tested as a function of a given stimulus specific to kinase activation and inhibition by kinase selective inhibitors. Table 1, provides staining combinations for the flow cytometry experiments used in this report. Kinase selective activators and inhibitors used are listed in Table 2, and FACS based kinase activity plots are illustrated in FIG. 1B. Kinase probes for p44/42, AKT, JNK, TYK2, p38, and phospho-tyrosine containing proteins exhibited the strongest resolution of peaks between uninduced and induced conditions (FIG. 1B). Kinase probes for PKC and PKA exhibited the lowest apparent induction from basal fluorescence levels as determined by FACS; this could have been dependent on the conditions we had established for induction and staining or the substrate motif recognition might not be optimal for these probes. We therefore determined that the fluorescence observed was due to a phosphorylation of a target protein by treating the sample prior to staining with one or more phosphatases to support the phospho-PKC-PAN, phospho-PKA substrate, and phospho-TYK2's probe phospho-specificity (FIG. 1 C). FIG. 1C highlights the phospho-PKC-PAN, phospholPKA-substrate and phospho-TYK2, probes are dependent on their respective phosphorylated substrate for recognition as phosphatase treatment diminishes their ability to recognize the stimulus induced phosphorylation product (s).

To exemplify that these probes can differentiate amongst varying levels of kinase activity a FACS dose response curve demonstrates there is excellent p44/42, activity to fluorescence correlation (FIG. 1B, bottom right panel). Furthermore, the mean fluorescence intensity values of the phospho-p44/42, probe had a correlation coefficient of 0.96, with the densitometry values of phosphorylated p44/42, in a dose response curve, validating the kinase probes as being able to measure small differences in kinase activity (FIG. 1D).

To demonstrate the ability of these probes to represent biologically relevant signaling events we activated peripheral blood mononuclear cells (PBMC), a population of cells that is likely to be heterogeneous in terms of potential kinase activities, to see if subsets of cells demonstrated differing kinase activation kinetics. Total PBMC in mixed culture were stimulated with CD3, and CD28, monoclonal antibodies to mimic physiological T cell activation of surface receptors. As another form of stimulus we activated these cells with the artificial T cell activation agents phorbal myristyl acetate (PMA) and ionomycin. Cell subsets were gated for CD4+, (a T cell subset marker) or CD19+, (a B cell marker). The T cell and B cell subsets were compared to discern differential kinase activity profiles between these two cell types upon a given stimulus. FIG. 2A illustrates that primary B and T cells have inherent differences with respect to kinase activity of p38, MAPK and p44/42, MAPK in an unstimulated state, and respond differently to the various stimulatory conditions applied. Dramatic differences for T cells in both p38, and p44/42, activity can be seen when comparing PMA/ionomycin and CD3/CD28, stimulation, suggesting that CD3/CD28, does not engage full activation of CD4+, T cells along the p38, or p44/42, pathway. Some activation of the CD19+, B cells is observed using combinations of CD3, and CD28, that we presume is due to T cell activation and their production of stimulatory cytokines: for B cells. Alternatively other T cell helper interactions with B cells could lead to the B cell activations observed with CD3, and CD28.

We also determined in a cell line differential responses to cytokines. Using CD69, an early T cell activator marker[10,11], as a surface antigen to distinguish between activated and non-activated Jurkat cells, CD69, expression was plotted as a function of p44/42, activity to a variety of T cell stimulatory agents (FIG. 2B). The differences observed in kinase activity and CD69, expression when comparing CD3/CD28, stimulation to that of PMA/ionomycin (artificial) would suggest that other co-stimulatory molecules exist and are necessary for optimal T cell activation with respect to p44/42, MAPK. In addition, experiments involving PMA/ionomycin stimulated Jurkat cells demonstrated decreased activation of TYK2, activity in CD69+, cells (data not shown) This would suggest that T cell activation could induce intrinsic regulatory mechanisms that cause cells to become hyporesponsive to further stimuli and point out that the kinase profiling probes can potentially be used to study anergic responses.

As an example of the type of information yielded by kinase-activity gating analysis, both traditional histogram analysis and kinase-activity gating analysis was undertaken and is presented as follows. Jurkat cells in either growth media or stimulated with PMA/ionomycin were assessed for multiple intracellular kinase activity and CD69, expression (FIG. 2C). Basal activity of PKC, p38 and p44/42, is observed, however, kinase activity for JNK, p38, p44/42, PKC, and PKA is dramatically altered for PMA/ionomycin stimulated cells (FIG. 2C). This is congruent with the observations for the CD69+, PBMC data (FIG. 2B). Thus, monitoring phosphorylation events in intact cells makes it possible to correlate activity with other parameters such as surface molecule expression, cell size, or cell granularity approaches not possible with conventional lysate analysis of kinase phosphorylation states.

To further explore subset analysis of cells we anisomycin-treated Jurkat cells and probed them for total p38, MAPK (using an antibody against a presumed nonphosphorylated region of p38) and with phospho-p38, MAPK probe. This would allow us to follow not only the changes to p38 phosphorylation but also to simultaneously measure steady state levels. Since FACS based kinase assays allow alternative analytical correlations to be made with cellular size (forward scatter) and shape of the cell (side scatter), we determined the status of the phosphorylation as a function of the side scatter parameter (a measurement of granularity). Cell granularity is a function of surface molecule distribution, cell structure and conformation, and can be influenced by internal cellular signals that result in outward cell surface modulation (events that are common for instance in the field of integrin "inside-out" signaling[12,13,14,15]). Contour plots depict a shift from non-phosphorylated to phosphorylated p38, as the granularity of the cell increases (FIG. 2D). Similarly, a direct correlation between elevated p44/42, kinase activity and increased cell size (forward scatter parameter) was observed when kinase activity was monitored as a function of cell size (data not shown). We note that the phospho-p38, fluorescence staining occurs at the expense of the apparent p38, nonphospho staining. We believe this might be due to occlusion of binding of the nonphospho-specific probe in the activated state by a cellular protein (see below).

We illustrate a three-kinase gating analysis by correlating the phosphorylated states of p38, and p44/42, to phospho-JNK for total PBMC stimulated with IL-1a (FIG. 2E). Excerpts from regions representing the lower end of phospho-JNK levels, up to higher levels, demonstrate an initial phosphorylation of p44/42, is followed by a phosphorylation in p38, as the intensity of JNK phosphorylation increases. Thus in the cell, higher levels of JNK activation correlate to an apparent passing of signals from p44/42, to p38. Although the phosphorylation events are not normalized according to time, the phosphorylation shifts observed in p38, and p44, as a function of JNK phosphorylation suggest pathway interplay, and could represent the result of one signaling cascade activating another (further experiments are underway to determine the cell subsets responsible for these shifts). Simultaneous monitoring of AKT, PKA, p44/42, and p38, kinase activity as a function of TYK2, activity in IL-1, p stimulated PBMC exemplifies that kinase cascades can be ordered with respect to their activation status when analyzed in a multi-parameter fashion (FIG. 2F). In regards to IL-1β stimulation, concomitant activation of p38, and p44/42, is observed when activation of TYK2, begins to be detected. However, a distinct profile is observed with respect to AKT and PKA activation, as the shift in detected phosphorylated AKT is correlated to lower levels of phospho-TYK2, and PKA phosphorylation of PKA substrates. The utility of these probes to spatially resolve as many as five simultaneous kinase activations allows global assessment of signaling pathways. In addition, population subsets can be distinguished based upon intracellular kinase activity and be correlated for phenotype by using multiple surface markers-(alternative data analysis not presented here). To demonstrate the ability of these kinase probes to screen for activation of individual signaling pathways to other specific stimuli, we treated human peripheral blood monocytes (PBMC) with several different cytokines. We used the phospho-kinase probes to correlate phospho-kinase profiles in the responding cells using polychromatic flow cytometry (11-color, 13, parameters).

In initial experiments functional characterization of T cells occasionally varied from donor to donor. Apparent donor variability was reduced when magnetically activated cell sorting (MACS) was used to isolate resting T cells by negative isolation prior to stimulation and analysis. This is most likely due to the depletion of pre-existing activated T cells and other cell types that might be producing cytokines. FIG. 3 illustrates a flow diagram of the protocol used to isolate, characterize, and analyze truly naive (CD3$^+$, CD4$^+$, CD8$^-$, CD62L$^+$, CD45RA$^+$, CD11a$^{dim}$CD28$^+$, CD27$^+$, ) and memory (CD3 $^+$, CD4$^+$, CD8$^-$, CD62L $^+$, CD45RA $^+$, CD11a $^{br}$CD28 $^-$, CD27$^-$, ) T cell intracellular kinase activities. We observed clear constitutive activation, for instance, of AKT in the CD4, and to a lesser degree CD8, positive subsets of naive T cells, as opposed to memory T cells, even in non-activated cell types (FIG. 3, bottom panels). Other differences were apparent as well in the non-stimulated cells, including differences in p38, phosphorylation. FIG. 4 demonstrates the power of polychromatic flow cytometry based kinase assays to identify functional differences in naive and memory T cells in their response to IL-1α, IL-1β, and IL-2, as measured by the phospho-kinase profiles. Interestingly, stimulation with any of these cytokines led to a drop in p44/42, phosphorylation in CD4+, naive cells relative to CD8+, cells. A less dramatic drop also occurs in JNK activity in these same cell subsets. Other kinase profiles are not effected.

Differences in kinase expression as consequences of stimuli are typically controlled for in standard western blot/ kinase analysis by protein content normalization or by running a comparative blot with a normalizing antibody that recognizes the kinase irrespective of phosphorylation. We determined whether we could simultaneously assess kinases in their active and inactive state using cognate non-phospho specific fluorescent probes for AKT, p44/42 MAPK, p38, MAPK, and JNK/SAPK (normalizing antibodies). In unstimulated cells, we observed strong staining using the normalization antibody to p44/42. After EGF stimulation, all cells showed phosphorylated p44/42, but the normalization antibody revealed a negative population. This result could be due to EGF-induced binding by an unknown protein to the site recognized by the p44/42, antibody probe, or a change in the structure of the p44/42, molecule that occludes the antibody binding site. For p38, we observed a strong increase after anisomycin stimulation in the levels of apparent p38, (or loss of a bound protein that occludes the normalization antibody recognition site) as well as a subset of cells that show increased phosphorylation of p38. For JNK, three distinct populations were observed before stimulation and four distinct populations could be visualized after stimulation.

One possibility is that the plots could depict two phosphorylation events of the p46, and p54 isoforms of JNK/SAPK, phosphorylation of JNK coupled by a rapid onset of JNK or p54, isoform expression, or if phosphorylation alters the capacity for interacting proteins to occlude/expose the antibody recognition site(s). For AKT, two distinct cellular populations that differed from the unstimulated state appeared after PDGF stimulation of Jurkat cells. The population of cells that had a higher AKT fluorescence intensity existed in both a mono and bi-phosphorylated state (FIG. 5A lower panel). The apparent AKT negative population of PDGF stimulated cells presented minimal phosphorylation as detected by the phospho-thr308, and the phospho-ser473, probes. It is unlikely that total AKT levels rapidly decrease within the 10, minutes of PDGF stimulation since this was not observed in standard western and kinase assays (see FIG. 1A) and thus we infer a new protein binds there or a signal induced change in structure prevent binding of the antibody.

These latter results lead us to believe that the changes in subpopulations observed represent changes in the binding of cellular proteins to the kinases. Thus, there are potential pitfalls in the simultaneous use of antibodies to normalize intracellular staining on the basis of a normalizing antibody-this warrants caution in the interpretation of such data. However, the results suggest that a series of antibodies, that recognize different epitopes on the same protein, could both infer the existence of cellular binding partners, map where they interact on the target protein structure, and derive specific functional correlations associated with such binding. We know of no other technique that allows protein interactions to be mapped on endogenous proteins in a cell-by cell analysis of subsets of cells in complex populations.

Summary

Utilizing multi-parameter flow cytometry, we demonstrate that lymphocyte subsets can be distinguished based upon levels of as many as five intracellular kinase activities. The power of the approach can be appreciated not only in dissection of intracellular signaling pathways, but presents for the first time the ability to perform multiple kinase activity measurements in a single cell by flow cytometry. Functional signaling dissection on a single cell level could be applicable to rare cell subpopulations such as stem cells or stem cell progenitors and can be extended to many systems where the rarity of certain cellular subsets preclude isolation of cells for in vitro functional characterization. The application of these kinase specific probes is the following: (1) To obtain a unique signaling profile for a stimulus to understand the biology of various cellular processes (2) To monitor signaling mechanisms in rare cell populations in the development, differentiation, or maintenance of cellular fates, (3) The potential to utilize these kinase probes (and others) in high-throughput FACS based screens for pharmacological inhibitors of specific kinase activity within mammalian cells, (4) the potential to temporally and spatially resolve kinase activation cascades on a global scale, and (5) the possibility that binding partners might be inferred before and after stimulation with appropriate antibody sets. Development of other intracellular kinase probes can contribute to the elucidation of signaling networks and in combination with polychromatic flow cytometry (11-color, 13, parameter) technology[9], could aid an understanding of the complexity of intracellular signals in the immune system. Furthermore, the utility of these probes might be extended to clinical settings to determine intracellular knase activities for cells derived from diseased patients as a diagnostic indicator of disease progression.

Experimental Procedures

Cell Culture and Primary Cell Isolation

Jurkat T cells were maintained in RPML1640, 10% FCS 1% PSQ (10% fetal calf serum, 1% penicillin-streptomycin (1000, units/ml and 2, mM L-glutamine PSQ). NIH3T3, cells were maintained in DMEM (Dulbecco modified eagle medium), 10% donar calf serum, 1% PSQ. For preparation of primary cells, mononuclear cells were isolated from blood of healthy donors (Stanford Blood Bank, Stanford, California). Human peripheral blood monocytes were obtained by Ficoll-plaque density centrifugation (Amersham Pharmacia, Uppsala, Sweden) of whole blood and depletion of adherent cells by adherence to plastic culture dishes. Isolated cells were maintained in complete media. Magnetically activated cell sorting (MACS, Miltenyl Biotech, Baraisch-Gladbach, Germany) was used in some experiments as noted to enrich for CD3+, T cells by negative isolation using combinations of CD16, CD14, CD44, HLA-DR, or CD19, biotinylated antibodies (Dynal, Oslo, Norway) and streptavidin-magnetic beads (Dynal, Oslo, Norway). Chemical and biological agents used were either obtained form Sigma (St. Louis, Mo.), Cell Signaling Technologies (Beverly, Mass.), Roche Biochemicals (Indianapolis, Ind.), or Peprotech (Rocky Hill, New Jersey): ionomycin (1-µM, Sigma), phorbal myristyl acetate (1, µM, Sigma), anisomycin (10, µM, Sigma), PDGF 10, pg/ml or as indicated (Roche Biochemicals), SB203580, (10, µM, Cell Signaling Technology), LY294002, (10, µM, Cell Signaling Technology), U0126, (10, µM, Cell Signaling Technology), Bisindolymaleimeide II (10, µM, Sigma), Calyculin A (10, µM, Sigma), staurosporine (1, µM, Sigma), genistein (10, µM, Sigma), IL-2, (10, pg/ml, Peprotech), IL-3, (10, pg/ml, Peprotech), IL-1α (Roche Biochemicals (10, pg/ml), epidermal growth factor (EGF, Roche Biochemicals), lambda phosphatase and calf intestinal phosphatase (CIP) (New England Biolabs, Beverly, Mass.), CD40L was a gift from Dr. Strobl (Department of Molecular Pharmacology, Stanford University). CD3, (OKT3) and CD28, endotoxin/azide free monoclonal antibodies where from PharMingen (La Jolla, Calif.).

For serum starvation, Jurkat cells were deprived of serum for 24, hours and were considered uninduced with respect to kinase activity. Kinase activity inhibition was done with the appropriate kinase inhibitor added 30, minutes prior to being stimulated by the kinase activating agent. Stimulation by either kinase activating agent or exogenous stimuli was performed for 30, minutes before cells were prepared for flow cytometry. Stimulation of Jurkat cells with PMA/Ionomycin was for 2, hours at 1, µM. Stimulation of PBMC was performed for 12, hours prior to 11-color analysis at 10, ng/ml of indicated cytokine. Chemical agents were dissolved in DMSO (Sigma), and uninduced cells received 0.1% DMSO carrier as control treatment. UV treatment for samples in FIG. 1A was performed by incubation under a UV light in a typical tissue culture hood for the indicated time. Lambda phosphatase treatment (1000, units at 37° C. for 15, min) and calf intestinal phosphatase treatment (CIP, 50, U at 37° C. for 15, min) was performed after FACS permeabilization prior to intracellular staining.

Immunoblotting

Cell extracts were prepared by washing $2\times10^6$, cells in ice cold PBS and harvesting in lysis buffer (20, mM Tris pH 7.5, 150, mM NaCl 1, mM EDTA 1, mM EGTA, 1% Triton X100, 2.5, mM $Na_2PO_4$, 1, mM β-glycerolphosphate, 1, mM Na3VO4,1, ug/ml Leupeptin, 1, mM PMSF, protease inhibitor cocktail tablet (Boehringer Mannheim, Basel, Switzerland). Extracts were centrifuged 14,000 RPM for 5, min at 4c and cell lysates (20, g as determine by BCA protein assay (Pierce, Rockford, Ill.) were fractionated on 12% or 15% SDS-polyacrylamide gel electrophoresis and transferred to PVDF membranes using standard procedures. Antibodies used are indicated adjacent to blots and were purchased from Cell Signaling Technologies) (Beverly, Mass.). Cell treatments are indicated where appropriate.

Kinase Assays

Kinase activity assay protocol was similar for AKT, p38, p44/42, JNK and substituted reagents used for respective kinase assay is noted. All reagents used for kinase activity assays were obtained from Cell Signaling Technologies (Beverly, Mass.). Kinase activity was detected by immunoprecipitation of kinase AKT, p38, p44/42, or JNK using immobilized AKT1G1 monoclonal antibody, immobilized phospho-p38, MAPK monoclonal antibody, immobilized phospho-p44/42, monoclonal antibody, or c-Jun fusion protein beads respectively, from cells. Immobilized kinase was used in a kinase assay with GSK3, fusion protein, ATF-2, fusion protein, Elk-1, fusion protein, or c-Jun fusion protein beads respectively. $2\times10^6$, NIH3T3, or $2\times10^6$ Jurkat cell were washed twice in PBS and lists were incubated with immobilized kinase antibody or beads (1:200) at 4° C. with gentle rocking motion for 2, hrs. Immunocomplexes were washed 4× with cell lysis buffer and resuspended in 40, µl kinase buffer (25, mM Tris pH 7.5, 5, mM β-glycerolphosphate, 2, mM DTT, 0.1, mM $Na_3VO_4$, 10, mM $MgCl_2$) supplemented with 200, µM ATP and 1, µg of fusion protein (except for JNK activity assay, in which ATP was sufficient to induce activation) for 30, min at 30° C. Kinase reaction was terminated with SDS sample buffer boiled for 5, min, and phosphorylation state of GSK3, ATF, EIK-1, or cJun was detected by immunoblotting with phospho specific antibodies phospho-GSK3αβ (ser21/9), phospho-Elk-1, (ser383), phospho-ATF2, (thr71) or phospho-cJun (ser63) respectively and visualized using ECL detection (Amersham). Immunoblots are representative of 3, independent experiments.

Kinase Probe Generation

Antibody conjugation was done using standard procedures ( http(colon)//drmr(dot)com(dot)abcon) or by using protein-protein/protein-dye crosslinking kits from Molecular Probes (Eugene, Oreg.). Phospho-specific and non-phospho specific antibodies were from Cell Signaling Technologies (Beverly, Mass.) or as indicated. Antibodies conjugated were the following: phospho-AKT Ser473, monoclonal anti-4E2, phospho p44/42, MAP Kinase (Thr202/Tyr204) monoclonal antibody, phospho-TYK2, (Tyr1054/1055) antibody, phospho-p38 MAP Kinase (Thr180/Tyr182) monoclonal antibody 28B10, phospho-PKC-PAN substrate antibody, phospho-PKA-substrate, phospho-SAPK JNK (Thr183, Tyr 185) G9, monoclonal antibody, phospho-tyrosine monoclonal antibody (P-tyr-100), p44/42, MAPK, p38, MAPK, JNK/SAPK, and phosphoAKTthr308. Anti-TYK2, was obtained from Santa Cruz Biotechnologies (Santa Cruz, Calif.). Phospho-PYK2, (pY402) antibody and phospho-FAK (pY397) were obtained from Biosource (Carillo, Calif.). ALEXA FLUOR® dyes (sulfonated amino-coumarin or rhodamine) (ALEXA FLUOR® 350, ALEXA FLUOR® 430, ALEXA FLUOR® 488, ALEXA FLUOR® 546, ALEXA FLUOR® 568, ALEXA FLUOR® 594, ALEXA FLUOR® 633, ALEXA FLUOR® 660, ALEXA FLUOR® 680), CASCADE BLUE® (pyrenyloxytrisulfonic acid), CASCADE YELLOW™ and Rphycoerythrin (PE) were purchased from Molecular Probes (Eugene, Oreg.). FITC, Rhodamine, and TEXAS RED® (tetramethylrhodamines with extra iulolidine rings) were purchased from Pierce (Rockford, Ill.). Cy5, Cy5.5, Cy7, were obtained from Amersham Life Science (Pittsburgh, Pa.). Tandem conjugate protocols for Cy5PE, Cy5.5PE, Cy7PE, Cy5.5APC, Cy7APC can be found at www (dot)drmr(dot)com/abcon. Quantitation of fluorescent probe conjugation was assessed to determine degree of labeling and protocols including dye spectral properties can be found at www.metazoa.com/UPL3419. In general, probes used had 2-9, moles of fluorescent dye per mole of protein.

Flow Cytometry and FACS Analysis

Intracellular and extracellular staining was initially performed as described (www(dot)metezoa(dot)com\UPL3287) but modified. Approximately $1-10\times10^7$, peripheral blood mononuclear cells were obtained by magnetically activated cell sorting, treated with a stimulatory condition for 12, hours, and prepared for flow cytometry. Surface stained for 20, minutes, and divided into aliquots for intracellular stain reagents (see below for details). Intracellular staining was achieved by permeabilizing with CytoFix/CytoPerm buffer (PharMingen, La Jolla, Calif.), intracellular stained for 30, minutes on ice, and final resuspension in 1% paraformaldehyde. Isotype control match antibodies were used for stain controls. Purified antibodies to cell surface markers listed in Table 1 in addition to the following where either obtained from PharMingen (La Jolla, Calif.) or conjugated to the indicated fluorophore in the Herzenberg laboratory (Department of Genetics, Stanford University): CD69-APC, CD69-PE, CD4-FITC, CD4-APC, CD4-PE, CD3-APC, CD3-PE, CD3-PERCP, CD19-FITC, CD19-APC.

For each blood sample, PBMC were stained with all the reagents in stain combination 4, 5, 6 (Table 1) except for FITC, PE, Alexa 594, and APC. The stained cells were divided into aliquots and then individually stained with different intracellular cocktail combinations as depicted in combinations 4, 5, 6, (Table 1). Intracellular FACS staining requires mild cell fixation and subsequent permeabilization. Though it has been possible to perform intracellular stains by using a two-step antibody staining protocol (primary plus conjugated secondary), optimal results were achieved with a primary conjugated antibody. Furthermore, conjugates comprised of phycobiliproteins such as phycoerythrin (PE) and allophycocyanin (APC), required significant optimization of permeabilization conditions perhaps because phycobiliproteins are large and might contribute to background binding to intracellular surfaces. For these reasons, the phospho-specific probes generated using the Alexa-Fluor dye series were used in multi-label experiments. In addition, several phospho-specific probes developed for other kinase activities (phospho-PYK2, phospho-FAK, among others) that recognize the phosphorylated form of these antibodies in standard western blots lost their ability to recognize the phosphoepitopes by FACS. This could be either due to the fixation process altering the epitope recognized by the antibody, or the epitope being occluded from antibody recognition in the protein's native form. After extensive testing we determined that in general, directly conjugated phospho-specific monoclonal antibodies exhibited the greatest signal to noise ratio.

Single and four color flow cytometry data acquisition was collected on a FACSCalibur machine (Beckton Dickinson, San Jose Calif.) using CELLQuest software, analyzed and presented using FlowJo software (Tree Star, San Carlos, California). Data for four or less colors are representative of 3, independent experiments of $10^6$, cells/sample and 50,000, events were collected and calibrated using Calibrite beads (Becton Dickinson, San Jose Calif.). 11-color data acquisition was collected on a modified FACStarPlus (Becton Dickinson, San Jose, Calif.) connected to MoFlo electronics (Cytomation, Fort Collins, Colorado). Data were collected by FACSDesk software and compensated, analyzed, and presented using FlowJo software. Data for 11-color flow cytometry collected a minimum of 200,000, events.

Table 1

Top table shows single, 3, and 4, color combinations were used for FIGS. 1 and 2A-D. The antibody-dye sets for these can be found in rows 1, 2, and 3, above. The antibody-dye combinations are grouped according to their excitation wavelength as determined by the laser line applied during the experiment. 11-color staining combinations (rows 4, 5, 6) were used to generate the data in FIGS. 2E-F, 3, 4, and 5. Regions left blank indicate no reagent used. Conditions used ethidium monoazide bromide (EMA) to identify dead cells by intercalating into DNA and forming a covalent adduct prior to permeabilization of the cells. Serum underlays, as well as forward and side scatter gating were used to physically remove and identify dead cells, respectively (FIG. 4).

Bottom table illustrates Alexa fluorescent dye labeled probes used in these experiments. The various kinases were conjugated with one or more of 7, different Phospho-specific antibodies labeled with Alexa dyes are referred in the above tables as p-probe to indicate phospho specific probe was used in that color. They were applied in the various stains in the top section of Table 1 to allow for complementary dye combinations for multiparameter analysis.

Table 2, shows agents used to induce and inhibit specific kinase activity in serum starved Jurkat cells are denoted[3,20-32]. 24, hour serum starvation reduced background phosphorylation significantly. Concentrations used other than those depicted is stated where appropriate. See Methods for treatment protocols.

References

1. Fiering, S, N. et al. Improved FACS-Gal: flow cytometric analysis and sorting of viable eukaryotic cells expressing reporter gene constructs. Cytometry 12, 291301. (1991).
2. Nolan, G. P., Fiering, S., Nicolas, J. F. & Herzenberg, L. A. Fluorescence activated cell analysis and sorting of viable mammalian cells based on beta-Dgalactosidase activity after transduction of *Escherichia*, cold lacZ. Proc Natl Acad Sci USA 85, 2603-7. (1988).
3. Spinozzi, F. et al. The natural tyrosine kinase inhibitor genistein produces cell cycle arrest and apoptosis in Jurkat T-leukemia cells. Leuk Res 18, 431-9. (1994)
4. Anderson, M. T. et al. Simultaneous fluorescence-activated cell sorter analysis of two distinct transcriptional elements within a single cell using engineered green fluorescent proteins. Proc Natl Acad Sci USA 93, 8508-11. (1996).
5. Song, X., Shi, J. & Swanson, B. Flow cytometry-based biosensor for detection of multivalent proteins. Anal Biochem 284, 3541. (2000).
6. Olsen, M. J. et al., Function-based isolation of novel enzymes from a large library. Nat Biotechnol 18,10714. (2000).
7. Dantuma, N. P., Lindsten, K., Glas, R., Jellne, M. & Masucci, M. G. Short-lived green fluorescent proteins for quantifying ubiquitin/proteasome-dependent proteolysis in living cells. Nat Biotechnol 18, 53843. (2000).
8. Hunter, T. Signaling-2000, and beyond. Cell 100, 113-27. (2000).
9. De Rosa, S. C., Herzenberg, L. A. & Roederer, M. 11-color, 13-parameter flow cytometry: Identification of human naive T cells by phenotype, function, and Tcell receptor diversity. Nat Med 7, 245-248. (2001).
10. Nielsen, S. D., Afzelius, P., Ersboll, A. K., Nielsen, J. O. & Hansen, J. E. Expression of the activation antigen CD69, predicts functionality of in vitro expanded peripheral blood mononuclear cells (PBMC) from healthy donors and HIV-infected patients. Clin Exp Immunol 114, 66-72. (1998).
11. Risso, A. et al. CD69, in resting and activated T lymphocytes. Its association with a GTP binding protein and biochemical requirements for its expression. J Immunol 146, 4105-14. (1991).
12. Dedhar, S. Integrins and signal transduction. Curr Opin Hematol 6, 37-43. (1999).
13. Faull, R. J. & Ginsberg, M. H. Inside-out signaling through integrins. J Am Soc Nephrol 7, 1091-7. (1996).
14. Kolanus, W. & Zeitlmann, L. Regulation of integrin function by inside-out signaling mechanisms. Curr Top Microbiol Immunol 231, 33-49. (1998).
15. Kolanus, W. & Seed, B. Integrins and inside-out signal transduction: converging signals from PKC and PIP3. Curr Opin Cell Biol 9, 725-31. (1997).
16. Bodor, J., Bodorova, J. & Gress, R. E. Suppression of T cell function: a potential role for transcriptional repressor ICER. J Leukoc Biol 67, 774-9. (2000).
17. Oberholzer, A., Oberholzer, C. & Moldawer, L. L. Cytokine signaling—regulation of the immune response in normal and critically ill states. Crit Care Med 28, N312. (2000).
18. Roncarolo, M. G. & Levings, M. K. The role of different subsets of T regulatory cells in controlling autoimmunity. Curr Opin Immunol 12, 676-83. (2000).
19. Honey, K., Cobbold, S. P. & Waldmann, H. Dominant regulation: a common mechanism of monoclonal antibody induced tolerance? Immunol Res 20, 1-14. (1999).
20. Fukuchi, K. et al. Phosphatidylinositol 3-kinase inhibitors, Wortmannin or LY294002, inhibited accumulation of p21, protein after gamma-irradiation by stabilization of the protein. Biochim Biophys Acta 1496, 207-20. (2000).
21. Duncia, J. V. et al. MEK inhibitors: the chemistry and biological activity of U0126, its analogs, and cyclization products. Bioorg Med Chem Lett 8, 2839-44. (1998).
22. Favata, M. F. et al. Identification of a novel inhibitor of mitogen-activated protein kinase kinase. J Biol Chem 273, 18623-32. (1998).
23. DeSilva, D. R. et al. Inhibition of mitogen-activated protein kinase kinase blocks T cell proliferation but does not induce or prevent energy. J Immunol 160, 4175-81. (1998).
24. Eyers, P. A., Craxton, M., Morrice, N., Cohen, P. & Goedert, M. Conversion of SB 20358-insensitive MAP 25. Bennecib, M., Gong, C., Grundke-Iqbal, I. & Iqbal, K. Role of protein phosphatase-2A and -1 in the regulation of GSK-3, cdk5, and cdc2, and the phosphorylation of tau in rat forebrain. FEBS Lett 485, 87-93. (2000).
26. Breittmayer, J. P., Pelassy, C. & Aussel, C. Effect of membrane potential on phosphatidylserine synthesis and calcium movements in control and CD3activated Jurkat T cells. J Lipid Mediat Cell Signal 13, 151-61. (1996).
27. Kiss, Z., Phillips, H. & Anderson, W. H. The bisindolylmaleimide GF 109203x, a selective inhibitor of protein kinase C, does not inhibit the potentiating effect of phorbol ester on ethano-induced phospholipase C-mediated hydrolysis of phosphatidylethanolamine. Biochim Biophys Acta 1265, 93-5. (1995).
28. Uddin, S., Chamdin, A. & Platanias, L. C. Interaction of the transcriptional activator Stat-2 with the type I interferon receptor. J Biol Chem 270, 24627-30. (1995).
29. Rolli-Derkinderen, M. & Gaestel, M. p38/SAPK2-dependent gene expression in Jurkat T cells. Biol Chem 381, 193-8. (2000).
30. Chini, C. C., Boos, M. D., Dick, C. J., Schoon, R. A. & Leibson, P. J. Regulation of p38 mitogen-activated protein kinase during NK cell activation. Eur J Immunol 30, 2791-8. (2000).
31. Sotsios, Y., Blair, P. J., Westwick, J. & Ward, S. G. Disparate effects of phorbol esters, CD3 and the costimulatory receptors CD2, and CD28, on RANTES secretion by human T lymphocytes. Immunology 101, 30-7. (2000).
32. Vlahos, C. J., Matter, W. F., Hui, K. Y. & Brown, R. F. A specific inhibitor of phosphatidylinositol 3-kinase, 2-(4-morpholinyl)-8-phenyl-4H-1-benzopyran-4, one (LY294002). J Biol Chem 269, 5241-8. (1994).

Example 2

LFA-1, Functionally Contributes to T-Cell Activation and Polarized Effector Cell Cytokine Production to a TH1, Profile In this Example, using the methods and compositions of the present invention, the present inventors (also referred to herein as "we") demonstrate that LFA-1, stimulation by ICAM-2 functionally contributes in activating human naïve T-cells (CD3$^+$, CD4$^4$CD8$^-$ CD62L$^+$, CD45RA$^+$, CD28$^+$, CD27$^+$, CD11a$^{dim}$) in the presence of CD3/CD28, co-stimulation as determined by simultaneous multidimensional (33, parameters) assessment of immunophenotype, phospho-protein signaling, cytokine production, and transcriptional activity. Soluble ICAM-2, (sICAM-2), upon interacting with LFA-1, initiated phosphorylation and release of LFA-1, binding proteins cytohesin-1, and JAB1, which induced activation of the p44/42, MAPK pathway and cJun respectively. sICAM-2, enforced rapid kinetics of multiple active kinases (p44/42, p38, JNK MAPKs, Ick, AKT, PLCy) when combined with CD3/CD28, stimulation, lowering the CD3/CD28, stimulus threshold by 10,000, fold as determined by activation markers CD25, and CD69. CD3/CD28/LFA-1, signal integration resulted in enhanced nuclear localization of NF-kB, Creb, Atf2, c-Fos, and c-Rel. These conditions optimized T-cell activation as measured by IL-2, expression, NFAT, NF-kB, and AP-1, activity, and cell cycle progression. Furthermore, the CD3/CD28/LFA-1, trio-stimulation polarized naïve human T cells towards a TH1, phenotype, with CD3/CD28, stimulus favoring a TH2, phenotype. These results demonstrate that ICAM-2 interaction with LFA-1, can functionally contribute in T cell activation and differentiation.

In particular, this Example demonstrates that polychromatic flow cytometry based on the methods and compositions of the present invention allow for the rapid identification of specific lymphocyte subsets with simultaneous measurement of multiple intracellular kinase activities. This approach provides functional signaling information on unique cellular processes, for example, T cell activation, at the single cell level.

Introduction

T-cell activation is a multi-step process involving integration of antigen receptor (TCR-CD3) signals with co-stimulatory signals such as B7/CD28, (Croft and Dubey, 1997). Engagement of the antigen-specific TCR-CD3, complex with a recognized peptide-MHC complex on antigen-presenting cells (APC) is necessary for in vivo T-cell activation. T-cell co-stimulatory surface molecules CD28, CD2, (LFA-2), and their APC counter receptors B7, (CD80-86), CD58, (LFA-3), initiate T cell activation (Bjorndahl et al., 1989; Cefai et al., 1996; Cerdan et al., 1992; Chambers and Allison, 1999; Lenschow et al., 1996). Adhesion between T-cells and APCs is necessary for the formation of the immunological synapse and is mediated by T-cell surface molecules LFA-1 (CD11a/CD18) (de Fougerolles et al., 1991; Dustin et al., 1989; Koopman et al., 1992) and the intercellular adhesion molecule ligands (ICAMs).

In contrast to the extensive data available concerning signals involved in TCR-CD3, and CD28 ligation, much less is known about specific signals generated by adhesion mediated events involved in T cell contact with APCs. However, there is evidence that optimal proliferation of T-cells and enhancement of IL-2, production requires stimulation other than TCR-CD3, and CD28 that results from adhesive interactions between costimulatory receptors on T-cells and their counter ligands on APCs (Fine and Kruisbeek, 1991; Salomon and Bluestone, 1998; Simmons, 1995; Starling et al., 1995; Zhang et al., 1997). Insect and fibroblast model systems utilized to study T cell activation have demonstrated that increasing antigen density by more than 10,000-fold fail to initiate naïve CD4+, T cell proliferation or cytokine synthesis in the absence of an ICAM/LFA-1, interaction (Abraham et al., 1999; Ragazzo et al., 2001). In addition, it has also been observed that the ICAM-1/LFA-1, interaction can promote the appearance of the hyper-phosphorylated p23, form of the TCR ζ chain (Ragazzo et al., 2001). Despite these and other observations that in co-ligation with TCR-CD3, LFA-1/ICAM interaction can lead to sustained intracellular calcium response, and increased inositol phospholipid hydrolysis (van Seventer 1992; Wulfing 1998; Rovere 1996), the specific functional consequences for an LFA-1, mediated "co-stimulatory" signal are not fully understood. Furthermore, these latter studies downplay a suggestion by some that LFA-1/ICAM interactions simply allow for longer TCR engagement and rather suggested to us that the LFA-1/ICAM interaction is capable by itself of initiating important intracellular signaling events.

Development of methodologies for intracellular phospho-protein staining has allowed us to simultaneously monitor multiple active kinases in up to 13, dimensions in single cells (Perez and Nolan, 2002). Utilizing this in conjunction with surface immunophenotyping, transcription factor nuclear profiling and cytokine bead arrays, we observed that human naïve T cells (CD3+CD4+CD8–CD62L+CD45RA+CD11a$^{dm}$CD27+, CD28+, ) are optimally activated upon CD3/CD28/LFA-1, stimulation. Co-stimulation with LFA resulted in an over 10,000, fold higer sensitivity to CD3/CD28, co-stimulation. In characterizing the mechanism of this observation, we demonstrate that cytohesin-1, an LFA-1, interacting protein, is released and phosphorylated upon LFA-1, stimulation, and mediates activation of the p44/42, MAPK pathway, correlated to activation of several downstream transcriptional regulators. In conjunction, JAB1, another interacting LFA-1 protein, is similarly released and phosphorylated upon LFA-1, stmulation, leading to c-Jun phosphorylation in the absence of JNK activity. The integration of signaling pathways from CD3, CD28, and LFA-1, converge to mediate activation of multiple pathways (MAPKs, PKC, Src kinases, and focal adhesion kinases) which enhanced NFAT, NF-κB, and AP-1, activities, cell cycle entry, and expression of IL-2, CD25, and CD69. Furthermore, the CD3/CD28/LFA-1 stimulus polarized T cell differentiation towards a TH1, phenotype as compared to the TH2 phenotype observed for a CD3/CD28, stimulus. Thus, the additional LFA-1, signal contributes functionally to both T cell activation and effector cell differentiation.

Results

ICAM-21LFA-1, Interaction Induces Release and Phosphorylation of JAB1, and Cytohesin-1

In a series of kinase profiling experiments we had observed that a solubilized version of membrane-ICAM-2, (sICAM-2, see Materials and Methods) induced activation of the p44/42 MAPK through LFA-1, activation (Perez and Nolan, manuscript submitted) that kinetically differed from CD3, or CD28, stimulation (data not shown). It was also observed that LFA-1, stimulation induced c-Jun phosphorylation in the absence of JNK activity (data not shown). We therefore decided to investigate the functional differences of the ICAM-2-induced signaling in human naïve CD4+, T cells.

LFA-1, stimulation induced phosphorylation and nuclear translocation of c-Jun, an effect that was additive with CD3/CD28, stimulation (FIG. 6A). Inhibition of JNK with the specific chemical inhibitor SP600125, (Bennett et al., 2001) did not abrogate the sICAM-2, induced cJun phosphorylation as determined by single cell analysis (FIG. 6B, top panel). Recently, JAB1, has been identified as an LFA-1, binding protein that mediated cJun phosphorylation in the absence of JNK activity (Bianchi et al., 2000). Intracellular delivery of α-JAB1, antibodies (see Materials and Methods), abrogated LFA-1, induced c-Jun phosphorylation (FIG. 6B, bottom panel). Visualizing both cytohesin-1, and JAB1, in T cells revealed membrane delocalization upon LFA-1, stimulation (FIG. 6C). Cells artificially loaded with anti-JAB1, exhibited membrane delocalized JAB1, in the absence of stimulus, and exhibited no change in cytohesin-1, localization (FIG. 6C). Thus, antibody disruption of JAB1, from LFA-1, blocked the LFA-1, induced c-Jun phosphorylation, indicating that the receptor-ligand interaction was necessary for receptor signaling to c-Jun through JAB1.

We assessed if modifications to cytohesin-1, and/or JAB1, occurred upon LFA-1, stimulus. It was observed that LFA-1, stimulation induced threonine phosphorylation of cytohesin-1, and serine phosphorylation of JAB1, an effect that was not observed after CD3, stimulation (FIG. 6D). We investigated if JAB1, or cytohesin-1, was responsible for LFA-1, induced p44/42, MAPK activity as previously observed (Reviewers please see attached manuscript) by using intracellular delivery of antibodies and/or peptides to functionally modulate respective protein's signaling. Intracellular delivery of an α-cytohesin-1, antibody to the C-terminal blocked the LFA-1, induced p44/42, MAPK activity, a property shared by intracellular delivery of a peptide corresponding to the cytohesin-1 C-terminal (FIG. 6E). Neither intracellular delivery of α-JAB1, or an IgG control affected the LFA-1, induced p44/42, MAPK activation (FIG. 6E). In contrast, intracellular delivery of antibodies directed at the cytohesin-1, N-terminal induced p44/42, MAPK activation (FIG. 6E). These results are supported by the observation that the N-terminal of Cytohesin-1, contains the domain that directly interacts with LFA-1, (Geiger et al., 2000; Kolanus et al., 1996). Therefore, the dissociation of cytohesin-1, from LFA-1, here induced by antibodies to the N-terminal, led to dissociation of the LFA-1/cytohesin interaction in vivo and consequently activated the p44/42 MAPK. The intracellular delivery of antibodies against JAB1, were capable of interfering with JAB1 binding and cJun phosphorylation whereas intracellular delivery of a corresponding C-terminal sequence of cytohesin-1, blocked LFA-1, induced p44/42, MAPK activity. Thus, intracellular delivery of antibodies can functionally modulate protein function and suggest that distinct signaling pathways are coupled to cytohesin-1, and JAB1, two LFA-1, interacting proteins that were mobilized upon stimulus.

Figure 7A:
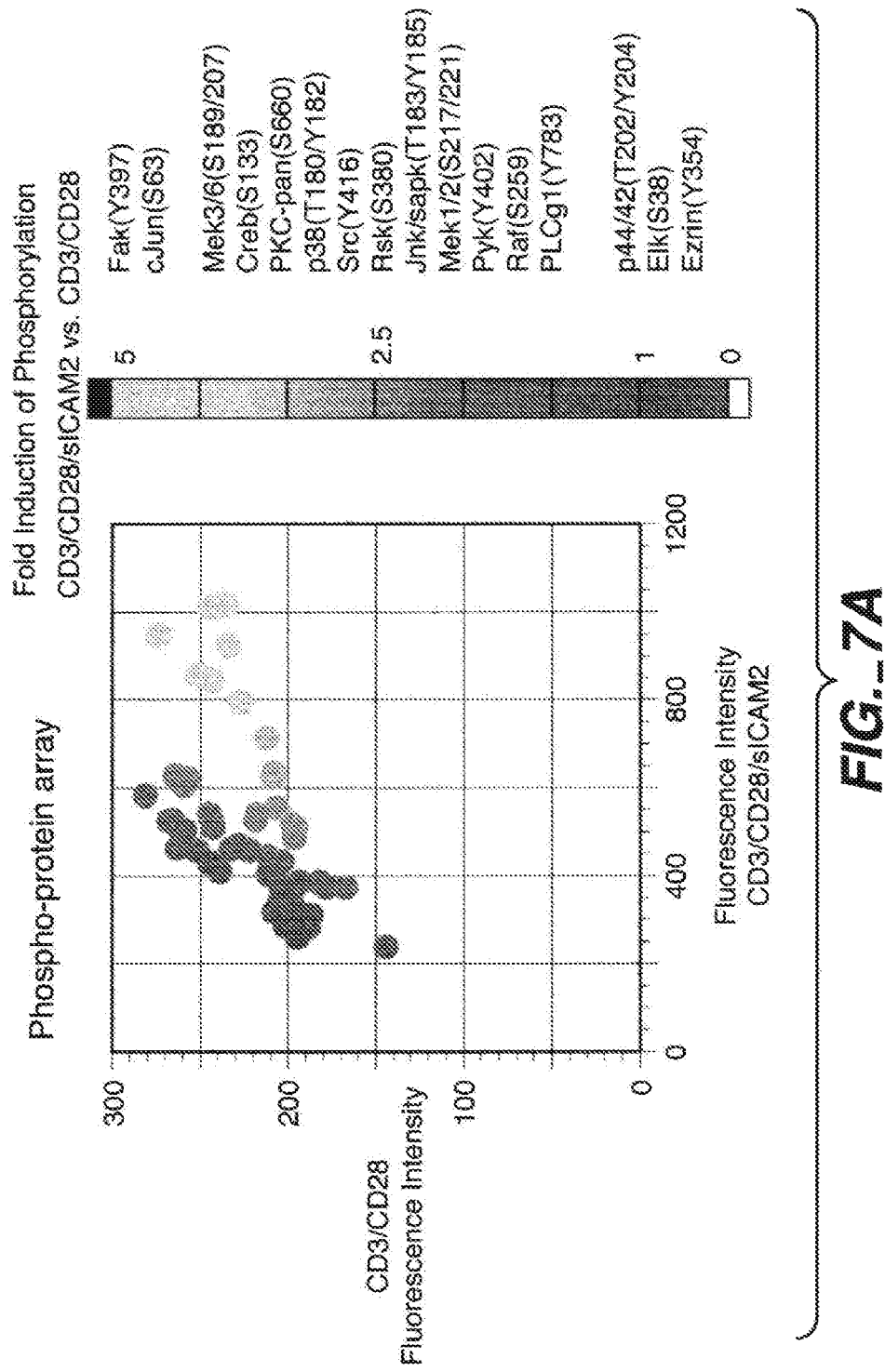

Integration of CD3, CD28, and LFA-1, Signaling Supercede Signaling Induced by CD3/CD28 Co-Stimulation We had performed kinetic analyses of multiple active kinases by flow cytometry to CD3, CD28 and LFA-1, stimulation (FIG. 6F). Since activation rates varied for individual stimuli tested (data not shown), we decided to study the combinations of CD3/CD28, versus CD3/CD28/LFA-1, in phospho-protein based analyses. We developed a phosphoprotein array by spotting a combination of 96, phospho and non-phospho specific antibodies for differential analysis of signaling proteins induced by CD31CD28, versus CD3/CD28/LFA-1, stimulation in purified human naïve CD4, T cells. (FIG. 7A). Enrichment of primary naïve T cells was performed by magnetically activated cell sorting using markers CD8, CD19, CD16, CD14, HLA-DR, and CD44 to remove cytotoxic T cells, B cells, NK cells, macrophages, and activated T cells from human PBMC respectively. After lysis of cells, equivalent protein lysates were labeled with Alexa532, or Alexa680, and the samples were co-hybridized to the array. The fluorescent intensities for both dyes were read by a fluorescent plate reader, and the log ratios were computed to obtain a differential signal between the stimulations tested. The fluorescent intensities for both channels is plotted on an XY coordinate grid (FIG. 7A). The fold induction in phosphorylation, as determined by the log ratios and is displayed on the plotted fluorescence intensity coordinates yielded for CD3/CD28, and CD3/CD28/LFA-1, stimulation (FIG. 7A). Analysis identified a 2-5 fold phospho-induction of MAPK kinases (p44/p42, p38, JNK, raf, mek1/2, mek3/6, rsk, raf), src related kinases (src, pyk2), and integrin signaling kinases (FAK), among others (FIG. 7A). Internal reference controls of non-phospho proteins (p44/42, MAPK, p38, MAPK, JNK, mek1/2, mek3/6, rsk, raf, src, pyk, fak) for these kinases showed induction in the range of 0.8-1.5, fold and were not expected to change significantly at the endpoint tested (data not shown). Antibodies against structural proteins (actinin, actin, tubulin) were used to verify equivalent protein quantities (data not shown). These results indicated that the triple CD3/CD28/LFA-1, stimulation induced overall phosphorylation of multiple proteins (kinases and transcription factors) to a greater extent than CD3/CD28, stimulation.

T cell activation requires cell cycle entry and subsequent cell proliferation, which is an important downstream outcome of cellular activity induced by signal transduction pathways. Cellular proliferation and concomitant cell cycle initiation was measured by flow cytometry staining for DNA content and Ki-67, proliferation antigen. FIG. 7C demonstrates cell cycle entry after 12 hours in CD3/CD28/LFA-1, stimulus as noted by >2n DNA content and expression of nuclear antigen Ki-67. Proliferation associated antigen Ki-67, and total DNA content quantify the cells residing within different cell cycle phases (Endl et al., 2001). As shown in FIG. 7C, CD3/CD28/LFA-1, stimulation invokes far greater percentages of cells in the S and G2/M phase than CD3/CD28, stimulation. Thus, a more profound cell cycle entry is observed in CD3/CD28/LFA-1, vs. CD3/CD28, stimulated cells.

Simultaneous Assessment of Immunophenotype, Intracellular Signaling, and Cellular Function in Single Cells We were interested in determining the contribution LFA-1, signaling possessed for naïve T cell activation in conjunction with CD3/CD28, co-stimulation. As evidenced below, we multiplexed magnetically activated cell sorting, 13-dimensional multiparameter flow cytometry (surface immunophenotyping, intracellular production of active kinases and cytokines) with profiling of secreted cytokines (cytometric bead arrays) and nuclear localized transcription factor profiling to obtain a multidimensional assessment of T cell activation and effector cell function. FIG. 8 represents a flow diagram of the various techniques multiplexed for functional analysis and these data sets were cross-referenced for correlatives of cell surface receptor activation, intracellular signaling, and functional outcomes.

Enrichment of primary naïve T cells was performed by magnetically activated cell sorting (MACS negative depletion) using markers CD8, CD19, CD16, CD14, HLA-DR, and CD44, to remove cytotoxic T cells, B cells, NK cells, macrophages, and activated T cells from PBMC respectively (FIG. 8). We utilized 8, markers to identify naïve human T cells (CD3$^+$, CD4$^+$, CD8$^-$ CD45RA$^+$, CD62L$^+$, CD11a$^{dim}$CD27$^+$, CD28$^+$, ). CD3, CD28, and LFA-1, single and combined stimulation was performed on enriched non-activated T cells. Mature naïve T cells, as determined by 8, immunophenotypical markers, were analyzed for CD69, CD25, and IL-2 expression, simultaneously by 13-dimensional flow cytometry as expression of these markers defines an activated T cell (Yu et al., 2000; Zola, 2000). Flow cytometric kinetic experiments identified signaling pathways as tested for individual stimulation to peak and subside within 0.5-4 hours post stimulation and were unique to each phospho-kinase tested (data not shown). We analyzed samples at 8, 12, and 24, hours post stimulation to observe the phospho-levels of stimulated cells. Post 8, hour stimulations, CD3, stimulation alone resulted in minor CD69 activation and low levels of phospho-p44/42, (FIG. 8, panel I). CD3/CD28, co-stimulation induced more CD69, activation, but the levels of phospho-p44/42, MAPK returned back to a basal level (FIG. 8, panel II). However, optimal activation of naïve T cells (CD3'CD4$^+$, CD8$^-$ CD45RA$^+$, CD62L$^+$, CD11a$^{dim}$CD27$^+$, CD28$^+$, ) was observed in the presence of LFA-1, plus CD3/CD28 stimulation at 8, hours (FIG. 8, panel III). sICAM-2, gave rise to some phospho-p44/42, induction and intermediate CD69, induction whereas CD28, stimulation alone was incapable of inducing either marker to express (FIG. 8B-C). At this timepoint, CD25, and IL-2, expression was observed for the CD3/CD28, stimulation, but the levels were greater in the CD3/CD28/LFA-1 stimulated cells (FIG. 8, panel III). Thus, these results suggested a signaling threshold was a consequence of 3, surface mediated signal integration for CD3, CD28, and LFA-1.

We performed titration and kinetic analyses for stimulus induced T cell activation as measured by IL-2, intracellular production and CD25, and CD69, surface expression by flow cytometry. The mean fluorescent intensities (MFI) of the intracellular IL-2, detection were computed, and the log ratio of the MFI$_{stimulated}$, to the MFI$_{unstimulated}$, was calculated and plotted as a function of the concentrations of the titrations for the stimulants used (both for single and the various ratios for the combined stimulants (FIG. 9)). A fluorescence intensity gradient was applied to the range of values to visually plot the differences (FIG. 9). At 6, hour stimulation, titration of LFA-1, and CD3/CD28, stimulation increased production of intracellular IL-2, depicting a threshold for IL-2 production at 0.1, µg/ml of a 1:1:1, ratio of CD3/CD28/LFA-1, stimulation (FIG. 9A, right panel).

Similar levels of CD3, and CD28, titrations showed lower levels of detected intracellular IL-2 (FIG. 9A, left panel). Higher levels than 0.1, µg/ml of CD3/CD28/LFA-1, demonstrated a linear response in concentration of stimulus to that of IL-2, production (FIG. 9A). Levels of inducer as high as 10, µg/ml of CD3/CD28, did not produce the same intracellular levels of IL-2, after 6, hr CD3/CD28/LFA-1, stimulation (FIG. 9A). Varying the ratio of either CD3, or CD28, up to 10,000 fold higher in the CD3/CD28/LFA-1, combination did not result in increased levels of intracellular IL-2, (data not shown). Therefore, ratiometric titration analyses indicates that the LFA-1, signal contribution cannot be compensated by increased CD3, or CD28, stimulation.

At 6, hr stimulation, 10,000, fold less CD3/CD28/LFA-1, stimulus was necessary than in CD3/CD28 costimulation for similar expression of CD69, and CD25, (FIG. 9B). After 6, hrs of CD3/CD28/LFA-1, stimulation we observed detectable secreted IL-2, contrasting the 12, hrs necessary for first detection of CD3/CD28, mediated IL-2, secretion (data not shown). At 12, hrs post stimulation, extracellular IL-2, after CD3/CD28/LFA-1, stimulation was reflected by significant production of intracellular IL-2, and correlated with enhanced CD69, expression (FIG. 9C). Furthermore, CD25, expression is maintained in the CD3/CD28/LFA-1, stimulated T cells at 48 hours, contrasting to a decrease observed in the CD3/CD28, stimulated cell population (FIG. 8B). Thus, the LFA-1, stimulus positively contributes to overcome the threshold of IL-2, production, allowing T cells to become activated more proficiently and with considerably enhanced longevity.

Stimulus Through LFA-1, Contributes to Transcription Factor Nuclear Translocation and Activity Transcription factor nuclear localization and activation profiling was performed in single CD3, CD28, and LFA-1, stimulations, as well as CD3/CD28, vs. CD3/CD28/LFA-1, stimulation. Luciferase reporter constructs were used to verify NFAT, NF-κB, and AP-1, activities. CD3/CD28/LFA-1 stimulus presented higher fold inductions of NFAT, NF-KB, and AP-1, transcriptional activity than CD3, or CD3/CD28, stimulation (FIG. 10A). Nuclear extracts of stimulated naïve CD4, T cells were bound to 96-well plates spotted with consensus sequences to the transcription factors NF-κB p65, NF-κB p50, cFos, CREB, aft2, and cRel. Detection of bound transcription factors was performed by standard ELISA techniques. Stimulation to CD3, CD28, and LFA-1, induced distinct profiles of nuclear localized transcription factors (FIGS. 10D-E). CD3/CD28, stimulus induced nuclear localization of all transcription factors tested here, with somewhat higher levels detected for the CD3/CD28/LFA-1, stimulus (FIG. 10B). The presence of the LFA-1, stimulus was slightly additive with CD3/CD28, in enhancing the levels of nuclear localized transcription factors. Titration experiments of NFAT activity verified that the LFA-1, signaling cannot be compensated for by increased concentrations of CD3/CD28, (FIG. 10C), results consistent with the expression of IL-2, (see FIG. 9A). Thus, the addition of the LFA-1, signaling integrates with that of CD3, and CD28 co-stimulation to enhance gene expression of at least the T cell transcription activities tested here.

LFA-1, Stimulation in the Presence of CD3/CD28, Polarizes T Cell Differentiation Towards a TH1, Phenotype We performed titration experiments of both CD3, vs. CD28, and CD3/CD28, vs. LFA-1, stimulation and monitored intracellular production of IL-4, and INFγ, Activated T cells, differentiate to either TH1, or TH2, effector T cells and can be preferentially directed towards one pathway by cytokines or additional stimuli (Asnagli and Murphy, 2001; Moser and Murphy, 2000). Effector cells can be identified by their cytokine secretion profile. TH1, cells are characterized by high IFNγ and low IL-4, whereas TH2, cells are characterized by high IL-4, and low IFNγ (Murphy et al., 2000). Computing the ratio of the median fluorescence of IL-4/IFNγ demonstrates that the LFA-1 stimulus, at all concentrations tested, favors a low IL-4/IFNγ ratio (FIG. 11). This is consistent with the TH1, phenotype. In the absence of the LFA-1, stimulus, CD3, and CD28, titrations favored a TH2, phenotype.

We used cytometric bead arrays to assess the secretion of IFNγ, IL-10, IL-2, IL-4, IL-5, and TNFα, in naïve T cells after 24, hours stimulation. The combination of CD3/CD28, presented high levels of IL-4, and low levels of IL-5, and IL-10. This contrasted CD3/CD28/LFA-1, stimulation which displayed similar levels of IFNγ, but significantly lower levels of IL-4, (FIG. 12). The triple stimulation reported elevated levels of IL-5, and IL-10, with similar levels of IL-2, at 24, hours (FIG. 12). Neither stimulation reported elevated levels of TNFα (FIG. 12) and this effects were not observed in single stimulated cells (FIG. 10E). Thus, the stimulation by LFA-1 polarizes T cell differentiation toward a TH1, phenotype in the presence of CD31CD28, stimulation.

Discussion

The work presented demonstrates that the ICAM-2/LFA-1, interaction contributes a distinct signal to CD3/CD28, co-stimulation and leads to rapid and optimal naïve T cell activation. Furthermore, it demonstrates that this accessory stimulation can, together with CD3, and CD28, and in the absence of additional signals, polarize T cell differentiation towards an apparent TH1, phenotype. Although it is expected that T cell signaling integrates numerous additional signals in the native environment, this finding suggests strongly that ICAM-2, induced LFA-1, signaling can be an important determinant of phenotypic outcomes in naïve T cell maturation.

Initiation of T cell activation requires cell-to-cell contact, an adhesion process primarily mediated by Leukocyte Function-Antigen 1, (LFA-1). Adhesive events involved in T cell contact have largely been unrecognized as transducing signals that may enhance T cell functions. However, there is increasing evidence for the importance of adhesion mediated events in optimal T cell activation (Neeson et al., 2000; Somersalo et al., 1995; Wulfing et al., 1998). Model systems of T cell stimulation using insect or fibroblast transfected cells report ICAM/LFA-1, interactions to be necessary for T proliferation (Damle et al., 1992a; Damle et al., 1993; Damle et al., 1992b; Damle et al., 1992c; Deeths and Mescher, 1999). We utilized a solubilized form of a normally surface-bound ligand of LFA-1, ICAM-2, to study the contribution of LFA-1, signaling to naïve T cell activation as ICAM-2, was able to mediate the active form of LFA-1, and induce a calcium influx (characterized in Perez and Nolan manuscript submitted [, reviewers please see manuscript in Appendix]). We report here that two LFA-1, binding proteins, JAB1, and cytohesin-1, are released, and subsequently phosphorylated upon ICAM-2, binding. Utilizing intracellular delivery of specific antibodies/peptides towards JAB1, and cytohesin-1, these LFA-1, interacting proteins mapped to distinct signaling pathways upon stimulation.

Cytohesin-1, is a guanine exchange factor that has recently been identified to be phosphorylated by PKCδ in vitro (Dierks et al., 2001) and enhances LFA-1, mediated leukocyte adhesion in T cell lines (Weber et al., 2001). Recently, a study identified the human herpesvirus 8, protein kaposin A as capable of mediating signaling by recruitment of cytohesin-1, and that a cytohesin-1, mutant (defective in guanine nucleotide exchange) was defective in p44/42, MAPK activation (Kliche et al., 2001). Interestingly, antibodies and a peptide directed to cytohesin-1's C-terminal (SECT domain), which contain the PKC consensus sites to threonine, blocked cytohesin-1, signaling to p44/42, MAPK. JAB1, another LFA-1, integrin binding protein, contains PKC serine consensus sites by sequence analysis, and has been identified as a mediator of cJun phosphorylation and AP-1, activity in cell culture models (Bianchi et al., 2000). Therefore these studies corroborate the direct observation that JAB1, and cytohesin-1, are involved in signaling upon LFA-1, stimulation in naïve CD4, T cells.

Multidimensional analysis of LFA-1, signaling events, in conjunction with CD3/CD28, stimulation, indicated that T cell activation was optimal upon triple stimulation. Differential phospho-protein analysis suggested that LFA-1, signaling induced phosphorylation of many signaling events. The integration of these signaling events mediated by LFA-1, in addition to CD3/CD28, costimulation is exemplified by the enhanced NFAT, NF-κB, and AP-1, activities. The presence of LFA-1, signaling lowered the threshold for IL-2, CD25, and CD69, expression (see FIG. 9) and initiated cell cycle progressions. Furthermore, the levels of nuclear translocated transcription factors as tested were greater in the CD3/CD28/LFA-1, stimulus vs. CD3/CD28, demonstrating the result of multiple kinase cascades. However the global analysis of transcriptional activity is expected to yield insights into the consequences of signal integration for factors not tested here as phosphorylation of other transcription factors, namely dun, Creb, Rsk, JNK, p44/42, and elk were also observed (see FIG. 7A).

Consequences of the LFA-1, integrin signaling included kinetically enhanced naïve T cell activation, lowering of the stimulus threshold for T cell activation, and apparent polarization of T cells to favor a TH1, phenotype, as determined by low IL-4, and high IFNγ levels. Of significance, T cell lines expressing a constitutively active LFA-1, respond to sub-threshold stimuli (Kaplan et al., 2000, (Damle et al., 1993) and blocking LFA-1/ICAM interactions has been demonstrated to favor TH2, cytokine production (Salomon and Bluestone, 1998). Therefore these results reconcile with the evidence provided here that LFA-1, plays an active role in T cell activation in addition to its adhesive properties. Based on these observations, it is predicted that LFA-1, knockout mice, will not only have impaired immune responses, but will be deficient in the ability to surmount an inflammatory response or recover from infections necessitating a TH1, response for clearance. Studies utilizing CD18, knockout mice, the β2, integrin of LFA-1, do indeed show impaired responses in a delayed-type hypersensitivity (DTH) inflammation model (Grabbe et al., 2002), as well as a defect in the induction of peripheral immune responses (Scharffetter-Kochanek et al., 1998). Thus, LFA-1, is important for in vivo TH1, responses.

In conclusion, LFA-1, contributes significantly to naïve T cell functionality as demonstrated by multiple independent assays. Most importantly, it greatly potentiates CD3/CD28, costimulation allowing for T cell maturation (as measured by CD69/CD25, expression, IL-2, secretion and progression to the S+G2/M phases of the cell cycle. Under the defined circumstances it also appears to contribute to commitment decisions as measured by the enhanced expression of TH1 cytokines. Underlying these outcomes we correlated these results with stimulation of multiple transcription factors and kinases, such as p44/p42, known to play roles in expression of these genes. Inhibition of LFA-1, by small molecules has also shown efficacy in various inflammation murine models although the molecular mechanisms for these observations remain unknown. The small molecule LFA-1, antagonist BIX 642, inhibited the DTH response in a trans-vivo DTH model (Winquist et al., 2001). Recently, an oral LFA-1, inhibitor LFA703, suppressed the inflammatory response in a murine model of peritonitis (Weitz-Schmidt et al., 2001). Furthermore, Leukocyte Adhesion Deficient (LAD) patients, a disease in which CD18, is either mutated or missing, display severe and recurrent bacterial infections (Hogg et al., 1999; Lipnick et al., 1996), in addition to LAD afflicted children having increased risk for infection of pseudomonoas aerguinos (Pollard et al., 2001), an infection typically cleared by a TH1, response (Fruh et al., 1995; Moser et al., 2002). Therefore, the clinical manifestations reported in both LAD patients and LFA-1, knockout mice can validate the physiological significance of LFA-1's signaling role demonstrated here in T cell activation and effector cell differentiation. We expect, given our current studies, that LFA-1 signaling will be further implicated in important immune cell regulatory events.

Materials and Methods
Immunological and Chemical Reagents

The following phospho-antibodies (p-Ab) were obtained from Cell Signaling Technologies (CST): p-Raf1, (Ser259), p-MEK1/2, (Ser217/221), p-p44/42, MAP kinase (Thr202/Tyr204), p-p44/42 MAPK (Thr202/Tyr204) mAb, p-Elk-1, (Ser383), p-p38, MAP kinase (Thr180/Tyr182), p-cJun (S63), non-phospho specific antibodies to the above proteins were also obtained from CST. Anti-Ki-67, mAb (Transduction Laboratories). All surface antibodies, cytokine antibodies, and isotype controls were obtained from PharMingen: CD3, CD4, CD8, CD69, CD25, IL-2, IL-4, IFNγ on FITC/PE/PerCp/APC. Alexa-Fluor dyes (350, 430, 488, 532, 546, 568, 594, 633, 660, 680), Cascade Blue, Cascade Yellow and R-phycoerythrin (PE) were purchased from Molecular Probes (Eugene, Oreg.). FITC and Texas Red were purchased from Pierce (Rockford, Ill.). Cy5, Cy5.5, Cy7, were obtained from Amersham Life Science (Pittsburgh, Pa.). Tandem conjugate protocols for Cy5PE, Cy5.5PE, Cy7PE, Cy5.5APC, Cy7APC can be found at www.drmr.com/abcon. Antibodies to CD62L, CD28, CD27, CD45RA, CD11a, CD3, CD4, CD8, IL-2, IL-4, IFNγ (PharMingen) were conjugated to FITC, PE, Cy5PE, Cy5.5PE, Cy7PE, Cy5.5APC, Cy7APC, cascade blue, cascade yellow, or alexa fluor dyes as needed. Quantitation of fluorescent probe conjugation was assessed to determine degree of labeling and protocols including dye spectral properties can be found at www.metazoa.com/UPL3419. In general, alexa conjugates used had 2-12, moles of fluorescent dye per mole of protein. The following antibodies were obtained from varying vendors: CD102-FITC (Research Diagnostics), anti-rabbit IgG HRP (CST), anti-mouse/rabbit Alexa 488/568/633, (Molecular Probes). Anti-JAB1, anti-cytohesin-1, C-terminal cytohesin-1, peptide, and anti-mouse IgG HRP (Santa Cruz Biotechnologies). Protein and chemical reagents used: DMSO, phorbol myristelated acetate (PMA) ionomycin, phytohemmagluttin A (PHA), propidium iodide (PI) RNASE (Sigma). U0126, PD98059, SB600125, (Calbiochem). Anti-CD3, (OKT3, NA/EN) and anti-CD28, mAb (NA/NE, PharMingen). ICAM-2-FC was purchased from Genzyme.

Cell Culture and Primary Cell Isolation

Jurkat T-cells were maintained in RPMI-1640, 10% FCS, 1% PSQ. Cells were maintained at 5% $CO_2$/37° C. humidified incubator and serum starved 12, hours for phospho analysis. For preparation of primary cells, mononuclear cells were isolated from blood of healthy donors (Stanford Blood Bank, Stanford, California). Human peripheral blood monocytes were obtained by Ficoll-plaque density centrifugation (Amersham Pharmacia, Uppsala, Sweden) of whole blood and depletion of adherent cells by adherence to plastic culture dishes. Isolated cells were maintained in complete media. Magnetically activated cell sorting was to enrich for naïve CD4, T cells by negative isolation using combinations of CD16, CD14, CD44, HLA-DR, CD8, or CD19 biotinylated antibodies (Dynal, Oslo, Norway) and streptavidin-magnetic beads (Dynal, Oslo, Norway).

Immunoprecipitations and Immunoblotting

Cell extracts were prepared by washing $2\times10^6$, cells (treated as indicated) in ice cold PBS and harvesting in lysis buffer (20, mM Tris pH 7.5, 150, mM NaCl 1, mM EDTA 1, mM EGTA, 1% Triton X-100, 2.5, mM $Na_2PO_4$, 1, mM $_R$-glycerolphosphate, 1, mM $Na_3VO_4$, 1, μg/ml Leupeptin, 1, mM PMSF, protease inhibitor cocktail tablet (Boehringer Mannheim). Extracts were centrifuged 14,000, RPM (5, min, 4° C.) and 10, μg (BCA protein assay (Pierce)) were immunoblotted using standard procedures. Immunoprecipitations (IP) were pre-cleared with protein NG plus-agarose beads, incubated with primary ab (1, h), protein NG plus-agarose beads (1, h) and washed 4× with lysis buffer. Blots were incubated with the indicated antibodies and developed using ECL (Amersham).

Flow Cytometry and FACS Analysis

Intracellular and extracellular staining was performed as described for phospho-staining (Perez and Nolan, 2002). Approximately $1-10\times10^7$, peripheral blood mononuclear cells (unactivated CD4+, T cells) were obtained by magnetically activated cell sorting (negative isolation), treated with a stimulatory condition for indicated time, and prepared for flow cytometry. Brefaldin A (10 μM) was added for intracellular cytokine detection for 6, hours (or as indicated). Isotype control match antibodies were used for stain controls. Kinetic analyses was done on synchronized 96-wells and directly fixed as described (Perez and Nolan, Submitted). Four or less color flow cytometry data acquisition was collected on a FACSCalibur machine (Beckton Dickinson, San Jose Calif.) using CELLQuest software, analyzed and presented using FlowJo software (Tree Star, San Carlos, California). Data for four or less colors are representative of 3 independent experiments of $10^6$, cells/sample and 50,000, events were collected and manually calibrated. 11-color data acquisition was collected on a modified FACStarPlus (Becton Dickinson, San Jose, Calif.) connected to MoFlo electronics (Cytomation, Fort Collins, Colorado). Data were collected by FACS-Desk software and compensated, analyzed, and presented using FlowJo software. Data for 11-color flow cytometry collected a minimum of 200,000, events. Cytometric bead arrays (CBA) were from PharMingen. Ratios of intracellular flow cytometric measurements were calculated from the following equation where MFI equals mean fluorescent intensity: Log $[(MFI_{experimental} - MFI_{isotype\ mAb})/(MFI_{control} - MFI_{isotype\ mAb})]$. Values were then designated a color intensity of two chosen colors to depict high and low, and displayed where appropriate.

Phospho-Protein Arrays

Protein A coated 96, well plates were coated with phospho and non-phospho specific antibodies (1, μg/ml) for 1, hr. Plates were washed twice with PBS, and antibodies were covalently coupled with dissuccimidyl succinate as suggested by manufacturer (Pierce). Plates were washed three times (PBS) and blocked with 4% BSA (in PBS, 30, min). Protein samples from stimulated CD4+ naïve T cells were quantified and equivalent amounts conjugated to either succimydyl ester reactive Alexa 532, and 680, dyes in 0.1, M pH8.0, sodium bicarbonate. After 1, hr the reactions were quenched (100, μL 1, M Tris pH 8.0) and washed in centricon YM-10, spin columns. Labeled protein samples were resuspended in PBST (plus 1% BSA). Plates were hybridized with 30, μg of Alexa532, and Alexa680, conjugated protein samples for 1, hr, 25° C. Plates were washed three times in PBST (PBS, 0.1% Tween-20) and three times in PBS. Fluorescent intensities were detected using a Molecular Devices Gemini Xs machine and fold induction was computed as the log ratio of the mean fluorescent intensities (MFI) of CD3/CD28/LFA-1, to CD3/CD28, stimulation, calculated from the following equation: Log.

Nuclear Transcription Factor Profiling

Mercury TransFactor kits (Clontech) spotted for consensus sequences for NF-κB p50, NF-κB p65, c-Rel, c-Fos, CREB, and ATF2, were used to hybridize transcription factors from nuclear extracts of $1\times10^1$ stimulated CD4+, naïve T cells (prepared as suggested by manufacturer). Detection of bound protein to DNA complex was made by standard ELISA methods.

Laser Scanning Confocal Microscopy

Cells were treated as indicated and adhered to poly-L-lysine (Sigma) coated sterilized coverslips (10, mg/ml, 30, minutes) by mild centrifugation (1000, RPM, 10, minutes), washed twice in phosphate buffered saline pH 7.4, (PBS) and fixed in 2.7% paraformaldehyde (in PBS). Cells were stained as described for flow cytometry: (primary at 0.1, mg/ml, secondary at 1:1000, dilution, in 4% FCS, with several washing steps in between). Stained coverslips were mounted onto glass slides with Prolong Antifade reagent (Molecular Probes) and visualized using a Zeiss laser scanning confocal microscope 510. Images were acquired using Zeiss LSM510, software and compiled using Adobe Photoshop 6.0.

Intracellular Delivery of Antibodies/Peptides

Antibodies were buffer exchanged into PBS by spin dialysis (centricon YM-100, spin columns) and mixed in 1:20, ratio of Fugene (Roche) for 30, min. Liposome/antibody complex was mixed with $1\times10^5$, cells in 50, μL, serum free media for 1, hr. Cells were washed twice (RPMI/4% FCS) and used for cellular assays within 2-4, hrs. Transfection efficiencies using FACS analysis of IgG-FITC was 30-40%.

Reporter Gene assays

Jurkat cells were transfected with 5, μg of NF-κB driven luciferase reporter gene (gift of S. Kinoshita, Stanford University) or AP-1, driven luciferase reporter gene (gift of J. F. Fortin, Stanford University) using Fugene 6, reagent (Boehringer Mannheim). NFAT-luciferase transfected cells were a gift of J. F. Fortin. Twenty-four hours after transfection, cells were stimulated as indicated for 6, hr at 37° C. Luciferase activity was analyzed in cell lysates of $1\times10^4$ cells (Promega).

References

Asnagli, H., and Murphy, K. M. (2001). Stability and commitment in T helper cell development. Curr Opin Immunol 13, 242-247.

Bennett, B. L., Sasaki, D. T., Murray, B. W., O'Leary, E. C., Sakata, S. T., Xu, W., Leisten, J. C., Motiwala, A., Pierce, S., Satoh, Y., et al. (2001). SP600125, an anthrapyrazolone inhibitor of Jun N-terminal kinase. Proc Natl Acad Sci USA 98, 13681-13686.

Bianchi, E., Denti, S., Granata, A., Bossi, G., Geginat, J., Villa, A., Rogge, L., and Pardi, R. (2000). Integrin LFA-1, interacts with the transcriptional co-activator JAB1, to modulate AP-1 activity. Nature 404, 617-621.

Bjorndahl, J. M., Sung, S. S., Hansen, J. A., and Fu, S. M. (1989). Human T cell activation: differential response to anti-CD28, as compared to anti-CD3, monoclonal antibodies. Eur J Immunol 19, 881-887.

Cefai, D., Cai, Y. C., Hu, H., and Rudd, C. (1996). CD28, co-stimulatory regimes differ in their dependence on phosphatidylinositol 3-kinase: common co-signals induced by CD80, and CD86. Int Immunol 8, 1609-1616.

Cerdan, C., Martin, Y., Courcoul, M., Brailly, H., Mawas, C., Birg, F., and Olive, D. (1992). Prolonged IL-2, receptor alpha/CD25, expression after T cell activation via the adhesion molecules CD2, and CD28. Demonstration of combined transcriptional and post-transcriptional regulation. J Immunol 149, 2255-2261.

Chambers, C. A., and Allison, J. P. (1999). Costimulatory regulation of T cell function. Curr Opin Cell Biol 11, 203-210.

Croft, M., and Dubey, C. (1997). Accessory molecule and costimulation requirements for CD4, T cell response. Crit Rev Immunol 17, 89-118.

Damle, N. K., Klussman, K., and Aruffo, A. (1992a). Intercellular adhesion molecule-2, a second counter-receptor for CD11a/CD18, (leukocyte function-associated antigen-1), provides a costimulatory signal for T-cell receptor-initiated activation of human T cells. J Immunol 148, 665-671.

Damle, N. K., Klussman, K., Leytze, G., Ochs, H. D., Aruffo, A., Linsley, P. S., and Ledbetter, J. A. (1993). Costimulation via vascular cell adhesion molecule-1, induces in T cells increased responsiveness to the CD28, counter-receptor B7. Cell Immunol 148, 144-156.

Damle, N. K., Klussman, K., Linsley, P. S., and Aruffo, A. (1992b). Differential costimulatory effects of adhesion molecules B7, ICAM-1, LFA-3, and VCAM-1, on resting and antigen-primed CD4+, T lymphocytes. J Immunol 148, 1985-1992.

Damle, N. K., Klussman, K., Linsley, P. S., Aruffo, A., and Ledbetter, J. A. (1992c). Differential regulatory effects of intercellular adhesion molecule-1, on costimulation by the CD28, counter-receptor B7. J Immunol 149, 2541-2548.

de Fougerolles, A. R., Stacker, S. A., Schwarting, R., and Springer, T. A. (1991). Characterization of ICAM-2, and evidence for a third counter-receptor for LFA-1. J Exp Med 174, 253-267.

Deeths, M. J., and Mescher, M. F. (1999). ICAM-1, and B7-1, provide similar but distinct costimulation for CD8+, T cells, while CD4+, T cells are poorly costimulated by ICAM-1. Eur J Immunol 29, 45-53.

Dierks, H., Kolanus, J., and Kolanus, W. (2001). Actin cytoskeletal association of cytohesin-1, is regulated by specific phosphorylation of its carboxyl-terminal polybasic domain. J Biol Chem 276, 37472-37481.

Dustin, M. L., Garcia-Aguilar, J., Hibbs, M. L., Larson, R. S., Stacker, S. A., Staunton, D. E., Wardlaw, A. J., and Springer, T. A. (1989). Structure and regulation of the leukocyte adhesion receptor LFA-1, and its counterreceptors, ICAM-1, and ICAM-2. Cold Spring Harb Symp Quant Biol 54, 753-765.

Endl, E., Hollmann, C., and Gerdes, J. (2001). Antibodies against the Ki-67, protein: assessment of the growth fraction and tools for cell cycle analysis. Methods Cell Biol 63, 399-418.

Fine, J. S., and Kruisbeek, A. M. (1991). The role of LFA-1/ICAM-1, interactions during murine T lymphocyte development. J Immunol 147, 2852-2859.

Fruh, R., Blum, B., Mossmann, H., Domdey, H., and von Specht, B. U. (1995). TH1, cells trigger tumor necrosis factor alpha-mediated hypersensitivity to Pseudomonas aeruginosa, after adoptive transfer into SCID mice. Infect Immun 63, 1107-1112.

Geiger, C., Nagel, W., Boehm, T., van Kooyk, Y., Figdor, C. G., Kremmer, E., Hogg, N., Zeitlmann, L., Dierks, H., Weber, K. S., and Kolanus, W. (2000). Cytohesin-1, regulates beta-2 integrin-mediated adhesion through both ARF-GEF function and interaction with LFA-1. Embo J 19, 2525-2536.

Grabbe, S., Varga, G., Beissert, S., Steinert, M., Pend, G., Seeliger, S., Bloch, W., Peters, T., Schwarz, T., Sunderkotter, C., and Scharffetter-Kochanek, K. (2002). Beta2, integrins are required for skin homing of primed T cells but not for priming naive T cells. J Clin Invest 109, 183-192.

Hogg, N., Stewart, M. P., Scarth, S. L., Newton, R., Shaw, J. M., Law, S. K., and Klein, N. (1999). A novel leukocyte adhesion deficiency caused by expressed but nonfunctional beta2, integrins Mac-1, and LFA-1. J Clin Invest 103, 97-106.

Kliche, S., Nagel, W., Kremmer, E., Atzler, C., Ege, A., Knorr, T., Koszinowski, U., Kolanus, W., and Haas, J. (2001). Signaling by human herpesvirus 8, kaposin A through direct membrane recruitment of cytohesin-1. Mol Cell 7, 833-843.

Kolanus, W., Nagel, W., Schiller, B., Zeitlmann, L., Godar, S., Stockinger, H., and Seed, B. (1996). Alpha L beta 2, integrin/LFA-1, binding to ICAM-1, induced by cytohesin-1, a cytoplasmic regulatory molecule. Cell 86, 233-242.

Koopman, G., de Graaff, M., Huysmans, A. C., Meijer, C. J., and Pals, S. T. (1992). Induction of homotypic T cell adhesion by triggering of leukocyte function-associated antigen-1, alpha (CD11a): differential effects on resting and activated T cells. Eur J Immunol 22, 1851-1856.

Lenschow, D. J., Walunas, T. L., and Bluestone, J. A. (1996). CD28/B7, system of T cell costimulation. Annu Rev Immunol 14, 233-258.

Lipnick, R. N., Iliopoulos, A., Salata, K., Hershey, J., Melnick, D., and Tsokos, G. C. (1996). Leukocyte adhesion deficiency: report of a case and review of the literature. Clin Exp Rheumatol 14, 95-98.

Moser, C., Jensen, P. O., Kobayashi, O., Hougen, H. P., Song, Z., Rygaard, J., Kharazmi, A., and N, H. b. (2002). Improved outcome of chronic Pseudomonas aeruginosa, lung infection is associated with induction of a Th1-dominated cytokine response. Clin Exp Immunol 127, 206-213.

Moser, M., and Murphy, K. M. (2000). Dendritic cell regulation of TH1-TH2, development. Nat Immunol 1, 199-205.

Murphy, K. M., Ouyang, W., Farrar, J. D., Yang, J., Ranganath, S., Asnagli, H., Afkarian, M., and Murphy, T. L. (2000). Signaling and transcription in T helper development. Annu Rev Immunol 18, 451-494.

Neeson, P. J., Thurlow, P. J., and Jamieson, G. P. (2000). Characterization of activated lymphocyte-tumor cell adhesion. J Leukoc Biol 67, 847-855.

Perez, O. D., and Nolan, G. P. (2002). Simultaneous measurement of multiple active kinase states using polychromatic flow cytometry. Nat Biotechnol 20, 155-162.

Pollard, A. J., Neale, J. P., Tsang, A., Massing, B., and Speert, D. P. (2001). Nonopsonic phagocytosis of Pseudomonas aeruginoas: insights from an infant with leukocyte adhesion deficiency. Pediatr Infect Dis J 20, 452-454.

Salomon, B., and Bluestone, J. A. (1998). LFA-1, interaction with ICAM-1, and ICAM-2, regulates Th2, cytokine production. J Immunol 161, 5138-5142.

Scharffetter-Kochanek, K., Lu, H., Norman, K., van Nood, N., Munoz, F., Grabbe, S., McArthur, M., Lorenzo, I., Kaplan, S., Ley, K., et al. (1998). Spontaneous skin ulceration and defective T cell function in CD18, null mice. J Exp Med 188, 119-131.

Simmons, D. L. (1995). The role of ICAM expression in immunity and disease. Cancer Surv 24, 141-155.

Somersalo, K., Carpen, O., Saksela, E., Gahmberg, C. G., Nortamo, P., and Timonen, T. (1995). Activation of natural killer cell migration by leukocyte integrin-binding peptide from intracellular adhesion molecule-2, (ICAM-2). J Biol Chem 270, 8629-8636.

Starling, G. C., McLellan, A. D., Egner, W., Sorg, R. V., Fawcett, J., Simmons, D. L., and Hart, D. N. (1995). Intercellular adhesion molecule-3, is the predominant co-stimulatory ligand for leukocyte function antigen-1, on human blood dendritic cells. Eur J Immunol 25, 2528-2532.

Weber, K. S., Weber, C., Ostermann, G., Dierks, H., Nagel, W., and Kolanus, W. (2001). Cytohesin-1, is a dynamic regulator of distinct LFA-1, functions in leukocyte arrest and transmigration triggered by chemokines. Curr Biol 11, 1969-1974.

Weitz-Schmidt, G., Welzenbach, K., Brinkmann, V., Kamata, T., Kallen, J., Bruns, C., Cottens, S., Takada, Y., and Hommel, U. (2001). Statins selectively inhibit leukocyte function antigen-1, by binding to a novel regulatory integrin site. Nat Med 7, 687-692.

Winquist, R. J., Desai, S., Fogal, S., Haynes, N. A., Nabozny, G. H., Reilly, P. L., Souza, D., and Panzenbeck, M. (2001). The role of leukocyte function-associated antigen-1, in animal models of inflammation. Eur J Pharmacol 429, 297-302.

Wulfing, C., Sjaastad, M. D., and Davis, M. M. (1998). Visualizing the dynamics of T cell activation: intracellular adhesion molecule 1, migrates rapidly to the T cell/B cell interface and acts to sustain calcium levels. Proc Natl Acad Sci USA 95, 6302-6307.

Yu, T. K., Caudell, E. G., Smid, C., and Grimm, E. A. (2000). IL-2, activation of NK cells: involvement of MKK1/2/ERK but not p38, kinase pathway. J Immunol 164, 6244-6251.

Zhang, Y. Q., Joost van Neerven, R. J., Van God, S. W., Coorevits, L., de Boer, M., and Ceuppens, J. L. (1997). B7-CD28, interaction is a late acting co-stimulatory signal for human T cell responses. Int Immunol 9, 1095-1102.

Zola, H. (2000). Markers of cell lineage, differentiation and activation. J Biol Regul Homeost Agents 14, 218-219.

Example 3

ICAM-2/LFA-1, Activates p44/42, MAPK Through PYK2, and SYK

In this Example, using the methods and compositions of the present invention, the present inventors (also referred to herein as "we") demonstrate that Leukocyte Function Antigen-1-(LFA-1) was found to activate the RAS/RAF/MEK/MAPK cascade upon engagement with ICAM-2. Dissection of the signaling pathway in revealed the ICAM-2/LFA-1, interaction depended on both PYK2, and SYK tyrosine kineses. Both PYK2, and SYK were found to associate with LFA-1, only after interaction with ICAM-2, and were rapidly re-distributed to the plasma membrane with concomitant phosphorylation of PYK2, and SYK as revealed by biochemical analysis and confocal microscopy. Chemical genetic approaches identify an LFA-1, mediated signal to phosphorylate PYK2, with subsequent signal relay to SYK to be contingent on PKC and PLCy activities. Furthermore, cell-to-cell contact of ICAM-2+, cells with LFA-1+, initiated the transactivation of the p44/42, MAPK pathway in LFA-1, expressing cells and simultaneously activated the AKT cell survival pathway ICAM-2, presenting cells, as determined by single cell kinase profiling by multiparameter flow cytometry. These results highlight that specific trans-signaling events occur upon cellular adhesion events mediated by the interaction of ICAM-2 and LFA-1, implicating the importance of ICAM interactions in consequential processes such as cellular adhesion and T cell activation.

Introduction

Leukocyte mediated functions are largely governed by their ability to localize to appropriate tissue compartments via adhesion molecule recognition of ligands on target tissues. Targeting of: leukocytes to distinct cellular environments is of pivotal importance in cellular processes such as blood clot formation (Bowes et al., 1995; Nagaoka et al., 2000; Schleef et al., 2001), immune surveillance (Patarroyo and Makgoba, 1989; Plate et al., 2000), inflammatory responses (Chihara et al., 2000; Cid et al., 2000; Krull et al., 1999; Zhang et al., 1999), angiogenesis (Griffoen et al., 1998; Melder et al., 1996; Patey et al., 1996; Radisavljevic et al., 2000; Verkarre et al., 1999), and cellular migration (All et al., 2000; Sans et al., 2001). Leukocyte targeting and adhesion is primarily mediated by the a and ~ integrin subunits and their intercellular adhesion molecule (ICAMs)-1, -2, -3, -4, -5, ligands (Douglas et al., 2000; Kruger et al., 2001; Sixt et al., 2001; Tian et al., 2000; van den Berg et al., 2001; Wang and Springer, 1998). The α and β integrin subunits form heterodimeric ICAM receptors such as leukocyte function antigen-1, (LFA-1, CD11a/CD18, or $\alpha_L\beta B2$), MAC-1, (macrophage receptor 1, CD11, β/CD18, or $\alpha_M\beta B2$), CD11, c/CD18, ($\alpha_x\beta B2$, or p150,95) and recently identified CD11d/CD18, ($\alpha_D\beta B2$) (Binnerts and van Kooyk, 1999; de Fougerolles et al., 1995; Gahmberg et al., 1998; Hayflick et al., 1998; Hermand et al., 2000). The ICAMs are members of the immunoglobin superfamily, a subclass of the adhesion molecules that include cadherins, integrins, and selecting. ICAMs show differences in their cell type distribution-which is believed to reflect their varying functions. In addition, they can be differentially induced by various inflammatory cytokines (Hayflick et al., 1998; Simmons, 1995; Somersalo, 1996). ICAM molecules are expressed on lymphoid lineages that include B cells, T-cells, red blood cells, macrophages (Hayflick et al., 1998), and also expressed on a subset of vascular endothelial cells (Griffioen et al., 1996) and neurons (Tian et al., 2000).

Deficiencies or augmentation of cellular adhesion properties are both detrimental and life-threatening, as exemplified in a variety of immunopathologies such as leukocyte adhesion deficiency type I (LAD I, allergic encephalomyelitis, tumor vasculature, vascular permeability diseases, hypertension, severe sepsis syndrome/septic shock, tumor metastasis, and osteoporosis among others (Allende et al., 2000; Angelopoulou et al., 1999; Collins et al., 2000; Etzioni and Tonetti, 2000; Ghaisas et al., 2000; Kiarash et al., 2001; Lalancette et al., 2000; Schnitzler et al., 1999; Tanaka et al., 2000; Weigand et al., 1999). Although extensive work has been conducted on leukocyte cell surface molecules to correlate mutations in, or absence of, the integrin receptors to the aforementioned immunopathologies it is not clear to what extent the ICAMs contribute to the progression of these diseases (Craig et al., 2000; Daniel et al., 2000; Koga et al., 2000; Mori et al., 2000; Muanza et al., 1999; Oishi et al., 2000). There is increasing evidence that elucidation of mechanisms involved in ICAM mediated cell-to-cell contact (Gottlieb et al., 2000) and in mechanisms that underscore the irregular production of soluble ICAM molecules may be of therapeutic interest (De Vita et al., 1998; Guo et al., 2000; Salmaggi et al., 1999). Blockade of LFA-1/ICAM interaction by peptides and monoclonal antibodies is proving to be effective in inhibiting processes such as T cell activation (Tibbetts et al., 2000), attenuation of organ transplant rejection and various adhesion related diseases (Gottlieb et al., 2000; Storck et al., 1994; Sun et al., 2000). Thus, ICAM molecules and their ligands are being recognized as important immunomodulators.

We have demonstrated that ICAM-2, can illicit a pro-survival signal upon surface clustering on human B cells rendering protection against FAS and TNFa induced apoptosis. Similarly, ICAM-1 has been shown to transmit an intracellular signal upon interaction with the extracellular matrix (Pluskota and D'Souza, 2000) and mice deficient in ICAM receptors or ICAM molecules have irregularities in a functional immune system (Ding et al., 1999; Gerwin et al., 1999; Igietseme et al., 1999; Schneeberger et al., 200p; van Den Engel et al., 2000). Crystallographic, molecular, and mutational analysis of ICAMs (1-4) and LFA-1, suggest that overlapping but not identical binding regions exist (Casasnovas et al., 1998; Casasnovas et al., 1999; Casasnovas et al., 1997; Edwards et al., 1998; Kotovuori et al., 1999, Hermand et al., 2000). In addition, dimerization requirements for ICAM-1, but not ICAM-2, or -3, binding to LFA-1, are indicative of differences in molecular interactions involving ICAM and LFA-1, and may allow differential cellular responses to distinct ICAM molecules (Casasnovas et al., 1998; Miller et al., 1995; Reilly et al., 1995). Finally, the repertoire of ICAM-binding integrin heterodimeric receptors and their subsequent signaling has not been investigated in depth.

Utilizing both retrovirally transduced NIH3T3, to express human ICAM-2, and a biochemically purified soluble ICAM-2, we demonstrate that in T cells, LFA-1, interaction with ICAM-2, induces activation of the RAS/RAF/MEK/ERK pathway (p44/42, Mitogen Activated Protein Kinase, MAPK). Monoclonal antibodies against LFA-1a (CD11a) or β2, integrin (CD18) blocked p44/42, MAPK activation. The signal was independent of ZAP-70, Src, FAK, and Lck as phosphorylation was not observed as a function of ICAM-21LFA-1, interaction. ICAM-2/LFA-1, induced p44/42, MAPK activity was dependent on proline-rich tyrosine kinase 2, (PYK2) and spleen tyrosine kinase (SYK), members of the Src family non-receptor tyrosine kineses, and p44/42, activity was abrogated with specific pharmacological inhibitors piceatannol and tyrphostin A9, respectively. Confocal microscopy reveals that there is a re-distribution of both PYK2, and SYK to the cellular membrane upon LFA-1, engagement with ICAM-2, and that this interaction yields phosphorylation of PYK2. Furthermore, PYK2, and SYK co immunoprecipated with LFA-1, only after engagement of ICAM-2, indicating a ligand induced conformational change was responsible for the interaction.

Development of a phospho-tyrosine protein elisa to screen for potential kineses involved in the LFA-1, to PYK2/SYK activation identify LFA-1, ligation to induce PYK2, phosphorylation, with subsequent SYK phosphorylation dependent on PCK and PLCy. Biochemical purification of ICAM-2, binding proteins not only identified β2, integrin, but also β1, and β3, integrins as being capable of interacting with ICAM-2, emphasizing that additional heterodimeric receptors involving β1, or β3, integrin subunits may exist for the ICAMs and that differential cellular responses can be regulated at the level of receptor subunit expression at the level of receptor avidity. Recently, other integrin heterodimeric receptors have been shown to influence the activity of β2, integrin receptors, illustrating that concerted cell adhesion might represent an additional level of intracellular signaling or regulation (May et al., 2000). Simultaneous measurement of intracellular kinase activities in mixed population experiments demonstrated that when ICAM-2 overexpressing fibroblasts engage LFA-1, expressing T-cells, activation of the AKT pathway is exclusively seen in the ICAM-2, expressing cells while activation of the p44/42, MAPK (ERK1/2) pathway is exclusively seen on the LFA-1, expressing T-cells. This trans-stimulatory effect of the ICAM-2/LFA-1, interaction is not dependent on additional co-stimulatory molecules, as ICAM2−/− fibroblasts did not result in either AKT or p44/42, MAPK activation. These results elucidate a previously unrecognized signaling mechanism for LFA-1, and have implications for its role in cellular adhesion and T cell activation.

Results

ICAM-2, Clustering Activates the RAF/MEK/ERK Pathway

Previous work utilizing retrovirally transduced NIH3T3, to overexpress human ICAM-2, allowed for the dissection of an ICAM-2, induced signaling pathway that was dependent on PKB/AKT and mediated through the intracellular C-terminal. In this work, clustering of surface expressed ICAM-2, molecules by monoclonal antibodies revealed a distinct and separate activation of the RAF/MEK/ERK mitogen activated protein kinase pathway (p44/42, MAPK) that was not abrogated in the presence of PI3K inhibitors (data not shown). The extracellular portion of ICAM-2, was sufficient to induce MAPK activity as both an ICAM-2, C-terminal truncated molecule (ICAM2-ΔC) and full length ICAM-2, induced activation of p44/p42, MAPK when clustered on the cell surface. The ICAM2-DC molecule was not capable of transducing the PI3K/AKT intracellular signal characterized to ICAM-2, in a separate study. Expression of human ICAM-2, and ICAM2-ΔC was verified to target to the cellular membrane by flow cytometry (FIG. 13A) and was confirmed by western blot analysis to present a similar electrophoretic mobility as the endogenous ICAM-2 protein in Jurkat cells (FIG. 13B). NIH3T3, fibroblasts do not express levels of murine ICAM-3 but do express low levels of murine ICAM-1, and ICAM-2, however, retrovirally enforced ectopic expression of human ICAM-2, was found to be 5, magnitudes higher than endogenous levels as determined by quantitative flow cytometry.

ICAM-2, clustering initiated activation of the RAF/MEK/ERK cascade (p44/42, MAPK pathway) in NIH3T3, cells as a function of time as observed by immunoblotting for each respective kinase's active phosphorylated state. (FIG. 13C). ERK kinase activity led, as expected, to phosphorylation of Elk-1. Phosphorylation of Elk-1, has been demonstrated to be sufficient for its activation and nuclear translocation (Wang and Prywes, 2000). Incidentally, other p44/42, MAPK activated proteins capable of transcription activity, namely Rsk-1, (FIG. 13C) and CREB (data not shown), were also phosphorylated as a function ICAM-2, clustering. The ICAM-2, induced phosphorylation of p44/42, MAPK was verified by kinase activity assays and was present in both ICAM-2, and ICAM2-ΔC transduced fibroblasts, and by endogenous ICAM-2, in Jurkat T cells when crosslinked (FIG. 13D). Furthermore, activation of JNK, p38, MAPK or activities of MEK3/6, or MEK 4/7, were not observed following ICAM-2, crosslinking (data not shown). Verification of the truncated ICAM2-ΔC expression by intracellular flow cytometry (see FIG. 13A) and its apparent inability to induce an intracellular signal led us to believe that the p44/42 MAPK activity observed was due by a surface-bound ICAM-2, interacting protein (discussed below).

ICAM-2, induced p44/42, MAPK Activity Attenuates Growth Kinetics and Augments Cellular Contact Inhibition The p44/42, MAPK family is important in a variety of cellular process that govern growth, survival, and differentiation of cells (Chang and Karin, 2001). Several assays were used to assess p44/42 MAPK mediated events. Cell cycle analysis was performed to determine if the ICAM-2, induced p44/42, MAPK activity was able to initiate cell cycle re-entry. ICAM-2, ICAM2-ΔC, vector control, and varying cell types were serum starved for 72, hours to synchronize cells in the absence of chemical agents. Cells were then crosslinked for ICAM-2, using a monoclonal antibody and analyzed 18, hours later. The percentage of cells in S-phase increased following ICAM-2 crosslinking (FIG. 14A). Cell cycle re-entry was dramatically apparent in ICAM2-ΔC (versus vector control and ICAM-2, cells). Continual stimulation of cell cycle re-entry is sufficient to override growth inhibition signals, often the case in cells that have lost the ability to arrest growth by contacting inhibition and exemplified in the metastatic spread of cancerous cells. Since ICAM-2, and ICAM2-AC presented p44/42, MAPK activity upon ICAM-2, clustering, we postulated that constitutive activation of the p44/42, MAPK pathway could potentially enhance growth kinetics, consequential to the cell cycle re-entry observed and may be sufficient to circumvent contact inhibitory mechanisms. We tested this by monitoring cellular respiration as a function of cell density to determine the extent of growth arrest induced, if any, by contact inhibition. We expected contact inhibition to induce a growth arrest in adherent cells, and therefore a decrease in cellular respiration as the cell density increased. Vector control cells (negative control) showed reduced cellular respiration at high cell densities in contrast to both Jurkat cells (suspension cells not capable of contact inhibition) and 293T cells (transformed fibroblast that fail to contact inhibit) (FIG. 14B). Both ICAM-2, and 1CAM2-ΔC expressing cells exhibited enhanced cellular respiration at high cell densities over vector control (FIG. 14B). Despite these observations, ICAM-2, and ICAM2-ΔC expressing cells were not found to be transformant, a property of cells that have lost contact inhibition, using a top agar transformation assay and did not form tumors when subcutaneously implanted in nude mice (data not shown). Irrespective of this, both ICAM-2 and ICAM2-ΔC expressing cells displayed enhanced growth kinetics over vector control cells (FIG. 14C). Since the ICAM2-ΔC construct elicited p44/42, MAPK activity and was able to initiate a robust cell cycle re-entry in comparison to vector controls, this suggested that an ICAM-2, surface interacting protein was responsible for the activation of p44/42, MAPK. The observation that the p44/42, MAPK induction effect was intensified when ICAM-2, was relieved of C-terminal cytoskeleton interactions (FIG. 14A) illustrates a potential role for cytoskeleton-mediated regulation of ICAM surface protein signal transduction (Heiska et al., 1998; Heiska et al., 1996; van Kooyk et al., 1999).

ICAM-2, Interacts with β Integrins 1, 2, and 3

A soluble form of ICAM-2, was used to verify the ability of ICAM-2, to bind to the cell surface. Full length ICAM-2, was immuno-depleted from ICAM-2, transduced cell lysates and conjugated to FITC (FIG. 15A). The ICAM-2-FITC probe was used to stain the surface of NIH3T3, fibroblast cells, Jurkat T cells, and BaF3, proB cells (FIG. 14B) on the presumption that ICAM-2, will bind, at least to its normal ligand partner β2, integrin on these cells. Pre-treatment of cells with the protease trypsin drastically decreased ICAM-2-FITC binding, suggesting that ICAM-2, was binding to a surface bound protein. The ICAM-2-FITC probe was found to be partially competed by antibodies to β2-integrin on NIH3T3, fibroblasts, a cell line that lacks LFA-1α expression (data not shown). ICAM-2-FITC binding was confirmed by epifluorescence microscopy and was titrateable and inhibited with an unlabeled control in a competition assay (data not shown). Since ICAM2-FITC binding was not completely inhibited by anti-β2, integrin antibodies in NIH3T3, in addition to these cells lacking expression of LFA-1α, it suggested that an additional molecule(s) capable of binding ICAM-2, existed on the surface of these cells.

A two-column affinity chromatography approach was utilized to determine surface bound target molecules capable of binding ICAM-2. ICAM-2, ICAM2-ΔC, and vector control cell surface proteins were biotinylated and subjected to affinity chromatography on an ICAM-2, coupled solid support, and subsequently passed through a streptavdin agarose support. A two-column system was preferred in order to identify proteins that were both surface expressed (biotinylated) and ICAM-2, binding. Final protein elusions were tested for both biotinylation by immunoblotting techniques and —ICAM-2, interaction by the use of the ICAM-2FITC probe in a farwestern approach (FIG. 15A). Protein bands of 112, 95, 67, kilodaltons (kDa) were gel eluted and sequenced by MALDI-MS. The biotinylation of the surface proteins interfered with a direct analysis of the proteins eluted, and fragments of peptide sequences generated suggested that the molecules contained RGD domains, with homologies to several surface bound receptors, although no apparent single protein could be identified from the peptide fragments generated. Therefore, we decided to test for integrin binding partners, given that ICAM-2, has been shown to bind β2, integrin. Immunoblotting the final two-column elusions confirmed β1, β2, and β3 integrins to be both surface expressed (biotinylated) and ICAM-2, interacting (FIG. 15C). β4, β5, and β6, integrins were not identified in immunoblotting final two-column elusions (data not shown). Performing reciprocal column systems (i.e. streptavidin-agarose support followed by ICAM-2, affinity column) in addition to, ICAM-2, immunoblots.

Monoclonal antibody (mAb) blocking experiments were used to distinguish the contribution of the integrin binding partners to the ICAM-2, induced p44/42, MAPK activation. Pretreatment of ICAM-2, ICAM2-ΔC, and vector control cells with mAbs for β1, β2, and β3, integrin prior to ICAM-2, clustering demonstrated occlusion of β2, integrin to selectively inhibit ICAM-2, induced p44/42, MAPK activity (FIG. 15C). Unexpected results were observed by using mAbs to β1, and β3, in that both partial inhibition and induction of p44/42, MAPK activity was observed (elaborated in the discussion). Therefore, differences observed in the antibody blocking experiments for β1 and β3, integrins cannot be differentiated between ICAM-2/integrin block or integrin-induced signaling given the nature of the experiment and were not explored any further. However, the experiments do illustrate that antibody blockade of β2, integrin is sufficient to abrogate ICAM-2's induced p44/42, MAPK activity. Since ICAM-2, clustering via the extracellular domain induced p44/42, MAPK activity in the ICAM2-ΔC transduced cell population and was blocked by β2 integrin monoclonal antibody, it suggested that the ICAM2-ΔC molecule was capable of interacting with β2, integrin on the same cell. Thus, the surface interaction of these two molecules mediated p44/42, MAPK activity through the β2, integrin. Interestingly, ICAM-2's natural receptor Leukocyte Function-Antigen-1, (LFA-1) is an αβ heterodimeric receptor composed of both β2, and α$_L$, integrins (CD11, a) (Kaplan et al., 2000). Therefore, we decided to test the ICAM-2, induced p44/42, MAPK activation in Jurkat T-cells, which endogenously express the low levels of the LFA-1, receptor subunits, with a biochemically purified soluble ICAM-2, protein. Treatment of Jurkat cells with soluble ICAM-2, induced p44/42, MAPK phosphorylation and activity and was blocked by monoclonal antibodies to both β2, and α$_L$, integrins (FIG. 15F).*indicating* that the ICAM-2/LFA-1, interaction can mediate activation of p44/42, MAPK in LFA-1, expressing cells.

ICAM-2 LFA-1, Engagement Induces p44/42, MAPK Activity Through PYK2, and SYK

To identify upstream kineses that would be responsible for signal transmission from LFA-1, to Raf (and subsequently to p44/42, MAPK), a series of kinase inhibitor screens were conducted. Tyrphostin A9, and piceatannol, specific inhibitors of proline-tyrosine kinase 2, (PYK2) and Spleen-tyrosine kinase (SYK) respectively (Avdi et al., 2001; Fuortes et al., 1999) were found to abrogate the ICAM-2, induced activation of Raf and subsequently p44/42, MAPK (FIG. 16A). Other protein kineses that include p38, MAPK, and two members of the src related tyrosine kineses p56Lck and Src were not found to be involved by the inability of specific pharmacological inhibitors of these kineses to block ICAM-2, induced p44/42, MAPK activity. Furthermore, immunoblotting for phosphotyrosine residues of immunoprecipitated tyrosine kineses involved in T-cell activation, namely LAT and ZAP-70, and tyrosine kineses involved in integrin signaling, FAK and Src, did not implicate these kineses in the ICAM-2/LFA-1, mediated signal (data not shown). However the ICAM-2/LFA-1, activation of p44/42, MAPK was dependent on guanosine triphosphate, implying the involvement of Ras (data not shown).

It was apparent that p44/42, MAPK activation was a function of an ICAM2/LFA-1, interaction that was initiated when ICAM-2, engaged LFA-1. It has been reported that adhesion molecule receptors require an activation step in order for intracellular signaling to occur that usually results in changes in it's the receptor's avidity and/or affinity for its respective ligand or in its formation if composed of a heterodimeric association (van Kooyk et al., 1999). This prompted us to test whether contact of ICAM-2, with LFA-1, induced an "activation state" that allowed for the subsequent binding of PYK2, or SYK to transmit the signal through an SH2/GRB/Ras dependent pathway to p44/42, MAPK. Typical exogenous treatments with phorbal esters to activate LFA-1 could not be used, since we noted eventual activation of the p44/42, MAPK pathway following treatment (data not shown). Therefore, the interaction of PYK2, and SYK with both subunits of LFA-1, β2, and αL integrins was tested by co-immunoprecipitation as a function of soluble ICAM-2, and various T cell activating stimulants. Tyrosine phosphorylation of neither β2, nor α$_L$ integrin was observed as a function of any stimulus tested (data not shown). An association between β2, and α$_L$, integrin was only observed after treatment with soluble ICANrr2, and was absent in unstimulated cells (FIG. 16B). This suggested that the formation of the LFA-1 receptor can be initiated by a ligand induced event mediated by ligand induced recruitment of the αβ subunits. LFA-1, receptor integrity was found to be stabilized by treatment with various T cell stimulants in addition to soluble ICAM-2, resulting in an enhanced interaction between β2, and α$_L$ integrin.

SYKs interaction with α$_L$, integrin was present under unstimulated conditions and was attenuated by stimulatory conditions with a concomitant association with β2, integrin. This suggested that the interaction of β2, and α$_L$, integrins induced by ICAM-2, resulted in an activation of SYK—a process that can result from a conformational change proceeding LFA-1, formation as suggested by studies reporting avidity changes in ligand binding of LFA-1. PYK2, presented a weak association with β2, integrin, an interaction that was enhanced upon ICAM-2, stimulus, and only interacted with αL integrin after the ICAM-2, stimulus was provided (FIG. 16B). Although the exact molecular details of the temporal kinetics of PYK2, and SYK association with LFA-1, as a function of stimulus were not investigated, the data would suggest that ICAM-2, could induce formation of its LFA-1 receptor by recruiting β2, and α$_L$, integrin. We speculate that "activated" LFA-1, induces a conformational change that is transmitted to PYK2, and SYK, either through direct physical contact, or exposure of binding sites that would in turn allow binding of PYK2, or SYK.

Ligand induced conformational changes of LFA-1, have been reported (Kotovuori et al., 1999; van Kooyk and Figdor, 2000), but lack linkage of LFA-1, to specific intracellular signaling mechanism. Furthermore, reciprocal coimmunoprecipitations of PYK2, and SYK association with β2, integrin was observed to be maximal in the presence of one or more stimuli (FIG. 16B). Both PYK2, and SYK2, were found to by phosphorylated in response to ICAM-2, as a function of time in LFA-1 expressing cells. Phosphorylation of PYK2, tyrosine residues tyr402, (autophosphorylation site) and tyr881, (SH2, binding site) was induced by ICAM-2, binding LFA-1, as determined by immunoblotting for respective phosphorylated residues. This confirmed that phosphorylation of PYK2, is mediated by an ICAM-2, induced LFA1, activation (FIG. 16C).

Confocal laser scanning microscopy was used to assess the cellular distribution of PYK2, and SYK, and their respective localization and/or phosphorylation after treatment of Jurkat cells with soluble ICAM-2. A cellular redistribution of both PYK2, and SYK upon ICAM-2/LFA-1, interaction was observed as diffused cytoplasmic PYK2, and SYK localized to the plasma membrane (FIG. 17, panel C and L). Phosphorylation of PYK2, was observed at the plasma membrane only after the ICAM-2, stimulus was provided as detected by a phospho-specific antibody to PYK2, at tyrosine 402, (FIG. 17, panel F and I). Recruitment of PYK2, to the plasma membrane by ICAM-2s interaction with LFA-1, resulted in PYK2, phosphorylation as PYK2, phosphorylation was not observed in the absence of the ICAM-2, stimulus. It is not clear which specific events mediate PYK2, or SYK recruitment to LFA-1, upon ligand interaction, at present, we hypothesize that a ligand induced conformational change to LFA-1, exposes protein binding sites for PYK2, and SYK interaction.

ICAM-2/LFA-1, Interaction Transmits Distinct Signals to Both Contacting Cells

LFA-1, and ICAM-have been implicated in cellular adhesion of leukocytes, in essential processes that include lymphocyte trafficking (Etienne-Manneville et al., 2000; Sato et al., 2000; Sigal et al., 2000), stabilizing T-cell:antigen-presenting cell contact (Hwang et al., 2000; Neeson et al., 2000), metastatic spread (Dosquet et al., 1997; Griffoen et al., 1996; Griffoen et al., 1996; Regidor et al., 1998; Tang and Honn, 1994), and organ transplant rejection (Rentsch et al., 2000). Considering the severity of diseases associated with the absence of ICAM/LFA-1, interactions, we sought to understand the signaling mechanisms initiated upon [celLto-cell] cell-to-cell contact that utilize ICAM-2, and LFA-1. To do this, we developed specific kinase probes for AKT and p44/42, MAPK, among others, to simultaneously monitor kinase activity within individual cells. These probes detect phosphorylated AKTser473, and phosphorylated p44/42, MAPK (Thr202/Tyr204) by flow cytometry and phosphorylation at these residues was found to correlate with respective kinase activity by immunoblotting and kinase activity assays. These probes, in conjunction with specific cell type markers, allowed us to test for the activation of signaling pathways in heterogeneous cell mixing experiments by flow cytometry.

NIH3T3, cells were engineered by retroviral transduction to overexpress human ICAM-2, and were used as a presenting cell to Jurkat T cells. NIH3T3, lack expression of costimulatory molecules CD86, and CD80, and express low levels of murine ICAM1, -3, as determined by flow cytometry (data not shown). The engineered ICAM-2, overexpressing cells present [106] $10^6$, fold surface human ICAM-2, protein compared to vector control as determined by quantitative flow cytometry. ICAM-2, cells and vector control cells were mixed with Jurkat T cells and prepared for flow cytometry by surface staining for T cell markers CD3, and CD4, and intracellular detection of phosphorylated p44/42, and AKT. FIG. 18 displays a FACS plot of both ICAM-2, (CD3, CD4−) and Jurkat cells (CD3+, CD4+, ) as distinguished by CD4, and CD3, markers. Forward and scatter voltages were experimentally determined to allow visualization of both cellular populations denoting the autofluorescence of fibroblast cells. Intracellular kinase activities for both AKT and p44/42, present two distinguishable peaks that can be attributed to distinct cell populations—only single peaks were observed in homogenous control populations (data not shown). AKT$^{high}$, activity is observed primarily in CD3/CD4, double negative cells while ERK$^{high}$, activity is observed primarily in CD3/CD4, double positive cells. Therefore, ICAM-2/LFA-1, interaction between a presenting cell and a leukocyte activates AKT and p44/42, within each cell respectively.

Discussion

The results presented demonstrate (1) ICAM-2/LFA-1, interaction activates the p44/p42, MAPK cascade in LFA-1, expressing cells and can be blocked by antibodies to both αL and β2, integrins, (2) LFA-1, transmits a signal to PYK2, and SYK upon ligand binding, (3) ICAM-2/LFA-1 engagement activates AKT in ICAM2, expressing cells and p44/42, in LFA-1, expressing cells, a concerted transstimulation to contacting cells upon celLto-cell contact respectively.

We have previously shown that ICAM-2, can intracellularly activate the PKB/AKT pathway protecting fibroblasts, T and B cells from apoptosis. Recently, it was shown that ICAM-1 interactions with fibrinogen can activate ERK1/2, and regulate endothelial cell survival (Pluskota and D'Souza, 2000). Therefore it is likely that ICAMs can transduce specific signals to their host cell upon engagement of LFA-1. Since the ICAMs are members of immunoglobulin superfamily, extensive work has been focused around their adhesive properties in cell-to-cell contact and lymphocyte recirculation (EtienneManneville et al., 2000; Geijtenbeek et al., 2000; Gerwin et al., 1999). This in part is due to the cell specific expression patterns exhibited by the ICAMs and their attenuation upon the presence of inflammatory cytokine (McLaughlin et al., 1999; Wolf et al., 2001). For example, ICAM-1, is expressed at low levels and is upregulated by inflammatory cytokines on leukocytes, endothelial cells, fibroblasts, and dendritic cells in contrast to ICAM-2 which is constitutively expressed on leukocytes, endothelial cells, and platelets (Staunton et al., 1989; Xu et al., 1996) and overexpressed in many lymphoproliferative diseases (Eichelmann et al., 1992; Molica et al., 1996).

Adhesion properties attributed to the ICAMs include cell migration (Ding et al., 1999; Nagaoka et al., 2000; Somersalo, 1996), lymphocyte trafficking (Devine et al., 1996; Geljtenbeek et al., 2000; Jutila, 1992), enhancing the avidity of the interaction between a T cell and antigen-presenting cell (APC) (Kotovuori et al., 1999; van Kooyk and Figdor, 2000; VanCompernolle et al., 2001; Wulfing et al., 1998) and contribute to the pathogenecity of viral infections (Belle and Rossmann, 1999; Hioe et al., 2001; Nagaoka et al., 2000; Shigeta, 1998). These adhesion roles partially overlap with the roles ascribed to the integrins, a distinct superfamily of $\alpha\beta$ heterodimeric transmembrane proteins that are essential in adhesion/migration and proliferation/differentiation cellular processes (Geginat et al., 1999). It is now becoming clear that integrins themselves can function as signal transducers in integrin-mediated T cell co-stimulation (Gaglia et al., 2000; Goldstein et al., 2000), in interactions involving the extracellular matrix (ECM), in addition to migratory properties (Epler et al., 2000; Holly et al., 2000; Tarone et al., 2000). Signal transduction for the Ig superfamily has largely gone unrecognized, with the majority of attention focused on other cellular adhesion molecules that include the integrin, selectin, and cadherin family of proteins (Braga, 1999; Elangbam et al., 1997; Gonzalez-Amaro and Sanchez-Madrid, 1999). Furthermore, a subset of integrins more commonly known by their CD number as leukocyte antigens-$\beta1$ (CD29), $\beta2$ (CD18), $\beta3$ (CD61) $\beta4$ (CD 104) $\alpha1$-6 (CD49a-f respectively), in addition to the ICAMs ICAM-1 (CD54), ICAM-2 (CD102), ICAM-3 (CD50) indirectly suggest that these molecules may possess specific signaling roles with functional consequences in lymphocyte populations.

Dissection of the downstream signaling pathways involving the LFA1/ICAM-2 interaction was found to be dependent on both PYK2 and SYK. PYK2 (also known as CAK-B or RAFTK) is a second member of the focal adhesion kinase family and activated by many types of cell surface receptors that include integrins, cytokines, immune receptors, stress stimuli, and PKC activation (Avraham et al., 2000; Hauck et al., 2000). Recently, phosphorylation of PYK2 has been associated with homotypic adhesion mediated by an LFA-1/ICAM-1 interaction in B cells (McDonald et al., 2000), and has also been implicated to be positively regulated by $\beta1$ and $\beta3$ integrin in myeloid cells (Litvak et al., 2000; Miura et al., 2000; van Seventer et al., 1998). Positive regulation of PYK2 by $\beta2$ integrins has been reported in regards to cell spreading and migration in macrophages (Duong and Rodan, 2000) and to induce apoptosis in neutrophils (Avdi et al., 2001). In addition, activation of PYK2 has been stated to be downstream of SYK in Fc$\epsilon$RI signaling in basophils (Okazaki et al., 1997). Therefore PYK2 is recently being regarded as a key signaling molecule in transmiting adhesion mediated events intracellularly.

SYK is a spleen non-receptor tyrosine kinase that is essential in signal transmission of $\alpha$III$\beta3$ inside out signaling (Saci et al., 2000), has roles in Fc$\epsilon$RI signaling (Jabril-Cuenod et al., 1996), and phosphorylated by integrin mediated signaling (Miller et al., 1999; Moores et al., 2000). Given the numerous reports depicting both PYK2 and SYK phosphorylation events, these events can be categorized by stimulatory conditions and present differential outcomes among different cell types: (1) signaling events involving $\beta3$ integrins with regards to B cell signaling (Babe et al., 2001; Li et al., 2001); (2) events involving $\beta2$ integrins with regards to cellular migration and invasion (Holly et al., 2000); (3) activation induced by immune receptors CD2 and CD28 (Fukai et al., 2000; Tsuchida et al., 1999). Here we report that PYK2 and SYK2 associate with LFA-1 components $\alpha$L and $\beta2$ upon LFA-1s interaction with ICAM-2 in Jurkat T cells as determined by both co-immunoprecipitation experiments and confocal microscopy to demonstrate that the ICAM-2/LFA-1 interaction mediates phosphorylation of PYK2 at the plasma membrane. Furthermore, we are the first group to report that both PYK2 and SYK2 are necessary in transmitting the ICAM-2/LFA-1 induced signal to Raf, the upstream kinase in the RAF/MEK/ERK cascade, as determined by usage of specific pharmacological inhibitors piceatannol and tryphostin A9 in Jurkat T cells. PYK2 and SYK interactions have been reported in G protein coupled MAPK activity in PC12 cells (Dikic et al., 1996) and activation of HL40 cells (Miura et al., 2000), supporting the notion of PYK2 and SYK interactions in cellular processes.

Activation of the RAF/MEK/ERK cascade was monitored as a function of time per induction of ICAM-2 clustering. Blockade of p44/42 MAPK activity with monoclonal antibodies to $\beta2$ and $\alpha_L$ integrins indicated the ICAM-2 induced activity was mediated in part by interaction of these integrins on the cellular surface. Since monoclonal antibody treatment to other $\beta$-integrins, namely $\beta1$ and $\beta3$ induced p44/42 MAPK activity in vector control cells, it could suggest a general role for p44/42. MAPK activation by these specific integrins in the fibroblast cell line used, since this was not observed in Jurkat cells. The results of $\beta1$ and $\beta3$ mAb treatment can be accounted for by at least three possible interpretations on the ICAM-2 and ICAM2-$\Delta$C expressing NIH3T3: (1) partial ICAM-2/partner inhibition; (2) partial integrin activation by antibody clustering; (3) combination of 1 and 2. Beta-integrins 1 and 3 have been reported to interact with Ras via G-proteins, and been implicated in the cellular adhesion/ECM signal transduction pathways resulting in p44/42 MAPK activity in adherent cell lines (Yokosaki et al., 1996; Zhu et al., 1999). Interestingly, $\beta1$ integrin was recently implicated in p44/42 MAPK activity and subsequent cell cycle reentry (Qiang et al., 2000). Furthermore, integrin clustering initiated by extracellular matrix attachment can initiate specific signals as observed by antibody clustering (Chen et al., 1996; Hotchin and Hall, 1995).

Studies involving dominant negative Ras implicated $\beta2$ integrin with the p44/42 MAPK in response to T cell receptor triggered ICAM-1 dependent adhesion (O'Rourke et al., 1998). Here we observed that p44/42 MAPK activity is due to ICAM-2 interacting with LFA-1, although both observations are not mutually exclusive and could suggest a mechanism in which low affinity ICAM/LFA-1 interactions are strengthened by a co-stimulatory condition such as that obtained through the T cell receptor in cell-to-cell contact processes. The ICAM-2 induced LFA-1 activation of p44/42 MAPK activity was confirmed by a soluble ICAM-2 molecule in Jurkat T cells and subsequently blocked by antibodies to the LFA-1 receptor subunits. Thus, LFA-1 is capable of initiating a signal to p44/42 MAPK after binding to its ligand ICAM-2. Although ICAM-1 and ICAM-3 also bind LFA-1, further studies are warranted to generalize the LFA-1 induced signal to binding of all its cognate ligands, in addition to elucidating signaling pathways for other ICAM-2 receptors such as DC-SIGN.

Development of intracellular kinase probes to monitor kinase activity in distinct cell populations allowed us to determine the activation of p44/42 MAPK and AKT in cell-to-cell contact in LFA-1 and ICAM-2 expressing cells respectively.

These trans signaling events initiated upon cellular contact were not only distinct to each participating cell type but illustrate that adhesion mediated events may transmit specific signaling events that have largely gone unrecognized. Detection of p44/42 MAPK and AKT activities in LFA-1/ICAM-2 engagement exemplify the significant impact that could result from deregulation of adhesion molecules, largely in part because p44/42 MAPK and AKT are two pivotal kineses involved in growth, proliferation, and survival pathways (Chang and Karin, 2001; Datta et al., 1999). The work presented herein brings to question the canonical segregation of integrins and leukocyte antigens as strictly playing adhesive/targeting roles and exemplifies that distinct signaling mechanisms are initiated upon ICAM-2 encountering LFA-1 to both interacting cells. Elucidating the roles of (I)CAM mediated adhesion in vivo could provide fundamental knowledge of their roles in functionally relevant cellular processes such as T cell activation, angiogenesis, and metastatic spread.

Materials and Methods
Immunological and Chemical Reagents

The following antibodies were obtained from Cell Signaling Technologies (CST): phospho-Raf1 (Ser259) polyclonal, phospho-MEK1/2 (Ser217/221) polyclonal, phospho-p44/42 MAP kinase (Thr202/Tyr204), phospho-p44/42 MAPK (Thr202/Tyr204), phospho-p90RSK (Ser381) polyclonal, phosphoElk-1 (Ser383) polyclonal, phospho-p38 MAP kinase (Thr180/Tyr182), polyclonal, immobilized phospho-p44/42 (Thr202/Tyr204) monoclonal, phospho-SAPK/JNK (Thr183/Tyr185) polyclonal, phospho-CREB (Ser133) polyclonal, phosphoSEK1/MKK4 (Thr261) polyclonal, phospho-Jun (Ser 63) polyclonal, phosphoMKK3/MKK6 (Sell 89/207) polyclonal, phosho-AKTSer473 monoclonal, nonphospho specific antibodies to the above proteins were also obtained from Cell Signal Technologies. The following antibodies were obtained from Transduction Laboratories: anti-β1 monoclonal, anti-β2 monoclonal, anti-β3 monoclonal, anti-$\alpha_L$ monoclonal, anti-α4 monoclonal, anti-α5 monoclonal, anti-α6 monoclonal, anti-LFA-1 monoclonal, anti-α5 monoclonal, anti-α1 monoclonal, anti-α4 monoclonal, anti-PYK2, anti-SYK, anti-CD3.

The following antibodies were obtained from varying vendors: ICAM-2 monoclonal (IC2/2 Research Diagnostics), ICAM-2 Cterminal polyclonal (Santa Cruz Biotechnologies; SCBT), anti-PYK2p402 (Biosource), anti-phosphotyrosine-FITC (CST), CD3-APC (PharMingen), CD4 PerCP (PharMingen), CD80-PE (PharMingen), CD86-FITC (PharMingen), CD54PE (PharMingen), CD50 (PharMingen), CD102-FITC (Research Diagnostics), anti-rabbit IgG HRP conjugated (CST), anti-mouse IgG HRP conjugated (SCBT), anti-mouse IgG FITC conjugated (PharMingen), anti-rabbit-PE conjugated (PharMingen), anti-goat rhodamine conjugated (SCBT), anti-mouse Alexa Fluor 488 conjugated (Molecular Probes), anti-rabbit ALEXA FLUOR® 488 conjugated (Molecular Probes) anti-rabbit ALEXA FLUOR® 568 conjugated (Molecular Probes), anti-rabbit ALEXA FLUOR® 568 conjugated (Molecular Probes), anti-rat IgG (PharMingen). Protein and chemical reagents used: streptavidin-FITC (SCBT), fluorescein isothiocyanate (FITC) (Pierce), R-phycoerythrin (Molecular Probes), ALEXA FLUOR® 488 (Molecular Probes), ALEXA FLUOR® 546 (Molecular Probes), Elk-1 fusion protein (CST), p42 MAP kinase (Erk2) (CST), Tyrphostin A9 (Calbiochem), tyrphostin 18 (Calbiochem), SB203580 (CST), herbimycin A (Sigma), emodin (Sigma), piceatannol (Calbiochem), genistein (Sigma), DMSO (Sigma), phorbal myristelated acetate (PMA) (Sigma), ionomycin (Sigma), propidium iodide (PI) (Sigma), RNASE (Sigma), MTT (Sigma), steptavidin-agarose (SCBT).

Cell Culture and cDNA Isolation and Retroviral Transduction

Full length ICAM2 cDNA was obtained from a retroviral cDNA library produced from Jurkat cDNA and cloned into retroviral vector PBM-Z-IN backbone (Kinoshita et al., 1998) at BamHI/Sal1 site. ICAM2-AC was generated by PCR and cloned into the BamHI/Sal1 site. Retroviral constructs containing ICAM-2 or ICAM2-AC were used to transduce NIH3T3 murine fibroblast. NIH3T3 cells were maintained in DMEM, 10% DCS, 1% PSQ (Duelbecco Modified Eagle Media, 10% Donor calf serum, 1% penicillinstreptomycin (1000 units/ml and 2 mM L-glutamine PSQ). Jurkat T-cells were maintained in RPMI-1640, 10% FCS, 1% PSQ. BaF3 pro-B-cells were maintained in RPML1640, 10% FCS, 1% PSQ, 400 U/ml IL-3 (Peprotech). HL60 myeloid leukemia cells were maintained in Opti-Mem 1, 10% FCS, 1% PSQ. 293T human fibroblast cells were maintained in DMEM, 10% FCS, 1% PSQ. Cells were maintained at 5% CO2/37° C. humidified incubator. Transduced cells were maintained in 500 1 µg/ml G418 (Sigma) and proper expression of construct was verified by western blots and FACS analysis of full length ICAM-2 and ICΔM2-AC as indicated. Vector controls consisted of pBMN-Z-IN (empty vector) transduction as indicated. The infection frequency of pBMN-Z-IN was 48%+/−10 for three independent viral transductions. Continual neomycin selection yielded homogenous ICAM-2, ICAM2-ΔC, or control vector populations as routinely monitored by flow cytometry for protein expression.

Cross-Linking

Antibody cross-linking experiments were performed using a mouse monoclonal anti-ICAM-2 that recognizes the N-terminal region (extracellular domain) (IC2/2 Research Diagnostics) at 10 µg/ml. Spin dialysis (Biorad) was used for buffer exchange of azide containing antibodies (0.01%) to phosphate buffered saline buffer pH 7.4. Anti-mouse IgG (Sigma) was used as a control antibody in crosslinking experiments. $10^6$ cells as indicated were serum starved for 3 hours or 4 hours respectively. Cells were incubated with either ICAM-2 (10 µg/ml) or mouse IgG (10 µg/ml) at 37° C. for the indicated time. Time points began post serum starvation to attenuate most of the signaling pathways or as indicated. Cells extracts were taken and subjected to either immunoprecipitation or immunoblotting.

Cell Growth Assays

Cell cycle analysis was performed as described www(dot)metazoan(dot)com/upI2072) and analyzed by flow cytometry. Cellular respiration was determined by the metabolic indicator dye 3-(4,5-cimethylthiazot 2-yl)-2,5-diphenyl tetrazolium bromide) (MTT) www(dot)metazoa(dot)com/upI2102) (Sigma).

Affinity Chromatography, ICAM-2-FITC Probe Generation, and Surface Protein Biotinylation Surface proteins of ICAM-2, ICAM2-AC, and vector control were biotinylated using sulfo-NHS-LC-Biotin (Pierce) as suggested by manufacturer and verified by flow cytometry and western blot techniques (data not shown). An ICAM-2 solid support was synthesized by coupling an anti-ICAM2 C-terminal antibody to an Affi-Prep 10 solid support (Biorad) as stated by manufacturer's instruction. The anti-ICAM-2 support was used to isolate ICAM-2 from retrovirally transduced ICAM-2 expressing NIH3T3 cells, thoroughly washed, and antibody/protein complex stabilized by chemical crosslinking with bis(sulfosuccinimidyl) suberate (Pierce) as suggested by manufacturer. Alternating washes with low/high pH solutions removed contaminating proteins and or chemicals. Solid support was tested for human ICAM-2 coupling by immunoblot techniques (data not shown). The ICAM-2 solid support was designed to orientate the anchored ICAM-2 molecule by the C-terminal (via an antibody), allowing the extracellular N-terminal to freely interact with passaged material (see Materials and Methods for elaboration).

Cell lysates were then passaged over the column and were initially subjected to a step gradient elusion using increments of 100, 250, 500 and 1 mM NaCl (in Tris pH 6.8) to elute binding proteins. Dual column system utilized the ICAM-2 solid support, binding proteins eluted with 500 mM NaCl (in Tris pH 6.8), concentrated (Centricon 3 kDa cutoff), dialyzed using dialysis membrane (3 kDa cutoff) in PBS pH 7.4 overnight, and depleted for biotinylated proteins by streptavidin-agarose. Further procedure was similar to immunoprecipitation protocol described below. Interacting proteins that survived the procedure were reduced in SDS-PAGE buffer, boiled for 5 minutes, and subjected to SDS-PAGE analysis. Bands appearing were gel eluted and subjected to protein sequencing by MALDI-MS. Verification of the identity of the interacting proteins was done using monoclonal antibodies as indicated in immunoblots. ICAM-2-FITC generation was achieved by immunodepleting ICAM-2, antibody complex stripped by using 4.5 M NaCl (in Tris pH 6.8), concentrated, dialyzed, and chemically conjugated to NHS-Fluorescein (Pierce) as suggested by manufacturer. ICAM-2-FITC probe was stored in PBS containing 0.1% azide.

Flow Cytometry

Intracellular and extracellular staining was performed as described www(dot)metazoa(dot)com/UPL3287). Intracellular probes for AKT and p44/42 MAPK activity was made by conjugating monoclonal anti-AKTser473 antibody or monoclonal anti-p44/42 phospho (Thr202/Tyr204) (Cell Signaling Technology) to ALEXA FLUOR® 568 dye or ALEXA FLUOR® 488 (Molecular Probes), using ALEXA FLUOR® protein conjugation kit (Molecular Probes) respectively. Phospho specificity was tested by western blotting and FACS analysis to a variety of P13K activators (platelet derived growth factor) and inhibitors (LY294002) for AKT activity, and to epidermal growth factor and MEK1/2 inhibitors U0126 (CST) for p44/42 MAPK activity (data not shown). Intracellular staining by phospho-AKTser473 ALEXA FLUOR®568 and phospho-p44/42 ALEXA FLUOR®488 reflected AKT kinase and p44/42 MAPK activity in Jurkat cells when stimulated and inhibited prior to stimulation. Quantitative FACS analysis was performed as described (Davis et al., 1998; Iyer et al., 1998; Lenkei et al., 1998).

In brief, R-phycoerythrin (PE) (Molecular Probes) was conjugated to indicated antibody as suggested by manufacturer of protein cross-linking kit (Molecular Probes), tested for proper stochiometry (data not shown) and quantitated using QuantiBRITE-PE beads (BD systems). A quantitative calibration curve was generated using QuantiBRITE-PE beads that contain a known amount of PE molecule/bead. A linear regression analysis is performed using the following equation: $\log_{10}(PE\ fluorescence) = slope*\log_{10}(PE\ molecules/bead) + intercept$. PE fluorescence is determined by taking the geometric mean of the PE channel. Quantitation is valid only for antibodies directly conjugated to PE. Using saturating amounts of antibody and thorough washing ensures all surface antigens are bound. Preparation of samples on ice reduces antibody internalization. Surface antigens of cells for an unknown cell population are determined by computing the PE geometric mean using the calibration curve. Quantitative FACS analysis provides approximate estimates for surface antigen expression. Numbers plotted represent relative surface antigen molecules and not absolute numbers since antibody valency was not investigated for the monoclonal antibodies used. Flow cytometry analysis was performed on a BD FACSCalibur machine and analyzed using FlowJo software (Tree Star). CellQuest was used for quantitative flow cytometry and linear regression analysis of QuantiBRITE-PE beads. Flow cytometry data are representative of 3 independent experiments of $10^6$ cells/sample analyzed. 50,000 events were collected or otherwise noted and calibrated using Calibrite beads (BD systems). Data plotted in bar graph format is expressed as the mean (bar)+/−SD of triplicate experiments.

Confocal Microscopy

Jurkat cells were treated as indicated and adhered to poly-L-lysine (Sigma) coated sterilized coverslips (10 mg/ml, 30 minutes) by mild centrifugation (1000 RPM, 10 minutes), washed twice in phosphate buffered saline pH 7.4 (PBS) and fixed in 2.7% paraformaldehyde (in PBS). Cells were permeabilized for 5 minutes with 0.1% saponin (in PBS), washed twice in PBS, blocked in 4% bovine serum albumin (BSA, in PBS), and subjected to antibody incubation: (primary at 0.1 mg/ml, secondary at 1:1000 dilution in 1% BSA, with several washing steps in between). Primary antibodies used: anti-PYK2 monoclonal, anti-SYK polyclonal, anti-PYK ptyr402 monoclonal, anti-SYK polyclonal, phospho-tyrosine-FITC. Secondaries used: anti-mouse-Alexa 488, anti-rabbit-Alexa 488, anti-rabbitAlexa-568, anti-rabbit-Alexa-568. Stained coverslips were mounted onto glass slides with Prolong Antifade reagent (Molecular Probes) and visualized using a Molecular Dynamics Multiprobe 2010 confocal laser scanning microscope. Images were compiled using Adobe Photoshop 6.0.

MAPK Kinase Assays

MAPK activity was detected by immunoprecipitation of active phosphorylated p44/42 from cells and used in a kinase assay with Elk-1 fusion protein (Cell Signaling Technologies; CST). $2 \times 10^6$ NIH3T3 or Jurkat cells were incubated with immobilized phospho-p44/42 monoclonal antibody (mAb) (1:200, CST) at 4° C. with gentle rocking motion for 2 hrs. Immunocomplexes were washed 4× with cell lysis buffer and resuspended in 40 µl kinase buffer (25 mM Tris pH 7.5, 5 mM, β-glycerolphosphate, 2 mM DTT, 0.1 mM $Na_3VO_4$, 10 mM $MgCl_2$) supplemented with 200 µM ATP and 1 µg of Elk-1 fusion protein (CST) for 30 min at 30° C. Kinase reaction was terminated with SDS sample buffer boiled for 5 min, and phosphorylation state of Elk-1 was detected by immunoblotting and visualized using ECL detection (Amersham). Immunoblots are representative of 3 independent virally transduced cell populations each repeated 3 times (n=9). MAPK activity was verified by MAPK phosphorylation by immunoblotting with phospho-specific antibodies Immunoprecipitations and Immunoblotting Cell extracts were prepared by washing $2 \times 10^6$ cells (treated as indicated) in ice cold PBS and harvesting in lysis buffer (20 mM Tris pH 7.5, 150 mM NaCl 1 mM EDTA 1 mM EGTA, 1% Triton X-100, 2.5 mM $Na_2PO_4$, 1 mM, β-glycerolphosphate, 1 mM $Na_3VO_4$, 1 µg/ml Leupeptin, 1 mM PMSF, protease inhibitor cocktail tablet (Boehringer Mannheim)). Extracts were centrifuged 14,000 RPM for 5 min at 4° C. and cell lysates (20 µg as determine by BCA protein assay (Pierce)) were fractionated on 15% SDS-polyacrylamide gel electrophoresis and transferred to PVDF membranes using standard procedures. Immunoprecipitations (IP) were pre-cleared with protein AIG plus-agarose beads (Santa Cruz Biotechnologies; SCBT). IP was incubated for 1 hr with primary antibody, 1 hr with protein A/G plus-agarose beads and washed 4× with lysis buffer. Blots were incubated with the indicated antibodies and developed using ECL (Amersham). Fluorescent blots were visualized on a Kodak Digital Image station 440 C station. Immunoblots stripped and reprobed (as indicated) were done by incubating with stripping buffer (62.5 mM Tris, pH 6.8, 10% SDS, 1% β-mercaptoethanol) for 30 minutes at 55° C. and subjected to a repeat of the entire immunoblot protocol.

References

Ali, S., Kaur, J., and Patel, K. D. (2000). Intercellular cell adhesion molecule-1, vascular cell adhesion molecule-1, and regulated on activation normal T cell expressed and secreted are expressed by human breast carcinoma cells and support eosinophil adhesion and activation. Am J Pathol 157, 313-21.

Allende, L. M., Hernandez, M., Corell, A., Garcia-Perez, M. A., Varela, P., Moreno, A., Caragol, I., Garcia-Martin, F., Guillen-Perales, J., Olive, T., Espanol, I T., and Arnalz-Villena, A. (2000). A novel CD18 genomic deletion in a patient with severe leucocyte adhesion deficiency: a possible CD2/lymphocyte function associated antigen-1 functional association in humans. Immunology 99, 440-50.

Angelopoulou, M. K., Kontopidou, F. N., and Pangalis, G. A. (1999). Adhesion molecules in B-chronic lymphoproliferative disorders. Semin Hematol 36, 178-97.

Avdi, N. J., Nick, J. A., Whitlock, B. B., Billstrom, M. A., Henson, P. M., Johnson, G. L., and Worthen, G. S. (2001). Tumor necrosis factor-alpha activation of the Jun Nterminal kinase pathway in human neutrophils. Integrin involvement in a pathway leading from cytoplasmic tyrosine kineses apoptosis. J Biol Chem 276, 2189-99.

Avraham, H., Park, S. Y., Schinkmann, K., and Avraham, S. (2000). RAFTK/Pyk2-mediated cellular signalling. Cell Signal 12, 123-33.

Baba, Y., Hashimoto, S., Matsushita, M., Watanabe, D., Kishimoto, T., Kurosaki, T., and Tsukada, S. (2001). BLNK mediates Syk-dependent Btk activation. Proc Natl Acad Sci USA 98, 2582-6.

Bella, J., and Rossmann, M. G. (1999). Review: rhinoviruses and their ICAM receptors. J Struct Biol 128, 69-74.

Binnerts, M. E., and van Kooyk, Y. (1999). How LFA-1 binds to different ligands. Immunol Today 20, 240-5.

Bowes, M. P., Rothlein, R., Fagan, S. C., and Zivin, J. A. (1995). Monoclonal antibodies preventing leukocyte activation reduce experimental neurologic injury and enhance efficacy of thrombolytic therapy. Neurology 45, 815-9.

Braga, V. M. (1999). Small GTPases and regulation of cadherin dependent celL cell adhesion. Mol Pathol 52, 197-202

Casasnovas, J. M., Bickford, J. K., and Springer, T. A. (1998). The domain structure of ICAM-1 and the kinetics of binding to rhinovirus. J Virol 72, 6244-6.

Casasnovas, J. M., Pieroni, C., and Springer, T. A. (1999). Lymphocyte function associated antigen-1 binding residues in intercellular adhesion molecule-2 (ICAM-2) and the integrin binding surface in the ICAM subfamily. Proc Natl Acad Sci USA 96, 3017-22.

Casasnovas, J. M., Springer, T. A., Liu, J. H., Harrison, S. C., and Wang, J. H. (1997). Crystal structure of ICAM-2 reveals a distinctive integrin recognition surface. Nature 387, 312-5.

Casasnovas, J. M., Stehle, T., Liu, J. H., Wang, J. H., and Springer, T. A. (1998). A dimeric crystal structure for the N-terminal two domains of intercellular adhesion molecule-1. Proc Natl Acad Sci USA 95, 4134-9.

Chang, L., and Karin, M. (2001). Mammalian MAP kinase signalling cascades. Nature 410, 3740.

Chen, Q., Lin, T. H., Der, C. J., and Juliano, R. L. (1996). Integrin-mediated activation of MEK and mitogen-activated protein kinase is independent of Ras 1. J Biol Chem 271, 18122-7.

Chihara, J., Kakazu, T., Higashimoto, I., Saito, N., Honda, K., Sannohe, S., Kayaba, H., and Urayama, O. (2000). Signaling through the beta2 integrin prolongs eosinophil survival. J Allergy Clin Immunol 106, S99-103.

Cid, M. C., Cebrian, M., Font, C., Col~Vinent, B., Ilernandez-Rodriguez, J., Esparza, J., Urbano-Marquez, A., and Grau, J. M. (2000). Cell adhesion molecules in the development of inflammatory infiltrates in giant cell arteritis: inflammation-induced angiogenesis as the preferential site of leukocyteendothelial cell interactions. Arthritis Rheum 43. 184-94.

Collins, R. G., Velji, R., Guevara, N. V., Hicks, M. J., Chan, L., and Beaudet, A. L. (2000). P-Selectin or intercellular adhesion molecule (ICAMi1 deficiency substantially protects against atherosclerosis in apolipoprotein E-deficient mice. J Exp Med 191, 189-94.

Craig, A., Fernandez-Reyes, D., Mesri, M., McDowall, A., Altieri, D. C., Hogg, N., and Newbold, C. (2000). A functional analysis of a natural variant of intercellular adhesion molecule-1 (ICAM-1Kilifi). Hum Mol Genet 9, 525-30.

Daniel, Y., Geva, E., Amit, A., Eshed-Englender, T., Baram, A., Fait, G., and Lessing, J. B. (2000). Do soluble cell adhesion molecules play a role in endometriosis? Am J Reprod Immunol 43, 160-6.

Datta, S. R., Brunet, A., and Greenberg, M. E. (1999). Cellular survival: a play in three Akts. Genes Dev 13, 2905-27.

de Fougerolles, A. R., Diamond, M. S., and Springer, T A. (1995). Heterogenous glycosylation of ICAM-3 and lack of interaction with Mac-1 and p150,95. Eur J Immunol 25,1 OQ8-12.

De V'ta, F., Orditura, M., Infusino, S., Auriemma, A., and Catalano, G. (1998). Increased serum levels of tumor necrosis factor-alpha are correlated to soluble intercellular adhesion molecule-1 concentrations in non-small cell lung cancer patients. Int J Mol Med 1, 605-8.

Devine, L., Lightman, S. L., and Greenwood, J. (1996). Role of LFA-1, ICAM-1, VLA4 and VCAM-1 in lymphocyte migration across retinal pigment epithelial monolayers in vitro. Immunology 88, 456-62.

Dikic, I., Tokiwa, G., Lev, S., Courtneidge, S. A., and Schlessinger, J. (1996). A role for Pyk2 and Src in linking G-protein-coupled receptors with MAP kinase activation. Nature 383, 547-50.

Ding, Z. M., Babensee, J. E., Simon, S. I., Lu, H., Perrard, J. L., Bullard, D. C., Dai, X. Y., Bromley, S. K., Dustin, M. L., Entman, M. L., Smith, C. W., and Ballantyne, C. M. (1999). Relative contribution of LFA-1 and Mac-1 to neutrophil ù adhesion and migration. J Immunol 163, 5029-38.

Dosquet, C., Coudert, M. C., Lepage, E., Cabane, J., and Richard, F. (1997). Are angiogenic factors, cytokines, and soluple adhesion molecules prognostic factors in patients with renal cell carcinoma? Clin Cancer Res 3, 2451-8.

Douglas, I. S., Leff, A. R., and Sperling, A. I. (2000). CD4+ T cell and eosinophil adhesion is mediated by specific ICAM-3 ligation and results in eosinophil activation. J Immunol 164, 3385-91.

Duong, L. T., and Rodan, G. A. (2000). PYK2 is an adhesion kinase in macrophages, localized in podosomes and activated by beta (2>integrin ligation. Cell Motil Cytoskeleton 47, 174-88.

Edwards, C. P., Fisher, K. L., Presta, L. G., and Bodary, S. C. (1998). Mapping the intercellular adhesion molecule-1 and -2 binding site on the inserted domain of leukocyte function-associated antigen-1. J Biol Chem 273, 2893744.

Eichelmann, A., Koretz, K., Mechtersheimer, G., and Moller, P. (1992). Adhesion receptor profile of thymic B-cell lymphoma. Am J Pathol 141, 72941. Perez and Nolan Elangbam, C. S., Qualls, C. W., Jr., and Dahigren, R. R. (1997). Cell adhesion molecules-update. Vet Pathol 34, 61-73.

Epler, J. A., Liu, R., and Shimizu, Y. (2000). From the ECM to the cytoskeleton and back: how integrins orchestrate T cell action. Dev Immunol 7, 155-70.

Etienne-Manneville, S., Manneville, J. B., Adamson, P., Wilbourn, B., Greenwood, J., and Couraud, P. O. (2000). ICAM-1-coupled cytoskeletal rearrangements and transendothelial lymphocyte migration involve intracellular calcium signaling in brain endothelial cell lines. J Immunol 165, 3375-83.

Etzioni, A., and Tonetti, M. (2000). Leukocyte adhesion deficiency 11-from A to almost Z. Immunol Rev 178, 13847.

Fukai, I., Hussey, R. E., Sunder-Plassmann, R., and Reinherz, E. L. (2000). A critical role for p59(fyn) in CD2-based signal transduction. Eur J Immunol 30, 3507-15.

Fuortes, M., Melchior, M., Han, H., Lyon, G. J., and Nathan, C. (1999). Role of the tyrosine kinase pyk2 in the integrin-dependent activation of human neutrophils by TN F. J Clin Invest 104, 327-35.

Gaglia, J. L., Greenfield, E. A., Mattoo, A., Sharpe, A. H., Freeman, G. J., and Kuchroo, V. K. (2000). 1 ntercellular adhesion molecule 1 is critical for activation of CD28-deficient T cells. J Immunol 165, 6091-8.

Gahmberg, C. G., Valmu, L., Fagerholm, S., Kotovuori, P., Ihanus, E., Tian, L., and Pessa-Morikawa, T. (1998). Leukocyte integrins and inflammation. Cell Mol Life Sci 54, 549-55.

Geginat, J., Bossi, G., Bender, J. R., and Pardi, R. (1999). Anchorage dependence of mitogen-induced G1 to S transition in primary T lymphocytes. J Immunol 162, 5085-93.

Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000). DC-SIGN-ICAM-2 interaction mediates dendritic cell trafficking. Nat Immunol 1, 353-7.

Gerin, N., Gonzalo, J. A., Lloyd, C., Coyle, A. J., Reiss, Y., Banu, N., Wang, B., Xu, H., Avraham, H., Engelhardt, B., Springer, T. A., and Gutierrez-Ramos, J. C. (1999). Prolonged eosinophil accumulation in allergic lung interstitium of ICAM-2 deficient mice results in extended hyperresponsiveness. Immunity 10, 9-19.

Ghaisas, N. K., Foley, J. B., O'Briain, D. S., Crean, P., Kelleher, D., and Walsh, M. (2000). Adhesion molecules in nonrheumatic aortic valve disease: endothelial expression, serum levels and effects of valve replacement. J Am Coll Cardiol 36, 2257-62.

Goldstein, J. S., Chen, T., Gubina, E., Pastor, R. W., and Koziowski, S. (2000). ICAM-1 enhances MHC-peptide activation of CD8(+) T cells without an organized immunological synapse. Eur J Immunol 30, 3266-70.

Gonzalez-Amaro, R., and Sanchez-Madrid, F. (1999). Cell adhesion molecules: selecting and integrins. Crit. Rev Immunol 19, 389429.

Gottlieb, A., Krueger, J. G., Bright, R., Ling, M., Lebwohl, M., Kang, S., Feldman, S., Spellman, M., Wittkowski, K., Ochs, H. D., Jardieu, P., Bauer, R., White, M., Dedrick, R., and Garovoy, M. (2000). Effects of administration of a single dose of a humanized monoclonal antibody to CD11a on the immunobiology and clinical activity of psoriasis. J Am Acad Dermatol 42, 428-35.

Griffoen, A. W., Damen, C. A., Blijham, G. H., and Groenewegen, G. (1996). Tumor angiogenesis is accompanied by a decreased inflammatory response of tumor-associated endothelium. Blood 88, 667-73.

Griffoen, A. W., Damen, C. A., Martinotti, S., Blijham, G. H., and Groenewegen, G. (1996). Endothelial intercellular adhesion molecule-1 expression is suppressed in human malignancies: the role of angiogenic factors. Cancer Res 56, 1111-17.

Griffoen, A. W., Tromp, S. C., and Hillen, H. F. (1998). Angiogenesis modulates the tumour immune response. Int J Exp Pathol 79, 363-8.

Guo, H., Tong, N., Turner, T., Epstein, L. G., McDermott, M. P., Kilgannon, P., and Gelbard, H. A. (2000). Release of the neuronal glycoprotein ICAM-5 in serum after hypoxic-ischemic injury. Ann Neurol 48, 590-602.

Hauck, C. R., Klingbeil, C. K., and Schlaepfer, D. D. (2000). Focal adhesion kinase functions as a receptor-proximal signaling component required for directed cell migration. Immunol Res 21, 293-303.

Hayflick, J. S., Kilgannon, P., and Gallatin, W. M. (1998). The intercellular adhesion molecule (ICAM) family of proteins. New members and novel functions. Immunol Res 17, 313-27.

Heiska, L., Alfthan, K., Gronholm, M., Vilja, P., Vaheri, A., and Carpen, O. (1998). Association of ezrin with intercellular adhesion molecule-1 and -2 (ICAM-1 and ICAM-2). Regulation by phosphatidylinositol 4,5-bisphosphate. J Biol Chem 273, 21893-900.

Heiska, L., Kantor, C., Parr, T., Critchley, D. R., Vilja, P., Gahmberg, C. G., and Carpen, O. (1996). Binding of the cytoplasmic domain of intercellular adhesion molecule-2 (ICAM-2) to alpha-actinin. J Biol Chem 271, 26214-9.

Hermand, P., Huet, M., Callebaut, I., Gane, P., Ihanus, E., Gahmberg, C. G., Cartron, J. P., and Bailly, P. (2000). Binding sites of leukocyte beta 2 integrins (LFA-1, Mac-1) on the human ICAM-4/LW blood group protein. J Biol Chem 275, 26002-10.

Hioe, C. E., Chien, P. C., Jr., Lu, C., Springer, T. A., Wang, X. H., Bandres, J., and Tuen, M. (2001). LFA-1 expression on target cells promotes human immunodeficiency virus type 1 infection and transmission. J Virol 75, 1077-82.

Holly, S. P., Larson, M. K., and Parise, L. V. (2000). Multiple roles of integrins in cell motility. Exp Cell Res 261, 69-74.

Hotchin, N. A., and Hall, A. (1995). The assembly of integrin adhesion complexes requires both extracellular matrix and intracellular rho/rac GTPases. J Cell Biol 131, 1857-65.

Hwang, I., Huang, J. F., Kishimoto, H., Brunmark, A., Peterson, P. A., Jackson, M. R., Surh, C. D., Cai, Z., and Sprent, J. (2000). T cells can use either T cell receptor or CD28 receptors to absorb and internalize cell surface molecules derived from antigen-presenting cells. J Exp Med 191, 113748.

Igietseme, J. U., Ananaba, G. A., Boller, J., Bowers, S., Moore, T., Belay, T., Lyn, D., and Black, C. M. (1999). The intercellular adhesion molecule type-1 is required for rapid activation of T helper type 1 lymphocytes that control early acute phase of genital chlamydial infection in mice. Immunology 98, 510-9.

JabriLCuenod, B., Zhang, C., Scharenberg, A. M., Paolini, R., Numerof, R., Beaven, M. A., and Kinet, J. P. (1996). Syk-dependent phosphorylation of Shc. A potential link between FcepsilonRI and the Ras/mitogen-activated protein kinase signaling pathway through SOS and Grb2. J Biol Chem 271, 16268-72.

Jutila, M. A. (1992). LeuRocyte traffic to sites of inflammation. Apmis 100, 191201.

Kaplan, M. J., Beretta, L., Yung, R. L., and Richardson, B. C. (2000). LFA-1 overexpression and T cell autoreactivity: mechanisms. Immunol Invest 29, 427 42.

Kiarash, A., Pagano, P. J., Tayeh, M., Rhaleb, N. E., and Carretero, O. A. (2001). Upregulated Expression of Rat Heart Intercellular Adhesion Molecule-1 in Angiotensin II-but Not Phenylephrine-Induced Hypertension. Hypertension 37, 58-65.

Koga, M., Matsuoka, T., Matsubara, T., Katayama, K., and Furukawa, S. (2000). Different expression of ICAM-1 and LFA-1 alpha by peripheral leukocytes during respiratory syncytial virus and influenza virus infection in young children. Scand J Infect Dis 32, 7-11.

Kotovuori, A., Pessa-Morikawa, T., Kotovuori, P., Nortamo, P., and Gahmberg, C. G. (1999). ICAM-2 and a peptide from its binding domain are efficient activators of leul~ocyte adhesion and integrin affinity. J Immunol 162, 6613-20.

Kruger, K., Buning, C., and Schriever, F. (2001). Activated T lymphocytes bind in situ to stromal tissue of colon carcinoma but lack adhesion to tumor cells. Eur J Immunol 31, 138-45.

Krull, M., Klucken, A. C., Wuppermann, F. N., Fuhrmann, O., Magerl, C., Seybold, J., Hippenstiel, S., Hegemann, J. H., Jantos, C. A., and Suttorp, N (1999). Signal transduction pathways activated in endothelial cells following infection with Chlamydia pneumoniae. J Immunol 162, 483441.

Lalancette, M., Aoudjit, F., Potworowski, E. F., and St-Pierre, Y. (2000). Resistance of ICAM-1-deficient mice to metastasis overcome by increased aggressiveness of lymphoma cells. Blood 95, 314-9.

Li, X., Martin, F., Oliver, A. M., Kearney, J. F., and Carter, R. H. (2001). Antigen receptor proximal signaling in splenic b-2 cell subsets. J Immunol 166, 3122-9.

Litvak, V., Tian, D., Shaul, Y. D., and Lev, S. (2000). Targeting of PYK2 to focal adhesions as a cellular mechanism for convergence between integrins and G protein-coupled receptor signaling cascacles. J Biol Chem 275, 3273646.

May, A. E., Neumann, F. J., Schomig, A., and Preissner, K. T. (2000). VLA4 (alpha (4)beta (1)) engagement defines a novel activation pathway for beta(2) integrin-dependent leukocyte adhesion involving the urokinase receptor. Blood 96, 506-13.

McDonald, J. T., Teague, R. M., Benedict, S. H., and Chan, M. A. (2000). Induction of PYK-2 phosphorylation during LFA-1/ICAM-1-dependent homotypic adhesion of fresh human B-cells. Immunol Invest 29, 71-80.

McLaughlin, F., Ludbrook, V. J., Kola, I., Campbell, C. J., and Randi, A. M. (1999). Characterisation of the tumour necrosis factor (TNF>(alpha) response elements in the human ICAM-2 promoter. J Cell Sci 112, 4695-703.

Melder, R. J., Koenig, G. C., Witwer, B. P., Safabakhsh, N., Munn, L. L., and Jain, R. K. (1996). During angiogenesis, vascular endothelial growth factor and basic fibroblast growth factor regulate natural killer cell adhesion to tumor endothelium. Nat Med 2, 992-7.

Miller, J., Knorr, R., Ferrone, M., Houdei, R, Carron, C. P., and Dustin, M. L. (1995). Intercellular adhesion molecule-1 dimerization and its consequences for adhesion mediated by lymphocyte function associated-1. J Exp Med 182, 123141.

Miller, L. A., Hong, J. J., Kinch, M. S., Harrison, M. L., and Geahlen, R. L. (1999). The engagement of beta1 integrins on promonocytic cells promotes phosphorylation of Syk and formation of a protein complex containing Lyn and beta1 integrin. Eur J Immunol 29, 1426-34.

Miura, Y., Tohyama, Y., Hishita, T., Lala, A., De Nardin, E., Yoshida, Y., Yamamura, H., Uchlyama, T., and Tohyama, K. (2000). Pyk2 and Syk participate in functional activation of granulocytic HL-60 cells in a different manner. Blood 96, 1733-9.

Molica, S., Dattilo, A., Mannella, A., and Levato, D. (1996). Intercellular adhesion molecules (ICAMs) 2 and 3 are frequently expressed in B cell chronic lymphocytic leukemia. Leukemia 10, 907-8.

Moores, S. L., Selfors, L. M., Fredericks, J., Breit, T., Fujikawa, K., Alt, F. W., Brugge, J. S., and Swat, W. (2000). Vav family proteins couple to diverse cell surface receptors. Mol Cell Biol 20, 6364-73.

Mori, N., Wada, A., Hirayama, T., Parks, T. P., Stratowa, C., and Yamamoto, N. (2000). Activation of intercellular adhesion molecule 1 expression by *Helicobacter pylori* is regulated by NF-kappaB in gastric epithelial cancer cells. Infect Immun 68, 1806-14.

Muanza, K., Traore, B., Gay, F., Krudsood, S., Danis, M., and Looareesuwan, S. (1999). Circulating receptors implicated in the cyto-adherence occurring in severe *Plasmodium falciparum* malaria in Thailand. Ann Trop Med Parasitol 93, 449-55.

Nagaoka, T., Kaburagi, Y., Hamaguchi, Y., Hasegawa, M., Takehara, K., Steeber, D. A., Tedder, T. F., and Sato, S. (2000). Delayed wound healing in the absence of-intercellular adhesion molecule-1 or L-selectin expression. Am J Pathol 157, 237-47.

Neeson, P. J., Thurlow, P. J., and Jamieson, G. P. (2000). Characterization of ùactivated lymphocyte-tumor cell adhesion. J Leukoc Biol 67, 847-55.

Oishi, Y., Wakatsuki, T., Nishikado, A., Oki, T., and Ito, S. (2000). Circulating adhesion molecules and severity of coronary atherosclerosis. Coron Artery Dis 11, 77-81.

Okazaki, H., Zhang, J., Hamawy, M. M., and Siraganian, R. P. (1997). Activation of protein-tyrosine kinase Pyk2 is downstream of Syk in FcepsilonRI signaling. J Biol Chem 272, 32443-7.

O'Rourke, A. M., Shao, H., and Kaye, J. (1998). A role for p21ras/MAP kinase in TCR-mediated activation of LFA-1. J Immunol 161, 5800-3.

Patarroyo, M., and Makgoba, M. W. (1989). Leucocyte adhesion to cells in immune and inflammatory responses. Lancet 2, 1139-42.

Patey, N., Vazeux, R., Canioni, D., Potter, T., Gallatin, W. M., and Brousse, N. (1996). Intercellular adhesion molecule-3 on endothelial cells. Expression in tumors but not in inflammatory responses. Am J Pathol 148, 465-72.

Plate, J. M., Long, B. W., and Kelkar, S. B. (2000). Role of beta2 integrins in the prevention of apoptosis induction in chronic lymphocytic leukemia B cells. Leukemia 14, 34-9.

Pluskota, E., and D'Souza, S. E. (2000). Fibrinogen interactions with ICAM-1 (CD54) regulate endothelial cell survival. Eur J Biochem 267, 4693-704.

Qiang, Y. W., Kitagawa, M., Higashi, M., Ishii, G., Morimoto, C., and Harigaya, K. (2000). Activation of mitogen-activated protein kinase through alpha5/beta1 integrin is required for cell cycle progression of B progenitor cell line, Reh, on human marrow stromal cells. Exp Hematol 28, 1147-57.

Radisavljevic, Z., Avraham, H., and Avraham, S. (2000). Vascular endothelial growth factor up-regulates ICAM-1 expression via the phosphatidylinositol 3 OHkinase/AKT/ Nitric oxide pathway and modulates migration of brain microvascular endothelial cells. J Biol Chem 275, 20770-4.

Regidor, P. A., Callies, R., Regidor, M., and Schindler, A. E. (1998). Expression of the cell adhesion molecules ICAM-1 and VCAM-1 in the cytosol of breast cancer tissue, benign breast tissue and corresponding sera. Eur J Gynaecol Oncol 19, 377-83.

Reilly, P. L., Woska, J. R., Jr., Jeanfavre, D. D., McNally, E., Rothlein, R., and Bormann, B. J. (1995). The native structure of intercellular adhesion molecule-1 (ICAM-1) is a dimer. Correlation with binding to LFA-1. J Immunol 155, 529-32.

Rentsch, M., Post, S., Palma, P., Lang, G., Menger, M. D., and Messmer, K. (2000). Anti-ICAM-1 blockade reduces postsinusoidal WBC adherence following cold ischemia and reperfusion, but does not improve early graft function in rat liver transplantation. J Hepatol 32, 821-8.

Saci, A., Rendu, F., and Bachelot-Loza, C. (2000). Platelet alpha IIb-beta 3 integrin engagement induces the tyrosine phosphorylation of Cbl and its association with phosphoinositide 3-kinase and Syk. Biochem J 351 Pt 3, 66976.

Salmaggi, A., Eoli, M., Frigerio, S., Ciusani, E., Silvani, A., and Boiardi, A. (1999). Circulating intercellular adhesion molecule-1 (ICAM-1), vascular cell adhesion molecule-1 (VCAM-1) and plasma thrombomodulin levels in glioblastoma patients. Cancer Lett 146, 169-72.

Sans, E., Delachanal, E., and Duperray, A. (2001). Analysis of the roles of ICAMin neutrophil transmigration using a reconstituted mammalian cell expression model: implication of ICAM-1 cytoplasmic domain and Rho-dependent signaling pathway. J Immunol 166, 544-51.

Sato, N., Suzuki, Y., Nishio, K., Suzuki, K., Naoki, K., Takeshita, K., Kudo, H., Miyao, N., Tsumura, H., Serizawa, H., Suematsu, M., and Yamaguchi, K. (2000). Roles of ICAM-1 for abnormal leukocyte recruitment in the microcirculation of bleomycin-induced fibrotic lung injury. Am J Respir Crit Care Med 161, 1681-8.

Schleef, R. R., Olman, M. A., Miles, L. A., and Chuang, J. L. (2001). Modulating the fibrinolytic system of peripheral blood mononuclear cells with adenovirus. Hum Gene Ther 12,43945.

Schneeberger, E. E., Vu, Q., LeBlanc, B. W., and Doerschuk, C. M. (2000). The accumulation of dendritic cells in the lung is impaired in CD18-/- but not in ICAM1-/- mutant mice. J Immunol 164, 2472-8.

Schnitzler, N., Haase, G., Podbielski, A., Lutticken, R., and Schweizer, K. G. (1999). A co-stimulatory signal through ICAM-beta2 integrin-binding potentiates neutrophil phagocytosis. Nat Med 5.231-5.

Shigeta, S. (1998). Approaches to antiviral chemotherapy for acute respiratory infections. Antivir Chem Chemother 9, 93-107.

Sigal, A., Bleijs, D. A., Grabovsky, V., van Vliet, S. J., Dwir, O., Figdor, C. G., van Kooyk, Y., and Alon, R. (2000). The LFA-1 integrin supports rolling adhesions on ICAM-1 under physiological shear flow in a permissive cellular environment. J Immunol 165, 442-52.

Simmons, D. L. (1995). The role of ICAM expression in immunity and disease. CancerSurv 24, 141-55.

Sixt, M., Hallmann, R., Wendler, O., Scharffetter-Kochanek, K., and Sorokin, L. M. (2001). Cell adhesion and migration properties of {Beta}2-integrin negative, polymorphonuclear granulocytes (PMN) on defined extracellular matrix molecules: Relevance for leukocyte extravasation. J Biol Chem 14, 14.

Somersalo, K. (1996). Migratory functions of natural killer cells. Nat Immun 15, 117-33.

Staquet, M. J., Peguet, J., Jacquet, C., Dezutter-Dambuyant, C., and Schmitt, D. (1995). Expression of ICAM-3 on human epidermal dendritic cells. Immunobiology 192, 249-61.

Staunton, D. E., Dustin, M. L., and Springer, T. A. (1989). Functional cloning of ICAM-2, a cell adhesion ligand for LFA-1 homologous to ICAM-1. Nature 339, 61-4.

Storck, M., Schilling, M., Burkhardt, K., Prestel, R., Abendroth, D., and Hammer, C. (1994). Production of proinflammatory cytokines and adhesion molecules in ex-vivo xenogeneic kidney perfusion. Transpl Int 7, S647-9.

Sun, J. J., Zhou, X. D., Liu, Y. K., Tang, Z. Y., Sun, R. X., Zhao, Y., and Uemura, T. (2000). Inhibitory effects of synthetic beta peptide on invasion and metastasis of liver cancer. J Cancer Res Clin Oncol 126, 595-600.

Tanaka, Y., Maruo, A., Fujii, K., Nomi, M., Nakamura, T., Eto, S., and Minami, Y. (2000). Intercellular adhesion molecule 1 discriminates functionally different populations of human osteoblasts: characteristic involvement of cell cycle regulators. J Bone Miner Res 15, 1912-23.

Tang, D. G., and Honn, K. V. (1994). Adhesion molecules and tumor metastasis: an update. Invasion Metastasis 14, 109-22.

Throne, G., Hirsch, E., Brancaccio, M., De Acetis, M., Barberis, L., Balzac, F., Retta, F., Botta, C., Altruda, F., and Silengo, L. (2000). Integrin function and regulation in development. Int J Dev Biol 44, 725-31.

Tian, L., Nyman, H., Kilgannon, P., Yoshlhara, Y., Mori, K., Andersson, L. C., Kaukinen, S., Rauvala, H., Gallatin, W. M., and Gahmberg, C. G. (2000). Intercellular adhesion molecule-5 induces dendritic outgrowth by homophilic adhesion. J Cell Biol 150, 243-52.

Tibbetts, S. A., Seetharama Jois, D., Siahaan, T. J., Benedict, S. H., and Chan, M. A. (2000). Linear and cyclic LFA-1 and ICAM-1 peptides inhibit T cell adhesion and function. Peptides 21, 1161-7.

Tsuchida, M., Knechtle, S. J., and Hamawy, M. M. (1999). CD28 ligation induces tyrosine phosphorylation of Pyk2 but not Fak in Jurkat T cells. J Biol Chem 274, 673540.

van den Berg, J. M., Mul, F. P., Schippers, E., Weening, J. J., Roos, D., and Kuijpers, T. W. (2001). Beta1 integrin activation on human neutrophils promotes beta2 integrin-mediated adhesion to fibronectin. Eur J Immunol 31, 276-84.

van Den Engel, N. K., Heidenthal, E., Vinke, A., Kolb, H., and Martin, S. (2000). Circulating forms of intercellular adhesion molecule (ICAMF1 in mice lacking membranous ICA~1. Blood 95, 1350-5.

van Kooyk, Y., and Figdor, C. G. (2000). Avidity regulation of integrins: the driving force in leukocyte adhesion. Curr Opin Cell Biol 12, 542-7 van Kooyk, Y., van Vliet, S. J., and Figdor, C. G. (1999). The actin cytoskeleton regulates LFA-1 ligand binding through avidity rather than affinity changes. J Biol Chem 274, 26869-77.

van Seventer, G. A., Mullen, M. M., and van Seventer, J. M. (1998). Pyk2 is differentially regulated by beta1 integrin- and CD28-mediated co-stimulation in human CD4+ T lymphocytes. Eur J Immunol 28, 3867-77.

VanCompernolle, S. E., Levy, S., and Todd, S. C. (2001). Anti-CD81 activates LFA-1 on T cells and promotes T cell-B cell collaboration. Eur J Immunol 31, 823-31.

ùVerkarre, V., Patey-Mariaud de Serre, N., Vazeux, R., Teillac-Hamel, D., Chretien-Marquet, B., Le Bihan, C., Leborgne, M., Fraitag, S., and Brousse, N. (1999). ICAM-3 and E-selectin endothelial cell expression differentiate two phases of angiogenesis in infantile hemangiomas. J Cutan Pathol 26, 17-24.

Wang, J., and Springer, T. A. (1998). Structural specializations of immunoglobulin superfamily members for adhesion to integrins and viruses. Immunol Rev 163, 197-215.

Wang, Y., and Prywes, R. (2000). Activation of the afos enhancer by the erk MAP kinase pathway through two sequence elements: the c-fos AP-1 and p62TCF sites. Oncogene 19, 1379-85.

Weigand, M. A., Schmidt, H., Pourmahmoud, M., Zhao, Q., Martin, E., and Bardenheuer, H. J. (1999). Circulating intercellular adhesion molecule-1 as an early predictor of hepatic failure in patients with septic shock. Crit Care Med 27, 2656-61.

Wolf, D., Hallmann, R., Sass, G., Sixt, M., Kusters, S., Fregien, B., Trautwein, C., and Tiegs, G. (2001). TNF-alpha-induced expression of adhesion molecules in the liver is under the control of TNFR1-relevance for concanavalin A-induced hepatitis. J Immunol 166, 1300-7.

Wulfing, C., Sjaastad, M. D., and Davis, M. M. (1998). Visualizing the dynamics of T cell activation: intracellular adhesion molecule 1 migrates rapidly to the T: cell/B cell interface and acts to sustain calcium levels. Proc Natl Acad Sci USA 95, 6302-7.

Xu, H., Bickford, J. K., Luther, E., Carpenito, C., Takei, F., and Springer, T. A. (1996). Characterization of murine intercellular adhesion molecule-2. J Immunol 156, 4909-14.

Yokosaki, Y., Monis, Fla., Chen, J., and Sheppard, D. (1996). Differential effects of the integrins alpha9beta1, alphavbeta3, and alphavbeta6 on cell proliferative responses to tenascin. Roles of the beta subunit extracellular and cytoplasmic domains. J Biol Chem 271, 24144-50. Perez and Nolan Zhang, R. L., Zhang, Z. G., Chopp, M., and Zivin, J. A. (1999). Thrombolysis with tissue plasminogen activator alters adhesion molecule expression in the ischemic rat brain. Stroke 30, 624-9.

Zhu, A. J., Haese, I., and Watt, F. M. (1999). Signaling via beta1 integrins and mitogen-activated protein kinase determines human epidermal stem cell fate in vitro. Proc Natl Aced Sci USA 96, 6728-33.

Example 4

Immune Cell Survival

Activation of the PKB/AKT

Pathway Intracellular Adhesion Molecule-2 (ICAM-2)

In this Example, using the methods and compositions of the present invention, the present inventors (also referred to herein as "we") using a retroviral cDNA library in a functional genetic screen, identified intracellular adhesion molecule-2 (ICAM-2), a member of the immunoglobin-family of adhesion molecules, as a potent inhibitor of several activators of apoptosis in varying cell types and induction settings. The anti-apoptotic effect was mapped to the activation of the PI3K/AKT pathway. ICAM-2 induced tyrosine phosphorylation of ezrin recruited PI3 kinase to the membrane and resulted in phosphatidylinositol 3,4,5 production, PDK-1 activity, AKT membrane translocation and activation and subsequent phosphorylation of AKT targets BAD, GSK3, FKHR and AFX. The ICAM-2 mediated survival function was abrogated by pharmacological inhibitors of Src (herbimycin A), Rho-dependent kineses (Y-27632), phosphoinositide turnover (Psi-tectorigenin), and of PI3 kinase (wortmannin and LY294002), indicating activation of AKT and its downstream effectors were dependent on PI3K recruitment to the plasma membrane by an ICAM-2 induced ezrin activation. Primary CD19+ cells were protected from TNFa and Fas mediated apoptosis following ICAM-2 clustering and presented elevated AKT activity and phosphatidylinositol 3, 4, 5 (PIP3) as detected by direct single cell flow cytometric measurements of intracellular AKT kinase activity and phosphatidylinositol levels. ICAM-2s engagement with its natural receptor, LFA-1, induced AKT activity similar to that of antibody crosslinking. This cell survival signal was shared only by ICAM-3 in primary B cells, and not by ICAM-1, CD43, and CD44, indicating that the binding of ezrin or interaction with LFA-1 is not sufficient for initiation of the cell survival signal as observed for ICAM-2. These results attribute a novel survival signaling function to ICAM-2 that might provide an explanation for both the role of ICAM-2 overexpression in B-cell lymphomas and mechanisms by which ICAM-2 might signal intracellular communication in cell-to-cell contact at various immunological synapses.

Introduction

A cell's commitment to cellular proliferation or programmed cell death is a balance of the survival and death signals communicated from both the immediate environs, such as extracellular matrix (ECM) interactions, cell-cell contact, or more distant sites through endocrine and paracrine factors (Ruoslahti and Reed, 1994). Survival pathways are proposed to function during early development where apoptosis plays a key role in shaping organogenesis (Raft, 1992) and are eminent in the maturation of the immune system. Clonal selection of antibody forming cells and maintenance of memory B cells are essential processes that require activation of cell survival pathways. Similarly, the lack of survival signals is exemplified in the phenomenon of anoikis, where epithelial cells undergo apoptosis when ECM-attachment is blocked (Frisch and Ruoslahti, 1997). ECM survival signals are presumably mediated by activation of cell-surface receptors via integrin clustering, contributes to the specificity of cell cell/cell-matrix interactions, and deregulation of ECM-integrin signaling leads to anchorage-independent growth (Hulleman and Boonstra, 2001). Identification of analogous molecules in lymphoid cells as those that can antagonize cell death or override growth inhibition programs would be pivotal in understanding intrinsic cell survival programs that can go awry in lymphatic disorders and possibly contribute to metastatic spread.

Functional characterization of molecules involved in cellular adhesion has been focused on signal transduction pathways attributed to integrins and cadherins, which can contribute to ECM-survival signals (de Fougerolles et al., 2000; Schneller, 2001; Shinohara et al., 2001). Adhesion molecules of the immunoglobin (Ig) superfamily have been largely overlooked as potential signaling molecules. ICAM-2 (CD102) is a member of the Ig-superfamily of cell surface proteins and mediates leukocyte binding to LFA-1 (CD11a/CD18) and MAC-1 (CD11 b/CD18) (van Kooyk and Figdor, 2000). As a cell surface adhesion member involved in leukocyte recruitment in tissues, ICAM-2 is expressed in low levels on most leukocytes including T and B lymphocytes, monocytes, platelets and early CD34[+] hematopoetic progenitor cells (de Fougerolles et al., 1991; Diacovo et al., 1994; Nortamo et al., 1991). In addition, ICAM-2 constitutive expression has been observed on all vascular endothelium (de Fougerolles et al., 1991). Based on the expression pattern of ICAM-2, it has been postulated to be involved in lymphocyte recirculation, trafficking, and extravasation. ICAM-2 deficient mice support this by demonstrating that eosinophil trafficking is augmented in inflammatory responses (Gerwin et al., 1999). Surprisingly, this phenotype is relatively mild considering the range of cell types upon which ICAM-2 is expressed. It suggests that the roles ICAM-2 plays are subtle or are redundant with other pathways. Thus, the ICAM-2 deficient mice do not sufficiently detail the roles of ICAM-2, warranting further characterizations of the mechanisms by which ICAM-2 acts are needed.

In contrast to ICAM-2's putative role as an adhesion molecule, it is surprising to find ICAM-2 highly expressed on both endothelial cells in lymphomas and CD5+ B cells from B-cell chronic lymphatic leukemia (B-CLL) patients (Molica et al., 1996; Renkonen et al., 1992). Lymphoproliferative diseases inevitably inhibit adhesion dependency-loss of adhesion is one of the primary means by which metastatic spread occurs. However, recent gene expression profiling of large B-cell lymphomas from patients indicated an elevated expression of ICAM-2 (Alizadeh et al., 2000). Interestingly, ICAM-2 is the only ICAM (1-5) that maps to chromosome 1 7q23-25 (Sansom et al., 1991), a segment associated with genomic instability and recently identified as a segment of high aberration in various cancers (Dion et al., 2000; Dobo et al., 1995; Russell et al., 2000; Sugai et al., 2000). Despite these observations, ICAM-2's role and molecular characterization in the progression of lymphatic disease states has not been addressed.

We devised a genetic screen to identify genes that are involved in regulation of apoptosis and augmented in malignant phenotypes. Cells transduced with a human lymphoid cell line (Jurkat) retroviral vector cDNA library were screened for an anti-apoptotic phenotype. One cDNA demonstrated reproducible antiapoptotic activity in a phenotypic transfer assay. This cDNA encoded full-length intracellular adhesion molecule-2 (ICAM-2). Here we show functional characterization of the ICAM-2 signal as being capable of mediating a cell survival signal upon its ligation and interaction with its endogenous receptor leukocyte function-antigen-1 (LFA-1). ICAM-2 mediates a survival signal sufficient to block apoptosis by activation of the PI3K/AKT pathway, being contingent on ezrin activation by Src tyrosine phosphorylation and Rho-kinase dependent threonine phosphorylation. Ezrin activation recruited PI3K to the cell membrane in lymphoid cells, thereby initiating activation of the PI3K/AKT pathway. Furthermore, development of probes to measure intracellular AKT and PI3K activity by flow cytometry allowed for the simultaneous measurement of kinase activity as a function of ICAM-2 clustering on human peripheral blood monocytes (PBMC). Multi-parameter FACS analysis confirmed ICAM-2 clustering led to phosphatidylinositol 3,4,5 production and AKT activity in CD19+ primary human cells and subsequent protection from Fas and TNFα mediated apoptosis. Interestingly, activation of the PI3K/AKT pathway was shared by ICAM-3 and not by ICAM-1, CD43, CD44 indicating that molecular differences exist amongst the 19 adhesion molecules that are capable of binding ezrin (Serrador et al., 1997; Yonemura and Tsukita, 1999). Ligation of ICAM-2 by its endogenous receptor LFA-1 was observed to induce AKT activity, illustrating that the ICAM-2/LFA-1 interaction is capable of activating the PI3K/AKT pathway. These observations identify a bimodal functional role for ICAM-2 in mediating cell survival. Overexpression of ICAM-2 conferred an anti-apoptotic phenotype, suggesting that inappropriate expression of ICAM-2 could contribute significantly to the antiapoptotic phenotypes in the cumulative process that leads to tumor progression and metastatic spread. The findings also underscore a novel positive role for ICAM-2 in signaling pathways involving Src/Rho-Kinase/Ezrin/PI3K/PDK-1/AKT and downstream effectors upon LFA-1 engagement in cell-to-cell contact with implications for other ICAM-2 interactions such as ICAM-2/DC-SIGN and ICAM2/Mac-1.

Results

Screening a Retroviral cDNA Library in an Anti-Apoptotic Functional Assay

We devised a retroviral library approach to screen for cDNAs that alter apoptotic signaling and encode for anti-apoptotic molecules (FIG. 19A). cDNAs from a malignant cell type (Jurkat T cell leukemia) were screened for anti-apoptotic function in a recipient non-malignant (fibroblast) cell. Apoptosis was induced with staurosporine (STP), a kinase-inhibiting plant-derived alkaloid, and a potent inducer of caspase-dependent cell death in most cell types. Induction conditions were determined that limited the level of spontaneous background while maximizing the extent of apoptotic death (minimal background of one surviving cell in a STP-treated mock library control in ~$10^4$ starting cells). $10^7$ NIH3T3 fibroblasts were infected with a retroviral cDNA library derived from Jurkat cells at an infection frequency of 40% to limit the number of integrations to a single event per cell. Control retroviruses were prepared expressing LacZ- or Bcl2, and infected into a similar number of NIH3T3 cells. Apoptosis was induced in the transduced cell culture by staurosporine treatment and the cells were then allowed to recover (FIG. 19A). Surviving cell clones were expanded, replated and retreated with staurosporine. The complexity of the expressed cDNAs in the surviving population was assessed with RT-PCR. A few major bands were observed following three rounds of selection (FIG. 19B).

Replication-competent Moloney murine leukemia virus (MMLV) was applied to the enriched cell populations. Upon integration and expression of the MMLV proteins, resident retroviral constructs from the library were co-packaged into infectious virions and transferred to naïve target NIH3T3 cells. The staurosporine selection process was then reapplied. In this manner true phenotype-inducing clones enrich at a rate of 1/background (see materials and methods for elaboration). Three of the pooled libraries showed enrichment for specific bands after PCR (see FIG. 19B lanes 1 and 2). Several bands were rescued by PCR cloning and one of these bands was sequenced and demonstrated to encode full-length ICAM-2 cDNA (Staunton et al., 1989), an immunoglobulin superfamily member that regulates leukocyte adhesion through interaction with its integrin counter-receptor, LFA-1 (de Fougerolles et al., 1991; Simmons, 1995).

ICAM-2 Mediates a Survival Signal

The ICAM-2 cDNA was cloned into a retroviral vector (pBMN-Z-IN) that carries an internal ribosome entry site (IRES) upstream of the neomycin resistance gene. NIH3T3 fibroblasts were infected with retroviruses capable of expressing the ICAM-2 gene, along with appropriate control vectors pBMN-Z-IN (vector control) and pBMN-Z-IN-GFP (GFP vector control). Expression of the 60 kD ICAM-2 glycoprotein in neomycin-selected NIH3T3 fibroblasts infected with the pBMN-Z-IN-ICAM-2 construct (referred to as ICAM-2 cells) was verified by immunoblotting (FIG. 19C), flow cytometry (FIG. 19D), and immunoprecipitation (FIG. 22A). The expressed ICAM-2 protein co-migrated with the native protein from Jurkat T cells (data not shown).

Staurosporine treatment is thought to mimic factor-withdrawal in cells (Raff, 1992), and induces apoptosis by inhibiting PKC, PKA, and PKG at nanomolar concentrations among other kineses (Meggio et al., 1995). ICAM-2 expression. in NIH3T3 cells limited the extent of apoptosis induced by staurosporine treatment as determined by an annexin-V binding assay (FIG. 20A), pyknotic nuclei count (FIG. 20B) and the BrdU TUNEL assay (data not shown confirming the clone's selection by phenotype in the screen. Interestingly, not all forms of apoptosis were inhibited by overexpression. ICAM-2 overexpressing Jurkat T cells did not inhibit apoptosis across a range of concentrations of a monoclonal antibody to the Fas receptor, contrasting inhibition of staurosporine induced apoptosis (FIG. 19E, panel 2-3, elaborated below).

Figure 20B:
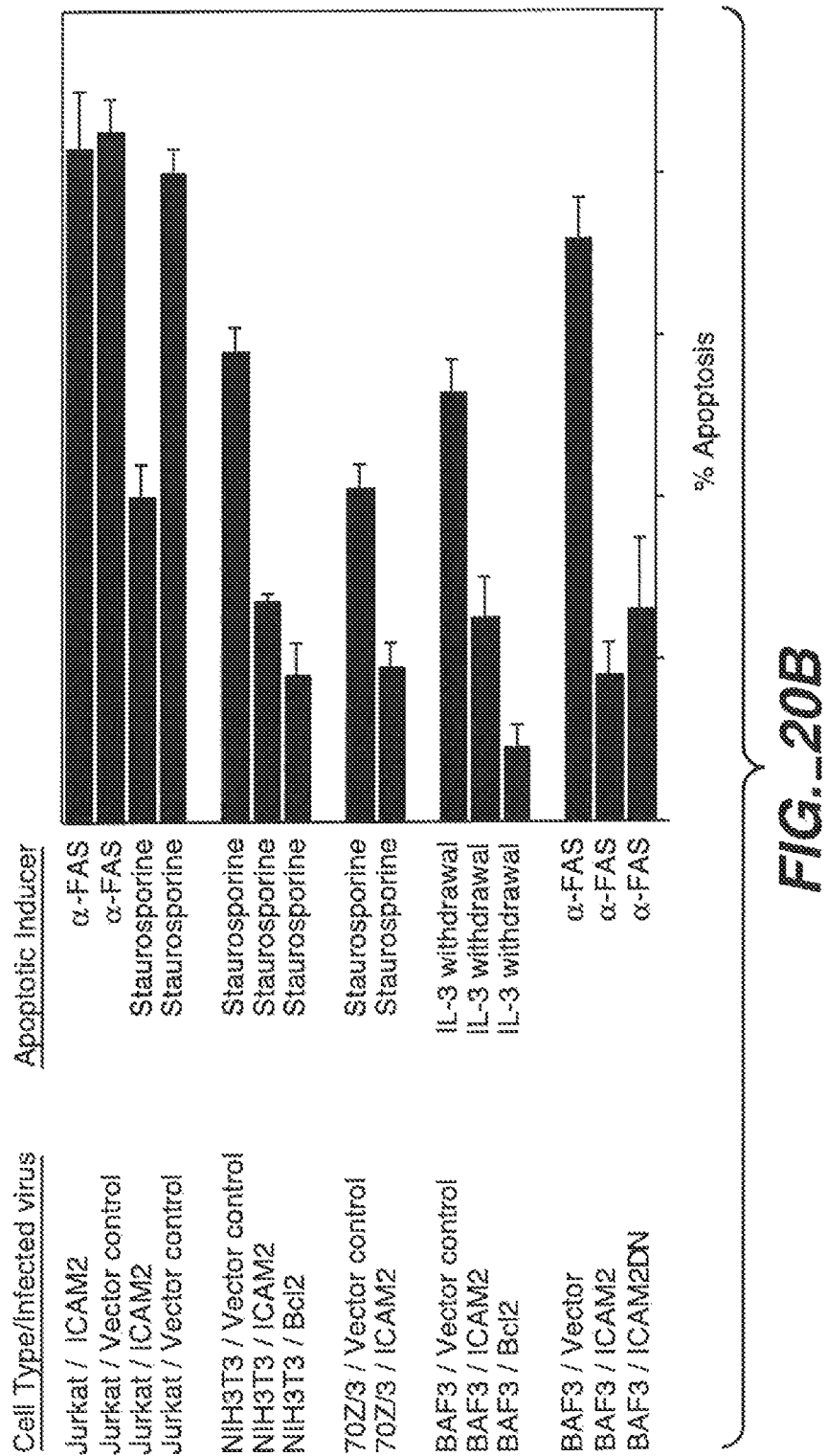

A report correlating ICAM-2 expression with a lymphoproliferative disorder, B-cell chronic lymphatic leukemia (B-CLL) (Molica et al., 1996), prompted us to test the anti-apoptotic activity of ICAM-2 in the mouse pre-B-cell line, 70Z/3. ICAM-2 expression inhibited staurosporine-induced apoptosis in 70Z/3 cells (FIG. 20B). Given the indication that staurosporine mimics factor withdrawal, we assessed the ability of ICAM-2 expression to protect factor-dependent cells from factor withdrawal. ICAM-2 expression in the IL-3-dependent pro-B cell line BaF3 resulted in a delayed onset of apoptosis following IL-3 deprivation (FIG. 20B). Furthermore, we tested the ability of ICAM-2 to rescue BaF3 cells from apoptosis induced by treatment with anti-Fas antibodies. ICAM-2 demonstrated a potent inhibition of apoptosis through the Fas-pathway in these cells (FIG. 20B). These results are as good as or better than transduction controls with Bcl2 and therefore the apparent effects cannot be attributed to modest effects on apoptosis or retroviral transduction (FIG. 20B, data not shown). There is, however, cell specificity to the anti-apoptotic effect by virtue of ICAM-2 ectopic expression as ICAM-2 overexpressing Jurkat T cells were not protected from Fas-induced apoptosis but were protected from staurosporine induced apoptosis (FIG. 20B). High throughput proteome analysis recently identified that in Jurkat T cells, Fas induced apoptosis results in a rapid destruction of 12 cytoskeletal proteins, alters phosphorylation states of various chaperone proteins and cytoskeletal structural proteins, and presents a more "aggressive" form of cell death than staurosporine induced apoptosis (Gerner et al., 2000). Therefore different cell death inducers have specific physiological characteristics in Jurkat T cells supporting the differences observed (Johnson et al., 2000). However, we later provide evidence for a bimodal function of ICAM-2, in which ligation of endogenous ICAM-2 on Jurkat cells is sufficient to block Fas induced apoptosis suggesting that overexpression is insufficient to initiate cell survival in this cell type (described below).

Figure 20C:
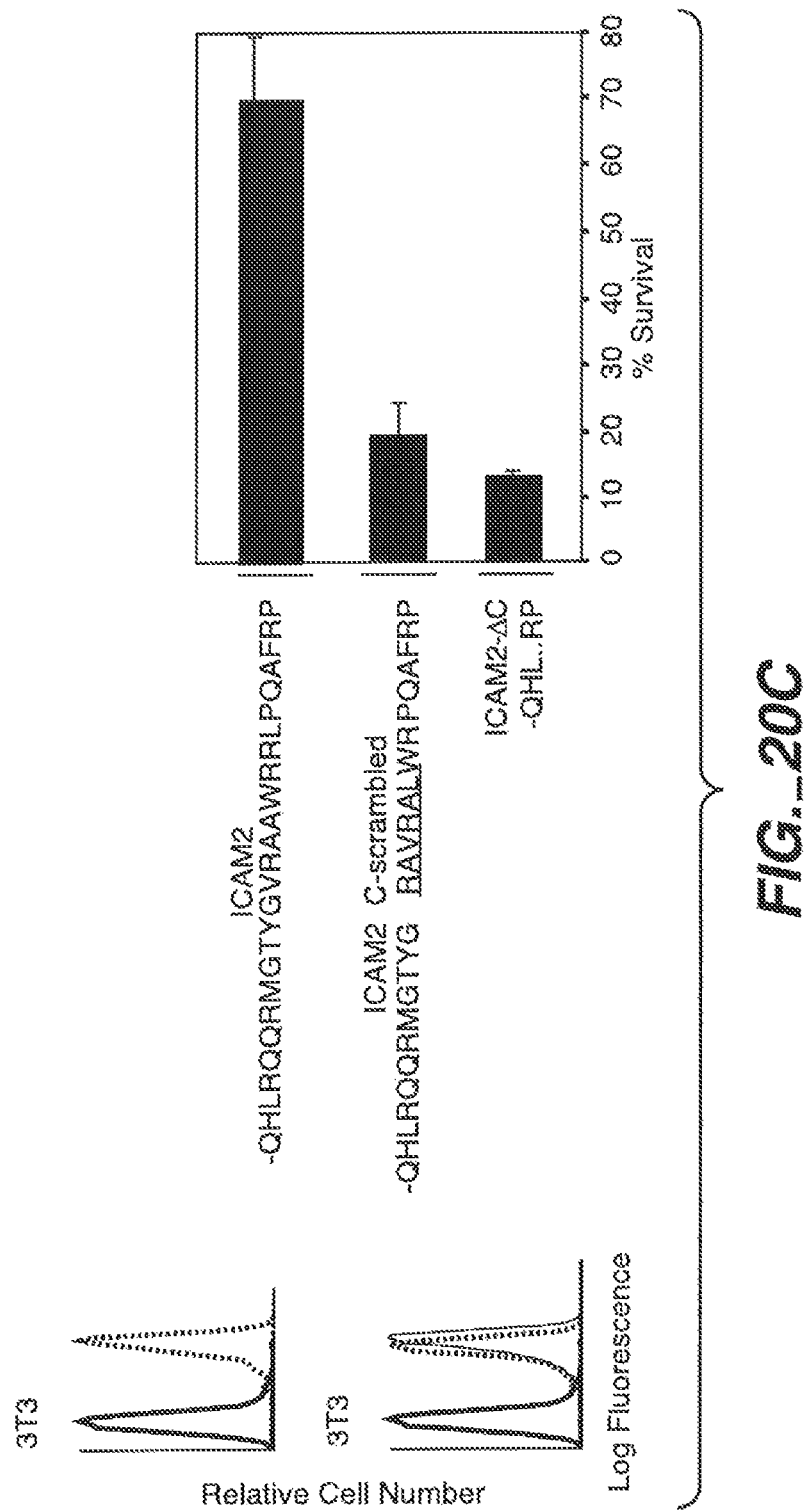

The initial screening was performed in fibroblasts, and it is therefore unlikely that ICAM-2's anti-apoptotic effect was mediated through its lymphocyte-specific integrin ligand, LFA-1 (CD11a/CD18), since NIH3T3 do not express LFA-1 (data not shown). To address this possibility in lymphoid cells, we prepared an extracellular domain-deleted ΔN version of ICAM-2 and tested it in BaF3 cells. Expression of the cytoplasmic domain was sufficient to impart full anti-apoptotic activity (FIG. 20B). This indicates that the cytoplasmic domain of ICAM-2 provides a survival signal when overexpressed ectopically, and likely exerts its effect by mimicking receptor crosslinking. Since signaling through ICAM-family cytoplasmic domains is poorly understood, we sought to identify the signaling pathway by which it conferred resistance to apoptosis. The ICAM-2 survival function maps to a membrane-cytoskeleton linker protein binding motif ICAM-2 is regarded as an adhesion molecule and has been shown to be interconnected with the actin cytoskeleton by linker proteins α-actinin and ezrin, both of which bind the ICAM-2 cytoplasmic domain. (Heiska et al., 1996; Helander et al., 1996). To assess the potential role of α-actinin in mediating the ICAM-2 anti-apoptotic signal, the α-actinin recognition sequence was changed to a scrambled sequence unable to bind α-actinin in vitro (Heiska et al., 1996). Retroviral constructs encoding ICAM-2, a C-terminal deletion mutant (ICAM2-ΔC) and a full-length ICAM-2 protein with the mutated α-actinin binding motif (ICAM2C scrambled) were used to transduce NIH3T3 cells (FIG. 20C). The infected cells were sorted by FACS using an ICAM-2 monoclonal antibody (IC2/2) recognizing only native N-terminal ICAM-2 (de Fougerolles et al., 1991). This verified that ICAM-2, ICAM2-ΔC, or ICAM2-C-scrambled proteins were properly folded and targeted to the outer face of the plasma membrane. The NIH3T3 cells expressing the ICAM-2 mutants were assayed for survival following both etoposide treatment (another potent inducer of apoptosis in NIH3T3 cells) and staurosporine treatment. ICAM-2 imparted potent long-term survival on NIH3T3 cells and the survival signal was lost when the terminal deletion of ICAM-2 (ICAM2-ΔC) was expressed in cells (FIG. 20C). Mutation of the α-actinin binding site in the ICAM-2 cytoplasmic tail also did not provide any protection against etoposide or staurosporine treatments. Although the motif within ICAM-2's C-terminal is identified as an α-actinin binding site, recent studies have shown that the positively charged amino acid cluster the cytoplasmic domain can also interact with ezrin, a member of the ezrin/radixin/moesin (ERM) cytoplasmic linker protein family (Yonemura et al., 1998). Whereas both α-actinin and ezrin co-immunoprecipitated with only full length ICAM-2, a significant difference in the quantity of ezrin binding protein was observed relative to α-actinin (FIG. 22A), supporting the postulate that these cytoskeleton linker proteins were necessary but may differentially relay an anti-apoptotic signal. Experiments designed to block activation steps of each of these cytoplasmic linker proteins elucidated differences between fibroblastoid and lymphoid cell types and their requirements for α-actinin and/or ezrin to relay the anti-apoptotic signal (elaborated below).

ICAM-2 Signals Through PI3K/AKT Kinase

As survival signaling through many adhesion molecules involves PI3 kinase (Frisch and Ruoslahti, 1997; Khwaja et al., 1997), we analyzed the role of this pathway in the ICAM-2 anti-apoptotic signal. Pretreatment of ICAM-2 expressing BaF3 cells with the PI3 kinase inhibitor wortmannin blocked the ICAM-2 mediated anti-apoptotic effect (FIG. 21A, left panel), implicating PI3 kinase in the ICAM-2 survival signaling cascade. Under these conditions vehicle-treated ICAM-2 expressing BaF3 cells were resistant to staurosporine induced apoptosis. Similarly, treating ICAM-2 transduced NIH3T3 with LY294002 abrogated ICAM-2's anti-apoptotic effect as measured by both annexin-V binding and BrdU TUNEL assay using flow cytometry (FIG. 21A, data not shown [, reviewers see Supplementary FIG. 19]). Anti-apoptotic effect was not abrogated with inhibitors to p44/42 MAPK (U0126 and PD98059), p38 MAPK (SB 203580), PKC isozymes (bisindolymaleimide I and 11), or PKA (H-89), excluding the involvement of these kinases in the signal transduction pathway (data not shown).

We utilized confocal microscopy to visualize the cellular distribution of PI3K, AKT, the p85 regulatory subunit of PI3K, and ezrin. We observe both PI3K and AKT to be concentrated at the outer periphery of ICAM-2 cells (FIG. 21B). Ezrin and the p85 subunit was visualized to co-localize more extensively in ICAM-2 cells versus vector control (FIG. 21C). ICAM-2 overexpression had augmented the distribution of PI3K and AKT to favor a membrane localization which is required for their respective activation. Alpha-actinin and ezrin both co-immunoprecipitated with ICAM-2 (FIG.

22A) and subsequently tested for PI3K interaction since direct PI3K interaction with ICAM-2 was not observed in the absence of either α-actinin or ezrin (data not shown).

Development of single cell based phosphatidylinositol 3,4,5 triphosphate (PIP3) and phosphatidylinositol 4,5 bisphosphate (PIP2) detection made it possible to assess PIP3/PIP2 levels within intact cells and reflect PI3K and PI4K/PLCγ1 kinase activities (Perez and Nolan, manuscript in preparation). ICAM-2 cells presented uniformly high levels of PIP3 versus the asynchronous production of PIP3 in vector controls and were inhibited by serum starvation and incubation with LY294002 (FIG. 22B). Production of PIP3 serves as a secondary messenger to recruit pleckstrin domain containing proteins, such as AKT, to the plasma membrane, and also serves to activate others, namely phosphatidylinositoL dependent kineses (PDK-1 and PDK-2) (Blume-Jensen and Hunter, 2001). The production of PIP3 in ICAM-2 cells paralleled the AKT localization pattern observed as expected for active PI3K.

PI3 kinase is known to regulate apoptosis through its downstream effector AKT (PKB) kinase (Downward, 1998). AKT kinase has a potent anti-apoptotic effect downstream of diverse apoptotic stimuli, including staurosporine (Marte and Downward, 1997)(data not shown). We assessed PDK-1 kinase activity in ICAM2 cells and found elevated PDK-1 activity in comparison with vector control (FIG. 22C). This effect reflected the increased levels of PIP3 detected in ICAM-2 cells as it was inhibited by incubation with LY294002, and to a lesser extent, Y-27632, a specific pharmacological inhibitor of Rho-associated protein kineses. Cytosolic/membrane fractionation of ICAM-2 cells confirmed localization of AKT to the membrane versus cytoplasmic localization in vector controls (FIG. 22D), congruent with confocal microscopy of AKT localization. ICAM-2 expressing fibroblast demonstrated an elevated level of AKT activation that was absent in ICAM2-ΔC or mock transduced cells (FIG. 22D). We further verified that this ICAM-2-dependent elevated AKT kinase activity is maintained following STP treatment using both kinase assays and by verifying phosphorylation of both ser473 and thr308 (FIG. 22E). A target of AKT kinase is the pro-apoptotic Bcl2 family member, BAD which is normally held in an inactive state by phosphorylation of serines 112 and 136, and is bound to 14-3-3. Upon induction of apoptosis, BAD is dephosphorylated at both ser112 and ser136, and dimerizes with Bcl2. As a result, the equilibrium of Bck2/Bcl-XL is shifted to favor release of BC~XL to mediate Cytochrome C release and apoptosis (Datta et al., 2000). BAD is dephosphorylated following staurosporine-treatment of ICAM2-ΔC and mock-transduced NIH3T3 cells, concomitant with the induction of apoptosis (FIG. 22F); however, ICAM-2 expression results in the maintenance of BAD phosphorylation consistent (FIG. 22F) with sustained AKT kinase activity (FIG. 22E).

BAD itself can integrate a number of signal transduction pathways with a similar outcome, possessing 3 phosphorylation sites that can be phosphorylated independent of one another: ser112 mediated by active p90Rsk1, ser136 mediated by active AKT, and ser155 mediated by both active PKA and active p90Rsk1. ICAM-2 and its role in connection to BAD ser112 phosphorylation is to be described elsewhere (Perez and Nolan, manuscript in preparation). Phosphorylation of BAD ser155 was not observed (data not shown). The anti-apoptotic signal had little apparent effects on the anti-apoptotic proteins Bcl-2 and Bcl-$x_{L/S}$ (FIG. 22E) and was found to be independent of caspase inhibitory proteins, cell cycle regulators, anti-apoptotic pathways using Bcl2 or additional cell survival programs (data not shown). This indicated that typical anti-apoptotic pathways did not mediate the survival signal (data not shown). Another target of AKT kinase involved in anti-apoptotic signaling, GSK3, was found to be phosphorylated in ICAM-2 expressing NIH3T3 and probably contributes to the anti-apoptotic effect (FIG. 22F, bottom panel). Additional AKT substrates, namely p70S6K and FKHR were also found to be phosphorylated in addition to a decreased detection of cleaved caspase products in ICAM-2 cells induced to apoptose (data not shown).

ICAM-2 Crosslinking Confirms a Role for Endogenous ICAM-2 in Providing an Anti-Apoptotic Signal The ICAM-2-dependent elevation of activated AKT levels in fibroblasts is independent of ligand interactions as determined by the fact that ICAM-2 ΔN can protect cells from apoptosis and ICAM2-ΔC cannot activate AKT. This is indicative of the signaling mechanism driven by oligomerization of surface ICAM-2 molecules, a common modus operandi for adhesion molecules. The surface oligomers may create interaction sites within their cytoplasmic domains, recruiting signaling molecules to participate in membrane proximal interactions. Quantitative FACS analysis revealed that the density of ICAM-2 molecules on the cell surface vary widely between cell types (FIG. 23A see Experimental Procedures for elaboration) and correlated with varied expression patterns as previously described (de Fougerolles et al., 1991). Basal expression levels of ICAM-2 on lymphocytes was 2-4 orders of magnitude less than the enforced expression from the retroviral vector as determined by the number of ICAM-2 surface molecules. We postulated that antibody cross-linking could emulate ICAM-2s interaction with its receptor, and therefore decided to test whether endogenous ICAM-2, when cross-linked, could confer the phenotypes observed as in the overexpression systems.

We cross-linked (clustered) endogenous Jurkat T cell ICAM-2 surface molecules with monoclonal antibodies and assayed activation of the PI3K/AKT pathway. Ezrin was found to associate and become tyrosine phosphorylated as a function of ICAM-2 cross-linking as detected by co-immunoprecipitation with ICAM-2 (FIG. 23B). This suggests that ezrin translocates to membrane in order to interact with the C-terminal of ICAM-2. Subsequently, ezrin becomes tyrosine phosphorylated upon interacting with ICAM-2 as a time delay is detected upon co-immunoprecipitation, indicating that phosphorylation is mediated by a membrane proximal protein tyrosine kinase, since ICAM-2 lacks tyrosine kinase activity (data not shown). Ezrin tyrosine phosphorylation and concomitant association with p85 was observed as a function of ICAM-2 cross-linking, with, a notable enhancement of ezrin threonine phosphorylation (FIG. 23D) effects of which were not shared by α-actinin (data not shown).

In order to identify upstream kineses capable of tyrosine phosphorylating ezrin as a function of ICAM-2 ligation, we developed a phosphotyrosine-protein based elisa to screen for the inhibition of ezrin tyrosine phosphorylation in vivo by various known inhibitors of protein kineses (Perez and Nolan, manuscript in preparation). Of the inhibitors screened, herbimycin A, a potent inhibitor of src tyrosine kinase family members src and p62$^{yes}$ (Haas et al., 2000; Schieven et al., 1992) was found to inhibit tyrosine phosphorylation of ezrin, comparable to genistein, which served as a control for general tyrosine kinase inhibition (FIG. 23C). Surprisingly, we also found inhibitors of ROCK, a Rho-dependent serine/threonine kinase (Y-27632), inhibitors of GTPases, and inhibitors of phosphoinositide turnover (Psi-Tectorigenin) to inhibit the tyrosine phosphorylation of ezrin, with minor affects by PKC isozyme inhibitors bisindolymaleimide I and II. Given the design of the screen to detect tyrosine residue phosphorylation, we speculate that activation of Rho-dependent processes may be a prerequisite for ezrin to be tyrosine phosphorylated by src (elaborated below).

Ligation of ICAM-2 on the surface of Jurkat T cells induced PDK-1 activity (FIG. 23E) and incidentally membrane localization of PI3K and AKT (FIG. 23F). Pursuant AKT activation, dual phosphorylation of AKTser473 and AKTthr308, and phosphorylation of AKT substrates BAD, GSK3, FKHR, and AFX followed ICAM-2 crosslinking in Jurkat T cells as a function of time (FIG. 24A). Crosslinking of ICAM-2 on a different cell type, pro-B cells, which also express low endogenous levels of ICAM-2 (see FIG. 23C) and displayed an antiapoptotic phenotype upon ICAM-2 transduction (FIG. 20B) similarly activated AKT and phosphorylation of AKT substrates BAD and FKHR in a time dependent manner (FIG. 24B). ICAM-2 crosslinking was found to protect Jurkat T cells from staurosporine induced apoptosis verifying the resultant outcome of the PI3K/AKT pathway activation (FIG. 24C). Incubation with LY294002 abrogated the antiapoptotic effects initiated by cross-linking ICAM-2 in Jurkat T cells and BaF3 cells (data not shown).

We had observed that overexpression of ICAM-2 was not sufficient to block Fas induced apoptosis in Jurkat T cells (FIG. 19E, 20C). Contrary but not necessarily contradictory, we observed crosslinking of endogenous ICAM-2 on Jurkat T cells to efficiently protect against Fas induced apoptosis and be abrogated in the presence of GTPγS, Psi-tectorigenin, Y-27632, and herbimycin A (FIG. 24D), inhibitors identified to block ezrin tyrosine phosphorylation (see FIG. 23C). These observations suggest that ICAM-2 clustering by virtue of antibody crosslinking is necessary for imparting the cell survival signal and that ICAM-2 overexpression in this cell type is not sufficient to block Fas induced apoptosis. Furthermore, the abated ICAM-2 induced cell survival signal by compounds GTPγS, Psi-tectorigenin, Y-27632, and herbimycin A in lymphoid cells contrasts the mild effects observed in ICAM-2 overexpressing NIH3T3 cell types (data not shown). This suggests that ezrin is the predominant linker between ICAM-2 and PI3K in lymphoid cells, since these compounds affect the activation of ezrin and not α-actinin (Freeman et al., 2000; Izaguirre et al., 1999; Morishige et al., 2001; Nakamura et al., 2000). This was verified by ezrin, and to a lesser extent α-actinin, predominantly coimmunoprecipitating with PI3K proceeding Jurkat ICAM-2 crosslinking (FIG. 24E), although PI3K co-immunoprecipitated with both ezrin and α-actinin in reciprocal co-immunoprecipitations in fibroblastoid cells (see FIG. 22C). In addition, we have observed ICAM-2 overexpressing fibroblastoid cells to dampen the dynamics of the cytoskeleton architecture and require this augmentation for maintenance of its survival signal, contrasting the requirements of a dynamic cytoskeleton architecture in lymphoid cells. Therefore, ICAM-2 ligation and ICAM-2 overexpression present molecular differences in their mode of activating the PI3K/AKT pathway in cells of different origins.

ICAM-2 Protects Primary CD19+ B Cells from TNFα and Fas Induced Apoptosis Via PI3K/AKT Activation and is Distinct from ICAM-1, ICAM-3, CD43, and CD44

Figure 25A:
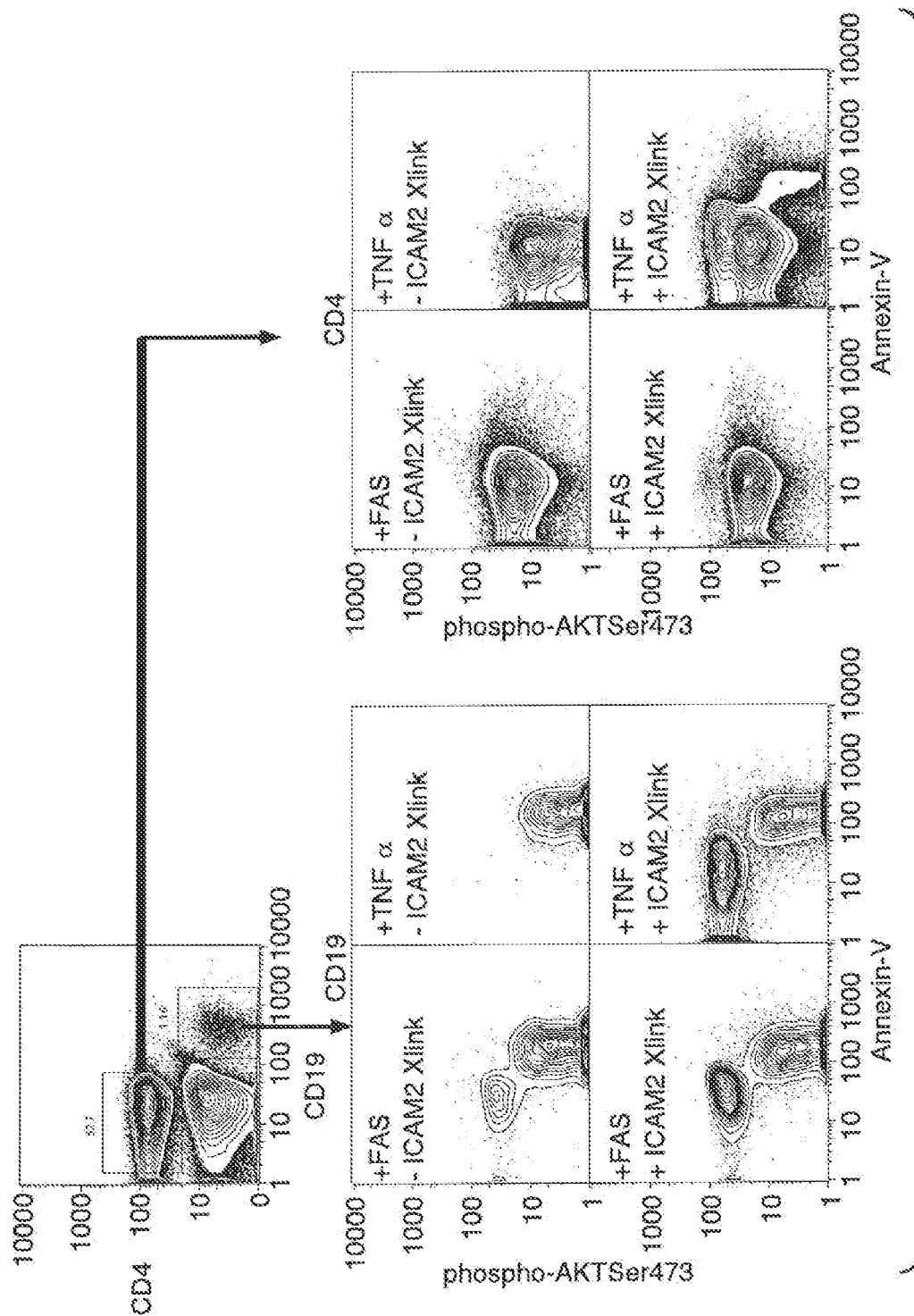
Figure 25B:
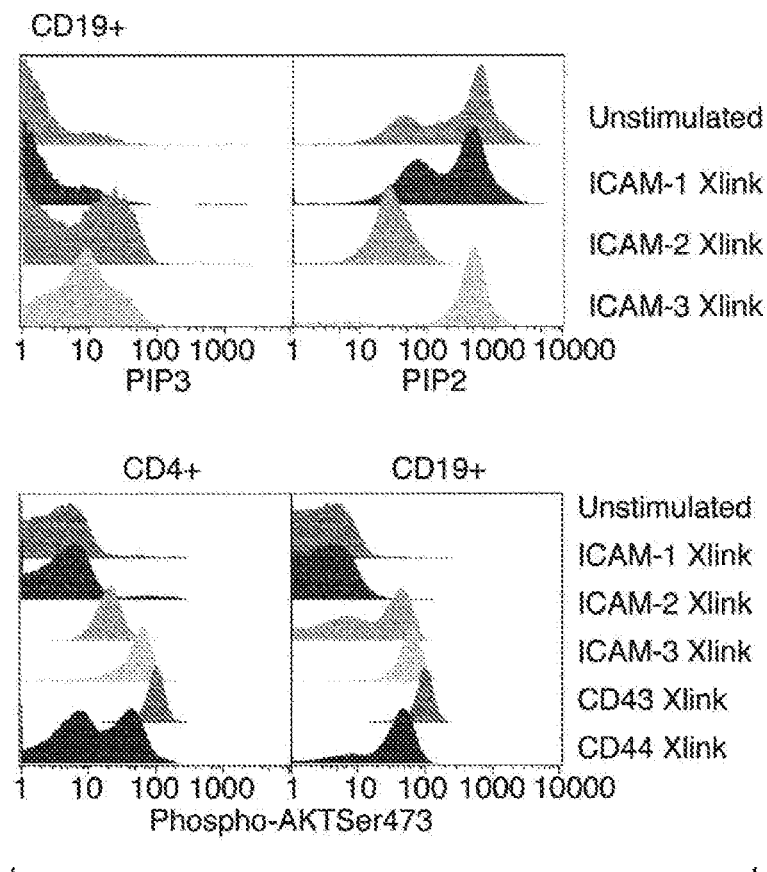
Figure 25C:
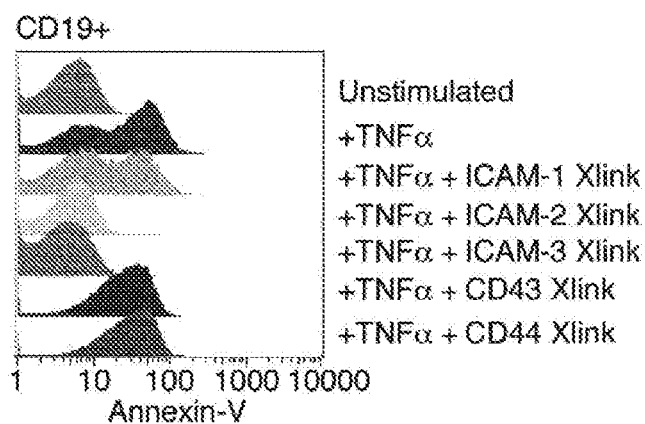

Although the results for AKT activity were reproducible, we were unsatisfied with the western blot analysis/kinase activity assays for whole blood derived cells and so developed a new procedure for single cell analysis of AKT activity by flow cytometry described below (Perez and Nolan). We also developed FACS based methodologies for phosphatidylinositol 3,4,5 triphosphate, and phosphatidylinositol 4,5 bisphosphate detection, reflective of phospholipid turnover, PI3K and PI4K/PLCγ activity respectively within single cells (Perez and Nolan, manuscript in preparation). We utilized FACS based AKT kinase assays and FACS based PIP3 and PIP2 measurements to attribute a physiological relevance for ICAM-2 in vivo. Human PBMC were crosslinked for ICAM-2 prior to treatment with TNFα and anti-Fas monoclonal antibody. Treated PBMC were subjected to flow cytometry, gated by immunophenotype for CD4 (T cell marker) and CD19 (B cell marker) and subsequently assayed for AKT activity and apoptosis by multi-parameter FACS. Intracellular AKT kinase activity measurements were achieved by development of a phospho-specific fluorescent probe for AKT-phospho ser473 phosphorylation site on AKT detectable by FACS (Perez and Nolan, submitted). Both CD4+ T cells and CD19+ B cells exhibited AKT activity when ICAM-2 was clustered and induced AKT activity preferentially protected B cells from apoptosis to Fas and TNFα induced apoptosis (FIG. 25A). There was little apparent antiapoptotic effect on CD4+ T cells perhaps due to the fact that these T cells were not strongly induced by Fas or TNFα to undergo apoptosis with our conditions and require prior stimulation with IL-2 or PMA/ionomycin (data not shown). Protection from apoptosis in primary B cells correlated perfectly with AKT phosphorylation at serine 473, confirming prior roles for this target serine in the protective effect of AKT against Fas and TNFα induced apoptosis. FACS based kinase activity measurements for AKT allow unique activation profiles in distinct lymphocyte populations to be assessed and circumvent the functional augmentation often observed in pre-sorting for such cell populations (data not shown). Differences were observed when ICAM-2 was compared to other ezrin binding surface molecules, namely ICAM-1, -3, CD43, and CD44. PIP3 and PIP2 FACS based measurements identify ICAM-2 as increasing the ratio of PIP3/PIP2, congruent with PI3K activity (FIG. 25B). ICAM-3 was found to increase both PIP3 and PIP2, with no effect on phosphoinositide levels by ICAM-1 (FIG. 25B). Although, ICAM-2, -3, CD44, and CD43 were found to activate AKT in primary CD4+ and CD19+ cells to varying extents (FIG. 25B, lower panel), only ICAM-2 and ICAM-3 effectively blocked TNFα induced apoptosis (FIG. 25C) and Fas induced apoptosis (data not shown) in CD19+ B cells, indicative of functionally distinct properties possessed by ICAM-3, CD44, and CD43. The ICAM-2 anti-apoptotic effect was abrogated by incubation with Psitectorigenin and Y-27632 in CD19+ human B cells (FIG. 25E), verifying the Rho kinase and phosphoinositide dependency in primary human cells. Incubation with GTPγS loading conditions and herbimycin A induced apoptosis in primary cells for unknown reasons (data not shown). Thus, ICAM-2 oligomerization leads to the apparent membrane recruitment of PI3-kinase, results in PIP3 production, and subsequent activation of AKT kinase, initiating a potent inhibition of apoptosis in Jurkat T cells, BaF3 pro-B cells, and human primary lymphoid cells.

ICAM-2 Interactions with its Natural Receptor LFA-1 Activates AKT

We decided to test whether ICAM-2 oligomerization by virtue of interacting with its natural receptor, LFA-1 was sufficient to activate the PI3K/AKT pathway as elucidated by antibody crosslinking experiments. We developed an overlay assay, using the ICAM-2 retrovirally transduced NIH3T3 cells as ICAM-2 presenting cells to LFA-1+ Jurkat cells, to see if mixing of these two cell populations would induce AKT activation in the ICAM-2 expressing cells. Pre-incubation of the ICAM-2 cells with LY294002 abolished the intrinsic AKT activity due to the consequences of ICAM-2 overexpression in these cells. Provided that PI3K inhibition for prolonged periods of time might present an irreversible inhibition, the overlay assay was designed to identify AKT activity in the ICAM-2 cells after one hour blockade of PI3K at a concentration (2 μM) close to the IC$_{50}$ of the compound. This time period and concentration was found to block AKT activity in control experiments and be inducible upon ICAM-2 crosslinking (data not shown). The overlay assay takes advantage of our recently developed FACS based AKT assay, in conjunction with immunophenotypic markers to identify which specific cells in a heterogeneous mixture present AKT kinase activity. Jurkat cells express low levels of LFA-1 and no detectable levels of Mac-1, two endogenous receptors for ICAM-2 (data not shown). ICAM-2 cells express full length human ICAM-2, and these NIH3T3 derived cells express low levels of mouse ICAM-1, -2 and no detectable levels of mouse ICAM-3 (data not shown), interactions of which are thought to be insignificant with human LFA-1, given the species and stoichiometric ratios of human ICAM-2 to murine ICAM-1, -2 (see FIG. 23C, data not shown). We mixed Jurkat cells with vector control and ICAM2 cells with conditions that included prior blocking of Jurkat surface LFA-1 and Mac-1 proteins by incubation with monoclonal antibodies (mAb). We identified the ICAM-2 cells by size differences and absence of the CD4 T cell marker. We observed that incubation of LFA-1 positive Jurkat cells activates AKT in ICAM-2 expressing cells and is inhibited by prior treatment of Jurkat cells with LFA-1 monoclonal antibodies when compared to Jurkat mixing with vector control cells (FIG. 25E, Reviewers see attached manuscript similar experiment in heterogenous lymphoid populations). Prior treatment of Jurkat cells with Mac-1 mAb also inhibited AKT activation of ICAM-2 expressing cells, indicating the common β2-integrin subunit between LFA-1 and Mac-1 is necessary in ICAM-2 oligomerization by these heterodimeric receptors. Because the ICAM-2 induced signal had to overcome the transient PI3K inhibition in our conditions, we did not expect to see a robust activation of AKT, but rather relied on the cell-by-cell analysis to see if activation of AKT was inducible in the presence of LFA-1+ Jurkat ceils and inhibited by LFA-1 monoclonal antibodies. Although additional studies are necessary to verify the activation state of LFA-1 and Mac-1, in addition to the extent of ICAM-2 oligomerization, the data suggests that a receptor induced ICAM-2 oligomerization is sufficient to activate ICAM-2s intracellular PI3K/AKT signal and attributes a physiological role for ICAM-2 as a signaling molecule in cell-to-cell contact. Wulfing et al have visualized ICAM-1 surface clustering upon cell-to-cell contact, supporting that LFA can induce ICAM surface oligomerization required for intracellular signaling by ICAM-2 (Wulfing and Davis, 1998; Wulfing et al., 1998). In a separate study, we have adopted the T cell/B cell mixing conditions of Wulfing et al, and find dual activation of the ICAM-2 AKT signal and a novel LFA-1 mediated p44/42 MAPK activation measured simultaneously in leukocyte mixing reactions by FACS based kineses assays (Perez and Nolan, submitted), further supporting an in vivo signaling role upon ICAM-2/LFA-1 contact.

Discussion

A Model for ICAM-2 Mediating a Cell Survival Signal

Our results demonstrate that ICAM-2 ectopic expression in a wide variety of cell types, and ligation of endogenous ICAM-2 in lymphoid cells including primary CD19+ B cells can initiate a survival signal. ICAM-2 induced AKT activation is a survival signal that can render a cell resistant to chemical (staurosporine and etoposide), and physiological TNFα and Fas ligand) apoptotic inducers and is contingent on ezrin activation, a tyrosine phosphorylation event requiring both src tyrosine kinase and Rho-dependent serine/threonine kinase. This results in PI3K recruitment to the plasma membrane, PIP3 production and subsequent activation of AKT, which is capable of initiating a variety of cell survival signals through phosphorylation of downstream targets.

Although interactions with critical membrane-cytoskeletal linker proteins α-actinin and ezrin was demonstrated through co-immunoprecipitation studies, we note apparent differences between the dependency of these linker proteins to relay the ICAM-2 survival signal in fibroblastoid and lymphoid cell types. ICAM-2's antiapoptotic effect was dependent on the 21 amino acid cytoplasmic domain known to bind α-actinin. Notably, α-actinin has been shown to interact directly with PI3 kinase through the p85 SH3-domain (Shibasaki et al., 1994) and was found to co-immunoprecipitate with PI3K in ICAM-2 overexpressing transduced NIH3T3 and associate with PI3K in ICAM-2 crosslinked Jurkat cells (FIG. 24E). We did not observe phosphorylation of α-actinin (data not shown), but did observe ezrin phosphorylation as a function of CAM-2 crosslinking (FIG. 23B), suggestive of an ICAM-2 induced ezrin activation mechanism.

The ICAM-2 cytoplasmic domain has been found to bind ezrin, a member of the ezrin/radixin/moesin (ERM) family of membrane-cytoskeleton linker proteins (Helander et al., 1996) and notably bound ICAM-2 in contrast to α-actinin in our experiments (FIG. 22A). ERM-proteins regulate cell morphology, adhesion and growth by promoting membrane-cytoplasmic linkages (Tsukita and Yonemura, 1997) and include the tumor suppressor, merlin/schwannomin, implicated in neurofibroblastomatosis type II. In addition, ezrin and other ERM proteins have been implicated in different diseases for their modulation of adhesion molecule distribution (Ichikawa et al., 1998; Stokowski and Cox, 2000; Turunen et al., 1998; Vinores et al., 1995). Interestingly, exrin overexpression has been shown to induce ICAM-2 clustering (Helander et al., 1996) suggesting that inappropriate surface protein clustering and subsequent signaling can be strongly influenced by ERM proteins. Additional studies are needed to address if the deregulation of the ICAM-2/ezrin protein stoichiometry by mutually exclusive pathways can impart similar cell survival capabilities.

Ezrin has recently been reported to mediate adhesion dependent survival in epithelial cells through a direct interaction with PI3-kinase and pursuant AKT activation (Gautreau et al., 1999). Here we report that ICAM-2 clustering induced ezrin tyrosine phosphorylation and enhanced threonine phosphorylation, concomitant with p85 and PI3K association in Jurkat T cells (FIGS. 23D and 24E). This was sufficient to translocate PI3K to the plasma membrane (FIG. 23F) and initiate production of PIP3 as measured directly by single cell analysis within primary cells (FIG. 25B) and indirectly through a PDK-1 activity assay (FIG. 23E). Although PI3K/AKT membrane localization, PIP3 production, ezrin phosphorylation, and PDK-1 activity was also observed in ICAM-2 overexpressing transduced NIH3T3 cells, the profound effects of ezrin tyrosine phosphorylation as induced by ICAM-2 clustering and inhibition of the ICAM-2 anti-apoptotic effect with Y-27632 and herbimycin A (FIG. 23D, 24D) preferentially in Jurkat cells lead us to propose that ICAM-2 mediates a cell survival signal through a Rho-dependent ezrin activation.

This then would initiate PI3K recruitment to the membrane and resultant PIP3 induced PDK-1 and AKT activity. We postulate that the increased binding of ezrin to the positively charged amino acid cluster in ICAM-2s C-terminal is probably enhanced by the oligomerization of ICAM-2 as induced by antibody clustering and LFA-1 interaction, since we did not detect ICAM-2 to be tyrosine phosphorylated. This could provide a mechanistic explanation as to why ezrin is strongly associated with ICAM-2 in overexpression models, but is only observed to associate with ICAM-2 upon ICAM-2 clustering of endogenous levels.

Current research focusing on the activating mechanisms of ezrin, report a variety of differences among different cell types. A two-step activation process has been proposed for ezrin (Bretscher et al., 2000). ERM proteins are believed to reside in a dormant closed conformation mediated by a C-to-N terminal interactions (Bretscher et al., 1997; Gary and Bretscher, 1995). Upon phosphorylation at threonine and possibly serine residues (Bretscher, 1989; Simons et al., 1998), a conformational change unmasks the F-actin binding sites in the C-terminal and the surface protein interacting sites in the N-terminal (Bretscher et al., 2000). RhoGDI (Rho-GDP-dissociation inhibitor) has been observed to bind only activated ERM proteins (Takahashi et al., 1998), suggesting that dissociation of Rho/RhoGDI is a prerequisite for Rho kinase activation (Straw et al., 1998; Yasui et al., 1998). Dissociation of RhoGDI is a prerequisite for activation of Rhodependent pathways, including ROCK, and is dependent for GTP to GDP conversion.

Evidence exists for ezrin functioning as both an upstream regulator and as a downstream regulator of small GTP binding proteins, making elucidation of molecular requirements and ordering of activation systems across cell types difficult (Kosako et al., 2000; Kotani et al., 1997; Mackay et al., 1997; Matsui et al., 1998; Shaw et al., 1998). In the systems utilized here, we observed the ICAM-2 anti-apoptotic effect to be abrogated by Y-27632 and GTPγS, suggesting the Rho-dependent kineses and GTP are necessary in relaying the ICAM-2 signal to PI3K. In addition, inhibitors of src/p62$^{yes}$ similarly antagonized the ICAM-2 induced tyrosine phosphorylation. We did not find a dependency on PCK isozymes, as PKC isozyme inhibitors bisindolymaleimide I, bisindolymaleimide II, and staurosporine did not abrogate the ICAM-2 induced survival signal and suggest that the PKCα and PCKδ dependent threonine phosphorylation of ezrin for its activation as reported by others contributes minimally in this system (Ng et al., 2001; Pietromonaco et al., 1998). We do note an increase of threonine phosphorylation of ezrin as a function of ICAM-2 crosslinking (FIG. 23D) but its presence at the zero time point and difference observed in the fold induction of tyrosine phosphorylation of ezrin lead us to believe that although the threonine phosphorylation state may be contributory zrin tyrosine phosphorylation is responsible for relaying the ICAM-2 survival signal. Furthermore, site-directed mutagenesis of ezrin tyrosine residue Y353 to phenylalanine (Y353F) has been shown to abrogate PI3K binding in epithelial cells (Gautreau et al., 1999), suggesting that kineses involved in phosphorylating Y353 may be key regulators in ezrins capability to activate the PI3K/AKT pathway. Additional tyrosine residues (Y154 and Y353) have been observed to be phosphorylated by several membrane proteins possessing tyrosine kinase activity, namely platelet derived growth factor receptor (PDGF-R), epidermal growth factor receptor (EGFR) and hepatocyte growth factor (HGF); however, mutants lacking both tyrosine residues are still observed to be tyrosine phosphorylated, with various augmentation in signaling properties (Bretscher et al., 2000; Crepaldi et al., 1997; Jiang et al., 1995). This indirectly suggests that ezrin's multiple tyrosine phosphorylation sites may possess distinct and unique signaling properties within different cells, suggestive of a potential explanation on how ezrin can integrate and respond differently to a variety of signals, either through direct interactions with key signaling molecules or indirectly via adapter proteins. The identification of protein kineses responsible for specific tyrosine residue phosphorylation remains controversial, although preliminary studies for tyrosine phosphorylation at Y353 have pointed to src and p62$^{yes}$ in vitro (Dumenil et al., 2000; Moller et al., 1994). We see ablation of ezrin tyrosine phosphorylation in the presence of herbimycin A in vivo, an inhibitor of both src and p62Yes, and further studies are needed to differentiate between these two src family protein tyrosine kineses and specific phosphorylation at Y353 or potentially other sites.

Our data suggest that ROCK is involved in the activation of ezrin that leads to its phosphorylation by src/p62$^{yes}$ since incubation with Y-27362, a specific ROCK inhibitor, abolished tyrosine phosphorylation of ezrin. We had noted hat ezrin threonine phosphorylation, though initially present, was intensified upon ICAM-2 ligation contrasting the induction of ezrin tyrosine phosphorylation (see FIG. 23D), and its ablation in the presence of inhibitors of Rho-dependent processes (see FIG. 23C). Although this suggests that src/p62$^{yes}$ tyrosine phosphorylation of ezrin is upstream of a Rho-dependent threonine phosphorylation, further studies are needed to conclusively delineate the temporal kinetics of ezrin activation as induced by ICAM-2 oligomerization. The ICAM-2 PI3K/AKT survival signal requirements for Rho-dependent kineses and phosphoinositides is apparent in Jurkat cells and in primary B cells (FIG. 24D, 26C), however these requirements are less constraining in ICAM-2 overexpressing cells (data not shown [, Reviewers see Supplementary FIG. 20B]) illustrating differences between the ICAM-2 overexpression and ICAM-2 clustering induced activation of the PI3K/AKT pathway.

The PI3K/AKT signaling system is a general mediator of extracellular stimuli, including growth factors, cytokines, as well as adhesion to extracellular matrices (Downward, 1998). The activation of AKT is dependent on phosphorylation at two sites, threonine-308 by PDK-1 and serine-473 by an unidentified PDK-2 (Downward, 1998). The amino terminus of AKT contains a pleckstrin homology (PH) domain that is thought to bind directly to phospholipid products of PI3K. This binding recruits AKT to the membrane, which has been proposed to induce a conformational change allowing phosphorylation at threonine-308 and serine-473 by PDKI and PDKII respectively (Alessi et al., 1996). Dually phosphorylated AKT is then active and can phosphorylate a number of downstream effectors contribute to cell survival that include, apart from those investigated here, human caspase 9, and eNOS (endothelial cells) which promotes angiogenesis of vascular endothelium (Cardone et al., 1998; Kureishi et al., 2000) AKT hyperactivity has been observed in a number of disorders (Haas-Kogan et al., 1998) (Kulik et al., 1997; Shan et al., 2000; Wick et al., 1999) and therefore, elucidating mechanism that initiate the activation of AKT may be of therapeutic interest. Here, we demonstrate that ICAM-2 induced activation of AKT kinase results in the activation of several downstream effectors as detected by phosphorylation of BAD, GSK3, FKHR and AFX, all of which can contribute to favor cell survival (Brunet et al., 1999; Graff et al., 2000; Pap and Cooper, 1998; Zha et al., 1996). These observations support that ICAM-2 activation would be expected to lead to an extremely powerful anti-apoptotic signal in a variety of cells. It is apparent that a major regulation of the PI3K/AKT survival pathway is conditional on the upstream activating events, since general PI3K activation is a commonly observed in a variety of cancers and tumor models (Blume-Jensen and Hunter, 2001; Roymans and Slegers, 2001). A graphical illustration of ICAM-2 activating the PI3K/AKT pathway is depicted in FIG. 25F, although differences in molecular mechanisms may exist at the ICAM-2/ezrin and ICAM2/α-actinin interface as alluded to above.

The data presented here illustrates that molecular differences exist between the induction of a cell survival signal in an ICAM-2 overexpression and ICAM-2 clustering model and further suggest that these processes may be cell type dependent. The anti-apoptotic effects mediated by ICAM-2 overexpression and by ICAM-2 clustering illustrate that inappropriate ICAM-2 expression may confer resistance to apoptotic stimuli but more importantly, ICAM-2 oligomerization can initiate a cell survival signal upon contact with LFA-1 bearing cells. This activation of the PI3K/AKT pathway by ICAM-2 can be viewed as both anti-apoptotic, if a cell where in an environment that predisposed it to apoptose, or as a cell survival signal that is mediated by cell-to-cell contact. As an adhesion molecule, ICAM-2 has been attributed a role in lymphocyte recirculation and a role in enhancing and stabilizing T-cell:B-cell contact via interactions with its receptor LFA-1 (Damle et al., 1992; Douglas et al., 2000). Here, we suggest that in addition to possessing adhesion molecule properties, ICAM-2 is capable of transmitting an intracellular signal when LFA-1 engagement clusters it on the cell surface. The significance of ICAM-2 clustering is twofold (1) by virtue of its overexpression it could lead to apoptotic resistance of cells otherwise destined to die by apoptosis; (2) receptor-mediated engagement of ICAM-2 can mediate cell survival selectively to cells that engage LFA-1 bearing cells, a process that occurs at the immunological synapse (Perez and Nolan, manuscript in preparation). We speculate that ICAM-2 clustering, as induced by antibody crosslinking or by engagement of its natural receptor LFA-1 presents a regulateable cell survival signal that is only initiated when an ICAM-2 cell comes in contact with an LFA-1 expressing cells. Such cell-to-cell contact is of functional necessity in T cell activation (Perez and Nolan, manuscript submitted) and may be important in other ICAM-2/receptor interactions such as those recently reported between ICAM-2/DC-SIGN interactions in lymphocyte extravasation and ICAM/LFA-1 enhanced HIV infection/transmission (Barbeau et al., 1998; Butini et al., 1994; Geijtenbeek et al., 2000; Hioe et al., 2001). Thus, differential physiological roles for CAM-2 may exist. ICAM-2 overexpression could lead to tumor drug resistance and cytoproliferative disorders such as B-cell chronic lymphatic leukemia (B-CLL) since it has been reported that ICAM-2 is highly expressed on CD5$^+$ B cells from B-CLL patients (Molica et al., 1996) and on large B-cell lymphomas derived from patients (Alizadeh et al., 2000). These observations, in conjunction with the work described, here proposes that ICAM-2 or other adhesion molecules may have a role in certain classes of leukemias. In normal fibroblastoid cells, ICAM-2 mediated PI3K activation may likely regulate the endothelial transmigration of eosinophils (Gerwin et al., 1999) and potentially dendritic cells (via DC-SIGN) (Geijtenbeek et al., 2000), in addition to lymphocyte extravasation, two pivotal cell-contact dependent processes.

Our results illustrate that ICAM-2 overexpression and clustering can provide an anti-apoptotic signal in cell lines and primary human B cells rendering them resistant to physiological death programs induced by TNFα and Fas ligand. Although ICAM-3, CD43, and CD44 induced AKT activity in primary cells as determined by single cell analysis, only ICAM-2 and ICAM-3 were able to block apoptosis to FAS and TNFa, with CD44 and CD43 actually perpetuating cell death. ICAM-3 crosslinking intensified PIP2 production in addition to a temporal delay in AKT activation (data not shown), which differed from ICAM-2 crosslinking and suggests that ICAM-3 is affecting other signaling pathways. Surprisingly, ICAM-1 was completely dissimilar to ICAM-2 in the experiments conducted. These observations illustrate that molecular differences exist in intracellular signaling pathways for adhesion molecules capable of binding the same ERM proteins and interacting with at least one shared receptor. Interestingly, it has been reported that inflammatory cytokines can modulate ICAM-2 expression on antigen presenting cells (APC) and that dendritic cell maturation upregulates expression of ICAM-3 (Maki et al., 1998; McLaughlin et al., 1998; McLaughlin et al., 1999; Ohh and Takei, 1996), suggesting that the similarities of ICAM-2 and ICAM-3 observed may have functionally similar roles in vivo. The work presented herein attributes a previously unrecognized function for ICAM-2. The finding that ICAM-2 can exert cell survival signaling, ectopically and endogenously, as well as elicit an anti-apoptotic phenotype in a variety of cell lines and human primary cells suggests that deregulation or induced clustering is likely to contribute significantly to the anti-apoptotic phenotype that leads to tumor progression and/or cell survival.

Development of anti-metastatic approaches targeted to block cancer cell adhesion by general blockade of adhesion molecules warrants caution as the development of such agents may have detrimental effects in normal physiological process that are dependent on cell-to-cell contact interaction such as those mediated by ICAM/LFA-1. Thus, pathways involved in the regulation of ICAM-2 or other adhesion molecule expression, distribution, and activation could be alternative targets to the development of anti-tumor therapies and potentially as immunosuppressants.

Experimental Procedures

Antibodies and Chemicals

The following antibodies were purchased from Cell Signaling Technologies (Beverly, Mass.): anti-phospho-AKT-ser473 mAb, anti-phospho-AKT-thr308, anti-AKT, anti-phospho FKHR, anti-FKHR, anti-phospho-Gsk3 alp21, anti-cleaved PARP, anti-cleaved caspase 9, anti-cleaved caspase 3, anti-cleaved caspase 7, anti-caspase 9, anti-caspase 7, anti-pAFX, anti-PARP, anti-BAD, anti-BADser112, anti-BADser136, anti-phospho-BADser155, anti-rabbit-HRP. Anti-ICAM-2IC2/2 mAb, anti-ICAM-2-FITC mAb (IC2/2) were purchased from Research Diagnostics (Flanders, N.J.) Anti-ICAM-2 N-terminal, anti-ICAM-2 Cterminal, anti-a-actinin, anti-Bcl2, anti-Bclx/s, anti-p27, anti-p21, anti-cFLIP, anti-MYC, anti-p53, anti-NFκB, anti-Ikkα, anti-Ikkβ anti-phospho-tyrosine, antiphospho-threonine, anti-mouse IgG-HRP, anti-goat-HRP, annexin-V-biotin, were purchased from Santa Cruz Biotechnologies (Santa Cruz, Calif.). Anti-ezrin mAb, anti-PI3K, were purchased from Transduction Laboratories (San Diego, Calif.). Anti-PDK-phospho-serine, anti-PDK-phospho-threonine, Y-27362, 00126, bisindolymaleimide I and II, psi-tectorigenin, etoposide, PD98059, LY294002, TNFα, IL-2 were purchased from Calbiochem (San Diego, Calif.). Staurosporine, wortmannin, acridine orange, ethidium bromide, propidium iodide, GTPγS were purchased from Sigma (St. Louis, Mo.). Anti-mouse-alexa fluor 568, anti-rabbit alexa flour 488, anti-mouse alexa fluor 488, anti-rabbit alexa fluor 568, Prolong antifade, annexin-633, annexin-488, streptavidin alexa fluor 488, streptavidin alexa fluor 633, anti-phosphoinositide 3,4,5 triphosphate, anti-phosphoinositide 4,5 bisphosphate, were purchased from Molecular Probes (Eugene, Oreg.). An nexin-V-FITC, anti-rabbit PE, anti-mouse-FITC, anti-goat FITC, anti-goat texas red, Streptavidin-PE, were from BD Biosciences (San Jose, Calif.). CD4-APC, CD19-PerCP, anti-ICAM-1, anti-CAM-3, anti-CD43, anti-CD44, ANTI-LFA-1, anti-Mac1, were purchased from PharMingen (San Diego, Calif.). Additional reagents are described where appropriate.

Retroviral cDNA Screening

Production and infection of retroviruses was carried out as described (Kitamura et al., 1995; Onishi et al., 1996; Rayner and Gonda, 1994). A cDNA library was prepared from Jurkat T cells in the pBabe-S vector (Hitoshi et al., 1998). The library ($2\times10^6$ primary transformants) was used to transfect $\sim10^7$ PHOENIX-E packaging cells. The pBMN-LacZ control vector was spiked into the library at 1:10 to monitor the transfection/infection efficiency. Viral supernatants were harvested and used to infect $\sim10^7$ exponentially growing NIH3T3 cells; 48 hours post infection the cells were split and analyzed for β-galactosidase activity. The library-transduced NIH3T3 cells were plated at ~25% confluency; 24 hours later the medium was replaced with DMEM containing 1 µM staurosporine (STP). After 24 hours treatment the STP-containing medium was replaced with complete DMEM/10% donor bovine serum. Surviving cells were allowed to reach ~80% confluency (7 days). Survivor cells were retreated as described two additional rounds.

Phenotypic Transfer Assay

An aliquot of the surviving library-infected cells were super-infected with Moloney Murine Leukemia Virus (gift of T. Kinsella, Stanford). Super-infected cells were passaged for two-weeks to allow efficient spread of the helper virus. Naive NIH3T3 cells were infected with viral supernatants and allowed to express for 48 hours. Re-infected cells were then treated with staurosporine as described above. Surviving cells were cultured for 7 days and analyzed for transfer by RT-PCR.

RT-PCR Cloning of Proviral-cDNA Inserts and Construct Generation

RNA was prepared by the acid-guanidium-phenol-chloroform method as described (Chomczynski and Sacchi, 1987). cDNA was prepared from 4 µg heat-denatured total RNA in a 50 .mu.l reaction volume (Promega, Madison, Wis.) and incubated at 42.degree. C. and 55.degree. C. for 45 minutes. The cDNA reaction products (5 µl) were amplified (primers: 5'-GATCCTCCCTTTATCCAG (SEQ ID NO: 02); 5'-GAAT-GAAAGACCCCACCTGT (SEQ ID NO: 03)) in a 50 µl PCR reaction mix (Perkin-Elmer, Foster City, Calif.) at 95° C./30 sec; 55° C./60 sec; 72° C./2 min for 25 cycles. Full length ICAM2 cDNA was cloned into retroviral vector PBM-Z-IN backbone (Kinoshita et al., 1998) at BamHI/Sal1 site. ICAM2-ΔC, ICAM2-ΔN and ICAM2-C -terminal scrambled were generated by PCR and cloned into the BamHI/Sal1 site.

Cell Culture and Preparation of Primary Cells

NIH3T3 murine fibroblast were maintained in DMEM, 10% DCS, 1% PSQ (Duelbecco Modified Eagle Media, 10% Donar calf serum, 1% penicillin-streptomycin (1000 units/ml and 2 mM L-glutamine PSQ). Jurkat T-cells and CH27 transformed B-cells were maintained in RPMI-1640, 10% FCS, 1% PSQ. BaF3 pro-B-cells were maintained in RPMI-1640, 10% FCS, 1% PSQ, 400 U/ml IL-3 (Peprotech). 70Z/3 pre-B-cells were maintained in RPMI-1640, 10% FCS, 1% PSQ, 50 µm β-mercaptoethanol. HL60 myeloid leukemia cells were maintained in Opti-Mem 1,10% FCS, 1% PSQ. 293T human fibroblast cells were maintained in DMEM, 10% FCS, 1% PSQ. Cells were maintained at 5% $CO_2$/37° C. humidified incubator. Transduced cells were maintained in 500 µg/ml G418 (Sigma) and proper expression of construct was verified by western blots and FACS analysis of full length ICAM-2, ICAM-2AC, ICAM-ΔN as indicated. Staurosporine treatment was for 24 hrs at 1 µM (unless otherwise indicated). LY294002 treatment was at 10 µm 30 minutes before any subsequent treatment. Wortmannin treatment was for 24 hrs at 100 nM. Chemicals were dissolved in DMSO (final being 1:1000 for solvent dilution) and vector controls were incubated with 1% DMSO as negative control. Vector controls consisted of pBMN-Z-IN (empty vector) transduction or pBMN-Z-IN-GFP as indicated. The infection frequency of pBMN-Z-IN-GFP was 48%±10 for three independent viral transductions. Continual neomycin selection yielded homogenous ICAM-2, ICAM2-ΔC, ICAM2-ΔN, or control vector populations as routinely monitored by flow cytometry for protein expression. For preparation of primary cells, mononuclear cells were isolated from human peripheral blood by Ficoll-plaque density centrifugation and depletion of adherent cells on adherent plastic culture dishes. Isolated cells were maintained in complete media and analyzed by FACS for CD4, CD3, CD19, and ICAM-2 expression.

Cross-Linking

Antibody cross-linking experiments were performed using mAbs to anti-ICAM-1, anti-ICAM-2, anti-ICAM-3, anti-CD43, or anti-CD44 that recognizes the N-terminal region (extracellular domain) at 10 µg/ml. Spin dialysis (Biorad) was used for buffer exchange of azide containing antibodies (0.01%) to phosphate buffered saline buffer pH 7.4. Anti-mouse IgG (Sigma) was used as a control antibody in cross-linking experiments. $1\times10^6$ Jurkat, $1\times10^6$ BaF3, or $1\times10^7$ PBMC cells were serum starved for 4 hours respectively (except PBMC). Cells were incubated with either mAb (10 µg/ml) or mouse IgG (10 µg/ml) at 37° C. for the indicated time. Time points began post serum starvation to attenuate most of the signaling pathways or as indicated. Serum starvation of 4 hrs lacked biochemical initiations of apoptosis as tested by caspase 3 activity, cell cycle analysis, annexin V/PI staining (data not shown). Cells extracts were taken and subjected to either immunoprecipitation or immunoblotting were appropriate. Primary cells were subjected to apoptotic treatment followed by preparation for flow cytometry. GTPγS was made cell permeant by pre-incubating compound with Fugene (Roche Biochemicals) in a 1:4 molar ratio for 30 minutes at 25° C. prior to being applied to cells. Liposome mediated delivery of radiolabeled/fluorescent triphosphates yields high cell incorporation of highly charged molecular species (Perez, O. D. unpublished results).

Apoptosis Assays

Apoptosis was determined either by counting pyknotic nuclei, annexin-V binding by flow cytometry, or TUNEL BrdU staining by flow cytometry as indicated. Apoptosis was induced either by staurosporine (1 µm), treatment with anti-mouse Fas (5 µq/ml Santa Cruz Biotechnology (SCB), anti-human Fas (5 µg/ml Jo2 Biomed) or anti-human Fas (10 ng/ml CH11 Kamiya Biomedical) as indicated in appropriate experiment, IL-3 withdrawal-(24 hrs) or as indicated. For pyknolic nuclei count, NIH3T3 cells were grown on glass coverslips and assayed for apoptosis. Suspension cells were analyzed by nuclear staining with 25 µM acridine orange/25 µm ethidium bromide or 5 µg/ml Hoechst 33342 (Molecular Probes, Eugene, Oreg.). Apoptosis was identified by the presence of characteristic pyknotic nuclei as described (Jacobson and Raff, 1995). At least 5 individual fields were photographed and counted using a Zeiss axioscope fluorescence microscope. For the survival assay $10^6$ NIH3T3 cells were plated in 10 cm dishes and incubated overnight at 37° C. The cells were treated with 1 µM staurosporine for 24 hours. The cells were washed and cultured for 24 hours in complete medium. The cells were trypsinized and viable cells counted following trypan blue staining. Untreated cells were counted at the time of treatment. % survival represents (number of viable cells post-treatment)/(number of viable cells pretreatment). FACS based annexin-V-FITC/PI staining was done as described (PharMingen). TUNEL assay was performed as described by manufacturer of Apoptosis BrdU kit (Promega).

Flow cytometry data acquisition was performed 24 post staurosporine treatment (1 μM) for both BrdU (10,000 events collected) and pyknotic nuclei count and 12 hr post-staurosporine treatment for annexin V binding (100,000 events collected). Annexin-V positive cells will have compromised membranes after 24 hr treatment. Flow cytometry analysis was performed on a BD FACSCalibur machine with CELLQuest and analyzed using FlowJo software (Tree Star).

Kinase Assays

PDK-1 activity was determined by a PDK-1 immunoprecipiation kinase assay kit (Upstate Biotecnology, Lake Placid, N.Y.) as recommended by manufacturer. In brief, PDK-1 was immunoprecipitated from $1\times10^6$ treated cells, incubated with inactivated SGK enzyme, and detection of ($\gamma$-$^{32}$P) ATP incorporation to a SGK peptide substrate was measured by scintillation counting. PI3K activity was detected by developed PI3K FACS based assay (see below). AKT activity was detected by immunoprecipitation of AKT1 from cells and used in a kinase assay with GSK3 fusion protein (CST). $2\times10^6$ NIH3T3, $2\times10^6$ Jurkat, or $5\times10^5$ BaF3 cells were incubated with immobilized AKT 1G1 monoclonal antibody (mAb) (1:200, CST) at 4° C. with gentle rocking motion for 2 hrs. Immunocomplexes were washed 4× with cell lysis buffer and resuspended in 40 μl kinase buffer (25 mM Tris pH 7.5, 5 mM p-glycerolphosphate, 2 mM DTT, 0.1 mM Na$_3$VO$_4$, 10 mM MgCl$_2$) supplemented with 200 μM ATP and 1 μg of GSK-3 fusion protein (CST) for 30 min at 30° C. Kinase reaction was terminated with SDS sample buffer boiled for 5 min, and phosphorylation state of GS3K was detected by immunoblotting and visualized using ECL detection (Amersham). Immunoblots are representative of 3 independent virally transduced cell populations each repeated 3 times (n=9). AKT activity was verified by AKT phosphorylation by immunoblotting with phospho-specific antibodies to ser473 and thr308 (NEB). Kinase assays are representative of at least three independent measurements and are represented as standard deviations were appropriate.

Cell Fractionation, Immunoprecipitations and Immunoblotting

Triton-X-100 fractionation was carried out as described [(Ref xxx)]. Cell extracts were prepared by washing $2\times10^6$ cells in ice cold PBS and harvesting in lysis buffer (20 mM Tris pH 7.5, 150 mM NaCl 1 mM EDTA 1 mM EGTA, 1% Triton X100, 2.5 mM Na$_2$PO$_4$, 1 mM β-glycerolphosphate, 1 mM Na$_3$VO$_4$, 1 μg/ml Leupeptin, 1 mM PMSF, protease inhibitor cocktail tablet (Boehringer Mannheim)). Extracts were centrifuged 14,000 RPM for 5 min at 4° C. and cell lysates (20 μg as determine by BCA protein assay (Pierce)) were fractionated on 12% or 15%

SDS-polyacrylamide gel electrophoresis and transferred to PVDF membranes using standard procedures. Immunoprecipitations were pre-cleared with protein A/G plus-agarose beads (SBC). IP was incubated for 1 hr or overnight with primary antibody, 1 hr with protein A/G plus-agarose beads and washed 4× with lysis buffer. Blots were incubated with the indicated antibodies. Secondary antibodies used: anti-rabbit HRP (1:5000 NEB), anti-mouse HRP or anti-goat HRP 1:5000, SBC) and visualized using ECL detection (Amersham) or with a Kodak Digital Science 440C station. Blots are representative of at least 3 independent experiments.

Flow Cytometry and FACS Analysis

Intracellular and extracellular staining was performed as described (www(dot)metazoa(dot)com/UPL3287). Intracellular probes for AKT and p44/42 MAPK activity was made by conjugating monoclonal anti-AKTser473 antibody or monoclonal anti-p44/42 phospho (Thr202/Tyr204) (Cell Signaling Technology) to ALEXA FLUOR® 568 dye or ALEXA FLUOR® 488 (Molecular Probes), using ALEXA FLUOR® protein conjugation kit (Molecular Probes) respectively. Phospho specificity was tested by western blotting and FACS analysis to a variety of PI3K activators (platelet derived growth factor) and inhibitors (LY294002) for AKT activity, and to epidermal growth factor and MEK1/2 inhibitors U0126 (CST) for p44/42 MAPK activity (data not shown). Intracellular staining by phospho-AKTser473 ALEXA FLUOR® 568 and phospho-p44/42 -Alexa ALEXA FLUOR® 488 reflected AKT kinase and p44/42 MAPK activity in Jurkat cells when stimulated and inhibited prior to stimulation. Quantitative FACS analysis was performed as described (Davis et al., 1998; Iyer et al., 1998; Lenkei et al., 1998). In brief, R-phycoerythrin (PE) (Molecular Probes) was conjugated to indicated antibody as suggested by manufacturer of protein cross-linking kit (Molecular Probes), tested for proper stochiometry (data not shown) and quantitated using QuantiBRITE-PE beads (BD systems). A quantitative calibration curve was generated using QuantiBRITE-PE beads that contain a known amount of PE molecule/bead. A linear regression analysis is performed using the following equation: $\log_{10}$(PE fluorescence)=slope*$\log_{10}$(PE molecules/bead)+intercept. PE fluorescence is determined by taking the geometric mean of the PE channel. Quantitation is valid only for antibodies directly conjugated to PE. Using saturating amounts of antibody and thorough washing ensures all surface antigens are bound. Preparation of samples on ice reduces antibody internalization. Surface antigens of cells for an unknown cell population are determined by computing the PE geometric mean using the calibration curve. Quantitative FACS analysis provides approximate estimates for surface antigen expression. Numbers plotted represent relative surface molecules and not absolute numbers since antibody valency was not investigated for the monoclonal antibodies used. Flow cytometry analysis was performed on a BD FACSCaliburx™ machine and analyzed using FlowJo™ software (Tree Star). CellQuest was used for quantitative flow cytometry and linear regression analysis of QuantiBRITET™-PE beads. Flow cytometry data are representative of 3 independent experiments of $10^6$ cells/sample analyzed. 50,000 events were collected or otherwise noted and calibrated using Calibrite™ beads (BD systems). Data plotted in bar graph format is expressed as the mean (bar)±SD of triplicate experiments.

Laser Scanning Confocal Microscopy

Cells were grown in coverslips, washed twice in phosphate buffered saline pH 7.4 (PBS) and fixed in 2.7% paraformaldehyde (in PBS). Cells were permeabilized for 5 minutes with 0.1% Triton-X-100 washed twice in PBS, blocked in 4% bovine serum albumin (BSA, in PBS), and subjected to antibody incubation: (primary at 0.1 mg/ml, secondary at 1:1000 dilution in 1% BSA, with several washing steps in between). Stained coverslips were mounted onto glass slides with Prolong Antifade reagent (Molecular Probes) and visualized using a Molecular Dynamics Multiprobe 2010 confocal laser scanning microscope. Images were compiled using Adobe Photoshop 6.0.

References

Alessi, D. R., Andjelkovic, M., Caudwell, B., Cron, P., Morrice, N., Cohen, P., and Hemmings, B. A. (1996). Mechanism of activation of protein kinase B by insulin and IGF-1. Embo J 15, 6541-51.

Alizadeh, A. A., Eisen, M. B., Davis, R. E., Ma, C., Lossos, I. S., Rosenwald, A., Boldrick, J. C., Sabet, H., Tran, T., Yu, X., Powell, J. I., Yang, L., Marti, G. E., Moore, T., Hudson, J., Jr., Lu, L., Lewis, D. B., Tibshirani, R., Sherlock, G., Chan, W. C., Greiner, T. C., Weisenburger, D. D., Armitage, J. O., Warnke, R., Staudt, L. M., and et al. (2000). Distinct types of diffuse large B-cell lymphoma identified by gene expression profiling. Nature 403, 503-11.

Brunet, A., Bonni, A., Zigmond, M. J., Lin, M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell 96, 857-68.

Budihardjo, I., Oliver, H., Lutter, M., Luo, X., and Wang, X. (1999). Biochemical pathways of caspase activation during apoptosis. Annu Rev Cell Dev Biol 15, 269-90.

Cardone, M. H., Roy, N., Stennicke, H. R., Salvesen, G. S., Franke, T. F., Stanbridge, E., Frisch, S., and Reed, J. C. (1998). Regulation of cell death protease caspase-9 by phosphorylation. Science 282, 1318-21.

Chomczynski, P., and Sacchi, N. (1987). Single-step method of RNA isolation by acid guanidinium thiocyanate-phenol-chloroform extraction. Anal Biochem 162, 156-9.

Damle, N. K., Klussman, K., and Aruffo, A. (1992). Intercellular adhesion molecule-2, a second counter-receptor for CD11a/CD18 (leukocyte function associated antigen-1), provides a costimulatory signal for T-cell receptor-initiated activation of human T cells. J Immunol 148, 665-71.

Datta, S. R., Katsov, A., Hu, L., Petros, A., Fesik, S. W., Yaffe, M. B., and Greenberg, M. E. (2000). 14-3-3 proteins and survival kineses cooperate to inactivate BAD by BH3 domain phosphorylation. Mol Cell 6, 41-51.

Davis, K. A., Abrams, B., Iyer, S. B., Hoffman, R. A., and Bishop, J. E. (1998). Determination of CD4 antigen density on cells: role of antibody valency, avidity, clones, and conjugation. Cytometry 33, 197-205.

de Fougerolles, A. R., Chi-Rosso, G., Bajardi, A., Gotwals, P., Green, C. D., and Koteliansky, V. E. (2000). Global expression analysis of extracellular matrixintegrin interactions in monocytes. Immunity 13, 749-58.

de Fougerolles, A. R., Stacker, S. A., Schwarting, R., and Springer, T. A. (1991). Characterization of ICAM-2 and evidence for a third counter-receptor for LFA-1. J Exp Med 174, 253-67.

Diacovo, T. G., deFougerolles, A. R., Bainton, D. F., and Springer, T. A. (1994). A functional integrin ligand on the surface of platelets: intercellular adhesion molecule-2. J Clin Invest 94, 1243-51.

Dion, F., Mes-Masson, A. M., Seymour, R. J., Provencher, D., and Tonin, P. N. (2000). Allelotyping defines minimal imbalance at chromosomal region 17q25 in non-serous epithelial ovarian cancers. Oncogene 19, 1466-72.

Dobo, K. L., Giver, C. R., Eastmond, D. A., Rumbos, H. S., and Grosovsky, A. J. (1995). Extensive loss of heterozygosity accounts for differential mutation rate on chromosome 17q in human lymphoblasts. Mutagenesis 10, 53-8.

Douglas, I. S., Leff, A. R., and Sperling, A. I. (2000). CD4+ T cell and eosinophil adhesion is mediated by specific ICAM-3 ligation and results in eosinophil activation. J Immunol 164, 3385-91.

Downward, J. (1998). Mechanisms and consequences of activation of protein kinase B/Akt. Curr Opin Cell Biol 10, 262-7.

Earnshaw, W. C., Martins, L. M., and Kaufmann, S. H. (1999). Mammalian caspases: structure, activation, substrates, and functions during apoptosis. Annu Rev Biochem 68, 383-424.

Frisch, S. M., and Ruoslahti, E. (1997). Integrins and anolkis. Curr Opin Cell Biol 9, 701-6.

Gautreau, A., Poullet, P., Louvard, D., and Arpin, M. (1999). Ezrin, a plasma membrane-microfilament linker, signals cell survival through the phosphatidylinositol 3-kinase/Akt pathway. Proc Natl Acad Sci USA 96, 7300-5.

Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000). DC-SIGN-ICAM-2 interaction mediates dendritic cell trafficking. Nat Immunol 1, 353-7.

Gerner, C., Frohwein, U., Gotzmann, J., Bayer, E., Gelbmann, D., Bursch, W., and Schulte-Hermann, R. (2000). The Fas-induced apoptosis analyzed by high throughput proteome analysis. J Biol Chem 275, 39018-26.

Gerwin, N., Gonzalo, J. A., Lloyd, C., Coyle, A. J., Reiss, Y., Banu, N., Wang, B., Xu, H., Avraham, H., Engelhardt, B., Springer, T. A., and Gutierrez-Ramos, J. C. (1999). Prolonged eosinophil accumulation in allergic lung interstitium of ICAM-2 deficient mice results in extended hyper-responsiveness. Immunity 10, 9-19.

Gottlieb, R. A. (2000). Mitochondria: execution central. FEBS Lett 482, 6-12.

Graff, J. R., Konicek, B. W., McNulty, A. M., Wang, Z., Houck, K., Allen, S., Paul, J. D., Hbalu, A., Goode, R. G., Sandusky, G. E., Vessella, R. L., and Neubauer, B. L. (2000). Increased AKT activity contributes to prostate cancer progression by dramatically accelerating prostate tumor growth and diminishing p27Kip1 expression. J Biol Chem 275' 24500-5.

Grutter, M. G. (2000). Caspases: key players in programmed cell death. Curr Opin Struct Biol 10, 649-55.

Haas-Kogan, D., Shalev, N., Wong, M., Mills, G., Yount, G., and Stokoe, D. (1998). Protein kinase B (PKB/Akt) activity is elevated in glioblastoma cells due to mutation of the tumor suppressor PTEN/MMAC. Curr Biol 8, 1195-8.

Heiska, L., Kantor, C., Parr, T., Critchley, D. R., Vilja, P., Gahmberg, C. G., and Carpen, O. (1996). Binding of the cytoplasmic domain of intercellular adhesion molecule-2 (ICAM-2) to alpha-actinin. J Biol Chem 271' 26214-9.

Helander, T. S., Carpen, O., Turunen, O., Kovanen, P. E., Vaheri, A., and Timonen, T. (1996). ICAM-2 redistributed by ezrin as a target for killer cells. Nature 382, 265-8.

Hitoshi, Y., Lorens, J., Kitada, S. I., Fisher, J., LaBarge, M., Ring, H. Z., Francke, U., Reed, J. C., Kinoshita, S., and Nolan, G. P. (1998). Toso, a cell surface, specific regulator of Fas-induced apoptosis in T cells. Immunity 8, 46171.

Holmstrom, T. H., and Eriksson, J. E. (2000). Phosphorylation-Based signaling in Fas receptor-mediated apoptosis. Crit. Rev Immunol 20, 121-52.

Hulleman, E., and Boonstra, J. (2001). Regulation of G1 phase progression by growth factors and the extracellular matrix. Cell Mol Life Sci 58, 80-93.

Ichikawa, T., Masumoto, J., Kaneko, M., Saida, T., Sagara, J., and Taniguchi, S. (1998). Expression of moesin and its associated molecule CD44 in epithelial skin tumors. J Cutan Pathol 25, 237-43.

Iyer, S. B., Hultin, L. E., Zawadzki, J. A., Davis, K. A., and Giorgi, J. V. (1998). Quantitation of CD38 expression using QuantiBRITE beads. Cytometry 33, 206-12.

Jacobson, M. D., and Raff, M. C. (1995). Programmed cell death and Bch2 protection in very low oxygen. Nature 374, 814-6.

Johnson, V. L., Ko, S. C., Holmstrom, T. H., Eriksson, J. E., and Chow, S. C. (2000). Effector caspases are dispensable for the early nuclear morphological changes during chemical-induced apoptosis. J Cell Sci 113, 2941-53.

Kennedy, S. G., Kandel, E. S., Cross, T. K., and Hay, N. (1999). AkVProtein kinase B inhibits cell death by preventing the release of cytochrome c from mitochondria. Mol Cell Biol 19, 5800-10.

Khwaja, A., Rodriguez-Viciana, P., Wennstrom, S., Warne, P. H., and Downward, J. (1997). Matrix adhesion and Ras transformation both activate a phosphoinositide 3-OH kinase and plotein kinase B/A cellular survival pathway. Embo J 16, 2783-93.

Kitamura, T., Onishi, M., Kinoshita, S., Shibuya, A., Miyajima, A., and Nolan, G. P. (1995). Efficient screening of retroviral cDNA expression libraries. Proc Natl Acad Sci USA 92, 9146-50.

Kroemer, G. (1999). Mitochondrial control of apoptosis: an overview. Biochem Soc Symp 66, 1-15.

Kruidering, M., and Evan, G. I. (2000). Caspase-8 in apoptosis: the beginning of "the end"? IUBMB Life 50, 85-90.

Kuida, K. (2000). Caspase-9. Int J Biochem Cell Biol 32, 121-4.

Kulik, G., Klippel, A., and Weber, M. J. (1997). Antiapoptotic signalling by the insulin-like growth factor I receptor, phosphatidylinositol 3-kinase, and Akt. Mol Cell Bid 17, 1595-606.

Kureishi, Y., Luo, Z., Shiojima, I., Bialik, A., Fulton, D., Lefer, D. J., Sessa, W. C., and Walsh, K. (2000). The HMG-CoA reductase inhibitor simvastatin activates the protein kinase Akt and promotes angiogenesis in normocholesterolemic animals. Nat Med 6, 1004-10.

Lenkei, R., Gratama, J. W., Rothe, G., Schmitz, G., D'Hautcourt J, L., Arekrans, A., Mandy, F., and Marti, G. (1998). Performance of calibration standards for antigen quantitation with flow cytometry. Cytometry 33, 188-98.

Marte, B. M., and Downward, J. (1997). PKB/Akt: connecting phosphoinositide 3-kinase to cell survival and beyond. Trends Biochem Sci 22, 355-8.

Molica, S., Dattilo, A., Mannella, A., and Levato, D. (1996). Intercellular adhesion molecules (ICAMs) 2 and 3 are frequently expressed in B cell chronic lymphocytic leukemia. Leukemia 10, 907-8.

Nortamo, P., Salcedo, R., Timonen, T., Patarroyo, M., and Gahmberg, C. G. (1991). A monoclonal antibody to the human leukocyte adhesion molecule intercellular adhesion molecule-2. Cellular distribution and molecular characterization of the antigen. J Immunol 146, 2530-5.

Onishi, M., Kinoshita, S., Morikawa, Y., Shibuya, A., Phillips, J., Lanier, L. L., Gorman, D. M., Nolan, G. P., Miyajima, A., and Kitamura, T. (1996). Applications of retrovirus-mediated expression cloning; Exp Hematol 24, 324-9.

Pap, M., and Cooper, G. M. (1998). Role of glycogen synthase kinase-3 in the phosphatidylinositol 3-Kinase/Akt cell survival pathway. J Biol Chem 273, 1992932.

Perez, O. D., and Nolan, G. P. (2001). Functional signaling analysis in single cells: Simultaneous measurement of multiple kinase activities using polychromatic flow cytometry. Submitted.

Raff, M. C. (1992). Social controls on cell survival and cell death. Nature 356, 397-400.

Rath, P. C., and Aggarwal, B. B. (1999). TNF-induced signaling in apoptosis. J Clin Immunol 19.350-64.

Rayner, J. R., and Gonda, T. J. (1994). A simple and efficient procedure for generating stable expression libraries by cDNA cloning in a retroviral vector. Mol Cell Biol 14, 880-7.

Renkonen, R., Paavonen, T., Nortamo, P., and Gahmberg, C. G. (1992). Expression of endothelial adhesion molecules in vivo. Increased endothelial ICAM-2 expression in lymphoid malignancies. Am J Pathol 140, 763-7.

Ruoslahti, E., and Reed, J. C. (1994). Anchorage dependence, integrins, and apoptosis. Cell 77, 477-8.

Russell, S. E., Mcilhatton, M. A., Burrows, J. F., Donaghy, P. G., Chanduloy, S., Petty, E. M., Kalikin, L. M., Church, S. W., Mcilroy, S., Harkin, D. P., Keilty, G. W., Cranston, A. N., Weissenbach, J., Hickey, I., and Johnston, P. G. (2000). Isolation and mapping of a human septin gene to a region on chromosome 17q, commonly deleted in sporadic epithelial ovarian tumors. Cancer Res 60, 4729-34.

Sansom, D., Borrow, J., Solomon, E., and Trowsdale, J. (1991). The human ICAM2 gene maps to 17q23-25. Genomics 11, 4624.

Schneider, P., and Tschopp, J. (2000). Apoptosis induced by death receptors. Pharm Acta Helv 74, 281-6.

Schneller, M. (2001). Identification of a candidate integrin-fraction associated with the activated form of the PDGF-receptor. Biochem Biophys Res Commun 281, 595-602.

Shan, X., Czar, M. J., Bunnell, S. C., Liu; P., Liu, Y., Schwartzberg, P. L., and Wange, R. L. (2000). Deficiency of PTEN in Jurkat T cells causes constitutive localization of Itk to the plasma membrane and hyperresponsiveness to CD3 stimulation. Mol Cell Biol 20, 6945-57.

Shibasaki, F., Fukami, K., Fukui, Y., and Takenawa, T. (1994). Phosphatidylinositol 3-kinase binds to alpha-actinin through the p85 subunit. Biochem J 302, 551-7.

Shinohara, M., Kodama, A., Matozaki, T., Fukuhara, A., Tachibana, K., Nakanishi, H., and Takai, Y. (2001). Roles of cell-cell adhesion-dependent tyrosine phosphorylation of Gab-1. J Biol Chem 21, 21.

Simmons, D. L. (1995). The role of ICAM expression in immunity and disease. Cancer Surv 24, 141-55.

Staunton, D. E., Dustin, M. L., and Springer, T. A. (1989). Functional cloning of ICAM-2, a cell adhesion ligand for LFA-1 homologous to ICAM-1. Nature 339, 614.

Stokowski, R. P., and Cox, D. R. (2000). Functional analysis of the neurofibromatosis type 2 protein by means of disease-causing point mutations. Am J Hum Genet. 66, 873-91.

Stolzenberg, I., Wulf, S., Mannherz, H. G., and Paddenberg, R. (2000). Different sublines of Jurkat cells respond with varying susceptibility of internucleosomal DNA degradation to different mediators of apoptosis. Cell Tissue Res 301, 273-82.

Sugai, T., Habano, W., Nakamura, S., Sato, H., Uesugi, N., Orli, S., Itoh, C., and Katoh, R. (2000). Allelic losses of 17p, 5q, and 18q loci in diploid and aneuploid populations of multiploid colorectal carcinomas. Hum Pathol 31, 925-30.

Tsukita, S., and Yonemura, S. (1997). ERM proteins: head-to-tail regulation of actin-plasma membrane interaction. Trends Biochem Sci 22, 53-8.

Turunen, O., Sainio, M., Jaaskelainen, J., Carpen, O., and Vaheri, A. (1998). Structure-function relationships in the ezrin family and the effect of tumorassociated point mutations in neurofibromatosis 2 protein. Biochim Biophys Acta 1387, 1-16.

van Kooyk, Y., and Figdor, C. G. (2000). Avidity regulation of integrins: the driving force in leukocyte adhesion. Curr Opin Cell Biol 12, 542-7.

Vinores, S. A., Henderer, J. D., Mahlow, J., Chiu, C., Derevjanik, N. L., Larochelle, W., Csaky, C., and Campochiaro, P. A. (1995). Isoforms of plateletderived growth factor and its receptors in epiretinal membranes: immunolocalization to retinal pigmented epithelial cells. Exp Eye Res 60, 607-19.

Wick, W., Furnari, F. B., Naumann, U., Cavenee, W. K., and Weller, M. (1999). PTEN gene transfer in human malignant glioma: sensitization to irradiation and CD95L-induced apoptosis. Oncogene 18, 393643.

Zha, J., Harada, H., Yang, E., Jockel, J., and Korsmeyer, S. J. (1996). Serine phosphorylation of death agonist BAD in response to survival factor results in binding to 14-3-3 not BCL-X(L). Cell 87, 619-28.

Example 5

Activation of PKB/AKT-Dependent Cell Survival by Intracellular Adhesion Molecule-2 (ICAM-2)

In this Example, using the methods and compositions of the present invention, the present inventors (also referred to herein as "we") using a retroviral cDNA library in a functional genetic screen identified intracellular adhesion molecule-2 (ICAM-2), a member of the immunoglobin-family of adhesion molecules, as a potent inhibitor of several activators of apoptosis. ICAM-2 expression blocked the onset of apoptosis in several cell types and induction settings. ICAM-2's anti-apoptotic effect was mapped to the activation of the PI3K/AKT pathway and resulted in subsequent phosphorylation of BAD, GSK3, and FKHR. ICAM-2's cell survival signal was found to be independent of caspase inhibitory proteins, cell cycle regulators, or anti-apoptotic pathways using Bcl-2. The survival function was dependent on the cytoplasmic tail of ICAM-2, a region that bound membrane-cytoskeleton linker proteins α-actinin and ezrin. The ICAM-2 mediated survival function was abrogated by two pharmacological inhibitors of PI3 kinase, wortmannin and LY294002, indicating activation of AKT and its downstream effectors were dependent on PI3K recruitment to the plasma membrane. Antibody clustering of endogenous ICAM-2 on BaF3 pro-B cells and Jurkat T-cells stimulated AKT kinase activity and phosphorylation of downstream effectors BAD, GSK3, FKHR, and AFX, congruent with the ectopic expression results. Primary CD4+ and CD19+ cells were protected from TNFα and Fas mediated apoptosis following ICAM-2 clustering and presented elevated AKT activity as detected by direct single cell flow cytometric measurement of intracellular AKT kinase activity. These results attribute a novel survival signaling function to ICAM-2 that might provide an explanation for both the role of ICAM-2 over-expression in B-cell lymphomas and mechanisms by which ICAM-2 might signal intracellular communication in a variety of important cell types.

Introduction

Cellular homeostasis is achieved through a tightly regulated balance of proliferation and apoptosis. Apoptosis is a distinct form of cell death that is initiated by a number of events including DNA damage, growth factor deprivation, receptor-mediated death signaling, or by xenobiotic induction, among others. Regulation of apoptotic signaling pathways is largely governed by a cell's ability to sense its environment. Cellular apoptotic death can occur by many paths with distinct apoptotic stimuli initiating varied cell death mechanisms. For instance, chemically induced apoptosis occurs with the release of cytochrome C and activation of caspase 9 (Budihardjo et al., 1999). Receptor induced apoptosis (Fas/TNFα) is mediated through activation of caspase 8 (Holmstrom and Eriksson, 2000; Kruidering and Evan, 2000; Rath and Aggarwal, 1999; Schneider and Tschopp, 2000) and can operate independent of the mitochondria (Gottlieb, 2000; Kroemer, 1999; Kuida, 2000). Both caspase 8 and 9 converge on effector caspases 3 and 7 to mediate the characteristic hallmarks of apoptosis (Earnshaw et al., 1999; Grutter, 2000).

A cell's commitment to cellular proliferation or programmed cell death is a balance of the survival and death signals communicated from both the immediate environs, such as extracellular matrix (ECM) interactions, cell-cell contact, or more distant sites through endocrine and paracrine factors (Ruoslahti and Reed, 1994). Survival pathways are proposed to function during early development where apoptosis plays a key role in shaping organogenesis (Raff, 1992). Similarly, the lack of survival signals is exemplified in the phenomenon of anoikis, where epithelial cells undergo apoptosis when ECM-attachment is blocked (Frisch and Ruoslahti, 1997). ECM survival signals are presumably mediated by activation of cell-surface receptors via integrin clustering, contributes to the specificity of cell-cell/cell-matrix interactions, and prevents unwarranted cell migration. ECM-interactions are required for growth factor signaling in adherent cells (Hulleman and Boonstra, 2001). Deregulation of ECM-integrin signaling leads to anchorage-independent growth, which correlates with malignancy. Hence it is clear that deregulation of ECM signaling can desensitize a cell to apoptotic stimuli and contribute to a malignant phenotype that allows cells to survive in foreign milieus and under adverse conditions.

Functional characterization of molecules involved in cellular adhesion has been focused on signal transduction pathways attributed to integrins and cadherins (de Fougerolles et al., 2000; Schneller, 2001; Shinohara et al., 2001). Adhesion molecules of the immunoglobin (Ig) superfamily have been largely overlooked as potential signaling molecules. ICAM-2 (CD102) is a member of the Ig-superfamily of cell surface proteins and mediates leukocyte binding to LFA-1 (CD11a/CD18) and MAC-1 (CD11b/CD18) whose expression is restricted to leukocytes (van Kooyk and Figdor, 2000). As a cell surface adhesion member involved in leukocyte recruitment in tissues, ICAM-2 is expressed in low levels on most leukocytes including T and B lymphocytes, monocytes, platelets and early CD34+ hematopoetic progenitor cells (de Fougerolles et al., 1991; Diacovo et al., 1994; Nortamo et al., 1991). In addition, ICAM-2 constitutive expression has been observed on all vascular endothelium (de Fougerolles et al., 1991). Based on the expression pattern of ICAM-2, it has been hypothesized to be involved in leukocyte recirculation. ICAM-2 deficient mice support this by demonstrating that eosinophil trafficking is augmented in inflammatory responses (Gerwin et al., 1999). Surprisingly, this phenotype is relatively mild considering the range of cell types upon which ICAM-2 is expressed. It suggests that the roles ICAM-2 plays are subtle or are redundant with other pathways. Thus, the ICAM-2 deficient mice do not sufficiently detail the roles of ICAM-2, warranting further characterizations of the mechanisms by which ICAM-2 acts are needed.

In contrast to ICAM-2's putative role as an adhesion molecule, it is surprising to find ICAM-2 highly expressed on both endothelial cells in lymphomas and CD5[+] B cells from B-cell chronic lymphatic leukemia (B-CLL) patients (Molica et al., 1996; Renkonen et al., 1992). Lymphoproliferative diseases inevitably inhibit adhesion dependency-loss of adhesion is one of the primary means by which metastatic spread occurs. However, recent gene expression profiling of large B-cell lymphomas from patients indicated an elevated expression of ICAM-2 (Alizadeh et al., 2000). Interestingly, ICAM-2 is the only ICAM (1-5) that maps to chromosome 17q23-25 (Sansom et al., 1991), a segment associated with genomic instability and recently identified as a segment of high aberration in various cancers (Dion et al., 2000; Dobo et al., 1995; Russell et al., 2000; Sugai et al., 2000). Despite these observations, ICAM-2's role and molecular characterization in the progression of lymphatic disease states has not been addressed.

We devised a genetic screen to identify genes that are involved in regulation of apoptosis and augmented in malignant phenotypes. Cells transduced with a human transformed T cell (Jurkat) retroviral vector cDNA library were screened for an anti-apoptotic phenotype. One cDNA demonstrated reproducible anti-apoptotic activity in a phenotypic transfer assay. This cDNA encoded full-length intracellular adhesion molecule-2 (ICAM-2). Here we show that ICAM-2 was identified as being capable of transducing an anti-apoptotic effect. Functional characterization of ICAM-2 reveals that it mediates a survival signal sufficient to block apoptosis by activation of the PI3K/AKT pathway. Furthermore, development of probes to measure intracellular AKT activity by flow cytometry allowed for the simultaneous measurement of AKT activity as a function of ICAM-2 clustering on human peripheral blood monocytes (PBMC). Multi-parameter FACS analysis confirmed ICAM-2 clustering led to AKT activity in CD4+ and CD19+ primary human cells and subsequent protection from Fas and TNFα mediated apoptosis. These observations identify ICAM-2 as having a role in mediating cell survival by activation of the PI3K/AKT cell survival pathway. These finding suggest that inappropriate expression of ICAM-2 could contribute significantly to the anti-apoptotic phenotypes in the cumulative process that leads to tumor progression and metastatic spread. The findings also underscore a positive role for ICAM-2 in signaling pathways involving AKT and downstream effectors.

Results

Screening a Retroviral cDNA Library in an Anti-Apoptotic Functional Assay

To identify genes that alter signaling in apoptosis we devised a retroviral library approach to screen for cDNAs that encode anti-apoptotic molecules (FIG. 26A). cDNAs from a malignant cell type (Jurkat T cell leukemia) were screened for anti-apoptotic function in a recipient non-malignant (fibroblast) cell. Apoptosis was induced with staurosporine (STP), a kinase-inhibiting plant-derived alkaloid, activity, and a potent inducer of caspase-dependent cell death in most cell types. Induction conditions were determined that limited the level of spontaneous background while maximizing the extent of apoptotic death (minimal background of one surviving cell in a STP-treated mock library control in ~$10^4$ starting cells). $10^7$ NIH3T3 fibroblasts were infected with a retroviral cDNA library derived from Jurkat cells at an infection frequency of 40% to limit the number of integrations to a single event per cell. Control retroviruses were prepared, expressing LacZ- or Bcl-2, and infected into a similar number of NIH3T3 cells. Apoptosis was induced in the transduced cell culture by staurosporine treatment and the cells were then allowed to recover (FIG. 26A). Surviving cell clones were expanded, replated and retreated with staurosporine. The complexity of the expressed cDNAs in the surviving population was assessed with RT-PCR. A few major bands were observed following three rounds of selection (FIG. 26 B).

Replication-competent Moloney murine leukemia virus (MMLV) was applied to the enriched cell populations. Upon integration and expression of the MMLV proteins resident retroviral constructs from the library were co-packaged into infectious virions that can be transferred to naïve target NIH3T3 cells. The staurosporine selection process was then reapplied. In this manner true phenotype-inducing clones enrich at a rate of 1/background (see materials and methods for elaboration). Three of the pooled libraries showed enrichment for specific bands after PCR (see FIG. 26B lanes 1 and 2). Several bands were rescued by PCR cloning and one of these bands was sequenced and demonstrated to encode full-length ICAM-2 cDNA (Staunton et al., 1989), an immunoglobulin superfamily member that regulates leukocyte adhesion through interaction with its integrin counter-receptor, LFA-1 (de Fougerolles et al., 1991; Simmons, 1995).

ICAM-2 Mediates a Survival Signal The ICAM-2 cDNA was cloned into a retroviral vector (pBMN-Z-IN) that carries an internal ribosome entry site (IRES) upstream of the neomycin resistance gene. NIH3T3 fibroblasts were infected with retroviruses capable of expressing the ICAM-2 gene, along with appropriate control vectors pBMN-Z-IN (vector control) and pBMN-Z-IN-GFP (GFP vector control). Expression of the 60 kD ICAM-2 glycoprotein in neomycin-selected NIH3T3 fibroblasts infected with the pBMN-Z-IN-ICAM-2 construct (referred to as ICAM-2) was verified by immunoblotting (FIG. 27A), flow cytometry (FIG. 27B, 28B), and immunoprecipitation (FIG. 28C). The expressed ICAM-2 protein co-migrated with the native protein from Jurkat T cells (data not shown).

Figure 27E:
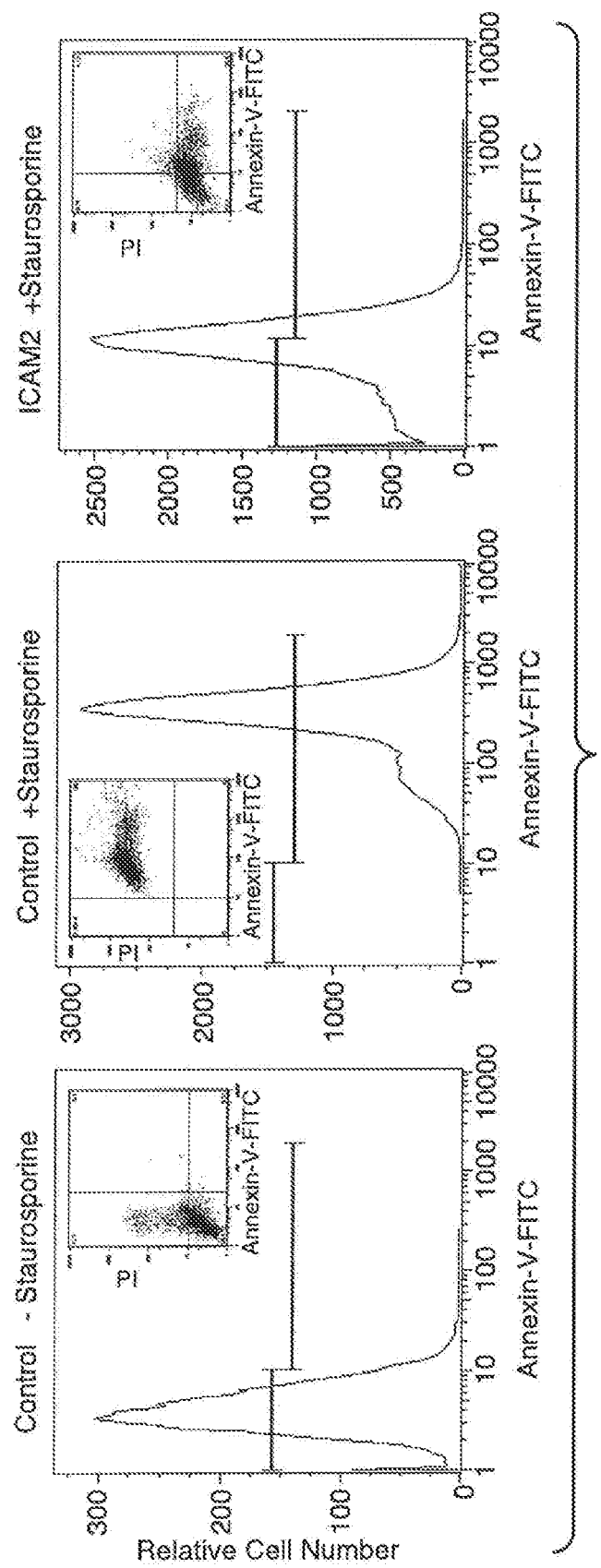

Staurosporine treatment is thought to mimic factor-withdrawal in cells (Raff, 1992), and induces apoptosis. ICAM-2 expression in NIH3T3 cells limited the extent of apoptosis induced by staurosporine treatment as determined by pyknotic nuclei count (FIG. 27C, 27D) as well as an annexin-V binding assay (FIG. 27E) and the BrdU TUNEL assay (FIG. 29B) confirming the clone's selection by phenotype in the screen. Interestingly, not all forms of apoptosis were inhibited. Fas induced apoptosis in ICAM-2 expressing Jurkat T cells was not inhibited across a range of concentrations of a monoclonal antibody to the Fas receptor (FIG. 27C, panel 3).

A report correlating ICAM-2 expression with a lymphoproliferative disorder, B-cell chronic lymphatic leukemia (B-CLL) (Molica et al., 1996), prompted us to test the anti-apoptotic activity of ICAM-2 in the mouse pre-B-cell line, 70Z/3. ICAM-2 expression inhibited staurosporine-induced apoptosis in 70Z/3 cells (FIG. 28A). Given the indication that staurosporine mimics factor withdrawal, we assessed the ability of ICAM-2 expression to protect factor-dependent cells from factor withdrawal. ICAM-2 expression in the IL-3-dependent pro-B cell line BaF3 resulted in a delayed onset of apoptosis following IL-3 deprivation (FIG. 28A). Furthermore, we tested the ability of ICAM-2 to rescue BaF3 cells from apoptosis induced by treatment with anti-Fas antibodies. ICAM-2 demonstrated a potent inhibition of apoptosis through the Fas pathway in these cells (FIG. 28A). These results are as good as or better than transduction controls with Bck2 and therefore the apparent effects cannot be attributed to modest effects on apoptosis (data not shown). There is, however, cell specificity to the anti-apoptotic effect as ICAM-2 over-expressing Jurkat T cells were not protected from Fas-induced apoptosis (FIG. 27C) but were protected from staurosporine induced apoptosis (FIG. 28A). High throughput proteome analysis recently identified that in Jurkat T cells, Fas induced apoptosis results in a rapid destruction of 12 cytoskeletal proteins, alters phosphorylation states of various chaperone proteins and cytoskeletal structural proteins, and presents a more "aggressive" form of cell death than staurosporine induced apoptosis (Gerner et al., 2000). Therefore different cell death inducers have specific physiological characteristics in Jurkat T cells supporting the differences observed. In addition, effector caspases have been demonstrated to be dispensable in chemical induced apoptosis (Johnson et al., 2000).

The initial screening was performed in fibroblasts, and it is therefore unlikely that ICAM-2's anti-apoptotic effect was mediated through its lymphocyte-specific integrin ligand, LFA-1 (CDT 1a/CD18). To address this possibility we prepared an extracellular domain-deleted (ΔN) version of ICAM-2 and tested it in the BaF3 cells. Expression of the cytoplasmic domain was sufficient to impart full anti-apoptotic activity (FIG. 28A). This indicates that the cytoplasmic domain of ICAM-2 provides a survival signal when overexpressed ectopically, and likely exerts its effect by mimicking receptor crosslinking. Since signaling through ICAM-family cytoplasmic domains is poorly understood, we sought to identify the signaling pathway by which it conferred resistance to apoptosis.

The ICAM-2 Survival Function Maps to a Membrane-Cytoskeleton Linker Protein Binding Motif.

ICAM-2 had been regarded as an adhesion molecule and has been shown to be interconnected with the actin cytoskeleton by linker proteins α-actinin and ezrin, which bind the ICAM-2 cytoplasmic domain. (Heiska et al., 1996; Helander et al., 1996). To assess the potential role of α-actinin in mediating the ICAM-2 antiapoptotic signal, the α-actinin recognition sequence was changed to a scrambled sequence unable to bind α-actinin in vitro (Heiska et al., 1996). Retroviral constructs encoding ICAM-2, a C-terminal deletion mutant (ICAM2-ΔC) and a full-length ICAM-2 protein with the mutated α-actinin binding motif (ICAM2-C scrambled) were used to transduce NIH3T3 cells (FIG. 28B). The infected cells were sorted by FACS using an ICAM-2 monoclonal antibody (IC2/2) recognizing only native N-terminal ICAM-2 (de Fougerolles et al., 1991). This verified that ICAM-2, ICAM2-ΔC, or ICAM2-C-scrambled proteins were properly folded and targeted to the outer face of the plasma membrane. The NIH3T3 cells expressing the ICAM-2 mutants were assayed for survival following both etoposide treatment (another potent inducer of apoptosis in NIH3T3 cells) and staurosporine treatment. ICAM-2 imparted potent long-term survival on NIH3T3 cells and the survival signal was lost when the C-terminal deletion of ICAM-2 (ICAM2-ΔC) was expressed in cells (FIG. 28B). Mutation of the α-actinin binding site in the ICAM2 cytoplasmic tail also did not provide any protection against etoposide or staurosporine treatments. Furthermore, both α-actinin and ezrin co-immunoprecipitated only with full length ICAM-2 (FIG. 28C), supporting the postulate that these cytoskeleton linker proteins were necessary to relay an anti-apoptotic signal.

ICAM-2 Signals Through AKT Kinase

As survival signaling through many adhesion molecules involves PI3 kinase (Frisch and Ruoslahti, 1997; Khwaja et al., 1997), we analyzed the role of this pathway in the ICAM-2 anti-apoptotic signal. Pretreatment of ICAM-2 expressing BaF3 cells with the PI3 kinase inhibitor wortmannin blocked the ICAM-2 mediated anti-apoptotic effect (FIG. 29A), implicating PI3 kinase in the ICAM-2 survival signaling cascade. Under these conditions vehicle-treated ICAM-2 expressing BaF3 cells were resistant to staurosporine induced apoptosis. Similarly, treating ICAM-2 transduced NIH3T3 with LY294002 abrogated ICAM-2's anti-apoptotic effect as measured by both annexin-V binding and BrdU TUNEL assay using flow cytometry (FIG. 29A, 29B, and, reviewers see APPENDIX for flow cytometry plots).

PI3 kinase is known to regulate apoptosis through its downstream effector AKT (PKB) kinase (Downward, 1998). AKT kinase has a potent anti-apoptotic effect downstream of diverse apoptotic stimuli, including staurosporine (Made and Downward, 1997) (data not shown). We assayed ICAM-2 expressing fibroblasts for AKT kinase activity. NIH3T3 fibroblasts expressing ICAM-2 showed an elevated level of activated AKT (FIG. 30A). This increase in AKT kinase activity was not seen in ICAM2-ΔC or mock transduced cells. We further verified that this ICAM-2-dependent increase in activated AKT is maintained following STP-treatment using both kinase assays and by verifying phosphorylation of both ser473 and thr308 (FIG. 30A). A target of AKT kinase is the pro-apoptotic BcL2 family member, BAD. BAD is normally held in an inactive state by phosphorylation of serines 112 and 136, and is bound to 14-3-3. Upon induction of apoptosis, BAD is dephosphorylated at both ser112 and ser136, and dimerizes with Bcl-2. As a result, the equilibrium of BcL-2/Bcl-$X_L$ is shifted to favor release of BCL-$X_L$ to mediate Cytochrome C release and apoptosis (Datta et al., 2000). BAD is dephosphorylpted following staurosporine-treatment of ICAM2-ΔC- and mock-transduced NIH3T3 cells, concomitant with the induction of apoptosis (FIG. 30B). However, ICAM-2 expression results in the maintenance of BAD-phosphorylation consistent (FIG. 30B) with sustained AKT kinase activity (FIG. 30A).

BAD has 3 phosphorylation sites, ser112 mediated by active p90Rsk1, ser136 mediated by active AKT, and ser155 mediated by both active PKA and active p90Rsk1. ICAM-2 and its role in connection to BAD ser112 phosphorylation is to be described elsewhere (Perez and Nolan, manuscript in preparation). Phosphorylation of BAD ser155 was not observed (data not shown). Another target of AKT kinase involved in anti-apoptotic signaling, GSK3, was found to be phosphorylated in ICAM-2 expressing NIH3T3 and probably contribute to the anti-apoptotic effect (FIG. 30B, bottom panel). The anti-apoptotic signal had no apparent effects on the anti-apoptotic proteins Bc1-2 and BCl-$X_L$ indicating that typical anti-apoptotic pathways did not mediate the survival signal (FIG. 30C).

ICAM-2 Crosslinking Confirms a Role for Endogenous ICAM-2 in Providing an Anti-Apoptotic Signal This ICAM-2-dependent elevation of activated AKT levels in fibroblasts is independent of ligand interactions as determined by the fact that ICAM-2ΔN can protect cells from apoptosis and ICAM2-ΔC cannot activate AKT. This is indicative of the signaling mechanism driven by oligomerization of surface ICAM-2 molecules, a common modus operandi for adhesion molecules. The surface oligomers create interaction sites within their cytoplasmic domains, recruiting signaling molecules to participate in membrane proximal interactions. Quantitative FACS analysis revealed that the density of ICAM-2 molecules on the cell surface vary widely between cell types (FIG. 30D, and, reviewers see APPENDIX for quantitative methodology; see Experimental Procedures for elaboration) and correlated with varied expression patterns as previously described (de Fougerolles et al., 1991). Basal expression levels of ICAM-2 on lymphocytes was 24 orders of magnitude less than the enforced expression from the retroviral vector as determined by the number of ICAM-2 surface molecules. We therefore decided to test whether endogenous ICAM-2, when cross-linked, could confer the phenotypes observed above.

To test this hypothesis in a physiological setting, we cross-linked (clustered) endogenous pro-B cell ICAM-2 surface molecules with monoclonal antibodies and assayed for activation of AKT kinase activity using GSK3 as a target. We first chose BaF3 cells as these displayed low endogenous ICAM-2 levels (FIG. 30D) and an anti-apoptotic phenotype upon ICAM-2 transduction (FIG. 28A). As shown in FIG. 31A, basal AKT activity is unaffected by incubation with isotype control sera. In contrast, AKT kinase activity increased 3.5-fold with fifteen minutes following addition of anti-ICAM-2 and resulted in the subsequent phosphorylation of BAD ser136, AKT ser473 thr308, and FKHR. This level of AKT kinase activity is congruent with that measured in following IGF-1-treatment of BaF3 cells (A. Bartels and J. B. L., unpublished results). Though the results for AKT-activity were reproducible we were unsatisfied with the western blot analysis and so developed a new procedure for single cell analysis of AKT activity by flow cytometry, described below (Perez and Nolan, submitted, reviewers please see attached manuscript). Cross-linking ICAM-2 on a different cell type, Jurkat T cells, also protected against staurosporine-induced apoptosis as assessed by flow cytometry analysis of annexin-V and propidium iodide staining (FIG. 31B-C). AKT phosphorylation and activation was observed within 15 minutes. Subsequently the AKT targets GSK3 and FKHR were phosphorylated by cross-linking of ICAM-2 in a time dependent manner (FIG. 31D). Incubation with LY294002 abrogated the anti-apoptotic effects initiated by cross-linking ICAM-2 in Jurkat T cells and BaF3 cells (data not shown).

It was of interest to understand if ICAM-2 antibody clustering can initiate a cell survival signal able to overcome the apoptotic machinery after induction of an apoptotic program. To test this, Jurkat T cells were treated with staurosporine for one hour to initiate an apoptotic program and then challenged to survive by ICAM-2 antibody clustering. After 1 hour of staurosporine treatment, hallmarks of apoptosis initiation were evident as detected by cleavage of PARP, cleavage of caspase 9, and cleavage of effector caspases 3 and 7 (FIG. 31E). Interestingly, detection of these cleavage apoptotic indexes decreased as ICAM-2 clustering stimulated AKT activity as a function of time (FIG. 31E-F). This was not observed in cells that were treated with staurosporine but ICAM-2 crosslinked (data not shown). ICAM-2 clustering initiated these hallmark cell survival signals in the presence of the staurosporine induced death signal as detected by increases in AKT phosphorylation and AKT activity. In addition, BAD phosphorylation also followed ICAM-2 clustering in these challenged T cells, demonstrating that activation of the PI3K/AKT pathway is sufficient to override apoptotic paradigms.

Figure 32B:
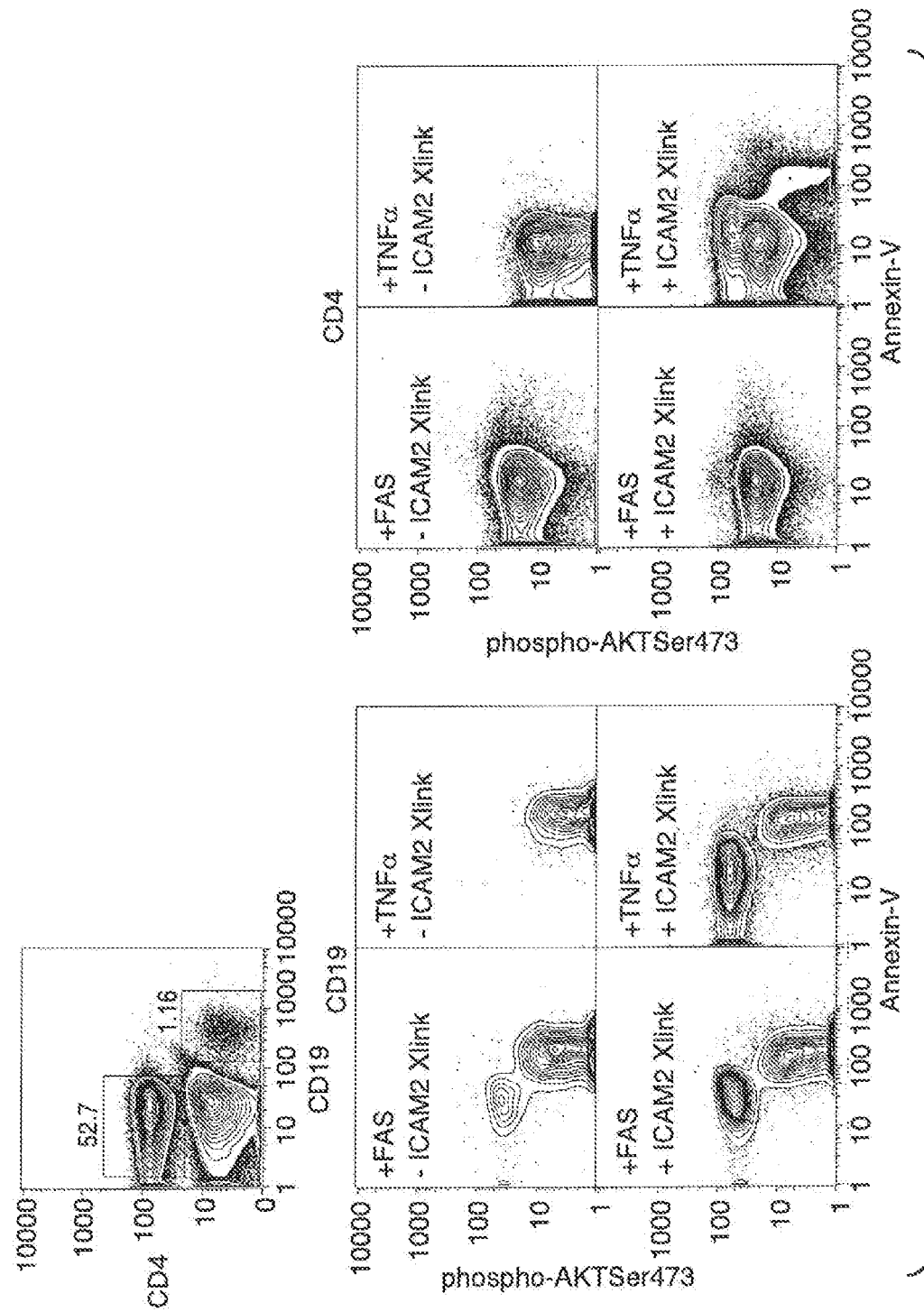

To attribute a physiological relevance to ICAM-2 induced AKT activity in vivo, human PBMC were crosslinked for ICAM-2 prior to treatment with TNFα and anti-Fas monoclonal antibody. Treated PBMC were gated by immunophenotype for CD4 and CD19 and subsequently assayed for AKT activity and apoptosis by muHi-parameter FACS. Intracellular AKT kinase activity measurements were achieved by development of a phospho-specific fluorescent probe for AKT-phospho ser473 phosphorylation site on AKT detectable by FACS (Perez and Nolan, submitted). Both ICAM-2+/CD4+ T cells and ICAM-2+/CD19+ B cells exhibited AKT activity when ICAM-2 was clustered (FIG. 32A). ICAM-2 induced AKT activity protected B cells from apoptosis to Fas and TNF-α induced apoptosis (FIG. 32B). There was little apparent anti-apoptotic effect on CD4+ T cells (FIG. 32B) perhaps due to the fact that these T cells were not strongly induced by Fas or TNF-α to undergo apoptosis with our conditions. Protection from apoptosis in primary B cells correlated perfectly with AKT phosphorylation at serine 473, confirming prior roles for this target serine in the protective effect of AKT against Fas and TNF-α induced apoptosis. Thus, ICAM-2 oligomerization leads to the apparent membrane recruitment of PI3-kinase and subsequent activation of AKT kinase, resulting in a potent inhibition of apoptosis in Jurkat T cells, BaF3 pro-B cells, and human primary T and B cells.

Discussion

A Model for ICAM-2 Mediating a Cell Survival Signal

Our results demonstrate that ectopic expression, or crosslinking of endogenous, ICAM-2 in a wide variety of cell types as well as in and primary CD19+ B cells can initiate a survival signal to cells. ICAM-2 induced AKT activation is a survival signal that can render a cell resistant to chemical (staurosporine and etoposide), and physiological (TNFα and Fas ligand) apoptotic inducers.

ICAM-2 co-immunoprecipitated with both α-actinin and ezrin, demonstrating interactions with critical membrane-cytoskeletal linker proteins. ICAM-2's anti-apoptotic effect was dependent on the 21 amino acid cytoplasmic domain known to bind α-actinin. Notably, α-actinin was shown to interact directly with PI3 kinase through the p85 SH3-domain (Shibasaki et al., 1994). Furthermore, the ICAM-2 cytoplasmic domain binds to members of the ezrin/radixin/moesin (ERM) family of membrane-cytoskeleton linker proteins (Helander et al., 1996). ERM-proteins regulate cell morphology, adhesion and growth by promoting membrane cytoplasmic linkages (Tsukita and Yonemura, 1997) and include the tumor suppressor, merlin/schwannomin, implicated in neurofibroblastomatosis type II. In addition, ezrin and other ERM proteins have been implicated in different diseases for their modulation of adhesion molecule distribution (Ichikawa et al., 1998; Stokowski and Cox, 2000; Turunen et al., 1998; Vinores et al., 1995). Adhesion dependent survival was recently reported to be mediated by ezrin in epithelial cells through a direct interaction with PI3-kinase and pursuant AKT activation (Gautreau et al., 1999). Interestingly, ICAM-2 clustering was induced by errin overexpression (Helander et al., 1996) suggesting that inappropriate surface protein clustering and subsequent signaling can be strongly influenced by ERM proteins. Hence, we propose that the ICAM-2 cytoplasmic domain interacts with membrane-cytoskeletal linker proteins such as α-actinin and/or ezrin, leading to the recruitment and activation of PI3 kinase to the membrane and the subsequent activation of AKT kinase-mediated survival activity.

The PI3K/AKT signaling system is a general mediator of extracellular stimuli, including growth factors, cytokines, as well as adhesion to extracellular matrices (Downward, 1998). The activation of AKT is dependent on phosphorylation at two sites, threonine-308 and serine-473 (Downward, 1998). The amino terminus of AKT contains a pleckstrin homology domain that is thought to bind directly to phospholipid products of PI3K. This binding recruits AKT to the membrane that has been proposed to induce a conformational change allowing phosphorylation at threonine-308 and serine-473 by PDKI and PDKII respectively (Alessi et al., 1996). Dually phosphorylated AKT is then active and can phosphorylate a number of downstream effectors. Another mode by which AKT is thought to inhibit cell death is by preventing release of cytochrome C from mitochondria (Kennedy et al., 1999). Activation of AKT kinase induced by ICAM-2 clustering resulted in activation of several downstream effectors as detected by phosphorylation of BAD, GSK3, FKHR and AFX. Phosphorylation of BAD at ser-136 results in binding to 14-3-3 instead of BCL-$X_L$ (Zha et al., 1996), shifting the equilibrium of Bcl-2 family members to favor cell survival. GSK3 activity has been shown to be necessary for apoptosis resulting from PI3K inhibition (Pap and Cooper, 1998). Phosphorylation of GSK3 inhibits its activity and therefore would present an anti-apoptotic signal. Phosphorylation of FKHR inhibits its ability to translocate to the nucleus and initiate FKHR-dependent transcription. Within the nucleus, dephosphorylated FKHR can induce target genes such as Fas ligand in certain cells and trigger apoptosis (Brunet et al., 1999). Phosphorylation of AFX inhibits transcriptional activation of p27, a cell cycle inhibitor (Graff et al., 2000). In addition, AKT has the ability to phosphorylate and inactivate caspase 9 (human caspase 9), phosphorylate eNOS (endothelial cells) and promote angiogenesis of vascular endothelium, and potentially other substrates (Cardone et al., 1998; Kureishi et al., 2000). AKT hyperactivity has been observed in a number of disorders (Haas-Kogan et al., 1998) (Kulik et al., 1997; Shan et al., 2000; Wick et al., 1999). All these data support the notion that ICAM-2 activation would be expected to lead to an extremely powerful anti-apoptotic signal in cells. A model of ICAM2's interaction with the PI3K/AKT pathway is depicted in FIG. 32C.

The anti-apoptotic effects mediated by ICAM-2 overexpression and by ICAM-2 clustering suggest that inappropriate ICAM-2 expression contributes an anti-apoptotic phenotype. As an adhesion molecule, ICAM-2 has been attributed a role in lymphocyte recirculation and through interactions with its receptor LFA-1, a role in enhancing and stabilizing T-cell:B-cell contact (Damle et al., 1992; Douglas et al., 2000). Here, we suggest that in addition to possessing adhesion molecule properties, ICAM-2 is capable of transmitting an intracellular signal when it is clustered on the cell surface. The significance of ICAM-2 clustering, by virtue of its overexpression in a cancer or by receptor-mediated engagement, could lead to survival in cells otherwise destined to die by apoptosis. This could lead to tumor drug resistance and cytoproliferative disorders such as B-cell chronic lymphatic leukemia (B-CLL). For instance, it was reported that ICAM-2 is highly expressed on CD5+ B cells from B-CLL patients (Molica et al., 1996) and on large B-cell lymphomas derived from patients (Alizadeh et al., 2000) indicating that ICAM-2 or other adhesion molecules may have a role in certain classes of leukemias. In normal cells, ICAM-2 mediated PI3K activation may likely regulate the endothelial transmigration of eosinophils (Gerwin et al., 1999), and potentially dendritic cells (via DC-SIGN) (Geijtenbeek et al., 2000).

Our results illustrate that ICAM-2 overexpression and clustering can provide an, anti-apoptotic signal in B cells rendering them resistant to physiological death 2 programs induced by TNFα and Fas ligand. Notably ICAM-2 expression is upregulated in many tissue culture cell lines in comparison to their normal counterparts, suggesting that cells in an ex vivo context need to initiate cell survival programs (de Fougerolles et al., 1991). The work presented herein attributes a previously unrecognized function for ICAM-2. The finding that ICAM-2 can exert cell survival signaling, ectopically and endogenously, as well as elicit an anti-apoptotic phenotype in a variety of cell lines and human primary cells suggests that deregulation or induced clustering is likely to contribute significantly to the anti-apoptotic phenotype that leads to tumor progression. Thus, pathways involved in the regulation of ICAM-2 expression and distribution or other adhesion molecules could be important in the development of anti-tumor therapies.

Experimental Procedures
Retroviral cDNA Screening

Production and infection of retroviruses was carried out as described (Kitamura et al., 1995; Onishi et al., 1996; Rayner and Gonda, 1994). A cDNA library was prepared from Jurkat T cells in the pBabe-S vector (Hitoshi et al., 1998). The library ($2\times10^6$ primary transformants) was used to transfect $\sim10^7$ PHOENIX-E packaging cells. The pBMN-LacZ control vector was spiked into the library at 1:10 to monitor the transfection/infection efficiency. Viral supernatants were harvested and used to infect $\sim10^7$ exponentially growing NIH3T3 cells; 48 hours post infection the cells were split and analyzed for β-galactosidase activity. The literary transduced NIH3T3 cells were plated at ~25% confluency; 24 hours later the medium was replaced with DMEM containing 1 μM staurosporine (STP; Sigma, St. Louis Mo.). After 24 hours treatment the STP-containing medium was replaced with complete DMEM/10% donor bovine serum. Surviving cells were allowed to reach ~80% confluency (7 days). Survivor cells were retreated as described two additional rounds.
phenotypic transfer assay An aliquot of the surviving library-infected cells were super-infected with Moloney Murine Leukemia Virus (gift of T. Kinsella, Stanford). Super-infected cells were passaged for two-weeks to allow efficient spread of the helper virus. Naive NIH3T3 cells were infected with viral supernatants and allowed to express for 48 hours. Re-infected cells were then treated with staurosporine as described above. Surviving cells were cultured for 7 days and analyzed for transfer by RT PCR.
RT-PCR Cloning of Provirap-cDNA Inserts and Construct Generation RNA was prepared by the acid-guanidium-phenol-chloroform method as described (Chomczynski and Sacchi, 1987). cDNA was prepared from 4 μg heat-denatured total RNA in a 50 μl reaction volume (Promega, Madison, Wis.) and incubated at 42° C. and 55° C. for 45 minutes. The cDNA reaction products (5 μl) were amplified (primers: 5'-GATCCTCCCT-TATCCAG (SEQ ID NO: 02); 5'GAATGAAAGACCCCAC-CTGT (SEQ ID NO: 03)) in a 50 μl PCR reaction mix (Perkin-Elmer, Foster City, Calif.) at 95° C./30 sec; 55° C./60 sec; 72° C/2 min for 25 cycles. Full length ICAM2 cDNA was cloned into retroviral vector PBM-Z-IN backbone (Kinoshita et al., 1998) at BamHI/Sal1 site. ICAM2-ΔC, ICAM2-ΔN and ICAM2-C-terminal scrambled were generated by PCR and cloned into the BamHI/Sal1 site.
Cell Culture and Preparation of Primary Cells NIH3T3 murine fibroblast were maintained in DMEM, 10% DCS, 1% PSQ (Duelbecco Modified Eagle Media, 10% Donar calf serum, 1% penicilli nstreptomycin (1000 units/ml and 2 mM L-glutamine PSQ). Jurkat T-cells and CH27 transformed B-cells were maintained in RPMI-1640, 10% FCS, 1% PSQ. BaF3 pro-B-cells were maintained in RPMk1640, 10% FCS, 1% PSQ, 400 U/ml IL-3 (Peprotech). 70Z/3 pre-B-cells were maintained in RPMI-1640, 10% FCS, 1% PSQ, 50 μm β-mercaptoethanol. HL60 myeloid leukemia cells were maintained in Opti-Mem 1,10% FCS, 1% PSQ. 293T human fibroblast cells were maintained in DMEM, 10% FCS, 1% PSQ. Cells were maintained at 5% $CO_2$/37° C. humidified incubator. Transduced cells were maintained in 500 μg/ml G418 (Sigma) and proper expression of construct was verified by western blots and FACS analysis of full length ICAM-2, ICAM-2ΔC, ICAM-ΔN as indicated. Staurosporine (Sigma) treatment was for 24 hrs at 1 μM (unless otherwise indicated). LY294002 (New England Biolabs) treatment was at 10 μm 30 minutes before any subsequent treatment. Wortmannin (Sigma) treatment was for 24 hrs at 100 nM. Chemicals were dissolved in DMSO (final being 1:1000 for solvent dilution) and vector controls were incubated with 1% DMSO as negative control. Vector controls consisted of pBMN-Z-IN (empty vector) transduction or pBMN-Z-IN-GFP (http://www.stanford.edu/group/nolan/plasmid_maps/pmaps.html) as indicated. The infection frequency of pBMN-Z-IN-GFP was 48%±10 for three independent viral transductions. Continual neomycin selection yielded homogenous ICAM-2, ICAM2-ΔC, ICAM2-ΔN, or control vector populations as routinely monitored by flow cytometry for protein expression. For preparation of primary cells, mononuclear cells were isolated from human peripheral blood by Ficoll-plaque density centrifugation and depletion of adherent cells on adherent plastic culture dishes. Isolated cells were maintained in complete media and analyzed by FACS for CD4, CD3, CD19, and ICAM-2 expression.

Cross-Linking

Antibody cross-linking experiments were performed using a mouse monoclonal anti-ICAM-2 that recognizes the N-terminal region (extracellular domain) at 10 µg/ml. Spin dialysis (Biorad) was used for buffer exchange of azide containing antibodies (0.01%) to phosphate buffered saline buffer pH 7.4. Anti-mouse IgG (Sigma) was used as a control antibody in cross-linking experiments. $10^6$ Jurkat or BaF3 cells were serum starved for 3 hours or 4 hours respectively. Cells were incubated with either ICAM-2 (10 µg/ml) or mouse IgG (10 µg/ml) at 37° C. for the indicated time. Time points began post serum starvation to attenuate most of the signaling pathways or as indicated. Serum starvation of 3 or 4 hrs lacked biochemical initiations of apoptosis as tested by caspase 3 activity, cell cycle analysis, annexin V/PI staining (data not shown). Cells extracts were taken and subjected to either immunoprecipitation or immunoblotting. ICAM-2 clustering of primary human cells was performed using anti-human ICAM-2 (IC2/2 Research Diagnostics) conjugated to FITC. The pursuant staining for ICAM-2 resulted in ICAM-2 clustering and signal transduction.

Apoptosis Assays

Apoptosis was determined either by counting pyknotic nuclei, annexin-V binding by flow cytometry, or TUNEL BrdU staining by flow cytometry as indicated. Apoptosis was induced either by staurosporine (11 lm), treatment with anti-mouse Fas (5 µg/ml Santa Cruz Biotechnology (SCB), anti-human Fas (5 µg/ml Jo2 Biomed) or anti-human Fas (10 ng/ml CH11 Kamiya Biomedical) as indicated in appropriate experiment, IL-3 withdrawal (24 hrs) or as indicated. For pyknotic nuclei count, NIH3T3 cells were grown on glass coverslips and assayed for apoptosis. Suspension cells were analyzed by nuclear staining with 25 µM acridine orange/25 µm ethidium bromide or 5 µg/ml Hoechst 33342 (Molecular Probes, Eugene, Oreg.). Apoptosis was identified by the presence of characteristic pyknotic nuclei as described (Jacobson and Raff, 1995). At least 5 individual fields were photographed and counted using a Zeiss axioscope fluorescence microscope. For the survival assay $10^6$ NIH3T3 cells were plated in 10 cm dishes and incubated overnight at 37° C. The cells were treated with 1 µM staurosporine for 24 hours. The cells were washed and cultured for 24 hours in complete medium. The cells were trypsinized and viable cells counted following trypan blue staining. Untreated cells were counted at the time of treatment. % survival represents (number of viable cells post-treatment)/(number of viable cells pretreatment). FACS based annexin-V-FITC(SCB)/PI (Clontech) staining was done as described (PharMingen). TUNEL assay was performed as described by manufacturer of Apoptosis BrdU kit (Promega). Flow cytometry data acquisition was performed 24 post staurosporine treatment (1 µM) for both BrdU (10,000 events collected) and pyknotic nuclei count and 12 hr post-staurosporine treatment for annexin V binding (100,000 events collected). Annexin-V positive cells will have compromised membranes after 24 hr treatment. Flow cytometry analysis was performed on a BD FACSCalibur machine with CELLQuest and analyzed using FlowJo software (Tree Star).

AKT Kinase Assays

AKT activity was detected by immunoprecipitation of AKT1 from cells and used in a kinase assay with GSK3 fusion protein (NEB). $2 \times 10^6$ NIH3T3, $2 \times 10^6$ Jurkat, or $5 \times 10^5$ BaF3 cells were incubated with immobilized AKT 1G1 monoclonal antibody (mAb) (1:200, NEB) at 4° C. with gentle rocking motion for 2 hrs. Immunocomplexes were washed 4× with cell lysis buffer and resuspended in 40 µl kinase buffer (25 mM Tris pH 7.5, 5 mM β-glycerolphosphate, 2 mM DTT, 0.1 mM $Na_3VO_4$, 10 mM $MgCl_2$) supplemented with 200 µM ATP and 1 µg of GSK-3 fusion protein (NEB) for 30 min at 30° C. Kinase reaction was terminated with SDS sample buffer boiled for 5 min, and phosphorylation state of GS3K was detected by immunoblotting and visualized using ECL detection (Amersham). Immunoblots are representative of 3 independent virally transduced cell populations each repeated 3 times (n=9). AKT activity was verified by AKT phosphorylation by immunoblotting with phospho-specific antibodies to ser473 and thr308 (NEB).

Immunoprecipitations and Immunoblotting

Cell extracts were prepared by washing $2 \times 10^6$ cells in ice cold PBS and harvesting in lysis buffer (20 mM Tris pH 7.5, 150 mM NaCl 1 mM EDTA 1 mM EGTA, 1% Triton X-100, 2.5 mM $Na_2PO_4$, 1 mM β-glycerolphosphate, 1 mM $Na_3VO_4$, 1 µg/ml Leupeptin, 1 mM PMSF, protease inhibitor cocktail tablet (Boehringer Mannheim)). Extracts were centrifuged 14,000 RPM for 5 min at $4^C$ and cell lysates (20 µg as determine by BCA protein assay (Pierce)) were fractionated on 12% or 15% SDS-polyacrylamide gel electrophoresis and transferred to PVDF membranes using standard procedures. Immunoprecipitations were pre-cleared with protein A/G plus-agarose beads (SBC). IP was incubated for 1 hr or overnight with primary antibody, 1 hr with protein N/G plus-agarose beads and washed 4× with lysis buffer. Blots were incubated with the following antibodies: ICAM2 N-terminal (1:500 SBC), anti-ICAM2 C-terminal (1:500 SBC), anti-ICAM2 IC2/2 mAb (1:500 BD Biosciences), anti-α-actinin (1:500 SBC), anti-ezrin mAb (1:500 Transduction Laboratories), anti-Bcl2 (1:500 SBC), anti-p27 (1:1000 SBC), anti-p21 (1:500 SBC), anti-cFLIP (1:500 SBC), anti-phospho-AKT-ser473 (1:1000 NEB), antiphospho-AKT-thr308 (1:1000 NEB), anti-AKT (1:1000 NEB), anti-phosphoBAD-ser155 (1:1000 NEB), anti-FKHR (1:1000 wb, 1:200 IP NEB), anti-phospho FKHR (1:1000 NEB), anti-phospho-Gsk3 α/021 (1:500, NEB), anti-cleaved PARP (1:1000 NEB), anti-cleaved caspase 9 (1:1000 NEB), anti-cleaved caspase 3 (1:1000 NEB), anti-cleaved caspase 7 (1:1000 NEB), anti-pAFX (1:1000 NEB), anti-caspase 9 (1:1000 NEB), anti-caspase 7 (1:1000 NEB), anti-PARP (1:1000 NEB). BAD phosphorylation was determined by immunoprecipitating total BAD (1:200 NEB) and immunoblotting with anti-BAD-ser112 (1:1000 NEB) and antiBADser136 (1:1000 NEB) as recommended by manufacturer of BAD phosphorylation detection kit (NEB). Secondary antibodies used: anti-rabbit HRP (1:5000 NEB), anti-mouse HRP or anti-goat HRP 1:5000, SBC) and visualized using ECL detection (Amersham) or with a Kodak Digital Science 440C station. Blots are representative of at least 3 independent experiments.

Flow Cytometry and FACS Analysis

Intracellular and extracellular staining was performed as described www(dot)metazoa(dot)com\UPL3287). Antibodies used: anti-ICAM2 N-terminal (SBC), anti-ICAM2 Nterminal (SBC), anti-ICAM2-FITC mAb (BD Biosciecnes/Fisher), annexin-V-FITC (BD 35 Biosciences), annexin-V-biotin (SBC), PI (Clonetech). Secondaries used: anti-rabbit PE (BD Biosciences), anti-mouse-FITC (BD Biosciences), anti-rabbit FITC (PharMingen), anti-goat FITC (BD Biosciences), anti-goat texas red (BD Biosciences), Streptavidin-PE (BD Biosciences), streptavidin-FITC (BD Biosciences), anti-human CD4-APC (PharMingen), anti-human CD19-PerCP (PharMingen), anti-human ICAM-2-FITC (Research Diagnostics IC212) Intracellular probe for AKT activity was made by conjugating monoclonal anti-AKTser473 antibody (Cell Signaling Technology) to ALEXA FLUOR® 568 dye (Molecular Probes), using ALEXA FLUOR® 568 protein conjugation kit (Molecular Probes). Phospho specificity was tested by western blotting and FACS analysis to a variety of P13K activators and inhibitors (data not shown), Intracellular staining by phospho-AKTser473 ALEXA FLUOR® 568 reflected AKT kinase activity when NIH3T3 cells were stimulated with platelet derived growth factor (Sigma) and inhibited by LY294002 prior to stimulation. Quantitative FACS analysis was performed as described (Davis et al., 1998; Iyer et al., 1998; Lenkei et al., 1998). In brief, R-phycoerythrin (PE) (Molecular Probes) was conjugated to a anti-ICAM2 N-terminal monoclonal antibody (Research Diagnostics IC2/2) as suggested by manufacturer of protein cross-linking kit (Molecular Probes), tested for proper stochiometry (data not shown) and quantitated using Quantibrite™-PE beads (BD systems). A quantitative calibration curve was generated using Quantibrite™-PE beads that contain a known amount of PE molecule/bead.

A linear regression analysis is performed using the following equation: $\log_{10}(PE\ fluorescence) = slope * \log_{10}(PE\ molecules/bead) + intercept$. PE fluorescence is determined by taking the geometric mean of the PE channel. Quantitation is valid only for antibodies directly conjugated to PK. Using saturating amounts of antibody and thorough washing ensures all surface antigens are bound. Preparation of samples on ice reduces antibody internalization. Surface antigens of cells for an unknown cell population are determined by computing the PE geometric mean using the calibration curve. Quantitative FACS analysis provides approximate estimates for surface antigen expression. Numbers plotted represent relative surface molecules and not absolute numbers since antibody valency was not investigated for the monoclonal antibodies used. Flow cytometry analysis was performed on a BD FACSCalibur machine and analyzed using FlowJo software (Tree Star). CellQuest was used for quantitative flow cytometry and linear regression analysis of Quantibrite-PE beads. Flow cytometry data are representative of 3 independent experiments of $10^6$ cells/sample analyzed. 100,000 events were collected or otherwise noted and calibrated using Calibrite beads (BD systems). Data plotted in bar graph format is expressed as the mean (bar)±SD of triplicate experiments.

References

Alessi, D. R., Andjelkovic, M., Caudwell, B., Cron, P., Morrice, N., Cohen, P., and Hemmings, B. A. (1996). Mechanism of activation of protein kinase B by insulin and IGF-1. Embo J 15, 6541-51.

Alizadeh, A. A., Eisen, M. B., Davis, R. E., Ma, C., Lossos, I. S., Rosenwald, A., Boldrick, J. C., Sabet, H., Tran, T., Yu, X., Powell, J. I., Yang, L., Marti, G. E., Moore, T., Hudson, J., Jr., Lu, L., Lewis, D. B., Tibshirani, R., Sherlock, G., Chan, W. C., Greiner, T. C., Weisenburger, D. D., Armitage, J. O., Warnke, R., Staudt, L. M., and et al. (2000). Distinct types of diffuse large B-cell lymphoma identified by gene expression profiling. Nature 403, 503-11.

Brunet, A., Bonni, A., Zigmond, M. J., Lin, M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell 96, 857-68.

Budihardjo, I., Oliver, H., Lutter, M., Luo, X., and Wang, X. (1999). Biochemical pathways of caspase activation during apoptosis. Annu Rev Cell Dev Biol 15, 269-90.

Cardone, M. H., Roy, N., Stennicke, H. R., Salvesen, G. S., Franke, T. F., Stanbridge, E., Frisch, S., and Reed, J. C. (1998). Regulation of cell death protease caspase-9 by phosphorylation. Science 282, 1318-21.

Chomczynski, P., and Sacchi, N. (1987). Single-step method of RNA isolation by acid guanidinium thiocyanate-phenol-chloroform extraction. Anal Biochem 162, 156-9.

Damle, N. K., Klussman, K., and Aruffo, A. (1992). Intercellular adhesion molecule-2, a second counter-receptor for CD11a/CD18 (leukocyte function-associated antigen-1), provides a costimulatory signal for T-cell receptor-initiated activation of human T cells. J Immunol 148, 665-71.

Datta, S. R., Katsov, A., Hu, L., Petros, A., Fesik, S. W., Yaffe, M. B., and Greenberg, M. E. (2000). 14-3-3 proteins and survival kineses cooperate to inactivate BAD by BH3 domain phosphorylation. Mol Cell 6, 41-51.

Davis, K. A., Abrams, B., Iyer, S. B., Hoffman, R. A., and Bishop, J. E. (1998). Determination of CD4 antigen density on cells: role of antibody valency, avidity, clones, and conjugation. Cytometry 33, 197-205.

de Fougerolles, A. R., Chi-Rosso, G., Bajardi, A., Gotwals, P., Green, C. D., and Koteliansky, V. E. (2000). Global expression analysis of extracellular matrix-integrin interactions in monocytes. Immunity 13, 749-58.

de Fougerolles, A. R., Stacker, S. A., Schwarting, R., and Springer, T. A. (1991). Characterization of ICAM-2 and evidence for a third counter-receptor for LFA-1. J Exp Med 174, 253-67.

Diacovo, T. G., deFougerolles, A. R., Bainton, D. F., and Springer, T. A. (1994). A functional integrin ligand on the surface of platelets: intercellular adhesion molecule-2. J Clin Invest 94, 1243-51.

Dion, F., Mes-Masson, A. M., Seymour, R. J., Provencher, D., and Tonin, P. N. (2000). Allelotyping defines minimal imbalance at chromosomal region 17q25 in non-serous epithelial ovarian cancers. Oncogene 19, 1466-72.

Dobo, K. L., Giver, C. R., Eastmond, D. A., Rumbos, H. S., and Grosovsky, A. J. (1995). Extensive loss of heterozygosity accounts for differential mutation rate on chromosome 17q in human lymphoblasts. Mutagenesis 10, 53-8.

Douglas, I. S., Leff, A. R., and Sperling, A. I. (2000). CD4+ T cell and eosinophil adhesion is mediated by specific ICAM-3 ligation and results in eosinophil activation. J Immunol 164, 3385-91.

Downward, J. (1998). Mechanisms and consequences of activation of protein kinase B/Akt. Curr Opin Cell Biol 10, 262-7.

Earnshaw, W. C., Martins, L. M., and Kaufmann, S. H. (1999). Mammalian caspases: structure, activation, substrates, and functions during apoptosis. Annu Rev Biochem 68, 383-424.

Frisch, S. M., and Ruoslahti, E. (1997). Integrins and anolkis. Curr Opin Cell Biol 9, 701-6.

Gautreau, A., Poullet, P., Louvard, D., and Arpin, M. (1999). Ezrin, a plasma membrane-microfilament linker, signals cell survival through the phosphatidylinositol 3-kinase/Akt pathway. Proc Natl Acad Sci USA 96, 7300-5.

Geijtenbeek, T. B., Krooshoop, D. J., Bleijs, D. A., van Vliet, S. J., van Duijnhoven, G. C., Grabovsky, V., Alon, R., Figdor, C. G., and van Kooyk, Y. (2000). DC-SIGN-ICAM-2 interaction mediates dendritic cell trafficking. Nat Immunol 1, 353-7.

Gerner, C., Frohwein, U., Gotzmann, J., Bayer, E., Gelbmann, D., Bursch, W., and Schulte-Hermann, R. (2000). The Fas-induced apoptosis analyzed by high throughput proteome analysis. J Biol Chem 275, 39018-26.

Gerwin, N., Gonzalo, J. A., Lloyd, C., Coyle, A. J., Reiss, Y., Banu, N., Wang, B., Xu, H., Avraham, H., Engelhardt, B., Springer, T. A., and Gutierrez-Ramos, J. C. (1999). Prolonged eosinophil accumulation in allergic lung interstitium of ICAM-2 deficient mice results in extended hyper-responsiveness. Immunity 10, 919.

Gottlieb, R. A. (2000). Mitochondria: execution central. FEBS Lett 482, 6-12.

Graff, J. R., Konicek, B. W., McNulty, A. M., Wang, Z., Houck, K., Allen, S., Paul, J. D., Hbaiu, A., Goode, R. G., Sandusky, G. E., Vessella, R. L., and Neubauer, B. L. (2000). Increased AKT activity contributes to prostate cancer progression by dramatically accelerating prostate tumor growth and diminishing p27Kip1 expression. J Biol Chem 275, 24500-5.

Grutter, M. G. (2000). Caspases: key players in programmed cell death. Curr Opin Struct Biol 10, 649-55.

Haas-Kogan, D., Shalev, N., Wong, M., Mills, G., Yount, G., and Stokoe, D. (1998). Protein kinase B (PKB/Akt) activity is elevated in glioblastoma cells due to mutation of the tumor suppressor PTEN/MMAC. Curr Biol 8, 1195-8.

Heiska, L., Kantor, C., Parr, T., Critchley, D. R., Villa, P., Gahmberg, C. G., and Carpen, O. (1996). Binding of the cytoplasmic domain of intercellular adhesion molecule-2 (ICAM-2) to alpha-actinin. J Biol Chem 271, 26214-9.

Helander, T. S., Carpen, O., Turunen, O., Kovanen, P. E., Vaheri, A., and Timonen, T. (1996). ICAM-2 redistributed by ezrin as a target for killer cells. Nature 382, 265-8.

Hitoshi, Y., Lorens, J., Kitada, S. I., Fisher, J., LaBarge, M., Ring, H. Z., Francke, U., Reed, J. C., Kinoshita, S., and Nolan, G. P. (1998). Toso, a cell surface, specific regulator of Fas-induced apoptosis in T cells. Immunity 8, 461-71.

Holmstrom, T. H., and Eriksson, J. E. (2000). Phosphorylation-Based signaling in Fas receptor-mediated apoptosis. Crit Rev Immunol 20, 121-52.

Hulleman, E., and Boonstra, J. (2001). Regulation of G1 phase progression by growth factors and the extracellular matrix. Cell Mol Life Sci 58, 80-93.

Ichikawa, T., Masumoto, J., Kaneko, M., Saida, T., Sagara, J., and Taniguchi, S. (1998). Expression of moesin and its associated molecule CD44 in epithelial skin tumors. J Cutan Pathol 25, 237-43.

Iyer, S. B., Hultin, L. E., Zawadzki, J. A., Davis, K. A., and Giorgi, J. V. (1998). Quantitation of CD38 expression using QuantiBRITE beads. Cytometry 33, 206-12.

Jacobson, M. D., and Raff, M. C. (1995). Programmed cell death and Bcl-2 protection in very low oxygen. Nature 374, 814-6.

Johnson, V. L., Ko, S. C., Holmstrom, T. H., Eriksson, J. E., and Chow, S. C. (2000). Effector caspases are dispensable for the early nuclear morphological changes during chemical-induced apoptosis. J Cell Sci 113, 2941-53.

Kennedy, S. G., Kandel, E. S., Cross, T. K., and Hay, N. (1999). Akt/Protein kinase B inhibits cell death by preventing the release of cytochrome c from mitochondria. Mol Cell Biol 19, 5800-10.

Khwaja, A., Rodriguez-Viciana, P., Wennstrom, S., Warne, P. H., and Downward, J. (1997). Matrix adhesion and Ras transformation both activate a phosphoinositide 3-OH kinase and protein kinase B/Akt cellular survival pathway. Embo J 16, 2783-93.

Kitamura, T., Onishi, M., Kinoshita, S., Shibuya, A., Miyajima, A., and Nolan, G. P. (1995). Efficient screening of retroviral cDNA expression libraries. Proc Natl Acad Sci USA 92, 9146-50.

Kroemer, G. (1999). Mitochondrial control of apoptosis: an overview. Biochem Soc Symp 66, 1-15.

Kruidering, M., and Evan, G. I. (2000). Caspase-8 in apoptosis: the beginning of "the end"? IUBMB Life 50, 85-90.

Kuida, K. (2000). Caspase-9. Int J Biochem Cell Biol 32, 121-4.

Kulik, G., Klippel, A., and Weber, M. J. (1997). Antiapoptotic signalling by the insulin-like growth factor I receptor, phosphatidylinositol 3-kinase, and Akt. Mol Cell Biol 17, 1595-606.

Kureishi, Y., Luo, Z., Shiojima, I., Bialik, A., Fulton, D., Lefer, D. J., Sessa, W. C., and Walsh, K. (2000). The HMG-CoA reductase inhibitor simvastatin activates the protein kinase Akt and promotes angiogenesis in normocholesterolemic animals. Nat Med 6, 1004-10.

Lenkei, R., Gratama, J. W., Rothe, G., Schmitz, G., D'Hautcourt J, L., Arekrans, A., Mandy, F., and Marti; G. (1998). Performance of calibration standards for antigen quantitation with flow cytometry. Cytometry 33, 188-96.

Marte, B. M., and Downward, J. (1997). PKB/Akt: connecting phosphoinositide 3-kinase to cell survival and beyond. Trends Biochem Sci 22, 355-8.

Molica, S., Dattilo, A., Mannella, A., and Levato, D. (1996). Intercellular adhesion molecules (ICAMs) 2 and 3 are frequently expressed in B cell chronic lymphocytic leukemia. Leukemia 10, 907-8.

Nortamo, P., Salcedo, R., Timonen, T., Patarroyo, M., and Gahmberg, C. G. (1991). A monoclonal antibody to the human leukocyte adhesion molecule intercellular adhesion molecule-2. Cellular distribution and molecular characterization of the antigen. J Immunol 146, 2530-5.

Onishi, M., Kinoshita, S., Morikawa, Y., Shibuya, A., Phillips, J., Lanier, L. L., Gorman, D. M., Nolan, G. P., Miyajima, A., and Kitamura, T. (1996). Applications of retrovirus-mediated expression cloning. Exp Hematol 24, 324-9.

Pap, M., and Cooper, G. M. (1998). Role of glycogen synthase kinase-3 in the phosphatidylinositol 3-Kinase/Akt cell survival pathway. J Biol Chem 273, 1992-932.

Perez, O. D., and Nolan, G. P. (2001). Functional signaling analysis in single cells: Simultaneous measurement of multiple kinase activities using polychromatic flow cytometry. Submitted.

Raff, M. C. (1992). Social controls on cell survival and cell death. Nature 356, 397-400.

Rath, P. C., and Aggarwal, B. B. (1999). TNF-induced signaling in apoptosis. J Clin Immunol 19, 350-64.

Rayner, J. R., and Gonda, T. J. (1994). A simple and efficient procedure for generating stable expression libraries by cDNA cloning in a retroviral vector. Mol Cell Biol 14, 880-7.

Renkonen, R., Paavonen, T., Nortamo, P., and Gahmberg, C. G. (1992). Expression of endothelial adhesion molecules in vivo. Increased endothelial ICAM-2 expression in lymphoid malignancies. Am J Pathol 140, 763-7.

Ruoslahti, E., and Reed, J. C. (1994). Anchorage dependence, integrins, and apoptosis. Cell 77, 477-8.

Russell, S. E., McIlhatton, M. A., Burrows, J. F., Donaghy, P. G., Chanduloy, S., Petty, E. M., Kalikin, L. M., Church, S. W., McIlroy, S., Harkin, D. P., Keilty, G W., Cranston, A. N., Weissenbach, J., Hickey, I., and Johnston, P. G. (2000). Isolation and mapping of a human septin gene to a region on chromosome 17q, commonly deleted in sporadic epithelial ovarian tumors. Cancer Res 60, 4729-34.

Sansom, D., Borrow, J., Solomon, E., and Trowsdale, J. (1991). The human ICAM2 gene maps to 17q23-25. Genomics 11, 462-4.

Schneider, P., and Tschopp, J. (2000). Apoptosis induced by death receptors. Pharm Acta Helv 74, 281-6.

Schneller, M. (2001). Identification of a candidate integrin-faction associated with the activated form of the PDGF-receptor. Biochem Biophys Res Commun 281, 595-602.

Shan, X., Czar, M. J., Bunnell, S. C., Liu, P., Liu, Y., Schwartzberg, P. L., and Wange, R. L. (2000). Deficiency of PTEN in Jurkat T cells causes constitutive localization of Itk to the plasma membrane and hyperresponsiveness to CD3 stimulation. Mol Cell Biol 20, 6945-57.

Shibasaki, F., Fukami, K, Fukui, Y., and Takenawa, T. (1994). Phosphatidylinositol 3-kinase binds to alpha-actinin through the p85 subunit. Biochem J 302, 551-7.

Shinohara, M., Kodama, A., Matozaki, T., Fukuhara, A., Tachi bane, K., Nakanishi, H., and Takai, Y. (2001). Roles of cell-cell adhesion-dependent tyrosine phosphorylation of Gab-1. J Biol Chem 21, 21.

Simmons, D. L. (1995). The role of ICAM expression in immunity and disease. Cancer Surv 24, 141-55.

Staunton, D. E., Dustin, M. L., and Springer, T. A. (1989). Functional cloning of ICAM-2, a cell adhesion ligand for LFA-1 homologous to ICAM-1. Nature 339, 61-4.

Stokowski, R. P., and Cox, D. R. (2000). Functional analysis of the neurofibromatosis type 2 protein by means of disease-causing point mutations. Am J Hum Genet. 66, 873-91.

Stolzenberg, I., Wulf, S., Mannherz, H. G., and Paddenberg, R. (2000). Different sublines of Jurkat cells respond with varying susceptibility of internucleosomal DNA degradation to different mediators of apoptosis. Cell Tissue Res 301, 273-82.

Sugai, T., Habano, W., Nakamura, S., Sato, H., Uesugi, N., Orli, S., Itoh, C., and Katoh, R. (2000). Allelic losses of 17p, 5q and 18q loci in diploid and aneuploid populations of multiploid colorectal carcinomas. Hum Pathol 31, 925-30.

Tsukita, S., and Yonemura, S. (1997). ERM proteins: head-to-tail regulation of actin-plasma membrane interaction. Trends Biochem Sci 22, 53-8.

Turunen, O., Sainio, M., Jaaskelainen, J., Carpen, O., and Vaheri, A. (1998). Structure-function relationships in the ezrin family and the effect of tumor-associated point mutations in neurofibromatosis 2 protein. Biochim Biophys Acta 1387, 1-16.

van Kooyk, Y., and Figdor, C. G. (2000). Avidity regulation of integrins: the driving force in leukocyte adhesion. Curr Opin Cell Biol 12, 542-7.

Vinores, S. A., Henderer, J. D., Mahlow, J., Chiu, C., Derev-janik, N. L., Larochelle, W., Csaky, C., and Campochiaro, P. A. (1995). Isoforms of platelet-derived growth factor and its receptors in epiretinal membranes: immunolocalization to retinal pigmented epithelial cells. Exp Eye Res 60, 607-19.

Wick, W., Furnari, F. B., Naumann, U., Cavenee, W. K., and Weller, M. (1999). PTEN gene transfer in human malignant glioma: sensitization to irradiation and CD95L-induced apoptosis. Oncogene 18, 3936-43.

Zha, J., Harada, H., Yang, E., Jockel, J., and Korsmeyer, S. J. (1996). Serine phosphorylation of death agonist BAD in response to survival factor results in binding to 14-3-3 not BCL-X(L). Cell 87, 619-28.

In this Example, using the methods and compositions of the present invention, the present inventors (also referred to herein as "we") show that Leukocyte Function Antigen-1 (LFA-1) is essential in the formation of immune cell synapses and has a role in the pathophysiology of various autoimmune diseases. In this Example, using the methods and compositions of the present invention, the present inventors demonstrate that ICAM-2 induced an LFA-1 signal transduction pathway that is linked to receptor clustering and activation by both the microtubule and actin cytoskeleton. ICAM-2 exhibited a 21.7 μM/cell binding affinity as determined by single cell analysis. ICAM-2/LFA-1 engagement induced activation of PKC and a reorganization of both the actin and microtubule cytoskeleton. These events resulted in a Syk dependent activation of the p44/42 MAPK pathway upon cytotoxic T cell effector-target cell binding via active LFA-1. ICAM-2 mediated human $CD56^+CD8^+$ perforin release and resultant cytotoxicity to target leukemia cells. In comparison to the other ICAMs, ICAM-3 was found to be most similar to ICAM-2's effect and dissimilar to ICAM-1. In IL-2 pre-activated human PBMC, ICAM-2>ICAM-3>>ICAM-1 in mediating perforin release of a $CD56^+CD8^{med}$ population. All ICAMs contributed to perforin and granzyme-A loss in $CD56^+CD8^{high}$ populations. These results identify a specific functional consequence for ICAM-2/LFA-1 in subset-specific cytotoxic T cell immunity.

Introduction

Leukocyte Function Antigen-1 (LFA-1) is an $\alpha,\beta$ heterodimer integrin involved in leukocyte adhesion (van Kooyk and Figdor, 2000). At present, it is well understood that LFA-1 participates in lymphocyte adhesion, with prominent roles in the formation of the immunological synapse (Dustin and Shaw, 1999), and lymphocyte extravasation and recirculation (Volkov et al., 2001). LFA-1 adhesion is governed by the intercellular adhesion molecule (ICAMs)-1, -2, and -3 ligands (van Kooyk and Figdor, 2000). Patients afflicted with Leukocyte Adhesion Deficiency disorder (LAD), a syndrome in which the LFA-1 integrin is mutated or missing, suffer sever recurrent bacterial infections and impaired overall immunity (Bunting et al., 2002). Among these clinical manifestations, the LFA-1 knockout mouse has suggested that LFA-1 may have a potential role in mediating tumor regression in adoptive immunotherapy (Mukai et al., 1999; Nishimura et al., 1999). Although these studies genetically link a lymphocyte adhesion molecule with impaired immune function, the molecular details that mediate these immunopathologies are less well understood.

Investigations of LFA-1 have primarily focused on the integrin's adhesive role. It is unclear as to how the physical processes of LFA-1 integrin activation and receptor clustering are interconnected and translated into cellular signals upon ligand binding. It is less understood how the absence of these events leads to the devastating effects of LAD and the impaired immune responses in LFA-1 knockout mice. We therefore sought to decipher the molecular details of a model interaction of ICAM-LFA-1 to understand LFA-1 signaling mechanisms initiated upon cell-to-cell contact. Utilizing multiparameter single cell analysis to monitor LFA-1 receptor dynamics upon treatment with a soluble ICAM-2, we found that both the actin and the microtubule cytoskeleton couple ICAM-2 adhesion to LFA-1 activation and clustering. The microtubule cytoskeleton constrained the LFA-1 conformational change (activation), an event that preceded LFA-1 clustering as measured by multiparameter flow cytometry. The induced LFA-1 activation led to the activation of the p44/42 Mitogen Activated Protein Kinase pathway (MAPK; RAF/MEK/ERK), an event that was dependent on both Pyk2 and Syk kinase activities.

The present inventors investigated these molecular details of the ICAM-2 mediated LFA-1 activation in the adhesion between cytotoxic T cells and a target leukemia cell, an event that requires cell-to-cell contact. ICAM-2 stimulation of human $CD56^+CD8^+$ T cells could induce perforin/granzyme-A mediated cytotoxicity of leukemia cells. This directed killing was shared by ICAM-3 and to a lesser extent by ICAM-1, two other LFA-1 ligands. These results distinguish a signaling mechanism for ICAM-2/LFA-1 directed cytotoxic T lymphocyte immunity and suggest possible mechanisms by which tumor secretion of ICAM-2 and possibly ICAM-3 might allow for evasion of a directed cytotoxic T cell immune response.

Results Recombinant ICAM-2 Promotes LFA-1 Mediated Adhesion

The present inventors chose a model Jurkat T cell line as a system to initially dissect the LFA-1 signaling mechanism and then verified the findings in human T cells. A biochemically purified ICAM-2 protein was produced to study ICAM-2/LFA-1 interactions in the absence of other ligands (FIG. 33E-H). We purified human ICAM-2 from retrovirally transduced NIH3T3 cells using immunoaffinity chromatography and subsequent gel filtration. We compared it to an ICAM-2-FC fusion protein produced in NSO murine myeloma cells. These murine based mammalian expression systems were chosen on the basis that they yielded a bioactive form of ICAM-2. Biochemical analysis of ICAM-2FC protein was consistent with the expected molecular weight of the fusion protein (76 kD, FIG. 33A) and purified human ICAM-2 displayed a molecular weight of 72-74 kD (FIG. 33A). This size was similar to the 75 kD ICAM-2 purified from Jurkat T cells (data not shown).

The present inventors generated a FITC conjugated ICAM-2 (ICAM-2-FITC) to study LFA-1 receptor dynamics by flow cytometry and laser scanning confocal microscopy (LSCM) (FIG. 33G). We tested for ligand binding of the LFA-1 receptor by monitoring the binding kinetics of ICAM2-FITC on single cells. Low binding was observed in the first 150 seconds, whereupon there was a progressive increase until 750 seconds, and leveled thereafter (FIG. 33B, middle panel). In contrast, an α-LFA-1 antibody displayed an initial spike in the first 50-100 seconds and equilibrated until 800 seconds (FIG. 33B, bottom panel). Pre-activating LFA-1 by treatment with PMA (McDowell et al., 1998) showed an immediate binding of ICAM-2 (FIG. 33C, top panel). The gradual ICAM-2 binding after 150 seconds suggested an enhanced LFA-1 binding for its ICAM-2 ligand after some binding-induced event—a property not observed using the α-LFA-1 or upon PMA activated LFA-1 (FIG. 33B). Binding of ICAM-2-FITC was not observed in trypsinized cells (data not shown) and was blocked by antibodies to LFA-1 (described below). Therefore, there appeared to be an increase in binding of the ICAM-2 ligand as a function of time, suggesting the presence of an induced binding site on the target cells.

Analysis of the ICAM-2 binding population by flow cytometry showed a dependency on both the actin cytoskeleton and temperature. ICAM-2 adhesion was enhanced at 37° C. vs. 4° C. (FIG. 33C). Pre-treatment with the actin depolymerizing agent cytochalisin D revealed two ICAM-2 binding populations at both 37° C. and 4° C., contrasting with the binding phenomena observed for α-LFA-1 (FIG. 33C). Saturation of ICAM-2-FITC was observed at 37° C. more readily than at 4° C. (data not shown, FIG. 33H). Single cell binding affinity measurements for ICAM-2 were obtained by computing the percent ICAM-2-FITC bound per cell (FIG. 33D). Curve fit analysis indicated a dissociation constant of $0.21\pm0.07$ μM/$10^4$ cells (FIG. 33D). This value equates to 21.7 μM/cell, representing the first ligand binding measurements reported for ICAM-2 within the physiological context of cell surface LFA-1. Thus, quantitative single cell analysis of ICAM-2 ligand binding suggests strong binding at physiological temperatures.

Soluble ICAM-2 Induces LFA-1 Clustering and Cytoskeleton Polarization

Figure 34C:
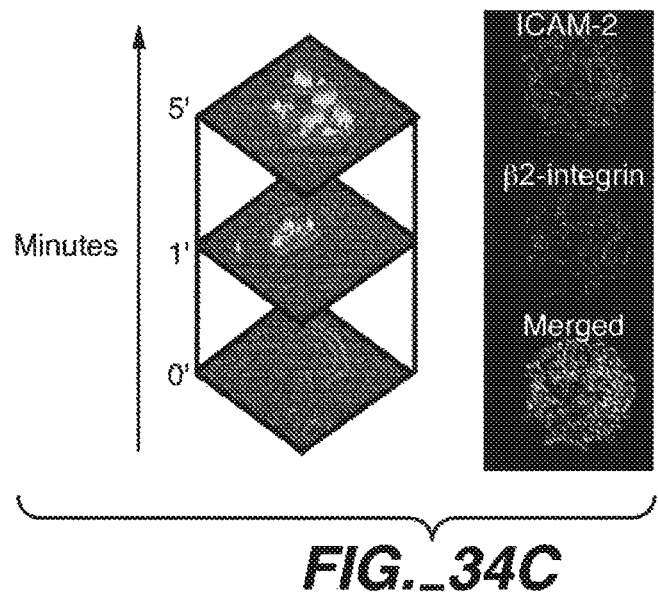

The present inventors investigated if LFA engagement altered cytoskeletal structures and observed a reorganization of both the actin and microtubule cytoskeleton upon ICAM-2 stimulus (FIG. 34A). The present inventors monitored the cytoskeletal architecture by flow cytometry and observed a simultaneous change in the actin and microtubule organization upon ICAM-2 binding (FIG. 34B), an effect consistent with depolymerization. ICAM-2 treatment induced a rapid clustering of LFA-1 within one minute, with multiple clustering events at five minutes (FIG. 34C, left panel). Using the ICAM-2-FITC ligand to visualize the cell surface, indicated that the ICAM-2 ligand induced clustering of the LFA-1 receptor (FIG. 34C, left panel). The clustering event showed some colocalization using a non-blocking β2 integrin antibody (clone CTB104) (FIG. 34C, right panel). Thus, we speculated that ICAM-2 binding to LFA-1 induced a signal that resulted in a reorganization of the LFA-1/ICAM-2 complex. We therefore decided to investigate this in relation to the observed changes in the actin/microtubule cytoskeleton.

Figure 34D:
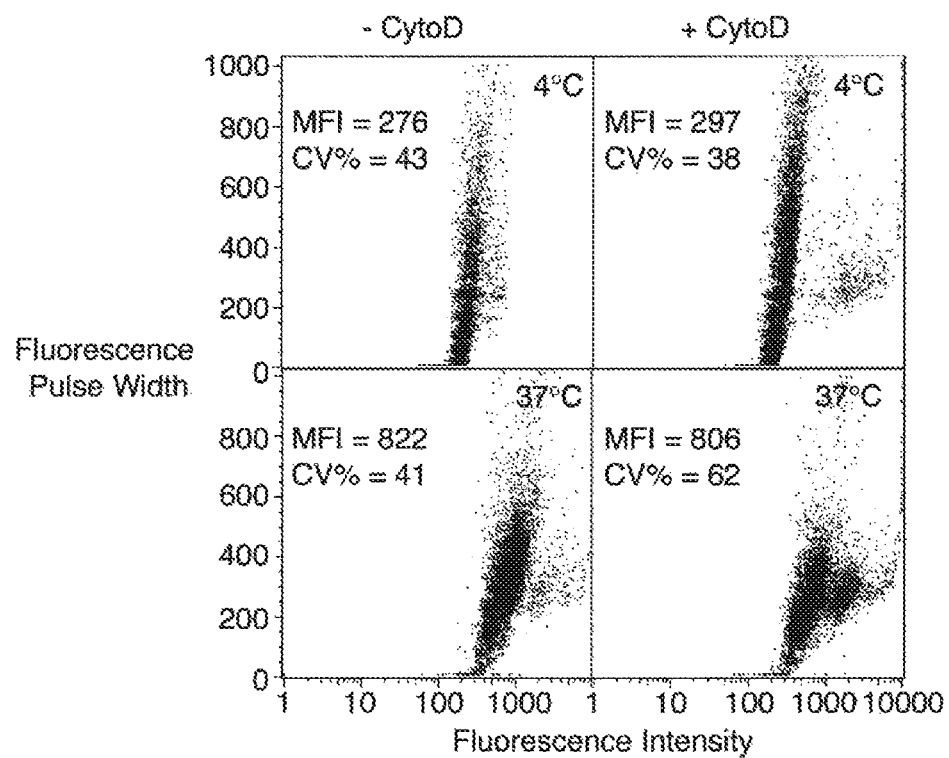

The present inventors assessed LFA-1 receptor dynamics by multiparameter flow cytometry upon ICAM-2 binding to correlate LFA-1 activation and clustering. We utilized the doublet discriminator module on a FACSCalibur machine to distinguish between distributed and focalized fluorescence pulses (FFP) upon laser excitation of single cells. Incubation of ICAM-2 at 37° C. vs. 4° C. displayed a decrease in the FFP, an effect that was greatly enhanced upon cytochalisin D treatment (FIG. 34D). ICAM-2-FITC surface binding was monitored by the fluorescence intensity and normalized against the time-of-flight (TOF) of the fluorescence pulse (FP). We interpreted the value of ICAM-2-FITC intensity per TOF as a quantitative assessment for LFA-1 clustering, as the TOF is proportional to the laser-excited cellular area. Computing this value as a function of time for an ICAM-2 stimulus (FIG. 34E) is proportional to the increased clustering events observed by LSCM (see FIG. 34C).

ICAM-2 Adhesion Induces a Conformational Change in LFA-1 that is Regulated by the Microtubule Cytoskeleton.

Although the enhanced ICAM-2 adhesion and induced LFA-1 clustering is reflective of overall increased avidity for the ICAM-2 ligand, it does not necessarily reflect an LFA-1 activation state (high affinity state) (McDowall et al., 1998). Upon LFA-1 activation, a conformational change exposes an epitope that is recognized by the mAb24 antibody (Neeson et al., 2000). A mAb24-Alexa633 conjugate was used to assess the activation state of LFA-1 upon ICAM-2 stimulus by flow cytometry. Unstimulated cells did not display mAb24 binding, contrasting the induction observed with PMA treatment (FIG. 34F). ICAM-2 stimulated cells displayed a bimodal population in active LFA-1, an effect that was attenuated by cytochalisin D (FIG. 34F). Treatment with microtubule disrupting agents, nocodazole and taxol, resulted in full activation of LFA-1 upon ICAM-2 stimulus (FIG. 34F). In contrast, disrupting the actin cytoskeleton via cytochalisin D diminished the ICAM-2 induced LFA-1 activation, although it enhanced LFA-1 receptor clustering and subsequent ICAM-2 binding (see FIG. 34D). Therefore, the actin and microtubule cytoskeletal network differentially impact LFA-1 activity and avidity.

The present inventors monitored LFA-1 activation and clustering simultaneously as a function of ICAM-2 stimulus per time by flow cytometry. Correlating the mean fluorescence of mAb24 antibody with the LFA-1 clustering value revealed LFA-1 activation preceeded LFA-1 clustering (FIG. 34G) within 30 seconds there was a significant increase in binding of the mAb24 antibody but only a modest increase in clustering. However, after another 30 seconds up to 30 minutes the relative binding of mAb24 increased somewhat but there was a significant increase in the clustering value (FIG. 34G). Thus, these results suggest that the ICAM-2 ligand induced activation of LFA-1 is followed by subsequent LFA-1 clustering.

Figure 35A:
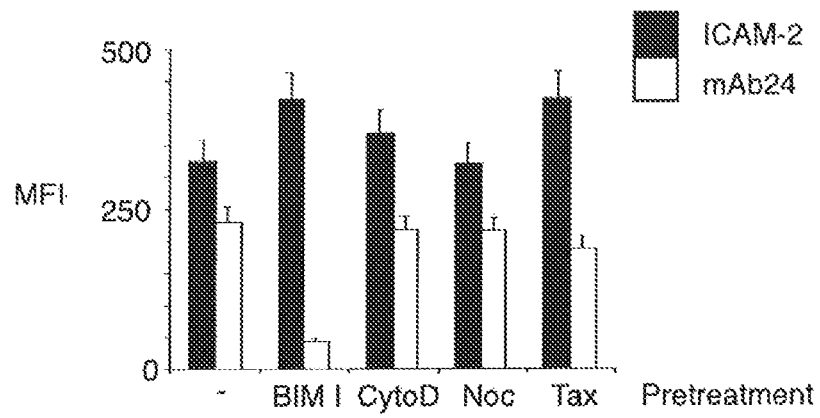

The present inventors observed that treating cells with a PKC inhibitor, bisindolymaleimide I (BIM I), inhibited ICAM-2 induced LFA-1 activation as measured by using mAb24 binding (FIG. 35A). ICAM-2 adhesion, as measured by the binding of ICAM-2-FITC, was not affected (FIG. 35A). This suggested that the ligand induced receptor conformational change was dependent on intracellular kinases. Interestingly, ICAM-2 induced a calcium influx, a component necessary in PKC activation (data not shown). Thus, these observations suggest that the ICAM-2 ligand induced exposure of the mAb24 neoepitope triggers a PKC dependent intracellular signaling event. We decided to investigate the downstream signaling consequences of ICAM-2 binding to LFA-1.

ICAM-2 Induces p44/42 MAPK Activity Through LFA-1

Figure 35B:
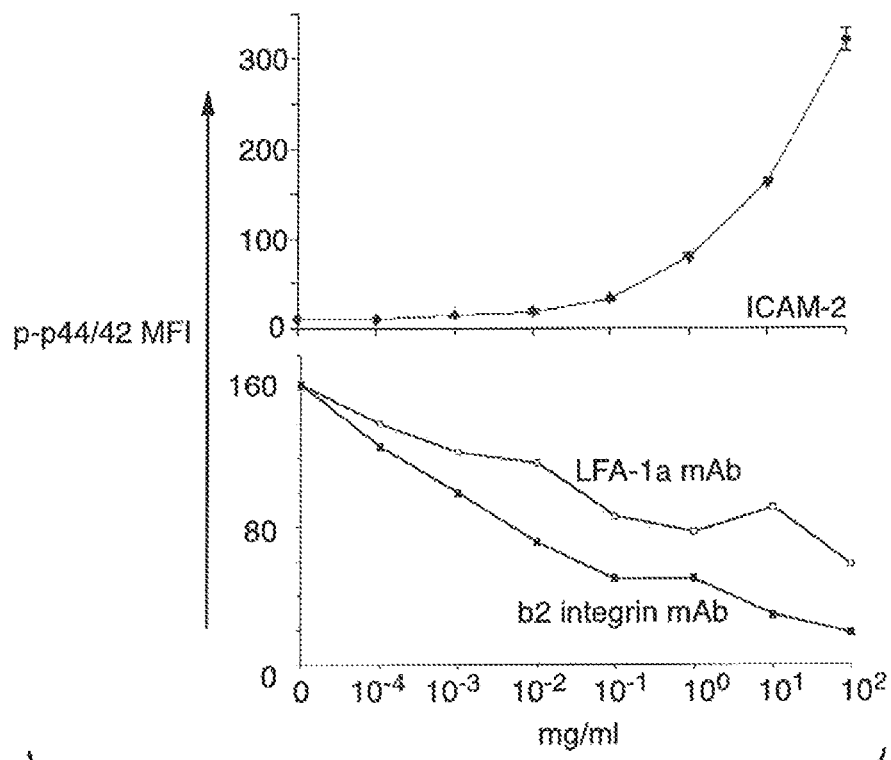

Flow cytometric based kinase profiling experiments were performed to identify a signaling pathway downstream of PKC activation upon ICAM-2 stimulus. Treatment with ICAM-2 induced both p44/42 MAPK phosphorylation and activation (FIG. 35B-D). An ICAM-2 titration correlated with phosphorylation of p44/42 MAPK as determined by single cell flow cytometric analysis (FIG. 35B, top panel), results congruent with kinase activity analysis (see FIG. 35C). Titration of mAbs to $\alpha_L$ and $\beta2$ integrins competed with ICAM-2 binding, and thus diminished the induced p44/42 MAPK phosphorylation (FIG. 35B, bottom panel). This inhibition was not observed after pretreatment with mAbs to $\beta1$, $\beta3$, $\alpha_M$, or $\alpha_X$ integrins (FIG. 35C) indicating that the ICAM-2/LFA-1 interaction was mediating the p44/42 MAPK activation.

Activation of PKC, PYK2, and SYK are Necessary for the ICAM-2/LFA-1 Induction of p44/42 MAPK Activity The present inventors undertook flow cytometric based p44/42 MAPK kinase inhibition and activation profiling to identify necessary components for LFA-1 signaling. PKC inhibitor BIM I, cytoskeletal disrupting agents cytochalisin D, taxol, nocodozole, and sequestering of divalent cations by EDTA diminished the ICAM-2 induced p44/42 MAPK signal (FIG. 35D), suggesting that the ligand-induced events of LFA-1 are mechanically linked to signal transduction by the actin-microtubule cytoskeleton. To identify upstream kinases that were responsible for signal transmission from LFA-1 to p44/42 MAPK, a series of kinase inhibitors were applied and tested for their ability to abrogate the ICAM-2 induced p44/42 MAPK activity (FIG. 34H-I), whereas Herbimycin A and Emodin, inhibitors of src and p56lck had no effect. Tyrphostin A9 and piceatannol, specific inhibitors of proline-tyrosine kinase 2 (Pyk2) and Spleen-tyrosine kinase (Syk), respectively (Avdi et al., 2001; Fuortes et al., 1999) abrogated the ICAM-2 induced activation of p44/42 MAPK and its upstream activator Raf-1 (FIG. 36A).

The present inventors tested whether Pyk2 and Syk interacted with the $\beta2$ integrin. Pyk2 and Syk were phosphorylated and co-immunoprecipitated with $\beta2$ integrin upon ICAM-2 treatment (FIG. 36B), indicating Pyk2 and Syk translocated to the membrane (FIG. 35E). This was coincident with phosphorylation of Pyk2 and Syk upon ICAM-2 stimulus as a function of time (FIG. 36B-C). Phosphorylation of PKC$\alpha/\beta_{II}$ and Pyk2 were detected at one minute, followed by Syk phosphorylation at 5 minutes (FIG. 36C). We confirmed that Pyk2 and Syk activities were dependent on PKC activation (data not shown FIG. 36D-E). Taken together with the above results, this suggested that the LFA-1 signaling mechanism imparted by ICAM-2 is at least initiated by PKC and relayed to the p44/42 MAPK pathway by Pyk2 and Syk.

LFA-1 is Involved in Effector-Target Cell Adhesion and Facilitates Human Cytotoxic T Cell Activation Since LFA-1 is involved in adhesion between lymphocytes, a process that occurs at several immunological synapses, we were interested in investigating the molecular events identified for the ICAM-2/LFA-1 interaction in a physiological context. It has been suggested that a clustered topographic presentation of ICAM-2, independent of expression levels, is an effective target structure by which natural killer cells initiated cytotoxicity (Helander et al., 1996). We first applied a FACS based effector-target killing assay to quantitatively monitor target cell lysis of HL60 leukemic cells upon treatment with stimulated human PBMC at various effector:target cell ratios. Flow cytometric detection of target cell lysis has been reported to be more sensitive than the standard chromium release assays (Lecoeur et al., 2001). We labeled HL60 cells with the fluorescent dye CFSE and monitored the cell quantity by flow cytometry in standard effector-target cell based assays. Soluble ICAM-2 could initiate target cell lysis in the presence of IL-2 but not in the absence of IL-2 (FIG. 37A). In IL-2 pre-activated cells, ICAM-1 and ICAM-3 did not initiate as potent a cytotoxic cell response in contrast to ICAM-2 (FIG. 37B).

Since natural killer cells (NK) comprise a heterogeneous population, namely specific cytotoxic T lymphocytes (CTL, with C8$^+$ subsets therein), NK cells (CD16$^+$ and subsets therein), and CD4$^+$ TH1 cells (Biron and Brossay, 2001), we determined if ICAM-2 was unique to a particular human NK cell subset. We utilized the multidimensional gating capability of flow cytometry to identify distinct cellular populations that were contributing to the cytolytic activity observed in human PBMC. We also monitored intracellular levels of perforin and granzyme-A by flow cytometry, two proteins that mediate target cell lysis by NK cells in these populations. We identified 6 distinct populations by CD8 and CD56 surface stains in human PBMC (FIG. 38 panel I) and gated on these subsets for all subsequent intracellular functional assays (FIG. 38A panels II-V). We performed effector-target cytotoxicity assays in the presence of ICAM-1, ICAM-2, and ICAM-3 soluble ligand and HL60 target cells. We did not observe significant changes in population subset frequencies post stimulation (FIG. 38A, panel I). The CD56$^+$CD8$^{low}$ population displayed no significant changes in intracellular perforin or granzyme-A upon stimulation with ICAM-1, -2, or -3 (FIG. 38A, panel II). The CD56$^+$CD8$^{med}$ population displayed a slight increase (1.5-2 fold) in the frequency of the perforin negative population for ICAM-2 and ICAM-3 (21.5% ICAM-2>19.8% ICAM-3>13.7% ICAM-1) (FIG. 38A panel III). The CD56$^+$CD8$^{high}$ population displayed a loss in both granzyme-A and perforin for ICAM-1, -2, -3 stimulations compared to unstimulated with a significant loss in the granzyme-A negative population for ICAM-2 (58.3%) compared to ICAM-1 (4.12%) or ICAM-3 (3.07%) (FIG. 38A, panel IV). The CD56$^-$CD8$^{high}$ also displayed a loss of both granzyme-A and perforin by all ICAM stimulations (FIG. 38A panel V). Since it was not possible to positively identify the subsets within the CD56$^-$CD8$^-$ population, they were omitted from analysis.

Quantifying the intracellular amounts of perforin and granzyme-A in the CD56CD8 subsets relative to unstimulated cells also identified similarities and differences for the ICAMs as evidenced below. ICAM-2 and ICAM-3 mediated loss of granzyme-A and perforin to a greater extent than ICAM-1 (FIGS. 38B-C). Additionally, in IL-2 pre-activated cells, differences where seen with the ICAM stimulations: ICAM-2>ICAM-3>>ICAM-1 displayed a loss of perforin, particularly in the CD56$^+$CD8$^{med/high}$ populations (FIG. 38B). ICAM-2 and ICAM-3 also induced perforin loss in the CD56$^+$CD8$^{low}$, however ICAM-2 required preactivation by IL-2 (FIG. 38B). There were lower levels of granzyme-A detected for the CD8$^{high}$ subsets (CD56$^+$ or CD56$^-$) for ICAM-2>ICAM-3>ICAM-1>unstimulated (FIG. 38C). In the presence of IL-2 pre-activation, all the ICAMs induced release of granzyme-A in the CD56$^+$CD8$^{high/med}$ populations, with a particular decrease by ICAM-2 (FIG. 38C). No significant changes were seen in the CD56$^+$CD8$^{low}$ population for granzyme-A (FIG. 38C). These differences were similar at various effector-target cell ratios (50:1, 25:1, 12.5:1) (data not shown). Thus, similarities and difference exist for ICAM-1, -2, and -3 stimulation of cytolytic activity in CD56CD8 subsets. All three ICAMs mediated perforin release in the CD56$^-$CD8$^{high}$ populations. ICAM-2 and ICAM-3 were most similar in mediating perforin/granzyme-A release in the CD56$^+$CD8$^{high}$ and CD56$^+$CD8$^{med}$ populations.

We focused on the CD56$^+$CD8$^+$ cells (both the CD8$^{med}$ and CD8$^{high}$ subsets) and tested if inhibition of Syk, p44/42 MAPK or disruption of the cytoskeleton detrimentally affected effector-target (E:T) cell conjugation as measured by a flow cytometric conjugate formation assay (Morgan et al., 2001). Disruption of cytoskeletal actin and microtubules enhanced E:T conjugate formation (FIG. 39A) congruent with prior results that disruption by these agents enhanced LFA-1 activation. Inhibition of Syk by piceatannol inhibited conjugate formation whereas inhibiting p44/42 MAPK by PD98059 did not (FIG. 39A). These results suggest that Syk activity is necessary for LFA-1 adhesion of effector-target cells and is consistent with a report indicating that Syk/ZAP-70 are necessary for LFA-1 to LFA-1 activation on the same cell (Soede et al., 1999). p44/42 MAPK appeared to not be necessary for E:T conjugate formation. Monitoring active LFA-1 and intracellular activation of p44/42 depicted a time dependent correlation between these two markers in CD56$^+$CD8$^+$ cells as stimulated by ICAM-2 (FIG. 39B).

Discussion

In this report it was observed that (1) ICAM-2 can induce LFA-1 clustering, activation, and cytoskeletal reorganization in the absence of exogenous activators such as cytokines or TCR signaling; (2) LFA-1 transmits a signal to the p44/42 MAPK pathway involving PKC, Pyk2, and Syk upon ligand binding; and (3) LFA-1 receptor dynamics are mechanically coupled to signal transduction by both the actin and microtubule cytoskeleton network. The physiological outcome of these molecular events triggered perforin and granzyme A mediated CD56$^+$CD8$^+$ T cell cytotoxicity that were mostly shared by ICAM-2 and ICAM-3 but not ICAM-1.

β2 integrin signaling mechanisms vary depending on the system of study and are centered on adhesive roles in cell morphology and motility (Dib, 2000). β2 integrin signaling has been shown to involve cytoskeletal reorganization via tyrosine phosphorylation of paxillin, vav, and GTPase activating proteins among others (Fuortes et al., 1994; Zheng et al., 1996). Studies focused on LFA-1 mediated leukocyte adhesion (CD11a/CD18) have shown a regulatory role for PKC in LFA-1 avidity (Bleijs et al., 2001; Hedman and Lundgren, 1992) and have demonstrated that TCR signaling can activate LFA-1 (Peterson et al., 2001). It has also been shown that chemokines, in the absence of TCR signaling, can serve as activators of LFA-1 during lymphocyte/endothelial contact (Constantin et al., 2000). It has not been clear how LFA-1 integrin adhesion, clustering, and activation are coupled to intracellular signaling events, in the absence of external (chemokine) or internal (TCR or costimulatory molecule) stimulation.

A synthesized peptide of ICAM-2's first Ig domain (P1, amino acids 21-42) can induce LFA-1 mediated adhesion at high concentrations (62 µM), which was comparable to a 48-fold lower ICAM-2 soluble protein concentration (1.3 µM) in a bulk cellular adhesion assay (Kotovuori et al., 1999). However, P1 binding did not induce the active conformation of LFA-1 and did not induce calcium influx (Kotovuori et al., 1999), whereas full length ICAM-2 binding resulted in active LFA-1 (see FIG. 34D) and a calcium influx event (data not shown). The calculated ICAM-2 affinity of 217±66 nM (per 10$^4$ cells) contrasts the 605±55 nM k$_D$ reported using BIA-core analysis of an engineered "active" locked I domain of LFA-1 (Shimaoka et al., 2001). The reported affinities for ICAM-2 binding here take advantage of single cell resolution within a physiological context, something not possible utilizing purified or genetically engineered LFA-1. The differences observed for peptide vs. protein concentrations are likely attributed to impurities in the peptide synthesis and/or presence of carbohydrate moieties native to the endogenous ICAM-2, which comprise greater than 30 kD of its approximate 66 kD molecular weight and have been suggested to orient ICAM-2 binding to LFA-1 (Casasnovas et al., 1997; de Fougerolles et al., 1991).

We investigated the role of the actin and microtubule cytoskeleton in LFA-1 receptor activation and clustering as induced by the ICAM-2 ligand by multiparameter flow cytometry. Disruption of the actin cytoskeleton enhanced LFA-1 clustering and ICAM-2 binding, corroborating previous studies that suggested the actin cytoskeleton constrains LFA-1 mobility (Lub et al., 1997). Interestingly, actin depolymerization abrogated the ICAM-2 induced LFA-1 activation. In contrast, disruption of the microtubules by both nocodazole and taxol enhanced LFA-1 activation as determined by exposure of the neo-epitope recognized by the mAb24. Recently, it has been reported that depolymerization of microtubules increases the lateral mobility of β2 integrins in macrophage cell lines (Zhou et al., 2001); therefore its conceivable that the microtubules regulate the conformational change upon ligand binding necessary for exposure of the LFA-1 activation epitope. These observations suggest the actin-microtubule cytoskeleton regulates both the high-avidity and high affinity state of LFA-1 upon ligand binding. We observed that LFA-1 signal transduction was abrogated in the presence of all cytoskeletal disrupting agents tested (cytochalisin D, nocodazole, and taxol) indicating that the LFA-1 receptor is linked to signal transduction machinery by the cytoskeleton. Thus, the mechanistic uncoupling of the high avidity and high affinity states of LFA-1 suggests that intracellular events that regulate/mediate these two states exist at the LFA-1 integrin-cytoskeletal juncture and relay the LFA-1 receptor dynamics to intracellular signaling proteins upon ligand binding.

Several chemical inhibition screens were designed to identify the proteins involved in the LFA-1 to p44/42 MAPK signaling event. Both Pyk2 and Syk were identified to be necessary for activation of the p44/42 MAPK pathway and were dependent on PKC activity upon ICAM-2 binding. Phosphorylation of Pyk2 has been associated with homotypic adhesion mediated by an LFA-1/ICAM-1 interaction in B cells (McDonald et al., 2000). In addition, Pyk2 activation has been shown to be necessary for p44/42 MAPK activity in other model systems (Barsacchi et al., 1999; Lev et al., 1995). Syk is a tyrosine kinase essential in αIIIβ3 signaling (Saci et al., 2000), and links FcεRI signaling to the ras/MAPK pathway (Jabril-Cuenod et al., 1996). Inhibition or ablation of Syk, either by pharmacological means (via inhibition by piceatannol), biochemical means (dominant negative Syk), or genetic means (Syk$^{-/-}$ mice) inhibits natural cytotoxicity (Brumbaugh et al., 1997; Colucci et al., 1999). Thus LFA-1 activation signaling to Syk, a kinase that has been shown to be important for NK cell function, provides a biochemical link between surface integrin activation and effector cell function.

The present inventors demonstrated that both Pyk2 and Syk are necessary in ICAM-2 induced LFA-1 signaling to Raf-1, the upstream kinase in the p44/42 MAPK (RAF/MEK/ERK) cascade. Inhibition of p44/42 MAPK did not prevent the occurrence of CD56$^+$CD8$^+$ cell conjugation. By immunofluorescence analysis, it has been shown that treatment of the NK leukemic cell line YT with the p44/42 MAPK inhibitor PD98059 inhibits perforin redistribution to the site of effector-target cell contact (Wei et al., 1998). In addition, the p44/42 MAPK pathway has been shown to be important in the regulation of cytoxicity in natural killer cells (Jiang et al., 2000). Thus, the p44/42 MAPK pathway, here demonstrated to become active upon LFA-1/ICAM-2 binding, has been shown to be connected to at least perforin granule exocytosis. Thus, the LFA-1 signaling pathway as elicited by ICAM-2 contains signaling junctures that map to both the effector-target cell adhesion event and activation of cytolytic machinery in the human CD56$^+$CD8$^+$ cytotoxic T cell population. These results provide direct evidence for a functional consequence of LFA-1 integrin adhesion with cytolytic signaling mechanisms.

We also observed that ICAM-2 was similar to ICAM-3 in mediating cytolytic activity as evidenced by release of perforin and granzyme-A in effector-cell conjugation, effects of which contrasted ICAM-1 (see FIG. 38). We have previously observed similarities between ICAM-2 and ICAM-3 intracellular signaling mechanism that also differed from that of ICAM-1 (Perez et al., 2002). However, the results do not exclude the possibility of ICAM-2 stimulating other yet to be identified cytotoxic capable subsets, as high cytolytic activity was observed in bulk PBMC (see FIG. 37).

Prior investigations into cytotoxic T cells have established that blocking the LFA-1/ICAM interactions inhibits effector-target cell adhesion and therefore concluded that it also blocks cytolytic activity in NK cells (Donskov et al., 1996; Krensky et al., 1984; Matsumoto et al., 2000). Functional studies of NK cells from LFA-1" mice have demonstrated that LFA-1 adhesion is necessary for IL-2 activated NK killing (Matsumoto et al., 2000) and also that LFA-1$^{-/-}$ CD8$^+$ T cells are defective for T cell activation and effector function (Shier et al., 1999). Interestingly, NK cell cytotoxicity is defective in NK cells from LAD patients (Shibuya et al., 1999). It has only recently been shown that the directed killing of cytotoxic T lymphocytes involves polarization of the microtubule-organizing center (MTOC) towards LFA-1 at the CTL-target site (Kuhn and Poenie, 2002), an indication that LFA-1 may possess a functional role other than strictly adhesion.

In conclusion we find that ICAM-2, as an LFA-1 ligand, can mediate activation and clustering of the LFA-1 receptor—an event that in turn polarizes the microtubule and actin cytoskeleton and activates the p44/42 MAPK pathway. These events were found to be necessary for effector-target cell binding of CD56$^+$CD8$^+$ T cells, and perforin/granzyme A mediated cytolytic activity. This effect was shared by ICAM-3. The mechanisms governing LFA-1 receptor dynamics and intracellular signaling reported here suggest LFA-1 signaling functionally contributes in CD56$^+$CD8$^+$ cytolytic activity in addition to possessing an adhesive role upon which other molecular interactions occur. Improper localization of the MTOC has been shown to inhibit exocytosis of lytic granules in CD8$^+$ tumor infiltrating T cells, thereby ablating perforin mediated cytolytic activity necessary for a CTL response in murine tumor models (Radoja et al., 2001b). Ironically, defective CD8$^+$ tumor infiltrating T cells can effectively mediate cell killing in vitro (Radoja et al., 2001a), suggesting tumor mediated inhibitory mechanisms exist within the tumor microenvironment. The production of soluble ICAMs (1 and 3) has been observed in sera from cancer and autoimmunity patients, though analysis has not been extended to ICAM-2 (Bloom et al., 2002). Only one report has indicated that elevated levels of soluble ICAM-2 were present in leukemia patients and decreased upon chemotherapy (Mustjoki et al., 2001). The etiology of these observations is unknown. In the context of the work presented here, it is plausible to speculate that either dysregulation of surface ICAM-2 or secretion of soluble ICAM-2 can prematurely trigger or block CD56$^+$CD8$^+$ cytolytic activity at the effector-target site and permit tumor escape from T cell lysis. Other, specific roles, of ICAM-2 in its interaction with other integrin ligands could lead to a better understanding of events that promulgate from the effector:target cell interface Materials and Methods Immunological and Chemical Reagents mAbs to β1, β2, β3, β4, β5, β6, α1, α4, α5, $α_L$, LFA-1, Pyk2, SyK, Mac-1, ICAM-1, and ICAM-3 (PharMingen). CD3, CD4, CD8, CD19, CD56, CD45 direct conjugates (FITC/PE/PERCP/APC/Biotin), granzyme-A-FITC (PharMingen). Perforin-CY5 and CD8-CY5PE (gift from the Herzenberg Laboratory, Stanford University). ICAM-2 mAb and ICAM-2-FITC (IC2/2 Research Diagnostics). Anti-phospho PYK2(Y402), anti-phospho-p44/42 (pT185Py187) (Biosource). Anti-phospho PKCα/β. (Thr638), anti-phospho-Syk(Tyr525/526), anti-phosphoRaf1 (Ser259) (Cell Signaling Technologies). Protein and chemical reagents used: fluorescein isothiocyanate (FITC) (Pierce), ALEXA FLUOR® dye series 488, 546, 568, 633, taxol-alexa546, phalloidin-alexa633, and CFSE (Molecular Probes). Tyrphostin A9 and 18, SB203580, piceatannol, bisindolylmaleimide I and II, herbimycin A (Calbiochem). Emodin, genistein, DMSO, PMA, PHA, staurosporine, ionomycin, propidium iodide, cytochalisin D (Sigma). Protein A/G agarose (SCBT). Recombinant human IL-2 (Roche), recombinant human ICAM-1-FC, ICAM2-FC, ICAM3-FC (Genzyme). Secondary antibodies to mouse and rabbit IgG (Santa Cruz). Mock treatments consisted of mouse IgG (for antibodies), 1% BSA (for proteins), or 0.001% DMSO vehicle (for chemicals).

Cell Culture

NIH3T3 cells were maintained in DMEM, 10% DCS, 1% PSQ (Duelbecco Modified Eagle Media, 10% Donor calf serum, 1% penicillin-streptomycin (1000 units/ml and 2 mM L-glutamine PSQ). Jurkat T-cells were maintained in RPMI-1640, 10% FCS, 1% PSQ at 1×10$^5$ cells/ml and serum starved 12 hours for all functional assays. Cells were maintained at 5% CO$_2$/37° C. humidified incubator. Human peripheral blood monocytes were obtained by Ficoll-plaque density centrifugation (Amersham Pharmacia, Uppsala, Sweden) of whole blood from healthy donors (Stanford Blood Bank) and depleted for adherent cells. Magnetically activated cell sorting was used to negatively isolate naïve CD8$^+$ T cells for studies as indicated (Dynal, Oslo, Norway).

Soluble ICAM-2 Generation and Synthesis of ICAM-2-FITC and ICAM2-Beads

Full length ICAM2 cDNA was obtained from Jurkat cells and cloned into retroviral vector PBM-Z-IN at the BamHI/Sal1 site as described (Perez et al., 2002). Human ICAM-2 was overexpressed in NIH3T3 cells by retroviral infection and harvested by immunoaffinity chromatography. ICAM-2 was affinity purified using a two step lysing procedure and subsequent purification on an anti-ICAM-2 solid support. Cells were lysed in buffer A (20 mM Tris pH 7.5, 150 mM NaCl 1 mM EDTA 1 mM EGTA, 0.1% NP40, 2.5 mM $Na_2PO_4$, 1 mM β-glycerolphosphate, 1 mM $Na_3VO_4$, 1 μg/ml Leupeptin, 1 mM PMSF, protease inhibitor cocktail tablet (Boehringer Mannheim) for 5 min 4° C., and subsequently permeabilized with 50% v/v with buffer B (Buffer A plus 1% Triton-X-100) for 30 min 4° C. Supernatant was harvested by centrifugation (14,000 RPM, 5 min, 4° C.). An Anti-ICAM-2 pAb to the C-terminal (4 mgs, Santa Cruz) was conjugated to an Affi-Gel Hz activated support (Biorad) as suggested by manufacturer. This support couples Ig molecules via the FC region, resulting in higher antigen binding capacity. Batch lysate of harvested supernatant was performed (4° C., for 2 hrs), and washed 4 times in buffer C (0.1% Tween-20, PBS pH 7.4). ICAM-2 protein was eluted by 4.5 M NaCl (in Tris pH 6.8), dialyzed overnight (in PBS pH 7.4, 0.001% azide, 0.01% glycerol, 4° C.), concentrated using size exclusion spin chromatography and stabilized using 0.01% glycerol. Anti-ICAM-2 solid support was re-equilibrated in buffer C, stored in 0.001% thimerosol and re-used up to 3 times. Purity was >98% as assessed by coomasie gel. Size exclusion chromatography removed higher molecular weight aggregates and were not observed on purified ICAM-2 by native gel electrophoresis. 20 mgs were purified by this method and used for this study. ICAM-2-FITC synthesis was achieved by chemical conjugation to NHS-Fluorescein (Pierce) and unreactive dye was removed by gel filtration. ICAM-2-FITC probe did not integrate into trypsinized Jurkat cells or bind when blocked by LFA-1 antibody clones TS1/22 or TS1/18 (Developmental Hybridoma Studies Bank) or unlabeled ICAM-2 protein as determined by flow cytometry. ICAM-2-FITC binding was not blocked by β2 integrin clone CT104 (Santa Cruz). Purified ICAM-2 was comparable to human recombinant ICAM-2FC fusion protein purified from NSO murine myeloma cells (Genzyme). ICAM-1 FC and ICAM-3FC were also purified from NSO cells (Genzyme). Proteins were spun at 14,000 RPM, 5 min prior to use. 1 mg of ICAM-2 protein was conjugated to $2 \times 10^8$ epoxy activated beads as suggested by manufacturer (Dynal). $4 \times 10^5$ beads containing a total of 2 μg ICAM-2 protein were used as indicated. Gel imaging was performed on a VersaDoc machine (Biorad) and analyzed using Quantity One quantitation software (Biorad).

Flow Cytometry

Intracellular and extracellular staining was performed as described (Perez and Nolan, 2002). Intracellular probes for active kinases were made by conjugating phospho-specific antibodies to the ALEXA FLUOR® dye series as described and used in phospho-protein optimized conditions (Perez and Nolan, 2002). Kinetic analyses was performed by direct application of fixation buffer in time synchronized 96-wells maintained at 37° C. Intracellular actin and microtubule staining was performed using phalloidin-Alexa633 and taxol-Alexa546 dyes (Molecular Probes). Adhesion and clustering assays were performed using ICAM-2-FITC as described in text. LFA-1 activation was assessed by either mAb24-Alexa633 or mAb24-Alexa546 conjugate, surface stained at 37° C. Flow cytometry data are representative of 3 independent experiments of $10^6$ cells/sample. 10-50,000 events were collected and manually calibrated on a FACSCalibur™ machine. Data plotted in bar graph format is expressed as geometric mean fluorescence intensity (MFI) and normalized for isotype controls. Log ratios are defined as the MFI of stimulus to the MFI of unstimulated cells. Data was analyzed using Flowjo™ software (Treestar).

Single Cell ICAM-2 Binding Measurements

Percentage of ICAM-2-FITC binding was expressed as $100*((MFI_{exp}-MFI_{ctl})/(MFI_{final}-MFI_{ctl}))$, where $MFI_{exP}$ equals the mean fluorescent intensity of experimental concentration, $MFI_{ctl}$ equals mean fluorescent intensity of unstained cells, $MFI_{final}$ equals mean fluorescent intensity of final concentration that saturated binding. The samples were incubated with final concentrations as indicted in Figure for 30 min at 37° C. in 50 μL staining media (def RPMI, 4% FCS), washed 1×(500 μL, PBS pH 7.4, containing 1 mM EDTA), and resuspended in 100 μL (1% paraformaldehyde). Dilution factor of staining conditions and molecular weight of 72.1 kD was used in determining molar concentrations. The staining buffer contained 2.4 mM calcium and 2 mM magnesium. The data were fit to the equation $V=V_{max}[S]/(Km+[S])$ where V is the percent bound, [S] is the ICAM-2-FITC concentration, and lc is the Michaelis-Menten binding constant using Kaleidagraph software.

Laser Scanning Confocal Microscopy

Jurkat cells were treated as indicated and adhered to poly-L-lysine (Sigma) coated sterilized coverslips (1 mg/ml, 30 min) by mild centrifugation (1000 RPM, 10 min), washed twice in phosphate buffered saline pH 7.4 (PBS) and fixed in 2.7% paraformaldehyde (in PBS). Cells were permeabilized (5 min, 0.1% Triton-X-100 in PBS), washed twice in PBS, blocked in 4% FCS, and subjected to antibody or intracellular staining as indicated. Stained coverslips were mounted and visualized using a Zeiss laser scanning confocal microscope 510.

Immunoprecipitations, Immunoblotting and Kinase Assays

Cell extracts were prepared by washing $2 \times 10^6$ cells (treated as indicated) in ice cold PBS and harvesting in lysis buffer (20 mM Tris pH 7.5, 150 mM NaCl 1 mM EDTA 1 mM EGTA, 1% Triton X-100, 2.5 mM $Na_2PO_4$, 1 mM β-glycerolphosphate, 1 mM $Na_3VO_4$, 1 μg/ml Leupeptin, 1 mM PMSF, protease inhibitor cocktail tablet (Boehringer Mannheim). Extracts were centrifuged 14,000 RPM (5 min, 4° C.) and 10-20 μg (BCA protein assay (Pierce)) were immunoblotted using standard procedures. Immunoprecipitations (IP) were pre-cleared with protein AlG plus-agarose beads, incubated with primary ab (1h), protein A/G plus-agarose beads (1h) and washed 4× with lysis buffer. Blots were incubated with the indicated antibodies and developed using ECL (Amersham). Immunoblots stripped and reprobed (as indicated) were done by incubating with stripping buffer (62.5 mM Tris, pH 6.8, 10% SDS, 1% β-mercaptoethanol) (30 min, 55° C.). MAPK activity was detected by a p44/42 MAPK kinase kit as suggested by manufacturer (Cell Signaling Technologies).

Cytolytic Activity, Perforin Release Assays, and Conjugate Formation Assays

Target cell lysis was measured by flow cytoemtric based detection of CFSE labeled HL60 cells. HL60 cells were labeled with 1 μg of CFSE (30 min, 37° C.). Targets were washed twice and mock treated, IL-2 activated (100 U/ml), CD3/CD28 activated (1 μg/ml), or treated with ICAM2 beads or soluble ICAM-1, -2, or 3 (10 μg/ml, 30 min, 37° C.) before plating at $10^4$ target cells/well of a 96-well round bottom plate. CTLs were added at 50:1, 25:1, and 12.5:1 E:T ratio, and incubated at 37° C. for 4 hrs. Cells were then processed for multiparameter flow cytometry and intracellular perforin stain. Percent specific lysis was calculated by the following equation: % specific lysis=100-100×(experimental HL60 count/total control HL60 count). HL60 counts were detectable by the CFSE fluorescence. Percent perforin was calculated by the following equation: % perforin=100×[(experimental perforin MFI–isotype mAb MFI)/(total perforin MFI–isotype mAb MFI)]. MFI refers to mean fluorescent intensity of flow cytoemtric based intracellular detection. Cell conjugates were determined by flow cytometry as described (Morgan et al., 2001). Chemical inhibition was done at 10 μM of indicated compound (30 min, 37° C.) prior to stimulation as indicated. All experiments were performed in triplicate.

References

Avdi, N. J., Nick, J. A., Whitlock, B. B., Billstrom, M. A., Henson, P. M., Johnson, G. L., and Worthen, G. S. (2001). Tumor necrosis factor-alpha activation of the c-Jun N-terminal kinase pathway in human neutrophils. Integrin involvement in a pathway leading from cytoplasmic tyrosine kinases apoptosis. J Biol Chem 276, 2189-2199.

Barsacchi, R., Heider, H., Girault, J., and Meldolesi, J. (1999). Requirement of pyk2 for the activation of the MAP kinase cascade induced by Ca(2+) (but not by PKC or G protein) in PC12 cells. FEBS Lett 461, 273-276.

Biron, C. A., and Brossay, L. (2001). NK cells and NKT cells in innate defense against viral infections. Curr Opin Immunol 13, 458-464.

Bleijs, D. A., van Duijnhoven, G. C., van Vliet, S. J., Thijssen, J. P., Figdor, C. G., and van Kooyk, Y. (2001). A single amino acid in the cytoplasmic domain of the beta 2 integrin lymphocyte function-associated antigen-1 regulates avidity-dependent inside-out signaling. J Biol Chem 276, 10338-10346.

Bloom, B. J., Miller, L. C., and Blier, P. R. (2002). Soluble adhesion molecules in pediatric rheumatic diseases. J Rheumatol 29, 832-836.

Brumbaugh, K. M., Binstadt, B. A., Billadeau, D. D., Schoon, R. A., Dick, C. J., Ten, R. M., and Leibson, P. J. (1997). Functional role for Syk tyrosine kinase in natural killer cell-mediated natural cytotoxicity. J Exp Med 186, 1965-1974.

Bunting, M., Harris, E. S., McIntyre, T. M., Prescott, S. M., and Zimmerman, G. A. (2002). Leukocyte adhesion deficiency syndromes: adhesion and tethering defects involving beta 2 integrins and selectin ligands. Curr Opin Hematol 9, 30-35.

Casasnovas, J. M., Springer, T. A., Liu, J. H., Harrison, S. C., and Wang, J. H. (1997). Crystal structure of ICAM-2 reveals a distinctive integrin recognition surface. Nature 387, 312-315.

Colucci, F., Turner, M., Schweighoffer, E., Guy-Grand, D., Di Bartolo, V., Salcedo, M., Tybulewicz, V. L., and Di Santo, J. P. (1999). Redundant role of the Syk protein tyrosine kinase in mouse NK cell differentiation. J Immunol 163, 1769-1774.

Constantin, G., Majeed, M., Giagulli, C., Piccio, L., Kim, J. Y., Butcher, E. C., and Laudanna, C. (2000). Chemokines trigger immediate beta2 integrin affinity and mobility changes: differential regulation and roles in lymphocyte arrest under flow. Immunity 13, 759-769.

de Fougerolles, A. R., Stacker, S. A., Schwarting, R., and Springer, T. A. (1991). Characterization of ICAM-2 and evidence for a third counter-receptor for LFA-1. J Exp Med 174, 253-267.

Dib, K. (2000). BETA 2 integrin signaling in leukocytes. Front Biosci 5, D438-451.

Donskov, F., Basse, P. H., and Hokland, M. (1996). Expression and function of LFA-1 on A-NK and T-LAK cells: role in tumor target killing and migration into tumor tissue. Nat Immun 15, 134-146.

Dustin, M. L., and Shaw, A. S. (1999). Costimulation: building an immunological synapse. Science 283, 649-650.

Fuortes, M., Jin, W. W., and Nathan, C. (1994). Beta 2 integrin-dependent tyrosine phosphorylation of paxillin in human neutrophils treated with tumor necrosis factor. J Cell Biol 127, 1477-1483.

Fuortes, M., Melchior, M., Han, H., Lyon, G. J., and Nathan, C. (1999). Role of the tyrosine kinase pyk2 in the integrin-dependent activation of human neutrophils by TNF. J Clin Invest 104, 327-335.

Hedman, H., and Lundgren, E. (1992). Regulation of LFA-1 avidity in human B cells. Requirements for dephosphorylation events for high avidity ICAM-1 binding. J Immunol 149, 2295-2299.

Helander, T. S., Carpen, O., Turunen, O., Kovanen, P. E., Vaheri, A., and Timonen, T. (1996). ICAM-2 redistributed by ezrin as a target for killer cells. Nature 382, 265-268.

Jabril-Cuenod, B., Zhang, C., Scharenberg, A. M., Paolini, R., Numerof, R., Beaven, M. A., and Kinet, J. P. (1996). Syk-dependent phosphorylation of Shc. A potential link between FcepsilonRI and the Ras/mitogen-activated protein kinase signaling pathway through SOS and Grb2. J Biol Chem 271, 16268-16272.

Jiang, K., Zhong, B., Gilvary, D. L., Corliss, B. C., Hong-Geller, E., Wei, S., and Djeu, J. Y. (2000). Pivotal role of phosphoinositide-3 kinase in regulation of cytotoxicity in natural killer cells. Nat Immunol 1, 419-425.

Kotovuori, A., Pessa-Morikawa, T., Kotovuori, P., Nortamo, P., and Gahmberg, C. G. (1999). ICAM-2 and a peptide from its binding domain are efficient activators of leukocyte adhesion and integrin affinity. J Immunol 162, 6613-6620.

Krensky, A. M., Robbins, E., Springer, T. A., and Burakoff, S. J. (1984). LFA-1, LFA-2, and LFA-3 antigens are involved in CTL-target conjugation. J Immunol 132, 2180-2182.

Kuhn, J. R., and Poenie, M. (2002). Dynamic polarization of the microtubule cytoskeleton during CTL-mediated killing. Immunity 16, 111-121.

Lecoeur, H., Fevrier, M., Garcia, S., Riviere, Y., and Gougeon, M. L. (2001). A novel flow cytometric assay for quantitation and multiparametric characterization of cell-mediated cytotoxicity. J Immunol Methods 253, 177-187.

Lev, S., Moreno, H., Martinez, R., Canoll, P., Peles, E., Musacchio, J. M., Plowman, G. D., Rudy, B., and Schlessinger, J. (1995). Protein tyrosine kinase PYK2 involved in Ca(2+)-induced regulation of ion channel and MAP kinase functions. Nature 376, 737-745.

Lub, M., van Kooyk, Y., van Vliet, S. J., and Figdor, C. G. (1997). Dual role of the actin cytoskeleton in regulating cell adhesion mediated by the integrin lymphocyte function-associated molecule-1. Mol Biol Cell 8, 341-351.

Matsumoto, G., Omi, Y., Lee, U., Nishimura, T., Shindo, J., and Penninger, J. M. (2000). Adhesion mediated by LFA-1 is required for efficient IL-12-induced NK and NKT cell cytotoxicity. Eur J Immunol 30, 3723-3731.

McDonald, J. T., Teague, R. M., Benedict, S. H., and Chan, M. A. (2000). Induction of PYK-2 phosphorylation during LFA-1/ICAM-1-dependent homotypic adhesion of fresh human B-cells. Immunol Invest 29, 71-80.

McDowall, A., Leitinger, B., Stanley, P., Bates, P. A., Randi, A. M., and Hogg, N. (1998). The I domain of integrin leukocyte function-associated antigen-1 is involved in a conformational change leading to high affinity binding to ligand intercellular adhesion molecule 1 (ICAM-1). J Biol Chem 273, 27396-27403.

Morgan, M. M., Labno, C. M., Van Seventer, G. A., Denny, M. F., Straus, D. B., and Burkhardt, S J. K. (2001). Superantigen-induced T cell:B cell conjugation is mediated by LFA-1 and requires signaling through Lck, but not ZAP-70. J Immunol 167, 5708-5718.

Mukai, S., Kagamu, H., Shu, S., and Plautz, G. E. (1999). Critical role of CD11a (LFA-1) in therapeutic efficacy of systemically transferred antitumor effector T cells. Cell Immunol 192, 122-132.

Mustjoki, S., Alitalo, R., Elonen, E., Carpen, O., Gahmberg, C. G., and Vaheri, A. (2001). Intercellular adhesion molecule-1 in extravasation of normal mononuclear and leukaemia cells. Br J Haematol 113, 989-1000.

Neeson, P. J., Thurlow, P. J., and Jamieson, G. P. (2000). Characterization of activated lymphocyte-tumor cell adhesion. J Leukoc Biol 67, 847-855.

Nishimura, T., Iwakabe, K., Sekimoto, M., Ohmi, Y., Yahata, T., Nakui, M., Sato, T., Habu, S., Tashiro, H., Sato, M., and Ohta, A. (1999). Distinct role of antigen-specific T helper type 1 (Th1) and Th2 cells in tumor eradication in vivo. J Exp Med 190, 617-627.

Perez, I. D., Kinoshita, S., Hitoshi, Y., Payan, D. G., Kitamura, T., Nolan, G. P., and Lorens, J. B. (2002). Activation of the PKB/AKT Pathway by ICAM-2. Immunity 16, 51-65.

Peterson, E. J., Woods, M. L., Dmowski, S. A., Derimanov, G., Jordan, M. S., Wu, J. N., Myung, P. S., Liu, Q. H., Pribila, J. T., Freedman, B. D., et al. (2001). Coupling of the TCR to integrin activation by Slap-130/Fyb. Science 293, 2263-2265.

Radoja, S., Saio, M., and Frey, A. B. (2001a). CD8+ tumor-infiltrating lymphocytes are primed for Fas-mediated activation-induced cell death but are not apoptotic in situ. J Immunol 166, 6074-6083.

Radoja, S., Saio, M., Schaer, D., Koneru, M., Vukmanovic, S., and Frey, A. B. (2001b). CD8(+) tumor-infiltrating T cells are deficient in perforin-mediated cytolytic activity due to defective microtubule-organizing center mobilization and lytic granule exocytosis. J Immunol 167, 5042-5051.

Saci, A., Rendu, F., and Bachelot-Loza, C. (2000). Platelet alpha IIb-beta 3 integrin engagement induces the tyrosine phosphorylation of Cbl and its association with phosphoinositide 3-kinase and Syk. Biochem J 351 Pt 3, 669-676.

Shibuya, K., Lanier, L. L., Phillips, J. H., Ochs, H. D., Shimizu, K., Nakayama, E., Nakauchi, H., and Shibuya, A. (1999). Physical and functional association of LFA-1 with DNAM-1 adhesion molecule. Immunity 11, 615-623.

Shier, P., Ngo, K., and Fung-Leung, W. P. (1999). Defective CD8+ T cell activation and cytolytic function in the absence of LFA-1 cannot be restored by increased TCR signaling. J Immunol 163, 4826-4832.

Shimaoka, M., Lu, C., Palframan, R. T., von Andrian, U. H., McCormack, A., Takagi, J., and Springer, T. A. (2001). Reversibly locking a protein fold in an active conformation with a disulfide bond: integrin alphaL I domains with high affinity and antagonist activity in vivo. Proc Natl Acad Sci USA 98, 6009-6014.

Soede, R. D., Driessens, M. H., Ruuls-Van Stalle, L., Van Hulten, P. E., Brink, A., and Roos, E. (1999). LFA-1 to LFA-1 signals involve zeta-associated protein-70 (ZAP-70) tyrosine kinase: relevance for invasion and migration of a T cell hybridoma. J Immunol 163, 4253-4261.

van Kooyk, Y., and Figdor, C. G. (2000). Avidity regulation of integrins: the driving force in leukocyte adhesion. Curr Opin Cell Biol 12, 542-547.

Volkov, Y., Long, A., McGrath, S., Ni Eidhin, D., and Kelleher, D. (2001). Crucial importance of PKC-beta(I) in LFA-1-mediated locomotion of activated T cells. Nat Immunol 2, 508-514.

Wei, S., Gamero, A. M., Liu, J. H., Daulton, A. A., Valkov, N. I., Trapani, J. A., Larner, A. C., Weber, M. J., and Djeu, J. Y. (1998). Control of lytic function by mitogen-activated protein kinase/extracellular regulatory kinase 2 (ERK2) in a human natural killer cell line: identification of perforin and granzyme B mobilization by functional ERK2. J Exp Med 187, 1753-1765.

Zheng, L., Sjolander, A., Eckerdal, J., and Andersson, T. (1996). Antibody-induced engagement of beta 2 integrins on adherent human neutrophils triggers activation of p21ras through tyrosine phosphorylation of the protooncogene product Vav. Proc Natl Acad Sci USA 93, 8431-8436.

Zhou, X., Li, J., and Kucik, D. F. (2001). The Microtubule Cytoskeleton Participates in Control of beta 2 Integrin Avidity. J Biol Chem 276, 44762-44769.

We claim:

1. A composition comprising:
   a first activation state specific binding element that is specific for an isoform corresponding to an activation state of a first activatable element; and
   a second activation state specific binding element that is specific for an isoform corresponding to an activation state of a second activatable element,
   wherein the first and second activation state specific binding elements are to be distinguishably detectable from one another, the first and second activatable elements are different from one another, and the first and the second activation state-specific binding elements are configured to detect binding to their corresponding activatable elements simultaneously or sequentially in single cells.

2. The composition according to claim 1, wherein the first and second activation state specific binding elements are antibodies or binding fragments thereof.

3. The composition according to claim 1, wherein the first and second activation state specific binding elements are labeled and the labels are distinguishable from one another.

4. The composition according to claim 3, wherein the first and second activation state specific binding elements are labeled with a directly detectable label.

5. The composition according to claim 4, wherein the directly detectable label is a fluorescent label.

6. The composition according to claim 3, wherein the first and second activation state specific binding elements are labeled with an indirectly detectable label.

7. The composition according to claim 6, wherein the indirectly detectable label is an enzyme.

8. The composition according to claim 1, wherein the composition further comprises a bioactive agent.

9. The composition according to claim 8, wherein the bioactive agent activates a signaling pathway.

10. The composition according to claim 9, wherein the bioactive agent is selected from the group consisting of polypeptides, nucleic acids and small binding molecules.

11. The composition according to claim 1, wherein the composition further comprises a fixation reagent.

12. The composition according to claim 1, wherein the composition further comprises a permeabilizing reagent.

13. The composition according to claim 1, wherein the composition is present in a vessel.

14. The composition according to claim 1, wherein the activation state of at least one activatable element of the first and second activatable elements is the phosphorylation state of the activatable element, and wherein the binding element that is specific for the activation state of the activatable element is specific for the phosphorylation state of the activatable element.

15. The composition according to claim 1, wherein the activation state of the first and second activatable elements is the phosphorylation state of the first and second activatable elements, and
   wherein the binding element that is specific for the activation state of the first activatable element is specific for the phosphorylation state of the first activatable element, and the binding element that is specific for the activation state of the second activatable element is specific for the phosphorylation state of the second activatable element.

\* \* \* \* \*

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial
<220> FEATURE:
<223> OTHER INFORMATION: Synthetic

<400> SEQUENCE: 1

Ser Lys Val Ile Leu Phe Glu
1               5

<210> SEQ ID NO 2
<211> LENGTH: 18
<212> TYPE: DNA
<213> ORGANISM: Artificial
<220> FEATURE:
<223> OTHER INFORMATION: Synthetic
```

-continued

```
<400> SEQUENCE: 2
gatcctccct ttatccag                                                 18

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
gaatgaaaga ccccacctgt                                               20

<210> SEQ ID NO 4
<211> LENGTH: 26
<212> TYPE: PRT
<213> ORGANISM: Artificial
<220> FEATURE:
<223> OTHER INFORMATION: Synthetic

<400> SEQUENCE: 4

Gln His Leu Arg Gln Gln Arg Met Gly Thr Tyr Gly Val Arg Ala Ala
1               5                   10                  15

Trp Arg Arg Leu Pro Gln Ala Phe Arg Pro
            20                  25

<210> SEQ ID NO 5
<211> LENGTH: 26
<212> TYPE: PRT
<213> ORGANISM: Artificial
<220> FEATURE:
<223> OTHER INFORMATION: Synthetic

<400> SEQUENCE: 5

Gln His Leu Arg Gln Gln Arg Met Gly Thr Tyr Gly Arg Ala Val Arg
1               5                   10                  15

Ala Leu Trp Arg Pro Gln Ala Phe Arg Pro
            20                  25
```